(12) United States Patent
Florjancic et al.

(10) Patent No.: US 8,841,334 B2
(45) Date of Patent: *Sep. 23, 2014

(54) COMPOUNDS AS CANNABINOID RECEPTOR LIGANDS AND USES THEREOF

(75) Inventors: Alan S. Florjancic, Kenosha, WI (US); Michael J. Dart, Highland Park, IL (US); Keith B. Ryther, Evansville, IN (US); Arturo Perez-Medrano, Grayslake, IL (US); William A. Carroll, Evanston, IL (US); Meena V. Patel, Green Oaks, IL (US); Karin Rosemarie Tietje, Mundelein, IL (US); Tongmei Li, Lake Bluff, IL (US); Teodozyj Kolasa, Lake Villa, IL (US); Megan E. Gallagher, Highland Park, IL (US); Sridhar Peddi, Grayslake, IL (US); Jennifer M. Frost, Grayslake, IL (US); Derek W. Nelson, Highland Park, IL (US); Xueqing Wang, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 252 days.

This patent is subject to a terminal disclaimer.

(21) Appl. No.: 12/274,105

(22) Filed: Nov. 19, 2008

(65) Prior Publication Data
US 2010/0093814 A1    Apr. 15, 2010

Related U.S. Application Data

(63) Continuation-in-part of application No. 11/755,434, filed on May 30, 2007, now Pat. No. 8,546,583.

(60) Provisional application No. 60/989,492, filed on Nov. 21, 2007, provisional application No. 60/809,712, filed on May 31, 2006.

(51) Int. Cl.
*A61K 31/426* (2006.01)
*C07D 277/08* (2006.01)

(52) U.S. Cl.
USPC .......... 514/371; 548/146; 548/190; 548/195; 514/365; 514/370

(58) Field of Classification Search
CPC ............................. A61K 31/426; C07D 277/08
USPC .......... 548/146, 190, 193, 195; 514/365, 370, 514/371
See application file for complete search history.

(56) References Cited

U.S. PATENT DOCUMENTS

| | | |
|---|---|---|
| 3,843,683 A | 10/1974 | Bell |
| 3,928,327 A | 12/1975 | Takamizawa et al. |
| 4,885,295 A | 12/1989 | Bell |
| 4,966,828 A | 10/1990 | Doenges et al. |
| 4,973,587 A | 11/1990 | Ward et al. |
| 4,978,664 A | 12/1990 | Bell |
| 5,013,837 A | 5/1991 | Ward et al. |
| 5,055,579 A | 10/1991 | Pawlowski et al. |
| 5,250,498 A | 10/1993 | Andree et al. |
| 5,468,722 A | 11/1995 | Shibata et al. |
| 5,530,019 A | 6/1996 | Okada et al. |
| 5,654,322 A | 8/1997 | Hirata et al. |
| 6,323,214 B1 | 11/2001 | Baraldi |
| 6,358,992 B1 | 3/2002 | Pamukcu et al. |

(Continued)

FOREIGN PATENT DOCUMENTS

| | | |
|---|---|---|
| CA | 2587667 A1 | 5/2006 |
| DE | 1522361 A1 | 7/1969 |

(Continued)

OTHER PUBLICATIONS

Araki et al (2003): STN International HCAPLUS database, (Columbus, Ohio), Accession No. 2003:931334.*
Ambartsumova, R.F. et al., "Effect of Various Factors on the Reaction of 2-Aminobenzothiazoles with Propylene Oxide," Chemistry of Heterocyclic Compounds, 2002, 994-999, vol. 38—Issue 8.

(Continued)

*Primary Examiner* — Golam M M Shameem
(74) *Attorney, Agent, or Firm* — Lisa V. Mueller; Michael Best & Friedrich LLP

(57) ABSTRACT

The present invention relates to compounds of formula (I), or pharmaceutical salts, prodrugs, salts of prodrugs, or combinations thereof,

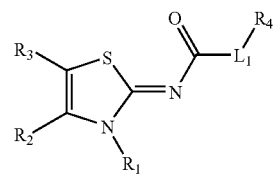

wherein $R_1$, $R_2$, $R_3$, $R_4$, and $L_1$ are defined in the specification, compositions comprising such compounds, and methods of treating conditions and disorders using such compounds and compositions. The present invention also relates to compounds of formula (II), or pharmaceutical salts, prodrugs, salts of prodrugs, or combinations thereof,

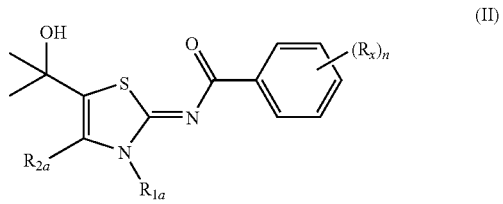

(II)

wherein $R_{1a}$, $R_{2a}$, $R_x$, and n are as defined in the specification, compositions comprising such compounds, and methods of treating conditions and disorders using such compounds and compositions.

18 Claims, No Drawings

(56) References Cited

U.S. PATENT DOCUMENTS

| | | | |
|---|---|---|---|
| 6,369,052 B1 | 4/2002 | Kellar et al. | |
| 6,559,186 B1 | 5/2003 | Campbell | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,560,456 B2 * | 7/2009 | Araki et al. | 514/224.2 |
| 7,560,481 B2 | 7/2009 | Frost et al. | |
| 7,674,912 B2 * | 3/2010 | Sams et al. | 548/195 |
| 7,683,084 B2 * | 3/2010 | Faghih et al. | 514/370 |
| 7,750,039 B2 | 7/2010 | Frost et al. | |
| 7,868,038 B2 | 1/2011 | Nelson et al. | |
| 7,872,006 B2 | 1/2011 | Moritani et al. | |
| 7,872,033 B2 | 1/2011 | Carroll et al. | |
| 7,875,639 B2 | 1/2011 | Florjancic et al. | |
| 7,875,640 B2 | 1/2011 | Kolasa et al. | |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |
| 8,236,822 B2 | 8/2012 | Wang et al. | |
| 8,288,428 B2 | 10/2012 | Wang et al. | |
| 8,338,467 B2 | 12/2012 | Kolasa et al. | |
| 8,481,574 B2 | 7/2013 | Meyer et al. | |
| 8,492,371 B2 | 7/2013 | Carroll et al. | |
| 8,501,794 B2 | 8/2013 | Carroll et al. | |
| 8,586,596 B2 | 11/2013 | Dart et al. | |
| 2004/0023862 A1 | 2/2004 | Smart et al. | |
| 2004/0029040 A1 | 2/2004 | Watanabe et al. | |
| 2004/0034090 A1 | 2/2004 | Barth et al. | |
| 2004/0077617 A1 | 4/2004 | Bennani et al. | |
| 2004/0166539 A1 | 8/2004 | Akhavan-Tafti et al. | |
| 2004/0259912 A1 | 12/2004 | Matsumoto et al. | |
| 2005/0176713 A1 | 8/2005 | Freyne et al. | |
| 2006/0199817 A1 | 9/2006 | Tasker et al. | |
| 2007/0061360 A1 | 3/2007 | Holcombe et al. | |
| 2007/0155738 A1 | 7/2007 | Steeneck et al. | |
| 2008/0058335 A1 | 3/2008 | Florjancic et al. | |
| 2008/0058355 A1 | 3/2008 | Westheim | |
| 2008/0139635 A1 | 6/2008 | Martin et al. | |
| 2008/0242654 A1 | 10/2008 | Kolasa et al. | |
| 2008/0287510 A1 | 11/2008 | Carroll et al. | |
| 2008/0312435 A1 | 12/2008 | Saito et al. | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105305 A1 | 4/2009 | Butlin et al. | |
| 2009/0105306 A1 | 4/2009 | Carroll et al. | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0041720 A1 | 2/2010 | Carroll et al. | |
| 2010/0063022 A1 | 3/2010 | Carroll et al. | |
| 2010/0069348 A1 | 3/2010 | Carroll et al. | |
| 2010/0069349 A1 | 3/2010 | Carroll et al. | |
| 2010/0093814 A1 | 4/2010 | Florjancic et al. | |
| 2010/0216760 A1 | 8/2010 | Frost et al. | |
| 2011/0065685 A1 | 3/2011 | Frost et al. | |
| 2011/0082116 A1 | 4/2011 | Carroll et al. | |
| 2011/0086832 A1 | 4/2011 | Kolasa et al. | |
| 2011/0086838 A1 | 4/2011 | Nelson et al. | |

FOREIGN PATENT DOCUMENTS

| | | | |
|---|---|---|---|
| DE | 1772867 | A1 | 6/1971 |
| DE | 2458933 | A1 | 6/1975 |
| DE | 3533331 | A1 | 3/1987 |
| EP | 412404 | A2 | 2/1991 |
| EP | 568096 | A1 | 11/1993 |
| EP | 0619316 | A1 | 10/1994 |
| EP | 0639569 | A1 | 2/1995 |
| EP | 1060734 | A2 | 12/2000 |
| EP | 1219612 | A1 | 7/2002 |
| EP | 1300401 | A1 | 4/2003 |
| EP | 1640369 | A1 | 3/2006 |
| EP | 1820504 | A1 | 8/2007 |
| FR | 2796643 | A1 | 1/2001 |
| JP | S57171986 | A | 10/1982 |
| JP | 6345736 | A | 12/1994 |
| WO | WO9507271 | A1 | 3/1995 |
| WO | WO-9531448 | A1 | 11/1995 |
| WO | WO-9601591 | A1 | 1/1996 |
| WO | WO-9700860 | A1 | 1/1997 |
| WO | WO9710223 | A1 | 3/1997 |
| WO | WO-0063207 | A1 | 10/2000 |
| WO | WO-0116138 | A1 | 3/2001 |
| WO | WO-0128557 | A1 | 4/2001 |
| WO | WO-0155139 | A1 | 8/2001 |
| WO | WO-0155140 | A1 | 8/2001 |
| WO | WO-0183422 | A1 | 11/2001 |
| WO | WO-0242269 | A1 | 5/2002 |
| WO | WO-02060447 | A1 | 8/2002 |
| WO | WO-02102232 | A2 | 12/2002 |
| WO | WO-03049741 | A1 | 6/2003 |
| WO | WO-03097605 | A1 | 11/2003 |
| WO | WO-2004050086 | A1 | 6/2004 |
| WO | WO-2004110453 | A1 | 12/2004 |
| WO | WO-2005023818 | A2 | 3/2005 |
| WO | WO-2005058887 | A1 | 6/2005 |
| WO | WO-2005075464 | A1 | 8/2005 |
| WO | WO2005099353 | A2 | 10/2005 |
| WO | WO-2005099353 | A3 | 10/2005 |
| WO | WO-2005115972 | A1 | 12/2005 |
| WO | WO-2005115986 | A1 | 12/2005 |
| WO | WO2006008754 | A1 | 1/2006 |
| WO | WO-2006051704 | A1 | 5/2006 |
| WO | WO-2006051704 | A1 | 5/2006 |
| WO | WO-2006070106 | A1 | 7/2006 |
| WO | WO2006100208 | A1 | 9/2006 |
| WO | WO-2007061360 | A2 | 5/2007 |
| WO | WO2007140385 | A2 | 12/2007 |
| WO | WO2007140439 | A2 | 12/2007 |
| WO | WO2007140439 | A3 | 1/2008 |
| WO | WO2007140385 | A3 | 2/2008 |
| WO | WO-2008063781 | A2 | 5/2008 |
| WO | WO2008079687 | A1 | 7/2008 |
| WO | WO-2008121558 | A1 | 10/2008 |
| WO | WO-2008130953 | A2 | 10/2008 |
| WO | WO2008144360 | A1 | 11/2008 |
| WO | WO-2009009550 | A1 | 1/2009 |
| WO | WO2009048936 | A1 | 4/2009 |
| WO | WO2009067613 | A1 | 5/2009 |
| WO | WO2009114566 | A1 | 9/2009 |
| WO | WO-2010019547 | A1 | 2/2010 |
| WO | WO-2010033543 | A2 | 3/2010 |
| WO | WO-2010054024 | A2 | 5/2010 |
| WO | WO-2010071783 | A1 | 6/2010 |
| WO | WO-2010111573 | A1 | 9/2010 |
| WO | WO-2010111574 | A1 | 9/2010 |

OTHER PUBLICATIONS

Arevalo-Martin, A., et al., "Therapeutic Action of Cannabinoids in a Murine Model of Multiple Sclerosis," Journal of Neuroscience, 2003, 2511-2516, vol. 23, No. 7.

Baker, T.J. et al., "Regiospecific Vinyl Phosphate/β-Keto Phosphonate Rearrangements Initiated by Halogen-Metal Exchange," Journal of Organic Chemistry, 1998, 2613-2618, vol. 63—Issue 8.

Benito, C, et al., "A Glial Endogenous Cannabinoid System Is Upregulated in the Brains of Macaques with Simian Immunodeficiency Virus-Induced Encephalitis," Journal of Neuroscience, 2005, 2530-2536, vol. 25—Issue 10.

(56) References Cited

OTHER PUBLICATIONS

Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.

Bouchard, J-F et al., "Contribution of endocannabinoids in the endothelial protection afforded by ischemic preconditioning in the isolated rat heart", Life Sciences, 2003, 1859-1870, vol. 72.

Boyle, W.J. et al., "Osteoclast differentiation and activation," (Binary/Image), 2003, 337-342, vol. 423.

Brennan, T.J. et al., "Characterization of a rat model of incisional pain," (Binary/Image), 1996, 493-501, vol. 64.

Buckley, N.E. et al., "Immunomodulation by cannabinoids is absent in mice deficient for the cannabinoid CB receptor," European Journal of Pharmacology, 2000, 141-149, vol. 396.

Carlisle, S.J. et al., "Differential expression of the CB2 cannabinoid receptor by rodent macrophages and macrophage-like cells in relation to cell activation," International Immunopharmacology, 2002, 69, vol. 2.

Carrier, E.J. et al., "Endocannabinoids in Neuroimmunology and Stress," Current Drug Targets CNS & Neurological Disorders, 2005, 657-665, vol. 4.

Casanova, M.L. et al., "Inhibition of skin tumor growth and angiogenesis in vivo by activation of cannabinoid receptors," Journal of Clinical Investigation, 2003, 43-50, vol. 111.

Chaplan, S.R. et al., "Quantitative assessment of tactile allodynia in the rat paw," Journal of Neuroscience Methods, 1994, 55-63, vol. 53.

Cichewicz, D.L. et al., "Synergistic interactions between cannabinoid and opioid analgesics," Life Sciences, 2004, 1317-1324, vol. 74.

Clayton, N. et al., "CB1 and CB2 cannabinoid receptors are implicated in inflammatory pain," (Binary/Image), 2002, 253-260, vol. 96.

Dixon, W.J. "Efficient analysis of experimental observations," Annual Review of Pharmacology and Toxicology, 1980, 441-462, vol. 20.

Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.

Galiégue, et al., "Expression of central and peripheral cannabinoid receptors in human immune tissues and leukocyte subpopulations," European Journal of Biochemistry, 1995, 54-61, vol. 232.

Golech, S.A. et al., "Human brain endothelium: coexpression and function of vannilloid and endocannabinoid receptors," Molecular Brain Research, 2004, 87-92, vol. 132.

Gouldson et al, "Mutational analysis and molecular modeling of the antagonist SR144528 binding site on the human cannabinoid CB2 receptor; figures 4 and 5," European Journal of Pharmacology, vol. 401, pp. 17-25, 2000.

Grotenhermen, F. et al., "IACM 2nd Conference on Cannabinoids in Medicine," Expert Opinion in Pharmacotherapy, 2003, 2367-2371, vol. 4—Issue 12.

Hanus, L. et al., "HU-308: A specific agonist for CB 2, a peripheral cannabinoid receptor," Proceedings of the National Academy of Science, 1999, 14228-14233, vol. 96.

Hargreaves, et al., "A new and sensitive method for measuring thermal nociception in cutaneous hyperalgesia," (Binary/Image), 1988, 77-88, vol. 32.

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.

Idris, A.I. et al., "Regulation of bone mass, bone loss and osteoclast activity by cannabinoid receptors," Nature Medicine, 2005, 774-779, vol. 11—Issue 7.

Ihenetu, K. et al., "Inhibition of interleukin-8 release in the human colonic epithelial cell line HT-29 by cannabinoids," European Journal of Pharmacology, 2003, 207-215, vol. 458.

International Search Report, European Patent Office (Nov. 27, 2008).

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14—Issue 22.

Kim, S.H. & Chung, J.M. "An experimental model for peripheral neuropathy produced by segmental spinal nerve ligation in the rat," (Binary/Image), 1992, 355-363, vol. 50—Issue 3.

Kreutzberg, G W "Microglia: a sensor for pathological events in the CNS," Trends in Neuroscience, 1996, 312-318, vol. 19.

Lepicier, P. et al., "Endocannabinoids protect the rat isolated heart against ischaemia," British Journal of Pharmacology, 2003, 805-815, vol. 139.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 627-634, vol. 15—Issue 2.

Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23—Issue 16.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Nunez, E. et al., "Cannabinoid CB2 Receptors Are Expressed by Perivascular Microglial Cells in the Human Brain: An Immunohistochemical Study," Synapse, 2004, 208-213, vol. 53.

Opposition filed by "Asociacion de Industrias Farmaceuticas Dominicanas Inc" for the Dominican Patent application Nr P2008-0060, received on Apr. 1, 2009, 8 pages.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology & Therapeutics, 2002, 165-174, vol. 95.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Genetic determinants of susceptibility to osteoporosis," Current Opinion in Pharmacology, 2003, 286-290, vol. 3.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

(56) References Cited

OTHER PUBLICATIONS

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.
Walter L. et al., "Cannabinoids and neuroinflammation," Pharmacology, 2004, 775-785, vol. 141.
Warhurst A.C. et al., "Interferon ? induces differential upregulation of a and β chemokine secretion in colonic epithelial cell lines," (Binary/Image), 1998, 208-213, vol. 42.
Watkins L.R. et al, "Glial activation: a driving force for pathological pain," Trends in Neuroscience, 2001, 450-455, vol. 24—Issue 8.
Werbel L.M. et al., "1-Alkyl-3-(3-alkyl-5-nitro-4-thiazolin-2-ylidene)-ureas and Related compounds as Schistosomicides" Journal of Medicinal Chemistry, 1972, 955-963, vol. 15—Issue 9.
Weyer et al., "Blutzuckersenkende Chinolin-8-carboxamidoalkyl-benzol sulfonamid derivate", Arzneimittel-Forschung, 1974, vol. 24, 269-275.
Wright K. et al., "Differential Expression of Cannabinoid Receptors in the Human Colon: Cannabinoids Promote Epithelial Wound Healing," Gastroenterology, 2005, 437-453, vol. 129.
Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.
Yoshihara S. et al., "Endogenous Cannabinoid Receptor Agonists Inhibit Neurogenic Inflammations in Guinea Pig Airways" Allergy and Immunology, 2005, 80-87, vol. 138.
Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.
Zimmer, A et al., "Increased mortality, hypoactivity, and hypoalgesia in cannabinoid CB1 receptor knockout mice," Proceedings of the National Academy of Science, 1999, 5780-5785, vol. 96.
Abreo M.A., et al., "Novel 3-Pyridyl Ethers with Subnanomolar Affinity for Central Neuronal Nicotinic Acetylcholine Receptors," Journal of Medicinal Chemistry, 1996, vol. 39 (4), pp. 817-825.
Araki, et al., (2003): STN International HCAPLUS database, (Columbus, OH). Accession No. 2003-931334.
Bennett G.J., et al., "A Peripheral Mononeuropathy in Rat that Produces Disorders of Pain Sensation like those Seen in Man," Pain, 1988, vol. 33 (1), pp. 87-107.
Berge, et al., "Pharmaceutical Salts," Journal of Pharmaceutical Sciences, 1977, vol. 66 (1), pp. 1-19.
Beylot, et al., "In Vivo Studies of Intrahepatic Metabolic Pathways," Diabetes Metabolism, 1997, vol. 23 (3), pp. 251-257.
Blagojevic, et al., "Role of heavy water in Boron Neutron Capture Therapy," Topics in Dosimetry & Treatment Planning for Neutron Capture Therapy, 1994, pp. 125-134.
Blake, et al., "Studies With Deuterated Drugs," Journal of Pharmaceutical Sciences, 1975, vol. 64 (3), pp. 367-391.
Bozidar, et al., "Transformations of 1,2,4-Thiadiazolo/2,3-X/ Azines," Heterocycles, 1987, vol. 26 (3), pp. 689-697.
Bozidar, et al., "Transformations of 1-(2-Chloropyridy1-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
"CAPLUS Record of U.S. Patent Application Publication No. 2008/0058335 by Westheim et al., 2007,".
"CAPLUS Record of U.S. Patent Application Publication No. 2008/0242654 by Kolasa et al., 2008,".
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, et al., "Effect of Deuterium Oxide on the Reproductive Potential of Mice," Annals of the New York Academy of Sciences, 1960, vol. 84, pp. 770-779.
Czajka, et al., "Physiological Effects of Deuterium on Dogs," American Journal of Physiology, 1961, vol. 201 (2), pp. 357-362.
Dart, et al (2007): STN International HCAPLUS database, Columbus (OH), Accession No. 2007:1396538.
Final Office Action mailed Mar. 10, 2010 for U.S. Appl. No. 11/755,434, filed May 30, 2007.
Final Office Action mailed Feb. 15, 2011 for U.S. Appl. No. 12/120,969, filed May 15, 2008.
Final Office Action mailed Mar. 24, 2011 for U.S. Appl. No. 11/755,434, filed May 30, 2007.
Final Office Action mailed Nov. 16, 2011 for U.S. Appl. No. 12/560,897, filed Sep. 16, 2009.
Final Office Action mailed Nov. 16, 2011 for U.S. Appl. No. 12/554,445, filed Sep. 4, 2009.
Final Office Action mailed Oct. 19, 2011 for U.S. Appl. No. 12/560,893, filed Sep. 16, 2009.
Florjancic, et al., (2009): Caplus Entry for WO2009067613, Accession No. 2009:649814.
Florjancic, et al., (2010): STN International HCAPLUS database, Columbus (OH), Accession No. 2010:478868.
Foster, et al., "Deuterium Isotope Effects in the Metabolism of Drugs and Xenobiotics: Implications for Drug Design," Advances in Drug Research, 1985, vol. 14, pp. 2-36.
Giron, D., "Applications of Thermal Analysis and Coupled Techniques in Pharmaceutical Industry," Journal of Thermal Analysis and Calorimetry, 2002, vol. 68, pp. 335-357.
Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Golub, et al., "Molecular Classification of Cancer: Class Discovery and Class Prediction by Gene Expression Monitoring," Science, 1999, vol. 286 (5439), pp. 531-537.
Greene, et al., "Protection for the Amino group," Protective Groups in Organic Synthesis, 1999, Third Edition, pp. 494-653.
Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.
International Search Report for Application No. PCT/US07/069921, mailed on Nov. 27, 2007, 4 pages.
International Search Report for Application No. PCT/US08/063648, mailed on Aug. 13, 2008, 3 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/068173, mailed on Feb. 5, 2010, 3 pages.
Joshi, et al., "Comparison of Antinociceptive Actoins of Standard Analgesics in Attenuating Capsaicin and Nerve-Injury-Induced Mechanical Hypersensitivty," Neuroscience, 2006, vol. 143, pp. 587-596.
Kato, et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Lizondo, et al., "Linezolid: Oxazolidinone antibacterial," Drugs of the Future, 1996, vol. 21 (11), pp. 1116-1123.
Maligres, et al., "Stereocontrolled Preparation of a Nonpeptidal (−)-Spirobicyclic NK-1 Receptor Antagonist," Journal of Organic Chemistry, 2002, vol. 67 (4), pp. 1093-1101.

(56) References Cited

OTHER PUBLICATIONS

Mallesham, et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.

Non-Final Office Action mailed Jun. 1, 2011 for U.S. Appl. No. 12/554,445, filed Sep. 4, 2009.

Non-Final Office Action mailed Jun. 1, 2011 for U.S. Appl. No. 12/560,897, filed Sep. 16, 2009.

Non-Final Office Action mailed Jun. 2, 2009 for U.S. Appl. No. 11/755,434, filed May 30, 2007.

Non-Final Office Action mailed Sep. 7, 2010 for U.S. Appl. No. 12/120,969, filed May 15, 2008.

Non-Final Office Action mailed Jan. 12, 2010 for U.S. Appl. No. 12/120,969, filed May 15, 2008.

Non-Final Office Action mailed May 17, 2011 for U.S. Appl. No. 12/560,893, filed Sep. 16, 2009.

Non-Final Office Action mailed Aug. 23, 2011 for U.S. Appl. No. 12/639,173, filed Dec. 16, 2009.

Non-Final Office Action mailed Jun. 29, 2010 for U.S. Appl. No. 11/755,434, filed May 30, 2007.

Non-Final Office Action mailed Nov. 30, 2010 for U.S. Appl. No. 11/755,434, filed May 30, 2007.

Ohta, et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.

Poste, et al., "Lipid Vesicles as Carriers for Introducing Biologically Active Materials into Cells," Methods in Cell Biology, 1976, vol. 14, pp. 33-71.

Radulescu, et al., "Actes Du Colloque Franco-Roumain De Chimie Appliquee, 3Rd, Bacau, Romania," 2004, pp. 117-120.

Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.

Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.

Rautio, et al, "Prodrugs: Design and Clinical Applications," Nature Reviews Drug Discovery, 2008, vol. 7 (3), pp. 255-270.

Rodriquez-Spong, et al., "General Principles of Pharmaceutical Solid Polymorphism: A Supramolecular Perspective," Advanced Drug Delivery Reviews, 2004, vol. 56 (3), pp. 241-274.

Ross, et al., "Antianaphylactic agents. 1. 2-(Acylamino)oxazoles," Journal of Medicinal Chemistry, 1979, vol. 22(4), pp. 412-417.

Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.

Smith, D., "Do Prodrugs Deliver?," Current Opinion in Drug Discovery and Development, 2007, vol. 10 (5), 550-559.

Souillac, et al, "Characterization of Delivery Systems, Differential Scanning Calorimetry," Encyclopedia of Controlled Drug Delivery, 1999, pp. 217-218.

Testa, B., "Prodrugs: Bridging Pharmacodynamic/Pharmacokinetic Gaps," Current Opinion in Chemical Biology, 2009, vol. 13 (3), pp. 338-344.

Thomson, J., "Physiological Effects of D20 in Mammals," Annals of the New York Academy of Sciences, 1960, vol. 84, pp. 736-744.

Wang, et al., Drug Delivery: Principles and Applications, John Wiley & Sons, Inc., 2005, pp. 136-137.

Widdowson, et al., "Palladium Catalysed Suzuki Reactions of Fluoroarenes," Chemical Communication (Camb), 2003, vol. 5, pp. 578-579.

Williams, et al., "Renin Inhibitors Containing Conformationally Restricted P1-P1 Dipeptide Mimetics," Journal of Medicinal Chemistry, 1991, vol. 34 (3), pp. 887-900.

Final Office Action mailed Dec. 28, 2011 for U.S. Appl. No. 12/639,173, filed Dec. 16, 2009.

Alfaro I., et al., "Dihydroaromatic Compounds in the Diels-Alder Reaction—III :In Situ Generation and Diels-Alder Reaction of Cyclohexa-1,3-Dienes," Tetrahedron, 1970, vol. 26, pp. 201-218.

Andreani, et al., "Ring-opened, etc.," Collection of Czechoslovak Chemical Communications, 1999, vol. 64, pp. 299-312.

Ansell M.F., et al., "The Synthesis of (+/−)-10a-Homo-11a-CarbathromboxaneA1, a Stable Thromboxane A Analogue," Journal of Chemical Society Perkin Trans, 1984, pp. 1061-1068.

Atwood B.K., et al., "CB : Therapeutic Target-in-Waiting," Progress in Neuro-Psychopharmacology & Biological Psychiatry, 2012, vol. 38 (1), pp. 16-20.

Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.

Bartlett P.A., et al., "Chorismate Mutase Inhibitors: Synthesis and Evaluation of Some Potential Transition-State Analogues," Journal of Organic Chemistry , 1988, vol. 53, pp. 3195-3210.

Bermudez-Silva, et al., "Role of Cannabinoid CB2 Receptors in Glucose Homeostasis in Rats," European Journal of Pharmacology, 2007, vol. 565 (1-3), pp. 207-211.

Bruson H.A., et al., "Action of Sulfuric Acid upon Unsaturated Isothiocyanates: Mercaptothiozolines ," Journal of American Chemical Society, 2011, vol. 59 (10), pp. 2011-2013.

Cai, et al., Ex Parte Appeal No. 2011005302, decided Jul. 12, 2011.

Campbell V.A., et al., "Alzheimer's Disease; Taking the Edge off with Cannabinoids?," British Journal of Pharmacology, 2007, vol. 152 (5), pp. 655-662.

Caplus Entry for International Application Publication No. WO2008130953, Accessed Aug. 14, 2012, with Structures Relevant to Claim 25 as Filed Aug. 11, 2011.

Caplus Entry for International Application Publication No. WO2008130953, Accessed Aug. 14, 2012, with Structures Relevant to Claim 35 as Filed Aug. 11, 2011.

CAS Registry No. 1061668-81-2, which entered STN on Oct. 15, 2008.

Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.

Chauhan M.S., "The Reaction of Some Heterocyclic Thiones with Ethyl Azidoformate," Canadian Journal of Chemistry, 1976, vol. 54 (24), pp. 3879-3883.

Chemical Abstracts Accession No. 1030770638, Jun. 26, 2008.

Cotarca L., et al., "Bis (trichloromethyl) Carbonate in Organic Synthesis," 1996, vol. 6, pp. 553-576.

Cross., et al., "Rules for the Nomenclature of Organic Chemistry, Section E: Stereochemistry," International Union of Pure and Applied Chemistry, 1976, vol. 45, pp. 11-30.

Database Registry [Online] Chemical Abstracts Service, Columbus, Ohio, US, Mar. 2, 2008, XP002687516, Database Accession No. 1006022-43-0.

Database Registry [Online] Chemical Abstracts Service, Columbus, Ohio, US, Mar. 2, 2008, XP002687517, Database Accession No. 1005993-02-1.

Database Registry [Online] Chemical Abstracts Service, Columbus, Ohio, US, Mar. 6, 2008, XP002687515, Database Accession No. 1006758-59-3.

Database Registry [Online] Chemical Abstracts Service, Columbus, Ohio, US, Mar. 7, 2008, XP002687514, Database Accession No. 1007004-94-5.

Database Registry [Online] Chemical Abstracts Service, Columbus, Ohio, US, Mar. 10, 2008, XP002687513, Database Accession No. 1007244-89-4.

Database Registry [Online] Chemical Abstracts Service, Columbus, Ohio, US, Feb. 29, 2008, XP002687518, Database Accession No. 1005931-81-6.

Dauben W.G., et al., "Organic Reactions at High Pressure Cycloadditions with Furans," Journal of the American Chemical Society, 1976, vol. 98 (7), pp. 1992-1993.

(56) References Cited

OTHER PUBLICATIONS

Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Ebata et al., "Synthesis of Both Enantiomers of 4-Hexanolide and 4-Dodecanolide," Agriculture Biochemical, 1991, vol. 55 (6), pp. 1685-1686.
Eckert H., et al., "Triphosgene, a Crystalline Phosgene Substitute," Angewandte Chemie International Edition in English, 1987, vol. 26 (9), pp. 894-895.
European Search Report for Application No. EP12187944, mailed on Nov. 20, 2012, 7 pages.
Ex Parte Quayle Action mailed Oct. 12, 2012 for U.S. Appl. No. 13/160,952, filed Jun. 15, 2011.
Fattori D., et al.,, "The Demjanov and Tiffeneau-Demjanov One-Carbon Ring Enlargements of 2-Aminomethy1-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Oct. 3, 2013 for U.S. Appl. No. 12/246,808, filed Oct. 7, 2008.
Final Office Action mailed Jul. 14, 2011 for U.S. Appl. No. 12/246,808, filed Oct. 7, 2008.
Final Office Action mailed Sep. 14, 2011 for U.S. Appl. No. 12/274,105, filed Nov. 19, 2008.
Final Office Action mailed Apr. 19, 2011 for U.S. Appl. No. 12/539,120, filed Aug. 11, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Goerdeler J., et al., "Uber Isothiazole, VIII. Synthese von Sulfonylamino-isothiazolen und Sulfonyliminoisothiazolinen aus Sulfonylsenfolen ," Chemische Berichte, 1969, vol. 102 (7), pp. 2273-2284.
Goodman A.J., et al., "CB2 Selective Sulfamoyl Benzamides; Optimization of the Amide Functionality," Bioorganic & Medicinal Chemistry Letters , 2009, vol. 19 (2), pp. 309-313.
Greene T.W., et al., in: Protective Groups in Organic Synthesis, 3rd Edition, John Wiley and Sons, Inc., 1999, Preface, Table of Contents, Abbreviations.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability and Written Opinion for Application No. PCT/US2010/028790, mailed on Sep. 27, 2008, 5 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US08/080253, mailed on Mar. 3, 2009, 3 pages.
International Search Report for Application No. PCT/US2005/0046480, mailed on Apr. 18, 2006, 5 pages.

(56) References Cited

OTHER PUBLICATIONS

International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/063318, mailed on May 6, 2010, 3 pages.
International Search Report for Application No. PCT/US2010/028790, mailed Jul. 19, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Izdebski J., et al., "A New Convenient Method for the Synthesis of Symmetrical and Unsymmetrical N,N'-Disubstituted Ureas," Synthesis, 1989, pp. 423-425.
Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Katritzky A.R., et al., "A General Synthesis of Unsymmetrical Tetrasubstituted Ureas," Journal of Organic Chemistry, 1997, vol. 62 (11), pp. 4155-4158.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.
Knolker H.J., et al., "A Novel Method for the Synthesis of Isocyanates Under Mild Conditions," Angewandte Chemie International Edition in English, 1995, vol. 34 (22), pp. 2497-2500.
Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.
Kolasa., "Thiazolylidene Derivatives as Cannabinoid Receptor Ligands and Their Preparation" Accession No. 2008:1184581, Mar. 22, 2011.
Kruijtzer J., et al., "Approaches to the Synthesis of Ureapeptoid Peptidomimetics," Tetrahedron Letters, 1997, vol. 38 (30), pp. 5335-5338.
Kubinyi, "3D QSAR in Drug Design: Ligand Protein Interactions & Molecular Similarity, 800 pages," Springer, 1998, vol. 2-3, pp. 243-244.
Lamothe M., et al., "A Simple One-Pot Preparation of N,N'-unsymmetrical ureas from N-Boc Protected Primary Anilines and Amines," Synlett, 1996, vol. 6, pp. 507-508.
Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.
Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.
Linn, et al., Journal of American Chemistry Society, 1963, 2032, vol. 85.
MacLennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Majer P., et al., "A Safe and Efficient Method for Preparation of N,"-Unsymmetrically Disubstituted Ureas Utilizing Triphosgene," Journal of Organic Chemistry, 1994, vol. 59, pp. 1937-1938.
Malan T.P., et al., "Inhibition of Pain Responses by Activation of CB(2) Cannabinoid Receptors," Chemistry and Physics of Lipids, 2002, vol. 121 (1-2), pp. 191-200.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.
Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Mayo clinic, Alzheimer's disease, [retrieved on Mar. 11, 2013]. Retrieved from the Internet:< URL: http://www.mayoclinic.com/health/alzheimers-disease/DS00161/DSECTION=prevention>.
Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.
Miyaura N., et al., ed., Topics in Current Chemistry: Cross-Coupling Reactions, Springer, 2002, Table of Contents.
Morii T., et al., "A General Strategy to Determine a Target DNA Sequence of a Short Peptide: Application to a [D]-Peptide," Journal American Chemical Society, 2002, vol. 124 (2), pp. 180-181.
Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.
Mucke L., "Neuroscience: Alzheimer's Disease," Nature, 2009, vol. 461 (7266), pp. 895-897.
Negishi E., et al., eds., Handbook of Organopalladium Chemistry for Organic Synthesis, vol. 1, John Wiley & Sons, 2002, Table of Contents.
Nieuwenhuijzen J.W., et al., "Solid and Solution Phase Combinatorial Synthesis of Ureas," Tetrahedron Letters, 1998, vol. 39, pp. 7811-7814.
Non-Final Office Action mailed Mar. 9, 2012 for U.S. Appl. No. 12/732,428, filed Mar. 26, 2010.
Non-Final Office Action mailed Jan. 27, 2011 for U.S. Appl. No. 12/274,105, filed Nov. 19, 2008.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Ozaki S., et al., "Recent Advances in Isocyanate Chemistry," Chemical Reviews, 1972, vol. 72 (5), pp. 457-496.
Padgett L.W., et al., "Recent Developments in Cannabinoid Ligands," Life Sciences, 2005, vol. 77 (14), pp. 1767-1798.
Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.
Rezoni G.E., et al., "Synthesis of 7-Carboxytricyclo[33103,7]nonan-3-ol," Journal of Organic Chemistry, 1983, vol. 48, pp. 5231-5236.
Sabnis R.W., et al., "2-Aminothiophenes by the Gewald Reaction," Journal of Heterocyclic Chemistry, 1999, vol. 36, pp. 333-345.
Schafer S.,et al., "Failure is an Option: Learning from Unsuccessful Proof-of-concept Trials," Drug Discovery Today, 2008, vol. 13 (21-22), pp. 913-916.
Schuart J., et al., "2-aminooxazoles and 2-iminooxazolines. 3. Selected Examples of a Homolog Series of 3 Substituted 2-imino-4-methyl-5-phenyloxazolines," Die Pharmazie, 1974, vol. 29 (3), pp. 170-172.
Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.

(56) References Cited

OTHER PUBLICATIONS

Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.
STN International HCAPLUS database Accession No. 2008:1184581, Columbus, Ohio, Lolasa et al, 2008.
Supplementary European Search Report for Application No. EP08837396, mailed on Jan. 16, 2012, 2 pages.
Supplementary European Search Report for Application No. EP08852528, mailed on Nov. 8, 2010, 2 pages.
Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.
Vasil'Eva V.F., et al., "Synthesis and Properties of 2-imino-3-benzyl-5-phenyl-1,3,4-oxadiazoline,"Caplus, 1970.
Viallet, et al., "2-Aminothiazoline, etc," 1980, CA 93:8074.
Vippagunta S.R., et al., "Crystalline Solids," Advanced Drug Delivery Reviews, 2001, vol. 48 (1), pp. 3-26.
Wermuth, "The practice of Medicinal chemistry," 2003, Chapters 9-10, 2nd edition,768 pages.
Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.
Williams K., et al., "Central Nervous System Perivascular Cells Are Immunoregulatory Cells that Connect the CNS tith the Peripheral mune System," Journal of Glia, 2001, vol. 36 (2), pp. 156-164.
Wu K.M., et al., "Regulatory Perspectives of Type II Prodrug Development and Time-Dependent Toxicity Management: Nonclinical Pharm/Tox Analysis and the Role of Comparative Toxicology," Toxicology, 2007, vol. 236 (1-2), pp. 1-6.
Yao B.B., et al., "In Vitro Pharmacological Characterization of Am1241: A Protean Agonist at the Cannabinoid Cb2 Receptor," British Journal of Pharmacology, 2006, vol. 149 (2), pp. 145-154.
Non-Final Rejection mailed Dec. 5, 2013 for U.S. Appl. No. 12/967,282, filed Dec. 14, 2010.
Office Action mailed Nov. 15, 2013 for European Application No. 05855099.7 filed Dec. 21, 2005.
Notice of Allowance mailed Jan. 17, 2014 for U.S. Appl. No. 12/120,969, filed May 15, 2008.
Final Office Action mailed Mar. 14, 2014 for U.S. Appl. No. 12/970,480, filed Dec. 16, 2010.
Notice of Allowance mailed Apr. 14, 2014 for U.S. Appl. No. 12/967,282, filed Dec. 14, 2010.
Final Office Action mailed May 23, 2014 for U.S. Appl. No. 12/246,808 filed Oct. 7, 2008.
Notice of Allowance mailed Jun. 2, 2014 for U.S. Appl. No. 12/554,445 filed Sep. 4, 2009.
Notice of Allowance mailed Jun. 9, 2014 for U.S. Appl. No. 12/560,893 filed Sep. 16, 2009.
Notice of Allowance mailed Jun. 9, 2014 for U.S. Appl. No. 12/639,173 filed Dec. 16, 2009.
Notice of Allowance mailed Jun. 9, 2014 for U.S. Appl. No. 12/970,435 filed Dec. 16, 2010.
Office Action mailed Jun. 30, 2014 for U.S. Appl. No. 12/970,480 filed Dec. 16, 2010.

\* cited by examiner

COMPOUNDS AS CANNABINOID RECEPTOR LIGANDS AND USES THEREOF

This application claims priority to U.S. Ser. No. 60/989,492 filed on Nov. 21, 2007 and is incorporated herein by reference in its entirety. The application is also a continuation-in-part of U.S. Ser. No. 11/755,434 filed on May 30, 2007 which in turn seeks priority from U.S. Ser. No. 60/809,712, filed on May 31, 2006, all of which are incorporated herein by reference in its entirety.

TECHNICAL FIELD

The present invention relates to compounds that are cannabinoid receptor ligands, compositions comprising such compounds, and methods of treating conditions and disorders using such compounds and compositions.

BACKGROUND $(-)$-$\Delta^9$-Tetrahydrocannabinol ($\Delta^9$-THC), the major psychoactive constituent of marijuana, exerts a broad range of therapeutic effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY

The present invention generally provides compounds that are $CB_2$ receptor ligands and pharmaceutical compositions and methods for the treatment of disorders using these compounds and pharmaceutical compositions.

One aspect of the invention is directed towards compounds of formula (I), or pharmaceutical salts, prodrugs, salts of prodrugs, or combinations thereof,

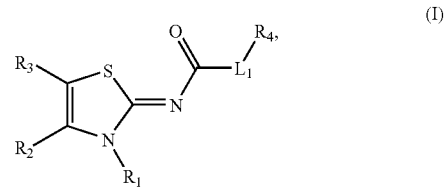

$R_1$ is alkoxyalkyl, alkoxyalkoxyalkyl, hydroxyalkyl, A, or A-alkylene-;

$R_2$ is hydrogen, alkoxy, alkoxyalkyl, alkoxycarbonyl, alkoxycarbonylalkyl, alkyl, alkyl-S(O)$_2$—, aryl, arylalkyl, arylalkenyl, azidoalkyl, cyano, cycloalkyl, halo, haloalkyl, heteroaryl, heterocycle, —(CR$_{21}$R$_{22}$)$_m$—OH, R$_a$R$_b$N—, R$_a$R$_b$N-alkyl-, R$_c$R$_d$NC(O)—, or R$_8$—R$_7$—;

$R_3$ is hydrogen, alkoxy, alkoxyalkyl, alkyl, alkylcarbonyl, alkyl-S(O)$_2$—, aryl, arylalkyl, arylalkenyl, cyano, cycloalkyl, halo, haloalkyl, heteroaryl, heterocycle, —(CR$_{31}$R$_{32}$)$_m$—OH, R$_a$R$_b$N—, R$_a$R$_b$N-alkyl-, or R$_8$—R$_7$—; or $R_2$ and $R_3$, together with the carbon atoms to which they are attached, form a 4-, 5-, 6-, or 7-membered monocyclic ring, optionally fused to benzo or oxadiazole, said monocyclic ring contains zero or one additional double bond, zero or one oxygen atom, and zero or one nitrogen atom as ring atoms; two non-adjacent atoms of said monocyclic ring are optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; with the proviso that when $R_2$ and $R_3$, together with the carbon atom to which they are attached, form a ring as represented by formula (viii), (ix), or (xi),

(viii)

(ix)

(xi)

then $R_1$ is A or A-alkylene-;

and with a further proviso that when $R_2$ and $R_3$ are other than forming a ring with the carbon atoms to which they are attached, then $R_1$ is alkoxyalkoxyalkyl, A or A-alkylene-;

$R_4$ is alkyl, alkynyl, cycloalkyl, cycloalkenyl, aryl, heteroaryl, heterocycle, cycloalkylalkyl, cycloalkenylalkyl, arylalkyl, heteroarylalkyl, heterocyclealkyl, or $R_{10}$-$L_2$-$R_9$—; wherein the alkyl group is optionally substituted with one substituent selected from the group consisting of alkoxy, alkoxycarbonyl, carboxy, halo, —OH, and $R_eR_fN$—;

$R_7$, $R_8$, and $R_9$, are each independently aryl, cycloalkyl, cycloalkenyl, heteroaryl, or heterocycle;

$R_{10}$ is aryl, cycloalkyl, cycloalkenyl, heteroaryl, heterocycle, or cycloalkylalkyl;

$R_a$ and $R_b$, at each occurrence, are each independently hydrogen, alkoxycarbonyl, alkyl, alkylcarbonyl, alkyl-S(O)$_2$—, or arylalkyl;

$R_c$ and $R_d$, are each independently hydrogen or alkyl;

$R_e$ and $R_f$, are each independently hydrogen, alkyl, or alkylcarbonyl;

A is a 4-, 5-, 6-, 7-, 8-, or 9-membered monocyclic heterocycle containing zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; or A is furanyl, oxazolyl, isoxazolyl, or oxadiazolyl; each ring A is optionally fused with a monocyclic ring selected from the group consisting of benzo, cycloalkyl, cycloalkenyl, heterocycle and heteroaryl; and each A is independently unsubstituted or substituted with 1, 2, 3, 4, 5, or 6 substituents independently selected from the group consisting of oxo, alkyl, halo, —OH, —O(alkyl), and haloalkyl;

$L_1$ is a single bond or —NR$_g$—;

$L_2$ is a single bond, alkylene, or —O—;

$R_g$ is hydrogen or alkyl;

the aryl, cycloalkyl, cycloalkenyl, heterocycle, or heteroaryl moieties, as a substituent, or as part of a substituent, as represented by $R_2$, $R_3$, $R_4$, $R_a$, $R_b$, $R_7$, $R_8$, $R_9$, and $R_{10}$, are each independently unsubstituted or substituted with 1, 2, 3, 4, 5, or 6 substituents independently selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$—(CR$_{41}$R$_{42}$)$_p$=C(R$_{41}$)—, alkyl-S(O)$_2$—(CR$_{41}$R$_{42}$)$_p$—, alkyl-S—, alkyl-S—(CR$_{41}$R$_{42}$)$_p$—, alkynyl, carboxy, carboxyalkyl, cyano, cyanoalkyl, formyl, formylalkyl, halogen, haloalkyl, haloalkoxy, hydroxy, hydroxyalkyl, oxo, —SH, N(O)$_2$, —C(R$_{41}$)=N—O(R$_{42}$), —(CR$_{41}$R$_{42}$)$_p$—C(R$_{41}$)=N—O(R$_{42}$), =N—O(alkyl), =N—OH, NZ$_1$Z$_2$—(CR$_{41}$R$_{42}$)$_p$—O—, —O—(CR$_{41}$R$_{42}$)$_p$-G$_1$, G$_1$, —NZ$_1$Z$_2$, —(CR$_{41}$R$_{42}$)$_p$—NZ$_1$Z$_2$, and (NZ$_3$Z$_4$)carbonyl;

G$_1$ is a 4-, 5-, 6-, or 7-membered monocyclic heterocycle containing one nitrogen atom and optionally 1 or 2 additional heteroatom in the ring, wherein said ring is attached to the parent moiety through the nitrogen atom, and said ring is optionally substituted with 1, 2, 3, 4, or 5 substituents selected from the group consisting of alkyl, alkenyl, alkynyl, halo, haloalkyl, =N—CN, =N—OR$_{51}$, —CN, oxo, —OR$_{51}$, —OC(O)R$_{51}$, —OC(O)N(R$_{51}$)$_2$, —S(O)$_2$R$_{52}$, —S(O)$_2$N(R$_{51}$)$_2$, —C(O)R$_{51}$, —C(O)OR$_{51}$, —C(O)N(R$_{51}$)$_2$, —N(R$_{51}$)$_2$, —N(R$_{51}$)C(O)R$_{51}$, —N(R$_{51}$)S(O)$_2$R$_{52}$, —N(R$_{51}$)C(O)O(R$_{52}$), —N(R$_{51}$)C(O)N(R$_{51}$)$_2$, —(CR$_{1c}$R$_{1d}$)$_q$—OR$_{51}$, —(CR$_{1c}$R$_{1d}$)$_q$—OC(O)R$_{51}$, —(CR$_{1c}$R$_{1d}$)$_q$—OC(O)N(R$_{51}$)$_2$, —(CR$_{1c}$R$_{1d}$)$_q$—S(O)$_2$R$_{52}$, —(CR$_{1c}$R$_{1d}$)$_q$—S(O)$_2$N(R$_{51}$)$_2$, —(CR$_{1c}$R$_{1d}$)$_q$—C(O)R$_{51}$, —(CR$_{1c}$R$_{1d}$)$_1$—C(O)OR$_{51}$, —(CR$_{1c}$R$_{1d}$)$_q$—C(O)N(R$_{51}$)$_2$, —(CR$_{1c}$R$_{1d}$)$_q$—N(R$_{51}$)$_2$, —(CR$_{1c}$R$_{1d}$)$_q$—N(R$_{51}$)C(O)R$_{51}$, —(CR$_{1c}$R$_{1d}$)$_q$—N(R$_{51}$)S(O)$_2$R$_{52}$, —(CR$_{1c}$R$_{1d}$)$_q$—N(R$_{51}$)C(O)O(R$_{52}$), —(CR$_{1c}$R$_{1d}$)$_q$—N(R$_{51}$)C(O)N(R$_{51}$)$_2$, and —(CR$_{1c}$R$_{1d}$)$_q$—CN;

$R_{51}$, at each occurrence, is independently hydrogen, $C_1$-$C_4$ alkyl, $C_1$-$C_4$ haloalkyl, —(CR$_{2c}$R$_{2d}$)$_u$—OR$^{53}$, monocyclic cycloalkyl, or —(CR$_{2c}$R$_{2d}$)$_u$-(monocyclic cycloalkyl); wherein $R_{53}$ is hydrogen, $C_1$-$C_4$ alkyl, $C_1$-$C_4$ haloalkyl, monocyclic cycloalkyl, or —(CR$_{2c}$R$_{2d}$)$_u$-(monocyclic cycloalkyl);

$R_{52}$, at each occurrence, is independently $C_1$-$C_4$ alkyl, $C_1$-$C_4$ haloalkyl, monocyclic cycloalkyl, or —(CR$_{2c}$R$_{2d}$)$_u$-(monocyclic cycloalkyl);

the monocyclic cycloalkyl moiety, as a substituent, or as part of a substituent, as represented by $R_{51}$, $R_{52}$, and $R_{53}$ are each independently unsubstituted or substituted with 1, 2, 3, or 4 substituents selected from the group consisting of $C_1$-$C_4$ alkyl, halo, hydroxy, $C_1$-$C_4$ alkoxy, $C_1$-$C_4$ haloalkoxy, and $C_1$-$C_4$ haloalkyl;

$R_{21}$, $R_{22}$, $R_{31}$, $R_{32}$, $R_{41}$, $R_{42}$, $R_{1c}$, $R_{1d}$, $R_{2c}$ and $R_{2d}$, at each occurrence, are each independently hydrogen, alkyl, haloalkyl, or halo;

m, p, q, and u, at each occurrence, are each independently 1, 2, 3, or 4;

$Z_1$ and $Z_2$ are each independently hydrogen, alkyl, alkoxyalkyl, alkylcarbonyl, cyanoalkyl, haloalkyl, or formyl; and $Z_3$ and $Z_4$ are each independently hydrogen, alkyl, haloalkyl, phenyl or benzyl wherein the phenyl moiety is optionally substituted with 1, 2, 3, or 4 substituents selected from the group consisting of alkyl, hydroxyl, and haloalkyl.

Another aspect of the invention relates to compounds of formula (II), or pharmaceutical salts, prodrugs, salts of prodrugs, or combinations thereof,

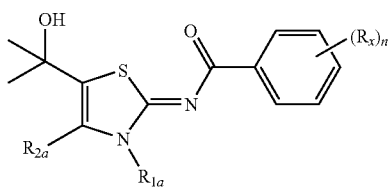

wherein
$R_{1a}$ is alkoxyalkyl, hydroxyalkyl, alkyl, haloalkyl, or cycloalkylalkyl wherein the cycloalkyl moiety is optionally substituted with 1, 2, 3, 4, 5, or 6 substituents independently selected from the group consisting of oxo, alkyl, halo, —OH, —O(alkyl), and haloalkyl;

$R_{2a}$ is hydrogen or alkyl;

$R_x$ is an optional substituent of phenyl, selected from the group consisting of alkyl, alkylcarbonyl, alkoxy, alkoxyalkoxy, cyano, formyl, halogen, haloalkoxy, hydroxy, hydroxyalkyl, haloalkyl, =N—OH, $NZ_{1a}Z_{2a}$—$(CR_{41a}R_{42a})_v$—O—, —O—$(CR_{41a}R_{42a})_v$-$G_{1a}$, —$(CR_{41a}R_{42a})_v$-$G_{1a}$, —$(CR_{41a}R_{42a})_v$—$NZ_{1a}Z_{2a}$, and $NZ_{1a}Z_{2a}$;

$G_{1a}$ is a 4-, 5-, 6-, or 7-membered monocyclic heterocycle containing one nitrogen atom and optionally 1 or 2 additional heteroatom in the ring, wherein said ring is attached to the parent moiety through the nitrogen atom, and said ring is optionally substituted with 1, 2, 3, 4, or 5 substituents selected from the group consisting of alkyl, alkenyl, alkynyl, halo, haloalkyl, =N—CN, =N—$OR_{51a}$, —CN, oxo, —$OR_{51a}$, —OC(O)$R_{51a}$, —OC(O)N$(R_{51a})_2$, S(O)$_2R_{52a}$, —S(O)$_2$N $(R_{51a})_2$, —C(O)$R_{51a}$, —C(O)O$R_{51a}$, —C(O)N$(R_{51a})_2$, —N$(R_{51a})_2$, —N$(R_{51a})$C(O)$R_{51a}$, —N$(R_{41a})$S(O)$_2R_{52a}$, —N$(R_{51a})$C(O)O$(R_{52a})$, —N$(R_{51a})$C(O)N$(R_{51a})_2$, —$(CR_{1e}R_{1f})_w$—$OR_{51}$, —$(CR_{1e}R_{1f})_w$—OC(O)$R_{51a}$, —$(CR_{1e}R_{1f})_w$—OC(O)N$(R_{51a})_2$, —$(CR_{1e}R_{1f})_w$—S(O)$_2$ $R_{52a}$, —$(CR_{1e}R_{1f})_w$—S(O)$_2$N$(R_{51a})_2$), —$(CR_{1e}R_{1f})_w$—C (O)$R_{51a}$, —$(R_{1e}R_{1f})_w$—C(O)O$R_{51a}$, $(CR_{1e}R_{1f})_w$—C(O)N $(R_{51a})_2$, —$(CR_{1e}R_{1f})_w$—N$(R_{51a})_2$, —$(CR_{1e}R_{1f})_w$—N$(R_{51})$C (O)$R_{51a}$, —$(CR_{1e}R_{1f})_w$—N$(R_{51a})$S(O)$_2R_{52a}$, —$(CR_{1e}R_{1f})_w$—N$(R_{51a})$C(O)O$(R_{52a})$, —$(CR_{1e}R_{1f})_w$—N$(R_{51a})$C(O)N $(R_{51a})_2$, and —$(CR_{1e}R_{1f})_w$—CN;

$R_{51a}$, at each occurrence, is independently hydrogen, $C_1$-$C_4$ alkyl, $C_1$-$C_4$haloalkyl, —$(CR_{2e}R_{2f})_y$—$OR^{53}$, monocyclic cycloalkyl, or —$(CR_{2e}R_{2f})_y$-(monocyclic cycloalkyl); wherein $R_{53a}$ is hydrogen, $C_1$-$C_4$ alkyl, $C_1$-$C_4$ haloalkyl, monocyclic cycloalkyl, or —$(CR_{2e}R_{2f})_y$-(monocyclic cycloalkyl);

$R_{52a}$, at each occurrence, is independently $C_1$-$C_4$alkyl, $C_1$-$C_4$haloalkyl, monocyclic cycloalkyl, or —$(CR_{2e}R_{2f})_y$-(monocyclic cycloalkyl);

the monocyclic cycloalkyl moiety, as a substituent, or as part of a substituent, as represented by $R_{51a}$, $R_{52a}$, and $R_{53a}$ are each independently unsubstituted or substituted with 1, 2, 3, or 4 substituents selected from the group consisting of $C_1$-$C_4$ alkyl, halo, hydroxy, $C_1$-$C_4$ alkoxy, $C_1$-$C_4$ haloalkoxy, and $C_1$-$C_4$ haloalkyl;

$R_{41a}$, $R_{42a}$, $R_{1e}$, $R_{1f}$, $R_{2e}$, and $R_{2f}$ at each occurrence, are each independently hydrogen, alkyl, haloalkyl, or halo;

v, w, and y, at each occurrence, are each independently 1, 2, 3, or 4;

$Z_{1a}$ and $Z_{2a}$ are each independently hydrogen, alkyl, alkoxyalkyl, alkylcarbonyl, cyanoalkyl, haloalkyl, or formyl; and n is 1, 2, 3, 4, or 5.

In another embodiment, the present invention provides a pharmaceutical composition comprising a therapeutically effective amount of a compound of the invention or a pharmaceutically acceptable salt thereof in combination with one or more pharmaceutically acceptable carriers. Such compositions can be administered in accordance with a method of the invention, typically as part of a therapeutic regimen for treatment or prevention of conditions and disorders related to cannabinoid (CB) receptor subtype, $CB_2$. More particularly, the method is useful for treating conditions related to neuropathic pain, nociceptive pain, inflammatory pain, inflammatory disorders, immune disorders, neurological disorders, cancers of the immune system, respiratory disorders, obesity, diabetes, cardiovascular disorders, or for providing neuroprotection.

Further, the present invention provides the use of compounds of the present invention or a pharmaceutically acceptable salt thereof, in the manufacture of a medicament for the treatment of the disease conditions described above, alone or in combination with one or more pharmaceutically acceptable carrier(s), particularly for the treatment of neuropathic pain, nociceptive pain, inflammatory pain, or combination thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION

Compounds of formulae (I) and (II) are disclosed in this invention,

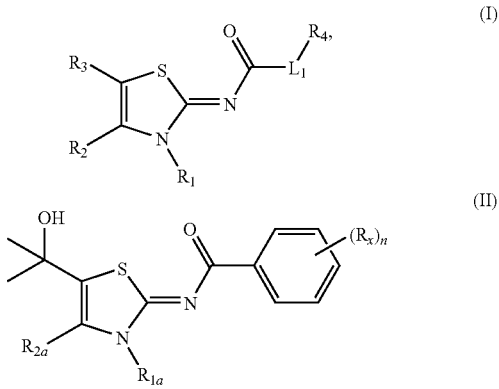

wherein $R_1$, $R_2$, $R_3$, $R_4$, $L_1$, $R_{1a}$, $R_{2a}$, $R_x$, and n are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond. Representative examples of alkenyl include, but are not limited to, ethenyl(vinyl), 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2, 3, or 4 carbon atoms and contains at least one carbon-carbon double bond. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. The term "$C_1$-$C_4$ alkoxy" a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 3-methoxy-3-methylbutoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, methoxymethyl, 2-methoxy-2-methylpropyl, and 3-methoxypropyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, ethoxycarbonylmethyl, 3-methoxycarbonylpropyl, 4-ethoxycarbonylbutyl, and 2-tert-butoxycarbonylethyl.

The term "alkyl" as used herein, means a straight or branched saturated hydrocarbon chain containing from 1 to 10 carbon atoms. The term "$C_{1-6}$ alkyl" or "$C_1$-$C_6$ alkyl" means a straight or branched saturated hydrocarbon chain containing from 1 to 6 carbon atoms. The term "$C_1$-$C_4$ alkyl" means a straight or branched saturated hydrocarbon chain containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 1-methylethyl, 2-methylbutyl, 3-methylbutyl, 1-methylpropyl, 1-ethylpropyl, 2-methylpropyl, 1,1-dimethylethyl, 1,1-dimethylpropyl, 1,2-dimethylpropyl, 2,2-dimethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein.

Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched saturated hydrocarbon chain of 1 to 10 carbon atoms. The term "$C_1$-$C_6$ alkylene" means a divalent group derived from a straight or branched saturated hydrocarbon chain of 1 to 6 carbon atoms. The term "$C_1$-$C_3$ alkylene" means a divalent group derived from a straight or branched saturated hydrocarbon chain of 1 to 3 carbon atoms. The term "$C_1$-$C_2$ alkylene" means a divalent group derived from a straight or branched saturated hydrocarbon chain of 1 to 2 carbon atoms. Representative examples of alkylene include, but are not limited to, —CH$_2$—, —CH(CH$_3$)—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 1-propylpent-3-ynyl, 3-butynyl, 2-pentynyl, and 1-butynyl.

The term "aryl," as used herein, means phenyl, a bicyclic aryl, or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, 1,2-dihydroacenaphthylenyl (including 1,2-dihydroacenaphthylen-5-yl), and tetrahydrophenanthrenyl. The phenyl, bicyclic and tricyclic aryls are attached to the parent molecular moiety through any carbon atom contained within the phenyl, bicyclic, and tricyclic aryls respectively.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 1-methyl-3-phenylpropyl, 2-methyl-1-phenylbutyl, 1-phenylpropyl, 3-phenylpropyl, and 2-naphth-2-ylethyl.

The term "azido" as used herein, means a —$N_3$ group.

The term "azidoalkyl" as used herein, means an azido group, as defined herein, appended to the parent molecular moiety through an alkylene group, as defined herein.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing zero heteroatoms in the ring. The monocyclic cycloalkenyl has three, four, five, six, seven or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. Representative examples of bicyclic ring systems include, but are not limited to 3a,4,5,6,7,7a-hexahydro-1H-indenyl, 4,5,6,7-tetrahydro-3aH-indene, and octahydronaphthalenyl. The monocyclic or the bicyclic cycloalkenyl ring can be appended to the parent molecular moiety through any substitutable carbon atom within the monocyclic or the bicyclic cycloalkenyl.

The term "cycloalkenylalkyl" as used herein, means a cycloalkenyl group as defined herein, appended to the parent molecular moiety through an alkylene group, as defined herein.

The term "cycloalkyl" as used herein, means a monocyclic, or a bicyclic ring system, or a spirocyclic cycloalkyl. The monocyclic cycloalkyl is a carbocyclic ring system containing 3, 4, 5, 6, 7, or 8 carbon atoms, zero heteroatoms and zero double bonds. Examples of monocyclic ring systems include cyclopropyl, cyclobutyl, cyclopentyl, cyclohexyl, cycloheptyl, and cyclooctyl. Bicyclic ring systems are exemplified by a monocyclic cycloalkyl ring fused to a monocyclic cycloalkyl ring. Representative examples of bicyclic ring systems include, but are not limited to, bicyclo[4.1.0]heptane, bicyclo[6.1.0]nonane, octahydroindene, and decahydronaphthalene. Spirocyclic cycloalkyl is exemplified by a monocyclic cycloalkyl ring wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic and spirocyclic cycloalkyl groups of the present invention can be appended to the parent molecular moiety through any substitutable carbon atom of the groups. The monocyclic and bicyclic cycloalkyl groups of the present invention, with the exception of $R^4$, may contain one or two alkylene bridges of 1, 2, 3, or 4 carbon atoms, each of which linking two non adjacent carbon atoms of the group. Examples of such a bridged system include, but are not limited to, adamantane (tricyclo[$3.3.1.1^{3,7}$]decane) and bicyclo[2.2.1]heptane.

The term "cycloalkylalkyl" as used herein, means a cycloalkyl group, as defined herein, appended to the parent molecular moiety through an alkylene group, as defined herein.

Representative examples of cycloalkylalkyl include, but are not limited to, cyclopentylmethyl, cyclohexylmethyl, cyclopropylmethyl, and 1-cyclopropylethyl.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means an alkoxy group, as defined herein, in which one, two, three, four, five or six hydrogen atoms are replaced by halogen. The term "$C_1$-$C_4$ haloalkoxy" as used herein, means a $C_1$-$C_4$ alkoxy group, as defined herein, in which one, two, three, four, five or six hydrogen atoms are replaced by halogen. Representative examples of haloalkoxy include, but are not limited to, trifluoromethoxy, difluoromethoxy, 2,2,2-trifluoroethoxy, and 2,2-difluoroethoxy.

The term "haloalkyl" as used herein, means an alkyl group, as defined herein, in which one, two, three, four, five, six, or seven hydrogen atoms are replaced by halogen. The term "$C_1$-$C_4$ haloalkyl" as used herein, means a $C_1$-$C_4$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

The term "heteroaryl," as used herein, means a monocyclic heteroaryl or a bicyclic heteroaryl.

The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl (including furan-3-yl, furan-2-yl), imidazolyl, isoxazolyl (including isoxazol-5-yl), isothiazolyl, oxadiazolyl (including 1,2,4-oxadiazol-3-yl), oxazolyl (including 1,3-oxazol-2-yl), pyridinyl (including pyridin-2-yl, pyridin-3-yl, pyridin-4-yl), pyridazinyl, pyrimidinyl, pyrazinyl, pyrazolyl (including pyrazol-5-yl), pyrrolyl, tetrazolyl, thiadiazolyl, thiazolyl, thienyl (including thien-2-yl), triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl (including benzofuran-5-yl), benzoxadiazolyl, 1,3-benzothiazolyl, benzimidazolyl, benzodioxolyl, benzothienyl, chromenyl, cinnolinyl, furopyridinyl, indolyl, indazolyl, isoindolyl, isoquinolinyl (including isoquinolin-5-yl), naphthyridinyl, oxazolopyridine, quinolinyl (including quinolin-4-yl, quinolin-5-yl, quinolin-8-yl), thienopyridinyl and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings may optionally be oxidized, and are contemplated within the scope of the invention.

The term "heteroarylalkyl" as used herein, means a heteroaryl group as defined herein, appended to the parent molecular moiety through an alkylene group, as defined herein. An example of heteroarylalkyl is 3-thienylpropyl.

The term "heterocycle" or "heterocyclic" as used herein, refers to a monocyclic, bicyclic, tricyclic, or a spirocyclic ring system, containing at least one heteroatom. The monocyclic heterocycle is a 3, 4, 5, 6, 7, or 8-membered ring containing at least one heteroatom independently selected from the group consisting of O, N, and S. The 3 or 4 membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6, 7, or 8-membered ring contains zero, one, or two double bonds, and one, two, or three heteroatoms in the ring selected from the group consisting of O, N and S. Representative examples of monocyclic heterocycle include, but are not limited to, azetidinyl (including azetidin-3-yl), azepanyl, aziridinyl, diazepanyl, 1,3-dioxanyl, 1,4-dioxanyl, 1,3-dioxolanyl, 4,5-dihydroisoxazol-5-yl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (pyrrolidin-3-yl), tetrahydrofuranyl (including tetrahydrofuran-2-yl tetrahydrofuran-3-yl), tetrahydropyranyl (including tetrahydro-2H-pyran-4-yl), tetrahydropyridinyl (including 1,2,3,6-tetrahydropyridin-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxolyl (including 1,3-benzodioxol-4-yl), 1,3-benzodithiolyl, 2,3-dihydro-1,4-benzodioxinyl, dihydrobenzofuranyl (including 2,3-dihydro-1-benzofuran-7-yl), 2,3-dihydro-1-benzothienyl, 2,3-dihydro-1H-indolyl, and 1,2,3,4-tetrahydroquinolinyl. Spirocyclic heterocycle means a 4,5-, 6-, 7-, or 8-membered monocyclic heterocycle ring wherein two of the substituents on the same carbon atom form a 4-, 5-, or 6-membered monocyclic cycloalkyl, wherein the cycloalkyl is optionally substituted with 1, 2, 3, 4, or 5 alkyl groups. One example of a spiroheterocycle is 5-oxaspiro[3,4]octane. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. The monocyclic, bicyclic, tricyclic, and spirocyclic heterocycle groups, unless otherwise noted, are connected to the parent molecular moiety through any substitutable carbon atom or any substitutable nitrogen atom contained within the group. The nitrogen and sulfur heteroatoms in the heterocycle rings may optionally be oxidized and the nitrogen atoms may optionally be quarternized.

The term "heterocyclealkyl" as used herein, means a heterocycle group as defined herein, appended to the parent molecular moiety through an alkylene group, as defined herein. An example includes, but is not limited to, tetrahydropyranmethyl (including tetrahydro-2H-pyran-4-ylmethyl).

The term "hydroxy" as used herein, means an —OH group.

The term "hydroxyalkyl" as used herein, means at least one hydroxy group, as defined herein, appended to the parent molecular moiety through an alkylene group, as defined herein. Representative examples of hydroxyalkyl include, but are not limited to, hydroxymethyl, 2-hydroxyethyl, 3-hydroxypropyl, 3-hydroxy-3-methylbutyl, 2,3-dihydroxypentyl, and 2-ethyl-4-hydroxyheptyl.

The term "hydroxy-protecting group" or "O-protecting group" means a substituent which protects hydroxy groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl(trityl).

The term "oxo" as used herein, means a =O moiety.

The term "sulfinyl" as used herein, means a —S(O)— group.

The term "tautomer" as used herein means a proton shift from one atom of a compound to another atom of the same compound wherein two or more structurally distinct compounds are in equilibrium with each other.

b. COMPOUNDS

Compounds of the invention have the formula (I) as described above.

Particular values of variable groups in compounds of formula (I) are as follows. Such values may be used where appropriate with any of the other values, definitions, claims or embodiments defined hereinbefore or hereinafter. In compounds of formula (I), $R_1$ is alkoxyalkyl, alkoxyalkoxyalkyl, hydroxyalkyl, A, or A-alkylene- wherein A is as disclosed in the Summary. Embodiments of the present invention include compounds wherein $R_1$ is A or A-alkylene- and A is a 4-, 5-, 6-, 7-, 8-, or 9-membered monocyclic heterocycle containing zero or one double bond, and one or two oxygen and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms, each ring A is optionally fused with a monocyclic ring selected from the group consisting of benzo, cycloalkyl, cycloalkenyl, heterocycle, and heteroaryl, and each Ring A is optionally substituted as described in the Summary. Some examples of Ring A are those that are represented by formula (i), (ii), (iii), (iv), (v), (vi), (vii), and (viia) wherein each ring is independently unsubstituted or substituted as described in the Summary. Certain examples of the optional substituents of Ring A include, but are not limited to, alkyl such as $C_{1-6}$ alkyl (for example, methyl, ethyl), haloalkyl (e.g. trifluoromethyl), and oxo.

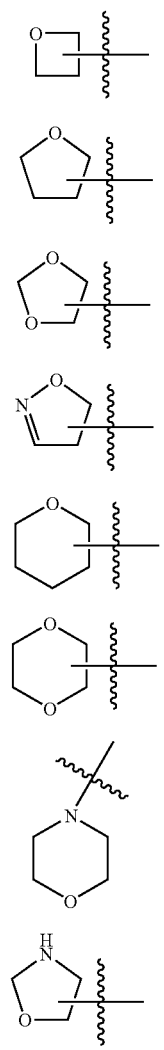

Examples of compounds of the invention include, but are not limited to, those wherein $R_1$ is oxetan-2-ylmethyl, oxetan-3-ylmethyl, tetrahydrofuran-2-ylmethyl, tetrahydrofuran-3-ylmethyl, tetrahydro-2H-pyran-2-ylmethyl, tetrahydro-2H-pyran-3-ylmethyl, tetrahydro-2H-pyran-4-ylmethyl, 2-tetrahydro-2H-pyran-4-ylethyl, 1,3-dioxolan-2-ylmethyl, 2-1,3-dioxolan-2-ylethyl, 1,3-dixoxolan-4-ylmethyl, 4,5-dihydroisoxazol-5-ylmethyl, 1,4-dioxan-2-ylmethyl, 2-morpholin-4-ylethyl, tetrahydro-2H-pyran-4-yl, and 1,3-oxazolidin-4-ylmethyl, wherein each of the oxetan-2-yl, oxetan-3-yl, tetrahydrofuran-2-yl, tetrahydrofuran-3-yl, tetrahydro-2H-pyran-2-yl, tetrahydro-2H-pyran-3-yl, tetrahydro-2H-pyran-4-yl, 1,3-dioxolan-2-yl, 1,3-dioxolan-4-yl, 4,5-dihydroisoxazol-5-yl, 1,4-dioxan-2-yl, morpholin-4-yl, and 1,3-oxazolidin-4-yl, is each independently unsubstituted or substituted with 1, 2, 3, or 4 substituents selected from the group consisting of alkyl (for example, methyl, ethyl), haloalkyl (e.g. trifluoromethyl), and oxo.

Yet other examples of compounds of formula (I) include those wherein $R_1$ is A-alkylene- and A is furanyl, oxazolyl, isoxazolyl, or oxadiazolyl, each of which is optionally substituted as described in the Summary. For example $R_1$ is furanylmethyl, oxazolylmethyl, isoxazolylmethyl, or oxadiazolylmethyl, wherein each of the furanyl, oxazolyl, isoxazolyl and oxadiazolyl is optionally substituted with the group consisting of alkyl (e.g. methyl, ethyl), halo, and haloalkyl (e.g. trifluoromethyl).

The alkylene moiety of A-alkylene-, for example, is $C_1$-$C_6$ alkylene. Further examples of the alkylene moiety of A-alkylene- is $C_1$-$C_3$ alkylene. Yet further examples of the alkylene moiety of A-alkylene- is $C_1$-$C_2$ alkylene.

Other examples of compounds of formula (I) include those wherein $R_1$ is alkoxyalkyl (e.g. 2-ethoxyethyl, 2-methoxymethyl, 2-methoxy2-methylpropyl, 3-methoxypropyl), alkoxyalkoxyalkyl (e.g. 2-(2-methoxyethoxy)ethyl), or hydroxyalkyl (e.g. 3-hydroxy-3-methylbutyl).

$R_2$ is hydrogen, alkoxy, alkoxyalkyl, alkoxycarbonyl, alkoxycarbonylalkyl, alkyl, alkyl-S(O)$_2$—, aryl, arylalkyl, arylalkenyl, azidoalkyl, cyano, cycloalkyl, halo, haloalkyl, heteroaryl, heterocycle, —(CR$_{21}$R$_{22}$)$_m$—OH, R$_a$R$_b$N—, R$_a$R$_b$N-alkyl-, R$_a$R$_a$NC(O)—, or R$_8$—R$_7$—; wherein R$_{21}$, R$_{22}$, m, R$_a$, R$_b$, R$_e$, R$_d$, R$_7$, and R$_8$, and the optional substituents of the aryl, cycloalkyl, heteroaryl and heterocycle moieties are as described in the Summary. Certain examples of compounds of formula (I) include those wherein $R_2$ is hydrogen, alkoxycarbonyl, alkoxycarbonylalkyl, alkyl (for example, methyl, ethyl, propyl, tert-butyl), aryl (for example, optionally substituted phenyl), halo, haloalkyl (e.g. trifluoromethyl), or —(CR$_{21}$R$_{22}$)$_m$—OH; wherein R$_{21}$, R$_{22}$, and m, and the optional substituents of the aryl moiety are as disclosed in the Summary. For example, the optional substituents of the aryl moiety are selected from the group consisting of alkyl and halo. Included, but not limited to, are compounds of formula (I) in which R$_{21}$ and R$_{22}$ are the same or different, and are each independently hydrogen, methyl, or ethyl, and m is 1. Embodiments of the present invention include compounds in which R$_2$ is hydrogen or alkyl (for example, methyl, ethyl, propyl, tert-butyl).

$R_3$ is hydrogen, alkoxy, alkoxyalkyl, alkyl, alkylcarbonyl, alkyl-S(O)$_2$—, aryl, arylalkyl, arylalkenyl, cyano, cycloalkyl, halo, haloalkyl, heteroaryl, heterocycle, —(CR$_{31}$R$_{32}$)$_m$—OH, R$_a$R$_b$N—, R$_a$R$_b$N-alkyl-, or R$_8$—R$_7$—; wherein R$_{31}$, R$_{32}$, m, R$_a$, R$_b$, R$_7$, and R$_8$, and the optional subtituents of the aryl, cycloalkyl, heteroaryl and heterocycle moieties are as disclosed in the Summary. Examples of compounds of formula (I) include, but are not limited to, those wherein R$_3$ is hydrogen, alkyl (for example, methyl, ethyl, n-propyl, tert-butyl), alkylcarbonyl (e.g. acetyl), aryl (for example, optionally substituted phenyl), cycloalkyl (for example, cyclopropyl, cyclohexyl, each of which is optionally substituted), halo, haloalkyl (e.g. trifluoromethyl), heterocycle (for example, morpholinyl), or —(CR$_{31}$R$_{32}$)$_m$—OH, wherein R$_{31}$, R$_{32}$, and m are as disclosed in the Summary. The optional substituents of aryl, cycloalkyl, and heterocycle moieties are as disclosed in the Summary, for example, the optional substituents are selected from the group consisting of alkyl (e.g. methyl), haloalkyl (e.g. trifluoromethyl), and halo. Non limiting examples of R$_{31}$ and R$_{32}$ (R$_{31}$ and R$_{32}$ can be the same or different) are alkyl (for example, methyl) or haloalkyl (for example, 2-iodoethyl, trifluoromethyl). m, for example, is 1. Embodiments of the present invention include compounds in which R$_3$ is alkyl (for example, methyl, ethyl, n-propyl, or tert-butyl) or —(CR$_{31}$R$_{32}$)$_m$—OH. Other examples include those wherein R$_3$ is —(CR$_{31}$R$_{32}$)$_m$—OH, wherein m is 1, and R$_{31}$ and R$_{32}$ are alkyl (such as, but not limited to, methyl) or haloalkyl (such as, but not limited to, trifluoromethyl).

In another embodiment, R$_2$ and R$_3$, together with the carbon atoms to which they are attached, form a 4-, 5-, 6-, or 7-membered monocyclic ring as described in the Summary. Embodiments of the present invention include compounds of formula (I) wherein R$_2$ and R$_3$, together with the carbon atoms to which they are attached, form a monocyclic ring as described in the Summary, containing zero heteroatoms in said monocyclic ring. Formulae (viii), (ix), (ixa), (xi), (xii), (xiii), and (xiv), each of which is optionally substituted as described in the Summary, represent some of these rings formed by R$_2$, R$_3$, and the carbon atoms to which they are attached, with the proviso that when said ring is represented by (viii), (ix) or (xi), then R$_1$ is A or A-alkylene, wherein A is as described in the Summary and the Detailed Description sections.

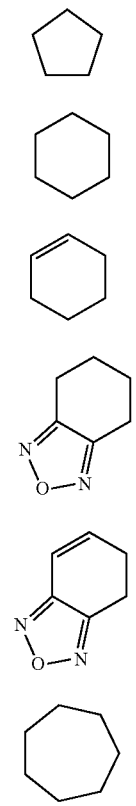

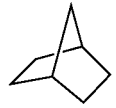

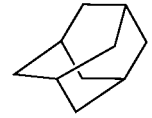

Yet other compounds of the present invention include those wherein R$_2$ and R$_3$, together with the carbon atoms to which they are attached, form a 4-, 5-, 6-, or 7-membered monocyclic ring optionally fused to benzo or oxadiazole, said monocyclic ring contains zero or one additional double bond, zero oxygen atom and zero nitrogen atom as ring atoms; and two non-adjacent atoms of said monocyclic ring are linked by an alkenylene bridge of 2, 3, or 4 carbon atoms, or linked by an alkylene bridge of 1, 2, 3, or 4 carbon atoms. Examples include, but are not limited to, formulae (xii), (xiii) and (xiv), each of which is optionally substituted.

Further examples of compounds of formula (I) include, but are not limited to, those wherein R$_2$ and R$_3$, together with the carbon atoms to which they are attached, form a monocyclic ring containing zero additional double bond, zero oxygen and zero nitrogen atom, such as those represented by (viii), (ix) or (xi).

Yet other compounds of the present invention include those wherein R$_2$ and R$_3$, together with the carbon atoms to which they are attached, form a 4-, 5-, 6-, or 7-membered monocyclic ring optionally fused to benzo or oxadiazole, said monocyclic ring contains zero or one additional double bond, and one oxygen atom and zero or one nitrogen atom as ring atoms; and two non-adjacent atoms of said monocyclic ring are optionally linked by an alkenylene bridge of 2, 3, or 4 carbon atoms, or optionally linked by an alkylene bridge of 1, 2, 3, or 4 carbon atoms. Examples include, but are not limited to, formula (xv)-(xxix), particularly, (xv), (xviii) and ((xxix).

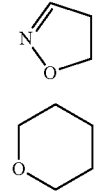

(xix)

(xx)

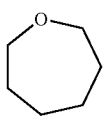
(xxi)

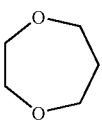
(xxii)

(xxiii)

(xxiv)

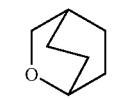
(xxv)

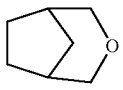
(xxvi)

(xxvii)

(xxviii)

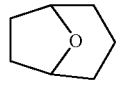
(xxix)

Each ring formed by $R_2$, $R_3$, and the carbon atoms to which they are attached is independently unsubstituted or substituted as described in the Summary, for example, these rings can be independently unsubstituted or substituted with 1, 2, 3, 4, 5 or 6 substituents independently selected from alkyl such as $C_{1-6}$ alkyl (for example, methyl), hydroxy, and oxo. Such rings are optionally fused with benzo or oxadiazole. Examples of such an optionally substituted fused ring are represented by formula (x) and (xa).

$R_4$ is alkyl, alkynyl, cycloalkyl, cycloalkenyl, aryl, heteroaryl, heterocycle, cycloalkylalkyl, cycloalkenylalkyl, arylalkyl, heteroarylalkyl, heterocyclealkyl, or $R_{10}$-$L_2$-$R_9$—; wherein the alkyl group is optionally substituted with one substituent selected from the group consisting of alkoxy, alkoxycarbonyl, carboxy, halo, —OH, and $R_eR_fN$—; $R_9$, $R_{10}$, $R_e$, and $R_f$ and the aryl moiety, cycloalkyl moiety, cycloalkenyl moiety, heteroaryl moiety and the heterocycle moiety are independently unsubstituted or substituted as described in the Summary. In one embodiment, $R_4$ is optionally substituted aryl. In another embodiment, $R_4$ is phenyl or naphthyl, each of which is optionally substituted. Yet other examples of compounds of formula (I) are those wherein $R_4$ is arylalkyl wherein the aryl moiety is optionally substituted. Other examples of compounds of formula (I) are those wherein $R_4$ is heteroaryl (for example, quinolinyl, isoquinolinyl, benzofuranyl, thienyl, pyrazolyl, pyridinyl), heterocycle (tetrahydropyranyl, dihydropyranyl, 2,3-dihydrobenzofuranyl, 1,3-benzodioxolyl), heteroarylalkyl (e.g. 3-thien-2-ylpropyl), or heterocyclealkyl (for example, tetrahydro-2H-pyranylmethyl), each of the heterocycl and heteroaryl moieties is optionally substituted as described in the Summary. Yet other examples are those wherein $R_4$ is alkynyl. Other examples are those wherein $R_4$ is alkyl optionally substituted with $R_eR_fN$—, —OH, or alkoxycarbonyl, wherein $R_e$ and $R_f$ are as disclosed in the Summary. Further examples are those wherein $R_4$ is cycloalkyl (e.g. cyclopropyl, cyclobutyl, cyclopentyl, cyclohexyl, cycloheptyl, spiro[2.5]octane) or cycloalkylalkyl (e.g. cyclopentylmethyl, cyclohexylmethyl) wherein the cycloalkyl moiety is optionally substituted.

Yet other examples of compounds of formula (I) are those wherein $R_4$ is $R_{10}$-$L_2$-$R_9$— wherein $R_9$ is aryl (for example, phenyl, naphthyl) or heteroaryl (e.g. pyrazolyl), $L_2$ is alkylene (e.g. $CH_2$, $CH_2CH_2$), and $R_{10}$ is heterocycle (e.g. tetrahydrofuranyl, azetidinyl, pyrrolidinyl, morpholinyl, thiomorpholinyl, piperazinyl) or aryl (e.g. phenyl); in other embodiments, $R_9$ is aryl (for example, phenyl, naphthyl) or heteroaryl (e.g. pyrazolyl), $L_2$ is O, and $R_{10}$ is cycloalkyl(cyclopropyl), cycloalkylalkyl (e.g. cyclopropylmethyl, cyclopentylmethyl), or heterocycle (e.g. tetrahydrofuranyl, azetidinyl, pyrrolidinyl, morpholinyl, thiomorpholinyl, piperazinyl). Each $R_9$ and $R_{10}$ is optionally substituted as described in the Summary and embodiments herein.

Examples of the optional substituents of $R_4$ and $R_{10}$ include, but are not limited to, alkyl (for example, methyl, ethyl), alkylcarbonyl (for example, acetyl), alkylcarbonylalkyl (e.g. acetylmethyl), alkoxy (for example, methoxy, ethoxy, isopropoxy, tert-butyoxy), alkoxyalkoxy (for example, 2-methoxyethoxy, 3-methyl-3-methoxybutoxy), alkoxycarbonyl (e.g. methoxycarbonyl), cyano, formyl, halogen (for example, Cl, Br, I, F), haloalkoxy (for example, trifluoromethoxy, difluoromethoxy, 2,2,2-trifluoroethoxy), hydroxy, haloalkyl (e.g. trifluoromethyl), alkyl-$S(O)_2$—$(CR_{41}R_{42})_p$=$C(R_{41})$—, alkyl-$S(O)_2$—$(CR_{41}R_{42})_p$—, alkyl-S— (e.g. $CH_3$—S—), alkenyl (e.g. vinyl), oxo, —$C(R_{41})$=N—O($R_{42}$), —$(CR_{41}R_{42})_p$—$C(R_{41})$=N—O($R_{42}$), =N—O(alkyl), $NZ_1Z_2$—$(CR_{41}R_{42})_p$—O—, —O—$(CR_{41}R_{42})_p$-$G_1$, $G_1$, —$NZ_1Z_2$, and —$(CR_{41}R_{42})_p$—$NZ_1Z_2$, wherein $Z_1$, $Z_2$, $R_{41}$, $R_{42}$, p, and $G_1$ are as described in the Summary. For example, $R_{41}$ and $R_{42}$ are the same or different, and at each occurrence, are each independently hydrogen or alkyl (e.g. methyl, ethyl). p, for example, is 1, 2, or 3. $Z_1$ and $Z_2$, are the same or different, and at each occurrence, are each, for example, independently hydrogen, alkyl (e.g. methyl, ethyl, tert-butyl), cyanoalkyl (e.g. cyanomethyl), or alkoxyalkyl (e.g. 2-methoxyethyl). $G_1$, for example, is morpholinyl, 1,2,3,6-tetrahydropyridinyl, piperidinyl, or thiomorpholinyl, each of which is optionally substituted as described in the Summary, for example, optionally substituted with 1, 2, or 3 substituents selected from alkyl (e.g. methyl), oxo, alkoxycarbonyl (e.g. tert-butoxycarbonyl). Examples of the optional substituents of $R_9$ include, but are not limited to, alkyl (e.g. methyl, tert-butyl, ethyl), haloalkyl (e.g. trifluoromethyl), and halogen.

$L_1$ is a single bond or —$NR_g$— wherein $R_g$ is hydrogen or alkyl. Certain compounds of the present invention include those wherein $L_1$ is a single bond. Yet others are those wherein $L_1$ is —$NR_g$— wherein $R_g$ is hydrogen or alkyl. Other examples include those wherein $L_1$ is —NH—.

It is appreciated that the present invention contemplates compounds of formula (I) with combinations of the above embodiments, including particular, more particular and preferred embodiments.

Accordingly, one aspect of the invention relates to a group of compounds of formula (I), or pharmaceutically acceptable salts thereof, wherein $R_1$ is A or A-alkylene-, $R_2$ is hydrogen, alkoxycarbonyl, alkoxycarbonylalkyl, alkyl (for example, methyl, ethyl, propyl, tert-butyl), aryl (for example, optionally substituted phenyl), halo, haloalkyl (e.g. trifluoromethyl), or —$(CR_{21}R_{22})_m$—OH; $R_3$ is hydrogen, alkyl (for example, methyl, ethyl, n-propyl, tert-butyl), alkylcarbonyl (e.g. acetyl), aryl (for example, optionally substituted phenyl), cycloalkyl (for example, cyclopropyl, cyclohexyl, each of which is optionally substituted), halo, haloalkyl (e.g. trifluoromethyl), heterocycle (for example, morpholinyl), or —$(CR_{31}R_{32})_m$—OH; A is a 4-, 5-, 6-, 7-, 8-, or 9-membered monocyclic heterocycle containing zero or one double bond, one or two oxygen, and zero or one nitrogen as ring atoms; two non-adjacent atoms of each A can be optionally linked by an alkenylene bridge of 2, 3, or 4 carbon atoms, or optionally linked by an alkylene bridge of 1, 2, 3, or 4 carbon atoms; each ring A is optionally fused with a monocyclic ring selected from the group consisting of benzo, cycloalkyl, cycloalkenyl, heterocycle, and heteroaryl; and each A is independently unsubstituted or substituted with 1, 2, 3, 4, 5, or 6 substituents independently selected from the group consisting of oxo, alkyl, halo, —OH, —O(alkyl), and haloalkyl; and $L_1$, $R_4$, $R_{21}$, $R_{22}$, $R_{31}$, $R_{32}$, m; and the optional substituents of the aryl, cycloalkyl, and heterocycle moieties are as disclosed in the Summary and the Detailed Description. Ring A, for example, is formula (i), (ii), (iii), (iv), (v), (vi), (vii), or (viia), wherein each ring is independently unsubstituted or substituted as described in the Summary and Detailed Description. The alkylene moiety of A-alkylene-, for example, is $C_1$-$C_6$ alkylene. Further examples of the alkylene moiety of A-alkylene- is $C_1$-$C_3$ alkylene. Yet further examples of the alkylene moiety of A-alkylene- is $C_1$-$C_2$ alkylene. Further examples of $R_1$ as A or A-alkylene include, but are not limited to, oxetan-2-ylmethyl, oxetan-3-ylmethyl, tetrahydrofuran-2-ylmethyl, tetrahydrofuran-3-ylmethyl, tetrahydro-2H-pyran-2-ylmethyl, tetrahydro-2H-pyran-3-ylmethyl, tetrahydro-2H-pyran-4-ylmethyl, 2-tetrahydro-2H-pyran-4-ylethyl, 1,3-dioxolan-2-ylmethyl, 2-1,3-dioxolan-2-ylethyl, 1,3-dioxolan-4-ylmethyl, 4,5-dihydroisoxazol-5-ylmethyl, 1,4-dioxan-2-ylmethyl, 2-morpholin-4-ylethyl, tetrahydro-2H-pyran-4-yl, and 1,3-oxazolidin-4-ylmethyl, wherein each of the oxetan-2-yl, oxetan-3-yl, tetrahydrofuran-2-yl, tetrahydrofuran-3-yl, tetrahydro-2H-pyran-2-yl, tetrahydro-2H-pyran-3-yl, tetrahydro-2H-pyran-4-yl, 1,3-dioxolan-2-yl, 1,3-dioxolan-4-yl, 4,5-dihydroisoxazol-5-yl, 1,4-dioxan-2-yl, morpholin-4-yl, and 1,3-oxazolidin-4-yl, is each independently unsubstituted or substituted with 1, 2, 3, or 4 substituents selected from the group consisting of alkyl (for example, methyl, ethyl), haloalkyl (e.g. trifluoromethyl), and oxo.

Another aspect of the invention relates to a group of compounds of formula (I), or pharmaceutically acceptable salts thereof, wherein $R_1$ is A-alkylene- and ring A is furanyl, oxazolyl, isoxazolyl, or oxadiazolyl, each of which is optionally substituted as described in the Summary and in Detailed Description; $R_2$ is hydrogen, alkoxycarbonyl, alkoxycarbonylalkyl, alkyl (for example, methyl, ethyl, propyl, tert-butyl), aryl (for example, optionally substituted phenyl), halo, haloalkyl (e.g. trifluoromethyl), or —$(CR_{21}R_{22})_m$—OH; $R_3$ is hydrogen, alkyl (for example, methyl, ethyl, n-propyl, tert-butyl), alkylcarbonyl (e.g. acetyl), aryl (for example, optionally substituted phenyl), cycloalkyl (for example, cyclopropyl, cyclohexyl, each of which is optionally substituted), halo, haloalkyl (e.g. trifluoromethyl), heterocycle (for example, morpholinyl), or —$(CR_{31}R_{32})_m$—OH, and $L_1$, $R_4$, $R_{21}$, $R_{22}$, $R_{31}$, $R_{32}$, m, and the optional substituents of the aryl, cycloalkyl, and heterocycle moieties are as disclosed in the Summary and Detailed Description. For example $R_1$ is furanylmethyl, oxazolylmethyl, isoxazolylmethyl, or oxadiazolylmethyl, wherein each of the furanyl, oxazolyl, isoxazolyl and oxadiazolyl is optionally substituted with the group consisting of alkyl (e.g. methyl, ethyl), halo, and haloalkyl (e.g. trifluoromethyl).

For the preceding two groups of compounds of formula (I), $R_{21}$ and $R_{22}$ are the same or different, and are each independently hydrogen, methyl, or ethyl. m, for example, is 1. $R_{31}$ and $R_{32}$ ($R_{31}$ and $R_{32}$ can be the same or different) are, for example, alkyl (for example, methyl) or haloalkyl (for example, 2-iodoethyl, trifluoromethyl).

In one embodiment, $R_3$ is alkyl (for example, methyl, ethyl, n-propyl, or tert-butyl) or —$(CR_{31}R_{32})_m$—OH, and $R_2$ is hydrogen or alkyl (for example, methyl, ethyl, propyl, tert-butyl); wherein $R_{31}$, $R_{32}$ and m are as described in the Summary and in embodiments described hereinabove. Examples include those wherein $R_2$ is hydrogen or alkyl (for example, methyl), and $R_3$ is —$(CR_{31}R_{32})_m$—OH wherein m is 1, and $R_{31}$ and $R_{32}$ are alkyl (such as, but not limited to, methyl) or haloalkyl (such as, but not limited to, trifluoromethyl). Other examples include those wherein $R_2$ is hydrogen or alkyl (for example, methyl), and $R_3$ is alkyl (for example, tert-butyl). Yet other examples include those wherein $R_2$ is hydrogen or alkyl (for example, methyl), and $R_3$ is —$(CR_{31}R_{32})_m$—OH, wherein $R_{31}$ and $R_{32}$ are alkyl (for example, methyl), and m is 1.

Another aspect of the invention provides a group of compounds of formula (I), or pharmaceutically acceptable salts thereof, wherein $R_1$ is A or A-alkylene-, $R_2$ and $R_3$, together with the carbon atoms to which they are attached form a monocyclic ring, and A, $R_4$, $L_1$, and said monocyclic ring are as described in the Summary. Some examples of ring A are as described herein above. Certain examples of the monocyclic ring formed by $R_2$, $R_3$, and the carbon atoms to which they are attached are represented by formulae (viii), (ix), (ixa), and (xi)-(xxix), each of which is optionally substituted with substituents as described in the Summary and in the Detailed Description, and each of which is optionally fused with benzo or oxadiazole. One example of such fused ring is represented by formula (x) or (xa). Examples of the optional substituents on the rings formed by $R_2$, $R_3$, and the carbon atoms to which they are attached include, but are not limited to, alkyl such as $C_{1-6}$ alkyl, hydroxy, and oxo.

Yet another aspect of the invention relates to a group of compounds of formula (I) or pharmaceutically acceptable salts thereof, wherein $R_1$ is alkoxyalkyl (e.g. 2-ethoxyethyl, 2-methoxymethyl, 2-methoxy2-methylpropyl, 3-methoxypropyl), alkoxyalkoxyalkyl (e.g. 2-(2-methoxyethoxy) ethyl), or hydroxyalkyl (e.g. 3-hydroxy-3-methylbutyl), $R_2$ and $R_3$, together with the carbon atoms to which they are attached, form a 4-, 5-, 6-, or 7-membered monocyclic ring, optionally fused to benzo or oxadiazole, said monocyclic ring contains zero or one additional double bond, zero oxygen atom and zero nitrogen atom as ring atoms; two non-adjacent atoms of said monocyclic ring are linked by an alkenylene bridge of 2, 3, or 4 carbon atoms, or linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; and $R_4$ and $L_1$ are as described in the Summary and Detailed Description. Some examples of the ring formed by $R_2$, $R_3$, and the carbon atoms to which they are attached are represented by formulae (xii), (xiii) and (xiv), each of which is optionally substituted as described in the Summary. Examples of the optional substituents include, but are not limited to, alkyl such as $C_{1-6}$ alkyl (e.g. methyl), hydroxy, and oxo.

A further aspect of the invention provides a group of compounds of formula (I) or pharmaceutically acceptable salts thereof, wherein $R_1$ is alkoxyalkyl (e.g. 2-ethoxyethyl, 2-methoxymethyl, 2-methoxy2-methylpropyl, 3-methoxypropyl), alkoxyalkoxyalkyl (e.g. 2-(2-methoxyethoxy) ethyl), or hydroxyalkyl (e.g. 3-hydroxy-3-methylbutyl), $R_2$ and $R_3$, together with the carbon atoms to which they are attached, form a 4-, 5-, 6-, or 7-membered monocyclic ring optionally fused to benzo or oxadiazole, containing zero or one additional double bond, and one oxygen atom, and zero or one nitrogen atom as ring atoms; and $R_4$ and $L_1$ are as described in the Summary and Detailed Description. Some examples of the monocyclic ring formed by $R_2$, $R_3$, and the carbon atoms to which they are attached are represented by formula (xv)-(xxix), each of which is optionally substituted as described in the Summary and Detailed Description. In one embodiment, the ring formed by $R_2$, $R_3$, and the carbon atoms to which they are attached are represented by formula (xv), (xviii), or (xxix), each of which is optionally substituted as described in the Summary and Detailed Description. Examples of the optional substituents of these rings include, but are not limited to, alkyl such as $C_{1-6}$ alkyl (e.g. methyl), hydroxy, and oxo.

Yet a further aspect of the invention provides a group of compounds of formula (I) or pharmaceutically acceptable salts thereof, wherein $R_1$ is alkoxyalkyl (e.g. 2-ethoxyethyl, 2-methoxymethyl, 2-methoxy2-methylpropyl, 3-methoxypropyl), alkoxyalkoxyalkyl (e.g. 2-(2-methoxyethoxy) ethyl), or hydroxyalkyl (e.g. 3-hydroxy-3-methylbutyl), and $R_2$ and $R_3$, together with the carbon atom to which they are attached, form a ring as represented by formula (x) or (xa), and $R_4$, $L_1$, and the optional substituents of formula (x) and (xa) are as described in the Summary and in the Detailed Description.

Within each group of compounds of formula (I) as described in the preceding paragraphs, $L_1$ and $R_4$ have values as described in the Summary and the Detailed Description.

Thus, within each group of the compounds as described in the preceding paragraphs, examples of a subgroup include those wherein $R_4$ is aryl (e.g. phenyl, naphthyl, 1,2-dihydroacenaphthylenyl), heteroaryl (for example, quinolinyl, isoquinolinyl, benzofuranyl, thienyl, pyrazolyl, pyridinyl), cycloalkyl (e.g. cyclopropyl, cyclobutyl, cyclopentyl, cyclohexyl, cycloheptyl, spiro[2.5]octane), heterocycle (tetrahydropyranyl, dihydropyranyl, 2,3-dihydrobenzofuranyl, 1,3-benzodioxolyl), arylalkyl, heteroarylalkyl (e.g. 3-thien-2-ylpropyl), heterocyclealkyl (for example, tetrahydro-2H-pyranylmethyl), cycloalkylalkyl (e.g. cyclopentylmethyl, cyclohexylmethyl), $R_9$-$L_2$-$R_{10}$, alkynyl, or alkyl, wherein the alkyl group is optionally substituted with $R_eR_fN$—, —OH, or alkoxycarbonyl, wherein $R_9$, $L_2$, $R_{10}$, $R_e$ and $R_f$ and the optional substituents of the aryl, heteroaryl, cycloalkyl, and heterocycle moieties are as described in the Summary and in the Detailed Description.

Examples of another subgroup of compounds of formula (I) include those wherein $L_1$ is a bond, and $R_4$ is aryl (e.g. phenyl, naphthyl, 1,2-dihydroacenaphthylenyl), heteroaryl (for example, quinolinyl, isoquinolinyl, benzofuranyl, thienyl, pyrazolyl, pyridinyl), cycloalkyl (e.g. cyclopropyl, cyclobutyl, cyclopentyl, cyclohexyl, cycloheptyl, spiro[2.5]octane), heterocycle (tetrahydropyranyl, dihydropyranyl, 2,3-dihydrobenzofuranyl, 1,3-benzodioxolyl), arylalkyl, heteroarylalkyl (e.g. 3-thien-2-ylpropyl), heterocyclealkyl (for example, tetrahydro-2H-pyranylmethyl), cycloalkylalkyl (e.g. cyclopentylmethyl, cyclohexylmethyl), $R_9$-$L_2$-$R_{10}$, alkynyl, or alkyl, wherein the alkyl group is optionally substituted with $R_eR_fN$—, —OH, or alkoxycarbonyl, wherein $R_9$, $L_2$, $R_{10}$, $R_e$ and $R_f$ and the optional substituents of the aryl, heteroaryl, cycloalkyl, and heterocycle moieties are as described in the Summary and in the Detailed Description.

Other examples of a subgroup include those wherein $L_1$ is a bond, and $R_4$ is optionally substituted phenyl or $R_{10}$-$L_2$-$R_9$—, wherein $R_9$ is aryl (for example, phenyl, naphthyl) or heteroaryl (e.g. pyrazolyl), $L_2$ is alkylene (e.g. $CH_2$, $CH_2CH_2$), and $R_{10}$ is as described in the Summary. For example, $R_{10}$ is heterocycle (e.g. tetrahydrofuranyl, azetidinyl, pyrrolidinyl, morpholinyl, thiomorpholinyl, piperazinyl) or aryl (e.g. phenyl); wherein the phenyl, aryl, heteroaryl, and heterocycle moieties of $R_4$, $R_9$, and $R_{10}$ are each optionally substituted as described in the Summary and the Detailed Description.

Other examples of a subgroup include those wherein $L_1$ is a bond, and $R_4$ is optionally substituted phenyl or $R_{10}$-$L_2$-$R_9$—, wherein $R_9$ is aryl (for example, phenyl, naphthyl) or heteroaryl (e.g. pyrazolyl), $L_2$ is O, and $R_{10}$ is as described in the Summary. for example, $R_{10}$ is cycloalkyl (cyclopropyl), cycloalkylalkyl (e.g. cyclopropylmethyl, cyclopentylmethyl), or heterocycle (e.g. tetrahydrofuranyl, azetidinyl, pyrrolidinyl, morpholinyl, thiomorpholinyl, piperazinyl); wherein the phenyl, aryl, heteroaryl, cycloalkyl, and heterocycle moieties of $R_4$, $R_9$, and $R_{10}$ are each optionally substituted as described in the Summary and the Detailed Description.

In certain embodiments of the subgroups described above, $R_9$ is optionally aryl (for example, phenyl), optionally further substituted as described in the Summary and in the Detailed Description.

Examples of another subgroup of compounds of formula (I) include those wherein $L_1$ is $NR_g$, and $R_4$ is arylalkyl, cycloalkyl, cycloalkylalkyl, or alkyl, wherein the alkyl group is optionally substituted with $R_eR_fN$—, —OH, or alkoxycarbonyl, and $R_e$, $R_g$, and $R_f$ and the optional substituents of the aryl and cycloalkyl moieties are as described in the Summary and in the Detailed Description.

Yet a further aspect of the invention provides compounds of formula (II) or pharmaceutically acceptable salts thereof,

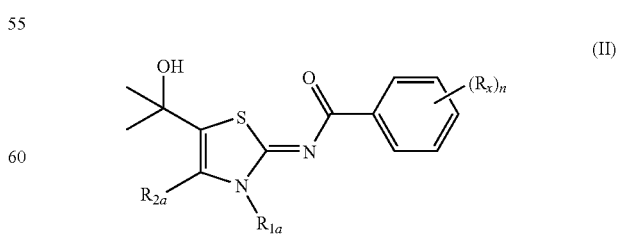

wherein
$R_{1a}$ is alkoxyalkyl, hydroxyalkyl, alkyl, haloalkyl, or cycloalkylalkyl wherein the cycloalkyl moiety is optionally substituted with 1, 2, 3, 4, 5, or 6 substituents independently selected from the group consisting of oxo, alkyl, halo, —OH, —O(alkyl), and haloalkyl;

$R_{2a}$ is hydrogen or alkyl;

$R_x$ is an optional substituent of phenyl, selected from the group consisting of alkyl, alkylcarbonyl, alkoxy, alkoxyalkyl, cyano, formyl, halogen, haloalkoxy, hydroxy, hydroxyalkyl, haloalkyl, =N—OH, $NZ_{1a}Z_{2a}$—$(CR^{41a}R_{42a})_v$—O—, —O—$(CR_{41a}R_{42a})_v$-$G_{1a}$, —$(CR_{41a}R_{42a})_v$-$G_{1a}$, —$(CR_{41a}R_{42a})_v$—$NZ_{1a}Z_{2a}$, and $NZ_{1a}Z_{2a}$;

$G_{1a}$ is a 4-, 5-, 6-, or 7-membered monocyclic heterocycle containing one nitrogen atom and optionally 1 or 2 additional heteroatom in the ring, wherein said ring is attached to the parent moiety through the nitrogen atom, and said ring is optionally substituted with 1, 2, 3, 4, or 5 substituents selected from the group consisting of alkyl, alkenyl, alkynyl, halo, haloalkyl, =N—CN, =N—$OR_{51a}$, —CN, oxo, —$OR_{51a}$, —$OC(O)R_{51a}$, —$OC(O)N(R_{51a})_2$, —$S(O)_2R_{52a}$, —$S(O)_2N(R_{51a})_2$, —$C(O)R_{51a}$, —$C(O)OR_{51a}$, —$C(O)N(R_{51a})_2$, —$N(R_{51a})_2$, —$N(R_{51a})C(O)R_{51a}$, —$N(R_{51a})S(O)_2R_{52a}$, —$N(R_{51a})C(O)O(R_{52a})$, —$N(R_{51a})C(O)N(R_{51a})_2$, —$(CR_{1e}R_{1f})_w$—$OR_{51}$, —$(CR_{1e}R_{1f})_w$—$OC(O)R_{51a}$, —$(CR_{1e}R_{1f})_w$—$OC(O)N(R_{51a})_2$, —$(CR_{1e}R_{1f})_w$—$S(O)_2R_{52a}$, —$(CR_{1e}R_{1f})_w$—$S(O)_2N(R_{51a})_2$, —$(CR_{1e}R_{1f})_w$—$C(O)R_{51a}$, —$(CR_{1e}R_{1f})_w$—$C(O)OR_{51a}$, —$(CR_{1e}R_{1f})_w$—$C(O)N(R_{51a})_2$, —$(CR_{1e}R_{1f})_w$—$N(R_{51a})_2$, —$(CR_{1e}R_{1f})_w$—$N(R_{51a})C(O)R_{51a}$, —$(CR_{1e}R_{1f})_w$—$N(R_{51a})S(O)_2R_{52a}$, —$(CR_{1e}R_{1f})_w$—$N(R_{51a})C(O)O(R_{52a})$, —$(CR_{1e}R_{1f})_w$—$N(R_{51a})C(O)N(R_{51a})_2$, and —$(CR_{1e}R_{1f})_w$—CN;

$R_{51a}$, at each occurrence, is independently hydrogen, $C_1$-$C_4$ alkyl, $C_1$-$C_4$ haloalkyl, —$(CR_{2e}R_{2f})_y$—$OR^{53}$, monocyclic cycloalkyl, or —$(CR_{2e}R_{2f})_y$-(monocyclic cycloalkyl); wherein $R_{53a}$ is hydrogen, $C_1$-$C_4$ alkyl, $C_1$-$C_4$ haloalkyl, monocyclic cycloalkyl, or —$(CR_{2a}R_{2f})_y$-(monocyclic cycloalkyl);

$R_{52a}$, at each occurrence, is independently $C_1$-$C_4$ alkyl, $C_1$-$C_4$ haloalkyl, monocyclic cycloalkyl, or —$(CR_{2e}R_{2f})_y$-(monocyclic cycloalkyl);

the monocyclic cycloalkyl moiety, as a substituent, or as part of a substituent, as represented by $R_{41a}$, $R_{52a}$, and $R_{53a}$ are each independently unsubstituted or substituted with 1, 2, 3, or 4 substituents selected from the group consisting of $C_1$-$C_4$ alkyl, halo, hydroxy, $C_1$-$C_4$ alkoxy, $C_1$-$C_4$ haloalkoxy, and $C_1$-$C_4$ haloalkyl;

$R_{41a}$, $R_{42a}$, $R_{1e}$, $R_{1f}$, $R_{2e}$, and $R_{2f}$ at each occurrence, are each independently hydrogen, alkyl, haloalkyl, or halo;

v, w, and y, at each occurrence, are each independently 1, 2, 3, or 4;

$Z_{1a}$ and $Z_{2a}$ are each independently hydrogen, alkyl, alkoxyalkyl, alkylcarbonyl, cyanoalkyl, haloalkyl, or formyl; and n is 1, 2, 3, 4, or 5.

In compounds of formula (II), $R_{2a}$ is hydrogen or alkyl such as $C_{1-6}$ alkyl. In one embodiment, $R_{2a}$ is hydrogen. In another embodiment, $R_{2a}$ is $C_{1-6}$ alkyl such as, but not limited to, methyl, or tert-butyl. Examples of $R_{1a}$ include, but are not limited to, cycloalkylalkyl wherein the cycloalkyl moiety include, but are not limited to, cyclopropyl, cyclobutyl, cyclopentyl and cyclohexyl, each of which is independently unsubstituted or substituted as described in the Summary. One example of the cycloalkyl moiety is cyclobutyl. Examples of the optional substituents of the cycloalkyl moiety include, but are not limited to, alkyl, haloalkyl, hydroxy, oxo, alkoxy, and haloalkoxy. In other embodiments, $R_{1a}$ is alkyl (such as, but not limited to, butyl). In yet another embodiment, $R_{1a}$ is halolakyl. In a further embodiment, $R_{1a}$, for example, is alkoxyalkyl (for example, 2-methoxyethyl).

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers (including enantiomers and diastereomers) and mixtures of various ratio thereof and are included within the scope of this invention. Individual stereoisomers of compounds of the present invention may be prepared synthetically from commercially available starting materials containing asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration; and substituents around a cycloalkyl or heterocycle are designated as being of cis or trans configuration.

Within the present invention it is to be understood that compounds disclosed herein may exhibit the phenomenon of tautomerism.

The formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. BIOLOGICAL DATA (i) In Vitro Methods—Human $CB_2$ and $CB_1$ Radioligand Binding Assays:

The $CB_1$ and $CB_2$ radioligand binding assays described herein are utilized to determine the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

Representative compounds of the present invention bound to $CB_2$ receptors with a $K_i$ of less than about 1,000 nM, preferably less than 400 nM, more preferably less than 200 nM and, most preferably lower than 100 nM.

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 unlabeled CP-55,940 (Tocris, Ellisville, Mo.) was used to assess nonspecific binding. Representative compounds of the present invention bound to $CB_1$ receptors with $K_1$ of about 10 fold to about 1000 fold or more higher than that for $CB_2$ receptors. These results show that the compounds of the present invention preferably bind to $CB_2$ receptors, therefore are selective ligands for the $CB_2$ receptor.

(ii) In Vivo Data:

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incisional Model of Postoperative Pain

A skin incision model of postoperative pain can be produced using the procedures described in Brennan et al., 1996, Pain, 64, 493. All rats are anesthetized with isoflurane delivered via a nose cone. Right hind paw incision is performed following sterilization procedures. The plantar aspect of the left hind paw is placed through a hole in a sterile plastic drape. A 1-cm longitudinal incision is made through the skin and fascia of the plantar aspect of the hind paw, starting 0.5 cm from the proximal edge of the heel and extending towards the toes, the plantar muscle is elevated and incised longitudinally leaving the muscle origin and insertion points intact. The skin is then closed with two mattress sutures (5-0 nylon). After surgery, animals are then allowed to recover for 2 hours, at which time tactile allodynia is assessed as described below. To evaluate the anti-nociceptive effects, animals are i.p. administered vehicle or test compound 90 minutes following skin incision and tactile allodynia is assessed 30 minutes after compound administration.

Tactile allodynia can be measured using calibrated von Frey filaments (Stoelting, Wood Dale, Ill.) as described in Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55. Rats are placed into inverted individual plastic cage (20×12.5×20 cm) on top of a suspended wire mesh grid, and are acclimated to the test chambers for 20 minutes. The von Frey filaments are applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses include an abrupt withdrawal of the hind paw from the stimulus, or flinching behavior immediately following removal of the stimulus. A 50% withdrawal threshold can be determined using an up-down procedure (Dixon, W. J., 1980, Efficient Analysis of Experimental Observations, Ann. Rev. Pharmacol. Toxicol., 20, 441).

Representative compounds of the present invention showed efficacy at less than about 300 micromoles/kg in the skin incision model of postoperative pain. In a more preferred embodiment, compounds described herein showed efficacy at less than about 100 micromoles/kg in the skin incision model of postoperative pain.

Complete Freund's Adjuvant (CFA) Model of Inflammatory Pain

Chronic inflammatory thermal hyperalgesia was induced by injection of 150 µL of a 50% solution of CFA in phosphate buffered saline (PBS) into the plantar surface of the right hind paw in rats; control animals received only PBS treatment. Thermal hyperalgesia was assessed 48 hours post CFA injection. Thermal hyperalgesia was determined using a commercially available thermal paw stimulator (University Anesthesiology Research and Development Group (UARDG), University of California, San Diego, Calif.) described by Hargreaves et al. (Hargreaves, et. al., 1988, Pain 32, 77). Rats were placed into individual plastic cubicles mounted on a glass surface maintained at 30° C., and allowed a 20 min habituation period. A thermal stimulus, in the form of radiant heat emitted from a focused projection bulb, was then applied to the plantar surface of each hind paw. The stimulus current was maintained at 4.50±0.05 amp, and the maximum time of exposure was set at 20.48 sec to limit possible tissue damage. The elapsed time until a brisk withdrawal of the hind paw from the thermal stimulus was recorded automatically using photodiode motion sensors. The right and left hind paw of each rat was tested in three sequential trials at approximately 5-minute intervals. Paw withdrawal latency (PWL) was calculated as the mean of the two shortest latencies.

Representative compounds of the present invention showed a statistically significant change in paw withdrawal latency versus a saline vehicle at less than about 300 micromoles/kg in the Complete Freund's Adjuvant (CFA) model of inflammatory pain.

Spinal Nerve Ligation Model of Neuropathic Pain

A model of spinal nerve ligation-induced (SNL model) neuropathic pain was produced using the procedure originally described in Kim, S. H. and J. M. Chung, 1992, An experimental model for peripheral neuropathy produced by segmental spinal nerve ligation in the rat, Pain, 50, 355. The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals a well as in the contralateral paws of nerve-injured rats.

Representative compounds of the present invention showed efficacy at less than about 300 micromoles/kg in the spinal nerve ligation model of neuropathic pain. In a more preferred embodiment, representative compounds of the present invention showed efficacy at less than about 100 micromoles/kg in the spinal nerve ligation model of neuropathic pain.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Representative compounds of the present invention showed a statistically significant change in paw withdrawal latency versus a saline vehicle at less than about 300 micromoles/kg. In a more preferred embodiment, representative compounds of the present invention showed efficacy at less than about 50 micromoles/kg.

MIA-Induced Knee Joint Osteoarthritic Pain Model

Unilateral knee joint osteoarthritis was induced in the rats by a single intra-articular (i.a.) injection of sodium monoiodoacetate (MIA, 3 mg in 0.05 mL sterile isotonic saline) into the right knee joint cavity under light isoflurane anesthesia using a 26G needle. The dose of the MIA (3 mg/i.a. injection) was selected based on results obtained from preliminary studies wherein an optimal pain behavior was observed at this dose. Pain behavioral assessment of hind limb grip force were conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of MIA. The vehicle control group for each compound being tested was assigned 0% whereas the age matched naïve group was assigned as being 100% (normal). The % effects for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than or equal to one day. A typical duration of repeated daily dosing is about 5 days to about 12 days.

Representative compounds of the present invention showed a statistically significant change in hind limb grip force strength versus a saline vehicle at less than about 300 micromoles/kg in the MIA model of osteoarthritic pain following a single dose. In a more preferred embodiment, representative compounds of the present invention showed a statistically significant change in hind limb grip force strength versus a saline vehicle at less than about 50 micromoles/kg in the MIA model of osteoarthritic pain following a single dose.

d. METHODS OF USING THE COMPOUNDS

The data contained herein above demonstrates that compounds of the present invention bind to the $CB_2$ receptor.

Certain compounds of the present invention were shown to have an analgesic effect in two types of animal pain models relating to neuropathic and nociceptive pain.

One embodiment of the present invention provides a method for treating pain (for example, neuropathic pain or nociceptive pain) in a mammal (including human) in need of such treatment. The method comprises administering to the mammal a therapeutically effective amount of any of the compounds described herein, or a pharmaceutically acceptable salt thereof, alone or in combination with one or more pharmaceutically acceptable carriers. The method further comprises administration of compounds of the invention as a single dose. The method also comprises repeated or chronic administration of compounds of the invention over a period of days, weeks, months, or longer. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID), or with other analgesic agent (e.g. acetaminophen), or a combination thereof Another embodiment of the present invention provides a method for treating a disorder selected from the group consisting of inflammatory disorders, immune disorders, neurological disorders, cancers of the immune system, respiratory disorders, and cardiovascular disorders in a mammal (including human) in need of such treatment. The method comprises administering to the mammal a therapeutically effective amount of any of the compounds described herein or a pharmaceutically acceptable salt thereof, alone or in combination with one or more pharmaceutically acceptable carriers.

Yet another embodiment of the present invention relates to a method for providing neuroprotection in a mammal (including human) in need of such treatment. The method comprises administering to the mammal a therapeutically effective amount of any of the compounds described herein or a pharmaceutically acceptable salt thereof, alone or in combination with one or more pharmaceutically acceptable carriers.

Another embodiment of the present invention provides a method of increasing the therapeutic effectiveness or potency of compounds of the invention by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Halms, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J.

Neurosci., 2003, 23(35), 11136-11141). In vitro, treatment with the $CB_2$ agonist JWH-133 abrogated □-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-□-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds of the invention may be required to achieve the desired therapeutic response. "Repeated or chronic administration" refers to the administration of compounds of the invention daily (i.e., every day) or intermittently (i.e., not every day) over a period of days, weeks, months, or longer. In particular, the treatment of chronic painful conditions is anticipated to require such repeated or chronic administration of compounds of the invention. Compounds of the invention may become more effective upon repeated or chronic administration such that the therapeutically effective doses on repeated or chronic administration may be lower than the therapeutically effective dose from a single administration.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds of the invention may be administered alone, or in combination with one or more other compounds of the invention, or in combination (i.e. co-administered) with one or more additional pharmaceutical agents. For example, a compound the invention, or a pharmaceutically acceptable salt or solvate thereof, may be administered in combination with acetaminophen, or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments of the invention, the nonsteroidal anti-inflammatory drug (NSAID) is ibuprofen. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R_g$, $R_1$, $R_2$, $R_3$, $R_4$, $R_9$, $R_{10}$, $R_{31}$, $R_{32}$, $R_{41}$, $R_{42}$, $Z_1$, $Z_2$, $G_1$, and $L_1$ have the meanings as set forth in the summary section unless otherwise noted, can be synthesized as shown in Schemes 1-15.

As used in the descriptions of the schemes and the examples, certain abbreviations are intended to have the following meanings: aq. for aqueous; DME for dimethoxyethane, DMF for N,N-dimethylformamide; dppf for, 1'-bis(diphenylphosphino)ferrocene, EtOAc for ethyl acetate, EtOH for ethanol, Et$_3$N for triethylamine, HATU for O-(7-azabenzotriazol-1-yl)-N,N,N',N'-tetramethyluronium hexafluorophosphate, Et$_2$O for diethyl ether, Et$_3$N for triethylamine, HPLC for high performance liquid chromatography, Ph for phenyl; mesyl for methanesulfonate; MeOH for methanol, min for minute or minutes; n-Bu for n-butyl; DMSO for dimethylsulfoxide; dppf for 1,1'-bis(diphenylphosphino)ferrocene; TFA for trifluoroacetic acid; THF for tetrahydrofuran; Ts or tosyl for p-CH$_3$PhS(O)$_2$O—; and Tf or triflate for CF$_3$S(O)$_2$O—.

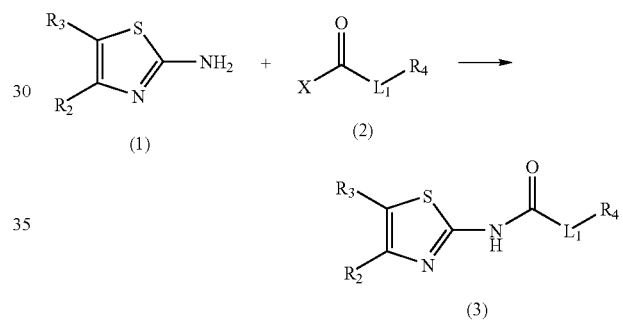

Scheme 1

As shown in Scheme 1, compounds of formula (1) containing an amine group when treated with compounds of formula (2), wherein X is chloro or —OH under coupling conditions known to one skilled in the art, will provide compounds of formula (3). Typical conditions for the reaction of compounds of formula (2) wherein X is chloro and compounds of formula (1) include but are not limited to stirring an equimolar mixture of the compounds in solvents such as chloroform, dichloromethane or THF in the presence of a base such as but not limited to diisopropylethylamine at 0-30° C. for 8-24 hours. Acid coupling conditions of compounds of formula (2), wherein X is —OH and compounds of formula (1), include stirring an equimolar mixture of the compounds with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU) along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine in a solvent such as, but not limited to, THF, N,N-dimethylacetamide, N,N-dimethylformamide, pyridine, chloroform, or mixtures thereof. Typical reactions can be carried out between 0-65° C. or may be carried out in a microwave reactor to facilitate the coupling.

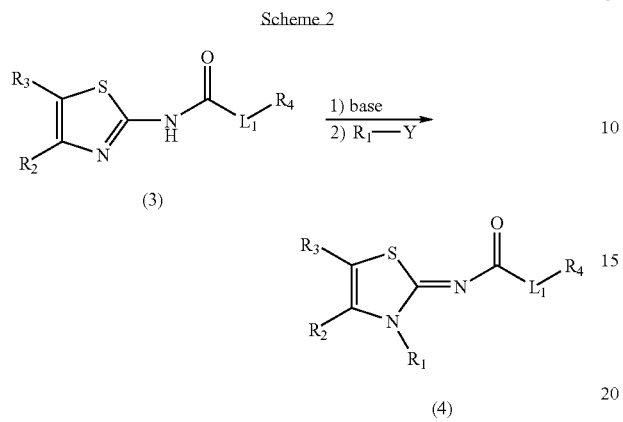

As shown in Scheme 2, compounds of formula (3) may be converted into compounds of formula (4) which are representative compounds of the present invention. Typical conditions include, but are not limited to, the treatment of compounds of formula (3) with sodium hydride in DMF at 0° C., followed by the addition of reagents such as $R_1$—Y, wherein $R_1$ is as defined in formula (I) and Y is chloro, bromo, iodo, tosyl, mesyl or triflate. Alternatively, other bases such as potassium hydroxide or potassium tert-butoxide in a mixture of THF and DMF, followed by treatment with $R_1$—Y will also provide compounds of formula (4).

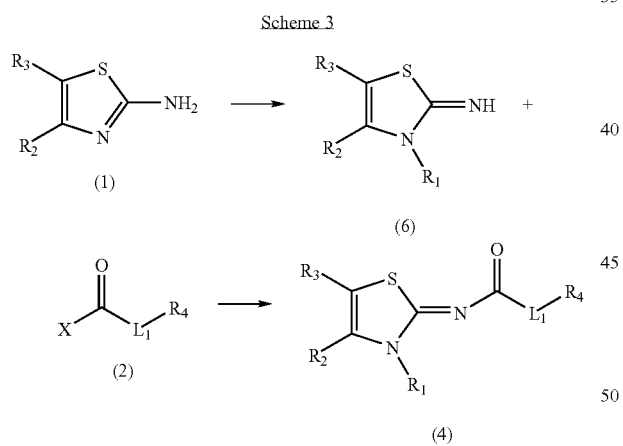

Alternatively, compounds of formula (4) may also be prepared according to the methods outlined in Scheme 3. Compounds of formula (1) when treated with sodium hydride in DMF at 0° C., followed by the addition of reagents such as $R_1$—Y, wherein Y is chloro, bromo, iodo, tosyl, mesyl or triflate provide compounds of formula (6). Alternatively, compounds of formula (1) may be heated neat or in the presence of a minimal amount of solvent to facilitate mixing with compounds of formula $R_1$—Y to obtain compounds of formula (6). Compounds of formula (6) may be isolated as a salt or a free base. The treatment of compounds of formula (6) with compounds of formula (2), wherein X is chloro or —OH, under coupling conditions as outlined in Scheme 1 can generate compounds of formula (4).

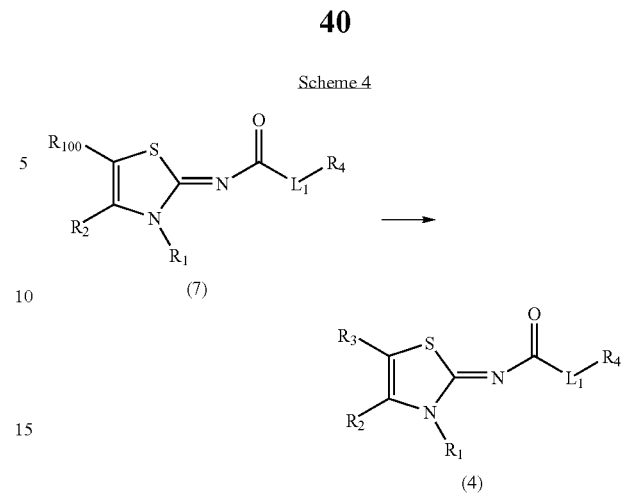

As outlined in Scheme 4, compounds of formula (7), wherein $R_{100}$ is halide or triflate and which can be prepared according to the methods outlined in Schemes 1-3, when treated with a boronic acid of formula $R_3B(OH)_2$, wherein $R_3$ is aryl, arylalkenyl, cycloalkyl, heterocycle or heteroaryl, a palladium catalyst such as dichlorobis(triphenyl)phosphine) palladium (II) and sodium carbonate in a mixture of solvents which include but are not limited to various mixtures of DME, ethanol and water under heated conditions provide compounds of formula (4) wherein $R_3$ is alkenyl, aryl, arylalkenyl, cycloalkyl, heterocycle or heteroaryl.

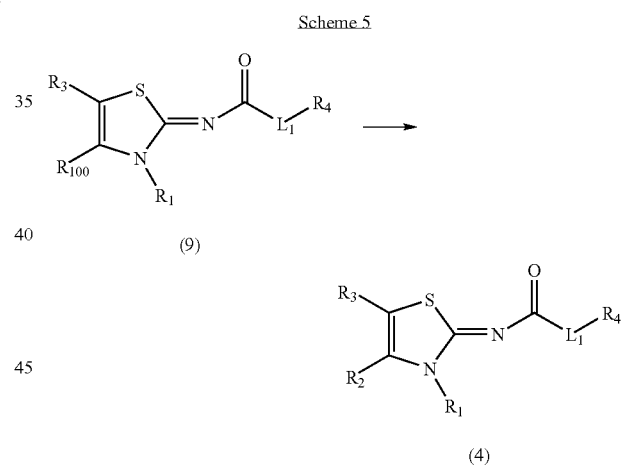

As outlined in Scheme 5, compounds of formula (9) wherein $R_{100}$ is halide or triflate and which can be prepared according to the methods outlined in Schemes 1-3, when treated with a boronic acid of formula $R_2B(OH)_2$, wherein $R_2$ is aryl, arylalkenyl, cycloalkyl, heterocycle or heteroaryl and a palladium catalyst according to the methods outlined is Scheme 4 can provide compounds of formula (4) wherein $R_2$ is aryl, arylalkenyl, cycloalkyl, heterocycle or heteroaryl.

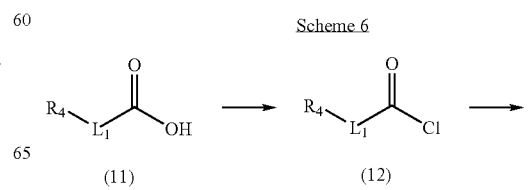

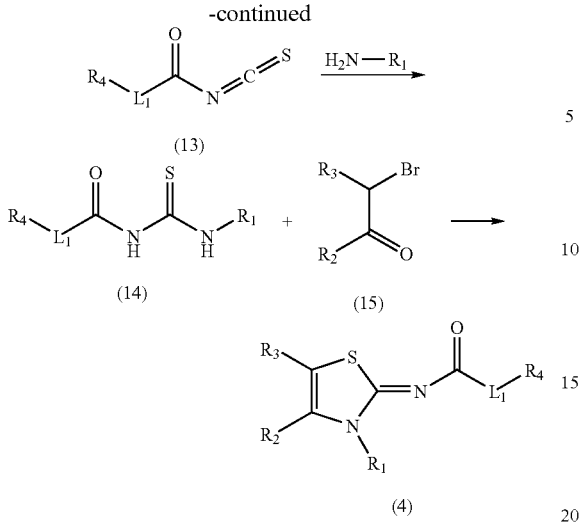

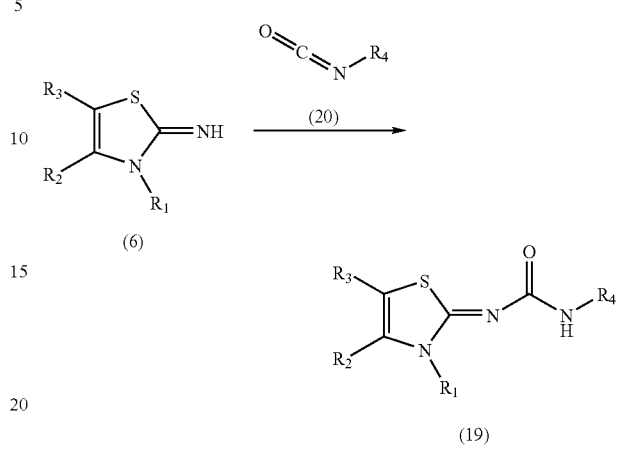

Scheme 6 describes another alternative method for the preparation of compounds of formula (4). Compounds of formula (11) when treated with oxalyl chloride in dichloromethane containing a catalytic amount of DMF will provide the acid chloride of formula (12). The acid chloride of formula (12) when treated with potassium thiocyanate in acetone can provide compounds of formula (13). Compounds of formula (13) when treated with an amine of formula $R_1$—$NH_2$ in solvents such as but not limited to THF can provide compounds of formula (14). Compounds of formula (14) when treated with substituted alpha-bromo-ketones of formula (15) in ethanol or mixtures of ethanol and toluene under heated conditions will provide compounds of formula (4).

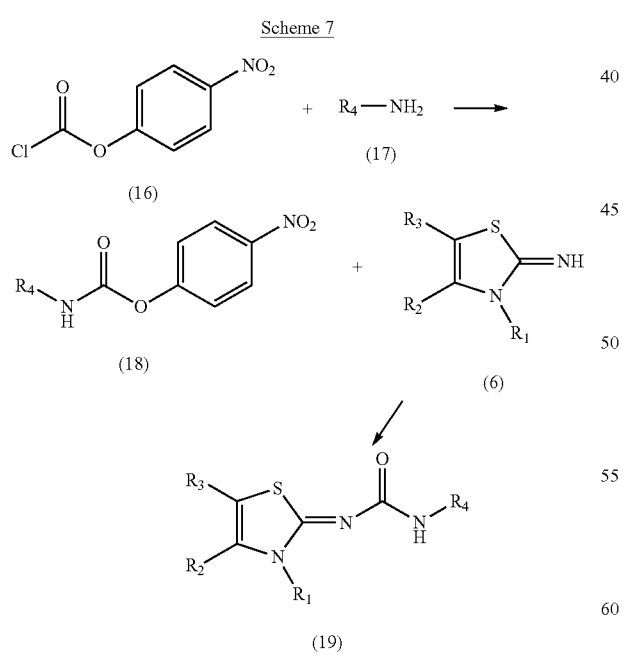

Compounds of formula (I) wherein $L_1$ is —NH—, may be prepared as outlined in Scheme 7. Compounds of formula (16) when treated with an amine of formula (17), wherein $R_4$ is defined in formula (I), will provide compounds of formula (18). Compounds of formula (18) when treated with compounds of formula (6) can provide compounds of formula (19).

Alternatively, compounds of formula (6) when treated with an isocyanate of formula (20) provide compounds of formula (19).

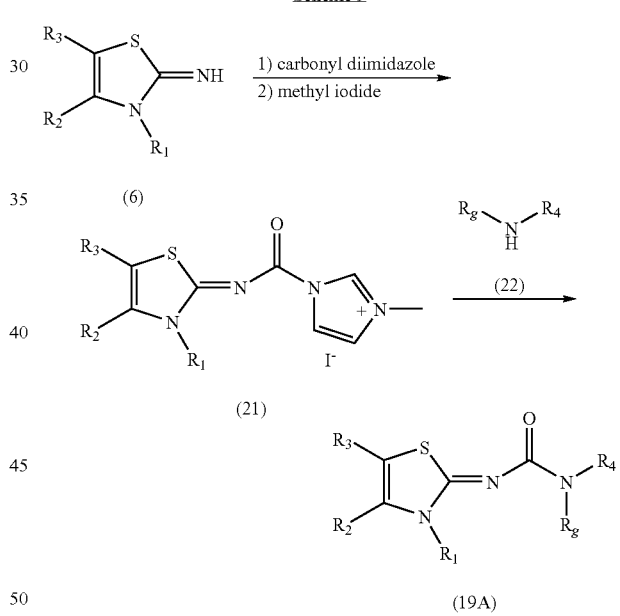

Similarly, compounds of formula (6) when treated with carbonyl diimidazole, followed by treatment with methyl iodide, can provide the imidazolide compounds of formula (21). Compounds of formula (21) when treated with an amine of formula (22) can provide compounds of formula (19A).

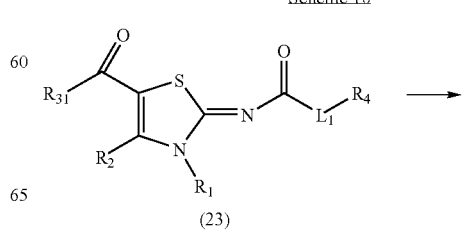

-continued

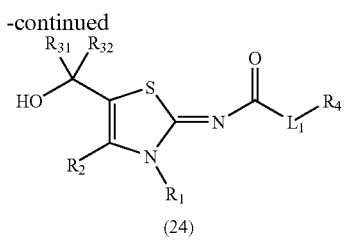

(24)

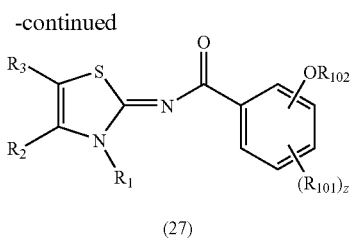

(27)

As shown in Scheme 10, compounds of formula (23) when treated at low temperatures with an organolithium reagent such as but not limited to $R_{32}Li$ or a Grignard reagent such as but not limited to $R_{32}MgBr$ can be converted to compounds of formula (24). The reaction is typically conducted in a solvent such as but not limited to diethyl ether.

Scheme 11

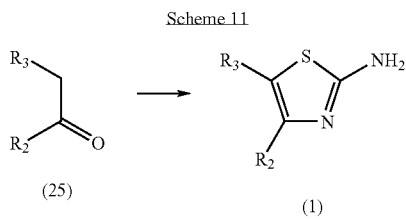

(25)  (1)

As shown in Scheme 11, compounds of formula (25) when treated with pyrrolidine and p-toluenesulfonic acid monohydrate in a solvent such as but not limited to cyclohexane at reflux followed by treatment with sulfur and cyanamide in a solvent such as but not limited to methanol at temperatures between 0-70° C., can provide compounds of formula (1).

Scheme 12

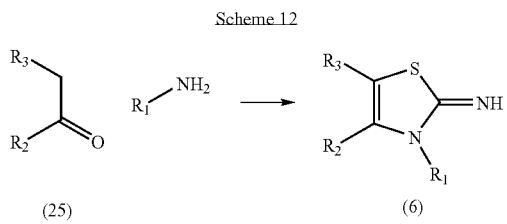

(25)  (6)

As shown in Scheme 12, compounds of formula (25) when treated with amines of formula $R_1NH_2$, in the presence of molecular sieves in a solvent such as, but not limited to, acetonitrile, at a temperatures ranging from about 25° C. to about 80° C., followed by treatment with potassium thiocyanate and iodine at temperatures between 40-80° C., provide compounds of formula (6).

Certain compounds of formula (I) where $R_4$ or $R_9$ is phenyl and said phenyl is substituted with the group $-OR_{102}$ can be prepared using the methods described in Scheme 13.

Scheme 13

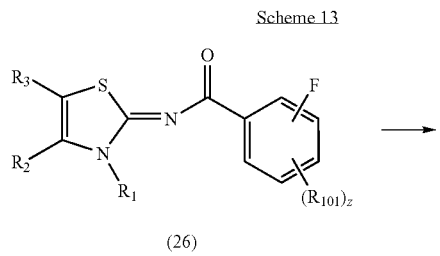

(26)

Compounds of formula (27), wherein $R_{101}$ represents the optional substituents of $R_4$ and $R_9$ of formula (I), z is 0, 1, 2, 3, or 4, and $R_{102}$ is $R_{10}$, alkyl, alkoxyalkyl, haloalkyl, $NZ_1Z_2-(CR_{41}R_{42})_p-$, or $G_1-(CR_{41}R_{42})_p-$ can be prepared from compounds of formula (26) by reaction with an alcohol $HOR_{102}$ in the presence of a base such as, but not limited to, potassium tert-butoxide or sodium tert-butoxide in a solvent such as, but not limited to, tetrahydrofuran or dimethylformamide at temperatures between about 0° C. and 50° C. In certain instances, a protecting group may be attached to a functional group present in $R_{102}$. Such protecting groups can be removed using methods well-known to those skilled in the art. The group $R_{102}$ can also be further transformed to provide other compounds of the invention using standard chemical techniques well-known to those skilled in the art such as alkylation, acylation, and reductive amination.

Certain compounds of formula (I) wherein $R_4$ or $R_9$ is phenyl and said phenyl is substituted with a group $R_{103}$, can be prepared according to the carbon-carbon bond forming reactions described in Scheme 14.

Scheme 14

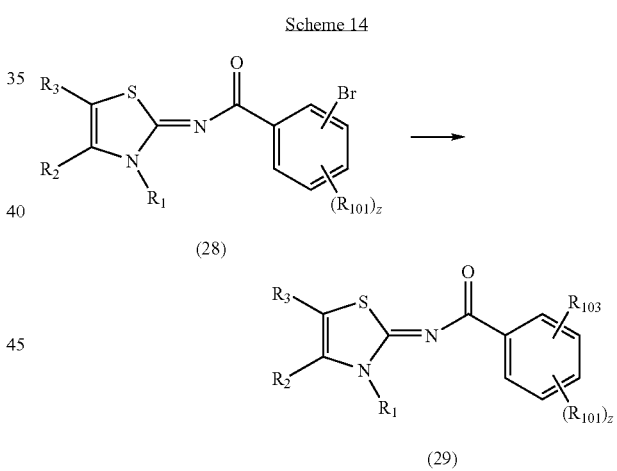

(28)

(29)

Compounds of formula (29), wherein $R_{101}$ represents the optional substituents of $R_4$ and $R_9$ of formula (I), z is 0, 1, 2, 3, or 4, and $R_{103}$ is selected from the group consisting of alkenyl, alkoxyalkoxyalkyl, alkoxyalkyl, alkoxycarbonylalkyl, alkyl, alkylcarbonylalkyl, alkylsulfinylalkyl, alkyl-S$(O)_2-(CR_{41}R_{42})_p=C(R_{41})-$, alkyl-S$(O)_2-(CR_{41}R_{42})_p-$, alkyl-S-$(CR_{41}R_{42})_p-$, alkynyl, carboxyalkyl, cyano, cyanoalkyl, formylalkyl, haloalkyl, hydroxyalkyl, $-C(R_{41})=N-O(R_{42})$, and $-(CR_{41}R_{42})_p-C(R_{41})=N-O(R_{42})$, can be prepared from compounds of formula (28). Reactions well-known in the chemical literature for effecting these transformations include the Suzuki, Heck, Stille, Sonogashira, and Negishi reactions. Typical reaction conditions for can be found in the following references: Negishi, E. A. Handbook of Organopalladium Chemistry for Organic Synthesis; Wiley-Interscience: New York, 2002; Miyaura, N. Cross-Coupling Reactions: A Practical Guide; Springer: New York, 2002. More specifically, where $R_{103}$ is alkyl-$S(O)_2$—$(CR_{41}R_{42})_p$=$C(R_{41})$—, or alkenyl, compounds can be prepared using palladium acetate, tri(o-tolyl)phosphine as the ligand, triethylamine as base with the corresponding vinyl sulfone, or alkene under microwave conditions at temperatures from 140-180° C. In the conversion of (28) to (29), the —Br of (28) may also be a triflate, —I, —Cl, a boronic acid (or derivative), stannyl or the like.

Certain compounds of formula (I) wherein $R_4$ or $R_9$ is phenyl, can be prepared according to the method shown in Scheme 15.

Scheme 15

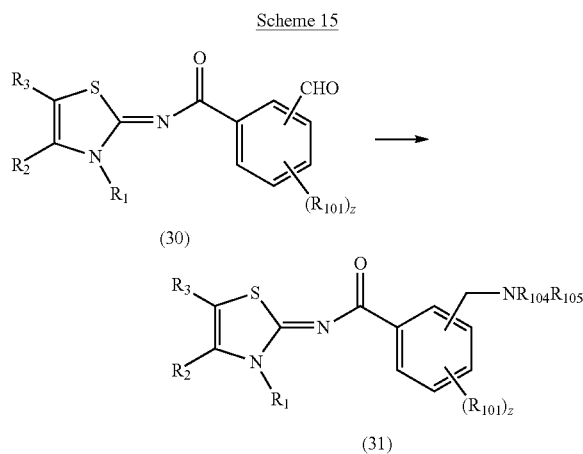

Compounds of the invention of formula (31), wherein $R_{101}$ represents the optional substituents of $R_4$ and $R_9$ of formula (I), z is 0, 1, 2, 3, or 4, and $NR_{104}R_{105}$ is $NZ_1Z_2$ or $G_1$, can be prepared from compounds of formula (30) by a reductive amination reaction. The reductive amination reaction is well known to those skilled in the art. For example, reaction of compounds (30) with amines $HNR_{104}R_{105}$ in solvents such as, but not limited to, acetonitrile, tetrahydrofuran, dichloromethane or dichloroethane, in the presence of a reducing agent such as, but not limited to, sodium cyanoborohydride or sodium triacetoxyborohydride, can provide compounds (31). The reaction may be conducted in the presence of an acid (e.g., acetic acid).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation. Following Examples may be used for illustrative purposes and should not be deemed to narrow the scope of the invention.

EXAMPLES

Example 1

N-[(2Z)-3-(2-methoxyethyl)-1,3-thiazol-2(3H)-ylidene]-2,2,3,3-tetramethylcyclopropanecarboxamide Example 1A 2,2,3,3-tetramethylcyclopropanecarbonyl chloride To a solution of 2,2,3,3-tetramethylcyclopropanecarboxylic acid (0.50 g, 3.5 mmol) in 18 mL of methylene chloride at 0° C. was added oxalyl chloride (0.61 mL, 7.0 mmol) and a catalytic amount of dimethylformamide (2 drops). The solution was stirred at ambient temperature for 1 hour, and then concentrated under reduced pressure to provide 0.56 g of the title compound.

Example 1B 2,2,3,3-tetramethyl-N-1,3-thiazol-2-ylcyclopropanecarboxamide

To a solution of 2-aminothiazole (0.39 g, 3.9 mmol) in 10 mL of methylene chloride at 0° C. was added a solution of the product from Example 1A in 8 mL of chloroform, followed by triethylamine (1.0 mL, 7.7 mmol). The mixture was stirred for 7 hours at 35° C., cooled to ambient temperature and diluted with water. The phases were separated and the aqueous phase was extracted with methylene chloride. The combined organic extracts were washed twice with water and then brine, dried over magnesium sulfate, filtered, and concentrated under reduced pressure. Purification by column chromatography (SiO$_2$, 30-60% ethyl acetate/hexanes gradient) afforded 0.11 g (14%) of the title compound. $^1$H NMR (CDCl$_3$, 300 MHz) δ ppm 1.18 (s, 1H), 1.25 (s, 6H), 1.35 (s, 6H), 6.92 (d, J=3.4 Hz, 1H), 7.39 (d, J=3.4 Hz, 1H), 10.7 (s, 1H); MS (DCI/NH$_3$) m/z 225 (M+H)$^+$. Anal. Calculated for C$_{11}$H$_{16}$N$_2$OS: C, 58.90; H, 7.19; N, 12.49. Found: C, 59.03; H, 7.34; N, 12.34.

Example 1C

N-[(2Z)-3-(2-methoxyethyl)-1,3-thiazol-2(3H)-ylidene]-2,2,3,3-tetramethylcyclopropanecarboxamide To a solution of Example 1B (0.16 g, 0.71 mmol) in 3.5 mL of 4:1 tetrahydrofuran:dimethylformamide at 0° C. was added potassium hydroxide (90 mg, 1.7 mmol). After stirring for 1 hour at room temperature, 2-bromoethyl methyl ether (73 μL, 7.1 mmol) was added and the solution was heated to 65° C. for 14 hours. The solution was allowed to cool to ambient temperature and then diluted with ethyl acetate and washed twice with water and then brine. The organic extract was dried over magnesium sulfate, filtered, and concentrated under reduced pressure. Purification by column chromatography (SiO$_2$, 30-50% ethyl acetate/hexanes gradient) afforded 22 mg (11%) of the title compound. $^1$H NMR (CDCl$_3$, 300 MHz) δ 1.25 (s, 12H), 1.75 (s, 1H), 3.32 (s, 3H), 3.74 (t, J=5.6 Hz, 2H), 4.44 (t, J=5.4 Hz, 2H), 6.95 (d, J=3.4 Hz, 1H), 7.48 (t, J=3.7 Hz, 1H); MS (DCI/NH$_3$) m/z 283 (M+H)$^+$. Anal. Calculated for C$_{14}$H$_{22}$N$_2$O$_2$S: C, 59.54; H, 7.85; N, 9.92. Found: C, 59.76; H, 7.97; N, 9.91.

Example 2

5-chloro-2-methoxy-N-[(2Z)-3-(2-methoxyethyl)-1,3-thiazol-2(3H)-ylidene]benzamide Example 2A 3-(2-methoxyethyl)-1,3-thiazol-2(3H)-imine hydrobromide A mixture of 2-aminothiazole (15 g, 0.15 mol) and 2-bromoethyl methyl ether (17 mL, 0.18 mol) were heated at 85° C. for 16 hours. After cooling to ambient temperature the resulting solid was triturated twice with isopropyl alcohol to afford 26 g (72%) of the title compound. $^1$H NMR (DMSO-d$_6$, 300 MHz) δ ppm 3.27 (s, 3H), 3.63 (t, J=5.1 Hz, 2H), 4.23 (t, J=4.9 Hz, 2H), 7.02 (d, J=4.7 Hz, 1H), 7.38 (d, J=4.4 Hz, 1H), 9.52 (s, 1H); MS (DCI/NH$_3$) m/z 159 (M+H)$^+$.

Example 2B

5-Chloro-2-methoxy-N-[(2Z)-3-(2-methoxyethyl)-1,3-thiazol-2(3H)-ylidene]benzamide To a solution of the product from Example 2A (0.77 g, 3.2 mmol) and 5-chloro-2-methoxybenzoic acid (0.50 g, 2.7 mmol) in 14 mL of THF at 0° C. was added O-(7-azabenzotriazol-1-yl)-N,N,N',N'-tetramethyluronium hexafluorophosphate (HATU, 1.24 g, 3.2 mmol) and N,N-diisopropylethylamine (1.1 mL, 6.2 mmol). The mixture was heated to 65° C. for 2.5 hours, cooled to ambient temperature and then diluted with ethyl acetate. The mixture was washed twice with water, then saturated aqueous sodium bicarbonate, and brine. The organic extract was dried over magnesium sulfate, and concentrated under reduced pressure. Purification by column chromatography (SiO$_2$, 20-35% ethyl acetate/hexanes gradient) afforded 0.38 g (43%) of the title compound. $^1$H NMR (CDCl$_3$, 300 MHz) δ ppm 3.35 (s, 3H), 3.72-3.81 (m, 2H), 3.91 (s, 3H), 4.41-4.48 (m, 2H), 6.65 (d, J=4.7 Hz, 1H), 6.92 (d, J=8.8 Hz, 1H), 7.16 (d, J=4.7 Hz, 1H), 7.34 (dd, J=8.8, 3.1 Hz, 1H), 7.99 (d, J=2.7 Hz, 1H); MS (DCI/NH$_3$) m/z 349 (M+H)$^+$. Anal. Calculated for C$_{18}$H$_{24}$N$_2$O$_3$S: C, 62.04; H, 6.94; N, 8.04. Found: C, 62.24; H, 7.08; N, 8.04.

Example 3

N-[(2Z)-3-(2-methoxyethyl)-1,3-thiazol-2(3H)-ylidene]cycloheptanecarboxamide

Cycloheptanecarboxylic acid (29 mg, 0.20 mmol), 3 equiv of polymer bound dicyclohexylcarbodiimide (PS-DCC), 1-hydroxybenzotriazole hydrate (HOBT, 22 mg, 0.16 mmol), N,N-diisopropylethylamine (62 mg, 0.50 mmol), and the product of Example 2A (39 mg, 0.16 mmol) were combined in dimethylacetamide (DMA, 2.8 mL) and heated in a microwave to 100° C. for 420 seconds. The mixture was filtered through Si-Carbonate (6 mL-1 g cartridge from Silicycle Chemical Division) and then concentrated to dryness. The residue was dissolved in 1:1 DMSO/MeOH and purified by reverse phase HPLC to afford the title compound. $^1$H NMR (500 MHz, DMSO-d$_6$) δ ppm 1.39-1.72 (m, 11H) 1.83-1.95 (m, 2H) 2.46-2.52 (m, 1H) 3.23-3.26 (m, 3H) 3.67 (t, 2H) 4.29 (t, 2H) 6.76-6.97 (d, 1H) 7.30-7.43 (d, 1H); MS (ESI) m/z 283 (M+H)$^+$.

Example 4

N-[(2Z)-3-(3-methoxypropyl)-1,3-thiazol-2(3H)-ylidene]-2,2,3,3-tetramethylcyclopropanecarboxamide Example 4A 3-(3-methoxypropyl)-1,3-thiazol-2(3H)-imine hydrobromide A mixture of 2-aminothiazole (1.0 g, 10 mmol) and 1-bromo-3-methoxypropane (1.8 g, 12 mmol) were heated at 85° C. for 16 hours. The solid was cooled to ambient temperature, triturated with ethanol, and then collected by filtration to provide 1.2 g (48%) of the title compound. MS (DCI/NH$_3$) m/z 173 (M+H)$^+$.

Example 4B

N-[(2Z)-3-(3-methoxypropyl)-1,3-thiazol-2(3H)-ylidene]-2,2,3,3-tetramethylcyclopropanecarboxamide The product of Example 4A (0.60 g, 2.4 mmol) and 2,2,3,3-tetramethylcyclopropanecarboxylic acid (0.34 g, 2.4 mmol) were processed using the method described in Example 2B. Purification by column chromatography (SiO$_2$, 20-40% ethyl acetate/hexanes gradient) afforded 0.33 g (47%) of the title compound. $^1$H NMR (CDCl$_3$, 300 MHz) δ ppm 1.21 (s, 6H), 1.34 (s, 6H), 1.56 (d, J=5.4 Hz, 1H), 2.00-2.13 (m, 2H), 3.31-3.39 (m, 5H), 4.23 (t, J=6.8 Hz, 2H), 6.50 (d, J=4.7 Hz, 1H), 6.88 (d, J=4.7 Hz, 1H); MS (DCI/NH$_3$) m/z 297 (M+H)$^+$. Anal. Calculated for $C_{15}H_{24}N_2O_2S$: C, 60.78; H, 8.27; N 9.45. Found: C, 60.78; H, 8.27; N, 9.34.

Example 5

N-[(2Z)-3-(2-methoxyethyl)-4-methyl-1,3-thiazol-2(3H)-ylidene]-2,2,3,3-tetramethylcyclopropanecarboxamide

Example 5A 3-(2-methoxyethyl)-4-methyl-1,3-thiazol-2(3H)-imine hydrobromide

A mixture of 4-methylthiazol-2-ylamine (0.75 g, 6.5 mmol) and 2-bromoethyl methyl ether (730 μL, 7.8 mmol) was heated at 85° C. for 15 hours. The mixture was cooled to ambient temperature and the resulting solid was triturated with isopropanol. Recrystallization from hot ethanol afforded 0.56 g (34%) of the title compound. $^1$H NMR (DMSO-d$_6$, 300 MHz) δ ppm 2.25 (d, J=1.4 Hz, 3H) 3.25 (s, 3H) 3.57 (t, J=5.1 Hz, 2H) 4.15 (t, J=5.1 Hz, 2H) 6.68 (d, J=1.4 Hz, 1H) 9.40 (s, 1H); MS (DCI/NH$_3$) m/z 173 (M+H)$^+$.

Example 5B

N-[(2Z)-3-(2-methoxyethyl)-4-methyl-1,3-thiazol-2(3H)-ylidene]-2,2,3,3-tetramethylcyclopropanecarboxamide The product of Example 5A (0.30 g, 1.2 mmol) and 2,2,3,3-tetramethylcyclopropanecarboxylic acid (0.19 g, 1.3 mmol) were processed using the method described in Example 2B. Purification by column chromatography (SiO$_2$, 20-40% ethyl acetate/hexanes gradient) afforded 0.14 g (41%) of the title compound. $^1$H NMR (CDCl$_3$, 300 MHz) δ ppm 1.21 (s, 6H), 1.34 (s, 6H), 1.59 (s, 1H), 2.30 (s, 3H), 3.30 (s, 3H), 3.70 (t, J=5.09 Hz, 2H), 4.25 (t, J=5.26 Hz, 2H), 6.09 (s, 1H); MS (DCI/NH$_3$) m/z 297 (M+H)$^+$. Anal. Calculated for $C_{15}H_{24}N_2O_2S$: C, 60.78; H, 8.16; N, 9.45. Found: C, 60.79; H, 7.82; N, 9.36.

Example 6 ethyl((2Z)-3-(2-methoxyethyl)-2-{[(2,2,3,3-tetramethylcyclopropyl)carbonyl]imino}-2,3-dihydro-1,3-thiazol-4-yl)acetate

Example 6A ethyl[2-imino-3-(2-methoxyethyl)-2,3-dihydro-1,3-thiazol-4-yl]acetate hydrobromide A mixture of (2-aminothiazol-4-yl)acetic acid ethyl ester (18.6 g, 100 mmol) and 2-bromoethyl methyl ether (15.3 g, 110 mmol) were processed using the method described in Example 2A to afford 14.1 g (83%) of the title compound. $^1$H NMR (300 MHz, DMSO-d$_6$) δ ppm 1.14-1.28 (m, 3H) 3.24 (s, 3H) 3.54 (t, J=5 Hz, 2H) 3.91 (s, 2H) 4.04-4.25 (m, 4H) 6.92 (s, 1H) 9.50 (s, 1H); MS (DCI/NH$_3$) m/z 231 (M+H)$^+$.

Example 6B ethyl((2Z)-3-(2-methoxethyl)-2-{[(2,2,3,3-tetramethylcyclopropyl)carbonyl]imino}-2,3-dihydro-1,3-thiazol-4-yl)acetate The product of Example 6A (2.3 g, 10 mmol) and 2,2,3,3-tetramethylcyclopropane carboxylic acid (1.6 g, 11 mmol) were processed as described using the method described in Example 2B to afford 2.1 g (54%) of the title compound. $^1$H NMR (300 MHz, DMSO-d$_6$) δ ppm 1.06-1.33 (m, 15H) 1.48 (s, 1H) 3.22 (s, 3H) 3.59 (t, J=5 Hz, 2H) 3.91 (s, 2H) 4.12 (t, J=7 Hz, 2H) 4.14-4.24 (m, 2H) 6.69 (s, 1H); MS (DCI/NH$_3$) m/z 369 (M+H)$^+$. Anal. Calculated for $C_{18}H_{28}N_2O_4S$ C, 68.67; H, 7.66; N, 7.62. Found: C, 68.67; H, 7.66; N, 7.60.

Example 7 ethyl(2Z)-3-(2-methoxyethyl)-2-{[(2,2,3,3-tetramethylcyclopropyl)carbonyl]imino}-2,3-dihydro-1,3-thiazole-4-carboxylate

Example 7A ethyl 2-imino-3-(2-methoxyethyl)-2,3-dihydro-1,3-thiazole-4-carboxylate hydrobromide A mixture of 2-aminothiazole-4-carboxylic acid ethyl ester (17.2 g, 100 mmol) and 2-bromoethyl methyl ether (15.3 g, 110 mmol) were processed using the method described in Example 2A to afford 17.1 g (83%) of the title compound. $^1$H NMR (300 MHz, DMSO-d$_6$) δ ppm 1.30 (t, J=7 Hz, 3H) 3.22 (s, 3H) 3.60 (t, J=5 Hz, 2H) 4.32 (t, J=7 Hz, 2H) 4.35-4.61 (m, 2H), 7.84 (s, 1H), 9.76 (s, 1H); MS (DCI/NH$_3$) m/z 231 (M+H)$^+$.

Example 7B ethyl(2Z)-3-(2-methoxyethyl)-2-{[(2,2,3,3-tetramethylcyclopropyl)carbonyl]imino}-2,3-dihydro-1,3-thiazole-4-carboxylate The product of Example 7A (2.3 g, 10 mmol) and 2,2,3,3-tetramethylcyclopropane carboxylic acid (1.6 g, 11 mmol) were processed using the method described in Example 2B to afford 1.9 g (53%) of the title compound. $^1$H NMR (300 MHz, DMSO-d$_6$) δ ppm 1.11-1.36 (m, 12H) 1.53 (s, 1H) 3.21 (s, 3H) 3.31 (s, 3H) 3.53-3.62 (m, 2H) 4.30 (q, J=7 Hz, 2H) 4.62-4.75 (m, 2H) 7.77 (s, 1H); MS (DCI/NH$_3$) m/z 355 (M+H); Anal. Calculated for $C_{17}H_{26}N_2O_4S$: C, 57.61; H, 7.39; N, 7.86. Found: C, 57.86; H, 7.67; N, 7.85.

Example 8

N-[(2Z)-4-(hydroxymethyl)-3-(2-methoxyethyl)-1,3-thiazol-2(3H)-ylidene]-2,2,3,3-tetramethylcyclopropanecarboxamide To a solution of the product of Example 7B (0.355 g, 1.00 mmol) in 100 mL of THF at 0° C. was added lithium borohydride (10 mL of a 2.0 M solution in THF) and the resulting solution was allowed to warm to ambient temperature and stirred overnight. The mixture was quenched with water and then diluted with saturated aqueous Na$_2$CO$_3$ and extracted twice with ethyl acetate. The combined organic extracts were dried over anhydrous $Na_2SO_4$, filtered, and concentrated. Purification by column chromatography ($SiO_2$, 0-50% ethyl acetate/hexanes gradient) afforded 0.278 g (89%) of the title compound. $^1$H NMR (300 MHz, DMSO-$d_6$) δ ppm 1.20 (d, 12H) 1.47 (s, 1H) 3.24 (s, 3H) 3.64 (t, J=6 Hz, 2H) 4.30 (t, J=6 Hz, 2H) 4.50 (d, J=5 Hz, 2H) 5.75 (s, 1H) 6.68 (s, 1H); MS (DCI/NH3) m/z 313 (M+H)$^+$; Anal. Calculated for $C_{15}H_{24}N_2O_3S \cdot 0.2H_2O$: C, 57.01; H, 7.78; N, 8.86. Found: C, 56.90; H, 7.61; N, 8.86.

Example 9

2-ethoxy-N-[(2Z)-3-(2-methoxyethyl)-4-(trifluoromethyl)-1,3-thiazol-2(3H)-ylidene]benzamide Example 9A 2-ethoxy-N-(4-trifluoromethyl-thiazol-2-yl)-benzamide A solution of 2-ethoxybenzoic acid (0.75 g, 4.5 mmol) in 23 mL of methylene chloride at 0° C. was treated with oxalyl chloride (0.44 mL, 4.9 mmol) followed by 2 drops of dimethylformamide. The solution was stirred at ambient temperature for 1 hour and then concentrated under reduced pressure to provide 0.83 g of 2-ethoxybenzoyl chloride. To a solution of 4-trifluoromethylthiazol-2-ylamine (0.50 g, 3.0 mmol) in 10 mL THF at 0° C. was added a solution of the freshly prepared acid chloride in 5 mL of THF and 2 mL of methylene chloride, followed by triethylamine (1.0 mL, 6.6 mmol). The reaction mixture was warmed to 65° C. and stirred 8 hours. The mixture was diluted with ethyl acetate and washed twice with water, then brine. The organic extract was dried over magnesium sulfate, filtered, and concentrated under reduced pressure. Purification by column chromatography ($SiO_2$, 30-50% ethyl acetate/hexanes gradient) afforded 0.47 g (50%) of the title compound. $^1$H NMR (CDCl$_3$, 300 MHz) δ ppm 1.66 (t, J=6.95 Hz, 3H), 4.38 (q, J=6.89 Hz, 2H), 7.03-7.10 (m, 2H), 7.17 (d, J=7.80 Hz, 1H), 7.42 (s, 1H), 8.29 (dd, J=7.97, 1.86 Hz, 1H). MS (DCI/NH$_3$) m/z 317 (M+H)$^+$.

Example 9B 2-ethoxy-N-[(2Z)-3-(2-methoxyethyl)-4-(trifluoromethyl)-1,3-thiazol-2(3H)-ylidene]benzamide The product of Example 9A (0.47 g, 1.5 mmol) and 1-bromo-2-methoxy-ethane (0.16 ml, 1.6 mmol) were processed using the method described in Example 1B. Purification by column chromatography ($SiO_2$, 30-40% ethyl acetate/hexanes gradient) afforded 0.06 g (11%) of the title compound. $^1$H NMR (DMSO-$d_6$, 300 MHz) δ ppm 1.24 (t, J=6.95 Hz, 3H), 3.02 (s, 3H), 3.36-3.63 (m, 2H), 3.86-4.02 (m, 1H), 4.13 (q, J=7.12 Hz, 2H), 4.21-4.33 (m, 1H), 7.08 (t, J=7.46 Hz, 1H), 7.17 (d, J=8.14 Hz, 1H), 7.40 (dd, J=7.46, 1.70 Hz, 1H), 7.46-7.56 (m, 1H), 8.09 (s, 1H); MS (DCI/NH$_3$) m/z 375 (M+H)$^+$. Anal. Calculated for $C_{16}H_{17}F_3N_2O_3S \cdot 0.2 H_2O$: C, 50.84; H, 4.64; N, 7.41. Found: C, 50.62; H, 4.35; N, 7.61.

Example 10

N-[(2Z)-3-(2-methoxyethyl)-5-methyl-1,3-thiazol-2 (3H)-ylidene]-2,2,3,3-tetramethylcyclopropanecarboxamide Example 10A 3-(2-Methoxyethyl)-5-methyl-3H-thiazol-2-ylideneamine hydrobromide A mixture of 5-methyl-thiazol-2-ylamine (1.0 g, 8.8 mmol) and 2-bromoethyl methyl ether (1.0 mL, 11 mmol) were heated at 85° C. for 16 hours. The mixture was cooled to ambient temperature, triturated with ethanol and the solid was collected by filtration to afford 0.90 g (40%) of the title compound. $^1$H NMR (CDCl$_3$, 300 MHz) δ ppm 2.25 (d, J=1.4 Hz, 3H), 3.36 (s, 3H), 3.72-3.81 (m, 2H), 4.36-4.43 (m, 2H), 6.61 (d, J=1.7 Hz, 1H), 9.54 (s, 1H); MS (DCI/NH$_3$) m/z 173 (M+H)$^+$.

Example 10B

N-[(2Z)-3-(2-methoxyethyl)-5-methyl-1,3-thiazol-2 (3H)-ylidene]-2,2,3,3-tetramethylcyclopropanecarboxamide The product of Example 10A (0.40 g, 1.6 mmol) and 2,2,3,3-tetramethylcyclopropanecarboxylic acid (0.25 g, 1.8 mmol) were processed using the method described in Example 2B. Purification by column chromatography ($SiO_2$, 20-40% ethyl acetate/hexanes gradient) afforded 0.30 g (63%) of the title compound. $^1$H NMR (CDCl$_3$, 300 MHz) δ ppm 1.21 (s, 6H), 1.33 (s, 6H), 1.52 (s, 1H), 2.22 (s, 3H), 3.35 (s, 3H), 3.68 (t, J=5.09 Hz, 2H), 4.24 (t, J=4.92 Hz, 2H), 6.67 (s, 1H); MS (DCI/NH$_3$) m/z 297 (M+H)$^+$. Anal. Calculated for $C_{15}H_{24}N_2O_2S$: C, 60.78; H, 8.16; N, 9.45. Found: C, 60.69; H, 8.31; N, 9.19.

Example 11

2-ethoxy-N-[(2Z)-3-(2-methoxyethyl)-5-methyl-1,3-thiazol-2(3H)-ylidene]benzamide To the product of Example 10A (0.55 g, 2.2 mmol) and 2-ethoxybenzoyl chloride (0.33 g, 1.8 mmol) in 10 mL of THF at 0° C. was added triethylamine (0.55 mL, 4.0 mmol). The solution was stirred at 65° C. for 4 hours then allowed to cool to ambient temperature and diluted with ethyl acetate. The solution was washed twice with water and then brine. The combined aqueous washings were extracted with ethyl acetate. The combined organic extracts were dried over magnesium sulfate, filtered, and concentrated under reduced pressure. Purification by column chromatography ($SiO_2$, 20-30% ethyl acetate/hexanes gradient) afforded 0.28 g (42%) of the title compound. $^1$H NMR (DMSO-$d_6$, 300 MHz) δ ppm 1.31 (t, J=7.0 Hz, 3H), 2.26 (d, J=1.4 Hz, 3H), 3.25 (s, 3H), 3.69 (t, J=5.3 Hz, 2H), 4.05 (q, J=7.1 Hz, 2H), 4.30 (t, J=5.3 Hz, 2H), 6.95 (t, J=7.5 Hz, 1H), 7.04 (d, J=7.8 Hz, 1H), 7.20 (d, J=1.4 Hz, 1H), 7.32-7.41 (m, 1H), 7.68 (dd, J=7.6, 1.9 Hz, 1H); MS (DCI/NH$_3$) m/z 321 (M+H)$^+$. Anal. Calculated for $C_{16}H_{20}N_2O_3S \cdot 0.2H_2O$: C, 59.31; H, 6.35; N, 8.65. Found: C, 59.18; H, 6.02; N, 8.29.

Example 12

3-fluoro-N-[(2Z)-3-(2-methoxyethyl)-4,5-dimethyl-1,3-thiazol-2(3H)-ylidene]-2-methylbenzamide

Example 12A 3-(2-Methoxyethyl)-4,5-dimethyl-3H-thiazol-2-ylideneamine hydrobromide A mixture of 4,5-dimethylthiazol-2-ylamine (9.0 g, 70 mmol) and 2-bromoethyl methyl ether (7.9 mL, 84 mmol) were heated at 85° C. for 12 hours. The mixture was cooled to ambient temperature and then triturated with isopropanol. The solid was collected by filtration and dried under vacuum to provide 10 g (56%) of the title compound. $^1$H NMR (DMSO-$d_6$, 300 MHz) δ ppm 2.17 (s, 3H), 2.19 (s, 3H), 3.25 (s, 3H) 3.56 (t, J=5.1 Hz, 2H) 4.16 (t, J=5.1 Hz, 2H) 9.41 (s, 1H); MS (DCI/NH$_3$) m/z 129 (M+H)$^+$.

Example 12B 3-fluoro-N-[(2Z)-3-(2-methoxyethyl)-4,5-dimethyl-1,3-thiazol-2(3H)-ylidene]-2-methylbenzamide The product of Example 12A (39 mg, 0.15 mmol) and 3-fluoro-2-methylbenzoic acid (31 mg, 0.22 mmol) were processed using the method described in Example 3 to afford the title compound. $^1$H NMR (500 MHz, DMSO-$d_6$) δ ppm 2.21-2.24 (m, 3H), 2.26-2.28 (m, 3H), 2.44-2.47 (m, 3H), 3.24 (s, 3H), 3.66-3.71 (m, 2H), 4.35 (t, 2H), 7.21-7.31 (m, 2H), 7.76 (d, 1H); MS (ESI) m/z 324 (M+H)$^+$.

Example 13

5-fluoro-N-[(2Z)-3-(2-methoxyethyl)-4,5-dimethyl-1,3-thiazol-2(3H)-ylidene]-2-methylbenzamide

Example 13A

5-Fluoro-2-methyl-benzoyl chloride

A solution of 5-fluoro-2-methylbenzoic acid (380 mg, 2.47 mmol) in thionyl chloride (5 mL) was heated to reflux for 3 hours. The solution was cooled to ambient temperature and the volatile components were removed under reduced pressure. The residue was dissolved in fresh toluene (10 mL) and concentrated under reduced pressure twice and then placed under high vacuum to afford the title compound (420 mg).

Example 13B 5-fluoro-N-[(2Z)-3-(2-methoxyethyl)-4,5-dimethyl-1,3-thiazol-2(3H)-ylidene]-2-methylbenzamide To a suspension of the product of Example 12A (549 mg, 2.05 mmol) and triethylamine (0.859 mL, 6.16 mmol) in THF (6 mL) were added a solution of the product from Example 13A in THF (2 mL). The mixture was heated at reflux for 14 hours, then cooled to ambient temperature and diluted with water and CH$_2$Cl$_2$. The phases were separated and the organic extract was washed with water and brine, dried (Na$_2$SO$_4$) and concentrated. The residue was dissolved in warm EtOAc (10 mL) and allowed to stand at room temperature for 14 hours. The crystals were isolated by filtration (EtOAc wash) to afford the title compound (450 mg, 68%). MS (ESI) m/z 324 (M+H)$^+$.

Example 14

3-methoxy-N-[(2Z)-3-(2-methoxyethyl)-4,5-dimethyl-1,3-thiazol-2(3H)-ylidene]-4-methylbenzamide The product of Example 12A (39 mg, 0.15 mmol) and 3-methoxy-4-methylbenzoic acid (37 mg, 0.22 mmol) were processed using the method described in Example 3 to afford the title compound. $^1$H NMR (500 MHz, DMSO-$d_6$) δ ppm 2.21 (d, 6H), 2.26 (s, 3H), 3.26 (s, 3H), 3.74 (t, 2H), 3.85 (s, 3H), 4.40 (t, 2H), 7.22 (d, 1H), 7.68-7.72 (m, 2H); MS (ESI) m/z 335 (M+H)$^+$.

Example 15

2-ethoxy-N-[(2Z)-3-(2-methoxyethyl)-4,5-dimethyl-1,3-thiazol-2(3H)-ylidene]benzamide The product of Example 12A (0.35 g, 1.3 mmol) and 2-ethoxybenzoic acid (0.43 g, 2.6 mmol) were processed using the methods described in Example 13. Purification by column chromatography (SiO$_2$, 30-50% ethyl acetate/hexanes gradient) afforded 0.078 g (18%) of the title compound. $^1$H NMR (CDCl$_3$, 300 MHz) δ ppm 1.46 (t, J=7.0 Hz, 3H), 2.18-2.31 (m, 6H), 3.30 (s, 3H), 3.78 (t, J=5.3 Hz, 2H), 4.17 (d, J=7.1 Hz, 2H), 4.37 (s, 2H), 6.89-7.04 (m, 2H), 7.36 (t, J=7.6 Hz, 1H), 7.96 (dd, J=7.8, 1.7 Hz, 1H); MS (DCI/NH$_3$) m/z 335 (M+H)$^+$. Anal. Calculated for C$_{17}$H$_{22}$N$_2$O$_3$S.0.1H$_2$O: C, 60.73; H, 6.65; N, 8.33. Found: C, 60.37; H, 6.42; N, 8.31.

Example 16

N-[(2Z)-3-(2-methoxyethyl)-4,5-dimethyl-1,3-thiazol-2(3H)-ylidene]-1-naphthamide The product of Example 12A (39 mg, 0.15 mmol) and 1-naphthoic acid (39 mg, 0.22 mmol) were processed using the method described in Example 3 to afford the title compound. $^1$H NMR (500 MHz, DMSO-$d_6$) δ ppm 2.25 (s, 3H), 2.28 (s, 3H), 3.26 (s, 3H), 3.72-3.77 (m, 2H), 4.37-4.43 (m, 2H), 7.52-7.60 (m, 3H), 7.95-7.99 (m, 1H), 8.02-8.06 (m, 1H), 8.28-8.31 (m, 1H), 9.03-9.07 (m, 1H); MS (ESI) m/z 341 (M+H)$^+$.

Example 17

N-[(2Z)-3-(2-methoxyethyl)-4,5-dimethyl-1,3-thiazol-2(3H)-ylidene]-2-naphthamide The product of Example 12A (39 mg, 0.15 mmol) and 2-napthoic acid (39 mg, 0.22 mmol) were processed using the method described in Example 3 to afford the title compound. $^1$H NMR (500 MHz, DMSO-$d_6$) δ ppm 2.24 (s, 3H) 2.29 (s, 3H) 3.28 (s, 3H) 3.80 (t, 2H) 4.49 (t, 2H) 7.55-7.62 (m, 2H) 7.95-7.99 (m, 2H) 8.08 (d, 1H) 8.26-8.29 (m, 1H) 8.76 (s, 1H); MS (ESI) m/z 341 (M+H)$^+$.

Example 18

5-chloro-2-methoxy-N-[(2Z)-3-(2-methoxyethyl)-4,5-dimethyl-1,3-thiazol-2(3H)-ylidene]benzamide The product of Example 12A (39 mg, 0.15 mmol) and 5-chloro-2-methoxybenzoic acid (41 mg, 0.22 mmol) were processed using the methods described in Example 13 to afford the title compound. MS (ESI) m/z 355 (M+H)$^+$.

Example 19

1-hydroxy-N-[(2Z)-3-(2-methoxyethyl)-4,5-dimethyl-1,3-thiazol-2(3H)-ylidene]-2-naphthamide The product of Example 12A (39 mg, 0.15 mmol) and 1-hydroxy-2-naphthoic acid (41 mg, 0.22 mmol) were processed using the methods described in Example 13 to afford the title compound. $^1$H NMR (500 MHz, DMSO-d$_6$) δ ppm 2.27 (s, 3H), 2.31 (s, 3H), 3.28 (s, 3H), 3.80 (t, 2H), 4.44 (t, 2H), 7.36 (d, 1H), 7.53 (t, 1H), 7.61 (t, 1H), 7.86 (d, 1H), 8.06 (d, 1H), 8.28 (d, 1H), 14.38 (s, 1H); MS (ESI) m/z 357 (M+H)$^+$.

Example 20

4-fluoro-N-[(2Z)-3-(2-methoxyethyl)-4,5-dimethyl-1,3-thiazol-2(3H)-ylidene]-1-naphthamide The product of Example 12A (39 mg, 0.15 mmol) and 4-fluoro-1-naphthoic acid (42 mg, 0.22 mmol) were processed using the method described in Example 3 to afford the title compound. $^1$H NMR (500 MHz, DMSO-d$_6$) δ ppm 2.25 (s, 3H) 2.28 (s, 3H) 3.26 (s, 3H) 3.74 (t, 2H) 4.41 (t, 2H) 7.38-7.44 (m, 1H) 7.65-7.72 (m, 2H) 8.12 (d, 1H) 8.37-8.41 (m, 1H) 9.23 (d, 1H) MS (ESI) m/z 359 (M+H)$^+$.

Example 21

2-methoxy-N-[(2Z)-3-(2-methoxyethyl)-4,5-dimethyl-1,3-thiazol-2(3H)-ylidene]-4-(methylthio)benzamide The product of Example 12A (39 mg, 0.15 mmol) and 2-methoxy-4-methylsulfanylbenzoic acid (44 mg, 0.22 mmol) were processed using the method described in Example 3 to afford the title compound. $^1$H NMR (500 MHz, DMSO-d$_6$) δ ppm 2.20 (s, 3H) 2.23 (s, 3H) 2.53 (s, 3H) 3.24 (s, 3H) 3.68 (t, 2H) 3.81 (s, 3H) 4.29 (t, 2H) 6.83-6.87 (m, 1H) 6.87-6.90 (m, 1H) 7.75 (d, 1H) MS (ESI) m/z 367 (M+H)$^+$.

Example 22

2-chloro-N-[(2Z)-3-(2-methoxyethyl)-4,5-dimethyl-1,3-thiazol-2(3H)-ylidene]-5-(methylthio)benzamide The product of Example 12A (39 mg, 0.15 mmol) and 2-chloro-5-methylsulfanylbenzoic acid (44 mg, 0.22 mmol) were processed using the method described in Example 3 to afford the title compound. $^1$H NMR (500 MHz, DMSO-d$_6$) δ ppm 2.23 (s, 3H) 2.27 (s, 3H) 3.24 (s, 3H) 3.29 (s, 3H) 3.69 (t, 2H) 4.33 (t, 2H) 7.30-7.33 (m, 1H) 7.39-7.42 (m, 1H) 7.67 (d, 1H) MS (ESI) m/z 371 (M+H)$^+$.

Example 23

N-[(2Z)-3-(2-methoxyethyl)-4,5-dimethyl-1,3-thiazol-2(3H)-ylidene]-4-(trifluoromethyl)nicotinamide The product of Example 12A (0.30 g, 1.1 mmol) and 4-trifluoromethylnicotinic acid (0.43 g, 2.2 mmol) were processed as in the methods of Example 13. Purification by column chromatography (SiO$_2$, 0-20% methanol/methylene chloride gradient) afforded 0.23 g (28%) of the title compound. $^1$H NMR (CDCl$_3$, 300 MHz) δ ppm 2.26 (s, 3H), 2.29 (s, 3H), 3.30 (s, 3H), 3.72 (t, J=5.1 Hz, 2H), 4.33 (t, J=5.1 Hz, 2H), 7.59 (d, J=5.1 Hz, 1H), 8.79 (d, J=5.1 Hz, 1H), 9.23 (s, 1H); MS (DCI/NH$_3$) m/z 360 (M+H)$^+$. Anal. Calculated for C$_{15}$H$_{16}$F$_3$N$_3$O$_2$S: C, 50.13; H, 4.49; N, 11.69. Found: C, 50.12; H, 4.33; N, 11.75.

Example 24

2-hydroxy-N-[(2Z)-3-(2-methoxyethyl)-4,5-dimethyl-1,3-thiazol-2(3H)-ylidene]benzamide The product of Example 12A (1.7 g, 9.4 mmol) and 2-hydroxybenzoic acid (1.6 g, 11 mmol) were processed using the method described in Example 2B. Purification by column chromatography (SiO$_2$, 20-40% ethyl acetate/hexanes gradient) afforded 0.91 g (32%) of the title compound. $^1$H NMR (CDCl$_3$, 300 MHz) δ ppm 2.26 (d, J=1.0 Hz, 3H), 2.29 (d, J=0.7 Hz, 3H), 3.31 (s, 3H), 3.78-3.86 (m, 2H), 4.34 (t, J=5.1 Hz, 2H), 6.89 (dt, J=7.9, 7.0, 1.0 Hz, 1H), 6.95 (dd, J=8.1, 1.0 Hz, 1H), 7.37 (dt, J=7.7, 1.9 Hz, 1H), 8.15 (dd, J=8.0, 1.9 Hz, 1H); MS (DCI/NH$_3$) m/z 307 (M+H)$^+$. Anal. Calculated for C$_{15}$H$_{18}$N$_2$O$_3$S: C, 58.80; H, 5.92; N, 9.14. Found: C, 58.60; H, 5.86; N, 9.01.

Example 25

2-(2-methoxyethoxy)-N-[(2Z)-3-(2-methoxyethyl)-4,5-dimethyl-1,3-thiazol-2(3H)-ylidene]benzamide

Example 25A

Methyl-2-(2-Methoxy-ethoxy)-benzoate

To a solution of triphenylphosphine (0.36 g, 1.40 mmol) in 10 mL of THF at 0° C. was added diisopropyl azodicarboxylate (275 µL, 1.40 mmol). The mixture was stirred for 0.5 hours and then methyl-2-hydroxybenzoate (400 mg, 1.3 mmol) and 2-methoxyethanol (110 µl, 1.40 mmol) were added. The mixture was allowed to warm to ambient temperature and stirred for 16 hours. The mixture was concentrated under reduced pressure and the residue was used without purification. MS (DCI/NH$_3$) m/z 211 (M+H)$^+$.

Example 25B 2-(2-Methoxy-ethoxy)-benzoic acid

A mixture of the product of Example 25A (0.27 g, 1.3 mmol) in 40% aqueous potassium hydroxide was stirred for 6 hours. The mixture was then diluted with water, made slightly acidic by the addition of 2 N aqueous HCl, and then extracted three times with ethyl acetate. The combined organic extracts were dried over magnesium sulfate, filtered, and concentrated under reduced pressure to afford 0.25 g of the title compound.

Example 25C 2-(2-Methoxy-ethoxy)-N-[3-(2-methoxyethyl)-4,5-dimethyl-3H-thiazol-2-ylidene]-benzamide The product of Example 25B (0.25 g, 1.3 mmol) and the product of Example 12A (0.28 g, 1.5 mmol) were processed using the methods described in Example 13. Purification by column chromatography (SiO$_2$, 30-60% ethyl acetate/hexanes gradient) afforded 35 mg (7%) of the title compound.

MS (DCI/NH$_3$) m/z 365 (M+H)$^+$. Anal. Calculated for C$_{18}$H$_{24}$N$_2$O$_4$S.0.5H$_2$O: C, 57.89; H, 6.75; N, 7.50. Found: C, 57.77; H, 6.59; N, 7.44.

Example 26

5-chloro-2-ethoxy-N-[(2Z)-3-(2-methoxyethyl)-4,5-dimethyl-1,3-thiazol-2(3H)-ylidene]benzamide The product of Example 12A (97 mg, 0.52 mmol) and 5-chloro-2-ethoxybenzoic acid (95 mg, 0.47 mmol) were processed using the methods described in Example 13 to afford the title compound. $^1$H NMR (CDCl$_3$, 400 MHz) δ ppm 1.45 (t, J=6.9 Hz, 3H), 2.24 (s, 3H), 2.28 (s, 3H), 3.31 (s, 3H), 3.78 (t, J=4.8 Hz, 2H), 4.15 (q, J=7.1 Hz, 2H), 4.45 (s, 2H), 6.90 (d, J=8.6 Hz, 1H), 7.30 (dd, J=8.9, 2.8 Hz, 1H), 7.89 (d, J=2.8 Hz, 1H); MS (DCI/NH$_3$) m/z 369 (M+H)$^+$. Anal. Calculated for C$_{17}$H$_{21}$ClN$_2$O$_3$S: C, 55.35; H, 5.74; N, 7.59. Found: C, 55.13; H, 5.59; N, 7.54.

Example 27

2-ethoxy-N-[(2Z)-3-(2-methoxyethyl)-4,5-dimethyl-1,3-thiazol-2(3H)-ylidene]nicotinamide The product of Example 12A (0.40 g, 2.2 mmol) and 2-ethoxynicotinic acid (0.40 g, 2.4 mmol) were processed using the method described in Example 2B. Purification by column chromatography (SiO$_2$, 0-30% methanol/methylene chloride gradient) afforded 0.34 g (45%) of the title compound. $^1$H NMR (CDCl$_3$, 300 MHz) δ ppm 1.45 (t, J=7.1 Hz, 3H), 2.23 (s, 3H), 2.26 (s, 3H), 3.31 (s, 3H), 3.78 (t, J=5.3 Hz, 2H), 4.37 (d, J=4.7 Hz, 2H), 4.52 (q, J=7.0 Hz, 2H), 6.91 (dd, J=7.5, 4.7 Hz, 1H), 8.21 (dd, J=4.7, 2.0 Hz, 1H), 8.32 (dd, J=7.5, 2.0 Hz, 1H); MS (DCI/NH$_3$) m/z 336 (M+H)$^+$. Anal. Calculated for C$_{16}$H$_{21}$N$_3$O$_3$S.0.2H$_2$O: C, 56.68; H, 6.36; N, 12.39. Found: C, 56.65; H, 6.32; N, 12.38.

Example 28

2-chloro-N-[(2Z)-3-(2-methoxyethyl)-4,5-dimethyl-1,3-thiazol-2(3H)-ylidene]nicotinamide A mixture of 2-chloronicotinic acid (0.42 g, 2.7 mmol) and 1,1'-carbonyldiimidazole (0.43 g, 2.7 mmol) in 3 mL of ethyl acetate was stirred at ambient temperature for 4 hours. The mixture was treated with water (3 mL) and the product of Example 12A (0.45 g, 2.4 mmol) and then heated at 65° C. for 13 hours. The mixture was cooled to ambient temperature, diluted with ethyl acetate and the layers separated. The organic phase was washed with twice with water and then brine, dried over magnesium sulfate, filtered and concentrated under reduced pressure. The residue was recrystallized from methylene chloride and afforded 0.14 g (18%) of the title compound. $^1$H NMR (CDCl$_3$, 300 MHz) δ ppm 2.26 (s, 3H), 2.28 (s, 3H), 3.30 (s, 3H), 3.76 (t, J=5.1 Hz, 2H), 4.36 (t, J=5.1 Hz, 2H), 7.28-7.32 (m, 1H), 8.28 (dd, J=7.5, 2.0 Hz, 1H), 8.42 (dd, J=4.7, 2.0 Hz, 1H); MS (DCI/NH$_3$) m/z 326 (M+H)$^+$. Anal. Calculated for C$_{14}$H$_{16}$ClN$_3$O$_2$S: C, 51.61; H, 4.95; N, 12.90. Found: C, 51.57; H, 4.76; N, 12.74.

Example 29

N-[(2Z)-3-(2-methoxyethyl)-4,5-dimethyl-1,3-thiazol-2(3H)-ylidene]-2-(trifluoromethoxy)benzamide A mixture of 2-trifluoromethoxybenzoyl chloride (0.59 g, 2.6 mmol) and the product of Example 12A were processed using the method described in Example 11 to afford the title compound. $^1$H NMR (CDCl$_3$, 300 MHz) δ ppm 2.24 (s, 3H), 2.28 (s, 3H), 3.29 (s, 3H), 3.76 (t, J=4.9 Hz, 2H), 4.45 (t, J=4.7 Hz, 2H), 7.27-7.39 (m, 2H), 7.46 (td, J=7.7, 1.9 Hz, 1H), 8.06 (dd, J=7.6, 1.9 Hz, 1H); Anal. Calculated for C$_{16}$H$_{17}$F$_3$N$_2$O$_3$S: C, 51.33; H, 4.58; N, 7.48. Found: C, 51.29; H, 4.40; N, 7.37.

Example 30

5-bromo-2-ethoxy-N-[(2Z)-3-(2-methoxyethyl)-4,5-dimethyl-1,3-thiazol-2(3H)-ylidene]benzamide The product of Example 12A (0.20 g, 1.1 mmol) and 5-bromo-2-ethoxybenzoyl chloride (0.28 g, 1.1 mmol) were processed using the method described in Example 11. Purification by column chromatography (SiO$_2$, 30-60% ethyl acetate/hexanes gradient) afforded 149 mg (38%) of the title compound. $^1$H NMR (CDCl$_3$, 300 MHz) δ ppm 1.46 (t, J=7.0 Hz, 3H), 2.25 (s, 3H), 2.29 (s, 3H), 3.31 (s, 3H), 3.79 (t, J=4.6 Hz, 2H), 4.09-4.23 (m, 2H), 4.44-4.61 (m, 2H), 6.85 (d, J=8.8 Hz, 1H), 7.42-7.48 (m, 1H), 8.02 (d, J=2.7 Hz, 1H); MS (DCI/NH$_3$) m/z 415 (M+H)$^+$. Anal. Calculated for C$_{17}$H$_{21}$BrN$_2$O$_3$S: C, 49.40; H, 5.12; N, 6.78. Found: C, 49.68; H, 5.03; N, 6.71.

Example 31

N-[(2Z)-3-(2-methoxyethyl)-4,5-dimethyl-1,3-thiazol-2(3H)-ylidene]-2-(trifluoromethyl)benzamide The product of Example 12A (0.50 g, 2.7 mmol) and 2-trifluoromethylbenzoyl chloride (0.62 g, 3.0 mmol) were processed using the method described in Example 11. Purification by column chromatography (SiO$_2$, 20-40% ethyl acetate/hexanes gradient) afforded 0.43 g (44%) of the title compound. $^1$H NMR (CDCl$_3$, 300 MHz) δ ppm 2.26 (s, 3H), 2.28 (s, 3H), 3.29 (s, 3H), 3.72 (t, J=4.7 Hz, 2H), 4.41 (t, J=4.6 Hz, 2H), 7.45-7.62 (m, 2H), 7.71 (d, J=7.1 Hz, 1H), 7.86 (d, J=7.1 Hz, 1H); MS (DCI/NH$_3$) m/z 359 (M+H)$^+$. Anal. Calculated for C$_{16}$H$_{17}$F$_3$N$_2$O$_2$S: C, 53.62; H, 4.78; N, 7.82. Found: C, 53.58; H, 4.51; N, 7.70.

Example 32

2-iodo-N-[(2Z)-3-(2-methoxyethyl)-4,5-dimethyl-1,3-thiazol-2(3H)-ylidene]benzamide The product of Example 12A (0.25 g, 1.3 mmol) and 2-iodobenzoyl chloride (0.37 g, 1.4 mmol) were processed using the method described in Example 11. Purification by preparative HPLC on a Waters Symmetry C8 column (40 mm×100 mm, 7 μm particle size) using a gradient of 20% to 95% acetonitrile:0.1% aqueous TFA over 12 minutes (15 minutes run time) at a flow rate of 70 mL/min afforded 0.12 g (23%) of the title compound. $^1$H NMR (CDCl$_3$, 300 MHz) δ ppm 2.30 (s, 3H), 2.31 (s, 3H), 3.29 (s, 3H), 3.72 (t, J=4.7 Hz, 2H), 4.41 (t, J=4.6 Hz, 2H), 7.45-7.62 (m, 2H), 7.71 (d, J=7.1 Hz, 1H), 7.86 (d, J=7.1 Hz, 1H); MS (DCI/NH$_3$) m/z 417 (M+H)$^+$.

Example 33

2-fluoro-N-[(2Z)-3-(2-methoxyethyl)-4,5-dimethyl-1,3-thiazol-2(3H)-ylidene]-5-(trifluoromethyl)benzamide The product of Example 12A (0.25 g, 1.3 mmol) and 2-fluoro-5-trifluoromethylbenzoyl chloride (0.32 g, 1.4 mmol) were processed using the method described in Example 11. Purification by preparative HPLC on a Waters Symmetry C8 column (40 mm×100 mm, 7 µm particle size) usinga gradient of 20% to 95% acetonitrile:0.1% aqueous TFA over 12 minutes (15 minutes run time) at a flow rate of 70 mL/min afforded 70 mg (14%) of the title compound. $^1$H NMR (CDCl$_3$, 300 MHz) δ ppm 2.29 (s, 3H), 2.31 (s, 3H), 3.33 (s, 3H), 3.73-3.89 (m, 2H), 4.44-4.57 (m, 2H), 7.18-7.24 (m, 1H), 7.68 (d, J=9.2 Hz, 1H), 8.38 (d, J=6.8 Hz, 1H); MS (DCI/NH$_3$) m/z 377 (M+H)$^+$. Anal. Calculated for C$_{16}$H$_{16}$F$_4$N$_2$O$_2$S.0.1H$_2$O: C, 51.06; H, 4.28; N, 7.44. Found: C, 50.54; H, 4.05; N, 7.27.

Example 34

2-bromo-5-methoxy-N-[(2Z)-3-(2-methoxyethyl)-4,5-dimethyl-1,3-thiazol-2(3H)-ylidene]benzamide The product of Example 12A (0.20 g, 1.1 mmol) and 2-bromo-5-methoxybenzoic acid (0.25 g, 1.1 mmol) were processed using the methods described in Example 13. Purification by preparative
HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 0.13 g (29%) of the title compound. $^1$H NMR (CDCl$_3$, 300 MHz) δ ppm 2.27 (s, 3H), 2.29 (s, 3H), 3.30 (s, 3H), 3.80 (t, J=4.7 Hz, 2H), 3.83 (s, 3H), 4.50-4.59 (m, 2H), 6.82 (dd, J=8.8, 3.1 Hz, 1H), 7.44 (d, J=3.1 Hz, 1H), 7.50 (d, J=8.8 Hz, 1H); MS (DCI/NH$_3$) m/z 401 (M+H)$^+$. Anal. Calculated for C$_{16}$H$_{19}$BrN$_2$O$_3$S: C, 48.13; H, 4.80; N, 7.02. Found: C, 47.88; H, 4.55; N, 6.89.

Example 35

5-fluoro-N-[(2Z)-3-(2-methoxyethyl)-4,5-dimethyl-1,3-thiazol-2(3H)-ylidene]-2-(trifluoromethyl)benzamide The product of Example 12A (0.20 g, 1.1 mmol) and 5-fluoro-2-trifluoromethylbenzoyl chloride (0.18 mL, 1.2 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 43 mg (11%) of the title compound. $^1$H NMR (CDCl$_3$, 300 MHz) δ ppm 2.27 (s, 3H), 2.29 (s, 3H), 3.30 (s, 3H), 3.65-3.76 (m, 2H), 4.37-4.48 (m, 2H), 7.13-7.20 (m, 1H), 7.56 (d, J=7.5 Hz, 1H), 7.71 (dd, J=9.2, 5.4 Hz, 1H); MS (DCI/NH$_3$) m/z 377 (M+H)$^+$. Anal. Calculated for C$_{16}$H$_{16}$F$_4$N$_2$O$_2$S.0.3H$_2$O: C, 50.34; H, 4.38; N, 7.34. Found: C, 49.95; H, 4.02; N, 7.09.

Example 36

N-[(2Z)-3-(2-methoxyethyl)-4,5-dimethyl-1,3-thiazol-2(3H)-ylidene]-2,5-bis(trifluoromethyl)benzamide The product of Example 12A (0.20 g, 1.1 mmol) and 2,5-bis-trifluoromethylbenzoyl chloride (0.33 g, 1.2 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 0.14 g (31%) of the title compound. $^1$H NMR (CDCl$_3$, 300 MHz) δ ppm 2.27 (s, 3H), 2.29 (s, 3H), 3.30 (s, 3H) 3.71 (t, J=4.9 Hz, 2H) 4.36 (t, J=5.1 Hz, 2H) 7.72-7.77 (m, 1H) 7.82-7.87 (m, 1H) 8.15 (s, 1H); MS (DCI/NH$_3$) m/z 427 (M+H)$^+$. Anal. Calculated for C$_{17}$H$_{16}$F$_6$N$_2$O$_2$S: C, 47.89; H, 3.78; N, 6.57. Found: C, 47.49; H, 3.42; N, 6.38.

Example 37

2-fluoro-N-[(2Z)-3-(2-methoxyethyl)-4,5-dimethyl-1,3-thiazol-2(3H)-ylidene]-6-(trifluoromethyl)benzamide The product of Example 12A (0.20 g, 1.1 mmol) and 2-fluoro-6-trifluoromethylbenzoyl chloride (0.17 mL, 1.2 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 0.13 g (32%) of the title compound. $^1$H NMR (CDCl$_3$, 300 MHz) δ ppm 2.27 (s, 3H), 2.28 (s, 3H), 3.27 (s, 3H), 3.69 (t, J=4.9 Hz, 2H), 4.37 (t, J=4.6 Hz, 2H), 7.28-7.33 (m, 1H), 7.38-7.50 (m, 2H); MS (DCI/NH$_3$) m/z 377 (M+H)$^+$. Anal. Calculated for C$_{16}$H$_{16}$F$_4$N$_2$O$_2$S: C, 51.06; H, 4.28; N, 7.44. Found: C, 50.98; H, 4.07; N, 7.36.

Example 38

2-chloro-6-fluoro-N-[(2Z)-3-(2-methoxyethyl)-4,5-dimethyl-1,3-thiazol-2(3H)-ylidene]benzamide The product of Example 12A (0.20 g, 1.1 mmol) and 2-chloro-6-fluorobenzoyl chloride (0.23 g, 1.2 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 66 mg (18%) of the title compound. $^1$H NMR (CDCl$_3$, 300 MHz) δ ppm 2.26 (s, 3H), 2.27 (s, 3H), 3.28 (s, 3H), 3.73 (t, J=4.9 Hz, 2H), 4.35 (t, J=4.7 Hz, 2H), 6.97-7.05 (m, 1H), 7.19-7.24 (m, 2H); MS (DCI/NH$_3$) m/z 343 (M+H)$^+$. Anal. Calculated for C$_{15}$H$_{16}$ClFN$_2$O$_2$S.0.2C$_2$HF$_3$O$_2$: C, 50.59; H, 4.47; N, 7.66. Found: C, 50.70; H, 4.34; N, 7.55.

Example 39

3-fluoro-N-[(2Z)-3-(2-methoxyethyl)-4,5-dimethyl-1,3-thiazol-2(3H)-ylidene]-2-(trifluoromethyl)benzamide The product of Example 12A (0.335 g, 1.9 mmol) and 3-fluoro-2-trifluoromethylbenzoyl chloride (0.47 g, 2.1 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 0.14 g (20%) of the title compound. $^1$H NMR (CDCl$_3$, 300 MHz) δ ppm 2.25 (d, J=0.7 Hz, 3H), 2.27 (s, 3H), 3.28 (s, 3H), 3.68 (t, J=5.1 Hz, 2H), 4.31 (t, J=5.1 Hz, 2H), 7.18 (dd, J=11.0, 8.3 Hz, 1H), 7.38-7.42 (m, 1H), 7.52 (td, J=8.0, 5.1 Hz, 1H); MS (DCI/NH$_3$) m/z 377 (M+H)$^+$.

Anal. Calculated for $C_{16}H_{16}F_4N_2O_2S$: C, 51.06; H, 4.28; N, 7.44. Found: C, 51.15; H, 3.96; N, 7.38.

Example 40

2-chloro-5-fluoro-N-[(2Z)-3-(2-methoxyethyl)-4,5-dimethyl-1,3-thiazol-2(3H)-ylidene]benzamide The product of Example 12A (0.20 g, 1.1 mmol) and 2-chloro-5-fluorobenzoyl chloride (0.23 g, 1.2 mmol) were processed using the method described in Example 11. Purification by preparative HPLC on a Waters Symmetry C8 column (40 mm×100 mm, 7 µm particle size) using a gradient of 20% to 95% acetonitrile:0.1% aqueous TFA over 12 minutes (15 minutes run time) at a flow rate of 70 mL/min afforded 17 mg (4%) of the title compound. $^1$H NMR (DMSO-$d_6$, 500 MHz) δ ppm 2.23 (s, 3H), 2.26 (s, 3H), 3.22 (s, 3H), 3.68 (t, J=5.3 Hz, 2H), 4.33 (t, J=5.3 Hz, 2H), 7.30 (td, J=8.4, 3.1 Hz, 1H), 7.52 (dd, J=8.9, 5.2 Hz, 1H), 7.64 (dd, J=9.1, 3.3 Hz, 1H); MS (DCI/NH$_3$) m/z 343 (M+H)$^+$. Anal. Calculated for $C_{15}H_{16}ClFN_2O_2S \cdot 0.1C_2HF_3O_2$: C, 51.54; H, 4.58; N, 7.91. Found: C, 51.68; H, 4.35; N, 7.95.

Example 41

N-[(2Z)-3-(2-methoxyethyl)-4,5-dimethyl-1,3-thiazol-2(3H)-ylidene]-2,2,3,3-tetramethylcyclopropanecarboxamide The product of Example 12A (1.5 g, 8.0 mmol) and 2,2,3,3-tetramethylcyclopropanecarboxylic acid (0.77 g, 5.4 mmol) were processed using the methods described in Example 13. Recrystallization from ethyl acetate afforded 0.99 g (60%) of the title compound. $^1$H NMR (DMSO-$d_6$, 300 MHz) δ ppm 1.16 (s, 6H), 1.23 (s, 6H), 1.44 (s, 1H), 2.13 (s, 3H), 2.19 (s, 3H), 3.24 (s, 3H), 3.61 (t, J=5.4 Hz, 2H), 4.21 (t, J=5.4 Hz, 2H); MS (DCI/NH$_3$) m/z 311 (M+H)$^+$. Anal. Calculated for $C_{16}H_{26}N_2O_2S$: C, 61.92; H, 8.44; N, 9.02. Found: C, 61.89; H, 8.38; N, 8.81.

Example 42

N-[(2Z)-3-(2-methoxyethyl)-4,5-dimethyl-1,3-thiazol-2(3H)-ylidene]-2-methylpentanamide The product of Example 12A (39 mg, 0.15 mmol) and 2-methylvaleric acid (26 mg, 0.22 mmol) were processed using the method described in Example 3 to afford the title compound. $^1$H NMR (DMSO-$d_6$, 300 MHz) δ ppm 0.85 (t, 3H) 1.09 (d, 3H) 1.20-1.28 (m, 2H) 1.32-1.40 (m, 1H) 1.59-1.67 (m, 1H) 2.19 (s, 3H) 2.22 (s, 3H) 2.52-2.57 (m, 1H) 3.24 (s, 3H) 3.63 (t, 2H) 4.26-4.33 (m, 2H) MS (ESI) m/z 285 (M+H)$^+$.

Example 43

N-[(2Z)-3-(2-methoxyethyl)-4,5-dimethyl-1,3-thiazol-2(3H)-ylidene]-2,2-dimethylbutanamide The product of Example 12A (39 mg, 0.15 mmol) and 2,2-dimethylbutyric acid (26 mg, 0.22 mmol) were processed using the method described in Example 3 to afford the title compound. $^1$H NMR (DMSO-$d_6$, 300 MHz) δ ppm 0.72 (t, 3H) 1.11 (s, 6H) 1.53-1.59 (m, 2H) 2.15 (s, 3H) 2.19 (s, 3H) 3.24 (s, 3H) 3.63 (t, 2H) 4.22 (t, 2H) MS (ESI) m/z 285 (M+H)$^+$.

Example 44

2-ethyl-N-[(2Z)-3-(2-methoxyethyl)-4,5-dimethyl-1,3-thiazol-2(3H)-ylidene]butanamide The product of Example 12A (39 mg, 0.15 mmol) and 2-ethylbutyric acid (26 mg, 0.22 mmol) were processed using the method described in Example 3 to afford the title compound. $^1$H NMR (DMSO-$d_6$, 300 MHz) δ ppm 0.80 (t, 6H) 1.48 (s, 2H) 1.56-1.65 (m, 2H) 2.19 (s, 3H) 2.23 (s, 3H) 2.27-2.33 (m, 1H) 3.23 (s, 3H) 3.63 (t, 2H) 4.24-4.33 (m, 2H) MS (ESI) m/z 285 (M+H)$^+$.

Example 45

N-[(2Z)-3-(2-methoxyethyl)-4,5-dimethyl-1,3-thiazol-2(3H)-ylidene]cyclohexanecarboxamide The product of Example 12A (39 mg, 0.15 mmol) and cyclohexanecarboxylic acid (28 mg, 0.22 mmol) were processed using the method described in Example 3 to afford the title compound. $^1$H NMR (DMSO-$d_6$, 300 MHz) δ ppm 1.23-1.32 (m, 2H) 1.34-1.43 (m, 2H) 1.58-1.65 (m, 1H) 1.67-1.74 (m, 2H) 1.83-1.89 (m, 2H) 2.19 (s, 3H) 2.23 (s, 3H) 2.35-2.42 (m, 1H) 3.24 (s, 3H) 3.64 (t, 2H) 4.31 (t, 3H) MS (ESI) m/z 297 (M+H)$^+$.

Example 46

N-[(2Z)-3-(2-methoxyethyl)-4,5-dimethyl-1,3-thiazol-2(3H)-ylidene]-1-methylcyclohexanecarboxamide The product of Example 12A (0.30 g, 1.1 mmol) and 1-methylcyclohexane-carboxylic acid (0.32 g, 2.2 mmol) were processed using the methods described in Example 13. Purification by column chromatography (SiO$_2$, 30-50% ethyl acetate/hexanes gradient) afforded 80 mg (23%) of the title compound. $^1$H NMR (CDCl$_3$, 300 MHz) δ ppm 1.16 (s, 3H), 1.19-1.58 (m, 10H), 2.18 (s, 3H), 2.20 (s, 3H), 3.30 (s, 3H), 3.69 (t, J=5.3 Hz, 2H), 4.19-4.31 (m, 2H); MS (DCI/NH$_3$) m/z 311 (M+H)$^+$. Anal. Calculated for $C_{16}H_{26}N_2O_2S$: C, 61.90; H, 8.44; N, 9.02. Found: C, 61.86; H, 8.80; N, 9.02.

Example 47 cis-N-[(2Z)-3-(2-Methoxyethyl)-4,5-dimethyl-1,3-thiazol-2(3H)-ylidene]-2-methylcyclohexanecarboxamide The product of Example 12A (0.30 g, 1.1 mmol) and (cis)-2-methyl-cyclohexanecarboxylic acid (0.32 g, 2.2 mmol) were processed using the methods described in Example 13. Purification by column chromatography (SiO$_2$, 30-50% ethyl acetate/hexanes gradient) afforded 0.24 g (68%) of the title compound. $^1$H NMR (CDCl$_3$, 300 MHz) δ ppm 0.85 (d, J=7.1 Hz, 3H), 1.36-1.84 (m, 8H), 2.17 (s, 3H), 2.20 (s, 3H), 2.31-2.42 (m, 1H), 2.53-2.65 (m, 1H), 3.29 (s, 3H), 3.69 (t, J=4.2 Hz, 2H), 4.17-4.29 (m, 2H); MS (DCI/NH$_3$) m/z 311 (M+H)$^+$. Anal. Calculated for $C_{16}H_{26}N_2O_2S$: C, 61.90; H, 8.44; N, 9.02. Found: C, 62.15; H, 8.70; N, 8.73.

Example 48

N-[(2Z)-3-(2-methoxyethyl)-4,5-dimethyl-1,3-thiazol-2(3H)-ylidene]-4-methylcyclohexanecarboxamide The product of Example 12A (39 mg, 0.15 mmol) and 4-methylcyclohexanecarboxylic acid (31 mg, 0.22 mmol)

were processed using the methods described in Example 13 to afford the title compound. $^1$H NMR (DMSO-$d_6$, 300 MHz) δ ppm 0.84-0.89 (m, 3H) 1.15-1.23 (m, 2H) 1.47-1.56 (m, 4H) 1.95-2.03 (m, 2H) 2.19 (s, 3H) 2.23 (s, 3H) 3.24 (s, 3H) 3.60-3.67 (m, 2H) 4.26-4.36 (m, 4H) MS (ESI) m/z 311 (M+H)$^+$.

Example 49

N-[(2Z)-3-(2-methoxyethyl)-4,5-dimethyl-1,3-thiazol-2(3H)-ylidene]cycloheptanecarboxamide The product of Example 12A (39 mg, 0.15 mmol) and cycloheptanecarboxylic acid (31 mg, 0.22 mmol) were processed using the methods described in Example 13 to afford the title compound. $^1$H NMR (DMSO-$d_6$, 300 MHz) δ ppm 1.45-1.52 (m, 4H) 1.54-1.56 (m, 2H) 1.60-1.70 (m, 4H) 1.85-1.92 (m, 2H) 2.19 (s, 3H) 2.23 (s, 3H) 2.55-2.61 (m, 1H) 3.24 (s, 3H) 3.61-3.66 (m, 2H) 4.27-4.34 (m, 2H) MS (ESI) m/z 311 (M+H)$^+$.

Example 50

(1S)—N-[(2Z)-3-(2-methoxyethyl)-4,5-dimethyl-1,3-thiazol-2(3H)-ylidene]spiro[2.5]octane-1-carboxamide The product of Example 12A and (1S)-spiro[2.5]octane-1-carboxylic acid (Bennani, Y. L., et al. US 20042043961) were processed using the methods described in Example 13 to provide the title compound. MS (DCI/NH$_3$) m/z 323 (M+H)$^+$.

Example 51

(2R)—N-[(2Z)-3-(2-methoxyethyl)-4,5-dimethyl-1,3-thiazol-2(3H)-ylidene]-2-propylhex-4-ynamide The product of Example 12A (0.30 g, 1.1 mmol) and (2R)-propyl-hex-4-ynoic acid (0.35 g, 2.2 mmol) were processed using the methods described in Example 13. Purification by column chromatography (SiO$_2$, 20-30% ethyl acetate/hexanes gradient) afforded 0.30 g (82%) of the title compound. $^1$H NMR (CDCl$_3$, 300 MHz) δ ppm 0.90 (t, J=7.5 Hz, 3H), 1.27-1.39 (m, 2H), 1.62-1.72 (m, 2H), 1.75 (t, J=2.4 Hz, 3H), 2.19 (s, 3H), 2.22 (s, 3H), 2.31-2.74 (m, 3H), 3.29 (s, 3H), 3.65-3.75 (m, 2H), 4.16-4.33 (m, 2H); MS (DCI/NH$_3$) m/z 323 (M+H)$^+$. Anal. Calculated for C$_{17}$H$_{26}$N$_2$O$_2$S: C, 63.32; H, 8.13; N, 8.69. Found: C, 63.12; H, 8.35; N, 8.51.

Example 52

(1S,3R,5S)—N-[(2Z)-3-(2-methoxyethyl)-4,5-dimethyl-1,3-thiazol-2(3H)-ylidene]-3,5-dimethylcyclohexanecarboxamide The product of Example 12A (0.30 g, 1.1 mmol) and (1S,3R,5S)-dimethylcyclohexanecarboxylic acid (0.35 g, 2.2 mmol) were processed using the methods described in Example 13. Purification by column chromatography (SiO$_2$, 20-40% ethyl acetate/hexanes gradient) afforded 0.12 g (33%) of the title compound. $^1$H NMR (CDCl$_3$, 300 MHz) δ ppm 0.91 (s, 3H), 0.92-0.94 (m, 3H), 1.01-1.13 (m, 2H), 1.61-1.69 (m, 3H), 1.90-2.00 (m, 3H), 2.19 (s, 3H), 2.21-2.25 (m, 3H), 2.26-2.30 (m, 1H), 3.30 (s, 3H), 3.71 (t, J=5.3 Hz, 2H), 4.19-4.44 (m, 2H); MS (DCI/NH$_3$) m/z 325 (M+H)$^+$. Anal. Calculated for C$_{17}$H$_{28}$N$_2$O$_2$S: C, 62.93; H, 8.70; N, 8.63. Found: C, 63.29; H, 8.91; N, 8.71.

Example 53

(9R,1R,8S)—N-[(2Z)-3-(2-methoxyethyl)-4,5-dimethyl-1,3-thiazol-2(3H)-ylidene]bicyclo[6.1.0]nonane-9-carboxamide (endo)-Bicyclo[6.1.0]nonane-9-carboxylic acid (0.38 g, 2.2 mmol, Bennani, Y. L., et al., US2004077617) and the product of Example 12A (0.30 g, 1.1 mmol) were processed using the methods described in Example 13. Purification by column chromatography (SiO$_2$, 20-35% ethyl acetate/hexanes gradient) afforded 0.27 g (72%) of the title compound. $^1$H NMR (CDCl$_3$, 300 MHz) δ ppm 1.03-1.20 (m, 1H), 1.29-1.51 (m, 6H), 1.52-1.77 (m, 6H), 2.07 (dd, J=14.1, 2.9 Hz, 2H), 2.17 (s, 3H), 2.20 (s, 3H), 3.31 (s, 3H), 3.70 (t, J=4.9 Hz, 2H), 4.20-4.30 (m, 2H); MS (DCI/NH$_3$) m/z 337 (M+H)$^+$. Anal. Calculated for C$_{18}$H$_{28}$N$_2$O$_2$S: C, 64.25; H, 8.39; N, 8.32. Found: C, 64.06; H, 8.54; N, 8.22.

Example 54

(9S,1R,8S)—N-[(2Z)-3-(2-methoxyethyl)-4,5-dimethyl-1,3-thiazol-2(3H)-ylidene]bicyclo[6.1.0]nonane-9-carboxamide (exo)-Bicyclo[6.1.0]nonane-9-carboxylic acid (0.38 g, 2.2 mmol, Bennani, Y. L., et al., US2004077617) and the product of Example 12A (0.30 g, 1.1 mmol) were processed using the methods described in Example 13. Purification by column chromatography (SiO$_2$, 20-30% ethyl acetate/hexanes gradient) afforded 70 mg (19%) of the title compound. $^1$H NMR (CDCl$_3$, 300 MHz) δ ppm 1.17-1.29 (m, 2H), 1.34-1.49 (m, 6H), 1.57-1.76 (m, 6H), 1.95-2.04 (m, 1H), 2.15 (s, 3H), 2.20 (s, 3H), 3.30 (s, 3H), 3.70 (t, J=5.3 Hz, 2H), 4.24 (t, J=5.3 Hz, 2H); MS (DCI/NH$_3$) m/z 337 (M+H)$^+$. Anal. Calculated for C$_{18}$H$_{28}$N$_2$O$_2$S: C, 64.25; H, 8.39; N, 8.32. Found: C, 64.33; H, 8.52; N, 8.23.

Example 55

(1R,6R,7R)—N-[(2Z)-3-(2-methoxyethyl)-4,5-dimethyl-1,3-thiazol-2(3H)-ylidene]-1-methylbicyclo[4.1.0]heptane-7-carboxamide The product of Example 12A (0.30 g, 1.1 mmol) and 1-methylbicyclo[4.1.0]heptane-7-carboxylic acid (0.35 g, 2.2 mmol, Bennani, Y. L., et al., US2004077617) were processed using the methods described in Example 13. Purification by column chromatography (SiO$_2$, 20-35% ethyl acetate/hexanes gradient) afforded 40 mg (11%) of the title compound. $^1$H NMR (CDCl$_3$, 300 MHz) δ ppm 1.15-1.42 (m, 7H), 1.58-1.72 (m, 3H), 1.77 (d, J=5.4 Hz, 1H), 1.84-2.04 (m, 2H), 2.15 (s, 3H), 2.19 (s, 3H), 3.28-3.33 (m, 3H), 3.69 (t, J=5.3 Hz, 2H), 4.12-4.39 (m, 2H); MS (DCI/NH$_3$) m/z 323 (M+H)$^+$. Anal. Calculated for C$_{17}$H$_{26}$N$_2$O$_2$S: C, 63.32; H, 8.13; N, 8.69. Found: C, 63.35; H, 8.3; N, 8.56.

Example 57

2,2,3,3-Tetramethylcyclopropanecarboxylic acid [4,5-dimethyl-3-(2-phenoxy-ethyl)-3H-thiazol-2-ylidene]-amide

Example 57A 4,5-Dimethyl-3-(2-phenoxy-ethyl)-3H-thiazol-2-ylideneamine hydrobromide A mixture of 4,5-dimethylthiazol-2-ylamine (1.0 g, 7.8 mmol) and (2-bromo-ethoxy)benzene (1.9 g, 9.4 mmol) were heated neat to 85° C. for 19 hours. The mixture was cooled to ambient temperature and the residue was crystallized from isopropanol. The solid was collected by filtration and dried under vacuum to afford 1.3 g (50%) of the title compound. MS (DCI/NH$_3$) m/z 249 (M+H)$^+$.

Example 57B 2,2,3,3-Tetramethylcyclopropanecarboxylic acid [4,5-dimethyl-3-(2-phenoxy-ethyl)-3H-thiazol-2-ylidene]-amide The product of Example 57A (0.40 g, 1.2 mmol) and 2,2,3,3-tetramethylcyclopropanecarboxylic acid (0.19 g, 1.3 mmol) were processed using the methods described in Example 13. Purification by column chromatography (SiO$_2$, 20-40% ethyl acetate/hexanes gradient) afforded 0.14 g (34%) of the title compound. $^1$H NMR (CDCl$_3$, 500 MHz) δ ppm 1.22 (s, 6H), 1.32-1.35 (m, 6H), 1.56 (s, 1H), 2.15 (s, 3H), 2.27 (s, 3H), 4.32 (t, J=5.5 Hz, 2H), 4.44 (t, J=5.3 Hz, 2H), 6.90 (d, J=8.1 Hz, 2H), 6.95 (t, J=7.3 Hz, 1H), 7.25-7.29 (m, 2H); MS (DCI/NH$_3$) m/z 373 (M+H)$^+$. Anal. Calculated for C$_{21}$H$_{28}$N$_2$O$_2$S: C, 67.71; H, 7.58; N, 7.52. Found: C, 67.31; H, 7.70; N, 7.30.

Example 58

N-[(2Z)-3-(2-methoxyethyl)-4,5-dimethyl-1,3-thiazol-2(3H)-ylidene]-2,2-dimethyltetrahydro-2H-pyran-4-carboxamide A mixture of the product of Example 12A (150 mg, 0.56 mmol), 2,2-dimethyl-tetrahydro-pyran-4-carboxylic acid (127 mg, 0.56 mmol), N-(3-dimethylaminopropyl)-N-ethyl-carbodiimide hydrochloride (133 mg, 0.70 mmol), 1-hydroxybenzotriazole (94.5 mg, 0.70 mmol) and triethylamine (312 µL, 2.24 mmol) in 5 mL of THF were stirred overnight at room temperature. The reaction mixture was diluted with ethyl acetate and washed with 1 M aqueous NaHCO$_3$ and brine. The organic extract was dried (Na$_2$SO$_4$), filtered and concentrated. Purification of the residue by chromatography afforded the title compound: $^1$H NMR (400 MHz, DMSO-d$_6$) δ 1.13 (s, 3H) 1.16 (s, 3H) 1.33-1.53 (m, 2H) 1.67-1.77 (m, 2H) 2.16 (s, 3H) 2.20 (s, 3H) 2.59-2.72 (m, 1H) 3.24 (s, 3H) 3.53-3.61 (m, 2H) 3.63 (t, J=5.1 Hz, 2H) 4.24 (t, J=5.4 Hz, 2H); MS (ESI+) m/z 327 (M+H)$^+$.

Example 59

2,2,3,3-tetrafluoro-N-[(2Z)-3-(2-methoxyethyl)-4,5-dimethyl-1,3-thiazol-2(3H)-ylidene]-1-methylcyclobutanecarboxamide The product of 12A (0.30 g, 1.6 mmol) and 2,2,3,3-tetrafluoro-1-methyl-cyclobutanecarborboxylic acid (0.37 g, 1.8 mmol) were processed using the methods described in Example 13. Purification by column chromatography (SiO$_2$, 30-45% ethyl acetate/hexanes gradient) afforded 0.15 g (27%) of the title compound. $^1$H NMR (CDCl$_3$, 300 MHz) δ ppm 1.59 (s, 3H), 2.23 (s, 3H), 2.25 (s, 3H), 2.29-2.43 (m, 1H), 3.29 (s, 3H), 3.31-3.46 (m, 1H), 3.70 (t, J=5.1 Hz, 2H), 4.26-4.48 (m, 2H); MS (DCI/NH$_3$) m/z 355 (M+H)$^+$. Anal. Calculated for C$_{14}$H$_{18}$F$_4$N$_2$O$_2$S: C, 47.45; H, 5.12; N, 7.91. Found: C, 47.41; H, 5.04; N, 7.81.

Example 60

1-hydroxy-N-[(2Z)-3-(2-methoxyethyl)-4,5-dimethyl-1,3-thiazol-2(3H)-ylidene]cyclohexanecarboxamide Commercially available 1-hydroxy-cyclohexanecarboxylic acid and the product of Example 12A were processed using the method described in Example 58 to afford the title compound. $^1$H NMR (300 MHz, DMSO-d$_6$) δ ppm 1.09-1.32 (m, 1H), 1.36-1.68 (m, 7H), 1.72-1.88 (m, 2H), 2.18 (s, 3H), 2.22 (s, 3H), 3.23 (s, 3H), 3.64 (t, J=5.3 Hz, 2H), 4.29 (t, J=5.4 Hz, 2H), 4.34 (s, 1H); MS (ESI$^+$) m/z 335 (M+Na)$^+$; Anal. Calculated for C$_{15}$H$_{24}$N$_2$O$_3$S: C, 57.66; H, 7.74; N, 8.97. Found: C, 57.76; H, 7.80; N, 8.88.

Example 61

1-({[(2Z)-4,5-dimethyl-1,3-thiazol-2(3H)-ylidene]amino}carbonyl)cyclohexyl propionate Propionyloxy-cyclohexanecarboxylic acid (Hartmann, Willy et al., *Synthesis* (1989), 4, 272-4) and the product from Example 12A were processed using the method described in Example 58 to afford the title compound. $^1$H NMR (300 MHz, DMSO-d$_6$) δ ppm 1.03 (t, J=7.5 Hz, 3H), 1.15-1.34 (m, 1H), 1.36-1.66 (m, 5H), 1.75 (td, J=13.1, 4.1 Hz, 2H), 2.01-2.13 (m, 2H), 2.16 (s, 3H), 2.20 (s, 3H), 2.32 (q, J=7.5 Hz, 2H), 3.22 (s, 3H), 3.58 (t, J=5.4 Hz, 2H), 4.19 (t, J=5.4 Hz, 2H); MS (ESI$^+$) m/z 369 (M+H)$^+$; Anal. Calculated for C$_{18}$H$_{28}$N$_2$O$_4$S: C, 58.67; H, 7.66; N, 7.60. Found: C, 58.46; H, 7.64; N, 7.75.

Example 62

N-[(2Z)-3-(2-methoxyethyl)-1,3-benzothiazol-2(3H)-ylidene]-2,2,3,3-tetramethylcyclopropanecarboxamide

Example 62A 2,2,3,3-Tetramethylcyclopropanecarboxylic acid benzothiazol-2-ylamide A mixture of 2,2,3,3-tetramethylcyclopropanecarboxylic acid (0.50 g, 3.5 mmol) and benzothiazol-2-ylamine (0.58 g, 3.9 mmol) were processed as in Example 9A. Purification by column chromatography (SiO$_2$, 20-40% ethyl acetate/hexanes gradient) afforded 0.26 g (27%) of the title compound. $^1$H NMR (CDCl$_3$, 300 MHz) δ ppm 1.22-1.27 (m, 6H), 1.36 (s, 6H), 1.67 (s, 1H), 2.07-2.18 (m, 2H), 3.34 (s, 3H), 3.41 (t, J=5.8 Hz, 2H), 4.39-4.53 (m, 2H), 7.20-7.26 (m, 1H), 7.37-7.42 (m, 2H), 7.60 (d, J=7.5 Hz, 1H); MS (DCI/NH$_3$) m/z 275 (M+H)$^+$.

Example 62B

2,2,3,3-Tetramethylcyclopropanecarboxylic acid [3-(2-methoxyethyl)-3H-benzothiazol-2-ylidene]-amide The product of Example 62A (0.12 g, 0.43 mmol), 2-bromoethyl methyl ether (0.44 mL, 4.7 mmol) and potassium hydroxide (56 mg, 1.0 mmol) were processed using the method described in Example 1B. Purification by column chromatography (SiO$_2$, 20-50% ethyl acetate/hexanes gradient) afforded 12 mg (8%) of the title compound. $^1$H NMR (CDCl$_3$, 300 MHz) δ ppm 1.25 (s, 6H), 1.36 (s, 6H), 1.66 (s, 1H), 3.34 (s, 3H), 3.79 (t, J=5.6 Hz, 2H), 4.53 (t, J=5.6 Hz, 2H), 7.21-7.25 (m, 1H), 7.37-7.42 (m, 2H), 7.58 (d, J=7.8 Hz, 1H); MS (DCI/NH$_3$) m/z 371 (M+H)$^+$. Anal. Calculated for C$_{18}$H$_{24}$N$_2$O$_2$S: C, 65.03; H, 7.28; N, 8.43. Found: C, 64.94; H, 7.10; N, 8.40.

Example 63

N-[(2Z)-3-(3-methoxypropyl)-1,3-benzothiazol-2(3H)-ylidene]-2,2,3,3-tetramethylcyclopropanecarboxamide

Example 63A

3-(3-Methoxy-propyl)-3H-benzothiazol-2-ylidene-amine hydrobromide

Benzothiazol-2-ylamine (1.0 g, 6.6 mmol) and 1-bromo-3-methoxy-propane (1.2 g, 7.9 mmol) were processed using the method described in Example 12A. Recrystallization from ethyl acetate provided 1.7 g (89%) of the title compound. $^1$H NMR (DMSO-d$_6$, 300 MHz) δ ppm 1.90-2.02 (m, 2H), 3.18 (s, 3H), 3.39 (t, J=5.9 Hz, 2H), 4.31 (t, J=7.1 Hz, 2H), 7.37-7.48 (m, 1H), 7.53-7.69 (m, 2H), 8.00 (dd, J=8.0, 0.8 Hz, 1H), 10.08 (s, 1H); MS (DCI/NH$_3$) m/z 233 (M+H)$^+$.

Example 63B

2,2,3,3-Tetramethylcyclopropanecarboxylic acid [3-(3-methoxy-propyl)-3H-benzothiazol-2-ylidene)-amide The product of Example 63A (0.40 g, 1.3 mmol) and 2,2,3,3-Tetramethylcyclopropanecarboxylic acid (0.19 g, 1.3 mmol) were processed using the methods described in Example 13. Purification by column chromatography (SiO$_2$, 20-30% ethyl acetate/hexanes gradient) afforded 0.32 g (70%) of the title compound. $^1$H NMR (CDCl$_3$, 300 MHz) δ ppm 1.26 (s, 6H), 1.36 (s, 6H), 1.64 (br s, 1H), 1.71 (s, 1H), 3.87 (s, 3H), 7.27-7.32 (m, 2H), 7.40-7.47 (m, 1H), 7.62 (d, J=7.5 Hz, 1H); MS (DCI/NH$_3$) m/z 289 (M+H)$^+$. Anal. Calculated for C$_{16}$H$_{20}$N$_2$O$_2$S: C, 65.86; H, 7.56; N, 8.08. Found: C, 65.54; H, 7.65; N, 7.81.

Example 64

N-[(2Z)-3-(2-methoxyethyl)-1,3-benzothiazol-2(3H)-ylidene]-3-phenylpropanamide

Example 64A

3-(2-Methoxyethyl)-3H-benzothiazol-2-ylideneamine hydrobromide

Benzothiazol-2-ylamine (10.0 g, 66.6 mmol) and 2-bromoethyl methyl ether (9.39 mL, 99.9 mmol) were combined and heated at 85° C. for 6 hours. The dark solid was triturated with EtOH then filtered and dried under vacuum to afford the title compound (15.8 g, 82%). $^1$H NMR (DMSO-d$_6$, 300 MHz) δ ppm 3.23 (s, 3H), 3.69 (t, J=5.1 Hz, 2H), 4.51 (t, J=5.1 Hz, 2H), 7.42 (dt, J=1.0, 8.0 Hz, 1H), 7.56 (m, 1H), 7.72 (d, J=8.0 Hz, 1H), 8.00 (dd, J=1.1, 8.0 Hz, 1H), 10.16 (br s, 2H); MS (DCI/NH$_3$) m/z 209 (M+H)$^+$.

Example 64B

N-[3-(2-Methoxyethyl)-3H-benzothiazol-2-ylidene]-3-phenylpropionamide

The product of Example 64A (39 mg, 0.14 mmol) and hydrocinnamic acid (26 mg, 0.17 mmol) were processed using the method described in Example 3 to afford the title compound. $^1$H NMR (500 MHz, DMSO-d$_6$) δ ppm 2.77-2.85 (m, 2H) 2.92-3.05 (m, 2H) 3.19-3.25 (m, 3H) 3.76 (t, 2H) 4.52 (t, 2H) 7.08-7.19 (m, 1H) 7.22-7.37 (m, 5H) 7.41-7.53 (m, 1H) 7.59-7.74 (m, 1H) 7.75-8.03 (m, 1H); MS(ESI) m/z 341 (M+H)$^+$.

Example 65

(2S)—N-[(2Z)-3-(2-methoxyethyl)-1,3-benzothiazol-2(3H)-ylidene]-2-phenylbutanamide The product of Example 64A (39 mg, 0.14 mmol) and (S)-(+)-2-phenylbutyric acid (26 mg, 0.17 mmol) were processed using the method described in Example 3 to afford the title compound. $^1$H NMR (500 MHz, DMSO-d$_6$) δ ppm 0.89 (t, 3H) 1.69-1.89 (m, 1H) 2.04-2.23 (m, 1H) 3.11-3.20 (m, 3H) 3.57-3.76 (m, 3H) 4.54 (t, 2H) 7.17-7.23 (m, 1H) 7.27-7.41 (m, 5H) 7.43-7.53 (m, 1H) 7.61-7.71 (m, 1H) 7.74-7.88 (m, 1H); MS(ESI) m/z 355 (M+H)$^+$.

Example 66

N-[(2Z)-3-(2-methoxyethyl)-1,3-benzothiazol-2(3H)-ylidene]-4-thien-2-ylbutanamide The product of Example 64A (39 mg, 0.14 mmol) and 4-(2-thienyl)butyric acid (29 mg, 0.17 mmol) were processed using the method described in Example 3 to afford the title compound. $^1$H NMR (500 MHz, DMSO-d$_6$) δ ppm 1.86-2.08 (m, 2H) 2.55 (t, 2H) 2.87 (t, 2H) 3.17-3.24 (m, 3H) 3.72 (t, 2H) 4.54 (t, 2H) 6.83-6.89 (m, 1H) 6.90-7.01 (m, 1H) 7.22-7.37 (m, 2H) 7.42-7.55 (m, 1H) 7.64-7.72 (m, 1H) 7.75-7.88 (m, 1H); MS(ESI) m/z 361 (M+H)$^+$.

Example 67

N$^2$-acetyl-N$^1$-[3-(2-methoxyethyl)-1,3-benzothiazol-2(3H)-ylidene]-L-leucinamide The product of Example 64A (39 mg, 0.14 mmol) and N-acetyl-L-leucine (29 mg, 0.17 mmol) were processed using the method described in Example 3 to afford the title compound. $^1$H NMR (500 MHz, DMSO-d$_6$) δ ppm 0.78-1.07 (m, 6H) 1.43-1.57 (m, 1H) 1.57-1.75 (m, 2H) 1.81-1.92 (m, 3H) 3.22-3.26 (m, 3H) 3.72 (t, 2H) 4.44-4.55 (m, 1H) 4.55-4.67 (m, 2H) 7.24-7.40 (m, 1H) 7.43-7.54 (m, 1H) 7.62-7.73 (m, 1H) 7.79-7.92 (m, 1H) 7.95-8.07 (m, 1H); MS(ESI) m/z 364 (M+H)$^+$.

Example 68

3-(2-chlorophenyl)-N-[(2Z)-3-(2-methoxyethyl)-1,3-benzothiazol-2(3H)-ylidene]propanamide The product of Example 64A (39 mg, 0.14 mmol) and 3-(2-chlorophenyl)propionic acid (31 mg, 0.17 mmol) were processed using the method described in Example 3 to afford the title compound. $^1$H NMR (500 MHz, DMSO-$d_6$) δ ppm 2.82 (t, 2H) 3.08 (t, 2H) 3.18-3.25 (m, 3H) 3.79 (t, 2H) 4.54 (t, 2H) 7.17-7.29 (m, 2H) 7.30-7.44 (m, 3H) 7.45-7.54 (m, 1H) 7.59-7.75 (m, 1H) 7.76-7.93 (m, 1H).

Example 69

N-[(2Z)-3-(2-methoxyethyl)-1,3-benzothiazol-2(3H)-ylidene]-3-methyl-2-phenylpentanamide The product of Example 64A (39 mg, 0.14 mmol) and 3-methyl-2-phenylvaleric acid (33 mg, 0.17 mmol) were processed using the method described in Example 3 to afford the title compound. $^1$H NMR (500 MHz, DMSO-$d_6$) δ ppm 0.59-0.68 (m, 2H) 0.72-0.82 (m, 2H) 0.84-0.98 (m, 3H) 1.08-1.27 (m, 1H) 2.21-2.39 (m, 1H) 3.11-3.24 (m, 3H) 3.38-3.50 (m, 1H) 3.65-3.82 (m, 2H) 4.57 (t, 2H) 7.16-7.23 (m, 1H) 7.25-7.36 (m, 3H) 7.37-7.54 (m, 3H) 7.60-7.73 (m, 1H) 7.75-7.88 (m, 1H); MS(ESI) m/z 383 (M+H)$^+$.

Example 70

4-ethyl-N-[(2Z)-3-(2-methoxyethyl)-1,3-benzothiazol-2(3H)-ylidene]benzamide

The product of Example 64A (39 mg, 0.14 mmol) and 4-ethylbenzoic acid (26 mg, 0.17 mmol) were processed using the method described in Example 3 to afford the title compound. $^1$H NMR (500 MHz, DMSO-$d_6$) δ ppm 1.22 (t, 3H) 2.66-2.72 (m, 2H) 3.25-3.26 (m, 3H) 3.85 (t, 2H) 4.75 (t, 2H) 7.31-7.42 (m, 3H) 7.47-7.60 (m, 1H) 7.68-7.79 (m, 1H) 7.85-7.94 (m, 1H) 8.12-8.23 (m, 2H); MS (ESI) m/z 341 (M+H)$^+$.

Example 71

3-fluoro-N-[(2Z)-3-(2-methoxyethyl)-1,3-benzothiazol-2(3H)-ylidene]-2-methylbenzamide The product of Example 64A (39 mg, 0.14 mmol) and 3-fluoro-2-methylbenzoic acid (26 mg, 0.17 mmol) were processed using the method described in Example 3 to afford the title compound. $^1$H NMR (500 MHz, DMSO-$d_6$) δ ppm 2.51-2.53 (m, 3H) 3.22-3.25 (m, 3H) 3.80 (t, 2H) 4.69 (t, 2H) 7.26-7.43 (m, 3H) 7.50-7.61 (m, 1H) 7.70-7.79 (m, 1H) 7.86-7.99 (m, 2H); MS (ESI) m/z 345 (M+H)$^+$.

Example 72

5-fluoro-N-[(2Z)-3-(2-methoxyethyl)-1,3-benzothiazol-2(3H)-ylidene]-2-methylbenzamide The product of Example 64A (39 mg, 0.14 mmol) and 5-fluoro-2-methylbenzoic acid (26 mg, 0.17 mmol) were processed using the method described in Example 3 to afford the title compound. $^1$H NMR (500 MHz, DMSO-$d_6$) δ ppm 2.51-2.53 (m, 3H) 3.22-3.25 (m, 3H) 3.80 (t, 2H) 4.69 (t, 2H) 7.26-7.43 (m, 3H) 7.50-7.61 (m, 1H) 7.70-7.79 (m, 1H) 7.86-7.99 (m, 2H); MS (ESI) m/z 345 (M+H)$^+$.

Example 73

3-fluoro-N-[(2Z)-3-(2-methoxyethyl)-1,3-benzothiazol-2(3H)-ylidene]-4-methylbenzamide The product of Example 64A (39 mg, 0.14 mmol) and 5-fluoro-4-methylbenzoic acid (26 mg, 0.17 mmol) were processed using the method described in Example 3 to afford the title compound. $^1$H NMR (500 MHz, DMSO-$d_6$) δ ppm 2.31-2.34 (m, 3H) 3.23-3.26 (m, 3H) 3.83 (t, 2H) 4.77 (t, 2H) 7.33-7.40 (m, 1H) 7.41-7.49 (m, 1H) 7.49-7.59 (m, 1H) 7.69-7.78 (m, 1H) 7.86-7.95 (m, 2H) 7.97-8.02 (m, 1H); MS (ESI) m/z 345 (M+H)$^+$.

Example 74

2,3-difluoro-N-[(2Z)-3-(2-methoxyethyl)-1,3-benzothiazol-2(3H)-ylidene]benzamide The product of Example 64A (39 mg, 0.14 mmol) and 2,3-difluorobenzoic acid (27 mg, 0.17 mmol) were processed using the method described in Example 3 to afford the title compound. $^1$H NMR (500 MHz, DMSO-$d_6$) δ ppm 3.20-3.26 (m, 3H) 3.82 (t, 2H) 4.72 (t, 2H) 7.28-7.36 (m, 1H) 7.37-7.43 (m, 1H) 7.51-7.59 (m, 1H) 7.59-7.67 (m, 1H) 7.73-7.81 (m, 1H) 7.90-8.00 (m, 2H); MS (ESI) m/z 349 (M+H)$^+$.

Example 75

2,5-difluoro-N-[(2Z)-3-(2-methoxyethyl)-1,3-benzothiazol-2(3H)-ylidene]benzamide The product of Example 64A (39 mg, 0.14 mmol) and 2,5-difluorobenzoic acid (27 mg, 0.17 mmol) were processed using the method described in Example 3 to afford the title compound. $^1$H NMR (500 MHz, DMSO-$d_6$) δ ppm 3.23 (s, 3H) 3.82 (t, 2H) 4.72 (t, 2H) 7.38 (s, 2H) 7.46 (s, 1H) 7.54 (s, 1H) 7.77 (s, 1H) 7.89 (s, 1H) 7.92-7.98 (m, 1H); MS (ESI) m/z 349 (M+H)$^+$.

Example 76

2-acetyl-N-[(2Z)-3-(2-methoxyethyl)-1,3-benzothiazol-2(3H)-ylidene]benzamide

The product of Example 64A (39 mg, 0.14 mmol) and 2-acetylbenzoic acid (28 mg, 0.17 mmol) were processed using the method described in Example 3 to afford the title compound. $^1$H NMR (500 MHz, DMSO-$d_6$) δ ppm 2.44-2.48 (m, 3H) 3.21-3.25 (m, 3H) 3.77 (t, 2H) 4.67 (t, 2H) 7.30-7.44 (m, 2H) 7.51-7.66 (m, 3H) 7.70-7.82 (m, 1H) 7.89-8.00 (m, 1H) 8.11-8.25 (m, 1H); MS (ESI) m/z 355 (M+H)$^+$.

Example 77

3-methoxy-N-[(2Z)-3-(2-methoxyethyl)-1,3-benzothiazol-2(3H)-ylidene]-4-methylbenzamide The product of Example 64A (39 mg, 0.14 mmol) and 3-methoxy-4-methylbenzoic acid (28 mg, 0.17 mmol) were processed using the method described in Example 3 to afford the title compound. $^1$H NMR (500 MHz, DMSO-$d_6$) δ ppm 2.21-2.26 (m, 3H) 3.25-3.28 (m, 3H) 3.85 (t, 2H) 3.88-3.90 (m, 3H) 4.76 (t, 2H) 7.26-7.31 (m, 1H) 7.32-7.39 (m, 1H)

7.47-7.57 (m, 1H) 7.71-7.78 (m, 2H) 7.79-7.84 (m, 1H) 7.88-7.93 (m, 1H); MS (ESI) m/z 357 (M+H)$^+$.

Example 78

2-ethoxy-N-[(2Z)-3-(2-methoxyethyl)-1,3-benzothiazol-2(3H)-ylidene]benzamide

The product of Example 64A (39 mg, 0.14 mmol) and 2-ethoxybenzoic acid (28 mg, 0.17 mmol) were processed using the method described in Example 3 to afford the title compound. $^1$H NMR (500 MHz, DMSO-d$_6$) δ ppm 2.21-2.26 (m, 3H) 3.25-3.28 (m, 3H) 3.85 (t, 2H) 3.88-3.90 (m, 3H) 4.76 (t, 2H) 7.26-7.31 (m, 1H) 7.32-7.39 (m, 1H) 7.47-7.57 (m, 1H) 7.71-7.78 (m, 2H) 7.79-7.84 (m, 1H) 7.88-7.93 (m, 1H); MS (ESI) m/z 357 (M+H)$^+$.

Example 79

N-[(2Z)-3-(2-methoxyethyl)-1,3-benzothiazol-2(3H)-ylidene]-4-(methylthio)benzamide The product of Example 64A (39 mg, 0.14 mmol) and 4-methylsulfanylbenzoic acid (29 mg, 0.17 mmol) were processed using the method described in Example 3 to afford the title compound. $^1$H NMR (500 MHz, DMSO-d$_6$) δ ppm 2.53-2.58 (m, 3H) 3.22-3.27 (m, 3H) 3.84 (t, 2H) 4.73 (t, 2H) 7.31-7.44 (m, 3H) 7.47-7.61 (m, 1H) 7.67-7.79 (m, 1H) 7.82-8.02 (m, 1H) 8.08-8.22 (m, 2H); MS (ESI) m/z 359 (M+H)$^+$.

Example 80

N-[(2Z)-3-(2-methoxyethyl)-1,3-benzothiazol-2(3H)-ylidene]-1-naphthamide

The product of Example 64A (39 mg, 0.14 mmol) and 1-naphthoic acid (29 mg, 0.17 mmol) were processed using the method described in Example 3 to afford the title compound. $^1$H NMR (500 MHz, DMSO-d$_6$) δ ppm 3.23-3.27 (m, 3H) 3.90 (t, 2H) 4.71 (t, 2H) 7.32-7.42 (m, 1H) 7.45-7.68 (m, 4H) 7.71-7.79 (m, 1H) 7.83-8.22 (m, 3H) 8.40-8.56 (m, 1H) 9.05-9.17 (m, 1H); MS (ESI) m/z 363 (M+H)$^+$.

Example 81

N-[(2Z)-3-(2-methoxyethyl)-1,3-benzothiazol-2(3H)-ylidene]-2-naphthamide

The product of Example 64A (39 mg, 0.14 mmol) and 2-naphthoic acid (29 mg, 0.17 mmol) were processed using the method described in Example 3 to afford the title compound. $^1$H NMR (500 MHz, DMSO-d$_6$) δ ppm 3.28-3.29 (m, 3H) 3.91 (t, 2H) 4.78 (t, 2H) 7.25-7.44 (m, 1H) 7.50-7.58 (m, 1H) 7.58-7.67 (m, 2H) 7.71-7.82 (m, 1H) 7.88-7.97 (m, 1H) 7.99-8.07 (m, 2H) 8.08-8.21 (m, 1H) 8.26-8.40 (m, 1H) 8.72-8.93 (m, 1H); MS (ESI) m/z 363 (M+H)$^+$.

Example 82

5-chloro-2-hydroxy-N-[(2Z)-3-(2-methoxyethyl)-1,3-benzothiazol-2(3H)-ylidene]benzamide The product of Example 64A (39 mg, 0.14 mmol) and 5-chloro-2-hydroxybenzoic acid (29 mg, 0.17 mmol) were processed using the method described in Example 3 to afford the title compound. $^1$H NMR (500 MHz, DMSO-d$_6$) δ ppm 3.22-3.25 (m, 3H) 3.85 (t, 2H) 4.73 (t, 2H) 6.94-7.08 (m, 2H) 7.36-7.53 (m, 2H) 7.57-7.67 (m, 1H) 7.79-7.92 (m, 1H) 7.96-8.09 (m, 2H); MS (ESI) m/z 363 (M+H)$^+$.

Example 83

5-chloro-2-methoxy-N-[(2Z)-3-(2-methoxyethyl)-1,3-benzothiazol-2(3H)-ylidene]benzamide The product of Example 64A (39 mg, 0.14 mmol) and 5-chloro-2-methoxybenzoic acid (32 mg, 0.17 mmol) were processed using the method described in Example 3 to afford the title compound. $^1$H NMR (500 MHz, DMSO-d$_6$) δ ppm 3.22-3.26 (m, 3H) 3.80 (t, 2H) 3.83-3.88 (m, 3H) 4.62 (t, 2H) 7.13-7.23 (m, 1H) 7.32-7.43 (m, 1H) 7.46-7.59 (m, 2H) 7.69-7.77 (m, 1H) 7.79-7.88 (m, 1H) 7.88-7.98 (m, 1H); MS (ESI) m/z 377 (M+H)$^+$.

Example 84

1-hydroxy-N-[(2Z)-3-(2-methoxyethyl)-1,3-benzothiazol-2(3H)-ylidene]-2-naphthamide The product of Example 64A (39 mg, 0.14 mmol) and 1-hydroxy-2-naphthoic acid (32 mg, 0.17 mmol) were processed using the method described in Example 3 to afford the title compound. $^1$H NMR (500 MHz, DMSO-d$_6$) δ ppm 3.25-3.28 (m, 3H) 3.89 (t, 2H) 4.75 (t, 2H) 7.35-7.47 (m, 2H) 7.53-7.63 (m, 2H) 7.63-7.70 (m, 1H) 7.79-7.93 (m, 2H) 7.96-8.06 (m, 1H) 8.04-8.19 (m, 1H) 8.23-8.40 (m, 1H); MS (ESI) m/z 379 (M+H)$^+$.

Example 85

4-fluoro-N-[(2Z)-3-(2-methoxyethyl)-1,3-benzothiazol-2(3H)-ylidene]-1-naphthamide The product of Example 64A (39 mg, 0.14 mmol) and 4-fluoro-1-naphthoic acid (32 mg, 0.17 mmol) were processed using the method described in Example 3 to afford the title compound. $^1$H NMR (500 MHz, DMSO-d$_6$) δ ppm 3.22-3.26 (m, 3H) 3.83 (t, 2H) 4.67 (t, 2H) 7.35-7.59 (m, 3H) 7.65-7.82 (m, 3H) 7.83-8.03 (m, 1H) 8.09-8.28 (m, 1H) 8.46-8.71 (m, 1H) 9.08-9.38 (m, 1H); MS (ESI) m/z 381 (M+H)$^+$.

Example 86

2-methoxy-N-[(2Z)-3-(2-methoxyethyl)-1,3-benzothiazol-2(3H)-ylidene]-4-(methylthio)benzamide The product of Example 64A (39 mg, 0.14 mmol) and 2-methoxy-4-methylsulfanylbenzoic acid (34 mg, 0.17 mmol) were processed using the method described in Example 3 to afford the title compound. $^1$H NMR (500 MHz, DMSO-d$_6$) δ ppm 2.53-2.61 (m, 3H) 3.21-3.25 (m, 3H) 3.79 (t, 2H) 3.82-3.89 (m, 3H) 4.58 (t, 2H) 6.73-7.05 (m, 2H) 7.25-7.38 (m, 1H) 7.47-7.61 (m, 1H) 7.60-7.78 (m, 1H) 7.80-7.91 (m, 1H) 7.89-8.09 (m, 1H); MS (ESI) m/z 389 (M+H)$^+$.

Example 87

2-chloro-N-[(2Z)-3-(2-methoxyethyl)-1,3-benzothiazol-2(3H)-ylidene]-5-(methylthio)benzamide The product of Example 64A (39 mg, 0.14 mmol) and 2-chloro-5-methylsulfanylbenzoic acid (34 mg, 0.17 mmol) were processed using the method described in Example 3 to afford the title compound. $^1$H NMR (500 MHz, DMSO-d$_6$) δ ppm 2.52-2.56 (m, 3H) 3.20-3.26 (m, 3H) 3.82 (t, 2H) 4.68 (t, 2H) 7.33-7.43 (m, 2H) 7.44-7.51 (m, 1H) 7.51-7.58 (m, 1H) 7.71-7.86 (m, 2H) 7.91-8.00 (m, 1H); MS (ESI) m/z 393 (M+H)$^+$.

Example 88

2-fluoro-N-[(2Z)-3-(2-methoxyethyl)-1,3-benzothiazol-2(3H)-ylidene]-5-(trifluoromethyl)benzamide The product of Example 64A (39 mg, 0.14 mmol) and 2-fluoro-5-trifluoromethylbenzoic acid (34 mg, 0.17 mmol) were processed using the method described in Example 3 to afford the title compound. $^1$H NMR (500 MHz, DMSO-d$_6$) δ ppm 3.23-3.26 (m, 3H) 3.84 (t, 2H) 4.67 (t, 2H) 7.30-7.47 (m, 1H) 7.52-7.64 (m, 2H) 7.72-7.89 (m, 1H) 7.91-8.07 (m, 2H) 8.34-8.58 (m, 1H); MS (ESI) m/z 399 (M+H)$^+$.

Example 89

2-benzyl-N-[(2Z)-3-(2-methoxyethyl)-1,3-benzothiazol-2(3H)-ylidene]benzamide

The product of Example 64A (39 mg, 0.14 mmol) and α-phenyl-o-toluic acid (36 mg, 0.17 mmol) were processed using the method described in Example 3 to afford the title compound. $^1$H NMR (500 MHz, DMSO-d$_6$) δ ppm 3.18-3.20 (m, 3H) 3.72 (t, 2H) 4.48-4.52 (m, 2H) 4.63 (t, 2H) 7.07-7.30 (m, 6H) 7.30-7.41 (m, 2H) 7.40-7.47 (m, 1H) 7.49-7.57 (m, 1H) 7.67-7.79 (m, 1H) 7.85-7.96 (m, 1H) 8.02-8.12 (m, 1H); MS (ESI) m/z 403 (M+H)$^+$.

Example 90

2-chloro-N-[(2Z)-3-(2-methoxyethyl)-1,3-benzothiazol-2(3H)-ylidene]-5-(trifluoromethyl)benzamide The product of Example 64A (39 mg, 0.14 mmol) and 2-chloro-5-trifluoromethylbenzoic acid (38 mg, 0.17 mmol) were processed using the method described in Example 3 to afford the title compound. $^1$H NMR (500 MHz, DMSO-d$_6$) δ ppm 3.20-3.25 (s, 3H) 3.80 (t, 2H) 4.70 (t, 2H) 7.35-7.45 (m, 1H) 7.50-7.65 (m, 1H) 7.76-7.83 (m, 2H) 7.84-7.91 (m, 1H) 7.94-8.03 (m, 1H) 8.22-8.32 (m, 1H); MS (ESI) m/z 415 (M+H)$^+$.

Example 91

N-[(2Z)-3-(2-methoxyethyl)-1,3-benzothiazol-2(3H)-ylidene]-2-(2-phenylethyl)benzamide The product of Example 64A (39 mg, 0.14 mmol) and 2-phenethylbenzoic acid (38 mg, 0.17 mmol) were processed using the method described in Example 3 to afford the title compound. $^1$H NMR (500 MHz, DMSO-d$_6$) δ ppm 2.78-2.95 (m, 2H) 3.16-3.22 (m, 3H) 3.32-3.37 (m, 2H) 3.76 (t, 2H) 4.65 (t, 2H) 6.99-7.46 (m, 9H) 7.49-7.57 (m, 1H) 7.67-7.80 (m, 1H) 7.82-7.97 (m, 1H) 7.97-8.15 (m, 1H); MS (ESI) m/z 417 (M+H)$^+$.

Example 92

2-bromo-5-methoxy-N-[(2Z)-3-(2-methoxyethyl)-1,3-benzothiazol-2(3H)-ylidene]benzamide The product of Example 64A (39 mg, 0.14 mmol) and 2-bromo-5-methoxybenzoic acid (39 mg, 0.17 mmol) were processed using the method described in Example 3 to afford the title compound. $^1$H NMR (500 MHz, DMSO-d$_6$) δ ppm 3.20-3.26 (m, 3H) 3.72-3.87 (m, 5H) 4.67 (t, 2H) 6.91-7.08 (m, 1H) 7.30-7.43 (m, 1H) 7.45-7.51 (m, 1H) 7.51-7.65 (m, 2H) 7.70-7.83 (m, 1H) 7.86-7.98 (m, 1H); MS (ESI) m/z 423 (M+H)$^+$.

Example 93

2-iodo-N-[(2Z)-3-(2-methoxyethyl)-1,3-benzothiazol-2(3H)-ylidene]benzamide

The product of Example 64A (39 mg, 0.14 mmol) and 2-iodobenzoic acid (42 mg, 0.17 mmol) were processed using the method described in Example 3 to afford the title compound. $^1$H NMR (500 MHz, DMSO-d$_6$) δ ppm 3.20-3.24 (m, 3H) 3.81 (t, 2H) 4.69 (t, 2H) 7.15-7.25 (m, 1H) 7.34-7.41 (m, 1H) 7.47-7.62 (m, 2H) 7.70-7.81 (m, 1H) 7.87-7.97 (m, 2H) 7.97-8.03 (m, 1H); MS (ESI) m/z 439 (M+H)$^+$.

Example 94

3-iodo-N-[(2Z)-3-(2-methoxyethyl)-1,3-benzothiazol-2(3H)-ylidene]benzamide

The product of Example 64A (39 mg, 0.14 mmol) and 3-iodobenzoic acid (42 mg, 0.17 mmol) were processed using the method described in Example 3 to afford the title compound. $^1$H NMR (500 MHz, DMSO-d$_6$) δ ppm 3.26-3.27 (m, 3H) 3.79 (t, 2H) 4.76 (t, 2H) 7.26-7.43 (m, 2H) 7.48-7.61 (m, 1H) 7.69-7.81 (m, 1H) 7.89-8.00 (m, 2H) 8.18-8.31 (m, 1H) 8.49-8.59 (m, 1H); MS (ESI) m/z 439 (M+H)$^+$.

Example 95

4-iodo-N-[(2Z)-3-(2-methoxyethyl)-1,3-benzothiazol-2(3H)-ylidene]benzamide

The product of Example 64A (39 mg, 0.14 mmol) and 4-iodobenzoic acid (42 mg, 0.17 mmol) were processed using the method described in Example 3 to afford the title compound. $^1$H NMR (500 MHz, DMSO-d$_6$) δ ppm 3.23-3.25 (m, 3H) 3.80 (t, 2H) 4.75 (t, 2H) 7.29-7.45 (m, 1H) 7.47-7.62 (m, 1H) 7.70-7.80 (m, 1H) 7.85-7.96 (m, 3H) 7.98-8.05 (m, 2H); MS (ESI) m/z 439 (M+H)$^+$.

Example 96

N-[(2Z)-3-(2-methoxyethyl)-1,3-benzothiazol-2(3H)-ylidene]-3-methylbutanamide

The product of Example 64A (39 mg, 0.14 mmol) and isovaleric acid (17 mg, 0.17 mmol) were processed using the method described in Example 3 to afford the title compound. $^1$H NMR (500 MHz, DMSO-d$_6$) δ ppm 0.93 (d, 6H) 2.10-2.23 (m, 1H) 2.37 (d, 2H) 3.21-3.25 (m, 3H) 3.74 (t, 2H) 4.57 (t, 2H) 7.31 (m, 1H) 7.48 (m, 1H) 7.66 (m, 1H) 7.83 (m, 1H); MS (ESI) m/z 393 (M+H)$^+$.

Example 97

N-[(2Z)-3-(2-methoxyethyl)-1,3-benzothiazol-2(3H)-ylidene]-2-methylpentanamide

The product of Example 64A (39 mg, 0.14 mmol) and 2-methylvaleric acid (20 mg, 0.17 mmol) were processed using the method described in Example 3 to afford the title compound. ¹H NMR (500 MHz, DMSO-d₆) δ ppm 0.88 (t, 3H) 1.14 (d, 3H) 1.21-1.34 (m, 2H) 1.35-1.47 (m, 1H) 1.63-1.76 (m, 1H) 2.53-2.62 (m, 1H) 3.22-3.26 (m, 3H) 3.75 (t, 2H) 4.58 (t, 2H) 7.31 (m, 1H) 7.49 (m, 1H) 7.66 (m, 1H) 7.83 (m, 1H); MS (ESI) m/z 307 (M+H)⁺.

Example 98

N-[(2Z)-3-(2-methoxyethyl)-1,3-benzothiazol-2(3H)-ylidene]-3-methylpentanamide

The product of Example 64A (39 mg, 0.14 mmol) and 3-methylvaleric acid (20 mg, 0.17 mmol) were processed using the method described in Example 3 to afford the title compound. ¹H NMR (500 MHz, DMSO-d₆) δ ppm 0.82-0.96 (m, 6H) 1.14-1.27 (m, 1H) 1.31-1.44 (m, 1H) 1.87-2.05 (m, 1H) 2.25-2.34 (m, 1H) 2.43-2.49 (m, 1H) 3.21-3.26 (m, 3H) 3.74 (t, 2H) 4.56 (t, 2H) 7.31 (m, 1H) 7.48 (m, 1H) 7.66 (m, 1H) 7.84 (m, 1H); MS (ESI) m/z 307 (M+H)⁺.

Example 99

N-[(2Z)-3-(2-methoxyethyl)-1,3-benzothiazol-2(3H)-ylidene]-4-methylpentanamide

The product of Example 64A (39 mg, 0.14 mmol) and 4-methylvaleric acid (20 mg, 0.17 mmol) were processed using the method described in Example 3 to afford the title compound. ¹H NMR (500 MHz, DMSO-d₆) δ ppm 0.90 (d, 6H) 1.49-1.61 (m, 3H) 2.45-2.50 (m, 2H) 3.21-3.26 (m, 3H) 3.74 (t, 2H) 4.58 (t, 2H) 7.32 (m, 1H) 7.48 (m, 1H) 7.66 (m, 1H) 7.84 (m, 1H); MS (ESI) m/z 307 (M+H)⁺.

Example 100

N-[(2Z)-3-(2-methoxyethyl)-1,3-benzothiazol-2(3H)-ylidene]-2,2-dimethylbutanamide The product of Example 64A (39 mg, 0.14 mmol) and 2,2-dimethylbutyric acid (20 mg, 0.17 mmol) were processed using the method described in Example 3 to afford the title compound. ¹H NMR (500 MHz, DMSO-d₆) δ ppm 0.76 (t, 3H) 1.11-1.23 (m, 6H) 1.62 (t, 2H) 3.18-3.27 (m, 3H) 3.75 (t, 2H) 4.58 (t, 2H) 7.26 (m, 1H) 7.46 (m, 1H) 7.66 (m, 1H) 7.84 (m, 1H); MS (ESI) m/z 307 (M+H)⁺.

Example 101

N-[(2Z)-3-(2-methoxyethyl)-1,3-benzothiazol-2(3H)-ylidene]-3,3-dimethylbutanamide The product of Example 64A (0.64 g, 2.2 mmol) and 3,3-dimethyl-butyric acid (0.26 mL, 2.0 mmol) were processed using the method described in Example 3. Purification by column chromatography (SiO₂, 20-30% ethyl acetate/hexanes gradient) afforded 0.44 g (71%) of the title compound. ¹H NMR (DMSO-d₆, 300 MHz) δ ppm 1.03 (s, 9H), 2.36-2.43 (s, 2H), 3.22 (s, 3H), 3.73 (t, J=5.4 Hz, 2H), 4.56 (t, J=5.4 Hz, 2H), 7.32 (m, 1H), 7.49 (td, J=7.8, 1.0 Hz, 1H), 7.67 (d, J=8.5 Hz, 1H), 7.84 (dd, J=8.0, 1.2 Hz, 1H); MS (DCI/NH₃) m/z 331 (M+H)⁺. Anal. Calculated for C₁₆H₂₂N₂O₂S: C, 62.71; H, 7.24; N, 9.14. Found: C, 62.79; H, 7.41; N, 9.06.

Example 102

2-ethyl-N-[(2Z)-3-(2-methoxyethyl)-1,3-benzothiazol-2(3H)-ylidene]butanamide

The product of Example 64A (39 mg, 0.14 mmol) and 2-ethylbutyric acid (20 mg, 0.17 mmol) were processed using the method described in Example 3 to afford the title compound. ¹H NMR (500 MHz, DMSO-d₆) δ ppm 0.84 (t, 6H) 1.47-1.59 (m, 2H) 1.60-1.72 (m, 2H) 2.27-2.39 (m, 1H) 3.21-3.26 (m, 3H) 3.75 (t, 2H) 4.58 (t, 2H) 7.32 (m, 1H) 7.48 (m, 1H) 7.65 (m, 1H) 7.82 (m, 1H); MS (ESI) m/z 307 (M+H)⁺.

Example 103

N-[(2Z)-3-(2-methoxyethyl)-1,3-benzothiazol-2(3H)-ylidene]cyclopentanecarboxamide The product of Example 64A (39 mg, 0.14 mmol) and cyclopentanecarboxylic acid (19 mg, 0.17 mmol) were processed using the method described in Example 3 to afford the title compound. ¹H NMR (500 MHz, DMSO-d₆) δ ppm 1.50-1.62 (m, 2H) 1.62-1.72 (m, 2H) 1.76-1.95 (m, 4H) 2.85-2.98 (m, 1H) 3.22-3.26 (m, 3H) 3.74 (t, 2H) 4.56 (m, 2H) 7.31 (m, 1H) 7.48 (m, 1H) 7.66 (m, 1H) 7.83 (d, 1H); MS (ESI) m/z 305 (M+H)⁺.

Example 104

2-cyclopentyl-N-[(2Z)-3-(2-methoxyethyl)-1,3-benzothiazol-2(3H)-ylidene]acetamide The product of Example 64A (39 mg, 0.14 mmol) and cyclopentylacetic acid (22 mg, 0.17 mmol) were processed using the method described in Example 3 to afford the title compound. ¹H NMR (500 MHz, DMSO-d₆) δ ppm 1.09-1.25 (m, 2H) 1.44-1.56 (m, 2H) 1.55-1.65 (m, 2H) 1.70-1.84 (m, 2H) 2.20-2.38 (m, 1H) 2.46-2.49 (m, 1H) 3.21-3.24 (m, 3H) 3.24-3.29 (m, 1H) 3.74 (t, 2H) 4.56 (t, 2H) 7.32 (m, 1H) 7.49 (m, 1H) 7.65 (m, 1H) 7.83 (m, 1H); MS (ESI) m/z 319 (M+H)⁺.

Example 105

N-[(2Z)-3-(2-methoxyethyl)-1,3-benzothiazol-2(3H)-ylidene]cyclohexanecarboxamide The product of Example 64A (39 mg, 0.14 mmol) and cyclohexanecarboxylic acid (22 mg, 0.17 mmol) were processed using the method described in Example 3 to afford the title compound. ¹H NMR (500 MHz, DMSO-d₆) δ ppm 1.13-1.36 (m, 3H) 1.37-1.52 (m, 2H) 1.58-1.67 (m, 1H) 1.66-1.80 (m, 2H) 1.84-2.00 (m, 2H) 2.32-2.46 (m, 1H) 3.22-3.25 (m, 3H) 3.75 (t, 2H) 4.56 (t, 2H) 7.30 (m, 1H) 7.48 (m, 1H) 7.65 (m, 1H) 7.83 (m, 1H); MS (ESI) m/z 319 (M+H)⁺.

Example 106

N-[(2Z)-3-(2-methoxyethyl)-1,3-benzothiazol-2(3H)-ylidene]-1-methylcyclohexanecarboxamide The product of Example 64A (39 mg, 0.14 mmol) and 1-methylcyclohexane-carboxylic acid (24 mg, 0.17 mmol) were processed using the method described in Example 3 to afford the title compound. ¹H NMR (500 MHz, DMSO-d₆) δ ppm 1.10-1.16 (m, 3H) 1.21-1.39 (m, 5H) 1.40-1.48 (m, 1H) 1.48-1.58 (m, 2H) 2.06-2.21 (m, 2H) 3.21-3.25 (m, 3H) 3.76 (t, 2H) 4.58 (t, 2H) 7.30 (m, 1H) 7.47 (m, 1H) 7.65 (m, 1H) 7.82 (m, 1H); MS (ESI) m/z 333 (M+H)⁺.

Example 107 cis-N-[(2Z)-3-(2-methoxyethyl)-1,3-benzothiazol-2(3H)-ylidene]-2-methylcyclohexanecarboxamide The product of Example 64A (39 mg, 0.14 mmol) and (cis)-2-methylcyclohexanecarboxylic acid (24 mg, 0.17 mmol) were processed using the method described in Example 3 to afford the title compound. $^1$H NMR (500 MHz, DMSO-d$_6$) δ ppm 0.79 (d, 3H) 1.14-1.87 (m, 8H) 2.24-2.39 (m, 1H) 2.56-2.65 (m, 1H) 3.19-3.23 (m, 3H) 3.72 (t, 2H) 4.54 (t, 2H) 7.22-7.37 (m, 1H) 7.42-7.50 (m, 1H) 7.58-7.67 (m, 1H) 7.75-7.88 (m, 1H); MS (ESI) m/z 333 (M+H)$^+$.

Example 108

N-[(2Z)-3-(2-methoxyethyl)-1,3-benzothiazol-2(3H)-ylidene]-4-methylcyclohexanecarboxamide The product of Example 64A (39 mg, 0.14 mmol) and 4-methylcyclohexanecarboxylic acid (24 mg, 0.17 mmol) were processed using the method described in Example 3 to afford the title compound. $^1$H NMR (500 MHz, DMSO-d$_6$) δ ppm 0.78-0.91 (m, 3H) 0.94-1.26 (m, 2H) 1.38-1.63 (m, 4H) 1.69-2.01 (m, 1H) 2.04-2.40 (m, 2H) 2.53-2.65 (m, 1H) 3.19-3.26 (m, 3H) 3.76 (t, 2H) 4.56 (t, 2H) 7.23-7.37 (m, 1H) 7.40-7.56 (m, 1H) 7.59-7.70 (m, 1H) 7.76-7.86 (m, 1H); MS (ESI) m/z 333 (M+H)$^+$.

Example 109

2-cyclohexyl-N-[(2Z)-3-(2-methoxyethyl)-1,3-benzothiazol-2(3H)-ylidene]acetamide The product of Example 64A (39 mg, 0.14 mmol) and cyclohexylacetic acid (24 mg, 0.17 mmol) were processed using the method described in Example 3 to afford the title compound. $^1$H NMR (500 MHz, DMSO-d$_6$) δ ppm 0.86-1.05 (m, 2H) 1.06-1.35 (m, 3H) 1.54-1.75 (m, 5H) 1.77-1.92 (m, 1H) 2.36 (d, 2H) 3.19-3.25 (m, 3H) 3.75 (t, 2H) 4.54 (t, 2H) 7.25-7.36 (m, 1H) 7.43-7.56 (m, 1H) 7.60-7.69 (m, 1H) 7.77-7.88 (m, 1H); MS (ESI) m/z 333 (M+H)$^+$.

Example 110

N-[(2Z)-3-(2-methoxyethyl)-1,3-benzothiazol-2(3H)-ylidene]cyclohepanecarboxamide The product of Example 64A (39 mg, 0.14 mmol) and cycloheptylacetic acid (24 mg, 0.17 mmol) were processed using the method described in Example 3 to afford the title compound. $^1$H NMR (500 MHz, DMSO-d$_6$) δ ppm 1.42-1.62 (m, 6H) 1.63-1.82 (m, 4H) 1.85-2.05 (m, 2H) 2.54-2.72 (m, 1H) 3.18-3.26 (m, 3H) 3.72 (t, 2H) 4.55 (t, 2H) 7.23-7.40 (m, 1H) 7.42-7.55 (m, 1H) 7.60-7.72 (m, 1H) 7.75-7.88 (m, 1H); MS (ESI) m/z 333 (M+H)$^+$.

Example 111

N-[(2Z)-3-(2-methoxyethyl)-1,3-benzothiazol-2(3H)-ylidene]-5-methylthiophene-2-carboxamide The product of Example 64A (39 mg, 0.14 mmol) and 5-methylthiophene-2-carboxylic acid (28 mg, 0.20 mmol) were processed using the method described in Example 3 to afford the title compound. $^1$H NMR (500 MHz, DMSO-d$_6$) δ ppm 2.51 (s, 3H) 3.26 (s, 3H) 3.82 (t, 2H) 4.66 (t, 2H) 6.91-6.93 (m, 1H) 7.35 (t, 1H) 7.51 (t, 1H) 7.68-7.72 (m, 2H) 7.89 (d, 1H); MS (ESI) m/z 332 (M+H)$^+$.

Example 112

N-[(2Z)-6-fluoro-3-(2-methoxyethyl)-1,3-benzothiazol-2(3H)-ylidene]-2,2,3,3-tetramethylcyclopropanecarboxamide Example 112A N-(6-fluoro-1,3-benzothiazol-2-yl)-2,2,3,3-tetramethylcyclopropanecarboxamide A mixture of 6-fluoro-benzothiazol-2-ylamine (1 equiv), N-(3-dimethylaminopropyl)-N-ethylcarbodiimide hydrochloride (1 equiv), 1-hydroxybenzotriazole, triethylamine (1.1 equiv), and 2,2,3,3-tetramethylcyclopropanecarboxylic acid (0.8 equiv) in 3:1 THF/Et$_3$N (1 M) and were stirred overnight at room temperature. The mixture was diluted with EtOAc, washed with 1 M aqueous NaHCO$_3$, dried (Na$_2$SO$_4$), filtered, and concentrated. Puried by silica gel chromatography afforded the title compound. MS (ESI$^+$) m/z 293 (M+H)$^+$.

Example 112B 2,2,3,3-Tetramethylcyclopropanecarboxylic acid [6-fluoro-3-(2-methoxyethyl)-3H-benzothiazol-2-ylidene]-amide To a solution of the product of Example 112A (1 equiv) in 1:1 DMF/THF (0.1 M) was added sodium hydride (60% dispersion in mineral oil, 1.2 equiv) and 2-bromoethyl methyl ether (1.2 equiv).

The mixture was stirred at 65° C. overnight then cooled to ambient temperature and diluted with EtOAc. The mixture was washed with 1 M saturated aqueous NaHCO$_3$, dried (Na$_2$SO$_4$), filtered and concentrated. Purifed by silica gel chromatography afforded the title compound. $^1$H NMR (300 MHz, DMSO-d$_6$) δ ppm 1.20 (s, 6H), 1.27 (s, 6H), 1.60 (s, 1H), 3.23 (s, 3H), 3.72 (t, J=5.4 Hz, 2H), 4.54 (t, J=5.4 Hz, 2H), 7.33 (td, J=9.0, 2.7 Hz, 1H), 7.65 (dd, J=8.8, 4.4 Hz, 1H), 7.75 (dd, J=8.1, 2.7 Hz, 1H); MS (ESI$^+$) m/z 351 (M+H)$^+$.

Example 113

2-cyclopentyl-N-[(2Z)-6-fluoro-3-(2-methoxyethyl)-1,3-benzothiazol-2(3H)-ylidene]acetamide Example 113A 6-Fluoro-3-(2-methoxyethyl)-3H-benzothiazol-2-ylideneamine hydrobromide Commercially available 6-fluoro-benzothiazol-2-ylamine and 2-bromoethyl methyl ether were processed as described for example 12A to afford the title compound. MS (ESI$^+$) m/z 227 (M+H)$^+$.

Example 113B 2-cyclopentyl-N-[(2Z)-6-fluoro-3-(2-methoxyethyl)-1,3-benzothiazol-2(3H)-ylidene]acetamide The product from Example 113A and cyclopentylacetyl chloride were processed as described for example 11 to afford the title compound. $^1$H NMR (400 MHz, DMSO-d$_6$) δ ppm 4.54 (d, J=5.76 Hz, 2H) 7.65 (t, J=8.14 Hz, 1H) 7.75 (dd, J=8.81, 2.71 Hz, 1H) 7.83 (dd, J=7.97, 1.53 Hz, 2H) 7.97 (dd, J=8.14, 1.36 Hz, 1H) 8.41 (d, J=3.05 Hz, 1H); MS (ESI$^+$) m/z 337 (M+H)⁺; Anal. Calculated for $C_{17}H_{21}FN_2O_2S$: C, 60.69; H, 6.29; N, 8.33. Found: C, 60.67; H, 6.41; N, 8.25.

Example 114

N-[(2Z)-6-fluoro-3-(2-methoxyethyl)-1,3-benzothiazol-2(3H)-ylidene]-2-tetrahydro-2H-pyran-4-ylacetamide Example 114A (Tetrahydro-pyran-4-yl)-acetyl chloride Commercially available (tetrahydro-pyran-4-yl)-acetic acid and oxalyl chloride were processed as described for example 9A to afford the title compound. MS (DCI/NH₃) m/z 159 (M+H)⁺.

Example 114B

N-[6-Fluoro-3-(2-methoxyethyl)-3H-benzothiazol-2-ylidene]-2-(tetrahydro-pyran-4-yl)-acetamide The product from Example 113A and the product from Example 114A were processed as described for Example 11 to afford the title compound. ¹H NMR (300 MHz, DMSO-d₆) δ ppm 1.13-1.35 (m, 2H), 1.52-1.66 (m, 2H), 2.05 (d, 1H), 2.43 (d, J=7.1 Hz, 2H), 3.22 (s, 3H), 3.72 (t, J=5.3 Hz, 2H), 3.78-3.88 (m, 4H), 4.56 (t, J=5.3 Hz, 2H), 7.36 (td, J=9.0, 2.7 Hz, 1H), 7.70 (dd, J=9.0, 4.2 Hz, 1H), 7.81 (dd, J=8.5, 2.7 Hz, 1H); MS (ESI⁺) m/z 353 (M+H)⁺; Anal. Calculated for $C_{17}H_{21}FN_2O_3S$: C, 57.94; H, 6.01; N, 7.95. Found: C, 58.03; H, 5.97; N, 7.87.

Example 115

5-fluoro-N-[(2Z)-6-fluoro-3-(2-methoxyethyl)-1,3-benzothiazol-2(3H)-ylidene]-2-methoxybenzamide The product from Example 113A and 5-fluoro-2-methoxybenzoic acid were processed using the methods described in Example 13 to afford the title compound. ¹H NMR (300 MHz, DMSO-d₆) δ ppm 3.23 (s, 3H), 3.72-3.87 (m, 5H), 4.65 (t, J=5.4 Hz, 2H), 7.15 (dd, J=9.3, 4.2 Hz, 1H), 7.37 (dd, 2H), 7.64 (dd, J=9.2, 3.4 Hz, 1H), 7.77 (dd, J=9.2, 4.4 Hz, 1H), 7.88 (dd, J=8.1, 2.7 Hz, 1H); MS (ESI⁺) m/z 379 (M+H)⁺; Anal. Calculated for $C_{18}H_{16}F_2N_2O_3S$: C, 57.13; H, 4.26; N, 7.40. Found: C, 57.05; H, 4.08; N, 7.35.

Example 116

5-chloro-N-[(2Z)-6-fluoro-3-(2-methoxyethyl)-1,3-benzothiazol-2(3H)-ylidene]-2-methoxybenzamide The product from Example 113A and 5-chloro-2-methoxybenzoic acid were processed using the methods described in Example 13 to afford the title compound. ¹H NMR (300 MHz, DMSO-d₆) δ ppm 3.24 (s, 3H), 3.79 (t, J=5.3 Hz, 2H), 3.83 (s, 3H), 4.65 (t, J=5.3 Hz, 2H), 7.17 (d, J=9.2 Hz, 1H), 7.41 (td, J=9.1, 2.5 Hz, 1H), 7.52 (dd, J=8.8, 2.7 Hz, 1H), 7.78 (dd, J=9.0, 4.2 Hz, 1H), 7.83 (d, J=2.7 Hz, 1H), 7.89 (dd, J=8.5, 2.7 Hz, 1H); MS (ESI⁺) m/z 395 (M+H)⁺; Anal. Calculated for $C_{18}H_{16}ClFN_2O_3S$: C, 54.75; H, 4.08; N, 7.09. Found: C, 54.29; H, 3.94; N, 6.99.

Example 117

N-[(2Z)-3-(2-methoxyethyl)-4-methyl-5-morpholin-4-yl-1,3-thiazol-2(3H)-ylidene]-2,2,3,3-tetramethylcyclopropanecarboxamide Example 117A 2,2,3,3-Tetramethylcyclopropanecarboxylic acid (4-methyl-5-morpholin-4-yl-thiazol-2-yl)-amide A mixture of 4-methyl-5-morpholin-4-yl-thiazol-2-ylamine (prepared using the method described in Christopher et al., *Bioorganic and Medicinal Chemistry Letters* 2004, 14(22), 5521-5525), N-(3-dimethylaminopropyl)-N-ethylcarbodiimide hydrochloride, 1-hydroxybenzotriazole, triethylamine, and 2,2,3,3-tetramethylcyclopropanecarboxylic acid were processed using the method described in Example 58 to afford the title compound. MS (ESI) m/z 324 (M+H)⁺.

Example 117B 2,2,3,3-Tetramethylcyclopropanecarboxylic acid [3-(2-methoxyethyl)-4-methyl-5-morpholin-4-yl-3H-thiazol-2-ylidene]-amide The product from Example 117A was processed using the method described in Example 112B to afford the title compound. ¹H NMR (300 MHz, DMSO-d₆) δ ppm 1.16 (s, 6H), 1.23 (s, 6H), 1.44 (s, 1H), 2.22 (s, 3H), 2.70-2.79 (m, 4H), 3.24 (s, 3H), 3.62 (t, J=5.3 Hz, 2H), 3.66-3.72 (m, 4H), 4.21 (t, J=5.4 Hz, 2H); MS (ESI) m/z 382 (M+H)⁺.

Example 118

N-[(2Z)-5-chloro-3-(2-methoxyethyl)-4-methyl-1,3-thiazol-2(3H)-ylidene]-2,2,3,3-tetramethylcyclopropanecarboxamide Example 118A 2,2,3,3-Tetramethylcyclopropanecarboxylic acid (5-chloro-4-methyl-thiazol-2-yl)-amide A mixture of 2-amino-5-chloro-2-methyl-thiazole (Matsuo, Masaaki; Ogino, Takashi; Igari, Norihiro; Seno, Hachiro; Shimomura, Kyoichi., EP 412404) (150 mg, 0.81 mmol), 2,2,3,3-tetramethylcyclopropanecarbonyl chloride (143 mg, 0.89 mmol), 4-dimethylaminopyridine (50.0 mg, 0.41 mmol) and triethylamine (226 μL, 1.62 mmol) in 15 mL of THF heated at reflux for 48 hours. The mixture was cooled to ambient temperature, diluted with EtOAc and washed with brine. The layers were separated and the aqueous phase was extracted with EtOAc (2×). The combined organic extracts were dried (Na₂SO₄), filtered, and concentrated. Purification by silica gel chromatography afforded the title compound: MS (LC/MS) m/z 273 (M+H)⁺.

Example 118B 2,2,3,3-Tetramethylcyclopropanecarboxylic acid (5-chloro-3-(2-methoxy-ethy)-4-methyl-3H-thiazol-2-ylidene]-amide A mixture of the product of Example 118A (150 mg, 0.55 mmol), NaH (60% dispersion in mineral oil, 29.0 mg, 0.71 mmol) and 2-bromoethyl methyl ether (57 μl, 0.61 mmol) in 20 mL of 2:1 THF/DMF was processed according to the method desribed in Example 112B to provide the title compound: ¹H NMR (300 MHz, DMSO-d₆) δ 1.18 (s, 6H) 1.23 (s, 6H) 1.50 (s, 1H) 2.29 (s, 3H) 3.25 (s, 3H) 3.63 (t, J=5.3 Hz, 2H) 4.27 (t, J=5.3 Hz, 2H); MS (DCI/NH₃) m/z 331 (M+H)⁺.

Example 119

N-[(2Z)-3-(2-methoxy ethyl)-5-methyl-4-phenyl-1,3-thiazol-2(3H)-ylidene]-2,2,3,3-tetramethylcyclopropane carboxamide Example 119A 3-(2-methoxyethyl)-5-methyl-4-phenyl-3H-thiazol-2-ylideneamine hydrobromide A mixture of 5-methyl-4-phenyl-thiazol-2-ylamine (300 mg, 1.58 mmol) and 2-bromoethyl methyl ether (300 μl, 3.20 mmol) was processed using the method described in Example 12A to provide the title compound.

Example 119B 2,2,3,3-Tetramethylcyclopropanecarboxylic acid [3-(2-methoxy-ethy)-5-methyl-4-phenyl-3H-thiazol-2-ylidene]-amide A mixture of the product of Example 119A (290 mg, 1.16 mmol), 2,2,3,3-tetramethylcyclopropanecarboxylic acid (182 mg, 1.28 mmol), HATU (661 mg, 1.74 mmol) and triethylamine (0.97 mL, 6.96 mmol) in 15 mL of DMF was processed according to the method of Example 2B to provide the title compound: ¹H NMR (400 MHz, DMSO-d₆) δ 1.17 (s, 6H) 1.26 (s, 6H) 1.49 (s, 1H) 2.01 (s, 3H) 3.02 (s, 3H) 3.43 (t, J=6.0 Hz, 2H) 4.06 (t, J=5.8 Hz, 2H) 7.39-7.43 (m, 2H) 7.50-7.57 (m, 3H); MS (DCI/NH₃) m/z 373 (M+H)⁺.

Example 120

N-[(2Z)-4-(4-chlorophenyl)-3-(2-methoxyethyl)-5-methyl-1,3-thiazol-2(3H)-ylidene]-2,2,3,3-tetramethylcyclopropanecarboxamide Example 120A 4-(4-chlorophenyl)-3-(2-methoxyethyl)-5-methyl-3H-thiazol-2-ylideneamine hydrobromide A mixture of 4-(4-chlorophenyl)-5-methyl-thiazol-2-ylamine (420 mg, 1.87 mmol) and 2-bromoethyl methyl ether (600 μL, 6.40 mmol) was processed according to the method of Example 12A to provide the title compound: MS (DCI/NH₃) m/z 283 (M+H)⁺.

Example 120B 2,2,3,3-Tetramethylcyclopropanecarboxylic acid [4-(4-chlorophenyl)-3-(2-methoxy-ethy)-5-methyl-3H-thiazol-2-ylidene]-amide A mixture of the product of Example 120A (156 mg, 0.55 mmol), 2,2,3,3-tetramethylcyclopropanecarboxylic acid (94 mg, 0.66 mmol), HATU (479 mg, 0.83 mmol) and triethylamine (0.46 mL, 3.30 mmol) in 10 mL of DMF was processed according to the method of Example 2B to provide the title compound: ¹H NMR (500 MHz, DMSO-d₆) δ 1.17 (s, 6H) 1.25 (s, 6H) 1.49 (s, 1H) 2.00 (s, 3H) 3.04 (s, 3H) 3.44 (t, J=5.8 Hz, 2H) 4.04 (t, J=5.8 Hz, 2H) 7.45 (d, J=8.2 Hz, 2H) 7.60 (d, J=8.5 Hz, 2H); MS (DCI/NH₃) m/z 407 (M+H)⁺.

Example 121

N-[(2Z)-3-(2-methoxyethyl)-4,5,6,7-tetrahydro-1,3-benzothiazol-2(3H)-ylidene]-2,2,3,3-tetramethylcyclopropanecarboxamide Example 121A 3-(2-methoxy-ethy)-4,5,6,7-tetrahydro-3H-benzothiazol-2-ylideneamine hydrobromide A mixture of 4,5,6,7-tetrahydro-benzothiazol-2-ylamine (300 mg, 1.94 mmol) and 2-bromoethyl methyl ether (600 μL, 6.40 mmol) was processed according to the method of Example 12A to provide the title compound as crude product: MS (LC/MS) m/z 213 (M+H)⁺.

Example 121B 2,2,3,3-Tetramethylcyclopropanecarboxylic acid [3-(2-methoxy-ethy)-4,5,6,7-tetrahydro-3H-benzothiazol-2-ylidene]-amide A mixture of the product of Example 121A (156 mg, 0.55 mmol), 2,2,3,3-tetramethylcyclopropanecarboxylic acid (94 mg, 0.66 mmol), HATU (479 mg, 0.83 mmol) and triethylamine (0.46 mL, 3.30 mmol) in 10 mL of DMF was processed according to the method of Example 2B to provide the title compound: ¹H NMR (500 MHz, DMSO-d₆) δ 1.16 (s, 6H) 1.23 (s, 6H) 1.45 (s, 1H) 1.69-1.82 (m, 4H) 2.43-2.48 (m, 2H) 2.54-2.59 (m, 2H) 3.24 (s, 3H) 3.60 (t, J=5.3 Hz, 2H) 4.16 (t, J=5.3 Hz, 2H); MS (DCI/NH₃) m/z 337 (M+H)⁺.

Example 122

N-[(2Z)-3-(2-methoxyethyl)-3,4,5,6-tetrahydro-2H-cyclopenta[d][1,3]thiazol-2-ylidene]-2,2,3,3-tetramethylcyclopropanecarboxamide Example 122A 2,2,3,3-Tetramethylcyclopropanecarboxylic acid (5,6-dihydro-4H-cyclopentathiazol-2-yl)-amide A mixture of 5,6-dihydro-4H-cyclopentathiazole-2-ylamine (177 mg, 1.26 mmol), 2,2,3,3-tetramethylcyclopropanecarboxylic acid (244 mg, 1.52 mmol), 4-dimethylaminopyridine (50.0 mg, 0.41 mmol) and triethylamine (351 μL, 2.52 mmol) in 20 mL of THF was processed according to the method of Example 118A to provide the title compound: MS (DCI/NH₃) m/z 265 (M+H)⁺.

Example 122B 2,2,3,3-Tetramethylcyclopropanecarboxylic acid [3-(2-methoxy-ethy)-(3,4,5,6-tetrahydro-cyclopentathiazol-2-ylidene)-amide A mixture of the product of Example 122A (254 mg, 0.95 mmol), NaH (60% dispersion in mineral oil, 50.0 mg, 1.22 mmol) and 2-bromoethyl methyl ether (100 μL, 1.07 mmol) in 30 mL of THF/DMF (2/1) was processed according to the method of Example 112B to provide the title compound: $^1$H NMR (500 MHz, DMSO-$d_6$) δ 1.16 (s, 6H) 1.23 (s, 6H) 1.45 (s, 1H) 2.31-2.38 (m, 2H) 2.72 (t, J=7.0 Hz, 2H) 2.78 (t, J=7.2 Hz, 2H) 3.24 (s, 3H) 3.61 (t, J=5.3 Hz, 2H) 4.15 (t, J=5.2 Hz, 2H); MS (DCI/NH$_3$) m/z 323 (M+H)$^+$.

Example 123

N-[(7Z)-8-(2-methoxyethyl)-5,8-dihydro[1,3]thiazolo[4,5-e][2,1,3]benzoxadiazol-7(4H)-ylidene]-2,2,3,3-tetramethylcyclopropanecarboxamide

Example 123A 4,5-dihydro[1,3]thiazolo[4,5-e][2,1,3]benzoxadiazol-7-amine hydrobromide To a solution of commercially available 5-bromo-6,7-dihydro-5H-benzo[1,2,5]oxadiazol-4-one (1.1 g, 5.1 mmol) in absolute ethanol (60 mL) was added thiourea. The reaction mixture was stirred at 60° C. for overnight and then concentrated. The residue was triturated in hexanes to afford 1.3 g (90%) of the title compound. MS (ESI$^+$) m/z 195 (M+H)$^+$.

Example 123B

N-4,5-dihydro[1,3]thiazolo[4,5-e][2,1,3]benzoxadiazol-7-yl-2,2,3,3-tetramethylcyclopropanecarboxamide Example 123A and 2,2,3,3-tetramethylcyclopropanecarbonyl chloride were processed as described for example 118A to afford the title compound. MS (ESI$^+$) m/z 319 (M+H)$^+$.

Example 123C

N-[(7Z)-8-(2-methoxyethyl)-5,8-dihydro[1,3]thiazolo[4,5-e][2,1,3]benzoxadiazol-7(4H)-ylidene]-2,2,3,3-tetramethylcyclopropanecarboxamide The product of Example 123B (1 equiv), potassium tert-butoxide (1.1 equiv) and 2-bromoethyl methyl ether (1 equiv) were combined in DMF (0.1 M) and heated in a SmithSynthesizer™ microwave at 250° C. for 15 minutes. The mixture was diluted with EtOAc and washed with 1 M aqueous NaHCO$_3$. The phases were separated and the aqueous phase was extracted with EtOAc (3×). The combined organic extracts were dried over Na$_2$SO$_4$, filtered, and concentrated. Purification by silica gel chromatography afforded the title compound and the product of Example 124. $^1$H NMR (400 MHz, DMSO-$d_6$) δ ppm 1.20 (s, 6H), 1.26 (s, 6H), 1.57 (s, 1H), 3.10 (t, J=7.5 Hz, 2H), 3.23 (s, 3H), 3.26 (t, J=7.4 Hz, 2H), 3.71 (t, J=5.8 Hz, 2H), 4.67 (t, J=5.8 Hz, 2H); MS (ESI$^+$) m/z 377 (M+H)$^+$.

Example 124

N-[(7Z)-8-(2-methoxyethyl)[1,3]thiazolo[4,5-e][2,1,3]benzoxadiazol-7(8H)-ylidene]-2,2,3,3-tetramethylcyclopropanecarboxamide The title compound was obtained as byproduct during the synthesis of example 123C. $^1$H NMR (400 MHz, DMSO-$d_6$) δ ppm 1.23 (s, 6H), 1.29 (s, 6H), 1.67 (s, 1H), 3.24 (s, 3H), 3.85 (t, J=5.7 Hz, 2H), 4.96 (t, J=5.5 Hz, 2H), 7.94 (d, J=9.2 Hz, 1H), 8.06 (d, J=9.5 Hz, 1H); MS (ESI$^+$) m/z 374 (M+H)$^+$.

Example 125

2-Ethoxy-N-[(2Z)-3-(2-methoxyethyl)-4,6-dihydro-furo[3,4-d]thiazol-2(3H)-ylidene]-benzamide

Example 125A

4-Bromo-dihydrofuran-3-one

The title compound was prepared according to the procedure using the method described in Baker, Tracy J, Wiemer, David F, *J. Org. Chem.*, 1998, 63(8), 2613-2618 and was used immediately using the method described in Example 125B.

Example 125B

3a-Ethoxy-3a,4,6,6a-tetrahydrofuro[3,4-d]thiazol-2-ylamine

The product of Example 125A and thiourea were processed using the method described in Example 123A to afford the title compound. MS (ESI$^+$) m/z 189 (M+H)$^+$.

Example 125C

3a-Ethoxy-3-(2-methoxy-ethyl)-tetrahydro-furo[3,4-d]thiazol-2-ylideneamine

The product from Example 125B and 1-bromo-2-methoxyethane were processed using the method described in Example 12A to afford the title compound. MS (ESI$^+$) m/z 247 (M+H)$^+$.

Example 125D

2-Ethoxy-N-[3a-ethoxy-3-(2-methoxy-ethyl)-tetrahydro-furo[3,4-d]thiazol-2-ylidene]-benzamide The product from Example 125B and 2-ethoxybenzoyl chloride were processed as described for example 118A to afford the title compound. MS (ESI$^+$) m/z 395 (M+H)$^+$.

Example 125E

2-Ethoxy-N-[3-(2-methoxyethyl)-4,6-dihydro-3H-furo[3,4-d]thiazol-2-ylidene]-benzamide To a solution of the product from Example 125D (15 mg, 0.04 mmol) in toluene (10 mL) was added p-toluenesulfonic acid monohydrate (2 mg). The mixture was refluxed for 3 hours and then cooled to room temperature, diluted with ethyl acetate, washed with 1M NaHCO$_3$, dried (Na$_2$SO$_4$), filtered and concentrated. Purification by preparative HPLC on a waters Symmetry C8 column (40 mm×100 mm, 7 μm particle size) using a gradient of 10% to 100% acetonitrile: ammonium acetate (10 mM) over 15 min at a flow rate of 70 mL/min afforded the title compound. $^1$H NMR (300 MHz, DMSO-$d_6$) δ ppm 1.33 (t, J=7.0 Hz, 3H), 3.24 (s, 3H), 3.65 (t, J=4.9 Hz, 2H), 4.07 (q, J=6.8 Hz, 2H), 4.25 (t, J=5.1 Hz, 2H), 4.96 (s, 4H), 6.92-7.01 (m, 1H), 7.07 (d, J=8.1 Hz, 1H), 7.36-7.44 (m, 1H), 7.74 (dd, J=7.5, 1.7 Hz, 1H); MS (ESI$^+$) m/z 349 (M+H)$^+$.

Example 126

3-chloro-2-fluoro-N-[(2Z)-3-(2-methoxyethyl)-4,5-dimethyl-1,3-thiazol-2(3H)-ylidene]-6-(trifluoromethyl)benzamide

Example 126A 3-(2-Methoxy-ethyl)-4,5-dimethyl-3H-thiazol-2-ylideneamine

The product of Example 12A was purified via flash column chromatography ($SiO_2$, 9:1:0.1 $CH_2Cl_2$:$CH_3OH$:$NH_4OH$) to provide the title compuond. $^1$H NMR (300 MHz, $CDCl_3$) δ ppm 2.18 (s, 6H) 3.32 (s, 3H) 3.78 (t, J=5.10 Hz, 2H) 4.39 (t, J=4.70 Hz, 2H) 9.45 (s, 2H); MS (DCI/$NH_3$) m/z 187 (M+H)$^+$.

Example 126B

3-Chloro-2-fluoro-N-[3-(2-methoxy-ethyl)-4,5-dimethyl-3H-thiazol-2-ylidene]-6-trifluoromethylbenzamide To a suspension of the product of Example 126A (0.20 g, 1.1 mmol) in 35 mL THF was added $Et_3N$ (0.37 mL, 2.7 mmol). This mixture was cooled to 0° C. and 3-chloro-2-fluoro-6-trifluoromethyl benzoyl chloride (Alfa Aesar, 0.35 g, 13 mmol) in 5 mL THF was added dropwise via syringe. The mixture was allowed to stir at ambient temperature for 1 hour, then was warmed to reflux and was allowed to stir for 8 hours. The mixture was then cooled to ambient temperature and filtered. The filtrate was concentrated under reduced pressure and purified via flash column chromatography ($SiO_2$, 7:3 hexanes:EtOAc) to provide the title compound (0.20 g, 0.50 mmol, 46% yield). $^1$H NMR (300 MHz, $CDCl_3$) δ ppm 2.27 (s, 3H), 2.28 (s, 3H), 3.27 (s, 3H), 3.68 (t, J=4.7 Hz, 2H), 4.28-4.37 (m, 2H), 7.37-7.43 (m, 1H), 7.44-7.52 (m, 1H); MS (DCI/$NH_3$) m/z 411 (M+H)$^+$; Anal. calculated for $C_{16}H_{15}ClF_4N_2O_2S$: C, 46.78; H, 3.68; N, 6.82. Found: C, 46.83; H, 3.30; N, 6.65.

Example 127

5-chloro-N-[(2Z)-3-(2-methoxyethyl)-4,5-dimethyl-1,3-thiazol-2(3H)-ylidene]-2-(trifluoromethyl)benzamide To the product of Example 126A (0.20 g, 1.1 mmol) in 35 mL THF at 0° C. was added $Et_3N$ (0.37 mL, 2.7 mmol) followed by 5-chloro-2-trifluoromethyl-benzoyl chloride (Matrix, 0.26 g, 1.3 mmol) in 5 mL THF dropwise via syringe. This mixture was stirred at ambient temperature for 1 hour then was warmed to reflux and allowed to stir for 8 hours. The mixture was then cooled to ambient temperature and filtered. The filtrate was concentrated under reduced pressure and the residue was purified via flash column chromatography ($SiO_2$, 4:1 hexanes:EtOAc) to provide the title compound (0.23 g, 0.57 mmol, 53% yield). $^1$H NMR (300 MHz, $CDCl_3$) δ ppm 2.26 (s, 3H), 2.28 (s, 3H), 3.30 (s, 3H), 3.71 (t, J=4.9 Hz, 2H), 4.36 (t, J=4.9 Hz, 2H), 7.45 (ddd, J=8.5, 2.0, 0.7 Hz, 1H), 7.64 (d, J=8.5 Hz, 1H), 7.84 (d, J=2.0 Hz, 1H); MS (DCI/$NH_3$) m/z 393 (M+H)$^+$; Anal. calculated for $C_{16}H_{16}ClF_3N_2O_2S$: C, 48.92; H, 4.11; N, 7.13. Found: C, 48.66; H, 3.81; N, 7.01.

Example 128

2,3-dichloro-N-[(2Z)-3-(2-methoxyethyl)-4,5-dimethyl-1,3-thiazol-2(3H)-ylidene]benzamide To the product of Example 126A (0.20 g, 1.1 mmol) in 35 mL THF was added $Et_3N$ (0.37 mL, 2.7 mmol). This mixture was cooled to 0° C. and 2,3-dichlorobenzoyl chloride (Lancaster, 0.27 g, 1.3 mmol) in 5 mL THF was added dropwise via syringe. This mixture stirred at ambient temperature for 1 hour then was warmed to reflux and was allowed to stir for 3 hours. The mixture was cooled to ambient temperature and was quenched with 5 mL saturated, aqueous $NH_4Cl$ and diluted with 10 mL EtOAc. The layers were separated and the aqueous layer was extracted 2×5 mL EtOAc and 2×5 mL $CH_2Cl_2$. The combined organics were washed 1×5 mL saturated, aqueous NaCl then were dried over anhydrous $Na_2SO_4$, filtered, concentrated under reduced pressure and purified via flash column chromatography ($SiO_2$, 10% $CH_3OH$:EtOAc). The material was still impure so it was purified again via flash column chromatography ($SiO_2$, 1:1 hexanes:EtOAc) to provide the title compound (0.105 g, 0.29 mmol, 27% yield). $^1$H NMR (300 MHz, $CDCl_3$) δ ppm 2.26 (s, 3H), 2.28 (s, 3H), 3.30 (s, 3H), 3.76 (t, J=4.6 Hz, 2H), 4.40 (t, J=4.2 Hz, 2H), 7.23 (t, J=7.7 Hz, 1H), 7.49 (dd, J=8.0, 1.5 Hz, 1H), 7.72 (dd, J=7.6, 1.5 Hz, 1H); MS (DCI/$NH_3$) m/z 359 (M+H)$^+$; Anal. calculated for $C_{15}H_{16}Cl_2N_2O_2S$: C, 50.15; H, 4.49; N, 7.80. Found: C, 50.17; H, 4.26; N, 7.69.

Example 129

N-[(2Z)-3-(2-methoxyethyl)-4,5-dimethyl-1,3-thiazol-2(3H)-ylidene]-2,2-dimethyl-2,3-dihydro-1-benzofuran-7-carboxamide To a solution of the product of Example 126A (0.20 g, 1.1 mmol) and $Et_3N$ (0.45 mL, 3.2 mmol) in 30 mL THF was added 2,2-dimethyl-2,3-dihydro-1-benzofuran-7-carbonyl chloride (Acros, 0.34 g, 1.6 mmol). This mixture was warmed to reflux and allowed to stir for 2 hours. The mixture was then cooled to ambient temperature and concentrated under reduced pressure. The residue was diluted with 10 mL EtOAc and washed with 5 mL saturated, aqueous $NH_4Cl$. The layers were separated and the aqueous layer was extracted 2×5 mL EtOAc. The combined organics were dried over anhydrous $Na_2SO_4$, filtered, concentrated under reduced pressure and purified via flash column chromatography ($SiO_2$, 4:1 hexanes:EtOAc) to provide the title compound (0.21 mmol, 0.57 mmol, 53% yield). $^1$H NMR (300 MHz, $CDCl_3$) δ ppm 1.55 (s, 6H), 2.22 (s, 3H), 2.27 (s, 3H), 3.02 (s, 2H), 3.31 (s, 3H), 3.77-3.89 (m, 2H), 4.33-4.50 (m, 2H), 6.85 (t, J=7.5 Hz, 1H), 7.22 (d, J=7.5 Hz, 1H), 8.00 (d, J=8.1 Hz, 1H); MS (DCI/$NH_3$) m/z 361 (M+H); Anal. calculated for $C_{19}H_{24}N_2O_3S$: C, 63.31; H, 6.71; N, 7.77. Found: C, 63.19; H, 6.50; N, 7.66.

Example 130

2,2-difluoro-N-[(2Z)-3-(2-methoxyethyl)-4,5-dimethyl-1,3-thiazol-2(3H)-ylidene]-1,3-benzodioxole-4-carboxamide To the product of Example 126A (0.20 g, 1.1 mmol) in 30 mL THF was added $Et_3N$ (0.37 mL, 2.7 mmol) followed by 2,2-difluoro-1,3-benzodioxole-4-carbonyl chloride (Lancaster, 0.29 g, 1.3 mmol). This mixture was stirred at ambient temperature for 17 hours then was warmed to reflux and allowed to stir for an additional 4 hours. The mixture was then cooled to ambient temperature and additional 2,2-difluoro-1,3-benzodioxole-4-carbonyl chloride (73 mg, 0.33 mmol) and Et$_3$N (0.37 mL, 2.7 mmol) were added. This mixture was warmed to reflux at which temperature it stirred for 2 hours. The mixture was then cooled to ambient temperature, diluted with 10 mL EtOAc and washed with 5 mL saturated, aqueous NH$_4$Cl. The layers were separated and the aqueous layer was extracted 2×5 mL EtOAc. The combined organics were dried over anhydrous Na$_2$SO$_4$, filtered, concentrated under reduced pressure and purified via flash column chromatography (SiO$_2$, 50% hexanes:EtOAc) to afford the title compound (0.22 g, 0.59 mmol, 55% yield). $^1$H NMR (300 MHz, CDCl$_3$) δ ppm 2.26 (s, 3H), 2.28 (s, 3H), 3.32 (s, 3H), 3.83 (t, J=5.1 Hz, 2H), 4.44 (t, J=5.1 Hz, 2H), 7.12 (d, J=4.4 Hz, 1H), 7.14 (s, 1H), 7.89 (dd, J=6.6, 2.9 Hz, 1H); MS (DCI/NH$_3$) m/z 371 (M+H)$^+$; Anal. calculated for C$_{16}$H$_{16}$F$_2$N$_2$O$_4$S: C, 51.89; H, 4.35; N, 7.56. Found: C, 52.27; H, 4.24; N, 7.53.

Example 131

5-bromo-N-[(2Z)-3-(2-methoxyethyl)-4,5-dimethyl-1,3-thiazol-2(3H)-ylidene]-2,3-dihydro-1-benzofuran-7-carboxamide The product of Example 126A (0.20 g, 1.1 mmol), Et$_3$N (0.45 mL, 3.2 mmol) and 5-bromo-2,3-dihydrobenzo[b]-furan-7-carbonyl chloride (Maybridge, 0.42 g, 1.6 mmol) in 35 mL THF were processed as in Example 126B. The resulting crude material was purified via flash column chromatography (SiO$_2$, 7:3 hexanes:EtOAc) to afford the title compound (0.16 g, 0.39 mmol, 36% yield). $^1$H NMR (300 MHz, CDCl$_3$) δ ppm 2.24 (s, 3H), 2.28 (s, 3H), 3.23 (t, J=8.5 Hz, 2H), 3.33 (s, 3H), 3.78-3.87 (m, 2H), 4.45-4.56 (m, 2H), 4.70-4.81 (m, 2H), 7.35-7.39 (m, 1H), 8.09 (d, J=2.0 Hz, 1H); MS (DCI/NH$_3$) m/z 411, 413 (M+H)$^+$; Anal. calculated for C$_{17}$H$_{19}$BrN$_2$O$_3$S.0.3H$_2$O: C, 49.00; H, 4.74; N, 6.72. Found: C, 48.91; H, 4.36; N, 6.57.

Example 132

2-bromo-N-[(2Z)-3-(2-methoxyethyl)-4,5-dimethyl-1,3-thiazol-2(3H)-ylidene]benzamide To a solution of the product of Example 126A (0.20 g, 1.1 mmol) and Et$_3$N (0.3 mL, 2.2 mmol) in 25 mL THF was added 2-bromobenzoyl chloride (Aldrich, 0.18 mL, 1.4 mmol). This mixture stirred at ambient temperature for 20 hours then was concentrated under reduced pressure and the residue was diluted with 10 mL EtOAc and washed with 5 mL NH$_4$Cl. The layers were separated and the aqueous layer was extracted (2×5 mL EtOAc). The combined organic layers were dried over anhydrous Na$_2$SO$_4$, filtered, concentrated under reduced pressure and purified via recrystallization with 50% hexanes/EtOAc to afford 0.18 g of the title compound (0.49 mmol, 46% yield). $^1$H NMR (300 MHz, CDCl$_3$) δ ppm 2.26 (s, 3H), 2.28 (s, 3H), 3.30 (s, 3H), 3.78 (t, J=5.1 Hz, 2H), 4.42 (t, J=5.1 Hz, 2H), 7.22 (dt, J=7.8, 1.7 Hz, 1H), 7.34 (dt, J=7.5, 1.4 Hz, 1H), 7.63 (dd, J=8.0, 1.2 Hz, 1H), 7.90 (dd, J=7.6, 1.9 Hz, 1H); MS (DCI/NH$_3$) m/z 369, 371 (M+H)$^+$; Anal. calculated for C$_{15}$H$_{17}$BrN$_2$O$_2$S: C, 48.79; H, 4.64; N, 7.59. Found: C, 48.84; H, 4.49; N, 7.40.

Example 133

2,6-dichloro-N-[(2Z)-3-(2-methoxyethyl)-4,5-dimethyl-1,3-thiazol-2(3H)-ylidene]benzamide The product of Example 126A (0.20 g, 1.1 mmol), Et$_3$N (0.3 mL, 2.2 mmol) and 2,6-dichlorobenzoyl chloride (Aldrich, 0.2 mL, 1.4 mmol) in 25 mL THF were processed as in Example 132 to afford the title compound (0.12 g, 0.32 mmol, 30% yield). $^1$H NMR (300 MHz, CDCl$_3$) δ ppm 2.28 (s, 6H), 3.27 (s, 3H), 3.74 (t, J=4.6 Hz, 2H), 4.34-4.44 (m, 2H), 7.19 (dd, J=8.8, 6.8 Hz, 1H), 7.28-7.34 (m, 2H); MS (DCI/NH$_3$) m/z 359 (M+H)$^+$.

Example 134

N-[(2Z)-3-(2-methoxyethyl)-4,5-dimethyl-1,3-thiazol-2(3H)-ylidene]quinoline-4-carboxamide Example 134A Quinoline-4-carbonyl chloride A solution of 4-quinolinecarboxylic acid (Aldrich, 0.25 g, 1.4 mmol) in 5 mL of thionyl chloride was warmed to reflux and allowed to stir for 1 hour. The mixture was then cooled to ambient temperature and concentrated under reduced pressure. This material was dissolved in 10 mL toluene and concentrated under reduced pressure (3×) to afford the title compound.

Example 134B

N-[(2Z)-3-(2-methoxyethyl)-4,5-dimethyl-1,3-thiazol-2(3H)-ylidene]quinoline-4-carboxamide To a suspension of the product of Example 126A (0.20 g, 1.1 mmol) in 25 mL THF was added Et$_3$N (0.3 mL, 2.2 mmol) followed by the freshly prepared quinoline-4-carbonyl chloride. This mixture was warmed to reflux and allowed to stir for 18 hours. The material was then concentrated under reduced pressure and 10 mL EtOAc, 5 mL H$_2$O and 5 mL NH$_4$OH were added. The layers were separated and the aqueous layer was extracted 2×5 mL EtOAc. The combined organic layers were dried over anhydrous Na$_2$SO$_4$, filtered, concentrated under reduced pressure and purified via flash column chromatography (SiO$_2$, 5% CH$_3$OH in EtOAc) to afford the title compound (0.12 g, 0.35 mmol, 33% yield). $^1$H NMR (300 MHz, CD$_3$OD) δ ppm 2.32 (d, J=0.7 Hz, 3H), 2.35 (d, J=0.7 Hz, 3H), 3.31 (s, 3H), 3.78 (t, J=5.3 Hz, 2H), 4.48 (t, J=5.1 Hz, 2H), 7.65 (ddd, J=8.5, 7.0, 1.2 Hz, 1H), 7.80 (ddd, J=8.4, 6.9, 1.4 Hz, 1H), 8.00 (d, J=4.4 Hz, 1H), 8.06-8.11 (m, 1H), 8.84 (ddd, J=8.5, 1.4, 0.7 Hz, 1H), 8.93 (d, J=4.4 Hz, 1H); MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 63.23; H, 5.46; N, 12.10.

Example 135

N-[(2Z)-3-(2-methoxyethyl)-4,5-dimethyl-1,3-thiazol-2(3H)-ylidene]quinoline-5-carboxamide The quinoline-5-carboxylic acid (Lancaster, 0.25 g, 1.4 mmol) was converted to quinoline-5-carbonyl chloride using 5 mL SOCl$_2$ using the method described in Example 134A. The product of Example 126A (0.20 g, 1.1 mmol), Et$_3$N (0.3 mL, 2.2 mmol) and quinoline-5-carbonyl chloride in 30 mL THF were processed as in Example 134B to afford the title compound (0.18 g, 0.53 mmol, 49% yield). $^1$H NMR (300 MHz, CD$_3$OD) δ ppm 2.30 (d, J=0.7 Hz, 3H), 2.34 (s, 3H), 3.31 (s, 3H), 3.80 (t, J=5.1 Hz, 2H), 4.49 (t, J=5.3 Hz, 2H), 7.60 (dd, J=8.6, 4.2 Hz, 1H), 7.83 (dd, J=8.5, 7.1 Hz, 1H), 8.15 (dt, J=8.5, 1.0 Hz, 1H), 8.40 (dd, J=7.3, 1.2 Hz, 1H), 8.87 (dd, J=4.1, 1.7 Hz, 1H), 9.55 (ddd, J=8.8, 1.7, 0.7 Hz, 1H);

MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 63.44; H, 5.05; N, 12.10.

Example 136

N-[(2Z)-3-(2-methoxyethyl)-4,5-dimethyl-1,3-thiazol-2(3H)-ylidene]isoquinoline-5-carboxamide The isoquinoline-5-carboxylic acid (Lancaster, 0.25 g, 1.4 mmol) was converted to the corresponding acid chloride with 5 mL of thionyl chloride using the method described in Example 134A. The product of Example 126A (0.20 g, 1.1 mmol), Et$_3$N (0.3 mL, 2.2 mmol) and the acid chloride in 30 mL THF were processed as in Example 134B to afford the title compound (98 mg, 0.29 mmol, 27% yield). $^1$H NMR (300 MHz, CD$_3$OD) δ ppm 2.31 (s, 3H), 2.35 (s, 3H), 3.31 (s, 3H), 3.81 (t, J=5.3 Hz, 2H), 4.50 (t, J=5.3 Hz, 2H), 7.76 (dd, J=7.5, 7.5 Hz, 1H), 8.23 (d, J=8.1 Hz, 1H), 8.48 (d, J=6.4 Hz, 1H), 8.61 (dd, J=7.1, 1.4 Hz, 1H), 9.03 (d, J=6.1 Hz, 1H), 9.27 (d, J=1.0 Hz, 1H); MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 62.97; H, 5.54; N, 12.07.

Example 137

N-[(2Z)-3-(2-methoxyethyl)-4,5-dimethyl-1,3-thiazol-2(3H)-ylidene]-2,3-dihydro-1-benzofuran-7-carboxamide The 2,3-dihydrobenzofuran-7-carboxylic acid (TCI-US, 0.25 g, 1.4 mmol) was converted to 2,3-dihydrobenzofuran-7-carbonyl chloride with 5 mL of thionyl chloride using the method described in Example 134A. The product of Example 126A (0.20 g, 1.1 mmol), Et$_3$N (0.3 mL, 2.2 mmol) and the freshly prepared 2,3-dihydrobenzofuran-7-carbonyl chloride in 30 mL THF were processed as in Example 134B. Purification of the crude material via recrystallization with 50% hexanes:EtOAc gave the title compound (0.12 g, 0.36 mmol, 34% yield). $^1$H NMR (300 MHz, CD$_3$OD) δ ppm 2.25 (s, 3H), 2.30 (s, 3H), 3.22 (t, J=8.8 Hz, 2H), 3.31 (s, 3H), 3.81 (t, J=5.3 Hz, 2H), 4.44 (t, J=5.3 Hz, 2H), 4.64 (t, J=8.8 Hz, 2H), 6.86 (t, J=7.5 Hz, 1H), 7.32 (dd, J=7.3, 1.2 Hz, 1H), 7.93 (dd, J=8.0, 0.8 Hz, 1H); MS (DCI/NH$_3$) m/z 333 (M+H)$^+$; Anal. calculated for C$_{17}$H$_{20}$N$_2$O$_3$S·0.1H$_2$O: C, 61.09; H, 6.09; N, 8.38. Found: C, 60.99; H, 5.91; N, 8.25.

Example 138

2-chloro-N-[(2Z)-3-(2-methoxyethyl)-4,5-dimethyl-1,3-thiazol-2(3H)-ylidene]quinoline-4-carboxamide The 2-chloroquinoline-4-carboxylic acid (TCI-JP, 0.29 g, 1.4 mmol) was converted to 2-chloroquinoline-4-carbonyl chloride with 5 mL of thionyl chloride using the method described in Example 134A. The product of Example 126A (0.20 g, 1.1 mmol), Et$_3$N (0.3 mL, 2.2 mmol) and 2-chloroquinoline-4-carbonyl chloride in 30 mL THF were processed as in Example 134B to afford the title compound (0.14 g, 0.37 mmol, 35% yield). $^1$H NMR (300 MHz, CD$_3$OD) δ ppm 2.33 (s, 3H), 2.35 (s, 3H), 3.31 (s, 3H), 3.78 (t, J=5.3 Hz, 2H), 4.49 (t, J=5.3 Hz, 2H), 7.66 (ddd, J=8.5, 7.1, 1.4 Hz, 1H), 7.81 (ddd, J=8.5, 7.1, 1.4 Hz, 1H), 7.94 (s, 1H), 7.99 (dt, J=8.5, 0.7 Hz, 1H), 8.83 (dd, J=8.6, 1.2 Hz, 1H); MS (DCI/NH$_3$) m/z 376 (M+H)$^+$; Anal. calculated for C$_{18}$H$_{18}$ClN$_3$O$_2$S: C, 57.52; H, 4.83; N, 11.18. Found: C, 57.44; H, 4.59; N, 10.97.

Example 139

N-[(2Z)-3-(2-methoxyethyl)-4,5-dimethyl-1,3-thiazol-2(3H)-ylidene]-1,2-dihydroacenaphthylene-5-carboxamide The acenaphthene-5-carboxylic acid (Aldrich, 0.29 g, 1.4 mmol) in 5 mL of thionyl chloride was converted to acenaphthene-5-carbonyl chloride using the method described in Example 134A. The product of Example 126A (0.20 g, 1.1 mmol), Et$_3$N (0.3 mL, 2.2 mmol) and acenaphthene-5-carbonyl chloride in 30 mL THF were processed as in Example 134B to afford the title compound (87 mg, 0.24 mmol, 22% yield). $^1$H NMR (300 MHz, CD$_3$OD) δ ppm 2.28 (d, J=0.7 Hz, 3H), 2.33 (d, J=0.7 Hz, 3H), 3.33 (s, 3H), 3.42 (s, 4H), 3.84 (t, J=5.3 Hz, 2H), 4.51 (t, J=5.3 Hz, 2H), 7.30-7.36 (m, 2H), 7.52 (dd, J=8.6, 7.0 Hz, 1H), 8.43 (d, J=7.5 Hz, 1H), 8.81 (d, J=8.8 Hz, 1H); MS (DCI/NH$_3$) m/z 367 (M+H)$^+$; Anal. calculated for C$_{21}$H$_{22}$N$_2$O$_2$S: C, 68.82; H, 6.05; N, 7.64. Found: C, 68.63; H, 5.72; N, 7.40.

Example 140

2,3-dichloro-N-[(2Z)-3-(2-methoxyethyl)-5-methyl-1,3-thiazol-2(3H)-ylidene]benzamide Example 140 A 3-(2-Methoxy-ethyl)-5-methyl-3H-thiazol-2-ylidene-amine The product of Example 10A (17.6 g, 70 mmol) was treated with ~50 mL 20% aqueous K$_2$CO$_3$ then the mixture was extracted with EtOAc (3×25 mL). The combined organics were dried over anhydrous Na$_2$SO$_4$, filtered and concentrated under reduced pressure to afford the title compound (5.9 g, 34 mmol, 49% yield). $^1$H NMR (300 MHz, CDCl$_3$) δ ppm 2.03 (d, J=1.70 Hz, 3H) 3.36 (s, 3H) 3.62 (t, J=5.10 Hz, 2H) 3.83 (t, J=4.80 Hz, 2H) 6.15-6.21 (m, 1H); MS (DCI/NH$_3$) m/z 173 (M+H)$^+$.

Example 140B 2,3-dichloro-N-[(2Z)-3-(2-methoxyethyl)-5-methyl-1,3-thiazol-2(3H)-ylidene]benzamide To the product of Example 140A (0.20 g, 1.2 mmol) in 15 mL THF was added Et$_3$N (0.48 mL, 3.5 mmol) followed by a solution of 2,3-dichlorobenzoyl chloride (Lancaster, 0.31 g, 1.5 mmol) in 5 mL THF. This mixture stirred at ambient temperature for 1 hour then was concentrated under reduced pressure, quenched with 5 mL saturated, aqueous NH$_4$Cl and extracted with EtOAc (3×5 mL). The combined organic extracts were dried over anhydrous Na$_2$SO$_4$, filtered and concentrated under reduced pressure. The resulting solids were recrystallized from 50% hexanes/EtOAc to afford the title compound (0.27 g, 0.78 mmol, 68% yield). $^1$H NMR (300 MHz, CDCl$_3$) δ ppm 2.32 (d, J=1.4 Hz, 3H), 3.34 (s, 3H), 3.71 (t, J=5.1 Hz, 2H), 4.34 (t, J=4.8 Hz, 2H), 6.82-6.86 (m, 1H), 7.22 (t, J=7.8 Hz, 1H), 7.49 (dd, J=8.1, 1.7 Hz, 1H), 7.73 (dd, J=7.5, 1.7 Hz, 1H); MS (DCI/NH$_3$) m/z 345 (M+H)$^+$; Anal. calculated for C$_{14}$H$_{14}$Cl$_2$N$_2$O$_2$S: C, 48.70; H, 4.09; N, 8.11. Found: C, 48.39; H, 3.70; N, 7.94.

Example 141

5-chloro-N-[(2Z)-3-(2-methoxyethyl)-5-methyl-1,3-thiazol-2(3H)-ylidene]-2-(trifluoromethyl)benzamide The product of Example 140A (0.20 g, 1.2 mmol), $Et_3N$ (0.48 mL, 3.5 mmol) and 5-chloro-2-(trifluoromethyl)benzoyl chloride (Matrix, 0.31 g, 1.5 mmol) in 20 mL THF were processed using the method described in Example 140B to afford the title compound (0.16 g, 0.42 mmol, 36% yield). $^1$H NMR (300 MHz, $CDCl_3$) δ ppm 2.33 (d, J=0.7 Hz, 3H), 3.34 (s, 3H), 3.69 (t, J=5.1 Hz, 2H), 4.34 (t, J=4.6 Hz, 2H), 6.85 (s, 1H), 7.42-7.48 (m, 1H), 7.64 (d, J=8.5 Hz, 1H), 7.85 (d, J=2.0 Hz, 1H); MS ($DCI/NH_3$) m/z 379 $(M+H)^+$; Anal. calculated for $C_{15}H_{14}ClF_3N_2O_2S$: C, 47.56; H, 3.73; N, 7.40. Found: C, 47.31; H, 3.30; N, 7.33.

Example 142

2-chloro-N-[(2Z)-3-(2-methoxyethyl)-4,5-dimethyl-1,3-thiazol-2(3H)-ylidene]benzamide The product of Example 126A (0.20 g, 1.1 mmol), $Et_3N$ (0.45 mL, 3.2 mmol) and 2-chlorobenzoyl chloride (Aldrich, 0.26 g, 1.4 mmol) in 15 mL THF were processed as in Example 132 to afford the title compound (0.13 g, 0.40 mmol, 37% yield). $^1$H NMR (300 MHz, $CD_3OD$) δ ppm 2.28 (s, 3H), 2.32 (s, 3H), 3.31 (s, 3H), 3.76 (t, J=5.3 Hz, 2H), 4.42 (t, J=5.1 Hz, 2H), 7.30-7.46 (m, 3H), 7.77-7.83 (m, 1H); MS ($DCI/NH_3$) m/z 325 $(M+H)^+$; Anal. calculated for $C_{15}H_{17}ClN_2O_2S$: C, 55.46; H, 5.28; N, 8.62. Found: C, 55.59; H, 4.81; N, 8.47.

Example 143

N-[(2Z)-5-tert-butyl-3-(2-methoxyethyl)-4-methyl-1,3-thiazol-2(3H)-ylidene]-2-ethoxybenzamide

Example 143A 5-tert-Butyl-3-(2-methoxyethyl)-4-methyl-1,3-thiazol-2(3H)-ylideneamine A mixture of 5-tert-butyl-4-methylthiazole-2-ylamine (1.5 g, 8.8 mmol) and 2-bromoethyl methyl ether (0.91 mL, 9.7 mmol) was warmed to 85° C. and allowed to stir for 24 hours. The crude material was dissolved in ~5 mL of a 1:1 mixture of $CH_2Cl_2$ and $CH_3OH$ and a small amount of silica gel was added. This mixture was concentrated to dryness and the residue was purified via flash column chromatography ($SiO_2$, 9:1:0.1 $CH_2Cl_2$:$CH_3OH$:$NH_4OH$) to afford the title compound (1.0 g, 4.4 mmol, 50% yield). $^1$H NMR (300 MHz, $CD_3OD$) δ ppm 1.41 (s, 9H) 2.38 (s, 3H) 3.35 (s, 3H) 3.66 (t, J=4.70 Hz, 2H) 4.16 (t, J=4.70 Hz, 2H); MS ($DCI/NH_3$) m/z 229 $(M+H)^+$.

Example 143B

N-[(2Z)-5-tert-butyl-3-(2-methoxyethyl)-4-methyl-1,3-thiazol-2(3H)-ylidene]-2-ethoxybenzamide A mixture of the product of Example 143A (0.15 g, 0.66 mmol), $Et_3N$ (0.28 mL, 2.0 mmol) and 2-ethoxybenzoyl chloride (Aldrich, 0.16 g, 0.86 mmol) in 15 mL THF were processed using the method described in Example 129 to afford the title compound (0.12 g, 0.33 mmol, 50% yield). $^1$H NMR (300 MHz, $CD_3OD$) δ ppm 1.41 (t, J=7.1 Hz, 3H), 1.45 (s, 9H), 2.47 (s, 3H), 3.31 (s, 3H), 3.77 (t, J=5.3 Hz, 2H), 4.11 (q, J=6.8 Hz, 2H), 4.43 (t, J=5.3 Hz, 2H), 6.95 (dt, J=7.5, 1.0 Hz, 1H), 7.04 (d, J=8.1 Hz, 1H), 7.37 (ddd, J=8.7, 6.9, 1.7 Hz, 1H), 7.78 (dd, J=7.6, 1.9 Hz, 1H); MS ($DCI/NH_3$) m/z 377 $(M+H)^+$; Anal. calculated for $C_{20}H_{28}N_2O_3S$: C, 63.80; H, 7.50; N, 7.44. Found: C, 64.19; H, 7.44; N, 7.19.

Example 144

N-[(2Z)-5-tert-butyl-3-(2-methoxyethyl)-4-methyl-1,3-thiazol-2(3H)-ylidene]-2,3-dichlorobenzamide A mixture of the product of Example 143A (0.15 g, 0.66 mmol), $Et_3N$ (0.28 mL, 2.0 mmol) and 2,3-dichlorobenzoyl chloride (Lancaster, 0.18 g, 0.86 mmol) in 15 mL THF were processed using the method described in Example 129 to afford the title compound (0.11 g, 0.27 mmol, 42% yield). $^1$H NMR (300 MHz, $CDCl_3$) δ ppm 1.43 (s, 9H), 2.43 (s, 3H), 3.30 (s, 3H), 3.74 (t, J=5.3 Hz, 2H), 4.36 (t, J=5.3 Hz, 2H), 7.22 (dd, J=8.0, 8.0 Hz, 1H), 7.48 (dd, J=8.1, 1.7 Hz, 1H), 7.72 (dd, J=7.6, 1.5 Hz, 1H); MS ($DCI/NH_3$) m/z 401 $(M+H)^+$; Anal. calculated for $C_{18}H_{22}Cl_2N_2O_2S$: C, 53.87; H, 5.53; N, 6.98. Found: C, 53.86; H, 5.37; N, 6.76.

Example 145

N-[(2Z)-5-tert-butyl-3-(2-methoxyethyl)-4-methyl-1,3-thiazol-2(3H)-ylidene]-5-chloro-2-(trifluoromethyl)benzamide A mixture of the product of Example 143A (0.15 g, 0.66 mmol), $Et_3N$ (0.28 mL, 2.0 mmol) and 5-chloro-2-trifluoromethylbenzoyl chloride (Matrix, 0.17 g, 0.86 mmol) in 15 mL THF were processed using the method described in Example 129 to afford the title compound (0.16 g, 0.37 mmol, 56% yield). $^1$H NMR (300 MHz, $CD_3OD$) δ ppm 1.46 (s, 9H), 2.49 (s, 3H), 3.31 (s, 3H), 3.70 (t, J=5.3 Hz, 2H), 4.41 (t, J=5.3 Hz, 2H), 7.56-7.62 (m, 1H), 7.71-7.76 (m, 2H); MS ($DCI/NH_3$) m/z 435 $(M+H)^+$; Anal. calculated for $C_{19}H_{22}ClF_3N_2O_2S$: C, 52.47; H, 5.10; N, 6.44. Found: C, 52.52; H, 4.94; N, 6.05.

Example 146

N-[(2Z)-3-(2-methoxyethyl)-5-methyl-1,3-thiazol-2(3H)-ylidene]-1-naphthamide

The product of Example 140A (0.20 g, 1.2 mmol), $Et_3N$ (0.48 mL, 3.5 mmol) and 1-naphthoyl chloride (Aldrich, 0.22 g, 1.5 mmol) in 15 mL THF were processed using the method described in Example 140B to afford the title compound (0.23 g, 0.69 mmol, 60% yield). $^1$H NMR (300 MHz, $CD_3OD$) δ ppm 2.36 (d, J=1.0 Hz, 3H), 3.35 (s, 3H), 3.78 (t, J=5.4 Hz, 2H), 4.45 (t, J=5.1 Hz, 2H), 7.10-7.15 (m, 1H), 7.46-7.58 (m, 3H), 7.88-7.94 (m, 1H), 7.97 (d, J=8.1 Hz, 1H), 8.17 (dd, J=7.3, 1.2 Hz, 1H), 8.83-8.90 (m, 1H); MS ($DCI/NH_3$) m/z 327 $(M+H)^+$; Anal. calculated for $C_{18}H_{18}N_2O_2S$: C, 66.23; H, 5.56; N, 8.58. Found: C, 66.10; H, 5.64; N, 8.51.

Example 147

N-[(2Z)-5-tert-butyl-3-(2-methoxyethyl)-4-methyl-1,3-thiazol-2(3H)-ylidene]-5-chloro-2-methoxybenzamide The 5-chloro-2-methoxybenzoic acid (Aldrich, 0.21 g, 1.1 mmol) was converted to 5-chloro-2-methoxybenzoyl chloride with 5 mL of thionyl chloride using the method described in Example 134A. A mixture of the product of Example 143A (0.20 g, 0.88 mmol), Et$_3$N (0.48 mL, 3.4 mmol) and 5-chloro-2-methoxybenzoyl chloride in 15 mL THF were processed using the method described in Example 129 to afford the title compound (0.13 g, 0.32 mmol, 37% yield). $^1$H NMR (300 MHz, CDCl$_3$) δ ppm 1.41 (s, 9H), 2.42 (s, 3H), 3.32 (s, 3H), 3.77 (t, J=5.3 Hz, 2H), 3.90 (s, 3H), 4.36 (t, J=5.1 Hz, 2H), 6.90 (d, J=8.8 Hz, 1H), 7.31 (dd, J=8.8, 3.1 Hz, 1H), 7.94 (d, J=2.7 Hz, 1H); MS (DCI/NH$_3$) m/z 397 (M+H)$^+$; Anal. calculated for C$_{19}$H$_{25}$ClN$_2$O$_3$S: C, 57.49; H, 6.35; N, 7.06. Found: C, 57.51; H, 6.30; N, 6.85.

Example 148

N-[(2Z)-3-(2-methoxyethyl)-5-methyl-1,3-thiazol-2(3H)-ylidene]-2-methylbenzamide The product of Example 140A (0.20 g, 1.2 mmol), Et$_3$N (0.48 mL, 3.5 mmol) and o-toloyl chloride (Aldrich, 0.23 g, 1.2 mmol) in 15 mL THF were processed using the method described in Example 140B to afford the title compound (0.26 g, 0.90 mmol, 78% yield). $^1$H NMR (300 MHz, CDCl$_3$) δ ppm 2.30 (s, 3H), 2.70 (s, 3H), 3.35 (s, 3H), 3.74 (t, J=5.1 Hz, 2H), 4.36 (t, J=4.8 Hz, 2H), 6.77-6.81 (m, 1H), 7.23 (t, J=7.3 Hz, 2H), 7.28-7.35 (m, 1H), 8.08-8.13 (m, 1H); MS (DCI/NH$_3$) m/z 291 (M+H)$^+$; Anal. calculated for C$_{15}$H$_{18}$N$_2$O$_2$S: C, 62.04; H, 6.25; N, 9.65. Found: C, 62.40; H, 6.11; N, 9.70.

Example 149

2,3-dichloro-N-[(2Z)-5-methyl-3-(tetrahydrofuran-2-ylmethyl)-1,3-thiazol-2(3H)-ylidene]benzamide Example 149A 5-Methyl-3-(tetrahydro-furan-2-ylmethyl)-3H-thiazol-2-ylideneamine A mixture of 2-amino-5-methylthiazole (1.0 g, 8.7 mmol) and 2-(bromomethyl)tetrahydrofuran (Maybridge, 1.1 mL, 10 mmol) was warmed to 85° C. and allowed to stir for 24 hours. The mixture was then cooled to ambient temperature and purified via column chromatography (SiO$_2$, 9:1:0.1 CH$_2$Cl$_2$:CH$_3$OH:NH$_4$OH) to afford the title compound (1.5 g, 7.5 mmol, 86% yield). $^1$H NMR (300 MHz, CD$_3$OD) δ ppm 1.55-1.70 (m, 1H) 1.89-2.01 (m, 2H) 2.07-2.20 (m, 1H) 2.28 (d, J=1.36 Hz, 3H) 3.72-3.82 (m, 1H) 3.86-4.00 (m, 2H) 4.08-4.24 (m, 2H) 6.98-7.04 (m, 1H); MS (DCI/NH$_3$) m/z 199 (M+H)$^+$.

Example 149B 2,3-dichloro-N-[(2Z)-5-methyl-3-(tetrahydrofuran-2-ylmethyl)-1,3-thiazol-2(3H)-ylidene]benzamide To a solution of the product of Example 149A (0.17 g, 0.86 mmol) in 10 mL THF and 1 mL DMF was added Et$_3$N (0.36 mL, 2.6 mmol) followed by 2,3-dichlorobenzoyl chloride (Lancaster, 0.27 g, 1.3 mmol). This mixture was warmed to 50° C. and allowed to stir for 2 hours. The mixture was cooled to ambient temperature, diluted with 10 mL EtOAc, and quenched with 10 mL NH$_4$Cl. The layers were separated and the aqueous layer was extracted 2×5 mL EtOAc. The combined organics were dried over anhydrous Na$_2$SO$_4$, filtered, concentrated under reduced pressure and purified via column chromatography (SiO$_2$, 20% hexanes/EtOAc) to afford the title compound (0.24 g, 0.64 mmol, 75% yield). $^1$H NMR (300 MHz, CDCl$_3$) δ ppm 1.58-1.68 (m, 1H), 1.78-1.94 (m, 2H), 2.00-2.13 (m, 1H), 2.32 (s, 3H), 3.72-3.91 (m, 2H), 4.06-4.15 (m, 1H), 4.24 (ddd, J=14.0, 7.0, 2.7 Hz, 1H), 4.47 (dd, J=13.6, 2.7 Hz, 1H), 6.91-6.95 (m, 1H), 7.22 (t, J=8.0 Hz, 1H), 7.49 (dd, J=8.1, 1.7 Hz, 1H), 7.72 (dd, J=7.5, 1.7 Hz, 1H); MS (DCI/NH$_3$) m/z 371 (M+H)$^+$; Anal. calculated for C$_{16}$H$_{16}$Cl$_2$N$_2$O$_2$S: C, 51.76; H, 4.34; N, 7.55. Found: C, 51.66; H, 4.17; N, 7.46.

Example 150

N-[(2Z)-3-(2-methoxyethyl)-4,5-dimethyl-1,3-thiazol-2(3H)-ylidene]-2-methylbenzamide The product of Example 126A (0.20 g, 1.1 mmol), Et$_3$N (0.45 mL, 3.2 mmol) and o-toloyl chloride (Aldrich, 0.22 g, 1.4 mmol) in 15 mL THF were processed using the method described in Example 129 to afford the title compound (0.15 g, 0.49 mmol, 46% yield). $^1$H NMR (300 MHz, CDCl$_3$) δ ppm 2.23 (d, J=0.7 Hz, 3H), 2.26 (s, 3H), 2.70 (s, 3H), 3.31 (s, 3H), 3.77 (t, J=5.3 Hz, 2H), 4.35 (t, J=5.3 Hz, 2H), 7.23 (t, J=7.5 Hz, 2H), 7.27-7.35 (m, 1H), 8.08-8.14 (m, 1H); MS (DCI/NH$_3$) m/z 305 (M+H)$^+$; Anal. calculated for C$_{16}$H$_{20}$N$_2$O$_2$S: C, 63.13; H, 6.62; N, 9.20. Found: C, 63.43; H, 6.53; N, 9.14.

Example 151

N-[(2Z)-3-(2-methoxyethyl)-4,5-dimethyl-1,3-thiazol-2(3H)-ylidene]benzamide

The product of Example 126A (0.20 g, 1.1 mmol), Et$_3$N (0.45 mL, 3.2 mmol) and benzoyl chloride (Aldrich, 0.16 mL, 1.4 mmol) in 15 mL THF were processed using the method described in Example 129 to afford the title compound (0.11 g, 0.38 mmol, 35% yield). $^1$H NMR (300 MHz, CDCl$_3$) δ ppm 2.24 (s, 3H), 2.27 (d, J=0.7 Hz, 3H), 3.32 (s, 3H), 3.82 (t, J=5.3 Hz, 2H), 4.41 (t, J=5.3 Hz, 2H), 7.38-7.51 (m, 3H), 8.27-8.34 (m, 2H); MS (DCI/NH$_3$) m/z 291 (M+H)$^+$; Anal: calculated for C$_{15}$H$_{18}$N$_2$O$_2$S: C, 62.04; H, 6.25; N, 9.65. Found: C, 62.02; H, 6.05; N, 9.56.

Example 152

2-chloro-4-fluoro-N-[(2Z)-3-(2-methoxyethyl)-4,5-dimethyl-1,3-thiazol-2(3H)-ylidene]benzamide The product of Example 126A (0.20 g, 1.1 mmol), Et$_3$N (0.37 mL, 2.7 mmol) and 2-chloro-4-fluorobenzene-1-carbonyl chloride (Acros, 0.25 g, 1.3 mmol) in 15 mL THF were processed using the method described in Example 132 to afford the title compound (0.19 g, 0.56 mmol, 52% yield). $^1$H NMR (300 MHz, CDCl$_3$) δ ppm 2.24 (s, 3H), 2.27 (s, 3H), 3.30 (s, 3H), 3.76 (t, J=5.1 Hz, 2H), 4.35 (t, J=5.1 Hz, 2H), 7.00 (ddd, J=8.5, 7.8, 2.4 Hz, 1H), 7.15 (dd, J=8.8, 2.4 Hz, 1H), 8.04 (dd, J=8.8, 6.4 Hz, 1H); MS (DCI/NH$_3$) m/z 343 (M+H)$^+$; Anal. calculated for C$_{15}$H$_{16}$ClFN$_2$O$_2$S: C, 52.55; H, 4.70; N, 8.17. Found: C, 52.60; H, 4.38; N, 8.06.

Example 153

2-chloro-4-fluoro-N-[(2Z)-3-(2-methoxyethyl)-5-methyl-1,3-thiazol-2(3H)-ylidene]benzamide The product of Example 140A (0.17 g, 1.0 mmol), Et$_3$N (0.35 mL, 2.5 mmol) and 2-chloro-4-fluorobenzene-1-carbonyl chloride (Acros, 0.23 g, 1.2 mmol) in 15 mL THF were processed using the method described in Example 140B to afford the title compound (0.15 g, 0.46 mmol, 46% yield). $^1$H NMR (300 MHz, CDCl$_3$) δ ppm 2.32 (d, J=1.4 Hz, 3H), 3.35 (s, 3H), 3.73 (t, J=5.4 Hz, 2H), 4.36 (t, J=4.7 Hz, 2H), 6.80-6.84 (m, 1H), 7.00 (ddd, J=8.6, 7.8, 2.5 Hz, 1H), 7.16 (dd, J=8.6, 2.5 Hz, 1H), 8.04 (dd, J=8.8, 6.4 Hz, 1H); MS (DCI/NH$_3$) m/z 329 (M+H)$^+$; Anal. calculated for C$_{14}$H$_{14}$ClFN$_2$O$_2$S: C, 51.15; H, 4.29; N, 8.52. Found: C, 51.11; H, 3.90; N, 8.43.

Example 154

2,5-dichloro-N-[(2Z)-3-(2-methoxyethyl)-4,5-dimethyl-1,3-thiazol-2(3H)-ylidene]benzamide The 2,5-dichlorobenzoic acid (Aldrich, 0.28 g, 1.4 mmol) was converted to 2,5-dichlorobenzoyl chloride with 5 mL of thionyl chloride using the method described in Example 134A.

The product of Example 126A (0.20 g, 1.1 mmol), Et$_3$N (0.45 mL, 3.2 mmol) and 2,5-dichlorobenzoyl chloride in 15 mL THF were processed using the method described in Example 132 to afford the title compound (0.10 g, 0.28 mmol, 26% yield). $^1$H NMR (300 MHz, CDCl$_3$) δ ppm 2.25 (d, J=1.0 Hz, 3H), 2.28 (d, J=1.0 Hz, 3H), 3.31 (s, 3H), 3.76 (t, J=5.3 Hz, 2H), 4.36 (t, J=5.3 Hz, 2H), 7.28 (d, J=2.4 Hz, 1H), 7.32-7.36 (m, 1H), 7.94 (d, J=2.4 Hz, 1H); MS (DCI/NH$_3$) m/z 359 (M+H)$^+$; Anal. calculated for C$_{15}$H$_{16}$Cl$_2$N$_2$O$_2$S: C, 50.15; H, 4.49; N, 7.80. Found: C, 50.22; H, 4.15; N, 7.63.

Example 155

2,5-dichloro-N-[(2Z)-3-(2-methoxyethyl)-5-methyl-1,3-thiazol-2(3H)-ylidene]benzamide The 2,5-dichlorobenzoic acid (Aldrich, 0.28 g, 1.4 mmol) was converted to 2,5-dichlorobenzoyl chloride with 5 mL of thionyl chloride using the method described in Example 134A. The product of Example 140A (0.20 g, 1.1 mmol), Et$_3$N (0.45 mL, 3.2 mmol) and 2,5-dichlorobenzoyl chloride in 15 mL THF were processed using the method described in Example 129 to afford the title compound (0.24 g, 0.70 mmol, 65% yield). $^1$H NMR (300 MHz, CDCl$_3$) δ ppm 2.32 (d, J=1.4 Hz, 3H), 3.35 (s, 3H), 3.73 (t, J=5.1 Hz, 2H), 4.37 (t, J=4.7 Hz, 2H), 6.83-6.86 (m, 1H), 7.28 (dd, J=8.5, 2.4 Hz, 1H), 7.35 (d, J=8.5 Hz, 1H), 7.94 (d, J=2.7 Hz, 1H); MS (DCI/NH$_3$) m/z 345 (M+H)$^+$; Anal. calculated for C$_{14}$H$_{14}$Cl$_2$N$_2$O$_2$S: C, 48.70; H, 4.09; N, 8.11. Found: C, 48.60; H, 3.78; N, 8.02.

Example 156

5-chloro-2-methoxy-N-[(2Z)-3-(2-methoxyethyl)-5-methyl-1,3-thiazol-2(3H)-ylidene]benzamide The 5-chloro-2-methoxybenzoic acid (Aldrich, 0.28 g, 1.5 mmol) was converted to 5-chloro-2-methoxybenzoyl chloride with 5 mL of thionyl chloride using the method described in Example 134A. The product of Example 140A (0.19 g, 1.1 mmol), Et$_3$N (0.45 mL, 3.2 mmol) and 5-chloro-2-methoxybenzoyl chloride in 15 mL THF were processed using the method described in Example 129 to afford the title compound (0.25 g, 0.72 mmol, 67% yield). $^1$H NMR (300 MHz, CDCl$_3$) δ ppm 2.30 (d, J=1.0 Hz, 3H), 3.36 (s, 3H), 3.74 (t, J=5.1 Hz, 2H), 3.90 (s, 3H), 4.36 (t, J=4.7 Hz, 2H), 6.82 (s, 1H), 6.90 (d, J=8.8 Hz, 1H), 7.33 (dd, J=8.8, 2.7 Hz, 1H), 7.96 (d, J=2.7 Hz, 1H); MS (DCI/NH$_3$) m/z 341 (M+H)$^+$; Anal. calculated for C$_{15}$H$_{17}$ClN$_2$O$_3$S: C, 52.86; H, 5.03; N, 8.22. Found: C, 52.84; H, 4.72; N, 8.13.

Example 157

2,3-dichloro-N-[(2Z)-5-methyl-3-(tetrahydro-2H-pyran-2-ylmethyl)-1,3-thiazol-2(3H)-ylidene]benzamide Example 157A 5-Methyl-3-(tetrahydro-pyran-2-ylmethyl)-3H-thiazol-2-ylideneamine A mixture of 2-amino-5-methylthiazole (1.2 g, 10.5 mmol) and 2-(bromomethyl)tetrahydro-2H-pyran (Aldrich, 1.5 mL, 11.6 mmol) was warmed to 85° C. and allowed to stir for 18 hours. The mixture was cooled to ambient temperature and purified by flash column chromatography (SiO$_2$, first 10% CH$_3$OH:EtOAc then 9:1:0.1 CH$_2$Cl$_2$:CH$_3$OH:NH$_4$OH) to afford the title compound (1.1 g, 5.2 mmol, 49% yield). $^1$H NMR (300 MHz, CDCl$_3$) δ ppm 1.12-1.32 (m, 1H) 1.44-1.63 (m, 2H) 1.79-1.95 (m, 2H) 2.06 (d, J=12.89 Hz, 1H) 2.25 (d, J=1.36 Hz, 3H) 3.33-3.45 (m, 1H) 3.65-3.78 (m, 1H) 3.86-4.01 (m, 2H) 4.44 (dd, J=14.92, 2.03 Hz, 1H) 6.56-6.65 (m, 1H) 9.48 (s, 1H); MS (DCI/NH$_3$) m/z 213 (M+H)$^+$.

Example 157B 2,3-dichloro-N-[(2Z)-5-methyl-3-(tetrahydro-2H-pyran-2-ylmethyl)-1,3-thiazol-2(3H)-ylidene]benzamide The product of Example 157A (0.15 g, 0.71 mmol), Et$_3$N (0.30 mL, 2.1 mmol) and 2,3-dichlorobenzoyl chloride (Lancaster, 0.19 g, 0.92 mmol) in 15 mL THF were processed as in Example 129 to afford the title compound (0.14 g, 0.36 mmol, 51% yield). $^1$H NMR (300 MHz, CDCl$_3$) δ ppm 1.16-1.33 (m, 1H), 1.46-1.56 (m, 3H), 1.64-1.73 (m, 1H), 1.80-1.92 (m, 1H), 2.32 (d, J=1.4 Hz, 3H), 3.30-3.43 (m, 1H), 3.69 (qt, J=11.5, 8.8, 2.0 Hz, 1H), 3.91-4.01 (m, 2H), 4.41 (dd, J=13.9, 2.7 Hz, 1H), 6.86 (d, J=1.4 Hz, 1H), 7.23 (t, J=7.8 Hz, 1H), 7.49 (dd, J=8.0, 1.5 Hz, 1H), 7.74 (dd, J=7.6, 1.5 Hz, 1H); MS (DCI/NH$_3$) m/z 385 (M+H)$^+$; Anal. calculated for C$_{17}$H$_{18}$Cl$_2$N$_2$O$_2$S: C, 52.99; H, 4.71; N, 7.27. Found: C, 53.15; H, 4.72; N, 7.14.

Example 158

2-ethoxy-N-[(2Z)-5-methyl-3-(tetrahydro-2H-pyran-2-ylmethyl-1,3-thiazol-2(3H)-ylidene]benzamide The product of Example 157A (0.15 g, 0.71 mmol), Et$_3$N (0.30 mL, 2.1 mmol) and 2-ethoxybenzoyl chloride (Aldrich, 0.18 g, 0.92 mmol) in 15 mL THF were processed as in Example 129 to afford the title compound (0.14 g, 0.39 mmol, 55% yield). $^1$H NMR (300 MHz, CDCl$_3$) δ ppm 1.20-1.32 (m, 1H), 1.46 (t, J=7.0 Hz, 3H), 1.50-1.54 (m, 3H), 1.63-1.79 (m, 1H), 1.80-1.90 (m, 1H), 2.29 (s, 3H), 3.32-3.43 (m, 1H), 3.64-3.76 (m, 1H), 3.92-4.00 (m, 2H), 4.16 (q, J=6.8 Hz, 2H), 4.37-4.47 (m, 1H), 6.76-6.84 (m, 1H), 6.93-7.00 (m, 2H), 7.35 (t, J=8.1 Hz, 1H), 7.96 (dd, J=8.0, 1.9 Hz, 1H); MS (DCI/NH$_3$) m/z 361 (M+H)$^+$; Anal. calculated for C$_{19}$H$_{24}$N$_2$O$_3$S: C, 63.61; H, 6.71; N, 7.77. Found: C, 63.56; H, 6.73; N, 7.26.

Example 159

5-chloro-2-methoxy-N-[(2Z)-5-methyl-3-(tetrahydrofuran-2-ylmethyl)-1,3-thiazol-2(3H)-ylidene]benzamide The 5-chloro-2-methoxybenzoic acid (Aldrich, 0.66 g, 3.5 mmol) was converted to 5-chloro-2-methoxybenzoyl chloride with 5 mL of thionyl chloride using the method described in Example 134A. The product of Example 149A (0.35 g, 0.18 mmol), Et$_3$N (0.74 mL, 5.3 mmol) and 5-chloro-2-methoxybenzoyl chloride in 20 mL THF were processed using the method described in Example 149B to afford the title compound (0.25 g, 0.68 mmol, 20% yield). $^1$H NMR (300 MHz, CD$_3$OD) δ ppm 1.67-1.78 (m, 1H), 1.84-1.96 (m, 2H), 2.00-2.13 (m, 1H), 2.34 (d, J=1.4 Hz, 3H), 3.71-3.81 (m, 1H), 3.85 (s, 3H), 3.86-3.93 (m, 1H), 4.20-4.42 (m, 3H), 7.07 (d, J=9.2 Hz, 1H), 7.12-7.16 (m, 1H), 7.39 (dd, J=8.8, 2.7 Hz, 1H), 7.81 (d, J=2.7 Hz, 1H); MS (DCI/NH$_3$) m/z 367 (M+H)$^+$; Anal. calculated for C$_{17}$H$_{19}$ClN$_2$O$_3$S.0.2H$_2$O: C, 55.12; H, 5.28; N, 7.56. Found: C, 54.90; H, 4.95; N, 7.55.

Example 160

5-chloro-2-methoxy-N-[(2Z)-5-methyl-3-(tetrahydro-2H-pyran-2-ylmethyl)-1,3-thiazol-2(3H)-ylidene]benzamide The 5-chloro-2-methoxybenzoic acid (Aldrich, 0.17 g, 0.92 mmol) was converted to 5-chloro-2-methoxybenzoyl chloride with 5 mL of thionyl chloride using the method described in Example 134A. A mixture of the product of Example 157A (0.15 g, 0.71 mmol), Et$_3$N (0.30 mL, 2.1 mmol) and 5-chloro-2-methoxybenzoyl chloride in 15 mL THF were processed using the method described in Example 129 to afford the title compound (0.11 g, 0.29 mmol, 41% yield). $^1$H NMR (300 MHz, CDCl$_3$) δ ppm 1.20-1.36 (m, 1H), 1.48-1.61 (m, 3H), 1.66-1.76 (m, 1H), 1.83-1.92 (m, 1H), 2.30 (d, J=1.0 Hz, 3H), 3.33-3.44 (m, 1H), 3.67-3.77 (m, 1H), 3.90 (s, 3H), 3.93-4.05 (m, 2H), 4.40 (dd, J=13.9, 2.4 Hz, 1H), 6.83 (s, 1H), 6.90 (d, J=8.8 Hz, 1H), 7.32 (dd, J=8.8, 2.7 Hz, 1H), 7.97 (d, J=2.7 Hz, 1H); MS (DCI/NH$_3$) m/z 381 (M+H)$^+$; Anal. calculated for C$_{18}$H$_{21}$ClN$_2$O$_3$S.0.15H$_2$O: C, 56.36; H, 5.60; N, 7.30. Found: C, 56.70; H, 5.41; N, 6.91.

Example 161

2-ethoxy-N-[(2Z)-5-methyl-3-(tetrahydrofuran-2-ylmethyl)-1,3-thiazol-2(3H)-ylidene]benzamide The product of Example 149A (0.20 g, 1.0 mmol), Et$_3$N (0.42 mL, 3.0 mmol) and the 2-ethoxybenzoyl chloride (Aldrich, 0.23 mL, 1.5 mmol) in 15 mL THF were processed using the method described in Example 149B to afford the title compound (0.18 g, 0.52 mmol, 52% yield). $^1$H NMR (300 MHz, CD$_3$OD) δ ppm 1.40 (t, J=7.0 Hz, 3H), 1.64-1.75 (m, 1H), 1.83-1.94 (m, 2H), 2.00-2.12 (m, 1H), 2.33 (d, J=1.4 Hz, 3H), 3.70-3.80 (m, 1H), 3.83-3.93 (m, 1H), 4.11 (q, J=7.1 Hz, 2H), 4.18-4.27 (m, 1H), 4.28-4.42 (m, 2H), 6.96 (dt, J=7.5, 1.0 Hz, 1H), 7.04 (d, J=8.1 Hz, 1H), 7.09-7.13 (m, 1H), 7.38 (ddd, J=8.4, 7.4, 1.9 Hz, 1H), 7.77 (dd, J=7.6, 1.9 Hz, 1H); MS (DCI/NH$_3$) m/z 347 (M+H)$^+$; Anal. calculated for C$_{18}$H$_{22}$N$_2$O$_3$S.0.1H$_2$O: C, 62.40; H, 6.40; N, 8.09. Found: C, 63.49; H, 5.90; N, 7.84.

Example 162

5-chloro-2-methoxy-N-[(2Z)-5-methyl-3-(tetrahydrofuran-3-ylmethyl)-1,3-thiazol-2(3H)-ylidene]benzamide

Example 162A

Toluene-4-sulfonic acid tetrahydro-furan-3-ylmethyl ester

To a solution of tetrahydro-3-furanmethanol (Aldrich, 1.0 mL, 10.4 mmol) in 5 mL CH$_2$Cl$_2$ and 5 mL pyridine was added para-toluenesulfonyl chloride (3.0 g, 15.6 mmol) portion-wise over 15 minutes. This mixture stirred at ambient temperature for 3 hours then 5 mL H$_2$O was added. The layers were separated and the aqueous layer was extracted 2×5 mL CH$_2$Cl$_2$. The combined organics were dried over Na$_2$SO$_4$, filtered, concentrated under reduced pressure and dried under vacuum (~1 mm Hg) to afford the title compound (2.62 g, 10.2 mmol, 98% yield). $^1$H NMR (300 MHz, CDCl$_3$) δ ppm 1.49-1.63 (m, 1H) 1.94-2.08 (m, 1H) 2.46 (s, 3H) 2.52-2.68 (m, 1H) 3.49 (dd, J=9.16, 5.09 Hz, 1H) 3.64-3.84 (m, 3H) 3.88-4.03 (m, 2H) 7.36 (d, J=8.14 Hz, 2H) 7.76-7.82 (m, 2H); MS (DCI/NH$_3$) m/z 257 (M+H)$^+$.

Example 162B

5-Methyl-3-(tetrahydro-furan-3-ylmethyl)-3H-thiazol-2-ylideneamine

A mixture of the product of Example 162A (1.62 g, 6.3 mmol), 2-amino-5-methylthiazole (0.72 g, 6.3 mmol) and LiBr (55 mg, 0.63 mmol) in 2 mL DMF was warmed to 85° C. and allowed to stir for 16 hours. The mixture was then allowed to cool to ambient temperature, diluted with 10 mL CH$_2$Cl$_2$ and washed with 1×5 mL 10% aqueous Na$_2$CO$_3$ solution. The layers were separated and the aqueous layer was extracted 2×5 mL CH$_2$Cl$_2$. The combined organics were dried over anhydrous Na$_2$SO$_4$, filtered, concentrated under reduced pressure and purified by column chromatography (SiO$_2$, 9:1: 0.1 CH$_2$Cl$_2$:CH$_3$OH:NH$_4$OH) to afford the title compound (0.31 g, 1.6 mmol, 25% yield). $^1$H NMR (300 MHz, CD$_3$OD) δ ppm 1.61-1.74 (m, 1H) 1.96-2.04 (m, 1H) 2.05 (d, J=1.36 Hz, 3H) 2.69-2.84 (m, 1H) 3.53 (dd, J=8.82, 5.76 Hz, 1H) 3.63 (dd, J=7.63, 2.20 Hz, 2H) 3.69-3.81 (m, 2H) 3.89 (ddd, J=8.31, 5.42 Hz, 1H) 6.36-6.42 (m, 1H); MS (DCI/NH$_3$) m/z 199 (M+H)$^+$.

Example 162C

5-chloro-2-methoxy-N-[(2Z)-5-methyl-3-(tetrahydrofuran-3-ylmethyl)-1,3-thiazol-2(3H)-ylidene]benzamide The 5-chloro-2-methoxybenzoic acid (Aldrich, 0.40 g, 2.1 mmol) was converted to 5-chloro-2-methoxybenzoyl chloride with 5 mL of thionyl chloride using the method described in Example 134A. The product of Example 162B (0.21 g, 1.1 mmol), Et$_3$N (0.44 mL, 3.2 mmol) and 5-chloro-2-methoxybenzoyl chloride in 15 mL THF were processed using the method described in Example 149B to afford the title compound (0.28 g, 0.76 mmol, 72% yield). $^1$H NMR (300 MHz, CD$_3$OD) δ ppm 1.69-1.83 (m, 1H), 1.96-2.09 (m, 1H), 2.34 (d, J=1.4 Hz, 3H), 2.84-3.00 (m, 1H), 3.64 (dd, J=8.8, 5.1 Hz, 1H), 3.72-3.81 (m, 2H), 3.85 (s, 3H), 3.89-3.99 (m, 1H), 4.17-4.33 (m, 2H), 7.06 (d, J=8.8 Hz, 1H), 7.14-7.17 (m, 1H), 7.39 (dd, J=8.8, 2.7 Hz, 1H), 7.84 (d, J=2.7 Hz, 1H); MS (DCI/NH$_3$) m/z 367 (M+H)$^+$; Anal. calculated for C$_{17}$H$_{19}$ClN$_2$O$_3$S: C, 55.66; H, 5.22; N, 7.64. Found: C, 55.77; H, 4.85; N, 7.26.

Example 163

2-ethoxy-N-[(2Z)-5-methyl-3-(tetrahydrofuran-3-ylmethyl)-1,3-thiazol-2(3H)-ylidene]benzamide The product of Example 162B (0.17 g, 0.86 mmol), Et$_3$N (0.36 mL, 2.6 mmol) and the 2-ethoxybenzoyl chloride (Aldrich, 0.15 mL, 0.94 mmol) in 10 mL THF were processed using the method described in Example 149B to afford the title compound (0.26 g, 0.74 mmol, 86% yield). $^1$H NMR (300 MHz, CD$_3$OD) δ ppm 1.39 (t, J=7.0 Hz, 3H), 1.68-1.82 (m, 1H), 1.92-2.05 (m, 1H), 2.34 (d, J=1.4 Hz, 3H), 2.85-3.02 (m, 1H), 3.63 (dd, J=8.8, 5.4 Hz, 1H), 3.70-3.80 (m, 2H), 3.88-3.97 (m, 1H), 4.12 (q, J=6.9 Hz, 2H), 4.17-4.33 (m, 2H), 6.96 (dt, J=7.5, 1.0 Hz, 1H), 7.05 (d, J=7.8 Hz, 1H), 7.11-7.16 (m, 1H), 7.38 (ddd, J=8.6, 7.0, 1.7 Hz, 1H), 7.79 (dd, J=7.8, 1.7 Hz, 1H); MS (DCI/NH$_3$) m/z 347 (M+H)$^+$; Anal. calculated for C$_{18}$H$_{22}$N$_2$O$_3$S: C, 62.40; H, 6.40; N, 8.09. Found: C, 62.43; H, 6.29; N, 7.96.

Example 164

2-ethoxy-N-[(2Z)-3-[2-(2-methoxyethoxy)ethyl]-5-methyl-1,3-thiazol-2(3H)-ylidene]benzamide

Example 164A

3-[2-(2-Methoxyethoxy)ethyl]-5-methyl-1,3-thiazol-2(3H)-ylideneamine

A mixture of 2-amino-5-methylthiazole (1.5 g, 13.0 mmol) and 1-bromo-2-(2-methoxyethoxy)ethane (Aldrich, 2.0 mL, 14.5 mmol) was processed as in Example 157A to afford the title compound (2.2 g, 10.9 mmol, 78% yield). $^1$H NMR (300 MHz, CD$_3$OD) δ ppm 2.29 (d, J=1.36 Hz, 3H) 3.34 (s, 3H) 3.49-3.54 (m, 2H) 3.60-3.66 (m, 2H) 3.80 (t, J=5.10 Hz, 2H) 4.13 (t, J=4.80 Hz, 2H) 6.99-7.04 (m, 1H); MS (DCI/NH$_3$) m/z 217 (M+H)$^+$.

Example 164B 2-ethoxy-N-[(2Z)-3-[2-(2-methoxyethoxy)ethyl]-5-methyl-1,3-thiazol-2(3H)-ylidene]benzamide The product of Example 164A (0.22 g, 1.0 mmol), Et$_3$N (0.23 mL, 2.0 mmol) and 2-ethoxybenzoyl chloride (Aldrich, 0.25 g, 1.3 mmol) in 15 mL THF were processed as in Example 129 to afford the title compound (0.15 g, 0.40 mmol, 40% yield). $^1$H NMR (300 MHz, CD$_3$OD) δ ppm 1.40 (t, J=7.0 Hz, 3H), 2.33 (d, J=1.4 Hz, 3H), 3.31 (s, 3H), 3.46-3.51 (m, 2H), 3.58-3.63 (m, 2H), 3.85 (t, J=5.3 Hz, 2H), 4.11 (q, J=6.8 Hz, 2H), 4.40 (t, J=5.3 Hz, 2H), 6.96 (dt, J=7.5, 1.0 Hz, 1H), 7.04 (d, J=8.5 Hz, 1H), 7.11-7.15 (m, 1H), 7.38 (ddd, J=8.4, 7.4, 1.9 Hz, 1H), 7.79 (dd, J=7.6, 1.9 Hz, 1H); MS (DCI/NH$_3$) m/z 365 (M+H)$^+$; Anal. calculated for C$_{18}$H$_{24}$N$_2$O$_4$S: C, 59.88; H, 6.86; N, 7.51. Found: C, 60.05; H, 6.81; N, 7.60.

Example 166

2,3-dichloro-N-[(2Z)-3-[2-(2-methoxyethoxy)ethyl]-5-methyl-1,3-thiazol-2(3H)-ylidene]benzamide The product of Example 164A (0.22 g, 1.0 mmol), Et$_3$N (0.23 mL, 2.0 mmol) and 2,3-dichlorobenzoyl chloride (Lancaster, 0.27 g, 1.3 mmol) in 15 mL THF were processed as in Example 129 to afford the title compound (95 mg, 0.24 mmol, 24% yield). $^1$H NMR (300 MHz, CD$_3$OD) δ ppm 2.36 (d, J=1.4 Hz, 3H), 3.31 (s, 3H), 3.46-3.50 (m, 2H), 3.57-3.62 (m, 2H), 3.83 (t, J=5.4 Hz, 2H), 4.40 (t, J=5.1 Hz, 2H), 7.18-7.21 (m, 1H), 7.33 (t, J=7.8 Hz, 1H), 7.58 (dd, J=8.0, 1.5 Hz, 1H), 7.64 (dd, J=7.6, 1.5 Hz, 1H); MS (DCI/NH$_3$) m/z 389 (M+H)$^+$; Anal. calculated for C$_{16}$H$_{18}$Cl$_2$N$_2$O$_3$S: C, 49.36; H, 4.66; N, 7.20. Found: C, 48.98; H, 4.60; N, 6.99.

Example 167

5-chloro-2-methoxy-N-[(2Z)-3-[2-(2-methoxyethoxy)ethyl]-5-methyl-1,3-thiazol-2(3H)-ylidene]benzamide The 5-chloro-2-methoxybenzoic acid (Aldrich, 0.24 g, 1.3 mmol) was converted to the 5-chloro-2-methoxybenzoyl chloride with 5 mL of thionyl chloride using the method described in Example 134A. The product of Example 164A (0.22 g, 1.0 mmol), Et$_3$N (0.42 mL, 3.0 mmol) and 5-chloro-2-methoxybenzoyl chloride in 15 mL THF were processed using the method described in Example 129 to afford the title compound (0.21 g, 0.55 mmol, 55% yield). $^1$H NMR (300 MHz, CD$_3$OD) δ ppm 2.34 (d, J=1.4 Hz, 3H), 3.31 (s, 3H), 3.47-3.52 (m, 2H), 3.59-3.64 (m, 2H), 3.86 (s, 3H), 3.88 (t, J=5.4 Hz, 2H), 4.41 (t, J=4.8 Hz, 2H), 7.07 (d, J=8.8 Hz, 1H), 7.14-7.17 (m, 1H), 7.39 (dd, J=9.0, 2.9 Hz, 1H), 7.83 (d, J=2.7 Hz, 1H); MS (DCI/NH$_3$) m/z 385 (M+H)$^+$; Anal. calculated for C$_{17}$H$_{21}$ClN$_2$O$_4$S: C, 53.05; H, 5.50; N, 7.28. Found: C, 52.93; H, 5.61; N, 7.26.

Example 168

2-methoxy-N-[(2Z)-5-methyl-3-(tetrahydrofuran-2-ylmethyl)-1,3-thiazol-2(3H)-ylidene]benzamide The product of Example 149A (0.15 g, 0.76 mmol), Et$_3$N (0.32 mL, 2.3 mmol) and the o-anisoyl chloride (Aldrich, 0.15 mL, 1.1 mmol) in 10 mL THF were processed using the method described in Example 149B to afford the title compound (88 mg, 0.26 mmol, 35% yield). $^1$H NMR (300 MHz, CD$_3$OD) δ ppm 1.66-1.76 (m, 1H), 1.84-1.95 (m, 2H), 2.02-2.12 (m, 1H), 2.33 (d, J=1.4 Hz, 3H), 3.71-3.79 (m, 1H), 3.85 (s, 3H), 3.84-3.92 (m, 1H), 4.22-4.28 (m, 1H), 4.29-4.41 (m, 2H), 6.98 (dt, J=7.6, 1.0 Hz, 1H), 7.07 (dd, J=8.5, 1.0 Hz, 1H), 7.10-7.12 (m, 1H), 7.42 (ddd, J=9.2, 7.5, 2.0 Hz, 1H), 7.85 (dd, J=7.8, 1.7 Hz, 1H); MS (DCI/NH$_3$) m/z 333 (M+H)$^+$; Anal. calculated for C$_{17}$H$_{20}$N$_2$O$_3$S: C, 61.42; H, 6.06; N, 8.43. Found: C, 61.35; H, 6.10; N, 8.28.

Example 169

1-(1,1-Dimethylpropyl)-3-[(2Z)-3-(2-methoxyethyl)-4,5-dimethyl-1,3-thiazol-2(3H)-ylidene]urea hydrochloride

Example 169A 1-(1,1-Dimethylpropyl)-3-[(2Z)-3-(2-methoxyethyl)-4,5-dimethyl-1,3-thiazol-2(3H)-ylidene]urea To a solution of 1,1-dimethylpropylamine (174 mg, 2.0 mmole) in 19 mL of THF and 1 mL of N,N-diisopropylethyl amine was added 4-nitrophenyl chloroformate (403 mg, 2.0 mmole). The solution was irradiated in a sealed tube placed in a single node microwave at 70° C. for 300 sec (maximum power 300 W) with stirring. The resulting solution was cooled to room temperature and 3-(2-methoxyethyl)-4,5-dimethyl-3H-thiazol-2-ylideneamine hydrobromide (587 mg, 2.2 mmole) from Example 12A was added. The sealed tube was irradiated at 120° C. for 1800 sec with stirring. The mixture was cooled and the volatile components were removed under reduced pressure. The residue was partitioned between water and ethyl acetate. The phases were separated and organic extract was dried over anhydrous $Na_2SO_4$, filtered, and concentrated. Purification by column chromatography ($SiO_2$, 0-70% ethyl acetate/hexanes gradient) afforded the title compound. $^1$H NMR (300 MHz, DMSO-$d_6$) δ ppm 0.76 (t, J=7 Hz, 3H) 1.20 (s, 6H) 1.66 (d, J=7 Hz, 2H) 2.06 (s, 3H) 2.11 (s, 3H) 3.30 (s, 3H) 3.55 (t, J=5 Hz, 2H) 4.06 (t, J=5 Hz, 2H) 6.13 (s, 1H)), MS (DCI/$NH_3$) m/z 300 (M+H)$^+$.

Example 169B 1-(1,1-Dimethylpropyl)-3-[(2Z)-3-(2-methoxyethyl)-4,5-dimethyl-1,3-thiazol-2(3H)-ylidene]urea hydrochloride To a solution of the product from Example 169A in MeOH was added a solution of HCl in $Et_2O$. The title compound was isolated by filtration. $^1$H NMR (300 MHz, DMSO-$d_6$) δ ppm 0.84 (t, J=7 Hz, 3H) 1.26 (s, 6H) 1.65 (q, J=7 Hz, 2H) 2.24 (s, 6H) 3.24 (s, 3H) 3.64 (t, J=5 Hz, 2H) 4.45 (s, 2H), MS (DCI/$NH_3$) m/z 300 (M+H)$^+$. Anal. Calculated for $C_{14}H_{25}ClN_3O_2S$: C, 50.06; H, 7.80; N, 12.51. Found: C, 50.11; H, 7.87; N, 12.35.

Example 170

1-(1,1-Dimethyl-propyl)-3-[(2Z)-3-(2-methoxyethyl)-1,3-benzothiazol-2(3H)-ylidene]urea To a solution of 1,1-dimethyl-propylamine (0.60 mL, 5.2 mmol) and triethylamine (0.40 mL, 2.9 mmol) in 12 mL of a 1:1 mixture of THF:DMF at 0° C. was added p-nitrophenylchloroformate (0.58 g, 2.9 mmol). After 30 minutes, the product of Example 64A (0.75 g, 2.6 mmol) and another aliquot of triethylamine (0.40 mL, 2.9 mmol) were added and the solution stirred at ambient temperature for 9 hours. The mixture was diluted with ethyl acetate then washed twice with water and brine. The organic extract was dried over magnesium sulfate, filtered, and concentrated under reduced pressure. Purification by column chromatography ($SiO_2$, 20-40% ethyl acetate/hexanes gradient) afforded 0.06 g (8%) of the title compound. $^1$H NMR ($CDCl_3$, 300 MHz) δ ppm 0.91 (t, J=7.46 Hz, 3H), 1.39 (s, 6H), 1.78 (q, J=7.46 Hz, 2H), 3.28 (s, 3H), 3.86 (t, J=4.92 Hz, 2H), 4.82 (t, J=4.58 Hz, 2H), 7.46 (t, J=7.63 Hz, 1H), 7.58 (t, J=7.63 Hz, 1H), 7.64-7.70 (m, 1H), 7.75 (d, J=7.80 Hz, 1H), 9.06 (s, 1H). MS (DCI/$NH_3$) m/z 322 (M+H)$^+$.

Example 171

1-[(2Z)-3-(2-Methoxyethyl)-4,5-dimethyl-1,3-thiazol-2(3H)-ylidene]-3-(3,3,5,5-tetramethylcyclohexyl)urea The product of Example 12A and 3,3,5,5-tetramethylcyclohexylamine were processed using the method described in Example 169A to afford the title compound. $^1$H NMR (300 MHz, DMSO-$d_6$) δ ppm 0.90 (s, 6H) 1.02 (s, 6H) 1.17-1.27 (m, 1H) 1.61 (d, J=12 Hz, 1H) 2.18-2.27 (m, 6H) 3.24 (s, 3H) 3.62 (t, J=5 Hz, 2H) 3.76-3.87 (m, J=5 Hz, 2H) 3.98 (s, 2H) 4.40 (s, 2H), MS (DCI/$NH_3$) m/z 366 (M+H)$^+$. Anal. Calculated for $C_{19}H_{14}ClN_3O_2S.0.7CH_4O$: C, 55.49; H, 8.7; N, 9.85. Found C, 55.81; H, 8.37; N, 9.52.

Example 172

1-[(2Z)-3-(2-Methoxyethyl)-4,5-dimethyl-1,3-thiazol-2(3H)-ylidene]-3-(1-methyl-3-phenylpropyl)urea The product of Example 12A and 1-methyl-3-phenylpropylamine were processed using the method described in Example 169A to afford the title compound. $^1$H NMR (300 MHz, DMSO-$d_6$) δ ppm 1.13 (d, J=6 Hz, 3H) 1.60-1.82 (m, 2H) 2.18 (s, 3H) 2.20 (s, 3H) 2.55-2.68 (m, 2H) 3.25 (s, 3H) 3.53-3.80 (m, 3H) 4.31 (s, 2H) 7.08-7.35 (m, 5H), MS (DCI/$NH_3$) m/z 362 (M+H)$^+$.

Example 173 ethyl N-({[(2Z)-3-(2-methoxyethyl)-4,5-dimethyl-1,3-thiazol-2(3H)-ylidene]amino}carbonyl)-L-leucinate The product of Example 12A and (2S)-ethyl-2-amino-4-methylpentanoate were processed using the method described in Example 169A to afford the title compound. $^1$H NMR (300 MHz, DMSO-$d_6$) δ ppm 0.87 (dd, J=9, 6 Hz, 6H) 1.37-1.50 (m, 1H) 1.51-1.65 (m, 2H) 1.84 (s, 3H) 2.17 (s, 3H) 2.21 (s, 3H) 3.22-3.23 (m, 3H) 3.62 (t, J=5 Hz, 2H) 4.18-4.33 (m, 2H) 4.37-4.48 (m, 1H) 7.88 (d, J=9 Hz, 1H)), MS (DCI/$NH_3$) m/z 342 (M+H)$^+$. Anal. Calculated for $C_{16}H_{27}N_3O_3S$: C, 56.26; H, 7.97; N, 12.31. Found C, 56.20; H, 8.04; N, 12.31.

Example 174

1-(1,1-Dimethylpropyl)-3-[(2Z)-5-methyl-3-(tetrahydropyran-2-ylmethyl)-1,3-thiazol-2(3H)-ylidene]urea The product of Example 157A and 2,2-dimethylpropylamine were processed using the method described in Example 169A to afford the title compound. $^1$H NMR (300 MHz, DMSO-$d_6$) δ ppm 0.76 (t, 3H) 1.12-1.17 (m, 1H) 1.20 (s, 6H) 1.38-1.49 (m, J=3 Hz, 3H) 1.50-1.59 (m, 1H) 1.66 (q, J=7 Hz, 2H) 1.75-1.82 (m, 1H) 2.12 (s, 3H) 3.22-3.30 (m, 1H) 3.54-3.65 (m, 1H) 3.80-3.93 (m, 3H) 6.19 (s, 1H) 6.79 (s, 1H), MS (DCI/$NH_3$) m/z 326 (M+H)$^+$. Anal. Calculated for $C_{16}H_{27}N_3O_2S$: C, 59.04; H, 8.36; N, 12.91. Found C, 59.06; H, 8.36; N, 12.91.

Example 175

1-(1,2-Dimethyl-propyl)-3-[(2Z)-5-methyl-3-(tetrahydropyran-2-ylmethyl)-1,3-thiazol-2(3H)-ylidene]urea hydrochloride The product of Example 157A and 1,2-dimethylpropylamine were processed according to the method described in Example 169A to afford the title compound. $^1$H NMR (300 MHz, DMSO-$d_6$) δ ppm 0.81 (dd, J=7, 3 Hz, 1H) 0.84-0.96 (m, 6H) 1.06 (d, J=7 Hz, 3H) 1.20 (t, 1H) 1.34-1.54 (m, 3H) 1.60-1.76 (m, 1H) 1.69-1.95 (m, 2H) 2.28 (s, 3H) 3.22-3.37 (m, 1H) 3.84 (d, J=11 Hz, 2H) 4.10-4.30 (m, 1H) 4.31-4.47 (m, 1H) 7.23-7.41 (m, 1H) 7.83-8.06 (m, 1H),), MS (DCI/$NH_3$) m/z 326 (M+H)$^+$. Anal. Calculated for $C_{16}H_{28}ClN_3O_2S$: C, 53.10; H, 7.80; N, 11.16. Found C, 52.73; H, 7.96; N, 10.82.

Example 176

1-Cyclohexyl-3-[(2Z)-4,5-dimethyl-3-tetrahydropyran-2-ylmethyl-1,3-thiazol-2(3H)-lidene]urea

Example 176A

4,5-Dimethyl-3-(tetrahydropyran-2-ylmethyl)-1,3-thiazol-2(3H)-ylideneamine hydrobromide A mixture of 2-amino-4,5-dimethylthiazole and 2-(bromomethyl)tetrahydro-2H-pyran were processed using the method described in Example 12A to afford the title compound $^1$H NMR (300 MHz, DMSO-d$_6$) δ ppm 1.13-1.31 (m, 1H) 1.36-1.52 (m, 3H) 1.64-1.85 (m, 2H) 2.18 (d, J=4 Hz, 6H) 3.19-3.33 (m, 1H) 3.49-3.63 (m, 1H) 3.77-3.89 (m, 1H) 3.94-4.02 (m, 2H) 9.34 (s, 2H),), MS (DCI/NH$_3$) m/z 227 (M+H)$^+$.

Example 176B

1-Cyclohexyl-3-[(2Z)-4,5-dimethyl-3-(tetrahydropyran-2-ylmethyl)-1,3-thiazol-2(3H)-ylidene]urea The product of Example 176A and cyclohexylamine were processed using the method described in Example 169A to afford the title compound. $^1$H NMR (300 MHz, DMSO-d$_6$) δ ppm 1.05-1.29 (m, 6H) 1.37-1.49 (m, 3H) 1.51-1.63 (m, 2H) 1.76 (m, 5H) 2.06 (s, 3H) 2.11 (s, 3H) 3.19-3.30 (m, 1H) 3.56-3.68 (m, 1H) 3.70-3.88 (m, 3H) 3.99 (dd, J=14, 3 Hz, 1H) 6.59 (d, J=8 Hz, 1H),), MS (DCI/NH$_3$) m/z 352 (M+H)$^+$. Anal. Calculated for C$_{18}$H$_{29}$N$_3$O$_2$S.0.1H$_2$O: C, 61.19; H, 8.33 N, 11.89. Found C, 61.03; H, 8.45; N, 11.69.

Example 177

1-(4-Methylcyclohexyl)-3-[(2Z)-5-methyl-3-(tetrahydropyran-2-ylmethyl)-1,3-thiazol-2(3H)-ylidene]urea The product of Example 157A and 4-methylcyclohexylamine were processed using the method described in Example 169A to afford the title compound. $^1$H NMR (300 MHz, DMSO-d$_6$) δ ppm 0.88 (dd, J=12, 7 Hz, 3H) 0.96 (d, J=3 Hz, 1H) 1.09-1.31 (m, 3H) 1.31-1.70 (m, 9H) 1.69-1.85 (m, 2H) 2.12 (s, 3H) 3.21-3.29 (m, 1H) 3.55-3.64 (m, J=3 Hz, 2H) 3.79-3.95 (m, 3H) 6.62 (t, J=8 Hz, 1H) 6.77-6.81 (m, J=1 Hz, 1H), MS (DCI/NH$_3$) m/z 352 (M+H)$^+$.

Example 178

1-(1,1-Dimethylpropyl)-3-[(2Z)-3-(tetrahydropyran-2-ylmethyl)-1,3-thiazol-2(3H)-ylidene]urea

Example 178A

3-(tetrahydropyran-2-ylmethyl)-1,3-thiazol-2(3H)-ylideneamine hydrobromide

A mixture of 2-aminothiazole and 2-(bromomethyl)tetrahydro-2H-pyran were processed using the method described in Example 12A to afford the title compound. MS (DCI/NH$_3$) m/z 199 (M+H)$^+$

Example 178B

1-(1,1-Dimethylpropyl)-3-[(2Z)-3-(tetrahydropyran-2-ylmethyl)-1,3-thiazol-2(3H)-ylidene]urea The product of Example 178A and 1,1-dimethylpropylamine were processed using the method described in Example 169A to afford the title compound. $^1$H NMR (300 MHz, DMSO-d$_6$) δ ppm 0.77 (t, J=7 Hz, 3H) 1.14-1.19 (m, 1H) 1.21 (s, 6H) 1.39-1.49 (m, 3H) 1.50-1.59 (m, 1H) 1.61-1.72 (m, 2H) 1.79 (s, 1H) 3.19-3.28 (m, 1H) 3.56-3.68 (m, 1H) 3.78-3.89 (m, 1H) 3.92-4.02 (m, 2H) 6.23 (s, 1H) 6.55 (d, J=5 Hz, 1H) 7.08 (d, J=5 Hz, 1H), MS (DCI/NH$_3$) m/z 312 (M+H)$^+$. Anal. Calculated for C$_{15}$H$_{25}$N$_3$O$_2$S: C, 57.85; H, 8.09; N, 13.49 Found C, 58.01; H, 8.23; N, 13.30.

Example 179

N-[(2Z)-4,5-dimethyl-3-(tetrahydro-2H-pyran-2-ylmethyl)-1,3-thiazol-2(3H)-ylidene]-N'-[(1S)-1,2,2-trimethylpropyl]urea The product of Example 176A and (1S)-1,2,2-trimethylpropylamine were processed using the method described in Example 169A to afford the title compound. $^1$H NMR (300 MHz, DMSO-d$_6$) δ ppm 0.84 (s, 9H) 0.98 (d, J=7 Hz, 3H) 1.12-1.28 (m, 1H) 1.40-1.49 (m, 3H) 1.47-1.64 (m, J=13 Hz, 1H) 1.73-1.84 (m, 1H) 2.12 (s, 3H) 3.23-3.30 (m, 1H) 3.50-3.68 (m, 2H) 3.80-4.03 (m, 3H) 6.46 (dd, J=9, 3 Hz, 1H) 6.80 (dd, J=5, 2 Hz, 1H), MS (DCI/NH$_3$) m/z 354 (M+H)$^+$. Anal. Calculated for C$_{18}$H$_{31}$N$_3$O$_2$S: C, 61.15; H, 8.84; N, 11.69. Found C, 60.80; H, 8.88; N, 11.69.

Example 180

1-(2,2-Dimethylpropyl)-3-[(2Z)-4,5-dimethyl-3-(tetrahydropyran-2-ylmethyl)-1,3-thiazol-2(3H)-ylidene]urea The product of Example 176A and 2,2-dimethylpropylamine were processed using the method described in Example 169A to afford the title compound. $^1$H NMR (300 MHz, DMSO-d$_6$) δ ppm 0.84 (s, 9H) 1.16-1.28 (m, 1H) 1.45 (s, 3H) 1.56-1.68 (m, 1H) 1.76-1.87 (m, 1H) 2.06 (s, 3H) 2.11 (s, 3H) 2.77-2.87 (m, 1H) 2.90-3.02 (m, 1H) 3.15-3.28 (m, 1H) 3.60-3.70 (m, 1H) 3.72-3.86 (m, 2H) 3.94-4.11 (m, 1H) 6.58-6.78 (m, 1H),), MS (DCI/NH$_3$) m/z 339 (M+H)$^+$. Anal. Calculated for C$_{17}$H$_{29}$N$_3$O$_2$S: C, 60.14; H, 8.61; N, 12.38. Found C, 60.22; H, 8.71; N, 12.35.

Example 181

N-[(2Z)-3-(tetrahydro-2H-pyran-2-ylmethyl)-1,3-thiazol-2(3H)-ylidene]-N'-[(1S)-1,2,2-trimethylpropyl]urea The product of Example 178A and (1S)-1,2,2-trimethylpropylamine were processed using the method described in Example 169A to afford the title compound. $^1$H NMR (300 MHz, DMSO-d$_6$) δ ppm 0.84 (s, 9H) 0.99 (d, J=7 Hz, 3H) 1.14-1.26 (m, J=11 Hz, 1H) 1.36-1.49 (m, 3H) 1.52-1.59 (m, 1H) 1.74-1.82 (m, 1H) 3.20-3.28 (m, 1H) 3.52-3.70 (m, 2H) 3.78-4.08 (m, 3H) 6.46-6.60 (m, 2H) 7.10 (t, J=5 Hz, 1H), MS (DCI/NH$_3$) m/z 326 (M+H)$^+$. Anal. Calculated for C$_{16}$H$_{27}$N$_3$O$_2$S: C, 59.04; H, 8.36; N, 12.91. Found C, 59.08; H, 8.28; N, 12.80.

Example 182

N-[(2Z)-5-methyl-3-(tetrahydro-2H-pyran-2-ylmethyl)-1,3-thiazol-2(3H)-ylidene]-N'-[(1S)-1,2,2-trimethylpropyl]urea The product of Example 157A and (1S)-1,2,2-trimethylpropylamine were processed using the method described in Example 169A to afford the title compound. $^1$H NMR (300 MHz, DMSO-d$_6$) δ ppm 0.84 (s, 9H) 0.98 (d, J=7 Hz, 3H) 1.11-1.30 (m, 1H) 1.45 (s, 3H) 1.51 (d, 2H) 2.12 (s, 4H) 3.21-3.30 (m, 1H) 3.48-3.70 (m, 2H) 3.78-4.05 (m, 3H) 6.46 (dd, J=9, 3 Hz, 1H) 6.80 (dd, J=5, 2 Hz, 1H), MS (DCI/NH$_3$) m/z 339 (M+H)$^+$. Anal. Calculated for C$_{17}$H$_{29}$N$_3$O$_2$S: C, 60.14; H, 8.61; N, 12.38. Found C, 60.10; H, 8.81; N, 12.02.

Example 183

1-(4-Methylcyclohexyl)-3-[(2Z)-4,5-dimethyl-3-(tetrahydropyran-2-ylmethyl)-1,3-thiazol-2(3H)-ylidene]urea The product of Example 176A and 4-methylcyclohexylamine were processed using the method described in Example 169A to afford the title compound. $^1$H NMR (300 MHz, DMSO-d$_6$) δ ppm 0.82-1.02 (m, 4H) 1.15-1.29 (m, 3H) 1.38-1.51 (m, 4H) 1.52-1.70 (m, 4H) 1.78 (s, 3H) 2.06 (s, 3H) 2.11 (s, 3H) 3.19-3.28 (m, 1H) 3.61 (s, 1H) 3.69-3.86 (m, 3H) 3.98 (dd, J=14, 3 Hz, 1H) 6.57 (d, J=8 Hz, 1H), MS (DCI/NH$_3$) m/z 366 (M+H)$^+$. Anal. Calculated for C$_{18}$H$_{23}$N$_3$O$_2$S: C, 62.45; H, 8.55; N, 11.50. Found C, 62.77; H, 8.86; N, 1150.

Example 184

1-(2,2-Dimethylpropyl)-3-[(2Z)-5-methyl-3-(tetrahydropyran-2-ylmethyl)-1,3-thiazol-2(3H)-ylidene]urea The product of Example 157A and 2,2-dimethylpropylamine were processed using the method described in Example 169A to afford the title compound. $^1$H NMR (300 MHz, DMSO-d$_6$) δ ppm 0.81 (s, 9H) 1.09-1.26 (m, 1H) 1.34-1.59 (m, 4H) 1.69-1.87 (m, 1H) 2.12 (d, J=1 Hz, 3H) 2.80-2.98 (m, 2H) 3.08-3.27 (m, 1H) 3.52-3.67 (m, 1H) 3.80-4.06 (m, 3H) 6.68-6.76 (m, 1H) 6.78-6.90 (m, 1H), MS (DCI/NH$_3$) m/z 326 (M+H)$^+$. Anal. Calculated for C$_{16}$H$_{27}$N$_3$O$_2$S: C, 59.04; H, 8.36; N, 12.91. Found C, 58.89; H, 8.56; N, 12.71.

Example 185

1-tert-Butyl-3-[(2Z)-4,5-dimethyl-3-(tetrahydropyran-2-ylmethyl)-1,3-thiazol-2(3H)-ylidene]urea The product of Example 176A and tert-butylamine were processed using the method described in Example 169A to afford the title compound. $^1$H NMR (300 MHz, DMSO-d$_6$) δ ppm 1.13-1.22 (m, 1H) 1.27 (s, 9H) 1.44 (d, J=4 Hz, 3H) 1.60 (d, J=12 Hz, 1H) 1.77 (s, 1H) 2.06 (s, 3H) 2.11 (s, 3H) 3.16-3.28 (m, 1H) 3.55-3.68 (m, 1H) 3.68-3.87 (m, 2H) 4.00 (dd, J=14, 3 Hz, 1H) 6.90 (d, J=9 Hz, 1H), MS (DCI/NH$_3$) m/z 326 (M+H)$^+$. Anal. Calculated for C$_{16}$H$_{27}$N$_3$O$_2$S.0.3H$_2$O: C, 58.02; H, 8.41; N, 12.70. Found C, 58.44; H, 8.12; N, 12.41.

Example 186

1-(1,1-Dimethylpropyl)-3-[(2Z)-4,5-dimethyl-3-(tetrahydrofuran-2-ylmethyl)-1,3-thiazol-2(3H)-ylidene]urea Example 186A 4,5-Dimethyl-3-(tetrahydrofuran-2-ylmethyl)-1,3-thiazol-2(3H)-ylideneamine hydrobromide A mixture of 2-amino-4,5-dimethylthiazole and 2-(bromomethyl)tetrahydrofuran were processed using the method described in Example 12A to afford the title compound. $^1$H NMR (300 MHz, DMSO-d$_6$) δ ppm 1.43-1.64 (m, 1H) 1.73-2.00 (m, 3H) 2.17 (s, 3H) 2.19 (s, 3H) 3.53-3.68 (m, 1H) 3.71-3.85 (m, 1H) 3.91-4.17 (m, 3H) 9.34 (s, 1H),), MS (DCI/NH$_3$) m/z 212 (M+H)$^+$.

Example 186B 1-(1,1-Dimethylpropyl)-3-[(2Z)-4,5-dimethyl-3-(tetrahydrofuran-2-ylmethyl)-1,3-thiazol-2(3H)-ylidene]urea The product of Example 186A and 1,1-dimethylpropylamine were processed using the method described in Example 169A to afford the title compound. $^1$H NMR (300 MHz, DMSO-d$_6$) δ ppm 0.84 (t, J=7 Hz, 3H) 1.22-1.31 (m, 6H) 1.53-1.72 (m, 3H) 1.75-1.86 (m, 1H) 1.91-2.05 (m, 1H) 2.08-2.20 (m, 1H) 2.24 (s, 6H) 3.55-3.71 (m, 1H) 3.76-3.88 (m, 1H) 4.09-4.20 (m, 1H) 4.30 (s, 1H) 4.40-4.54 (m, 1H) 6.94 (d, J=9 Hz, 1H), MS (DCI/NH$_3$) m/z 326 (M+H)$^+$.

Example 187

1-(2,2-Dimethylpropyl)-3-[(2Z)-4,5-dimethyl-3-(tetrahydrofuran-2-ylmethyl)-1,3-thiazol-2(3H)-ylidene]urea The product of Example 186A and 2,2-dimethylpropylamine were processed using the method described in Example 169A to afford the title compound. $^1$H NMR (300 MHz, DMSO-d$_6$) δ ppm 0.86 (s, 9H) 1.54-1.65 (m, 1H) 1.77-1.97 (m, 3H) 2.07 (s, 3H) 2.10-2.14 (m, 3H) 2.78-2.97 (m, 2H) 3.54-3.65 (m, 1H) 3.71-3.85 (m, 2H) 3.98-4.11 (m, 1H) 4.14-4.31 (m, 1H) 6.66 (t, J=7 Hz, 1H), MS (DCI/NH$_3$) m/z 326 (M+H)$^+$. Anal. Calculated for C$_{16}$H$_{27}$N$_3$O$_2$S: C, 59.04; H, 8.36; N, 12.91. Found C, 58.91; H, 8.64; N, 12.77.

Example 188

1-[(2Z)-4,5-Dimethyl-3-(tetrahydropyran-2-ylmethyl)-1,3-thiazol-2(3H)-ylidene]-3-(3,3,5,5-tetramethylcyclohexyl)urea The product of Example 176A and 3,3,5,5-tetramethylcyclohexylamine were processed using the method described in Example 169A to afford the title compound. $^1$H NMR (300 MHz, DMSO-d$_6$) δ ppm 0.88 (s, 6H) 0.91-1.01 (m, 2H) 1.01-1.05 (m, 6H) 1.20 (d, J=14 Hz, 2H) 1.37-1.62 (m, 7H) 1.77 (d, J=4 Hz, 1H) 2.04-2.09 (m, 3H) 2.09-2.15 (m, 3H) 3.09-3.28 (m, 1H) 3.55-3.87 (m, 4H) 3.98 (dd, J=14, 3 Hz, 1H) 6.56 (d, J=8 Hz, 1H), MS (DCI/NH$_3$) m/z 408 (M+H)$^+$. Anal. Calculated for C$_{22}$H$_{37}$N$_3$O$_2$S.0.4H$_2$O: C, 63.7; H, 89.18N, 10.13. Found C, 63.49; H, 8.93; N, 10.12.

Example 189

N-[(2Z)-4,5-dimethyl-3-(tetrahydrofuran-2-ylmethyl)-1,3-thiazol-2(3H)-ylidene]-N'-[(1S)-1,2,2-trimethylpropyl]urea The product of Example 186A and (1S)-1,2,2-trimethylpropylamine were processed using the method described in Example 169A to afford the title compound. $^1$H NMR (300 MHz, DMSO-d$_6$) δ ppm 0.83 (s, 9H) 0.98 (dd, J=7, 2 Hz, 3H) 1.53-1.64 (m, 1H) 1.76-1.99 (m, 3H) 2.06 (s, 3H) 2.11 (s, 3H) 3.53-3.65 (m, 2H) 3.73-3.84 (m, 2H) 4.05-4.14 (m, 1H) 4.17-4.22 (m, 1H) 6.34-6.42 (m, 1H), MS (DCI/NH$_3$) m/z 339

(M+H)⁺. Anal. Calculated for C₁₇H₂₉N₃O₂S: C, 60.14; H, 8.61 N, 12.38. Found C, 60.06; H, 8.95; N, 12.29.

Example 190

N-[(2Z)-4,5-dimethyl-3-(tetrahydro-2H-pyran-2-ylmethyl)-1,3-thiazol-2(3H)-ylidene]-N'-[(1R)-1,2,2-trimethylpropyl]urea The product of Example 176A and (1R)-1,2,2-trimethylpropylamine were processed using the method described in Example 169A to afford the title compound. ¹H NMR (300 MHz, DMSO-d₆) δ ppm 0.84 (s, 9H) 0.99 (dd, J=7, 5 Hz, 3H) 1.13-1.30 (m, 1H) 1.38-1.50 (m, 3H) 1.54-1.68 (m, J=11 Hz, 1H) 1.74-1.85 (m, 1H) 2.06 (s, 3H) 2.11 (s, 3H) 3.19-3.27 (m, 1H) 3.53-3.66 (m, 1H) 3.71-3.88 (m, 3H) 3.95-4.12 (m, 1H) 6.37 (d, J=9 Hz, 1H), MS (DCI/NH₃) m/z 354 (M+H)⁺. Anal. Calculated for C₁₈H₃₁N₃O₂S: C, 61.15; H, 9.04; N, 11.89. Found C, 61.36; H, 9.08; N, 11.80.

Example 191

1-tert-Butyl-3-[(2Z)-5-methyl-3-(tetrahydropyran-2-ylmethyl)-1,3-thiazol-2(3H)-ylidene]urea The product of Example 157A and tent-butyl amine were processed using the method described in Example 169A to afford the title compound. ¹H NMR (300 MHz, DMSO-d₆) δ ppm 1.11-1.22 (m, 1H) 1.27 (s, 9H) 1.42-1.47 (m, J=1 Hz, 3H) 1.47-1.60 (m, 1H) 1.78 (d, J=5 Hz, 1H) 2.12 (s, 3H) 3.17-3.26 (m, 1H) 3.55-3.66 (m, J=6 Hz, 1H) 3.80-3.95 (m, 3H) 6.34 (s, 1H) 6.79 (s, 1H), MS (DCI/NH₃) m/z 326 (M+H)⁺. Anal. Calculated for C₁₆H₂₇N₃O₂S.0.3H₂O: C, 58.08; H, 8.41; N, 12.70. Found C, 58.44; H, 8.12; N, 12.41.

Example 192

1-(2,3-Dichlorophenyl)-3-[(2Z)-4,5-dimethyl-3-(tetrahydrofuran-2-ylmethyl)-1,3-thiazol-2(3H)-ylidene]urea The product of Example 186A and 2,3-dichlorophenylamine were processed using the method described in Example 169A to afford the title compound. ¹H NMR (300 MHz, DMSO-d₆) δ ppm 1.50-1.67 (m, 1H) 1.75-2.06 (m, 3H) 2.15 (s, 3H) 2.18 (s, 3H) 3.57-3.69 (m, 1H) 3.72-3.83 (m, 1H) 3.83-3.96 (m, 1H) 4.10-4.30 (m, 2H) 7.30 (s, 1H) 7.32 (d, J=1 Hz, 1H) 7.97-8.03 (m, 1H) 8.22 (s, 1H), MS (DCI/NH₃) m/z 400, 401 (M+H)⁺. Anal. Calculated for C₁₃H₂₃Cl₃N₃O₂S.0.3MeOH: C, 54.15; H, 8.23; N, 14.20. Found C, 54.47; H, 7.91N, 13.99.

Example 193

1-(2,2-Dimethylpropyl)-3-[(2Z)-3-(2-methoxyethyl)-4-methyl-1,3-thiazol-2(3H)-ylidene]urea The product of Example 5A and 2,2-dimethylpropylamine were processed using the method described in Example 169A to afford the title compound. ¹H NMR (300 MHz, DMSO-d₆) δ ppm 0.77 (t, J=7 Hz, 3H) 1.21 (s, 6H) 1.66 (q, J=7 Hz, 2H) 2.21 (s, 3H) 3.23 (s, 3H) 3.57 (t, J=5 Hz, 2H) 4.07 (t, J=5 Hz, 2H) 6.21 (s, 1H) 8.10 (d, J=9 Hz, 1H),), MS (DCI/NH₃) m/z 286 (M+H)⁺. Anal. Calculated for C₁₃H₂₃N₃O₂S.0.1MeOH: C, 54.70; H, 8.15; N, 14.26. Found C, 54.47; H, 7.91; N, 13.99.

Example 194

N-[(2Z)-4,5-dimethyl-3-(tetrahydrofuran-2-ylmethyl)-1,3-thiazol-2(3H)-ylidene]-N'-[(1R)-1,2,2-trimethylpropyl]urea The product of Example 186A and (1R)-1,2,2-trimethylpropylamine were processed using the method described in Example 169A to afford the title compound. ¹H NMR (300 MHz, DMSO-d₆) δ ppm 0.84 (s, 9H) 0.98 (dd, J=7, 2 Hz, 3H) 1.49-1.66 (m, 1H) 1.74-1.99 (m, 3H) 2.06 (s, 3H) 2.11 (s, 3H) 3.52-3.67 (m, 2H) 3.72-3.88 (m, 2H) 4.10 (dt, J=14, 4 Hz, 1H) 4.16-4.27 (m, 1H) 6.37 (dd, J=10, 4 Hz, 1H), m/z 339 (M+H)⁺. Anal. Calculated for C₁₇H₂₉N₃O₂S: C, 60.14; H, 8.61; N, 12.38. Found C, 60.18; H, 8.88; N, 12.33.

Example 195

N-[(1S)-1,2-dimethylpropyl]-N'-[(2Z)-4,5-dimethyl-3-(tetrahydrofuran-2-ylmethyl)-1,3-thiazol-2(3H)-ylidene]urea The product of Example 186A and (1S)-1,2,2-trimethylpropylamine were processed using the method described in Example 169A to afford the title compound. ¹H NMR (300 MHz, DMSO-d₆) δ ppm 0.83 (s, 9H) 0.98 (dd, J=7, 2 Hz, 3H) 1.52-1.66 (m, 1H) 1.75-1.97 (m, 3H) 2.06 (s, 3H) 2.11 (s, 3H) 3.51-3.66 (m, 2H) 3.72-3.86 (m, 2H) 4.10 (dt, J=14, 4 Hz, 1H) 4.19 (s, 1H) 6.37 (dd, J=10, 4 Hz, 1H), m/z 339 (M+H)⁺. Anal. Calculated for C₁₇H₂₉N₃O₂S: C, 60.14; H, 8.61; N, 12.38. Found C, 60.06; H, 8.95; N, 12.29.

Example 196

1-(1-Cyclopropylethyl)-3-[(2Z)-4,5-dimethyl-3-(tetrahydrofuran-2-ylmethyl)-1,3-thiazol-2(3H)-ylidene]urea The product of Example 12A and 1-cyclopropylethylamine were processed using the method described in Example 169A to afford the title compound. ¹H NMR (300 MHz, DMSO-d₆) δ ppm 0.05-0.15 (m, 1H) 0.18-0.55 (m, 3H) 0.78-0.92 (m, 1H) 1.11 (dd, J=7, 2 Hz, 3H) 1.51-1.64 (m, 1H) 1.75-1.99 (m, 3H) 2.07 (s, 3H) 2.12 (s, 3H) 3.06-3.22 (m, 1H) 3.61 (dd, 1H) 3.73-3.85 (m, 2H) 4.02-4.14 (m, 1H) 4.15-4.25 (m, 1H) 6.57-6.70 (m, 1H); m/z 324 (M+H)⁺. Anal. Calculated for C₁₆H₂₅N₃O₂S: C, 59.41; H, 7.79; N, 12.99. Found C, 59.13; H, 7.78; N, 12.88.

Example 197

1-[(2Z)-5-(2,4-Difluorophenyl)-3-(2-methoxyethyl)-1,3-thiazol-2(3H)-ylidene]-3-(1,1-dimethylpropyl)urea Example 197A N-[5-chloro-3-(2-methoxyethyl)-1,3-thiazol-2(3H)-ylidene]acetamide A flask was charged with 2-acetamido-5-chlorothiazole (Lancaster, 19.3 g, 110 mmol) in 200 mL of 2:1 THF/DMF. To the solution was added sodium hydride (60% dispersion in mineral oil, 5.44 g, 142 mmol). The mixture was stirred at room temperature for 15 min and then 2-bromoethyl methyl ether (18.3 g, 131 mmol) was added. The reaction mixture was warmed to 85° C. and stirred overnight. After cooling to room temperature, the mixture was diluted with ethyl acetate and washed with water. The organic extract was dried (MgSO$_4$), filtered, and concentrated. The residue was purified by flash chromatography on SiO$_2$ using a gradient of 0% to 100% ethyl acetate:hexane to provide 10.3 g (42%) of the title compound as the more polar regioisomer: $^1$H NMR (300 MHz, CDCl$_3$) δ 2.28 (s, 3H) 3.35 (s, 3H) 3.65-3.71 (m, 2H) 4.28-4.36 (m, 2H) 7.00 (s, 1H); MS (ESI$^+$) m/z 235 (M+H)$^+$.

Example 197B

N-[5-(2,4-difluorophenyl)-3-(2-methoxyethyl)-1,3-thiazol-2(3H)-ylidene]acetamide A flask was charged with the product from Example 197A (10.2 g, 42.6 mmol), 2,6-difluorophenylboronic acid (8.08 g, 51.1 mmol), Na$_2$CO$_3$ (64.0 mL of a 2 M aqueous solution, 128 mmol) and PdCl$_2$(PPh$_3$)$_2$ (1.5 g, 2.13 mmol) in 100 mL of DME/H$_2$O/ethanol (7:3:2). The mixture was warmed to 85° C. and stirred overnight. After cooling to room temperature, the mixture was diluted with ethyl acetate and washed with water. The organic extract was dried (MgSO$_4$), filtered, and concentrated. The residue was purified by flash chromatography on SiO$_2$ using a gradient of 0% to 100% ethyl acetate:hexane to provide 11.5 g (86%) of the title compound: $^1$H NMR (300 MHz, CDCl$_3$) δ 2.17 (s, 3H) 3.27 (s, 3H) 3.71 (t, J=5.3 Hz, 2H) 4.37 (t, J=5.4 Hz, 2H) 7.17-7.24 (m, 1H) 7.38-7.48 (m, 1H) 7.64-7.74 (m, 1H) 7.88 (s, 1H); MS (ESI$^+$) m/z 313 (M+H)$^+$.

Example 197C

N-5-(2,4-difluoro-phenyl)-3-(2-methoxyethyl)-1,3-thiazol-2(3H)-ylideneamine

To a solution of the product from Example 197B (11.5 g, 36.8 mmol) in 100 mL of THF was added 25 mL of 5 N aqueous HCl. The mixture was warmed to 40° C. and stirred overnight. After cooling to room temperature, the solvent was removed under reduced pressure and the residue diluted with ethyl acetate. The mixture was neutralized to pH 7 with saturated aqueous NaHCO$_3$ and then washed with water. The organic extract was dried (MgSO$_4$), filtered and concentrated. The residue was purified by flash chromatography on SiO$_2$ using a gradient of 0% to 100% ethyl acetate:hexane to provide 8.5 g (85%) of the title compound: $^1$H NMR (300 MHz, DMSO-d$_6$) δ 3.27 (s, 3H) 3.57 (t, J=5.3 Hz, 2H) 3.86 (t, J=5.4 Hz, 2H) 7.06-7.14 (m, Hz, 1H) 7.25 (s, 1H) 7.29 (dd, J=9.2, 2.7 Hz, 2H) 7.34 (dd, J=5.9, 3.2 Hz, 1H) 7.94 (s, 1H); MS (ESI$^+$) m/z 271 (M+H)$^+$.

Example 197D

1-[(2Z)-5-(2,4-Difluorophenyl)-3-(2-methoxyethyl)-1,3-thiazol-2-ylidene]-3-(1,1-dimethylpropyl)urea A mixture of the product of Example 197C and 1,1-dimethylpropylamine were processed using the method described in Example 169A to afford the title compound. $^1$H NMR (400 MHz, DMSO-d$_6$) δ ppm 0.78 (t, J=7.06 Hz, 3H) 1.24 (s, 6H) 1.68 (q, J=7.67 Hz, 2H) 3.27 (s, 3H) 3.66 (t, J=5.52 Hz, 2H) 4.20 (t, J=5.22 Hz, 2H) 6.49 (m, 1H) 7.16 (td, J=7.98, 1.84 Hz, 1H) 7.38 (m, 1H) 7.58 (m, 1H) 7.61 (s, 1H); MS (DCI/NH$_3$) m/z 384 (M+H)$^+$.

Example 198

1-[(2Z)-5-(2,4-Difluorophenyl)-3-(2-methoxyethyl)-1,3-thiazol-2-ylidene]-(1-methylpropyl)urea A mixture of the product of Example 197C and sec-butylamine were processed using the method described in Example 169A to afford the title compound. $^1$H NMR (500 MHz, DMSO-d$_6$) ppm 0.84 (t, J=7.32 Hz, 3H) 1.05 (d, J=6.41 Hz, 3H) 1.42 (m, 2H) 3.27 (s, 3H) 3.59 (m, 1H) 3.66 (t, J=5.49 Hz, 2H) 4.21 (t, J=5.80 Hz, 2H) 6.93 (d, J=8.54 Hz, 1H) 7.18 (td, J=8.24, 2.44 Hz, 1H) 7.39 (m, 1H) 7.57 (td, J=8.85, 6.41 Hz, 1H) 7.62 (brs, 1H); MS (DCI/NH$_3$) m/z 370 (M+H)$^+$.

Example 199

1-Cyclopentyl-3-[(2Z)-5-(2,4-difluorophenyl)-3-(2-methoxyethyl)-1,3-thiazol-2(3H)-ylidene]urea A mixture of the product of Example 197C and cyclopentylamine were processed using the method described in Example 169A to afford the title compound. $^1$H NMR (500 MHz, DMSO-d$_6$) δ ppm 1.47 (m, 4H) 1.65 (m, 2H) 1.80 (m, 2H) 3.27 (s, 3H) 3.66 (t, J=5.49 Hz, 2H) 3.95 (m, 1H) 4.20 (t, J=5.19 Hz, 2H) 7.10 (d, J=7.63 Hz, 1H) 7.18 (td, J=8.24, 2.44 Hz, 1H) 7.39 (m, 1H) 7.57 (m, 1H) 7.63 (s, 1H); MS (DCI/NH$_3$) m/z 382 (M+H)$^+$.

Example 200

1-[(2Z)-5-(2,4-Difluorophenyl)-3-(2-methoxyethyl)-1,3-thiazol-2(3H)-ylidene]-3-(4-methylcyclohexyl)urea A mixture of the product of Example 197C and 4-methylcyclohexylamine were processed using the method described in Example 169A to afford the title compound. $^1$H NMR (400 MHz, DMSO-d$_6$) δ ppm 0.90 (m, 3H) 0.98 (m, 2H) 1.49 (m, 8H) 3.27 (s, 3H) 3.66 (m, 2H) 4.21 (m, 2H) 6.93 (t, J=8.90 Hz, 1H) 7.17 (td, J=7.06, 2.45 Hz, 1H) 7.38 (m, 1H) 7.56 (m, 1H) 7.62 (m, 1H); MS (DCI/NH$_3$) m/z 410 (M+H)$^+$.

Example 202

N-[(2Z)-5-tert-butyl-3-(2-methoxyethyl)-1,3-thiazol-2(3H)-ylidene]-2-ethoxybenzamide

Example 202A 5-tert-butylthiazol-2-amine

To a flask equipped with a Dean-Stark trap was added 3,3-dimethylbutanal (Aldrich, 5.0 g, 50 mmol), pyrrolidine (Aldrich, 4.4 mL, 52 mmol) and p-toluenesulfonic acid monohydrate (10 mg) in cyclohexane (70 mL). The mixture was heated to reflux for 3 hours, the water was removed and the organic phase was concentrated under reduced pressure. The residue was dissolved in methanol (20 mL) and cooled to 0° C. Sulfur (Aldrich, 1.6 g, 50 mmol) and a solution of cyanamide (Aldrich, 2.1 g, 50 mmol) in methanol (5 mL) were added. The reaction mixture was allowed to warm to ambient temperature, stirred for 12 hours, and was concentrated under reduced pressure. The residue was purified by column chromatography (SiO$_2$, 2% methanol in CH$_2$Cl$_2$) to afford the title compound. MS (ESI$^+$) m/z 157 (M+H)$^+$.

Example 202B 5-tert-butyl-3-(2-methoxyethyl)thiazol-2(3H)-imine hydrobromide A mixture of Example 202A and commercially available 2-bromoethyl methyl ether (Aldrich) were processed according to the method described in Example 12A to afford the title compound. MS (ESI$^+$) m/z 215 (M+H)$^+$.

Example 202C

N-[(2Z)-5-tert-butyl-3-(2-methoxyethyl)-1,3-thiazol-2(3H)-ylidene]-2-ethoxybenzamide Commercially available 2-ethoxybenzoic acid (Aldrich) and Example 202B were processed using the method described in Example 58 to afford the title compound. $^1$H NMR (300 MHz, dimethylsulfoxide-d$_6$) δ ppm 1.28-1.36 (m, 12H), 3.26 (s, 3H), 3.71 (t, J=5.4 Hz, 2), 4.06 (q, J=6.9 Hz, 2H), 4.31 (t, J=5.4 Hz, 2H), 6.95 (td, J=7.4, 0.8 Hz, 1H), 7.05 (dd, J=8.5, 0.7 Hz, 1H), 7.21 (s, 1H), 7.32-7.42 (m, 1H), 7.67 (dd, J=7.6, 1.9 Hz, 1H)); MS (ESI$^+$) m/z 363 (M+H)$^+$.

Example 203

2-ethoxy-N-[(2Z)-5-methyl-3-(tetrahydro-2H-pyran-4-ylmethyl)-1,3-thiazol-2(3H)-ylidene]benzamide

Example 203A (tetrahydro-2H-pyran-4-yl)methyl 4-methylbenzenesulfonate

To a solution of tetrahydro-2H-pyran-4-ylmethanol (Combi-Blocks, 2.0 g, 17.2 mmol) in 10 mL of of CH$_2$Cl$_2$ and 10 mL of of pyridine was added p-toluenesulfonyl chloride (3.5 g, 18.1 mmol) in portions over 15 minutes. The mixture stirred at ambient temperature for 16 hours and was quenched with 10 mL of saturated, aqueous NaHCO$_3$. The layers were separated and the aqueous layer was extracted with three 10 mL portions of CH$_2$Cl$_2$. The combined organic extracts were dried over anhydrous Na$_2$SO$_4$, filtered and concentrated under reduced pressure to afford the title compound. $^1$H NMR (300 MHz, dimethylsulfoxide-d$_6$) δ ppm 1.05-1.25 (m, 2H), 1.40-1.53 (m, 2H), 1.73-1.94 (m, 1H), 2.43 (s, 3H), 3.14-3.28 (m, 2H), 3.71-3.84 (m, 2H), 3.88 (d, J=6.4 Hz, 2H), 7.48 (d, J=8.5 Hz, 2H), 7.79 (d, J=8.5 Hz, 2H); MS (DCI/NH$_3$) m/z 288 (M+NH$_4$)$^+$.

Example 203B 5-methyl-3-((tetrahydro-2H-pyran-4-yl)methyl)thiazol-2(3H)-imine A mixture of Example 203A (1.9 g, 7.0 mmol), 2-amino-5-methylthiazole (0.80 g, 7.0 mmol) and tetrabutylammonium iodide (1.3 g, 3.5 mmol) in 3 mL of N,N-dimethylformamide was warmed to 85° C. and was allowed to stir for 24 hours. The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 213 (M+H)$^+$.

Example 203C 2-ethoxy-N-[(2Z)-5-methyl-3-(tetrahydro-2H-pyran-4-ylmethyl)-1,3-thiazol-2(3H)-ylidene]benzamide To a solution of Example 203B (0.11 g, 0.52 mmol) in 10 mL of tetrahydrofuran and 1 mL of N,N-dimethylformamide at ambient temperature was added triethylamine (0.22 mL, 1.6 mmol) followed by 2-ethoxybenzoyl chloride (0.11 g, 0.57 mmol). This mixture was warmed to 50° C., stirred for 3 hours, was quenched with 10 mL of saturated aqueous NH$_4$Cl, and diluted with 10 mL of CH$_2$Cl$_2$. The layers were separated and the aqueous layer was extracted with three 5 mL portions of CH$_2$Cl$_2$. The combined organic extracts were dried over anhydrous Na$_2$SO$_4$, filtered and concentrated under reduced pressure. Purification via flash column chromatography (SiO$_2$, 50% hexanes in ethyl acetate) afforded the title compound. $^1$H NMR (300 MHz, CDCl$_3$) δ ppm 1.46 (t, J=7.0 Hz, 3H), 1.52-1.61 (m, 1H), 1.57 (s, 3H), 2.14-2.26 (m, 1H), 2.29 (d, J=1.4 Hz, 3H), 3.36 (dt, J=11.7, 2.4 Hz, 2H), 3.98 (ddd, J=11.4, 4.1, 1.5 Hz, 2H), 4.06 (d, J=7.5 Hz, 2H), 4.17 (q, J=6.8 Hz, 2H), 6.59-6.62 (m, 1H), 6.93-7.01 (m, 2H), 7.36 (ddd, J=8.3, 7.5, 1.9 Hz, 1H), 7.97 (dd, J=8.0, 1.9 Hz, 1H); MS (DCI/NH$_3$) m/z 361 (M+H)$^+$. Anal. Calculated for C$_{19}$H$_{24}$N$_2$O$_3$S: C, 63.31; H, 6.71; N, 7.77. Found: C, 63.27; H, 6.57; N, 7.48.

Example 204

2,4-dimethoxy-N-[(2Z)-5-methyl-3-(tetrahydrofuran-2-ylmethyl)-1,3-thiazol-2(3H)-ylidene]benzamide

Example 204A 5-methyl-3-((tetrahydrofuran-2-yl)methyl)thiazol-2(3H)-imine

A mixture of 2-amino-5-methylthiazole (1 g, 8.7 mmol) and 2-(bromomethyl)tetrahydrofuran (1.1 mL, 10 mmol) was warmed to 85° C. and was allowed to stir for 24 hours. The mixture was cooled to ambient temperature and purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 199 (M+H)$^+$.

Example 204B 2,4-dimethoxybenzoyl chloride

A solution of 2,4-dimethoxybenzoic acid (0.25 g, 1.4 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 204C 2,4-dimethoxy-N-[(2Z)-5-methyl-3-(tetrahydrofuran-2-ylmethyl)-1,3-thiazol-2(3H)-ylidene]benzamide To a solution of Example 204A (0.18 g, 0.91 mmol) in 10 mL of tetrahydrofuran at ambient temperature was added triethylamine (0.38 mL, 2.7 mmol) followed by Example 204B (1.4 mmol) in 3 mL of tetrahydrofuran via cannula. This mixture was warmed to 50° C., stirred for 3 hours, then quenched with 10 mL of saturated aqueous NH$_4$Cl, and diluted with 10 mL of CH$_2$Cl$_2$. The layers were separated and the aqueous phase was extracted three 5 mL portions of CH$_2$Cl$_2$. The combined organic extracts were dried over anhydrous Na$_2$SO$_4$, filtered and concentrated under reduced pressure. Purification via column chromatography (SiO$_2$, 50% hexanes in ethyl acetate) afforded the title compound. $^1$H NMR (300 MHz, CD$_3$OD) δ ppm 1.65-1.79 (m, 1H), 1.84-1.96 (m, 2H), 1.99-2.15 (m, 1H), 2.31 (d, J=1.4 Hz, 3H), 3.71-3.81 (m, 1H), 3.84-3.93 (m, 1H), 3.85 (s, 3H), 3.86 (s, 3H), 4.19-4.42 (m, 3H), 6.51-6.62 (m, 2H), 7.05-7.10 (m, 1H), 8.03 (d, J=8.8 Hz, 1H); MS (DCI/NH$_3$) m/z 363 (M+H)$^+$. Anal. Calculated for C$_{18}$H$_{22}$N$_2$O$_4$S: C, 59.65; H, 6.12; N, 7.73. Found: C, 59.47; H, 6.01; N, 7.62.

Example 205

5-chloro-2-methoxy-N-[(2Z)-4-methyl-3-(tetrahydro-2H-pyran-2-ylmethyl)-1,3-thiazol-2(3H)-ylidene]benzamide Example 205A 4-methyl-3-((tetrahydro-2H-pyran-2-yl)methyl)thiazol-2(3H)-imine A mixture of 2-amino-4-methylthiazole (1.0 g, 8.8 mmol) and 2-(bromomethyl)tetrahydropyran (1.1 mL, 8.8 mmol) was warmed to 85° C. and was allowed to stir for 24 hours. The mixture was cooled to ambient temperature and the crude material was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 213 (M+H)$^+$.

Example 205B 5-chloro-2-methoxybenzoyl chloride

A solution of 2-methoxy-5-chlorobenzoic acid (0.37 g, 2.0 mmol) in 10 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1$H NMR (300 MHz, dimethylsulfoxide-d$_6$) δ ppm 3.82 (s, 3H), 7.16 (d, J=8.8 Hz, 1H), 7.49-7.59 (m, 1H), 7.61 (d, J=2.7 Hz, 1H).

Example 205C 5-chloro-2-methoxy-N-[(2Z)-4-methyl-3-(tetrahydro-2H-pyran-2-ylmethyl)-1,3-thiazol-2(3H)-ylidene]benzamide To a solution of Example 205A (0.21 g, 1.0 mmol) in 10 mL of tetrahydrofuran at ambient temperature was added triethylamine (0.41 mL, 3.0 mmol) followed by Example 205B (2.0 mmol) in 5 mL of tetrahydrofuran via cannula. This mixture was warmed to 50° C., stirred for 2 hours, then quenched with 10 mL of saturated aqueous NH$_4$Cl, and diluted with 10 mL of CH$_2$Cl$_2$. The layers were separated and the aqueous phase was extracted with three 5 mL portions of CH$_2$Cl$_2$. The combined organic extracts were dried over anhydrous Na$_2$SO$_4$, filtered and concentrated under reduced pressure. Purification via column chromatography (SiO$_2$, 50% hexanes in ethyl acetate) afforded the title compound. $^1$H NMR (300 MHz, CD$_3$OD) δ ppm 1.31-1.48 (m, 1H), 1.47-1.67 (m, 3H), 1.70-1.82 (m, 1H), 1.84-1.98 (m, 1H), 2.40 (d, J=1.0 Hz, 3H), 3.26-3.40 (m, 1H), 3.82-3.94 (m, 2H), 3.87 (s, 3H), 4.00-4.11 (m, 1H), 4.42 (dd, J=13.9, 2.7 Hz, 1H), 6.55 (d, J=1.0 Hz, 1H), 7.07 (d, J=8.8 Hz, 1H), 7.40 (dd, J=8.8, 2.7 Hz, 1H), 7.87 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.58; H, 5.43; N, 7.19.

Example 206

5-chloro-2-methoxy-N-[(2Z)-5-methyl-3-(tetrahydro-2H-pyran-4-ylmethyl)-1,3-thiazol-2(3H)-ylidene]benzamide To Example 203B (0.11 g, 0.52 mmol) and triethylamine (0.22 mL, 1.6 mmol) in 10 mL of tetrahydrofuran and 1 mL of N,N-dimethylformamide was added Example 205B (0.68 mmol) in 2 mL of tetrahydrofuran. This mixture was warmed to 50° C., stirred for 2 hours, then quenched with 10 mL of saturated aqueous NH$_4$Cl, and diluted with 10 mL of CH$_2$Cl$_2$. The layers were separated and the aqueous phase was extracted with three 5 mL portions of CH$_2$Cl$_2$. The combined organic extracts were dried over anhydrous Na$_2$SO$_4$, filtered and concentrated under reduced pressure. Purification via flash column chromatography (SiO$_2$, 50% hexanes in ethyl acetate) resulted in the title compound. $^1$H NMR (300 MHz, CD$_3$OD) δ ppm 1.34-1.60 (m, 4H), 2.18-2.32 (m, 1H), 2.34 (d, J=1.4 Hz, 3H), 3.38 (dt, J=11.6, 2.5 Hz, 2H), 3.86 (s, 3H), 3.94 (ddd, J=11.6, 4.2, 1.9 Hz, 2H), 4.14 (d, J=7.5 Hz, 2H), 7.07 (d, J=8.8 Hz, 1H), 7.12 (q, J=1.4 Hz, 1H), 7.40 (dd, J=8.8, 2.7 Hz, 1H), 7.83 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.48; H, 5.46; N, 7.23.

Example 207

5-chloro-2-methoxy-N-[(2Z)-3-(tetrahydro-2H-pyran-2-ylmethyl)-1,3-thiazol-2(3H)-ylidene]benzamide Example 207A 3-((tetrahydro-2H-pyran-2-yl)methyl)thiazol-2(3H)-imine A mixture of 2-aminothiazole (1.0 g, 10 mmol) and 2-(bromomethyl)tetrahydro-2H-pyran (1.3 mL, 10 mmol) was warmed to 85° C. and was allowed to stir for 24 hours. The mixture was cooled to ambient temperature and the crude material was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 199 (M+H)$^+$.

Example 207B 5-chloro-2-methoxy-N-[(2Z)-3-(tetrahydro-2H-pyran-2-ylmethyl)-1,3-thiazol-2(3H)-ylidene]benzamide To a solution of Example 207A (0.19 g, 0.96 mmol) in 10 mL of tetrahydrofuran at ambient temperature was added triethylamine (0.40 mL, 2.9 mmol) followed by Example 205B (2.0 mmol) in 5 mL of tetrahydrofuran via cannula. This mixture was warmed to 50° C., stirred for 2 hours, then quenched with 10 mL of saturated aqueous $NH_4Cl$, and diluted with 10 mL of $CH_2Cl_2$. The layers were separated and the aqueous phase was extracted with three 5 mL portions of $CH_2Cl_2$. The combined organic extracts were dried over anhydrous $Na_2SO_4$, filtered and concentrated under reduced pressure. Purification via column chromatography ($SiO_2$, 50% hexanes in ethyl acetate) afforded the title compound. $^1H$ NMR (300 MHz, $CD_3OD$) δ ppm 1.20-1.41 (m, 1H), 1.46-1.63 (m, 3H), 1.67-1.77 (m, 1H), 1.82-1.96 (m, 1H), 3.35-3.45 (m, 1H), 3.75-3.85 (m, 1H), 3.86 (s, 3H), 3.89-4.00 (m, 1H), 4.19-4.27 (m, 1H), 4.38-4.46 (m, 1H), 6.91 (d, J=4.7 Hz, 1H), 7.08 (d, J=8.8 Hz, 1H), 7.38 (d, J=4.7 Hz, 1H), 7.41 (dd, J=8.8, 3.1 Hz, 1H), 7.85 (d, J=3.1 Hz, 1H); MS ($DCI/NH_3$) m/z 367 $(M+H)^+$. Anal. Calculated for $C_{17}H_{19}ClN_2O_3S$: C, 55.66; H, 5.22; N, 7.64. Found: C, 55.72; H, 5.08; N, 7.55.

Example 208

5-chloro-2-methoxy-N-[(2Z)-5-methyl-3-[(2R)-tetrahydrofuran-2-ylmethyl]-1,3-thiazol-2(3H)-ylidene] benzamide Example 208A (R)-(tetrahydrofuran-2-yl)methyl 4-methylbenzenesulfonate To a solution of (R)-tetrahydrofurfuryl alcohol (Lancaster, 1.0 g, 9.8 mmol) in 5 mL of $CH_2Cl_2$ and 5 mL of pyridine was added p-toluenesulfonyl chloride (2.8 g, 14.7 mmol) in portions over 15 minutes. The mixture was stirred at ambient temperature for 3 hours and was quenched with 10 mL of saturated, aqueous $NaHCO_3$. The layers were separated and the aqueous layer was extracted with three 5 mL portions of $CH_2Cl_2$. The combined organic extracts were dried over anhydrous $Na_2SO_4$, filtered and concentrated under reduced pressure to afford the title compound. MS ($DCI/NH_3$) m/z 257 $(M+H)^+$, 274 $(M+NH_4)$.

Example 208B (R)-5-methyl-3-((tetrahydrofuran-2-yl)methyl)thiazol-2(3H)-imine

A mixture of Example 208A (1.5 g, 5.9 mmol), 2-amino-5-methylthiazole (0.68 g, 5.9 mmol) and tetrabutylammonium iodide (1.1 g, 3.0 mmol) in 3 mL of N,N-dimethylformamide was warmed to 85° C. and was allowed to stir for 48 hours. The mixture was diluted with 10 mL of $CH_2Cl_2$ and the solution was quenched with 10 mL of saturated, aqueous $NaHCO_3$. The layers were separated and the aqueous layer was extracted twice with 10 mL portions of $CH_2Cl_2$. The combined organic extracts were dried over anhydrous $Na_2SO_4$, filtered and concentrated under reduced pressure. Purification via column chromatography ($SiO_2$, 10% methanol in ethyl acetate then 9:1:0.1 $CH_2Cl_2$:methanol:$NH_4OH$) afforded the title compound. MS ($DCI/NH_3$) m/z 199 $(M+H)^+$.

Example 208C 5-chloro-2-methoxybenzoyl chloride

A solution of 2-methoxy-5-chlorobenzoic acid (0.22 g, 1.2 mmol) in 10 mL of $SOCl_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1H$ NMR (300 MHz, dimethylsulfoxide-$d_6$) δ ppm 3.82 (s, 3H), 7.16 (d, J=8.8 Hz, 1H), 7.49-7.59 (m, 1H), 7.61 (d, J=2.7 Hz, 1H).

Example 208D 5-chloro-2-methoxy-N-[(2Z)-5-methyl-3-[(2R)-tetrahydrofuran-2-ylmethyl]-1,3-thiazol-2(3H)-ylidene] benzamide To a solution of Example 208B (0.23 g, 1.2 mmol) in 10 mL of tetrahydrofuran at ambient temperature was added triethylamine (0.49 mL, 3.5 mmol) followed by Example 208C (1.2 mmol) in 5 mL of tetrahydrofuran via cannula. This mixture was warmed to 50° C. and was allowed to stir for 3 hours and was quenched with 10 mL of $NH_4Cl$ and diluted with 10 mL of $CH_2Cl_2$. The layers were separated and the aqueous layer was extracted with three 5 mL portions of $CH_2Cl_2$. The combined organic extracts were dried over anhydrous $Na_2SO_4$, filtered and concentrated under reduced pressure. Purification via flash column chromatography ($SiO_2$, 1:1:1 hexanes:ethyl acetate:$CH_2Cl_2$) afforded the title compound. $^1H$ NMR (300 MHz, $CD_3OD$) δ ppm 1.64-1.79 (m, 1H), 1.84-1.96 (m, 2H), 2.00-2.14 (m, 1H), 2.34 (d, J=1.4 Hz, 3H), 3.69-3.81 (m, 1H), 3.84-3.93 (m, 1H), 3.85 (s, 3H), 4.20-4.43 (m, 3H), 7.07 (d, J=8.8 Hz, 1H), 7.14 (q, J=1.1 Hz, 1H), 7.39 (dd, J=9.0, 2.9 Hz, 1H), 7.81 (d, J=2.7 Hz, 1H); MS ($DCI/NH_3$) m/z 367 $(M+H)^+$. Anal. Calculated for $C_{17}H_{19}ClN_2O_3S$: C, 55.66; H, 5.22; N, 7.64. Found: C, 55.42; H, 5.08; N, 7.58.

Example 209

5-chloro-2-methoxy-N-[(2Z)-5-methyl-3-[(2S)-tetrahydrofuran-2-ylmethyl]-1,3-thiazol-2(3H)-ylidene] benzamide Example 209A (S)-(tetrahydrofuran-2-yl)methyl 4-methylbenzenesulfonate To a solution of (S)-tetrahydrofurfuryl alcohol (Codexis, 1.6 g, 15.2 mmol) in 5 mL of $CH_2Cl_2$ and 5 mL of pyridine was added p-toluenesulfonyl chloride (4.3 g, 22.8 mmol) in portions over 15 minutes. The mixture stirred at ambient temperature for 3 hours and was quenched with 10 mL of saturated, aqueous $NaHCO_3$. The layers were separated and the aqueous layer was extracted with three 5 mL portions of $CH_2Cl_2$. The combined organic extracts were dried over anhydrous $Na_2SO_4$, filtered and concentrated under reduced pressure to afford the title compound. MS ($DCI/NH_3$) m/z 257 $(M+H)^+$, 274 $(M+NH_4)$.

Example 209B (S)-5-methyl-3-((tetrahydrofuran-2-yl)methyl)thiazol-2(3H)-imine

A mixture of Example 209A (1.6 g, 6.1 mmol), 2-amino-5-methylthiazole (0.7 g, 6.1 mmol) and tetrabutylammonium iodide (2.3 g, 6.1 mmol) in 5 mL of N,N-dimethylformamide was warmed to 85° C. and was allowed to stir for 18 hours.

The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 199 (M+H)$^+$.

Example 209C 5-chloro-2-methoxy-N-[(2Z)-5-methyl-3-[(2S)-tetrahydrofuran-2-ylmethyl]-1,3-thiazol-2(3H)-ylidene]benzamide Example 209B (0.32 g, 1.6 mmol), triethylamine (0.67 mL, 4.8 mmol) and Example 205B (1.9 mmol) in 20 mL of tetrahydrofuran were processed as in Example 208D to afford the title compound. $^1$H NMR (300 MHz, CD$_3$OD) δ ppm 1.64-1.79 (m, 1H), 1.84-1.96 (m, 2H), 2.00-2.13 (m, 1H), 2.34 (d, J=1.4 Hz, 3H), 3.71-3.81 (m, 1H), 3.84-3.93 (m, 1H), 3.85 (s, 3H), 4.20-4.43 (m, 3H), 7.07 (d, J=8.8 Hz, 1H), 7.14 (q, J=1.4 Hz, 1H), 7.39 (dd, J=9.0, 2.9 Hz, 1H), 7.81 (d, J=2.7 Hz, 1H); MS (DCI/NH$_3$) m/z 367 (M+H)$^+$. Anal. Calculated for C$_{17}$H$_{19}$ClN$_2$O$_3$S: C, 55.66; H, 5.22; N, 7.64. Found: C, 55.48; H, 4.96; N, 7.52.

Example 210

2,2,3,3-tetrafluoro-1-methyl-N-[(2Z)-5-methyl-3-(tetrahydrofuran-2-ylmethyl)-1,3-thiazol-2(3H)-ylidene]cyclobutanecarboxamide Example 204A (0.20 g, 1.0 mmol), triethylamine (0.42 mL, 3.0 mmol) and 2,2,3,3-tetrafluoro-1-(methyl)cyclobutanecarbonyl chloride (ABCR, 0.27 g, 1.3 mmol) in 15 mL of tetrahydrofuran were processed as in Example 208D to afford the title compound. $^1$H NMR (300 MHz, CD$_3$OD) δ ppm 1.53 (s, 3H), 1.62-1.73 (m, 1H), 1.81-1.93 (m, 2H), 1.95-2.10 (m, 1H), 2.27-2.44 (m, 1H), 2.32 (d, J=1.4 Hz, 3H), 3.33-3.43 (m, 1H), 3.69-3.79 (m, 1H), 3.80-3.90 (m, 1H), 4.20-4.36 (m, 3H), 7.11 (dd, J=1.4, 0.7 Hz, 1H); MS (DCI/NH$_3$) m/z 367 (M+H)$^+$. Anal. Calculated for C$_{15}$H$_{18}$F$_4$N$_2$O$_2$S: C, 49.17; H, 4.95; N, 7.65. Found: C, 49.27; H, 4.88; N, 7.58.

Example 211

5-chloro-2-methoxy-N-[(2Z)-5-methyl-3-(oxetan-2-ylmethyl)-1,3-thiazol-2(3H)-ylidene]benzamide Example 211A oxetan-2-ylmethyl 4-methylbenzenesulfonate To a solution of 2-hydroxymethyloxetane (TCI-US, 2.0 g, 23 mmol) in 10 mL of CH$_2$Cl$_2$ and 10 mL of pyridine was added p-toluenesulfonyl chloride (6.5 g, 34 mmol) in portions over 15 minutes. The mixture was stirred at ambient temperature for 3 hours and was quenched with 10 mL of saturated, aqueous NaHCO$_3$. The layers were separated and the aqueous layer was extracted with three 5 mL portions of CH$_2$Cl$_2$. The combined organic extracts were dried over anhydrous Na$_2$SO$_4$, filtered and concentrated under reduced pressure. Purification via column chromatography (SiO$_2$, 70% hexanes in ethyl acetate) afforded the title compound. MS (DCI/NH$_3$) m/z 243 (M+H)$^+$, 260 (M+NH$_4$)$^+$.

Example 211B 5-methyl-3-(oxetan-2-ylmethyl)thiazol-2(3H)-imine

A mixture of Example 211A (1.1 g, 4.6 mmol), 2-amino-5-methylthiazole (0.53 g, 4.6 mmol) and tetrabutylammonium iodide (0.85 g, 2.3 mmol) in 5 mL of N,N-dimethylformamide was warmed to 85° C. and was allowed to stir for 18 hours. The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 185 (M+H)$^+$.

Example 211C 5-chloro-2-methoxy-N-[(2Z)-5-methyl-3-(oxetan-2-ylmethyl)-1,3-thiazol-2(3H)-ylidene]benzamide Example 211B (0.26 g, 1.4 mmol), triethylamine (0.59 mL, 4.2 mmol) and Example 205B (1.7 mmol) in 15 mL of tetrahydrofuran were processed as in Example 208D to afford the title compound. $^1$H NMR (300 MHz, CD$_3$OD) δ ppm 2.35 (d, J=1.4 Hz, 3H), 2.43-2.59 (m, 1H), 2.70-2.85 (m, 1H), 3.85 (s, 3H), 4.37-4.51 (m, 2H), 4.57-4.71 (m, 2H), 5.15-5.25 (m, 1H), 7.06 (d, J=9.2 Hz, 1H), 7.18 (q, J=1.1 Hz, 1H), 7.39 (dd, J=8.8, 2.7 Hz, 1H), 7.79 (d, J=2.7 Hz, 1H); MS (DCI/NH$_3$) m/z 353 (M+H)$^+$. Anal. Calculated for C$_{16}$H$_{17}$ClN$_2$O$_3$S: C, 54.46; H, 4.86; N, 7.94. Found: C, 54.41; H, 4.88; N, 7.80.

Example 212

5-chloro-N-[(2Z)-3-(1,3-dioxolan-2-ylmethyl)-5-methyl-1,3-thiazol-2(3H)-ylidene]-2-methoxybenzamide Example 212A 3-((1,3-dioxolan-2-yl)methyl)-5-methylthiazol-2(3H)-imine A mixture of 2-amino-5-methylthiazole (1 g, 8.7 mmol) and 2-bromomethyl-1,3-dioxolane (0.98 mL, 9.6 mmol) was warmed to 85° C. and was allowed to stir for 18 hours. The mixture was cooled to ambient temperature and purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 201 (M+H)$^+$.

Example 212B 5-chloro-N-[(2Z)-3-(1,3-dioxolan-2-ylmethyl)-5-methyl-1,3-thiazol-2(3H)-ylidene]-2-methoxybenzamide Example 212A (0.25 g, 1.3 mmol), triethylamine (0.52 mL, 3.8 mmol) and Example 205B (1.5 mmol) in 15 mL of tetrahydrofuran were processed as in Example 208D to afford the title compound. $^1$H NMR (300 MHz, CD$_3$OD) δ ppm 2.33 (d, J=1.4 Hz, 3H), 3.86 (s, 3H), 3.87-3.99 (m, 4H), 4.41 (d, J=4.1 Hz, 2H), 5.27 (t, J=4.1 Hz, 1H), 7.07 (d, J=8.8 Hz, 1H), 7.12 (q, J=1.4 Hz, 1H), 7.40 (dd, J=8.8, 2.7 Hz, 1H), 7.87 (d, J=2.7 Hz, 1H); MS (DCI/NH$_3$) m/z 369 (M+H)$^+$, Anal. Calculated for C$_{16}$H$_{17}$ClN$_2$O$_4$S: C, 52.10; H, 4.65; N, 7.60. Found: C, 52.15; H, 4.42; N, 7.44.

Example 213

5-chloro-N-[(2Z)-3-[2-(1,3-dioxolan-2-yl)ethyl]-5-methyl-1,3-thiazol-2(3H)-ylidene]-2-methoxybenzamide

Example 213A 3-(2-(1,3-dioxolan-2-yl)ethyl)-5-methylthiazol-2(3H)-imine

A mixture of 2-amino-5-methylthiazole (1.0 g, 8.7 mmol) and 2-(2-bromoethyl)-1,3-dioxolane (1.1 mL, 8.7 mmol) was warmed to 85° C. and was allowed to stir for 18 hours. The mixture was cooled to ambient temperature and purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 215 (M+H)$^+$.

Example 213B 5-chloro-N-[(2Z)-3-[2-(1,3-dioxolan-2-yl)ethyl]-5-methyl-1,3-thiazol-2(3H)-ylidene]-2-methoxybenzamide Example 213A (0.25 g, 1.2 mmol), triethylamine (0.49 mL, 3.5 mmol) and Example 205B (1.3 mmol) in 10 mL of tetrahydrofuran were processed as in Example 208D to afford the title compound. $^1$H NMR (300 MHz, CD$_3$OD) δ ppm 2.18-2.25 (m, 2H), 2.33 (d, J=1.0 Hz, 3H), 3.82-3.87 (m, 2H), 3.86 (s, 3H), 3.93-4.01 (m, 2H), 4.36 (dd, J=7.1 Hz, 2H), 4.93 (t, J=4.4 Hz, 1H), 7.07 (d, J=8.8 Hz, 1H), 7.10 (q, J=1.4 Hz, 1H), 7.40 (dd, J=8.8, 2.7 Hz, 1H), 7.96 (d, J=3.1 Hz, 1H); MS (DCI/NH$_3$) m/z 383 (M+H)$^+$. Anal. Calculated for C$_{17}$H$_{19}$ClN$_2$O$_4$S: C, 53.33; H, 5.00; N, 7.32. Found: C, 53.02; H, 4.52; N, 7.22.

Example 214

N-[(2Z)-3-(1,3-dioxolan-2-ylmethyl)-5-methyl-1,3-thiazol-2(3H)-ylidene]-2-ethoxybenzamide Example 212A (0.20 g, 1.0 mmol), triethylamine (0.42 mL, 3.0 mmol) and 2-ethoxybenzoyl chloride (0.17 g, 1.1 mmol) in 10 mL of tetrahydrofuran were processed as in Example 208D to afford the title compound. $^1$H NMR (300 MHz, CD$_3$OD) δ ppm 1.41 (t, J=7.0 Hz, 3H), 2.33 (d, J=1.4 Hz, 3H), 3.82-4.01 (m, 4H), 4.12 (q, J=6.9 Hz, 2H), 4.40 (d, J=4.4 Hz, 2H), 5.27 (t, J=4.2 Hz, 1H), 6.96 (dt, J=7.5, 0.8 Hz, 1H), 7.05 (d, J=8.5 Hz, 1H), 7.09 (q, J=1.4 Hz, 1H), 7.39 (ddd, J=8.7, 6.9, 1.7 Hz, 1H), 7.83 (dd, J=7.6, 1.9 Hz, 1H); MS (DCI/NH$_3$) m/z 349 (M+H)$^+$. Anal. Calculated for C$_{17}$H$_{20}$N$_2$O$_4$S: C, 58.60; H, 5.79; N, 8.04. Found: C, 58.22; H, 5.32; N, 7.93.

Example 215

5-bromo-2-ethoxy-N-[(2Z)-5-methyl-3-[(2R)-tetrahydrofuran-2-ylmethyl]-1,3-thiazol-2(3H)-ylidene]benzamide

Example 215A 5-bromo-2-ethoxybenzoic acid

To a solution of 2-ethoxybenzoic acid (3.3 g, 20.0 mmol) in 75 mL of acetonitrile at 0° C. was added N-bromosuccinimide (3.7 g, 21 mmol) in 15 mL of acetonitrile. The reaction mixture was warmed to ambient temperature and the mixture was allowed to stir for 48 hours. The mixture was quenched with 20 mL of H$_2$O and the layers were separated. The aqueous layer was extracted with three 15 mL portions of CH$_2$Cl$_2$ and the combined organic extracts were dried over anhydrous Na$_2$SO$_4$, filtered and concentrated under reduced pressure. Purification via column chromatography (SiO$_2$, 10% hexanes in ethyl acetate) afforded the title compound. MS (DCI/NH$_3$) m/z 262, 264 (M+NH$_4$)$^+$.

Example 215B 5-bromo-2-ethoxybenzoyl chloride

A solution of Example 215A (0.21 g, 0.86 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 215C 5-bromo-2-ethoxy-N-[(2Z)-5-methyl-3-[(2R)-tetrahydrofuran-2-ylmethyl]-1,3-thiazol-2(3H)-ylidene]benzamide Example 208B (0.17 g, 0.86 mmol), triethylamine (0.36 mL, 2.6 mmol) and Example 215B (0.86 mmol) in 10 mL of tetrahydrofuran were processed as in Example 208D to afford the title compound. $^1$H NMR (300 MHz, CD$_3$OD) δ ppm 1.39 (t, J=7.0 Hz, 3H), 1.63-1.78 (m, 1H), 1.84-1.96 (m, 2H), 2.00-2.15 (m, 1H), 2.34 (d, J=1.4 Hz, 3H), 3.69-3.81 (m, 1H), 3.84-3.95 (m, 1H), 4.10 (q, J=7.0 Hz, 2H), 4.19-4.43 (m, 3H), 6.99 (d, J=8.8 Hz, 1H), 7.14 (q, J=1.2 Hz, 1H), 7.49 (dd, J=8.8, 2.7 Hz, 1H), 7.87 (d, J=2.7 Hz, 1H); MS (DCI/NH$_3$) m/z 425, 427 (M+H)$^+$. Anal. Calculated for C$_{18}$H$_{21}$BrN$_2$O$_3$S: C, 50.83; H, 4.98; N, 6.59. Found: C, 50.89; H, 4.87; N, 6.51.

Example 216

5-chloro-2-ethoxy-N-[(2Z)-5-methyl-3-[(2R)-tetrahydrofuran-2-ylmethyl]-1,3-thiazol-2(3H)-ylidene]benzamide

Example 216A 5-chloro-2-ethoxybenzoic acid

To a solution of 2-ethoxybenzoic acid (4.4 g, 26.6 mmol) in 80 mL of acetonitrile at 0° C. was added N-chlorosuccinimide (3.7 g, 28 mmol) in 20 mL of acetonitrile dropwise over 30 minutes. The reaction mixture was warmed to ambient temperature and the mixture was allowed to stir for 70 hours. The mixture was quenched with 20 mL of H$_2$O and the layers were separated. The aqueous layer was extracted with three 15 mL portions of CH$_2$Cl$_2$ and the combined organic extracts were dried over anhydrous Na$_2$SO$_4$, filtered and concentrated under reduced pressure. Purification via recrystallization with ether and hexanes afforded the title compound. MS (DCI/NH$_3$) m/z 201 (M+H)$^+$, 218 (M+NH$_4$)$^+$.

Example 216B

5-chloro-2-ethoxybenzoyl chloride

A solution of Example 216A (0.25 g, 1.0 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 216C

5-chloro-2-ethoxy-N-[(2Z)-5-methyl-3-[(2R)-tetrahydrofuran-2-ylmethyl]-1,3-thiazol-2(3H)-ylidene]benzamide Example 208B (0.20 g, 1.0 mmol), triethylamine (0.42 mL, 3.0 mmol) and Example 216B (1.0 mmol) in 10 mL of tetrahydrofuran were processed as in Example 208D to afford the title compound. $^1$H NMR (300 MHz, CD$_3$OD) δ ppm 1.39 (t, J=7.0 Hz, 3H), 1.62-1.77 (m, 1H), 1.83-1.97 (m, 2H), 1.99-2.14 (m, 1H), 2.34 (d, J=1.4 Hz, 3H), 3.70-3.80 (m, 1H), 3.84-3.93 (m, 1H), 4.10 (q, J=6.9 Hz, 2H), 4.20-4.44 (m, 3H), 7.04 (d, J=8.8 Hz, 1H), 7.14 (q, J=1.4 Hz, 1H), 7.35 (dd, J=8.8, 2.7 Hz, 1H), 7.73 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.36; H, 5.28; N, 7.25.

Example 217

4-chloro-2-methoxy-N-[(2Z)-5-methyl-3-(tetrahydrofuran-2-ylmethyl)-1,3-thiazol-2(3H)-ylidene]benzamide

Example 217A

4-chloro-2-methoxybenzoyl chloride

A solution of the 4-chloro-2-methoxybenzoic acid (0.24 g, 1.3 mmol) in 7 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 217B

4-chloro-2-methoxy-N-[(2Z)-5-methyl-3-(tetrahydrofuran-2-ylmethyl)-1,3-thiazol-2(3H)-ylidene]benzamide Example 204A (0.20 g, 1.0 mmol), triethylamine (0.42 mL, 3.0 mmol) and Example 217A (1.3 mmol) in 15 mL of tetrahydrofuran and 1 mL of N,N-dimethylformamide were processed as in Example 208D to afford the title compound. $^1$H NMR (300 MHz, CDCl$_3$) δ ppm 1.61-1.74 (m, 1H), 1.77-1.98 (m, 2H), 1.99-2.14 (m, 1H), 2.30 (d, J=1.4 Hz, 3H), 3.72-3.82 (m, 1H), 3.82-3.90 (m, 1H), 3.91 (s, 3H), 4.11-4.20 (m, 1H), 4.27 (ddd, J=13.7, 6.8, 2.9 Hz, 1H), 4.41-4.51 (m, 1H), 6.87-6.91 (m, 1H), 6.93-6.99 (m, 2H), 7.97 (d, J=8.8 Hz, 1H); MS (DCI/NH$_3$) m/z 367 (M+H)$^+$. Anal. Calculated for C$_{17}$H$_{19}$ClN$_2$O$_3$S: C, 55.66; H, 5.22; N, 7.64. Found: C, 55.40; H, 5.31; N, 7.48.

Example 218

5-chloro-2-methoxy-N-[(2Z)-1-(2-methoxyethyl)-1,4,6,7-tetrahydro-2H-pyrano[4,3-d][1,3]thiazol-2-ylidene]benzamide

Example 218A

6,7-dihydro-4H-pyrano[4,3-d][1,3]thiazol-2-amine

To a solution of tetrahydro-4H-pyran-4-one (Aldrich) (7.22 g, 72.11 mmol) in cyclohexane (70 mL) were added pyrrolidine (6.26 mL, 7.57 mmol) and p-toluenesulfonic acid monohydrate (13.72 mg, 0.07 mmol). The reaction mixture was refluxed for 3 hours with a Dean-Stark trap, cooled and concentrated. The residue was dissolved in methanol (20 mL) and then sulfur (2.31 g, 72.11 mmol) was added followed by a solution of cyanamide (3.03 g, 72.11 mmol) in methanol (5 mL) at 0° C. The reaction mixture was stirred at room temperature overnight, filtered, concentrated and purified by column chromatography using an Analogix® Intelliflash280™ (SiO$_2$, 0-5% methanol in dichloromethane) to afford the title compound. MS (ESI$^+$) m/z 157 (M+H)$^+$.

Example 218B

1-(2-methoxyethyl)-6,7-dihydro-1H-pyrano[4,3-d]thiazol-2(4H)-imine hydrobromide A mixture of product of Example 218A (1.0 g, 6.4 mmol) and 2-bromoethyl methyl ether (3.0 mL, 32.0 mmol) was processed according to the method of Example 2A to afford the title compound: MS (LC/MS) m/z 213 (M+H)$^+$.

Example 218C

5-chloro-2-methoxy-N-[(2Z)-1-(2-methoxyethyl)-1,4,6,7-tetrahydro-2H-pyrano[4,3-d][1,3]thiazol-2-ylidene]benzamide To a solution of Example 218B (150.0 mg, 0.51 mmol) in tetrahydrofuran (10 mL) was added N-(3-dimethylaminopropyl)-N-ethylcarbodiimide hydrochloride (97.0 mg, 0.51 mmol), 1-hydroxybenzotriazole (69.0 mg, 0.51 mmol), triethylamine (178.0 μL, 1.28 mmol), and 5-chloro-2-methoxybenzoic acid (Aldrich) (95.0 mg, 0.51 mmol). The mixture was stirred overnight at 80° C., and then diluted with ethyl acetate, washed with 1 M aqueous NaHCO$_3$, dried (Na$_2$SO$_4$), filtered and concentrated. Purification by preparative HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded the title compound. $^1$H NMR (300 MHz, dimethylsulfoxide-d$_6$) δ 2.75 (t, J=5.4 Hz, 2H), 3.25 (s, 3H), 3.69 (t, J=5.3 Hz, 2H), 3.80 (s, 3H), 3.95 (t, J=5.4 Hz, 1H), 4.27 (t, J=5.3 Hz, 2H), 4.58 (s, 2H), 7.12 (d, J=8.8 Hz, 1H), 7.46 (dd, J=9.0, 2.9 Hz, 1H), 7.69 (d, J=2.7 Hz, 1H); MS (ESI$^+$) m/z 383 (M+H)$^+$. Anal. Calculated for C$_{17}$H$_{19}$ClN$_2$O$_4$S: C, 53.33; H, 5.00; N, 7.32. Found: C, 53.21; H, 4.80; N, 7.27.

Example 219

5-bromo-2-methoxy-N-[(2Z)-5-methyl-3-[(2R)-tetrahydrofuran-2-ylmethyl]-1,3-thiazol-2(3H)-ylidene]benzamide

Example 219A 5-bromo-2-methoxybenzoic acid

To a solution of 2-methoxybenzoic acid (6 g, 39.4 mmol) in 80 mL of acetonitrile was added N-bromosuccinimide (7.4 g, 41.4 mmol) in 20 mL of acetonitrile. The reaction mixture was warmed to ambient temperature and the mixture was allowed to stir for 16 hours. Additional N-bromosuccinimide (14.8 g, 82.8 mmol) was added and the reaction mixture stirred for an additional 48 hours. The mixture was quenched with 25 mL of $H_2O$ and the layers were separated. The aqueous layer was extracted with three 15 mL of portions of $CH_2Cl_2$ and the combined organic extracts were dried over anhydrous $Na_2SO_4$, filtered and concentrated under reduced pressure. Purification via column chromatography ($SiO_2$, 50% hexanes in ethyl acetate) afforded the title compound. MS ($DCI/NH_3$) m/z 248, 250 $(M+NH_4)^+$.

Example 219B 5-bromo-2-methoxybenzoyl chloride

A solution of Example 219A (0.28 g, 1.4 mmol) in 5 mL of $SOCl_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 219C 5-bromo-2-methoxy-N-[(2Z)-5-methyl-3-[(2R)-tetrahydrofuran-2-ylmethyl]-1,3-thiazol-2(3H)-ylidene]benzamide Example 208B (0.25 g, 1.3 mmol), triethylamine (0.53 mL, 3.8 mmol) and Example 219B (1.4 mmol) in 15 mL of tetrahydrofuran were processed as in Example 208D to afford the title compound. $^1$H NMR (300 MHz, $CD_3OD$) δ ppm 1.65-1.80 (m, 1H), 1.85-1.96 (m, 2H), 2.01-2.14 (m, 1H), 2.34 (d, J=1.4 Hz, 3H), 3.71-3.80 (m, 1H), 3.85 (s, 3H), 3.85-3.93 (m, 1H), 4.21-4.41 (m, 3H), 7.02 (d, J=9.2 Hz, 1H), 7.14 (q, J=1.1 Hz, 1H), 7.53 (dd, J=8.8, 2.7 Hz, 1H), 7.95 (d, J=2.4 Hz, 1H); MS ($DCI/NH_3$) m/z 411, 413 $(M+H)^+$. Anal. Calculated for $C_{17}H_{19}BrN_2O_3S$: C, 49.64; H, 4.66; N, 6.81. Found: C, 49.48; H, 4.53; N, 6.72.

Example 220

5-chloro-2-methoxy-N-[(2Z)-5-methyl-3-(2-tetrahydro-2H-pyran-4-ylethyl)-1,3-thiazol-2(3H)-ylidene]benzamide

Example 220A 2-(tetrahydro-2H-pyran-4-yl)ethyl 4-methylbenzenesulfonate

To a solution of 2-(tetrahydropyran-4-yl)-ethanol (1.5 g, 11.5 mmol) in 10 mL of $CH_2Cl_2$ and 7 mL of pyridine was added p-toluenesulfonyl chloride (2.4 g, 12.7 mmol) portion wise over 15 minutes. The mixture stirred at ambient temperature for 3 hours and was quenched with 10 mL of saturated, aqueous $NaHCO_3$. The layers were separated and the aqueous layer was extracted with three 5 mL of portions of $CH_2Cl_2$. The combined organic extracts were dried over anhydrous $Na_2SO_4$, filtered and concentrated under reduced pressure. Purification via column chromatography ($SiO_2$, 70% hexanes in ethyl acetate) afforded the title compound. MS ($DCI/NH_3$) m/z 302 $(M+NH_4)^+$.

Example 220B 5-methyl-3-(2-(tetrahydro-2H-pyran-4-yl)ethyl)thiazol-2(3H)-imine A mixture of Example 220A (1.9 g, 6.7 mmol), 2-amino-5-methylthiazole (0.77 g, 6.7 mmol) and tetrabutylammonium iodide (1.1 g, 3.3 mmol) in 2 mL of N,N-dimethylformamide was warmed of 10 to 85° C. and was allowed to stir for 18 hours. The mixture was diluted with 10 mL of $CH_2Cl_2$, washed with 10 mL of 10% aqueous $NaHCO_3$, dried over anhydrous $Na_2SO_4$, filtered and concentrated under reduced pressure. Purification via column chromatography ($SiO_2$, 10% methanol in ethyl acetate then 9:1:0.1 $CH_2Cl_2$:methanol:$NH_4OH$) afforded the title compound. MS ($DCI/NH_3$) m/z 227 $(M+H)^+$.

Example 220C 5-chloro-2-methoxy-N-[(2Z)-5-methyl-3-(2-tetrahydro-2H-pyran-4-ylethyl)-1,3-thiazol-2(3H)-ylidene]benzamide Example 220B (0.20 g, 0.9 mmol), triethylamine (0.37 mL, 0.26 mmol) and Example 205B (0.9 mmol) in 10 mL of tetrahydrofuran were processed as in Example 208D to afford the title compound. $^1$H NMR (300 MHz, $CD_3OD$) δ ppm 1.26-1.44 (m, 2H), 1.47-1.65 (m, 1H), 1.71-1.89 (m, 4H), 2.34 (d, J=1.4 Hz, 3H), 3.32-3.41 (m, 2H), 3.86 (s, 3H), 3.86-3.94 (m, 2H), 4.26-4.35 (m, 2H), 7.07 (d, J=8.8 Hz, 1H), 7.14 (q, J=1.4 Hz, 1H), 7.40 (dd, J=9.0, 2.9 Hz, 1H), 7.89 (d, J=3.1 Hz, 1H); MS ($DCI/NH_3$) m/z 395 $(M+H)^+$. Anal. Calculated for $C_{19}H_{23}ClN_2O_3S$: C, 57.79; H, 5.87; N, 7.09. Found: C, 57.54; H, 5.67; N, 7.07.

Example 221

5-chloro-N-[(2Z)-5-ethyl-3-(tetrahydrofuran-2-ylmethyl)-1,3-thiazol-2(3H)-ylidene]-2-methoxybenzamide

Example 221A 5-ethyl-3-((tetrahydrofuran-2-yl)methyl)thiazol-2(3H)-imine

A mixture of 5-ethylthiazol-2-amine and 2-(bromomethyl)tetrahydrofuran were processed using the method described in Example 2A to afford the title compound. MS (ESI) m/z 213 $(M+H)^+$.

Example 221B 5-chloro-N-[(2Z)-5-ethyl-3-(tetrahydrofuran-2-ylmethyl)-1,3-thiazol-2(3H)-ylidene]-2-methoxybenzamide Example 221A and 5-chloro-2-methoxybenzoic acid were processed using the method described in Example 2B to afford the title compound. $^1$H NMR (500 MHz, dimethylsulfoxide-$d_6$) δ ppm 1.21 (t, J=7.63 Hz, 3H) 1.59-1.68 (m, 1H) 1.77-1.85 (m, 2H) 1.89-1.97 (m, 1H) 2.67 (dd, J=15.56, 7.63 Hz, 2H) 3.65 (dd, J=14.95, 7.02 Hz, 1H) 3.75-3.82 (m, 1H) 3.78 (s, 3H) 4.13-4.24 (m, 2H) 4.24-4.30 (m, 1H) 7.10 (d, J=8.85 Hz, 1H) 7.26 (t, J=1.22 Hz, 1H), 7.44 (dd, J=8.85, 2.75 Hz, 1H) 7.64 (d, J=2.75 Hz, 1H); MS (ESI) m/z 381 (M+H)$^+$.

Example 222

5-chloro-2-methoxy-N-[(2Z)-5-propyl-3-(tetrahydrofuran-2-ylmethyl)-1,3-thiazol-2(3H)-ylidene]benzamide Example 222A 5-propyl-3-((tetrahydrofuran-2-yl)methyl)thiazol-2(3H)-imine A mixture of 5-propylthiazol-2-amine and 2-(bromomethyl)tetrahydrofuran were processed using the method described in Example 2A to afford the title compound. MS (ESI) m/z 227 (M+H)$^+$.

Example 222B 5-chloro-2-methoxy-N-[(2Z)-5-propyl-3-(tetrahydrofuran-2-ylmethyl)-1,3-thiazol-2(3H)-ylidene]benzamide Example 222A and 5-chloro-2-methoxybenzoic acid were processed using the method described in Example 2B to afford the title compound. $^1$H NMR (500 MHz, dimethylsulfoxide-$d_6$) δ ppm 0.93 (t, J=7.32 Hz, 3H) 1.56-1.67 (m, 3H) 1.77-1.85 (m, 2H) 1.93 (dt, J=19.22, 7.02 Hz, 1H) 2.62 (t, J=7.02 Hz, 2H) 3.65 (dd, J=14.95, 6.71 Hz, 1H) 3.74-3.80 (m, 1H) 3.77-3.79 (m, 3H) 4.15-4.24 (m, 2H) 4.24-4.30 (m, 1H) 7.10 (d, J=8.85 Hz, 1H) 7.25-7.28 (m, 1H) 7.44 (dd, J=8.85, 2.75 Hz, 1H) 7.64 (d, J=2.75 Hz, 1H); MS (ESI) m/z 395 (M+H)$^+$.

Example 223

5-chloro-N-[(2Z)-5-chloro-3-(tetrahydrofuran-2-ylmethyl)-1,3-thiazol-2(3H)-ylidene]-2-methoxybenzamide Example 223A 5-chloro-N-(5-chlorothiazol-2-yl)-2-methoxybenzamide A mixture of 5-chlorothiazol-2-amine hydrochloride (513 mg, 3 mmol), 5-chloro-2-methoxybenzoic acid (670 mg, 3.6 mmol), 1-ethyl-3-[3-(dimethylamino)propyl]-carbodiimide hydrochloride (1.15 g, 6 mmol), 1-hydroxybenzotriazole hydrate (810 mg, 6 mmol) and 4-(dimethylamino)pyridine (73 mg, 0.6 mmol) in pyridine was stirred at room temperature for 2 hours. The volatiles were removed under vacuum, and the resulting mixture was diluted with water and extracted with ethyl acetate. The organic extract was dried ($Na_2SO_4$), filtered and concentrated. The residue was washed with a small amount of ethyl acetate, and filtered to afford the title compound. MS (ESI) m/z 303 (M+H)$^+$.

Example 223B 5-chloro-N-[(2Z)-5-chloro-3-(tetrahydrofuran-2-ylmethyl)-1,3-thiazol-2(3H)-ylidene]-2-methoxybenzamide Example 223A (250 mg, 0.83 mmol) in tetrahydrofuran/N,N-dimethylformamide (1:2) (9 mL) was treated with NaH (60%) (40 mg, 1.0 mmol) for 10 minutes then 2-mL) was treated with NaH (60%) (40 mg, 1.0 mmol) for 10 minutes then 2-(bromomethyl)tetrahydrofuran (164 mg, 1.0 mmol) was added. The mixture was heated at 150° C. for ethyl acetate. The organic extract was dried ($Na_2SO_4$), filtered and concentrated. Purification by reverse phase HPLC afforded the title compound. $^1$H NMR (400 MHz, dimethylsulfoxide-$d_6$) δ ppm 1.60-1.70 (m, 1H) 1.79-1.89 (m, 2H) 1.92-2.01 (m, 1H) 3.66 (dd, J=15.04, 7.06 Hz, 1H) 3.76-3.83 (m, 1H) 3.79-3.81 (m, 3H) 4.15-4.23 (m, 1H) 4.24-4.33 (m, 2H) 7.14 (d, J=8.90 Hz, 1H) 7.49 (dd, J=8.90, 2.76 Hz, 1H) 7.74 (d, J=3.07 Hz, 1H) 7.77 (s, 1H). MS (ESI) m/z 387 (M+H)$^+$.

Example 224

4,5-dichloro-2-methoxy-N-[(2Z)-5-methyl-3-[(2R)-tetrahydrofuran-2-ylmethyl]-1,3-thiazol-2(3H)-ylidene]benzamide Example 224A 4,5-dichloro-2-methoxybenzoic acid To a solution of 4-chloro-2-methoxybenzoic acid (5 g, 26.8 mmol) in 200 mL of acetonitrile ambient temperature and was quenched with 50 mL of $H_2O$. The layers were separated and the aqueous layer was extracted with three 25 mL portions of $CH_2Cl_2$. The combined organic extracts were dried over anhydrous $Na_2SO_4$, filtered and concentrated under reduced pressure. Purification via column chromatography ($SiO_2$, 25% hexanes in ethyl acetate) afforded the title compound. MS (DCI/$NH_3$) m/z 238 (M+$NH_4$)$^+$.

Example 224B 4,5-dichloro-2-methoxybenzoyl chloride

A solution of Example 224A (0.18 g, 0.81 mmol) in 5 mL of $SOCl_2$ was warmed to reflux and under reduced pressure. The crude material was diluted with 5 mL of toluene and concentrated under reduced pressure. This dilution with toluene and concentration was repeated two additional times to afford the title compound which was used without additional purification or characterization.

Example 224C 4,5-dichloro-2-methoxy-N-[(2Z)-5-methyl-3-[(2R)-tetrahydrofuran-2-ylmethyl]-1,3-thiazol-2(3H)-ylidene]benzamide Example 208B (0.16 g, 0.81 mmol), triethylamine (0.34 mL, 2.4 mmol) and Example 224B compound. $^1$H NMR (300 MHz, $CD_3OD$) δ ppm 1.64-1.79 (m, 1H), 1.83-1.96 (m, 2H), 2.03-2.15 (m, 1H), 2.34 (d, J=1.4 Hz, 3H), 3.70-3.80 (m, 1H), 3.83-3.93 (m, 1H), 3.87 (s, 3H), 4.20-4.44 (m, 3H), 7.15 (q, J=1.1 Hz, 1H), 7.26 (s, 1H), 7.99 (s, 1H); MS (DCI/NH$_3$) m/z 401 (M+H)$^-$. Anal. Calculated for C$_{17}$H$_{18}$Cl$_2$N$_2$O$_3$S: C, 50.88; H, 4.52; N, 6.98. Found: C, 50.63; H, 4.41; N, 6.83.

Example 225

5-chloro-2-methoxy-N-[(2Z)-5-methyl-3-(tetrahydro-2H-pyran-3-ylmethyl)-1,3-thiazol-2(3H)-ylidene]benzamide

Example 225A (tetrahydro-2H-pyran-3-yl)methyl 4-methylbenzenesulfonate

To a solution of (tetrahydropyran-3-yl)-methanol (Matrix, 1.67 g, 14.4 mmol) in 15 mL of CH$_2$Cl$_2$ and 15 mL of pyridine was added p-toluenesulfonyl chloride (2.9 g, 15.1 mmol) in portions over 10 minutes. The mixture stirred at ambient temperature for 18 hours and was quenched with 10 mL of saturated, aqueous NaHCO$_3$. The layers were separated and the aqueous phase was extracted three 5 mL of portions of CH$_2$Cl$_2$. The combined organic extracts were dried over anhydrous Na$_2$SO$_4$, filtered and concentrated under reduced pressure. Purification via column chromatography (SiO$_2$, 70% hexanes in ethyl acetate) afforded the title compound. MS (DCI/NH$_3$) m/z 288 (M+NH$_4$)$^+$.

Example 225B 5-methyl-3-((tetrahydro-2H-pyran-3-yl)methyl)thiazol-2(3H)-imine A mixture of Example 225A (1.0 g, 3.7 mmol), 2-amino-5-methylthiazole (0.42 g, 3.7 mmol) and tetrabutylammonium iodide (0.68 g, 1.85 mmol) in 1 mL of N,N-dimethylformamide was warmed to 85° C. and was allowed to stir for 16 hours. The mixture was diluted with 10 mL of CH$_2$Cl$_2$, washed with 10 mL of 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 213 (M+H)$^+$.

Example 225C 5-chloro-2-methoxy-N-[(2Z)-5-methyl-3-(tetrahydro-2H-pyran-3-ylmethyl)-1,3-thiazol-2(3H)-ylidene]benzamide Example 225B (0.19 g, 0.89 mmol), triethylamine (0.29 mL, 2.1 mmol) and Example 205B (0.63 mmol) in 10 mL of tetrahydrofuran were processed as in Example 208D to afford the title compound. $^1$H NMR (300 MHz, CD$_3$OD) δ ppm 1.33-1.49 (m, 1H), 1.50-1.67 (m, 1H), 1.69-1.86 (m, 2H), 2.20-2.32 (m, 1H), 2.34 (d, J=1.4 Hz, 3H), 3.32-3.38 (m, 1H), 3.50 (ddd, J=11.5, 9.5, 3.1 Hz, 1H), 3.72-3.82 (m, 2H), 3.86 (s, 3H), 4.17 (d, J=7.5 Hz, 2H), 7.07 (d, J=8.8 Hz, 1H), 7.11 (q, J=1.4 Hz, 1H), 7.40 (dd, J=8.8, 2.7 Hz, 1H), 7.85 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.84; H, 5.32; N, 7.29.

Example 226

2-chloro-N-[(2Z)-4,5-dimethyl-3-(tetrahydrofuran-2-ylmethyl)-1,3-thiazol-2(3H)-ylidene]nicotinamide A mixture of Example 186A (0.15 g), 2-chloronicotinic acid (99 mg), 1-hydroxybenzotriazole hydrate (80 mg), 1-ethyl-3-[3-(dimethylamino)propyl]-carbodiimide hydrochloride (120 mg) and triethylamine (0.15 mL) in N,N-dimethylformamide was stirred overnight at room temperature, poured into water and extracted with ether (3×). The combined organic extracts were dried (Na$_2$SO$_4$), filtered and the solvent evaporated. The crude material was purified by gradient flash chromatography over silica gel eluting with ethyl acetate:hexane (1:4 to 1:1) to afford the title compound. $^1$H NMR (300 MHz, dimethylsulfoxide-d$_6$) δ ppm 1.65 (m, 1H), 1.85 (m, 2H), 2.0 (m, 1H), 2.25 (s, 3H), 2.28 (s, 3H), 3.62 (dd, 1H), 3.77 (dd, 1H), 4.08 (dd, 1H), 4.28 (m, 1H), 4.38 (dd, 1H), 7.50 (dd, 1H), 8.24 (dd, 1H), 8.45 (dd, 1H); MS (ESI+) m/z 352 (M+H)$^+$.

Example 227

5-chloro-N-[(2Z)-4,5-dimethyl-3-[(3-methyl-4,5-dihydroisoxazol-5-yl)methyl]-1,3-thiazol-2(3H)-ylidene]-2-methoxybenzamide

Example 227A 3-allyl-4,5-dimethylthiazol-2(3H)-imine hydrobromide

A mixture of 4,5-dimethyl-1,3-thiazol-2-amine (1 g) and allylbromide (0.95 g) in toluene (5 mL) was heated to 85° C. for 12 hours, cooled, diluted with ether, filtered and the solvent was evaporated to afford crude product that was taken on to the next step without further characterization.

Example 227B (Z)—N-(3-allyl-4,5-dimethylthiazol-2(3H)-ylidene)-5-chloro-2-methoxybenzamide A mixture of Example 227A (1.3 g), Example 205B (1.36 g) and triethylamine (1.0 g) in tetrahydrofuran (40 mL) was heated to 60° C. for 4 hours, cooled and solvent was evaporated. The crude material was triturated with ether, filtered and solvent evaporated. The crude was flash chromatographed over silica gel gradient eluting with ethyl acetate: hexane (2:3 to 3:2) to afford the title compound. $^1$H NMR (300 MHz, dimethylsulfoxide-d$_6$) δ ppm 2.22 (s, 3H), 2.23 (s, 3H), 3.78 (s, 3H), 4.85 (m, 2H), 4.96, (dq, J=17.3, 1.3 Hz, 1H), 5.19 (dq, J=10.5, 1.3 Hz, 1H), 5.92-6.05 (m, 1H), 7.10 (d, 1H), 7.44 (dd, 1H), 7.66 (d, 1H); MS (ESI+) m/z 337 (M+H)$^+$.

Example 227C 5-chloro-N-[(2Z)-4,5-dimethyl-3-[(3-methyl-4,5-dihydroisoxazol-5-yl)methyl]-1,3-thiazol-2(3H)-ylidene]-2-methoxybenzamide To a solution of acetaldoxime (56 mg, 1.48 mmol) in CHCl$_3$ (10 mL) under N$_2$ was added N-chlorosuccinimide (200 mg) and pyridine (10 µL). After 4.5 hours at room temperature, Example 227B (100 mg) was added, followed by triethylamine (0.15 g) and the reaction continued to stir at room temperature for 21 hours. The reaction mixture was washed with water and partitioned. The aqueous layer was extracted again with $CH_2Cl_2$ and the combined organic extracts were dried ($MgSO_4$), filtered, and solvent evaporated. The crude was purified by flash chromatography over silica gel eluting with ethyl acetate:hexane (1:1) to afford the title compound. $^1H$ NMR (300 MHz, dimethylsulfoxide-$d_6$) δ ppm 1.93 (s, 3H), 2.23 (s, 6H), 2.90 (dd, 1H), 3.14 (dd, 1H), 3.79 (s, 3H), 4.11 (dd, 1H), 4.27, (dd, 1H), 4.98 (m, 1H), 7.11 (d, 1H), 7.44 (dd, 1H), 7.67 (d, 1H). MS (ESI+) m/z 394 $(M+H)^+$.

Example 228

N-[(2Z)-4,5-dimethyl-3-(tetrahydrofuran-2-ylmethyl)-1,3-thiazol-2(3H)-ylidene]-4-(trifluoromethyl)nicotinamide Example 186A (0.15 g) and 4-(trifluoromethyl)nicotinic acid (0.12 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1H$ NMR (300 MHz, dimethylsulfoxide-$d_6$) δ ppm 1.63 (m, 1H), 1.85 (m, 2H), 1.96 (m, 1H), 2.25 (s, 3H), 2.29 (s, 3H), 3.62 (dd, 1H), 3.77 (dd, 1H), 4.07 (dd, 1H), 4.25 (m, 1H), 4.38 (dd, 1H), 7.80 (d, 1H), 8.89 (d, 1H), 9.12 (s, 1H). MS (ESI+) m/z 386 $(M+H)^+$.

Example 229

N-[(2Z)-4,5-dimethyl-3-(tetrahydrofuran-2-ylmethyl)-1,3-thiazol-2(3H)-ylidene]-2-ethoxynicotinamide Example 186A (0.15 g) and 2-ethoxynicotinic acid (0.1 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1H$ NMR (300 MHz, dimethylsulfoxide-$d_6$) δ ppm 1.32 (t, 3H), 1.66 (m, 1H), 1.85 (m, 2H), 1.97 (m, 1H), 2.22 (s, 3H), 2.26 (s, 3H), 3.62 (dd, 1H), 3.78 (dd, 1H), 4.06 (dd, 1H), 4.3-4.42 (m, 3H), 7.02 (dd, 1H), 8.13 (dd, 1H), 8.22 (dd, 1H). MS (ESI+) m/z 362 $(M+H)^+$.

Example 230

N-[(2Z)-4,5-dimethyl-3-(tetrahydrofuran-2-ylmethyl)-1,3-thiazol-2(3H)-ylidene]-2,3,6-trifluoroisonicotinamide Example 186A (0.15 g) and 2,3,6-trifluoroisonicotinic acid (0.11 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1H$ NMR (300 MHz, dimethylsulfoxide-$d_6$) δ ppm 1.67 (m, 1H), 1.86 (m, 2H), 2.00 (m, 1H), 2.27 (s, 3H), 2.30 (s, 3H), 3.62 (dd, 1H), 3.78 (dd, 1H), 4.15 (dd, 1H), 4.28 (m, 1H), 4.43 (dd, 1H), 7.57 (t, 1H). MS (ESI+) m/z 372 $(M+H)^+$.

Example 231

6-chloro-N-[(2Z)-4,5-dimethyl-3-(tetrahydrofuran-2-ylmethyl)-1,3-thiazol-2(3H)-ylidene]-4-(trifluoromethyl)nicotinamide Example 186A (0.15 g) and 6-chloro-4-(trifluoromethyl)nicotinic acid (0.17 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1H$ NMR (300 MHz, dimethylsulfoxide-$d_6$) δ ppm 1.62 (m, 1H), 1.85 (m, 2H), 1.96 (m, 1H), 2.25 (s, 3H), 2.29 (s, 3H), 3.62 (dd, 1H), 3.77 (dd, 1H), 4.08 (dd, 1H), 4.24 (m, 1H), 4.38 (dd, 1H), 7.99 (s, 1H), 9.00 (s, 1H); MS (ESI+) m/z 420 $(M+H)^+$.

Example 232

5-chloro-2-methoxy-N-[(2Z)-5-methyl-3-[(3-methyl-4,5-dihydroisoxazol-5-yl)methyl]-1,3-thiazol-2(3H)-ylidene]benzamide Example 232A 3-allyl-5-methylthiazol-2(3H)-imine hydrobromide A mixture of 2-amino-5-methylthiazole (2.5 g) and allylbromide (3.31 g) was processed according to the method of Example 227A to afford the title compound that was taken directly to the next step. MS (ESI+) m/z 155 $(M+H)^+$.

Example 232B (Z)—N-(3-allyl-5-methylthiazol-2(3H)-ylidene)-5-chloro-2-methoxybenzamide A mixture of Example 232A (0.5 g) and 5-chloro-2-methoxybenzoylchloride (0.57 g) were processed according to the method of Example 227B to afford the title compound. $^1H$ NMR (300 MHz, dimethylsulfoxide-$d_6$) δ ppm 2.28 (d, J=1.4 Hz, 3H), 3.78 (s, 3H), 4.77 (d, 2H), 5.13 (dq, J=16.9, 1.3 Hz, 1H), 5.24 (dq, J=10.5, 1.4 Hz, 2H), 5.94-6.07 (m, 1H), 7.11 (d, 1H), 7.23 (q, J=1.4 Hz, 1H), 7.43 (dd, 1H), 7.68 (d, 1H); MS (ESI+) m/z 323 $(M+H)^+$.

Example 232C 5-chloro-2-methoxy-N-[(2Z)-5-methyl-3-[(3-methyl-4,5-dihydroisoxazol-5-yl)methyl]-1,3-thiazol-2(3H)-ylidene]benzamide Example 232B was processed according to the method of Example 227C to afford the title compound. $^1H$ NMR (300 MHz, dimethylsulfoxide-$d_6$) δ ppm 1.90 (s, 3H), 2.28 (s, 3H), 2.87 (dd, 1H), 3.11 (dd, 1H), 4.23 (d, 2H), 4.94 (m, 1H), 7.11 (d, 1H), 7.25 (s, 1H), 7.45 (dd, 1H), 7.67 (d, 1H); MS (ESI+) m/z 380 (M+H)$^+$.

Example 233

N-[(2Z)-4,5-dimethyl-3-(tetrahydrofuran-2-ylmethyl)-1,3-thiazol-2(3H)-ylidene]-2-(ethylamino)benzamide Example 186A (0.15 g) and 2-ethylaminobenzoic acid (Pellon *Syn. Lett.* 2005, 10, 1606) (0.1 g) were processed according to the method of Example 226. The crude was purified by flash chromatography over silica gel gradient eluting with ethyl acetate:hexane (1:9 to 1:3) to afford the title compound. $^1$H NMR (300 MHz, dimethylsulfoxide-d$_6$) δ ppm 1.25 (t, 3H), 1.70 (m, 1H), 1.87 (m, 2H), 2.01 (m, 1H), 2.20 (s, 3H), 2.26 (s, 3H), 3.20 (m, 2H), 3.62 (dd, 1H), 3.79 (dd, 1H), 4.12 (dd, 1H), 4.28 (m, 1H), 4.38 (dd, 1H), 6.55 (t, 1H), 6.67 (d, 1H), 7.27 (t, 1H), 8.22 (dd, 1H), 8.52 (t, 1H); MS (ESI+) m/z 360 (M+H)$^+$.

Example 234

N-[(2Z)-4,5-dimethyl-3-(tetrahydrofuran-2-ylmethyl)-1,3-thiazol-2(3H)-ylidene]-5-iodo-2-(methylamino)benzamide Example 186A (0.15 g) and 5-iodo-2-methylaminobenzoic acid (0.17 g) were processed according to the method of Example 226. The crude was purified by flash chromatography over silica gel gradient eluting with ethyl acetate:hexane (1:19 to 1:10) to afford the title compound. $^1$H NMR (300 MHz, dimethylsulfoxide-d$_6$) δ ppm 1.7-1.82 (m, 1H), 1.84-1.95 (m, 2H), 1.95-2.08 (m, 1H), 2.22 9 s, 3H), 2.27 (s, 3H), 2.84 (d, 3H), 3.65 (dd, 1H), 3.82 (dd, 1H), 4.12 (dd, 4.28 (m, 1H), 4.36 (dd, 1H), 6.52 (d, 1H), 7.53 (dd, 1H), 8.46 (d, 1H), 8.52 (q, 1H); MS (ESI+) m/z 472 (M+H)$^+$.

Example 235

5-bromo-N-[(2Z)-5-tert-butyl-3-[(2R)-tetrahydrofuran-2-ylmethyl]-1,3-thiazol-2(3H)-ylidene]-2-methoxybenzamide To a mixture of 3,3-dimethylbutyraldehyde (Aldrich) (5 mL, 39.8 mmol) and Example 278A (641.0 mg, 4.0 mmol) was added a mixture of dimethylsulfoxide (560 µL, 8 mmol) and 12 N aqueous HCl (667 µL, 8 mmol). The reaction mixture was heated at 40° C. overnight. The mixture was concentrated and the residue was dried under vacuum for 2 hours. The residue (252 mg 0.9 mmol) was dissolved in tetrahydrofuran (10 mL). To this solution was added 5-bromo-2-methoxy-benzoic acid (209.0 mg, 0.9 mmol), N-(3-dimethylaminopropyl)-N-ethylcarbodiimide hydrochloride (73 mg, 0.9 mmol), 1-hydroxybenzotriazole (122.0 mg, 0.9 mmol) and triethylamine (315.0 µL, 2.3 mmol). The mixture was stirred overnight at 80° C., and cooled to room temperature. The mixture was diluted with ethyl acetate, washed with 1 M aqueous NaHCO$_3$, dried (Na$_2$SO$_4$), filtered and concentrated. The residue was purified by flash chromatography using an Analogix® Intelliflash280™ (SiO$_2$, 0-75% ethyl acetate in hexanes) to afford the title compound. $^1$H NMR (300 MHz, dimethylsulfoxide-d$_6$) δ 1.32 (s, 9H), 1.58-1.71 (m, 1H), 1.75-1.86 (m, 2H), 1.87-2.00 (m, 1H), 3.64 (dd, J=15, 6.8 Hz, 1H), 3.78 (s, 3H), 3.79-3.83 (m, 1H), 4.19 (d, J=5.8 Hz, 2H), 4.23-4.35 (m, 1H), 7.05 (d, J=8.8 Hz, 1H), 7.25 (s, 1H), 7.56 (dd, J=8.8, 2.7 Hz, 1H), 7.76 (d, J=2.7 Hz, 1H.

Example 236

5-chloro-2-(cyclopropyloxy)-N-[(2Z)-5-methyl-3-[(2R)-tetrahydrofuran-2-ylmethyl]-1,3-thiazol-2(3H)-ylidene]benzamide

Example 236A methyl 5-chloro-2-(2-chloroethoxy)benzoate

A mixture of methyl-5-chlorosalicylate (19.5 g, 105 mmol), 2-chloroethyl p-toluenesulfonate (19.3 mL, 107 mmol) and K$_2$CO$_3$ (28.9 g, 210 mmol) in 105 mL of N,N-dimethylformamide was warmed to 50° C. and allowed to stir for 18 hours. The mixture was cooled to ambient temperature, diluted with 25 mL of ethyl acetate and 25 mL of H$_2$O. The layers were separated and the organic layer was dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 249 (M+H)$^+$, 266 (M+NH$_4$)$^+$.

Example 236B 5-chloro-2-(vinyloxy)benzoic acid

To Example 236A (15 g, 60 mmol) in 100 mL of tetrahydrofuran at 0° C. was added potassium t-butoxide (8.9 g, 75.6 mmol) portion wise with the internal reaction temperature being maintained below 5° C. After the addition was complete, the mixture was allowed to warm to ambient temperature and was allowed to stir for 18 hours. The mixture was diluted with 25 mL of H$_2$O and 25 mL of ethyl acetate and the layers were separated. The aqueous layer was acidified with 1 N aqueous HCl to pH 7 and was extracted with three 15 mL portions of ethyl acetate. These organic extracts (excluding the original organic layer before acidification) were combined and dried over anhydrous Na$_2$SO$_4$, filtered and concentrated under reduced pressure to afford the title compound. MS (DCI/NH$_3$) m/z 216 (M+NH$_4$)$^+$.

Example 236C methyl 5-chloro-2-(vinyloxy)benzoate

To Example 236B (5.1 g, 26 mmol) in 30 mL of N,N-dimethylformamide was added K$_2$CO$_3$ (10.7 g, 78 mmol) followed by CH$_3$I (1.8 mL, 29 mmol). The mixture stirred at ambient temperature for 3 hours and was diluted with 20 mL of H$_2$O and 20 mL of ether. The layers were separated and the aqueous layer was extracted twice with 10 mL of ether. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 213 (M+H)$^+$, 230 (M+NH$_4$)$^+$.

Example 236D methyl 5-chloro-2-cyclopropoxybenzoate

To a solution of Example 236C (1.29 g, 6.1 mmol) in 15 mL of dichloroethane at −5° C. was added chloro-iodomethane (1.4 mL, 19.4 mmol) A solution of diethylzinc (1M solution in hexanes, 9.7 mL, 9.7 mmol) was added dropwise over 1 hour using a syringe pump. After the addition was complete, the mixture was allowed to warm to ambient temperature and was stirred for 45 minutes. The mixture was cooled to 0° C. and quenched with 5 mL of saturated, aqueous NH$_4$Cl and 1 mL of concentrated NH$_4$OH. This mixture was diluted with 10 mL of ethyl acetate and the layers were separated. The aqueous layer was extracted twice with 10 mL of ethyl acetate and the combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 227 (M+H)$^+$, 244 (M+NH$_4$)$^+$.

Example 236E 5-chloro-2-cyclopropoxybenzoic acid

To a solution of Example 236D (1.24 g, 5.5 mmol) in 10 mL of ethanol at ambient temperature was added 5 mL of 40% aqueous KOH. The mixture was stirred at ambient temperature for 2 hours and was partially concentrated to remove the ethanol. The aqueous residue was extracted with three 10 mL of portions of CH$_2$Cl$_2$. The aqueous layer was acidified with 10% aqueous HCl to ~pH 1 and then extracted with three 10 mL of portions of CH$_2$Cl$_2$. The combined organic extracts (from both extractions) were dried over anhydrous Na$_2$SO$_4$, filtered and concentrated under reduced pressure to afford the title compound. MS (DCI/NH$_3$) m/z 213 (M+H)$^+$, 230 (M+NH$_4$)$^+$.

Example 236F 5-chloro-2-(cyclopropyloxy)-N-[(2Z)-5-methyl-3-[(2R)-tetrahydrofuran-2-ylmethyl]-1,3-thiazol-2(3H)-ylidene]benzamide A mixture of Example 236E (0.30 g, 1.4 mmol) and 1,1'-carbonyldiimidazole (0.27 g, 1.7 mmol) in 10 mL of ethyl acetate was stirred at ambient temperature for 4 hours. Example 208B (0.28 g, 1.4 mmol) in 2 mL of ethyl acetate and 2 mL of tetrahydrofuran was added and the mixture was warmed to reflux for 16 hours. The mixture was cooled to ambient temperature and was quenched with 10 mL of H$_2$O and 5 mL 5% aqueous HCl and was diluted with 10 mL of ethyl acetate. The layers were separated and the aqueous layer was extracted twice with 5 mL of ethyl acetate. The combined organic extracts were dried over anhydrous Na$_2$SO$_4$, filtered and concentrated under reduced pressure. Purification via column chromatography (SiO$_2$, 40% hexanes in ethyl acetate) afforded the title compound. $^1$H NMR (300 MHz, CD$_3$OD) δ ppm 0.76-0.82 (m, 2H), 1.63-1.77 (m, 1H), 1.84-1.96 (m, 2H), 2.01-2.14 (m, 1H), 2.33 (d, J=1.4 Hz, 3H), 3.69-3.93 (m, 4H), 4.18-4.43 (m, 4H), 7.13 (q, J=1.4 Hz, 1H), 7.38-7.41 (m, 2H), 7.74 (dd, J=2.0, 1.0 Hz, 1H); MS (DCI/NH$_3$) m/z 393 (M+H)$^+$. Anal. Calculated for C$_{19}$H$_{21}$ClN$_2$O$_3$S: C, 58.08; H, 5.39; N, 7.13. Found: C, 57.77; H, 5.45; N, 7.09.

Example 237

5-chloro-N-[(2Z)-3-(1,4-dioxan-2-ylmethyl)-5-methyl-1,3-thiazol-2(3H)-ylidene]-2-methoxybenzamide Example 237A 3-((1,4-dioxan-2-yl)methyl)-5-methylthiazol-2(3H)-imine A mixture of 2-amino-5-methylthiazole (0.77 g, 6.7 mmol) and 2-iodomethyl-1,4-dioxane (Synchem-OHG, 1.5 g, 6.7 mmol) was warmed to 85° C. and was allowed to stir for 18 hours. The mixture was cooled to ambient temperature and the crude material was purified via column chromatography (SiO$_2$, 10% methanol in ethyl acetate then 9:1:0.1 CH$_2$Cl$_2$: methanol:NH$_4$OH) to afford the title compound. MS (DCI/NH$_3$) m/z 215 (M+H)$^+$.

Example 237B 5-chloro-N-[(2Z)-3-(1,4-dioxan-2-ylmethyl)-5-methyl-1,3-thiazol-2(3H)-ylidene]-2-methoxybenzamide Example 237A (0.20 g, 0.93 mmol), triethylamine (0.39 mL, 2.8 mmol) and Example 205B (0.93 mmol) in 10 mL of tetrahydrofuran were processed as described in Example 208D to afford the title compound. $^1$H NMR (300 MHz, CD$_3$OD) δ ppm 2.33 (d, J=1.4 Hz, 3H), 3.34 (dd, J=11.5, 9.5 Hz, 1H), 3.50-3.71 (m, 3H), 3.82 (dt, J=10.5, 3.1 Hz, 2H), 3.86 (s, 3H), 3.99-4.09 (m, 1H), 4.19-4.36 (m, 2H), 7.08 (d, J=8.8 Hz, 1H), 7.09 (q, J=1.0 Hz, 1H), 7.40 (dd, J=9.0, 2.9 Hz, 1H), 7.81 (d, J=2.7 Hz, 1H); MS (DCI/NH$_3$) m/z 383 (M+H)$^+$. Anal. Calculated for C$_{17}$H$_{19}$ClN$_2$O$_4$S: C, 53.33; H, 5.00; N, 7.32. Found: C, 53.51; H, 4.93; N, 7.29.

Example 238

N-[(2Z)-5-acetyl-4-methyl-3-[(2R)-tetrahydrofuran-2-ylmethyl]-1,3-thiazol-2(3H)-ylidene]-5-chloro-2-methoxybenzamide Example 238A N-(5-acetyl-4-methylthiazol-2-yl)-5-chloro-2-methoxybenzamide To a solution of 5-acetyl-2-amino-4-methylthiazole (5.0 g, 32 mmol) in 50 mL of tetrahydrofuran was added triethylamine (13.4 mL, 96 mmol) followed by Example 205B (32 mmol) in 10 mL of tetrahydrofuran via cannula. The mixture was warmed to 50° C. and was allowed to stir for 18 hours. The mixture was cooled to ambient temperature quenched with 15 mL of NH$_4$Cl and diluted with 15 mL of ethyl acetate. The layers were separated and the aqueous layer was extracted with three 10 mL of portions of ethyl acetate. The combined organic extracts were dried over anhydrous Na$_2$SO$_4$, filtered and concentrated under reduced pressure. The residue was washed with ethyl acetate and the remaining solids were pure title compound. MS (DCI/NH$_3$) m/z 325 (M+H)$^+$.

Example 238B

N-[(2Z)-5-acetyl-4-methyl-3-[(2R)-tetrahydrofuran-2-ylmethyl]-1,3-thiazol-2(3H)-ylidene]-5-chloro-2-methoxybenzamide A mixture of Example 238A (1.1 g, 3.2 mmol), Example 208A (1.0 g, 3.9 mmol), tetrabutylammonium iodide (0.36 g, 0.98 mmol) and potassium t-butoxide (0.58 g, 4.9 mmol) in 12 mL of N,N-dimethylformamide was warmed to 65° C. and was allowed to stir for 16 hours. The mixture was cooled to ambient temperature quenched with 10 mL of NH$_4$Cl and diluted with 10 mL of ethyl acetate. The layers were separated and the aqueous layer was extracted twice with 10 mL of ethyl acetate. The combined organic extracts were dried over anhydrous Na$_2$SO$_4$, filtered and concentrated under reduced pressure. Purification via column chromatography (SiO$_2$, 30% hexanes in ethyl acetate) afforded the title compound. $^1$H NMR (300 MHz, CD$_3$OD) δ ppm 1.73-1.87 (m, 1H), 1.89-2.05 (m, 2H), 2.09-2.22 (m, 1H), 2.52 (s, 3H), 2.79 (s, 3H), 3.69-3.78 (m, 1H), 3.85-3.94 (m, 1H), 3.88 (s, 3H), 4.21-4.31 (m, 1H), 4.38-4.49 (m, 1H), 4.59 (dd, J=13.9, 3.1 Hz, 1H), 7.10 (d, J=9.2 Hz, 1H), 7.44 (dd, J=8.8, 2.7 Hz, 1H), 7.94 (d, J=2.7 Hz, 1H); MS (DCI/NH$_3$) m/z 409 (M+H)$^+$. Anal. Calculated for C$_{19}$H$_{21}$ClN$_2$O$_4$S.0.12H$_2$O: C, 55.52; H, 5.21; N, 6.81. Found: C, 55.83; H, 5.21; N, 6.41.

Example 239

5-chloro-N-[(2Z)-5-(1-hydroxy-1-methylethyl)-4-methyl-3-[(2R)-tetrahydrofuran-2-ylmethyl]-1,3-thiazol-2(3H)-ylidene]-2-methoxybenzamide To Example 238B (0.11 g, 0.27 mmol) in 5 mL of tetrahydrofuran at −78° C. was added a solution of methyl lithium (1.6 M in ether, 0.50 mL, 0.81 mmol) dropwise over 5 minutes. The mixture stirred at −78° C. for 1 hour and was slowly warmed to ambient temperature and was allowed to stir for 18 hours. The mixture was quenched with 5 mL of NH$_4$Cl and diluted with 5 mL of ethyl acetate. The layers were separated and the aqueous layer was extracted twice with 5 mL of ethyl acetate. The combined organic extracts were dried over anhydrous Na$_2$SO$_4$, filtered and concentrated under reduced pressure. Purification via column chromatography (SiO$_2$, 20% hexanes in ethyl acetate) afforded the title compound. $^1$H NMR (300 MHz, CD$_3$OD) δ ppm 1.26 (none, 1H), 1.61 (s, 6H), H), 1.73-1.85 (m, 1H), 1.88-2.01 (m, 2H), 2.05-2.19 (m, 1H), 2.52 (s, 3H), 3.69-3.78 (m, 1H), 3.85 (s, 3H), 3.87-3.93 (m, 1H), 4.02-4.19 (m, 2H), 4.36-4.45 (m, 1H), 4.50 (dd, J=13.9, 3.1 Hz, 1H), 7.06 (d, J=8.8 Hz, 1H), 7.39 (dd, J=8.8, 2.7 Hz, 1H), 7.83 (d, J=2.7 Hz, 1H); MS (DCI/NH$_3$) m/z 425 (M+H)$^+$. Anal. Calculated for C$_{20}$H$_{25}$ClN$_2$O$_4$S.0.1H$_2$O: C, 56.29; H, 5.95; N, 6.56. Found: C, 55.95; H, 5.87; N, 6.47.

Example 240

N-[(2Z)-5-tert-butyl-3-[(2R)-tetrahydrofuran-2-ylmethyl]-1,3-thiazol-2(3H)-ylidene]-5-chloro-2-methoxybenzamide Example 240A 5-tert-butylthiazol-2-amine To a solution of 3,3-dimethylbutyraldehyde (10 g, 99.8 mmol) in 200 mL of cyclohexane was added pyrrolidine (8.7 mL, 0.11 mol) followed by p-toluenesulfonic acid monohydrate (0.95 g, 5.0 mmol). This reaction flask was equipped with a Dean-Stark trap and the mixture was warmed to reflux and was allowed to stir for 3 hours. The mixture was cooled to ambient temperature, filtered and concentrated under reduced pressure. The residue was dissolved in 75 mL of CH$_3$OH, sulfur was added (3.2 g, 99.8 mmol), and the mixture was cooled to 0° C. Cyanamide (4.2 g, 99.8 mmol) was added portion wise over 10 minutes and the mixture was allowed to warm to ambient temperature and stir for 18 hours. The reaction mixture was concentrated under reduced pressure and purified by column chromatography (SiO$_2$, ethyl acetate then 10% methanol in ethyl acetate) to afford the title compound. MS (DCI/NH$_3$) m/z 157 (M+H)$^+$.

Example 240B (R)-(tetrahydrofuran-2-yl)methyl 4-methylbenzenesulfonate

To a solution of (R)-tetrahydrofurfuryl alcohol (Lancaster, 1.0 g, 9.8 mmol) in 5 mL of CH$_2$Cl$_2$ and 5 mL of pyridine was added p-toluenesulfonyl chloride (2.8 g, 14.7 mmol) in portions over 15 minutes. The mixture was stirred at ambient temperature for 3 hours and was quenched with 5 mL of saturated, aqueous NaHCO$_3$. The layers were separated and the aqueous layer was extracted with three 5 mL of portions of CH$_2$Cl$_2$. The combined organic extracts were dried over anhydrous Na$_2$SO$_4$, filtered and concentrated under reduced pressure to afford the title compound. MS (DCI/NH$_3$) m/z 257 (M+H)$^+$, 274 (M+NH$_4$)$^+$.

Example 240C (R)-5-tert-butyl-3-((tetrahydrofuran-2-yl)methyl)thiazol-2(3H)-imine 4-methylbenzenesulfonate A mixture of Example 240A (9.8 g, 62.7 mmol), Example 240B (23.5 g, 91.7 mmol) and tetrabutylammonium iodide (11.6 g, 31.4 mmol) in 35 mL of N,N-dimethylformamide was warmed to 85° C. and was allowed to stir for 72 hours. The mixture was diluted with 50 mL of CH$_2$Cl$_2$ and the layers were separated. The organic layer was washed with 15 mL of saturated, aqueous NaHCO$_3$ and the combined aqueous layers were extracted with three 10 mL of portions of CH$_2$Cl$_2$. The combined organic extracts were dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 241 (M+H)$^+$.

Example 240D 5-chloro-2-methoxybenzoyl chloride

A solution of 2-methoxy-5-chlorobenzoic acid (6.9 g, 37 mmol) in 15 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1$H NMR (300 MHz, dimethylsulfoxide-d$_6$) δ ppm 3.82 (s, 3H), 7.16 (d, J=8.8 Hz, 1H), 7.49-7.59 (m, 1H), 7.61 (d, J=2.7 Hz, 1H).

Example 240E

N-[(2Z)-5-tert-butyl-3-[(2R)-tetrahydrofuran-2-ylmethyl]-1,3-thiazol-2(3H)-ylidene]-5-chloro-2-methoxybenzamide To a solution of Example 240C (13.9 g, 34 mmol) in 120 mL of tetrahydrofuran at ambient temperature was added triethylamine (19 mL, 135 mmol) followed by Example 240D (7.6 g, 37 mmol) in 30 mL of tetrahydrofuran via cannula. This mixture was warmed to 60° C. and was allowed to stir for 3 hours and was quenched with 30 mL of NH$_4$Cl and diluted with 50 mL of ethyl acetate. The layers were separated and the aqueous layer was extracted with three 5 mL of portions of ethyl acetate. The combined organic extracts were dried over anhydrous Na$_2$SO$_4$, filtered and concentrated under reduced pressure. Purification via flash column chromatography (SiO$_2$, 50% hexanes:ethyl acetate) afforded the title compound. $^1$H NMR (300 MHz, CDCl$_3$) δ ppm 1.35 (s, 9H), 1.64-1.92 (m, 3H), 2.00-2.14 (m, 1H), 3.72-3.88 (m, 2H), 3.90 (s, 3H), 4.19-4.34 (m, 2H), 4.40 (dd, J=12.9, 2.4 Hz, 1H), 6.86 (s, 1H), 6.90 (d, J=9.2 Hz, 1H), 7.32 (dd, J=9.0, 2.9 Hz, 1H), 7.95 (d, J=3.1 Hz, 1H); MS (DCI/NH$_3$) m/z 409 (M+H)$^+$. Anal. Calculated for C$_{20}$H$_{25}$ClN$_2$O$_3$S: C, 58.74; H, 6.16; N, 6.85. Found: C, 58.74; H, 6.27; N, 6.81.

Example 241

N-[(2Z)-5-tert-butyl-3-(1,3-dioxolan-2-ylmethyl)-1,3-thiazol-2(3H)-ylidene]-5-chloro-2-methoxybenzamide Example 241A 3-((1,3-dioxolan-2-yl)methyl)-5-tert-butylthiazol-2(3H)-imine A mixture of Example 240A (0.17 g, 1.1 mmol) and 2-bromomethyl-1,3-dioxolane (0.21 g, 1.2 mmol) was warmed to 85° C. and was allowed to stir for 18 hours. The mixture was cooled to ambient temperature and the crude material was purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 243 (M+H)$^+$.

Example 241B

N-[(2Z)-5-tert-butyl-3-(1,3-dioxolan-2-ylmethyl)-1,3-thiazol-2(3H)-ylidene]-5-chloro-2-methoxybenzamide Example 241A (64 mg, 0.26 mmol), triethylamine (0.11 mL, 0.79 mmol) and Example 205B (0.26 mmol) in 2 mL of tetrahydrofuran and 0.5 mL of N,N-dimethylformamide were processed as in Example 208D to afford the title compound. $^1$H NMR (300 MHz, CD$_3$OD) δ ppm 1.38 (s, 9H), 3.86 (s, 3H), 3.88-3.98 (m, 4H), 4.42 (d, J=4.1 Hz, 2H), 5.29 (dd, J=4.1 Hz, 1H), 7.07 (d, J=8.8 Hz, 1H), 7.12 (s, 1H), 7.40 (dd, J=9.0, 2.9 Hz, 1H), 7.87 (d, J=2.7 Hz, 1H); MS (DCI/NH$_3$) m/z 411 (M+H)$^+$. Anal. Calculated for C$_{19}$H$_{23}$ClN$_2$O$_4$S: C, 55.54; H, 5.64; N, 6.82. Found: C, 55.43; H, 5.60; N, 6.62.

Example 242

5-chloro-N-[(2Z)-5-chloro-3-[(2R)-tetrahydrofuran-2-ylmethyl]-1,3-thiazol-2(3H)-ylidene]-2-methoxybenzamide Example 242A 5-chloro-N-(5-chlorothiazol-2-yl)-2-methoxybenzamide A mixture of 2-amino-5-chlorothiazole hydrochloric acid (1.0 g, 5.9 mmol), 5-chloro-2-methoxybenzoic acid (1.3 g, 7.0 mmol), 1-ethyl-(3-dimethylaminopropyl)carbodiimide hydrochloride (Chem-Impex International, 2.2 g, 12 mmol), 1-hydroxbenzotriazole (0.95 g, 7.0 mmol) and 4-dimethylaminopyridine (0.14 g, 1.2 mmol) in 6 mL of pyridine was allowed to stir at ambient temperature for 72 hours. The reaction mixture was concentrated under reduced pressure and 10 mL of H$_2$O was added. The resulting solids were isolated by filtration, washed with 5 mL of H$_2$O and twice with 5 mL of ethyl acetate, and dried to afford the title compound. MS (DCI/NH$_3$) m/z 303 (M+H)$^+$.

Example 242B 5-chloro-N-[(2Z)-5-chloro-3-[(2R)-tetrahydrofuran-2-ylmethyl]-1,3-thiazol-2(3H)-ylidene]-2-methoxybenzamide To a slurry of sodium hydride (40 mg of a 60% dispersion, 1.0 mmol) in 4 mL of N,N-dimethylformamide at 0° C. was added Example 242A (0.20 g, 0.66 mmol). This mixture was allowed to warm to ambient temperature and stirred for 1 hour. The mixture was cooled to 0° C. and Example 208A (0.19 g, 0.73 mmol) was added. The mixture was warmed to 80° C. and allowed to stir for 24 hours and cooled to ambient temperature. The reaction mixture was quenched with ice and 5 mL of saturated, aqueous NH$_4$Cl and diluted with 5 mL of ethyl acetate. The layers were separated and the aqueous layer was extracted with three 5 mL of portions of ethyl acetate. The combined organic extracts were dried over anhydrous Na$_2$SO$_4$, filtered and concentrated under reduced pressure. Purification via flash column chromatography (SiO$_2$, 50% hexanes:ethyl acetate) afforded the title compound. $^1$H NMR (300 MHz, CD$_3$OD) δ ppm 1.65-1.80 (m, 1H), 1.85-1.97 (m, 2H), 2.02-2.18 (m, 1H), 3.72-3.82 (m, 1H), 3.84-3.94 (m, 1H), 3.87 (s, 3H), 4.21-4.38 (m, 2H), 4.40-4.48 (m, 1H), 7.09 (d, J=8.8 Hz, 1H), 7.43 (dd, J=9.0, 2.9 Hz, 1H), 7.50 (s, 1H), 7.90 (d, J=2.7 Hz, 1H); MS (DCI/NH$_3$) m/z 387 (M+H)$^+$. Anal. Calculated for C$_{16}$H$_{16}$Cl$_2$N$_2$O$_3$S: C, 49.62; H, 4.16; N, 7.23. Found: C, 50.49; H, 4.03; N, 6.70.

Example 243

5-chloro-N-[(2Z)-5-chloro-3-(tetrahydro-2H-pyran-4-ylmethyl)-1,3-thiazol-2(3H)-ylidene]-2-methoxybenzamide Example 242A (0.20 g, 0.66 mmol), Example 203A (0.20, 0.73 mmol) and NaH (40 mg, 1 mmol) in 4 mL of tetrahydrofuran and 1 mL of N,N-dimethylformamide were processed as in Example 242B to afford the title compound. $^1$H NMR (300 MHz, CD$_3$OD) δ ppm 1.36-1.52 (m, 2H), 1.53-1.61 (m, 2H), 2.19-2.38 (m, 1H), 3.40 (dt, J=11.7, 2.4 Hz, 2H), 3.88 (s, 3H), 3.92-4.00 (m, 2H), 4.19 (d, J=7.1 Hz, 2H), 7.10 (d, J=8.8 Hz, 1H), 7.44 (dd, J=9.0, 2.9 Hz, 1H), 7.55 (s, 1H), 7.91 (d, J=2.7 Hz, 1H); MS (DCI/NH$_3$) m/z 401 (M+H)$^+$.

Example 244

N-[(2Z)-5-tert-butyl-3-[(3-methyl-4,5-dihydroisoxazol-5-yl)methyl]-1,3-thiazol-2(3H)-ylidene]-5-chloro-2-methoxybenzamide Example 244A N-(5-tert-butylthiazol-2-yl)-5-chloro-2-methoxybenzamide To a solution of Example 202A (0.94 g, 6.0 mmol) in tetrahydrofuran (40 mL) was added Example 205B (1.23 g, 6.0 mmol), triethylamine (2.4 mL, 18 mmol), and 4-dimethylaminopyridine (7.5 mg, 0.06 mmol). The reaction mixture was stirred at 60° C. for 14 hours and then cooled to ambient temperature, diluted with saturated aqueous NaHCO$_3$ (20 mL) and extracted with ethyl acetate (3×30 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. MS (ESI$^+$) m/z 325 (M+H)$^+$

Example 244B

N-[(2Z)-3-allyl-5-tert-butyl-1,3-thiazol-2(3H)-ylidene]-5-chloro-2-methoxybenzamide To a solution of Example 244A (410 mg, 1.3 mmol) in 5 mL of tetrahydrofuran:N,N-dimethylformamide (4/1) at 0° C. was added potassium tert-butoxide (230 mg, 1.9 mmol). The reaction mixture was stirred for 1 hour then allyl bromide (0.16 mL, 1.9 mmol) was added. The mixture was warmed to 65° C. and stirred overnight. The mixture was cooled to ambient temperature, concentrated, diluted with CH$_2$Cl$_2$ and washed with water and brine. The organic layer was dried over magnesium sulfate, filtered, and concentrated under reduced pressure. Purification by chromatography (20-50% ethyl ccetate/hexane gradient) afforded the title compound. $^1$H NMR (CDCl$_3$, 300 MHz) δ ppm 1.34 (s, 9H), 3.90 (s, 3H), 4.78-4.85 (m, 3H), 5.22-5.36 (m, 2H), 5.90-6.09 (m, J=17.0, 10.17 Hz, 1H), 6.62 (s, 1H), 6.90 (d, J=9.2 Hz, 1H), 7.32 (dd, J=8.8, 3.1 Hz, 1H), 8.00 (d, J=2.7 Hz, 1H); MS (DCI/NH$_3$) m/z 365 (M+H)$^+$.

Example 244C

N-[(2Z)-5-tert-butyl-3-[(3-methyl-4,5-dihydroisoxazol-5-yl)methyl]-1,3-thiazol-2(3H)-ylidene]-5-chloro-2-methoxybenzamide Example 244B was processed according to the method of Example 227C to afford the title compound. MS (DCI/NH$_3$) m/z 422 (M+H)$^+$.

Example 245

N-[(2Z)-5-tert-butyl-3-[(2R)-tetrahydrofuran-2-ylmethyl]-1,3-thiazol-2(3H)-ylidene]-2,2-dimethyl-4-oxo-3,4-dihydro-2H-pyran-6-carboxamide To a solution of the product from Example 240C (300 mg, 0.94 mmol) and 2,2-dimethyl-4-oxo-3,4-dihydro-2H-pyran-6-carboxylic acid (180 mg, 1.0 mmol) in 5 mL of N,N-dimethylformamide were added 1-hydroxybenzotriazole hydrate (190 mg, 1.4 mmol), triethylamine (0.30 mL, 2.1 mmol), and 1-ethyl-3-[3-(dimethylamino)propyl]-carbodiimide hydrochloride (260 mg, 1.4 mmol). The mixture was warmed to 65° C. and stirred overnight. The mixture was cooled to ambient temperature, diluted with CH$_2$Cl$_2$ and washed with water and brine. The organic extract was dried (MgSO$_4$), filtered, and concentrated under reduced pressure. Purification by column chromatography (SiO$_2$, 20-40% ethyl acetate/hexanes gradient) afforded the title compound. $^1$H NMR (500 MHz, CDCl$_3$) δ ppm 1.34 (s, 9H), 1.57 (s, 6H), 1.72-1.84, (m, 1H), 1.83-1.94 (m, 1H), 2.00-2.12 (m, 2H), 2.55 (s, 2H), 3.73-3.88 (m, 2H), 4.10-4.27 (m, 2H), 4.39 (dd, J=13.7, 2.8 Hz, 1H), 6.48 (s, 1H), 6.91 (s, 1H); MS (DCI/NH$_3$) m/z 393 (M+H)$^+$.

Example 246

N-[(2Z)-5-tert-butyl-3-(tetrahydro-2H-pyran-4-ylmethyl)-1,3-thiazol-2(3H)-ylidene]-5-chloro-2-methoxybenzamide To a solution of Example 244A (1.0 g, 3.1 mmol) in 4:1 N,N-dimethylformamide/tetrahydrofuran (20 mL) were added potassium tert-butoxide (Aldrich, 0.42 g, 3.7 mmol) and 4-(iodomethyl)tetrahydro-2H-pyran (Maybridge, 0.97 g, 4.3 mmol). The reaction mixture was stirred at 80° C. for 16 hours, cooled to room temperature, quenched with saturated aqueous NaHCO$_3$ (20 mL) and extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, dimethylsulfoxide-d$_6$) δ ppm 1.21-1.51 (m, 4H), 1.32 (s, 9H), 2.06-2.35 (m, 1H), 3.20-3.30 (m, 2H), 3.79 (s, 3H), 3.80-3.91 (m, J=9.3, 2.2, 2.0 Hz, 2H), 4.06 (d, J=7.1 Hz, 2H), 7.11 (d, J=8.8 Hz, 1H), 7.30 (s, 1H), 7.45 (dd, J=8.8, 3.1 Hz, 1H), 7.64 (d, J=2.7 Hz, 1H); MS (ESI$^+$) m/z 423 (M+H)$^+$; Anal. Calculated for C$_{21}$H$_{27}$ClN$_2$O$_3$S: C, 59.63; H, 6.43; N, 6.62. Found: C, 59.66; H, 6.36; N, 6.56.

Example 247

5-chloro-2-methoxy-N-[(2Z)-3-(tetrahydro-2H-pyran-4-ylmethyl)-4,5,6,7-tetrahydro-1,3-benzothiazol-2(3H)-ylidene]benzamide

Example 247A 5-chloro-2-methoxy-N-(4,5,6,7-tetrahydrobenzo[d]thiazol-2-yl)benzamide Commercially available 4,5,6,7-tetrahydrobenzo[d]thiazol-2-amine (Aldrich) and 5-chloro-2-methoxybenzoic acid (Aldrich) were processed using the method described in Example 58 to afford the title compound. MS (ESI$^+$) m/z 323 (M+H)$^+$

Example 247B 5-chloro-2-methoxy-N-[(2Z)-3-(tetrahydro-2H-pyran-4-ylmethyl)-4,5,6,7-tetrahydro-1,3-benzothiazol-2(3H)-ylidene]benzamide Example 203A and Example 247A were processed using the method described in Example 246 to afford the title compound. $^1$H NMR (300 MHz, dimethylsulfoxide-d$_6$) δ ppm 1.25-1.55 (m, 4H), 1.69-1.94 (m, 4H), 2.07-2.30 (m, 1H), 2.52-2.59 (m, 2H), 2.58-2.66 (m, 2H), 3.18-3.30 (m, 2H), 3.80 (s, 3H), 3.81-3.89 (m, 2H), 4.03 (d, J=7.1 Hz, 2H), 7.11 (d, J=8.8 Hz, 1H), 7.45 (dd, J=8.8, 2.7 Hz, 1H), 7.69 (d, J=3.1 Hz, 1H); MS (ESI$^+$) m/z 421 (M+H)$^+$.

Example 248

5-chloro-2-methoxy-N-[(2Z)-3-(2-methoxyethyl)-4,4,6,6-tetramethyl-4,6-dihydrofuro[3,4-d]-[1,3]thiazol-2(3H)-ylidene]benzamide

Example 248A 4-bromo-2,2,5,5-tetramethyldihydrofuran-3(2H)-one

To a solution of commercially available 2,2,5,5-tetramethyldihydrofuran-3(2H)-one (Aldrich, 10.0 g, 0.07 mol) in CH$_2$Cl$_2$ (100 mL) was added bromine (Aldrich, 3.6 mL, 0.07 mol,) dropwise at room temperature. The reaction mixture was stirred for 2 hours over which time the reaction mixture became clear. Then, the reaction mixture was cooled to 0° C., quenched with NaHCO$_3$ powder in small portions, filtered and concentrated under reduced pressure to afford the title compound. $^1$H NMR (300 MHz, dimethylsulfoxide-d$_6$) δ ppm 1.26 (s, 3H), 1.27 (s, 3H), 1.30 (s, 3H), 1.39 (s, 3H), 5.22 (s, 1H).

Example 248B 4,4,6,6-tetramethyl-4,6-dihydrofuro[3,4-d]thiazol-2-amine

To a solution of Example 248A (10.0 g, 0.045 mol) in ethanol (100 mL) were added thiourea (3.8 g, 0.05 mol) and triethylamine (6.3 mL, 0.045 mol). The reaction mixture was heated at reflux overnight, then cooled, and concentrated under reduced pressure. The residue was diluted with water (25 mL) and extracted with ethyl acetate (3×50 mL). The combined organic extracts were dried (Na$_2$SO$_4$), filtered and concentrated. The residue was purified by column chromatography (SiO$_2$, 0-5% methanol in CH$_2$Cl$_2$) to afford the title compound. MS (ESI$^+$) m/z 199 (M+H)$^+$.

Example 248C 5-chloro-2-methoxy-N-(4,4,6,6-tetramethyl-4,6-dihydrofuro[3,4-d]thiazol-2-yl)benzamide Example 248B and Example 205B were processed using the method described in Example 244A to afford the title compound. MS (ESI$^+$) m/z 367 (M+H)$^+$.

Example 248D 5-chloro-2-methoxy-N-[(2Z)-3-(2-methoxyethyl)-4,4,6,6-tetramethyl-4,6-dihydrofuro[3,4-d][1,3]thiazol-2(3H)-ylidene]benzamide Example 248C and commercially available 2-bromoethyl methyl ether (Aldrich) were processed using the method described in Example 246 to afford the title compound. $^1$H NMR (300 MHz, dimethylsulfoxide-d$_6$) δ ppm 1.48 (s, 6H), 1.55 (s, 6H), 3.25 (s, 3H), 3.71-3.81 (s, 3H), 4.20 (t, J=5.6 Hz, 2H), 7.13 (d, J=9.2 Hz, 1H), 7.48 (dd, J=9.0, 2.9 Hz, 1H), 7.68 (d, J=2.7 Hz, 1H); MS (ESI$^-$) m/z 425 (M+H)$^+$ Example 249

5-chloro-2-methoxy-N-[(2Z)-3-(2-methoxyethyl)-6,6-dimethyl-4-oxo-4,6-dihydrofuro[3,4-d][1,3]thiazol-2(3H)-ylidene]benzamide Example 249A tert-butyl 6,6-dimethyl-4-oxo-4,6-dihydrofuro[3,4-d]thiazol-2-ylcarbamate To a solution of diisopropylamine (23.5 mL, 165 mmol) in tetrahydrofuran (200 mL) was added butyllithium (103 mL, 1.6 M in hexanes, 165 mmol) dropwise at –78° C. The solution was stirred at –78° C. for 30 minutes then transferred via cannula into a solution of methyl 2-(tert-butoxycarbonylamino)thiazole-4-carboxylate (Combi-Blocks, 14.2 g, 55 mmol) in tetrahydrofuran (300 mL) at –78° C. After stirring at –78° C. for 30 minutes, dry acetone (Acros, 16.2 mL, 220 mmol) was added dropwise and the reaction mixture was allowed to warm to room temperature and stirred overnight. The reaction mixture was quenched with saturated aqueous NH$_4$Cl solution (200 mL) and the aqueous layer was extracted with ethyl acetate (4×200 mL). The combined organic extracts were dried (Na$_2$SO$_4$), filtered and concentrated. The residue was purified by column chromatography (SiO$_2$, 0-100% ethyl acetate in hexanes) to afford the title compound. MS (ESI$^+$) m/z 285 (M+H)$^+$.

Example 249B 2-amino-6,6-dimethylfuro[3,4-d]thiazol-4(6H)-one

To a solution of Example 249A (7.4 g, 26.0 mmol) in CH$_2$Cl$_2$ (20 mL) was added trifluoroacetic acid (20.0 mL, 260 mmol) slowly at 0° C. The reaction mixture was stirred at room temperature for 3 hours, and then concentrated under vacuum. The residue was diluted with ethyl acetate (100 mL) and neutralized with saturated aqueous NaHCO$_3$ solution. The layers were separated and the aqueous phase was extracted with ethyl acetate (5×100 mL). The combined organic extracts were dried (Na$_2$SO$_4$), filtered and concentrated to afford the title compound. MS (ESI$^+$) m/z 185 (M+H)$^+$ Example 249C 2-imino-3-(2-methoxyethyl)-6,6-dimethyl-2,3-dihydrofuro[3,4-d]thiazol-4(6H)-one hydrobromide A mixture of Example 249B and commercially available 2-bromoethyl methyl ether (Aldrich) was processed at 120° C. using the method described in Example 12A to afford the title compound. MS (ESI$^+$) m/z 243 (M+H)$^+$ Example 249D 5-chloro-2-methoxy-N-[(2Z)-3-(2-methoxyethyl)-6,6-dimethyl-4-oxo-4,6-dihydrofuro[3,4-d][1,3]thiazol-2(3H)-ylidene]benzamide Example 249C and Example 205B were processed using the method described in Example 244A to afford the title compound. $^1$H NMR (300 MHz, dimethylsulfoxide-d$_6$) δ ppm 1.71 (s, 6H), 3.26 (s, 3H), 3.78 (t, J=5.6 Hz, 2H), 3.82 (s, 3H), 4.46 (t, J=5.6 Hz, 2H), 7.17 (d, J=8.8 Hz, 1H), 7.53 (dd, J=9.0, 2.9 Hz, 1H), 7.77 (d, J=2.7 Hz, 1H)); MS (ESI$^+$) m/z 411 (M+H)$^+$; Anal. Calculated for C$_{18}$H$_{19}$ClN$_2$O$_5$S: C, 52.62; H, 4.66; N, 6.82. Found: C, 52.72; H, 4.49; N, 6.90.

Example 250

N-[(2Z)-5-acetyl-4-methyl-3-(oxetan-2-ylmethyl)-1,3-thiazol-2(3H)-ylidene]-5-chloro-2-methoxybenzamide Example 238A and Example 211A were processed using the method described in Example 246 to afford the title compound. $^1$H NMR (300 MHz, CDCl$_3$) δ ppm 2.49 (s, 3H), 2.54-2.67 (m, 1H), 2.74-2.82 (m, 1H), 2.84 (s, 3H), 3.93 (s, 3H), 4.45-4.74 (m, 4H), 5.30 (d, 1H), 6.93 (d, J=9.2 Hz, 1H), 7.38 (dd, J=8.8, 2.7 Hz, 1H), 7.97 (d, J=2.7 Hz, 1H); MS (ESI$^+$) m/z 493 (M+H)$^+$; Anal. Calculated for C$_{18}$H$_{19}$ClN$_2$O$_4$S: C, 54.75; H, 4.85; N, 7.09. Found: C, 54.68; H, 4.70; N, 7.07.

Example 251

5-chloro-N-[(2Z)-4,4-dimethyl-1-(oxetan-2-ylmethyl)-1,4,6,7-tetrahydro-2H-pyrano[4,3-d][1,3]thiazol-2-ylidene]-2-methoxybenzamide

Example 251A ethyl 2-(2-(tert-butoxycarbonylamino)thiazol-4-yl)acetate

The title compound was obtained from commercially available ethyl 2-(2-aminothiazol-4-yl)acetate (Aldrich) as per the procedure described in JP 06345736. MS (ESI$^+$) m/z 287 (M+H)$^+$.

Example 251B tert-butyl 4-(2-hydroxyethyl)thiazol-2-ylcarbamate

To a cooled solution of Example 251A in tetrahydrofuran (100 mL) was added lithium borohydride (Aldrich, 100 mL, 2 M solution in tetrahydrofuran) at 0° C. The reaction mixture was heated at reflux overnight, then cooled to 0° C., quenched with water and extracted with ethyl acetate (3×100 mL). The combined organic extracts were dried (Na$_2$SO$_4$), filtered and concentrated. The residue was purified by column chromatography (SiO$_2$, 0-5% methanol in CH$_2$Cl$_2$) to afford the title compound. MS (ESI$^+$) m/z 245 (M+H)$^+$

Example 251C tert-butyl 4-(2-(tetrahydro-2H-pyran-2-yloxy)ethyl)thiazol-2-ylcarbamate To a solution of Example 251B (6.3 g, 27.4 mmol) in CH$_2$Cl$_2$ (100 mL) was added commercially available 3,4-dihydro-2H-pyran (Aldrich, 21 g, 250 mmol) and pyridinium-p-toluenesulfonic acid (Aldrich, 3.5 g, 14.0 mmol). The reaction mixture was stirred overnight at room temperature and was diluted with CH$_2$Cl$_2$, washed with water, dried (Na$_2$SO$_4$), filtered and concentrated. The residue was purified by column chromatography (SiO$_2$, 0-100% ethyl acetate in hexanes) to afford the title compound. MS (ESI$^+$) m/z 329 (M+H)$^+$

Example 251D tert-butyl 5-(2-hydroxypropan-2-yl)-4-(2-(tetrahydro-2H-pyran-2-yloxy)ethyl)thiazol-2-ylcarbamate Example 251C, diisopropylamine, butyllithium, and dry acetone (Acros) were processed as described for Example 249A to obtain the title compound. MS (ESI$^+$) m/z 387 (M+H)$^+$.

Example 251E 4,4-dimethyl-6,7-dihydro-4H-pyrano[4,3-d]thiazol-2-amine

To a solution of Example 251D (4.6 g, 11 mmol) in tetrahydrofuran was added concentrated HCl (6.9 mL). The reaction mixture was heated at reflux for overnight and then cooled. The mixture was basified with 5N NaOH (17 mL) and extracted with ethyl acetate (3×50 mL). The combined organic extracts were dried (Na$_2$SO$_4$), filtered and concentrated. The residue was purified by column chromatography (SiO$_2$, 0-10% methanol in CH$_2$Cl$_2$) to afford the title compound. MS (ESI$^+$) m/z 185 (M+H)$^+$.

Example 251F 5-chloro-N-(4,4-dimethyl-6,7-dihydro-4H-pyrano[4,3-d]thiazol-2-yl)-2-methoxybenzamide Example 251E and Example 205B were processed using the method described in Example 244A to afford the title compound. MS (ESI$^+$) m/z 353 (M+H)$^+$

Example 251G 5-chloro-N-[(2Z)-4,4-dimethyl-1-(oxetan-2-ylmethyl)-1,4,6,7-tetrahydro-2H-pyrano[4,3-d][1,3]thiazol-2-ylidene]-2-methoxybenzamide Example 251F and Example 211A were processed using the method described in Example 246 to afford the title compound. $^1$H NMR (300 MHz, dimethylsulfoxide-d$_6$) δ ppm 1.45 (s, 3H), 1.46 (s, 3H), 2.67-2.75 (m, 2H), 2.74-2.83 (m, 2H), 3.79 (s, 3H), 3.90-4.01 (m, 2H), 4.32-4.44 (m, 2H), 4.45-4.58 (m, 2H), 5.06 (d, 1H), 7.11 (d, J=8.8 Hz, 1H), 7.45 (dd, J=8.8, 2.7 Hz, 1H), 7.62 (d, J=2.7 Hz, 1H); MS (ESI$^+$) m/z 423 (M+H)$^+$; Anal. Calculated for C$_{20}$H$_{23}$ClN$_2$O$_4$S.0.2C$_4$H$_8$O$_2$: C, 56.71; H, 5.63; N, 6.36. Found: C, 56.33; H, 5.39; N, 6.41.

Example 252

5-chloro-N-{(2Z)-4,4-dimethyl-1-[(2R)-tetrahydrofuran-2-ylmethyl]-1,4,6,7-tetrahydro-2H-pyrano[4,3-d][1,3]thiazol-2-ylidene}-2-methoxybenzamide Example 251F and Example 208A were processed using the method described in Example 246 to afford the title compound. $^1$H NMR (300 MHz, dimethylsulfoxide-d$_6$) δ ppm 1.45 (s, 6H), 1.61-2.04 (m, 4H), 2.71 (t, J=5.8 Hz, 2H), 3.56-3.70 (m, 1H), 3.73-3.84 (m, 1H), 3.79 (s, 3H), 3.96 (t, J=5.3 Hz, 2H), 4.00-4.05 (m, 1H), 4.20-4.38 (m, 2H), 7.11 (d, J=8.8 Hz, 1H), 7.46 (dd, J=9.0, 2.9 Hz, 1H), 7.66 (d, J=3.1 Hz, 1H); MS (ESI$^+$) m/z 437 (M+H)$^+$; Anal. Calculated for C$_{21}$H$_{25}$ClN$_2$O$_4$S: C, 57.72; H, 5.77; N, 6.41. Found: C, 57.58; H, 5.86; N, 6.33.

Example 253

N-[(2Z)-5-acetyl-4-methyl-3-(tetrahydro-2H-pyran-2-ylmethyl)-1,3-thiazol-2(3H)-ylidene]-5-chloro-2-methoxybenzamide Commercially available 2-(bromomethyl)tetrahydro-2H-pyran (Aldrich) and Example 238A were processed using the method described in Example 246 to afford the title compound. $^1$H NMR (300 MHz, dimethylsulfoxide-d$_6$) δ ppm 1.28-1.38 (m, 1H), 1.41-1.52 (m, 2H), 1.62-1.71 (m, 1H), 1.78-1.88 (m, 1H), 2.50 (s, 3H), 2.61-2.84 (m, 3H), 3.64-3.93 (m, 3H), 3.83 (s, 3H), 4.14 (dd, J=14.1, 8.6 Hz, 1H), 4.37 (dd, J=14.2, 3.1 Hz, 1H), 7.16 (d, J=8.8 Hz, 1H), 7.51 (dd, J=9.0, 2.9 Hz, 1H), 7.79 (d, J=2.7 Hz, 1H); MS (ESI$^+$) m/z 423

(M+H)⁺; Anal. Calculated for C₂₀H₂₃ClN₂O₄S: C, 56.80; H, 5.48; N, 6.62. Found: C, 56.53; H, 5.27; N, 6.55.

Example 254

N-[(2Z)-5-acetyl-4-methyl-3-(tetrahydro-2H-pyran-3-ylmethyl)-1,3-thiazol-2(3H)-ylidene]-5-chloro-2-methoxybenzamide Example 225A and Example 238A were processed using the method described in Example 246 to afford the title compound. ¹H NMR (300 MHz, dimethylsulfoxide-d₆) δ ppm 1.47 (s, 6H) 1.52 (s, 6H) 3.72 (s, 3H) 5.35 (s, 2H) 7.07 (d, 3H) 7.32 (d, 1H) 7.37 (d, J=2.71 Hz, 1H) 7.40-7.50 (m, J=8.81 Hz, 1H); MS (ESI⁺) m/z 423 (M+H)⁺; Anal. Calculated for C₂₀H₂₃ClN₂O₄S.0.2H₂O: C, 56.32; H, 5.53; N, 6.57. Found: C, 56.19; H, 5.50; N, 6.62.

Example 255

5-chloro-N-[(2Z)-5-(1-hydroxy-1-methylethyl)-4-methyl-3-(tetrahydro-2H-pyran-2-ylmethyl)-1,3-thiazol-2(3H)-ylidene]-2-methoxybenzamide A solution of methyllithium (Aldrich, 1.6 M in diethyl ether, 0.41 mL, 0.66 mmol) was added slowly a solution of Example 253 (0.14 g, 0.33 mmol) in tetrahydrofuran (3 mL) at −78° C. The reaction mixture was stirred at −78° C. for 30 minutes and was allowed to reach room temperature. The reaction mixture was quenched with water (6 mL) and extracted with ethyl acetate (2×10 mL). The combined organic extracts were dried over anhydrous Na₂SO₄, filtered and concentrated under reduced pressure. The residue was purified by column chromatography using an Analogix® Intelliflash280™ (SiO₂, 0-5% methanol in CH₂Cl₂) to afford the title compound. ¹H NMR (300 MHz, dimethylsulfoxide-d₆) δ ppm 1.21-1.36 (m, 1H), 1.41-1.48 (m, 3H), 1.49 (s, 3H), 1.50 (s, 3H), 1.57-1.67 (m, 1H), 1.74-1.85 (m, 1H), 2.42 (s, 3H), 3.68-3.89 (m, 3H), 3.79 (s, 3H), 3.92-4.09 (m, 1H), 4.17-4.38 (m, 1H), 5.60 (s, 1H), 7.10 (d, J=8.8 Hz, 1H), 7.44 (dd, J=8.8, 2.7 Hz, 1H), 7.68 (d, J=2.7 Hz, 1H); MS (ESI⁺) m/z 439 (M+H)⁻; Anal. Calculated for C₂₁H₂₇ClN₂O₄S: C, 57.46; H, 6.20; N, 6.38. Found: C, 57.44; H, 5.88; N, 6.06.

Example 256

5-chloro-2-methoxy-N-[(2Z)-4-methyl-3-[(2R)-tetrahydrofuran-2-ylmethyl]-5-[2,2,2-trifluoro-1-hydroxy-1-(trifluoromethyl)ethyl]-1,3-thiazol-2(3H)-ylidene]benzamide

Example 256A 2-(2-amino-4-methylthiazol-5-yl)-1,1,1,3,3,3-hexafluoropropan-2-ol The title compound was prepared from commercially available of 4-methylthiazol-2-amine (Aldrich) and hexafluoroacetone trihydrate (Aldrich) using the procedure described in European Journal of Organic Chemistry, (21), 4286-4291; 2003. MS (ESI⁺) m/z 281 (M+H)⁺.

Example 256B 5-chloro-N-(5-(1,1,1,3,3,3-hexafluoro-2-hydroxypropan-2-yl)-4-methylthiazol-2-yl)-2-methoxybenzamide Commercially available 5-chloro-2-methoxybenzoic acid (Aldrich) and Example 256A were processed using the method described in Example 58 to afford the title compound. MS (ESI⁺) m/z 449 (M+H)⁺.

Example 256C 5-chloro-2-methoxy-N-[(2Z)-4-methyl-3-[(2R)-tetrahydrofuran-2-ylmethyl]-5-[2,2,2-trifluoro-1-hydroxy-1-(trifluoromethyl)ethyl]-1,3-thiazol-2(3H)-ylidene]benzamide Example 256B and Example 208A were processed using the method described in Example 246 to afford the title compound. ¹H NMR (300 MHz, dimethylsulfoxide-d₆) δ ppm 1.62-1.76 (m, 1), 1.78-1.93 (m, 2H), 1.93-2.09 (m, 1H), 2.57 (s, 3H), 3.57-3.70 (m, 1H), 3.74-3.88 (m, 1H), 3.80 (s, 3H), 4.12-4.26 (m, 1H), 4.39 (d, 2H), 7.14 (d, J=8.8 Hz, 1H), 7.49 (dd, J=8.8, 2.7 Hz, 1H), 7.74 (d, J=2.7 Hz, 1H), 9.34 (s, 1H); MS (ESI⁺) m/z 533 (M+H)⁺.

Example 257

5-chloro-N-[(2Z)-5-(1-hydroxy-1-methylethyl)-4-methyl-3-(tetrahydro-2H-pyran-3-ylmethyl)-1,3-thiazol-2(3H)-ylidene]-2-methoxybenzamide Example 254 and commercially available methyllithium (Aldrich, 1.6 M in diethyl ether) were processed using the method described in Example 255 to afford the title compound. ¹H NMR (300 MHz, dimethylsulfoxide-d₆) δ ppm 1.32-1.48 (m, 2H), 1.51 (s, 6H), 1.57-1.80 (m, 2H), 2.02-2.23 (m, 1H), 2.41 (s, 3H), 3.19-3.28 (m, 1H), 3.35-3.43 (m, 1H), 3.55-3.73 (m, 2H), 3.79 (s, 3H), 3.95-4.29 (m, 2H), 5.60 (s, 1H), 7.10 (d, J=8.8 Hz, 1H), 7.44 (dd, J=8.8, 3.1 Hz, 1H), 7.67 (d, J=2.7 Hz, 1H); MS (ESI⁺) m/z 439 (M+H)⁺; Anal. Calculated for C₂₁H₂₇ClN₂O₄S: C, 57.46; H, 6.20; N, 6.38. Found: C, 57.14; H, 6.23; N, 6.53.

Example 258

5-chloro-N-[(2Z)-3-{[(4R)-2,2-dimethyl-1,3-dioxolan-4-yl]methyl}-5-(1-hydroxy-1-methylethyl)-4-methyl-1,3-thiazol-2(3H)-ylidene]-2-methoxybenzamide

Example 258A 5-chloro-N-(5-(2-hydroxypropan-2-yl)-4-methylthiazol-2-yl)-2-methoxybenzamide Example 238A and methyllithium (Aldrich, 1.6M in diethyl ether) were processed using the method described in Example 255 to afford the title compound. MS (ESI⁺) m/z 341 (M+H)⁺.

Example 258B 5-chloro-N-[(2Z)-3-{[(4R)-2,2-dimethyl-1,3-dioxolan-4-yl]methyl}-5-(1-hydroxy-1-methylethyl)-4-methyl-1,3-thiazol-2(3H)-ylidene]-2-methoxybenzamide Example 258A and commercially available (S)-(2,2-dimethyl-1,3-dioxolan-4-yl)methyl 4-methylbenzenesulfonate (Aldrich) were processed using the method described in Example 246 to afford the title compound. $^1$H NMR (300 MHz, dimethylsulfoxide-$d_6$) δ ppm 1.25 (s, 3H), 1.31 (s, 3H), 1.50 (s, 6H), 2.45 (s, 3H), 3.78 (s, 3H), 3.84 (dd, J=8.8, 6.1 Hz, 1H), 4.04 (dd, J=8.5, 6.4 Hz, 1H), 4.18-4.29 (m, 1H), 4.32-4.42 (m, 1H), 4.46-4.58 (m, 1H), 5.63 (s, 1H), 7.10 (d, J=8.8 Hz, 1), 7.43 (dd, J=8.8, 2.7 Hz, 1H), 7.64 (d, J=2.7 Hz, 1H); MS (ESI$^+$) m/z 455 (M+H)$^+$; Anal. Calculated for $C_{21}H_{27}ClN_2O_5S$: C, 55.44; H, 5.98; N, 6.16. Found: C, 55.34; H, 5.79; N, 6.21.

Example 259

5-chloro-N-[(2Z)-6,6-dimethyl-4-oxo-3-[(2R)-tetrahydrofuran-2-ylmethyl]-4,6-dihydrofuro[3,4-d][1,3]thiazol-2(3H)-ylidene]-2-methoxybenzamide

Example 259A 5-chloro-N-(6,6-dimethyl-4-oxo-4,6-dihydrofuro[3,4-d]thiazol-2-yl)-2-methoxybenzamide Example 249B, triethylamine, 4-dimethylaminopyridine, and Example 205B were processed as described for Example 244A to obtain the title compound. MS (ESI$^+$) m/z 353 (M+H)$^+$.

Example 259B 5-chloro-N-[(2Z)-6,6-dimethyl-4-oxo-3-[(2R)-tetrahydrofuran-2-ylmethyl]-4,6-dihydrofuro[3,4-d][1,3]thiazol-2(3H)-ylidene]-2-methoxybenzamide Example 259A and Example 208A were processed using the method described in Example 246 to afford the title compound. $^1$H NMR (300 MHz, dimethylsulfoxide-$d_6$) δ ppm 1.71 (s, 6H), 1.73-2.05 (m, 4H), 3.60-3.69 (m, 1H), 3.72-3.81 (m, 1H), 3.82 (s, 3H), 4.18-4.35 (m, 2H), 4.35-4.47 (m, 1H), 7.17 (d, J=8.8 Hz, 1H), 7.53 (dd, J=8.8, 2.7 Hz, 1H), 7.76 (d, J=2.7 Hz, 1H); MS (ESI$^+$) m/z 437 (M+H)$^+$; Anal. Calculated for $C_{20}H_{21}ClN_2O_5S \cdot 0.4H_2O$: C, 54.09; H, 4.95; N, 6.31. Found: C, 53.81; H, 4.55; N, 5.99.

Example 260

5-chloro-N-[(2Z)-3-{[(4S)-2,2-dimethyl-1,3-dioxolan-4-yl]methyl}-5-(1-hydroxy-1-methylethyl)-4-methyl-1,3-thiazol-2(3H)-ylidene]-2-methoxybenzamide Example 258A and commercially available (R)-(2,2-dimethyl-1,3-dioxolan-4-yl)methyl 4-methylbenzenesulfonate (Aldrich) were processed using the method described in Example 246 to afford the title compound. $^1$H NMR (300 MHz, dimethylsulfoxide-$d_6$) δ ppm 1.25 (s, 3H), 1.31 (s, 3H), 1.50 (s, 6H), 2.45 (s, 3H), 3.78 (s, 3H), 3.84 (dd, J=8.5, 6.1 Hz, 1H), 4.04 (dd, J=8.8, 6.4 Hz, 1H), 4.14-4.30 (m, 1H), 4.32-4.43 (m, 1H), 4.43-4.63 (m, 1H), 5.63 (s, 1H), 7.10 (d, J=9.2 Hz, 1H), 7.43 (dd, J=9.0, 2.9 Hz, 1H), 7.64 (d, J=2.7 Hz, 1H); MS (ESI$^+$) m/z 455 (M+H)$^+$; Anal. Calculated for $C_{21}H_{27}ClN_2O_5S$: C, 55.44; H, 5.98; N, 6.16. Found: C, 55.73; H, 6.07; N, 6.07.

Example 261

N-[(2Z)-5-acetyl-3-(1,4-dioxan-2-ylmethyl)-4-methyl-1,3-thiazol-2(3H)-ylidene]-5-chloro-2-methoxybenzamide Example 238A and commercially available 2-(iodomethyl)-1,4-dioxane (Synchem) were processed using the method described in Example 246 to afford the title compound. $^1$H NMR (300 MHz, dimethylsulfoxide-$d_6$) δ ppm 2.50 (s, 3H), 2.72 (s, 3H), 3.33-3.42 (m, 1H), 3.45-3.56 (m, 2H), 3.59-3.77 (m, 2H), 3.78-3.87 (m, 1H), 3.83 (s, 3H), 4.00-4.11 (m, 1H), 4.12-4.25 (m, 1H), 4.31-4.43 (m, 1H), 7.16 (d, J=8.8 Hz, 1H), 7.52 (dd, J=8.8, 3.1 Hz, 1H), 7.79 (d, J=2.7 Hz, 1H); MS (ESI$^+$) m/z 425 (M+H)$^+$; Anal. Calculated for $C_{19}H_{21}ClN_2O_5S$: C, 53.71; H, 4.98; N, 6.59. Found: C, 53.32; H, 4.73; N, 6.59.

Example 262

5-chloro-N-[(2Z)-5-(1-hydroxy-1-methylethyl)-4-methyl-3-(oxetan-2-ylmethyl)-1,3-thiazol-2(3H)-ylidene]-2-methoxybenzamide Example 258A and Example 211A were processed using the method described in Example 246 to afford the title compound. $^1$H NMR (300 MHz, dimethylsulfoxide-$d_6$) δ ppm 1.50 (s, 6H), 2.47 (s, 3H), 2.59-2.84 (m, 1H), 3.78 (s, 3H), 4.25-4.64 (m, 5H), 5.00-5.19 (m, 1H), 5.63 (s, 1H), 7.09 (d, J=9.2 Hz, 1H), 7.43 (dd, J=8.8, 3.1 Hz, 1H), 7.60 (d, J=2.7 Hz, 1H); MS (ESI$^+$) m/z 411 (M+H)$^+$; Anal. Calculated for $C_{19}H_{23}ClN_2O_4S$: C, 55.54; H, 5.64; N, 6.82. Found: C, 55.41; H, 5.51; N, 6.78.

Example 263

5-chloro-N-[(2Z)-5-(1-hydroxy-1-methylethyl)-4-methyl-3-(tetrahydrofuran-3-ylmethyl)-1,3-thiazol-2(3H)-ylidene]-2-methoxybenzamide Example 258A and Example 162A were processed using the method described in Example 246 to afford the title compound. $^1$H NMR (300 MHz, dimethylsulfoxide-$d_6$) δ ppm 1.51 (s, 6H), 1.65-1.82 (m, 1H), 1.84-2.03 (m, 1H), 2.43 (s, 3H), 2.68-2.89 (m, 1H), 3.48-3.71 (m, 3H), 3.78 (s, 3H), 3.80-3.93 (m, 1H), 4.08-4.34 (m, 2H), 5.62 (s, 1H), 7.09 (d, J=8.8 Hz, 1H), 7.43 (dd, J=8.8, 3.1 Hz, 1H), 7.65 (d, J=2.7 Hz, 1H); MS (ESI$^+$) m/z 425 (M+H)$^+$; Anal. Calculated for $C_{20}H_{25}ClN_2O_4S$: C, 56.53; H, 5.93; N, 6.59. Found: C, 56.35; H, 5.55; N, 6.56.

Example 264

5-chloro-N-[(2Z)-3-(1,4-dioxan-2-ylmethyl)-5-(1-hydroxy-1-methylethyl)-4-methyl-1,3-thiazol-2(3H)-ylidene]-2-methoxybenzamide Example 258A and commercially available 2-(iodomethyl)-1,4-dioxane (Synchem) were processed using the method described in Example 246 to afford the title compound. $^1$H NMR (300 MHz, dimethylsulfoxide-$d_6$) δ ppm 0.93 (t, J=7.46 Hz, 3H) 1.28-1.38 (m, 2H) 1.45 (s, 6H) 1.63-

1.78 (m, 2H) 2.69 (t, J=5.42 Hz, 2H) 3.79 (s, 3H) 3.97 (t, J=5.42 Hz, 2H) 4.07-4.17 (m, 2H) 7.11 (d, J=8.81 Hz, 1H) 7.46 (dd, J=8.81, 2.71 Hz, 1H) 7.69 (d, J=2.71 Hz, 1H); LCMS (ESI+) m/z 441 (M+H)+; Anal. Calculated for $C_{20}H_{25}ClN_2O_5S$: C, 54.48; H, 5.71; N, 6.35. Found: C, 54.54; H, 5.38; N, 6.43.

Example 265

N-[(2Z)-5-tert-butyl-3-[(2R)-tetrahydrofuran-2-ylmethyl]-1,3-thiazol-2(3H)-ylidene]-3-methoxy-2-naphthamide Commercially available 3-methoxy-2-naphthoic acid (Aldrich) and Example 240C were processed using the method described in Example 240E to afford the title compound. $^1$H NMR (300 MHz, dimethylsulfoxide-$d_6$) δ ppm 1.32 (s, 9H), 1.58-1.74 (m, 1H), 1.75-1.88 (m, 2H), 1.88-1.97 (m, 1H), 3.60-3.71 (m, 1H), 3.74-3.85 (m, 1H), 3.88 (s, 3H), 4.15-4.26 (m, 2H), 4.27-4.41 (m, 1H), 7.24 (s, 1H), 7.31-7.43 (m, 2H), 7.45-7.55 (m, 1H), 7.86 (dd, J=13.6, 8.5 Hz, 2H), 8.12 (s, 1H); MS (ESI+) m/z 425 (M+H)+; Anal. Calculated for $C_{20}H_{23}ClN_2O_4S.0.2C_4H_8O_2.0.2H_2O$: C, 66.82; H, 6.78; N, 6.28. Found: C, 66.70; H, 6.65; N, 6.33.

Example 266

N-[(2Z)-5-tert-butyl-3-[(3-methyloxetan-3-yl)methyl]-1,3-thiazol-2(3H)-ylidene]-5-chloro-2-methoxybenzamide To a solution of Example 244A (0.75 g, 2.31 mmol) in N,N-dimethylformamide/tetrahydrofuran (1:4, 20 mL) were added potassium tert-butoxide (0.39 g, 3.46 mmol), tetrabutylammonium iodide (0.09 mg, 0.23 mmol) and commercially available 3-(chloromethyl)-3-methyloxetane (TCI, 0.28 g, 2.31 mmol). The reaction mixture was stirred at 80° C. for 16 hours, cooled, diluted with ethyl acetate (20 mL) and quenched with saturated aqueous $NaHCO_3$ (20 mL). The aqueous layer was extracted with ethyl acetate (2×20 mL). The combined organic layers were washed with water (1×25 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% ethyl acetate in hexanes) to afford the title compound. $^1$H NMR (300 MHz, dimethylsulfoxide-$d_6$) δ ppm 1.24 (s, 3H), 1.33 (s, 9H), 3.77 (s, 3H), 4.19 (d, J=6.1 Hz, 2H), 4.38 (s, 2H), 4.69 (d, J=6.1 Hz, 2H), 7.10 (d, J=9.2 Hz, 1H), 7.29 (s, 1H), 7.44 (dd, J=9.0, 2.9 Hz, 1H), 7.58 (d, J=2.7 Hz, 1H); MS (ESI+) m/z 409 (M+H)+; Anal. Calculated for $C_{20}H_{25}ClN_2O_3S$: C, 58.74; H, 6.16; N, 6.85. Found: C, 58.92; H, 6.04; N, 6.84.

Example 267

5-chloro-2-methoxy-N-[(2Z)-3-(tetrahydrofuran-2-ylmethyl)-3,4,5,6-tetrahydro-2H-cyclopenta[d][1,3]thiazol-2-ylidene]benzamide

Example 267A 5,6-dihydro-4H-cyclopenta[d]thiazol-2-amine

A mixture of 2-chlorocyclopentanone (5.0 g, 40 mmol) and thiourea (3.0 g, 40 mmol) was heated at 70° C. for 3 hours. After cooling, the solid was triturated with ethanol and collected by filtration to afford the title compound. MS (ESI) m/z 141 (M+H)+.

Example 267B

Example 267A and 5-chloro-2-methoxybenzoic acid were processed using the method described in Example 223A to afford the title compound. MS (ESI) m/z 309 (M+H)+.

Example 267C 5-chloro-2-methoxy-N-[(2Z)-3-(tetrahydrofuran-2-ylmethyl)-3,4,5,6-tetrahydro-2H-cyclopenta[d][1,3]thiazol-2-ylidene]benzamide Example 267B (150 mg, 0.49 mmol) in tetrahydrofuran/N,N-dimethylformamide (2:1)(10 mL) was treated with NaH (60%) (24 mg, 0.58 mmol). After 10 minutes, 2-(bromomethyl)tetrahydrofuran (96 mg, 0.58 mmol) was added and the mixture was heated at 95° C. for 12 hours. After cooling to ambient temperature, the mixture was diluted with water, and extracted with ethyl acetate. The organic extract was dried ($Na_2SO_4$), filtered and concentrated. Purification by chromatography afforded the title compound. $^1$H NMR (400 MHz, dimethylsulfoxide-$d_6$) δ ppm 1.62-1.73 (m, 1H) 1.79-1.88 (m, 2H) 1.91-2.02 (m, 1H) 2.35-2.44 (m, 2H) 2.77-2.91 (m, 4H) 3.64 (dd, J=14.7, 7.1 Hz, 1H) 3.74-3.81 (m, 1H) 3.79 (s, 3H) 4.00 (dd, J=13.5, 8.0 Hz, 1H) 4.23 (dd, J=13.5, 3.7 Hz, 1H) 4.26-4.33 (m, 1H) 7.11 (d, J=8.9 Hz, 1H) 7.44 (dd, J=8.9, 2.8 Hz, 1H) 7.68 (d, J=2.8 Hz, 1H); MS (ESI) m/z 393 (M+H)−.

Example 268

5-chloro-2-methoxy-N-[(2Z)-3-(tetrahydro-2H-pyran-4-ylmethyl)-3,4,5,6-tetrahydro-2H-cyclopenta[d][1,3]thiazol-2-ylidene]benzamide Example 267B and 4-(bromomethyl)tetrahydro-2H-pyran were processed using the method described in Example 267C to afford the title compound. $^1$H NMR (500 MHz, dimethylsulfoxide-$d_6$) δ ppm 1.33 (ddd, J=24.7, 11.90, 4.3 Hz, 2H) 1.40-1.54 (m, 2H) 1.83-1.86 (m, 1H) 2.15-2.26 (m, 1H) 2.36-2.45 (m, 2H) 2.82 (dt, J=20.8, 6.7 Hz, 4H) 3.26 (td, J=11.9, 1.8 Hz, 1H) 3.80 (s, 3H) 3.84 (dd, J=11.6, 2.4 Hz, 2H) 3.99 (d, J=7.3 Hz, 2H) 7.11 (d, J=8.9 Hz, 1H) 7.45 (dd, J=8.9, 2.8 Hz, 1H) 7.70 (d, J=2.8 Hz, 1H); MS (ESI) m/z 407 (M+H)+.

Example 269

N-[(2Z)-4,5-dimethyl-3-(tetrahydro-2H-pyran-4-ylmethyl)-1,3-thiazol-2(3H)-ylidene]-2,2-dimethyltetrahydro-2H-pyran-4-carboxamide

Example 269A

A mixture of 4,5-dimethylthiazol-2-amine (Aldrich) and 2,2-dimethyltetrahydro-2H-pyran-4-carboxylic acid (Chembridge Building Block Library) were processed using the method described in Example 223A to afford the title compound. MS (ESI) m/z 269 (M+H)+.

Example 269B

N-[(2Z)-4,5-dimethyl-3-(tetrahydro-2H-pyran-4-ylmethyl)-1,3-thiazol-2(3H)-ylidene]-2,2-dimethyltetrahydro-2H-pyran-4-carboxamide Example 269A and 4-(bromomethyl)tetrahydro-2H-pyran were processed using the method described in Example 267C to afford the title compound. $^1$H NMR (300 MHz, dimethylsulfoxide d$_6$) δ ppm 1.11-1.14 (m, 3H) 1.15-1.18 (m, 3H) 1.30-1.43 (m, 4H) 1.43-1.56 (m, 2H) 1.68-1.80 (m, 2H) 2.14-2.18 (m, 3H) 2.19-2.23 (m, 3H) 2.55-2.71 (m, 1H) 3.16-3.26 (m, 2H) 3.35-3.41 (m, 1H) 3.60 (dd, J=11.9, 2.4 Hz, 1H) 3.63-3.68 (m, 1H) 3.79-3.83 (m, 1H) 3.83-3.87 (m, 1H) 4.01-4.03 (m, 1H) 4.03-4.06 (m, 1H); MS (ESI) m/z 376 (M+H)$^+$.

Example 270

N-[(2Z)-5-tert-butyl-3-(oxetan-2-ylmethyl)-1,3-thiazol-2(3H)-ylidene]-5-chloro-2-methoxybenzamide Example 244A and the product from Example 211A were processed using the method described in Example 244B to afford the title compound. $^1$H NMR (400 MHz, CDCl$_3$) δ ppm 1.35 (s, 9H) 2.39-2.56 (m, 1H) 2.68-2.83 (m, 1H) 3.86-3.90 (s, 3H) 4.34-4.38 (m, 1H) 4.37-4.43 (m, 1H) 4.55 (dd, J=14.1, 5.8 Hz, 1H) 4.62-4.68 (m, 1H) 5.15-5.22 (m, 1H) 6.89 (d, J=8.9 Hz, 1H) 6.93-6.94 (m, 1H) 7.31 (dd, J=8.9, 2.8 Hz, 1H) 7.89 (d, J=2.8 Hz, 1H); MS (ESI) m/z 395 (M+H)$^+$.

Example 271

N-[(2Z)-5-tert-butyl-3-(tetrahydro-2H-pyran-2-ylmethyl)-1,3-thiazol-2(3H)-ylidene]-5-chloro-2-methoxybenzamide Example 244A and 2-(bromomethyl)tetrahydro-2H-pyran were processed using the method described in Example 246 to afford the title compound. $^1$H NMR (500 MHz, CDCl$_3$) δ ppm 1.20-1.34 (m, 2H) 1.34 (s, 9H) 1.51-1.55 (m, 2H) 1.71 (dt, J=12.8, 1.8 Hz, 1H) 1.85-1.92 (m, 1H) 3.39 (td, J=14.3, 11.3, 3.4 Hz, 1H) 3.70-3.77 (m, 1H) 3.90 (s, 3H) 3.94-4.00 (m, 2H) 4.40 (dd, J=14.0, 3.0 Hz, 1H) 6.78 (s, 1H) 6.90 (d, J=8.9 Hz, 1H) 7.32 (dd, J=8.9, 2.8 Hz, 1H) 7.95 (d, J=2.8 Hz, 1H); MS (ESI) m/z 423 (M+H)$^+$.

Example 272

N-[(2Z)-5-tert-butyl-3-(1,4-dioxan-2-ylmethyl)-1,3-thiazol-2(3H)-ylidene]-5-chloro-2-methoxybenzamide Example 244A and 2-(iodomethyl)-1,4-dioxane were processed using the method described in Example 246 to afford the title compound. $^1$H NMR (500 MHz, CDCl$_3$) δ ppm 1.34 (s, 9H) 3.32 (dd, J=11.60, 10.1 Hz, 1H) 3.52-3.62 (m, 1H) 3.68-3.76 (m, 2H) 3.80 (dd, J=11.0, 2.8 Hz, 1H) 3.85-3.91 (m, 1H) 3.90 (s, 3H) 4.00-4.06 (m, 1H) 4.05 (dd, J=19.5, 6.71 Hz, 1H) 4.33 (dd, J=10.7, 3.1 Hz, 1H) 6.74 (s, 1H) 6.90 (d, J=8.9 Hz, 1H) 7.33 (dd, J=8.9, 2.8 Hz, 1H) 7.92 (d, J=2.8 Hz, 1H); MS (ESI) m/z 425 (M+H)$^+$.

Example 273

N-[(2Z)-5-tert-butyl-3-{[(4S)-2,2-dimethyl-1,3-dioxolan-4-yl]methyl}-1,3-thiazol-2(3H)-ylidene]-5-chloro-2-methoxybenzamide Example 244A and (R)-(2,2-dimethyl-1,3-dioxolan-4-yl)methyl 4-methylbenzenesulfonate were processed using the method described in Example 246 to afford the title compound. $^1$H NMR (500 MHz, CDCl$_3$) δ ppm 1.34 (s, 9H) 1.36 (s, 3H) 1.37 (s, 3H) 3.76 (dd, J=8.9, 6.7 Hz, 1H) 3.90 (s, 3H) 4.11 (dd, J=8.9, 6.4 Hz, 1H) 4.31-4.42 (m, 2H) 4.47-4.53 (m, 1H) 6.80 (s, 1H) 6.90 (d, J=8.9 Hz, 1H) 7.32 (dd, J=8.9, 2.75 Hz, 1H) 7.90 (d, J=3.1 Hz, 1H); MS (ESI) m/z 439 (M+H)$^+$.

Example 274

N-[(2Z)-5-tert-butyl-3-{[(4R)-2,2-dimethyl-1,3-dioxolan-4-yl]methyl}-1,3-thiazol-2(3H)-ylidene]-5-chloro-2-methoxybenzamide Example 244A and (S)-(2,2-dimethyl-1,3-dioxolan-4-yl)methyl 4-methylbenzenesulfonate were processed using the method described in Example 246 to afford the title compound. $^1$H NMR (500 MHz, CDCl$_3$) δ ppm 1.35 (s, 9H) 1.36 (s, 3H) 1.37 (s, 3H) 3.76 (dd, J=8.9, 6.71 Hz, 1H) 3.90 (s, 3H) 4.11 (dd, J=8.9, 6.4 Hz, 1H) 4.33-4.43 (m, 2H) 4.48-4.54 (m, 1H) 6.81 (s, 1H) 6.90 (d, J=8.9 Hz, 1H) 7.33 (dd, J=8.9, 2.8 Hz, 1H) 7.89 (d, J=2.8 Hz, 1H); MS (ESI) m/z 439 (M+H)$^+$.

Example 275

N-[(2Z)-5-tert-butyl-3-(tetrahydrofuran-3-ylmethyl)-1,3-thiazol-2(3H)-ylidene]-5-chloro-2-methoxybenzamide Example 244A and the product from Example 162A were processed using the method described in Example 246 to afford the title compound. $^1$H NMR (500 MHz, CDCl$_3$) δ ppm 1.35 (s, 9H) 1.71-1.79 (m, 1H) 1.98-2.10 (m, 1H) 2.90-3.02 (m, 1H) 3.64 (dd, J=9.15, 5.19 Hz, 1H) 3.76-3.83 (m, 2H) 3.90 (s, 3H) 3.95-4.01 (m, 1H) 4.08 (dd, J=13.43, 7.93 Hz, 1H) 4.24 (dd, J=13.12, 7.32 Hz, 1H) 6.63 (s, 1H) 6.91 (d, J=8.85 Hz, 1H) 7.33 (dd, J=8.85, 3.05 Hz, 1H) 7.97 (d, J=3.05 Hz, 1H); MS (ESI) m/z 409 (M+H)$^+$.

Example 276

N-[(2Z)-5-tert-butyl-3-(tetrahydro-2H-pyran-3-ylmethyl)-1,3-thiazol-2(3H)-ylidene]-5-chloro-2-methoxybenzamide Example 244A and the product from Example 225A were processed using the method described in Example 246 to afford the title compound. $^1$H NMR (500 MHz, CDCl$_3$) δ ppm 1.34 (s, 9H) 1.39-1.48 (m, 1H) 1.56-1.67 (m, 1H) 1.69-1.77 (m, 1H) 1.78-1.89 (m, 1H) 2.23-2.34 (m, 1H) 3.34 (dd, J=11.0, 8.2 Hz, 1H) 3.53 (ddd, J=9.2, 3.1 Hz, 1H) 3.74-3.85 (m, 2H) 3.90 (s, 3H) 4.04-4.16 (m, 2H) 6.60 (s, 1H) 6.90 (d, J=8.9 Hz, 1H) 7.33 (dd, J=8.9, 2.75 Hz, 1H) 7.98 (d, J=2.8 Hz, 1H); MS (ESI) m/z 423 (M+H)$^+$.

Example 277

N-[(2Z)-5-tert-butyl-3-{[(2S)-5-oxotetrahydrofuran-2-yl]methyl}-1,3-thiazol-2(3H)-ylidene]-5-chloro-2-methoxybenzamide

Example 277A (S)-(5-oxotetrahydrofuran-2-yl)methyl 4-methylbenzenesulfonate

A mixture of (S)-5-(hydroxymethyl)dihydrofuran-2(3H)-one, para-toluenesulfonyl chloride and pyridine were processed using the method described in Example 162A to afford the title compound. MS (ESI) m/z 288 (M+18)$^+$.

Example 277B

N-[(2Z)-5-tert-butyl-3-{[(2S)-5-oxotetrahydrofuran-2-yl]methyl}-1,3-thiazol-2(3H)-ylidene]-5-chloro-2-methoxybenzamide Example 244A and the product from Example 277A were processed using the method described in Example 246 to afford the title compound. $^1$H NMR (400 MHz, CDCl$_3$) δ ppm 1.34 (s, 9H) 2.07-2.20 (m, 1H) 2.34-2.48 (m, 2H) 2.49-2.61 (m, 1H) 3.90 (s, 3H) 4.39 (dd, J=14.4, 6.1 Hz, 1H) 4.55 (dd, J=14.4, 3.1 Hz, 1H) 4.92-5.01 (m, 1H) 6.75 (s, 1H) 6.92 (d, J=8.9 Hz, 1H) 7.35 (dd, J=8.9, 2.8 Hz, 1H) 7.92 (d, J=2.8 Hz, 1H); MS (ESI) m/z 423 (M+H)$^+$.

Example 278

N-[(2Z)-5-acetyl-4-methyl-3-[(2R)-tetrahydrofuran-2-ylmethyl]-1,3-thiazol-2(3H)-ylidene]-1-benzofuran-5-carboxamide

Example 278A (R)-1-((tetrahydrofuran-2-yl)methyl)thiourea

To a 0° C. solution of (R)-(tetrahydrofuran-2-yl)methanamine (5.0 g, 49.5 mmol) and triethylamine (690 uL, 4.95 mmol) in tetrahydrofuran (100 mL) was added carbon disulfide (5.65 g, 74.3 mmol). Stirring was continued for 0.5 hour followed by the dropwise addition of 30% hydrogen peroxide (5.6 g, 49.5 mmol) so that the temperature was maintained below 40° C. The reaction mixture was poured into water, and extracted with ethyl acetate. The organic extract was dried (Na$_2$SO$_4$), filtered and concentrated to afford an oil. The residue was dissolved in tetrahydrofuran, and treated with 7 N ammonia in methanol (14.3 mL, 100 mmol). The precipitate was collected by filtration and washed with water to afford the title compound.

Example 278B (R)-1-(2-imino-4-methyl-3-((tetrahydrofuran-2-yl)methyl)-2,3-dihydrothiazol-5-yl)ethanone To a solution of pentane-2,4-dione (451 mg, 4.5 mmol) and the product from Example 278A (786 mg, 4.5 mmol) in tetrahydrofuran (5 mL) was added a mixture of dimethylsulfoxide (0.64 mL, 9.0 mmol) and concentrated HCl (0.75 mL, 9.0 mmol). The reaction mixture was heated at 40° C. for 12 hours. After cooling to ambient temperature, the mixture was diluted with ethyl acetate and washed with saturated aqueous NaHCO$_3$. The organic extract was dried (Na$_2$SO$_4$), filtered and concentrated to afford the title compound. MS (ESI) m/z 241 (M+H)$^+$.

Example 278C

N-[(2Z)-5-acetyl-4-methyl-3-[(2R)-tetrahydrofuran-2-ylmethyl]-1,3-thiazol-2(3H)-ylidene]-1-benzofuran-5-carboxamide Example 298B and benzofuran-5-carboxylic acid were processed using the method described in Example 223A to afford the title compound. $^1$H NMR (400 MHz, CDCl$_3$) δ ppm 1.73-1.84 (m, 1H) 1.91-2.03 (m, 2H) 2.16-2.26 (m, 1H) 2.50 (s, 3H) 2.81 (s, 3H) 3.75 (dd, J=14.12, 6.44 Hz, 1H) 3.90 (dd, J=14.1, 7.4 Hz, 1H) 4.16 (dd, J=13.8, 8.0 Hz, 1H) 4.41-4.51 (m, 1H) 4.71 (dd, J=13.8, 3.4 Hz, 1H) 6.88 (s, 1H) 7.55 (d, J=8.6 Hz, 1H) 7.68 (t, J=2.2 Hz, 1H) 8.30 (dt, J=8.6, 1.5 Hz, 1H) 8.57-8.59 (m, 1H); MS (ESI) m/z 385 (M+H)$^+$.

Example 279

N-[(2Z)-5-(1-hydroxy-1-methylethyl)-4-methyl-3-[(2R)-tetrahydrofuran-2-ylmethyl]-1,3-thiazol-2(3H)-ylidene]-1-benzofuran-5-carboxamide Example 278C (300 mg, 0.78 mmol) in tetrahydrofuran (20 mL) was treated with a solution of methyllithium in diethyl ether (1.56 mL, 1.56 mmol) at −78° C. The reaction mixture was stirred at −78° C. for 4 hours and quenched with saturated aqueous NH$_4$Cl, warmed to ambient temperature and extracted with ethyl acetate. The organic extract was dried (Na$_2$SO$_4$), filtered and concentrated. Purification by reverse phase HPLC afforded the title compound. $^1$H NMR (500 MHz, CDCl$_3$) δ ppm 1.65 (s, 3H) 1.67 (s, 3H) 1.74-1.84 (m, 1H) 1.89-2.00 (m, 2H) 1.99-2.02 (m, 1H) 2.12-2.22 (m, 1H) 2.55 (s, 3H) 3.76 (dd, J=14.3, 7.6 Hz, 1H) 3.90 (dd, J=15.0, 6.7 Hz, 1H) 4.06 (dd, J=13.7, 7.3 Hz, 1H) 4.40-4.49 (m, 1H) 4.64 (dd, J=14.0, 3.7 Hz, 1H) 6.85 (dd, J=2.1, 0.9 Hz, 1H) 7.52 (d, J=8.5 Hz, 1H) 7.66 (d, J=2.1 Hz, 1H) 8.30 (dd, J=8.5, 1.5 Hz, 1H) 8.57 (d, J=1.5 Hz, 1H); MS (ESI) m/z 401 (M+H)$^+$.

Example 280

N-[(2Z)-5-acetyl-4-methyl-3-[(2R)-tetrahydrofuran-2-ylmethyl]-1,3-thiazol-2(3H)-ylidene]-5-chloro-2-(2,2,2-trifluoroethoxy)benzamide

Example 280A

N-((2Z)-5-acetyl-4-methyl-3-(((2R)-tetrahydrofuran-2-yl)methyl)thiazol-2(3H)-ylidene)-5-chloro-2-fluorobenzamide Example 278B and 5-chloro-2-fluorobenzoic acid were processed using the method described in Example 223A to afford the title compound. MS (ESI) m/z 397 (M+H)$^+$.

Example 280B

N-[(2Z)-5-acetyl-4-methyl-3-[(2R)-tetrahydrofuran-2-ylmethyl]-1,3-thiazol-2(3H)-ylidene]-5-chloro-2-(2,2,2-trifluoroethoxy)benzamide To the solution of the product from Example 280A (360 mg, 0.91 mmol) in tetrahydrofuran (4 mL) was added 2,2,2-trifluoroethanol (227 mg, 2.27 mmol) and a 1.0 M solution of potassium tert-butoxide in tetrahydrofuran (2.27 mL, 2.27 mmol). The reaction mixture was stirred at room temperature for 24 hours. The mixture was diluted with water, and extracted with ethyl acetate. The organic extract was dried (Na$_2$SO$_4$), filtered and concentrated. Purification by reverse phase HPLC afforded the title compound. $^1$H NMR (500 MHz, CDCl$_3$) δ ppm 1.64-1.75 (m, 1H) 1.90-2.00 (m, 2H) 2.10-2.20 (m, 1H) 2.51 (s, 3H) 2.80 (s, 3H) 3.73 (dd, J=15.9, 7.3 Hz, 1H) 3.88 (dd, J=15.3, 6.7 Hz, 1H) 4.07 (dd, J=13.7, 8.2 Hz, 1H) 4.33-4.41 (m, 1H) 4.47 (dd, J=16.8, 8.2 Hz, 2H)

4.62 (dd, J=13.7, 2.8 Hz, 1H) 7.03 (d, J=8.5 Hz, 1H) 7.39 (dd, J=8.5, 2.8 Hz, 1H) 8.02 (d, J=2.8 Hz, 1H); MS (ESI) m/z 477 (M+H)+.

Example 281

N-[(2Z)-5-tert-butyl-3-[(5-methyltetrahydrofuran-2-yl)methyl]-1,3-thiazol-2(3H)-ylidene]-5-chloro-2-methoxybenzamide

Example 281A hex-5-en-2-ol

A solution of hex-5-en-2-one (10 g, 102 mmol) in ether (60 mL) was treated with lithium aluminum hydride (4.0 g, 110 mmol) and the mixture was stirred at room temperature for 1 hour. The reaction mixture was quenched with saturated aqueous NH₄Cl, and extracted with ether. The organic extract was dried (Na$_2$SO$_4$), filtered and concentrated to afford the title compound.

Example 281B 2-(bromomethyl)-5-methyltetrahydrofuran

A solution of the product from Example 281A (6.9 g, 69 mmol) in CH$_2$Cl$_2$ (100 mL) was treated with N-bromosuccinimide (14.7, 83 mmol). The reaction mixture was stirred at room temperature for 48 hours, poured into water, and extracted with CH$_2$Cl$_2$. The organic extract was dried (Na$_2$SO$_4$), filtered and concentrated to afford the title compound. MS (ESI) m/z 179 (M+H)+.

Example 281C

N-[(2Z)-5-tert-butyl-3-[(5-methyltetrahydrofuran-2-yl)methyl]-1,3-thiazol-2(3H)-ylidene]-5-chloro-2-methoxybenzamide Example 244A and the product from Example 281B were processed using the method described in Example 246 to afford the title compound. $^1$H NMR (500 MHz, CDCl$_3$) δ ppm 1.22 (d, J=6.1 Hz, 3H) 1.33-1.37 (m, 9H) 1.46-1.54 (m, 2H) 1.67-1.76 (m, 1H) 1.91-2.00 (m, 1H) 3.90 (s, 3H) 4.01-4.08 (m, 1H) 4.29-4.34 (m, 2H) 4.39-4.46 (m, 1H) 6.89-6.90 (m, 1H) 6.90-6.91 (m, 1H) 7.32 (dd, J=8.5, 3.1 Hz, 1H) 7.94 (d, J=2.8 Hz, 1H); MS (ESI) m/z 423 (M+H)+.

Example 282

N-[(2Z)-5-tert-butyl-3-[(5,5-dimethyltetrahydrofuran-2-yl)methyl]-1,3-thiazol-2(3H)-ylidene]-5-chloro-2-methoxybenzamide

Example 282A 2-methylhex-5-en-2-ol

A 0° C. solution of hex-5-en-2-one (10 g, 102 mmol) in ether (200 mL) was treated dropwise with a 3.0 M solution of methylmagnesium iodide in ether (102 mL, 306 mmol) over 20 minutes. The reaction mixture was gradually warmed to room temperature, and stirred for 1 hour, quenched with water, and filtered through Celite (ether wash). The filtrate was concentrated and the resulting residue was distilled (27-30° C. at 5 mm Hg) to afford the title compound. $^1$H NMR (500 MHz, CDCl$_3$) δ ppm 1.23 (s, 6H) 1.54-1.62 (m, 2H) 2.11-2.19 (m, 2H) 4.96 (dq, J=11.29, 1.83, 1.22 Hz, 1H) 5.05 (dq, J=17.39, 1.53 Hz, 1H) 5.80-5.91 (m, 1H).

Example 282B 5-(bromomethyl)-2,2-dimethyltetrahydrofuran

The product from 282A was processed using the method described in Example 281B to afford the title compound. $^1$H NMR (400 MHz, CDCl$_3$) δ ppm 1.23 (s, 3H) 1.29 (s, 3H) 1.73-1.82 (m, 2H) 1.81-1.91 (m, 1H) 2.10-2.22 (m, 1H) 3.32 (dd, J=10.13, 7.06 Hz, 1H) 3.43 (dd, J=9.82, 4.60 Hz, 1H) 4.16-4.27 (m, 1H).

Example 282C

N-[(2Z)-5-tert-butyl-3-[(5,5-dimethyltetrahydrofuran-2-yl)methyl]-1,3-thiazol-2(3H)-ylidene]-5-chloro-2-methoxybenzamide Example 244A and the product from Example 282B were processed using the method described in Example 246 to afford the title compound. $^1$H NMR (400 MHz, dimethylsulfoxide-d$_6$) δ ppm 1.13 (s, 3H) 1.17 (s, 3H) 1.31 (s, 9H) 1.54-1.62 (m, 1H) 1.64-1.72 (m, 1H) 1.72-1.80 (m, 1H) 1.93-2.04 (m, 1H) 3.78 (s, 3H) 4.12 (dd, J=15.34, 6.75 Hz, 1H) 4.29-4.39 (m, 2H) 7.10 (d, J=8.59 Hz, 1H) 7.20 (s, 1H) 7.44 (dd, J=8.59, 2.76 Hz, 1H) 7.64 (d, J=2.76 Hz, 1H); MS (ESI) m/z 437 (M+H)+.

Example 283

N-[(2Z)-5-tert-butyl-3-[(2R)-tetrahydro furan-2-ylmethyl]-1,3-thiazol-2(3H)-ylidene]-5-chloro-2-(2-methoxyethoxy)benzamide

Example 283A

Example 240C and 5-chloro-2-fluorobenzoic acid were processed using the method described in Example 223A to afford the title compound. MS (ESI) m/z 397 (M+H)+.

Example 283B

N-[(2Z)-5-tert-butyl-3-[(2R)-tetrahydro furan-2-ylmethyl]-1,3-thiazol-2(3H)-ylidene]-5-chloro-2-(2-methoxyethoxy)benzamide Example 283A and 2-methoxyethanol were processed using the method described in Example 280B to afford the title compound. $^1$H NMR (500 MHz, CDCl$_3$) δ ppm 1.36 (s, 9H) 1.62-1.71 (m, 1H) 1.74-1.83 (m, 1H) 1.84-1.93 (m, 1H) 2.02-2.11 (m, 1H) 3.42 (s, 3H) 3.77 (m, 3H) 3.84 (dd, J=15.0, 6.71 Hz, 1H) 4.21 (t, J=5.2 Hz, 2H) 4.22-4.31 (m, 2H) 4.43 (dd, J=10.4 Hz, 1H) 6.90 (s, 1H) 6.97 (d, J=8.9 Hz, 1H) 7.30 (dd, J=8.5, 2.8 Hz, 1H) 7.89 (d, J=2.8 Hz, 1H) MS (ESI) m/z 477 (M+H)+.

Example 284

N-[(2Z)-5-tert-butyl-3-[(2R)-tetrahydrofuran-2-ylmethyl]-1,3-thiazol-2(3H)-ylidene]-6-chloroquinoline-8-carboxamide Example 240C and 6-chloroquinoline-8-carboxylic acid were processed using the method described in Example 223A to afford the title compound. $^1$H NMR (400 MHz, CDCl$_3$) δ ppm 1.38 (s, 9H) 1.63-1.74 (m, 1H) 1.74-1.83 (m, 1H) 1.82-1.93 (m, 1H) 1.98-2.08 (m, 1H) 3.72-3.88 (m, 2H) 4.18-4.30 (m, 2H) 4.40 (dd, J=13.2, 2.5 Hz, 1H) 6.90 (s, 1H) 7.40 (dd, J=8.3, 4.0 Hz, 1H) 7.82 (d, J=2.5 Hz, 1H) 7.99 (d, J=2.2 Hz, 1H) 8.06 (dd, J=8.3, 1.84 Hz, 1H) 9.02 (dd, J=4.3, 1.84 Hz, 1H); MS (ESI) m/z 430 (M+H)$^+$.

Example 285

5-chloro-2-methoxy-N-[(2Z)-5-(1-methylcyclopropyl)-3-[(2R)-tetrahydrofuran-2-ylmethyl]-1,3-thiazol-2(3H)-ylidene]benzamide Example 285A 2-(2-aminothiazol-5-yl)propan-2-ol To a −78° C. solution of thiazol-2-amine (7.0 g, 69.9 mmol) in tetrahydrofuran (200 mL) was added a 10.0 M solution of butyllithium in hexane (14 mL, 140 mmol). The mixture was stirred at −78° C. for 1 hour and chlorotrimethylsilane (15.2 g, 140 mmol) was added dropwise. The mixture was allowed to warm up to −40° C., cooled to −78° C. and a 10.0 M solution of butyllithium in hexane (7.0, 70 mmol) was added. After 10 minutes, propan-2-one (8.12 g, 140 mmol) was added and the mixture was stirred for 12 hours. The reaction mixture was quenched with saturated aqueous NH$_4$Cl and extracted with ether. The organic extract was dried (Na$_2$SO$_4$), filtered and concentrated. The residue was purified by column chromatography using an Analogix® Intelliflash280™ (SiO$_2$, 0-100% ethyl acetate in hexanes) to afford the title compound. $^1$H NMR (500 MHz, CDCl$_3$) δ ppm 1.61 (s, 6H) 5.04-5.19 (brs, 2H) 6.89 (s, 1H); MS (ESI) m/z 159 (M+H)$^+$.

Example 285B (R)-5-(prop-1-en-2-yl)-3-((tetrahydrofuran-2-yl)methyl)thiazol-2(3H)-imine Example 285A and the product from Example 208A were processed using the method described in Example 240C to afford the title compound. MS (ESI) m/z 225 (M+H)$^+$.

Example 285C (R,Z)-5-chloro-2-methoxy-N-(5-(prop-1-en-2-yl)-3-((tetrahydrofuran-2-yl)methyl)thiazol-2(3H)-ylidene)benzamide Example 285B and the product from Example 205B were processed using the method described in Example 223A to afford the title compound. MS (ESI) m/z 393 (M+H)$^+$.

Example 285D 5-chloro-2-methoxy-N-[(2Z)-5-(1-methylcyclopropyl)-3-[(2R)-tetrahydrofuran-2-ylmethyl]-1,3-thiazol-2(3H)-ylidene]benzamide A 20 mL vial was charged with 1 mL of CH$_2$Cl$_2$ and 1,2-dimethoxyethane (110 mg, 1.22 mmol). The solution was cooled to −10° C. and diethylzinc (151 mg, 1.22 mmol) was added. To this mixture was added dropwise diiodomethane (654 mg, 2.44 mmol). After the addition was complete, the resulting clear solution was stirred for 10 minutes at −10° C. A solution of Example 285C (80 mg, 0.204 mmol) was added. The mixture was allowed to warm to room temperature, stirred for 16 hours, then concentrated. Purification by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minutes) afforded Example 285D and Example 286. Characterization for Example 285D: $^1$H NMR (400 MHz, CDCl$_3$) δ ppm 0.97-1.02 (m, 2H) 1.02-1.08 (m, 2H) 1.50 (s, 3H) 1.62-1.72 (m, 1H) 1.82-1.91 (m, 1H) 1.93-2.04 (m, 1H) 2.21-2.31 (m, 1H) 3.72-3.86 (m, 2H) 4.04 (s, 3H) 4.29-4.39 (m, 1H) 4.48-4.61 (m, 1H) 4.80-4.93 (m, 1H) 7.02 (d, J=9.2 Hz, 1H) 7.54 (dd, J=8.9, 2.8 Hz, 1H) 7.53-7.55 (m, 1H) 8.04 (d, J=2.8 Hz, 1H); MS (ESI) m/z 407 (M+H)$^−$.

Example 286

5-chloro-N-[(2Z)-5-(1-hydroxy-3-iodo-1-methylpropyl)-3-[(2R)-tetrahydrofuran-2-ylmethyl]-1,3-thiazol-2(3H)-ylidene]-2-methoxybenzamide See Example 285D for experimental details $^1$H NMR (500 MHz, CDCl$_3$) δ ppm 1.61 (d, J=1.53 Hz, 3H) 1.63-1.72 (m, 1H) 1.79-1.96 (m, 2H) 2.03-2.14 (m, 2H) 2.40-2.47 (m, 2H) 3.02-3.11 (m, 1H) 3.19 (dd, J=17.4, 9.2 Hz, 1H) 3.78 (dd, J=15.0, 7.0 Hz, 1H) 3.83-3.89 (m, 1H) 3.91 (s, 3H) 4.15-4.22 (m, 1H) 4.25-4.31 (m, 1H) 6.91 (d, J=8.9 Hz, 1H) 7.11 (d, J=5.5 Hz, 1H) 7.34 (dd, J=8.5, 3.1 Hz, 1H) 7.96 (d, J=2.8 Hz, 1H); MS (ESI) m/z 550 (M+H)$^+$.

Example 287

N-[(2Z)-5-tert-butyl-3-[(2R)-tetrahydrofuran-2-ylmethyl]-1,3-thiazol-2(3H)-ylidene]-5-chloro-2-[(1-methylcyclopropyl)methoxy]benzamide The product from 283A and (1-methylcyclopropyl)methanol were processed using the method described in Example 280B to afford the title compound. $^1$H NMR (500 MHz, CDCl$_3$) δ ppm 0.36 (t, J=4.8 Hz, 2H) 0.55 (t, J=4.6 Hz, 2H) 1.22 (s, 3H) 1.36 (s, 9H) 1.61-1.70 (m, 1H) 1.74-1.83 (m, 1H) 1.83-1.92 (m, 1H) 2.01-2.10 (m, 1H) 3.77 (dd, J=14.3, 7.6 Hz, 1H) 3.81 (s, 2H) 3.84 (dd, J=15.9, 8.2 Hz, 1H) 4.21 (dd, J=13.4, 6.41 Hz, 1H) 4.23-4.29 (m, 1H) 4.42 (dd, J=13.4, 2.4 Hz, 1H) 6.86 (d, J=9.5 Hz, 1H) 6.87-6.88 (m, 1H) 7.26 (dd, J=7.9, 3.7 Hz, 1H) 7.81 (d, J=2.8 Hz, 1H); MS (ESI) m/z 463 (M+H)$^+$.

Example 288

N-[(2Z)-5-tert-butyl-3-[(2R)-tetrahydrofuran-2-ylmethyl]-1,3-thiazol-2(3H)-ylidene]-5-chloro-2-isopropoxybenzamide Example 283A and propan-2-ol were processed using the method described in Example 280B to afford the title compound. $^1$H NMR (500 MHz, CDCl$_3$) δ ppm 1.35 (s, 9H) 1.35 (d, J=5.8 Hz, 6H) 1.63-1.71 (m, 1H) 1.75-1.82 (m, 1H) 1.83-1.92 (m, 1H) 2.01-2.10 (m, 1H) 3.77 (dd, J=14.65, 7.32 Hz, 1H) 3.85 (dd, J=14.7, 6.7 Hz, 1H) 4.20 (dd, J=13.7, 6.4 Hz, 1H) 4.24-4.30 (m, 1H) 4.42 (dd, J=13.4, 2.8 Hz, 1H) 4.49-4.57 (m, 1H) 6.86 (s, 1H) 6.89 (d, J=8.9 Hz, 1H) 7.26 (dd, J=8.9, 2.8 Hz, 1H) 7.84 (d, J=2.8 Hz, 1H); MS (ESI) m/z 437 (M+H)$^+$.

Example 289

N-[(2Z)-5-tert-butyl-3-[(2R)-tetrahydrofuran-2-ylmethyl]-1,3-thiazol-2(3H)-ylidene]-5-chloro-2-ethoxybenzamide Example 283A and ethanol were processed using the method described in Example 280B to afford the title compound. ¹H NMR (500 MHz, CDCl₃) δ ppm 1.35 (s, 9H) 1.44 (t, J=7.02 Hz, 3H) 1.62-1.73 (m, 1H) 1.75-1.83 (m, 1H) 1.84-1.92 (m, 1H) 2.01-2.11 (m, 1H) 3.77 (dd, J=13.7, 7.6 Hz, 1H) 3.84 (dd, J=14.7, 6.7 Hz, 1H) 4.13 (dd, J=14.0, 7.2 Hz, 2H) 4.22 (dd, J=13.4, 6.0 Hz, 1H) 4.25-4.31 (m, 1H) 4.41 (dd, J=13.4, 2.8 Hz, 1H) 6.86 (s, 1H) 6.89 (d, J=8.9 Hz, 1H) 7.29 (dd, J=8.9, 2.8 Hz, 1H) 7.91 (d, J=2.8 Hz, 1H); MS (ESI) m/z 423 (M+H)⁻.

Example 290

N-[(2Z)-5-tert-butyl-3-[(2R)-tetrahydrofuran-2-ylmethyl]-1,3-thiazol-2(3H)-ylidene]-5-chloro-2-(tetrahydrofuran-3-yloxy)benzamide Example 283A and tetrahydrofuran-3-ol were processed using the method described in Example 280B to afford the title compound. ¹H NMR (500 MHz, CDCl₃) δ ppm ¹H NMR (500 MHz, CDCl₃) δ ppm 1.36 (s, 9H) 1.61-1.70 (m, 1H) 1.76-1.83 (m, 1H) 1.84-1.93 (m, 1H) 2.03-2.10 (m, 1H) 2.11-2.25 (m, 2H) 3.77 (dd, J=14.0, 7.3 Hz, 1H) 3.82-3.91 (m, 2H) 3.98 (dd, J=15.3, 8.5 Hz, 1H) 4.02 (d, J=3.7 Hz, 2H) 4.20 (ddd, J=6.4, 1.5 Hz, 1H) 4.23-4.30 (m, 1H) 4.41 (dd, J=13.7, 3.1 Hz, 1H) 4.88-5.00 (m, 1H) 6.83 (dd, J=8.9, 0.6 Hz, 1H) 6.88 (d, J=0.9 Hz, 1H) 7.28 (dd, J=8.9, 2.75 Hz, 1H) 7.87 (t, J=3.1 Hz, 1H); MS (ESI) m/z 423 (M+H)⁺.

Example 291

N-[(2Z)-5-tert-butyl-3-[(2R)-tetrahydrofuran-2-ylmethyl]-1,3-thiazol-2(3H)-ylidene]-5-chloro-2-[(2-methoxyethyl)(methyl)amino]benzamide A mixture of the product from Example 283A (120 mg, 0.3 mmol), 2-methoxy-N-methylethanamine (54 mg, 0.6 mmol) and triethylamine (127 ul, 0.91 mmol) in tetrahydrofuran (1 mL) was heated at 120° C. in a microwave (CEM) for 2 hours. The reaction mixture was diluted with water and extracted with ethyl acetate. The organic extract was dried (Na₂SO₄), filtered, and concentrated. Purification by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound afforded the title compound. ¹H NMR (500 MHz, CDCl₃) δ ppm 1.36 (s, 9H) 1.62-1.71 (m, 1H) 1.78-1.86 (m, 1H) 1.86-1.93 (m, 1H) 2.01-2.11 (m, 1H) 2.89 (s, 3H) 3.26 (s, 3H) 3.29 (t, J=6.1 Hz, 2H) 3.54 (t, J=6.4 Hz, 2H) 3.78 (dd, J=14.7, 7.3 Hz, 1H) 3.85 (dd, J=15.0, 8.2 Hz, 1H) 4.18 (dd, J=13.7, 6.4 Hz, 1H) 4.23-4.30 (m, 1H) 4.40 (dd, J=13.7, 3.1 Hz, 1H) 6.85 (s, 1H) 6.92 (d, J=8.9 Hz, 1H) 7.20 (dd, J=8.9, 2.8 Hz, 1H) 7.67 (d, J=2.4 Hz, 1H); MS (ESI) m/z 466 (M+H)⁺.

Example 292

N-[(2Z)-5-tert-butyl-3-[(2R)-tetrahydrofuran-2-ylmethyl]-1,3-thiazol-2(3H)-ylidene]-5-chloro-2-(difluoromethoxy)benzamide Example 240C and 5-chloro-2-(difluoromethoxy)benzoic acid were processed using the method described in Example 223A to afford the title compound. ¹H NMR (500 MHz, CDCl₃) δ ppm 1.36 (s, 9H) 1.60-1.69 (m, 1H) 1.76-1.84 (m, 1H) 1.85-1.93 (m, 1H) 2.02-2.12 (m, 1H) 3.78 (dd, J=13.7, 7.3 Hz, 1H) 3.85 (dd, J=15.0, 6.7 Hz, 1H) 4.20 (dd, J=13.4, 6.4 Hz, 1H) 4.24-4.30 (m, 1H) 4.44 (dd, J=13.7, 2.8 Hz, 1H) 6.73 (t, J=6.3 Hz, 1H) 6.91 (s, 1H) 7.17 (d, J=8.5 Hz, 1H) 7.38 (dd, J=8.5, 2.8 Hz, 1H) 8.05 (d, J=2.8 Hz, 1H); MS (ESI) m/z 445 (M+H)⁺.

Example 293

N-[(2Z)-5-tert-butyl-3-[(2R)-tetrahydrofuran-2-ylmethyl]-1,3-thiazol-2(3H)-ylidene]-5-chloro-2-(trifluoromethoxy)benzamide Example 240C and 5-chloro-2-(trifluoromethoxy)benzoic acid were processed using the method described in Example 223A to afford the title compound. ¹H NMR (500 MHz, CDCl₃) δ ppm 1.36 (s, 9H) 1.58-1.67 (m, 1H) 1.75-1.83 (m, 1H) 1.84-1.93 (m, 1H) 2.01-2.11 (m, 1H) 3.77 (dd, J=13.7, 6.4 Hz, 1H) 3.84 (dd, J=15.0, 6.7 Hz, 1H) 4.18 (dd, J=13.7, 6.7 Hz, 1H) 4.22-4.29 (m, 1H) 4.46 (dd, J=13.7, 2.8 Hz, 1H) 6.91 (s, 1H) 7.23 (dd, J=8.5, 1.2 Hz, 1H) 7.40 (dd, J=8.9, 2.8 Hz, 1H) 8.06 (d, J=2.8 Hz, 1H); MS (ESI) m/z 463 (M+H)⁺.

Example 294

N-[(2Z)-5-tert-butyl-3-[(2R)-tetrahydrofuran-2-ylmethyl]-1,3-thiazol-2(3H)-ylidene]-5-chloro-2-(2,2,2-trifluoroethoxy)benzamide The product from 283A and 2,2,2-trifluoroethanol were processed using the method described in Example 280B to afford the title compound. ¹H NMR (500 MHz, CDCl₃) δ ppm 1.37 (s, 9H) 1.60-1.69 (m, 1H) 1.76-1.84 (m, 1H) 1.85-1.93 (m, 1H) 2.02-2.11 (m, 1H) 3.78 (dd, J=13.7, 7.3 Hz, 1H) 3.85 (dd, J=15.0, 7.0 Hz, 1H) 4.21 (dd, J=13.4, 6.4 Hz, 1H) 4.24-4.29 (m, 1H) 4.43 (dd, J=11.0, 2.8 Hz, 1H) 4.47 (dd, J=17.1, 8.5 Hz, 2H) 6.91 (s, 1H) 7.01 (d, J=8.9 Hz, 1H) 7.33 (dd, J=8.5, 2.8 Hz, 1H) 7.99 (d, J=2.8 Hz, 1H); MS (ESI) m/z 477 (M+H)⁻.

Example 295

N-[(2Z)-5-tert-butyl-3-[(2R)-tetrahydrofuran-2-ylmethyl]-1,3-thiazol-2(3H)-ylidene]-5-chloro-2-[3-(dimethylamino)propoxy]benzamide The product from 283A and 3-(dimethylamino)propan-1-ol were processed using the method described in Example 280B to afford the title compound. ¹H NMR (500 MHz, CDCl₃) δ ppm 1.38 (s, 9H) 1.62-1.71 (m, 1H) 1.84-1.91 (m, 1H) 1.91-1.98 (m, 1H) 2.09-2.19 (m, 1H) 2.29-2.36 (m, 2H) 3.04-3.09 (m, J=4.9 Hz, 2H) 3.81 (dd, J=13.7, 6.4 Hz, 1H) 3.87 (dd, J=15.0, 7.0 Hz, 1H) 4.25-4.34 (m, 4H) 4.51 (d, J=12.8 Hz, 1H) 6.93 (d, J=9.2 Hz, 1H) 7.00-7.02 (m, 1H) 7.44 (dd, J=8.9, 2.9 Hz, 1H) 8.20 (d, J=2.8 Hz, 1H) 10.35-10.51 (m, 1H); MS (ESI) m/z 480 (M+H)⁺.

Example 296

5,6-dichloro-N-[(2Z)-4,5-dimethyl-3-(tetrahydrofuran-2-ylmethyl)-1,3-thiazol-2(3H)-ylidene]quinoline-8-carboxamide A mixture of Example 186A (145 mg), 5,6-dichloroquinoline-8-carboxylic acid (99.65 mg) (Bailey J. Heterocycl. Chem. 1974, 11, 229), 1-hydroxybenzotriazole hydrate (55 mg), 1-ethyl-3-[3-(dimethylamino)propyl]-carbodiimide hydrochloride (79 mg) and triethylamine (0.14 mL) in tetrahydrofuran (3 mL) was heated at 70° C. on a shaker overnight, cooled, quenched in saturated NaHCO₃ and extracted with ethyl acetate (2×). The organic extracts were dried (Na$_2$SO$_4$), filtered and the solvent was evaporated. The crude material was purified by reverse phase preparative HPLC on a Waters Symmetry C8 column (25 mm×100 mm, 7 µm particle size) using a gradient of 10% to 100% acetonitrile:10 mM ammonium acetate over 8 minutes (10 minutes run time) at a flow rate of 40 mL/minutes) to afford the title compound. $^1$H NMR (300 MHz, CDCl$_3$) δ ppm 1.62-1.75 (m, 1H), 1.85-1.95 (m, 2H), 2.0-2.1 (m, 1H), 2.26 (s, 3H), 2.30 (s, 3H), 3.70-3.77 (m, 1H), 3.83-3.90 (m, 1H), 3.97 (dd, 1H), 4.35-4.42 (m, 1H), 4.55 (dd, 1H), 7.53 (dd, 1H), 8.60 (dd, 1H), 9.07 (m, 1H); MS (DCI/NH$_3$) m/z 436, 438 (M+H)$^+$.

Example 297

6-chloro-N-[(2Z)-4,5-dimethyl-3-(tetrahydrofuran-2-ylmethyl)-1,3-thiazol-2(3H)-ylidene]quinoline-8-carboxamide A mixture of Example 186A (106 mg), 6-chloro-quinoline-8-carboxylic acid (73 mg) (Weyer et al, *Arzneim. Forsch* 1974, 24, 269), 1-hydroxybenzotriazole hydrate (47 mg), 1-ethyl-3-[3-(dimethylamino)propyl]-carbodiimide hydrochloride (69 mg), and triethylamine (0.15 mL) in tetrahydrofuran (2 mL) was heated to 70° C. on a shaker overnight, cooled, poured into saturated NaHCO$_3$ and extracted with ethyl acetate (2×). The organic extracts were dried (Na$_2$SO$_4$), filtered and the solvent was evaporated. The crude material was dissolved in warm methanol and allowed to cool overnight. The solid precipitate was discarded, the filtrate was concentrated to dryness, triturated with cold methanol, and collected to afford the title compound. $^1$H NMR (300 MHz, dimethylsulfoxide-d$_6$) δ ppm 1.56-1.64 (m, 1H), 1.70-1.95 (m, 3H), 2.26 (s, 3H), 2.27 (s, 3H), 3.57-3.65 (m, 1H), 3.73-3.80 (m, 1H), 3.97-4.05 (m, 1H), 4.24-4.35 (m, 2H), 7.60 (dd, 1H), 7.78 (d, 1H), 8.15 (d, 1H), 8.38 (dd, 1H), 8.91 (dd, 1H); MS (DCI/NH$_3$) m/z 402 (M+H)$^+$.

Example 298

6-chloro-N-[(2Z)-5-methyl-3-(tetrahydrofuran-2-ylmethyl)-1,3-thiazol-2(3H)-ylidene]quinoline-8-carboxamide A mixture of Example 149A (142 mg), 6-chloro-quinoline-8-carboxylic acid (105 mg) (Weyer et al, *Arzneim. Forsch* 1974, 24, 269), 1-hydroxybenzotriazole hydrate (67 mg), 1-ethyl-3-[3-(dimethylamino)propyl]-carbodiimide hydrochloride (94 mg), and triethylamine (0.15 mL) in tetrahydrofuran (3 mL) was heated to 70° C. for 24 hours, cooled, poured into saturated NaHCO$_3$ and extracted with ethyl acetate (2×). The organic extracts were dried (Na$_2$SO$_4$), filtered and the solvent was evaporated. The crude material was purified by reverse phase preparative HPLC on a Waters Symmetry C8 column (25 mm×100 mm, 7 µm particle size) using a gradient of 10% to 100% acetonitrile: 10 mM ammonium acetate over 8 minutes (10 minutes run time) at a flow rate of 40 mL/minutes) to afford the title compound. $^1$H NMR (300 MHz, CDCl$_3$) δ ppm 1.65-1.72 (m, 1H), 1.80-1.95 (m, 2H), 2.0-2.1 (m, 1H), 2.34 (d, J=1.4 Hz, 3H), 3.74-3.90 (m, 2H), 4.14 (dd, 1H), 4.2-4.3 (m, 1H), 4.47 (dd, 1H), 6.95 (q, J=1.4 Hz, 1H), 7.42 (dd, 1H), 7.84 (d, 1H), 8.03 (d, 1H), 8.08 (dd, 1H), 9.04 (dd, 1H); MS (DCI/NH$_3$) m/z 388 (M+H)$^+$.

Example 299

5,6-dichloro-N-[(2Z)-5-methyl-3-(tetrahydrofuran-2-ylmethyl)-1,3-thiazol-2(3H)-ylidene]quinoline-8-carboxamide A mixture of Example 149A (117 mg), 5,6-dichloroquinoline-8-carboxylic acid (71 mg), 1-hydroxybenzotriazole hydrate (51 mg), 1-ethyl-3-[3-(dimethylamino)propyl]-carbodiimide hydrochloride (79 mg) and triethylamine (0.15 mL) in tetrahydrofuran was processed and purified according to the method of Example 298 to afford the title compound. $^1$H NMR (300 MHz, CDCl$_3$) δ ppm 1.6-1.71 (m, 1H), 1.78-1.95 (m, 2H), 2.0-2.1 (m, 1H), 2.34 (d, J=1.4 Hz, 3H), 3.72-3.90 (m, 2H), 4.12 (dd, 1H), 4.2-4.3 (m, 1H), 4.46 (dd, 1H), 6.94 (q, J=1.4 Hz, 1H), 7.53 (dd, 1H), 8.60 (dd, 1H), 9.06 (dd, 1H); MS (DCI/NH$_3$) m/z 422 (M+H)$^+$.

Example 300

3-methoxy-N-[(2Z)-5-methyl-3-(tetrahydrofuran-2-ylmethyl)-1,3-thiazol-2(3H)-ylidene]-2-naphthamide A mixture of Example 149A (113 mg), 3-methoxy-2-naphthoic acid (Aldrich) (69 mg), 1-hydroxybenzotriazole hydrate (50 mg), 1-ethyl-3-[3-(dimethylamino)propyl]-carbodiimide hydrochloride (79 mg) and triethylamine (0.15 mL) in tetrahydrofuran (2 mL) was shaken over the weekend at room temperature, poured into saturated NaHCO$_3$ and extracted with ethyl acetate (2×). The organic extracts were dried (Na$_2$SO$_4$), filtered and the solvent was evaporated. The crude material was purified by flash chromatography over silica gel eluting with ethyl acetate:hexane (7:3) to afford the title compound. $^1$H NMR (300 MHz, CDCl$_3$) δ ppm 1.64-1.78 (m, 1H), 1.80-1.95 (m, 2H), 2.02-2.15 (m, 1H), 2.32 (d, J=1.4 Hz, 3H), 3.74-3.92 (m, 2H), 4.01 (s, 3H), 4.2 (dd, 1H), 4.27-4.35 (m, 1H), 4.51 (d, 1H), 6.91 (br s, 1H), 7.20 (s, 1H), 7.33 (m, 1H), 7.46 (m, 1H), 7.73 (d, 1H), 7.81 (d, 1H), 8.42 (s, 1H); MS (DCI/NH$_3$) m/z 383 (M+H)$^-$.

Example 301

N-[(2Z)-5-tert-butyl-3-[(cis)-(3-methoxycyclobutyl)methyl]-1,3-thiazol-2(3H)-ylidene]-5-chloro-2-methoxybenzamide Example 301A cis-3-benzyloxymethylcyclobutanol methyl ether To a solution of cis-3-benzyloxymethylcyclobutanol (Albany Molecular Research Institute, 1.0 g, 5.2 mmol) in 10 mL of tetrahydrofuran at 0° C. was added NaH (0.62 g, 15.6 mmol). The mixture stirred for 15 minutes and iodomethane (0.49 mL, 7.8 mmol) was added and the mixture was allowed to warm to ambient temperature and stirred for 16 hours. Some starting material remained by TLC so additional NaH (0.21, 5.2 mmol) and iodomethane (0.32 mL, 5.2 mmol) were added and the mixture stirred for an additional 2 hours. The mixture was quenched with 10 mL of NH$_4$Cl and diluted with 10 mL of ethyl acetate. The layers were separated and the aqueous layer was extracted twice with 5 mL portions of ethyl acetate. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 207 (M+H)$^+$.

Example 301B (cis-3-methoxycyclobutyl)methanol

A solution of Example 301A (1.05 g, 5.2 mmol) in 10 mL of ethanol was degassed and the flask was filled with N$_2$. This was repeated two additional times. Pd/C (0.1 g, 10 wt %) was added and the mixture was degassed again and flushed with N$_2$. This was repeated two additional times and the flask was put under 1 atm. of H$_2$ and the mixture was allowed to stir at ambient temperature for 72 hours. The mixture was degassed and the flask was filled with N$_2$. The reaction mixture was filtered, concentrated under reduced pressure and purified by column chromatography (SiO$_2$, 25% hexanes in ethyl acetate) to afford the title compound. MS (DCI/NH$_3$) m/z 134 (M+NH$_4$)$^+$.

Example 301C (cis-3-methoxycyclobutyl)methyl 4-methylbenzenesulfonate

Example 301B (0.49 g, 4.2 mmol) and p-toluenesulfonyl chloride (0.80 g, 4.2 mmol) in 5 mL of CH$_2$Cl$_2$ and 5 mL of pyridine were processed as in Example 203A to afford the title compound. MS (DCI/NH$_3$) m/z 288 (M+NH$_4$)$^+$.

Example 301D 5-tert-butyl-3-((cis-3-methoxycyclobutyl)methyl) thiazol-2(3H)-imine Example 240A (0.25 g, 1.6 mmol), Example 301C (0.44 g, 1.6 mmol) and tetrabutylammonium iodide (0.30 g, 0.81 mmol) in 0.5 mL of N,N-dimethylformamide were processed as in Example 240C to afford the title compound. MS (DCI/NH$_3$) m/z 266 (M+H)$^+$.

Example 301E

N-[(2Z)-5-tert-butyl-3-[(cis)-(3-methoxycyclobutyl) methyl]-1,3-thiazol-2(3H)-ylidene]-5-chloro-2-methoxybenzamide Example 301D (0.19 g, 0.75 mmol), triethylamine (0.31 mL, 2.2 mmol) and Example 205B (0.75 mmol) in 10 mL of tetrahydrofuran were processed as in Example 208D to afford the title compound (0.105 g, 0.25 mmol, 33% yield). $^1$H NMR (300 MHz, CD$_3$OD) δ ppm 1.38 (s, 9H), 1.71-1.84 (m, 2H), 2.31-2.47 (m, 3H), 3.21 (s, 3H), 3.71-3.83 (m, 1H), 3.86 (s, 3H), 4.29 (d, J=6.4 Hz, 2H), 7.07 (d, J=8.8 Hz, 1H), 7.14 (s, 1H), 7.40 (dd, J=8.8, 3.1 Hz, 1H), 7.83 (d, J=2.7 Hz, 1H); MS (DCI/NH$_3$) m/z 423 (M+H)$^+$. Anal. Calculated for C$_{21}$H$_{27}$ClN$_2$O$_3$S: C, 59.63; H, 6.43; N, 6.62. Found: C, 59.66; H, 6.28; N, 6.44.

Example 302

N-[(2Z)-5-tert-butyl-3-[(cis)-(3-hydroxycyclobutyl) methyl]-1,3-thiazol-2(3H)-ylidene]-5-chloro-2-methoxybenzamide Example 302A (cis-3-(benzyloxymethyl)cyclobutoxy)(tert-butyl) dimethylsilane To a solution of cis-3-benzyloxymethylcyclobutanol (Albany Molecular Research Institute, 1.0 g, 5.2 mmol) in 50 mL of CH$_2$Cl$_2$ was added imidazole (2.7 g, 39 mmol) followed by tert-butyldimethylsilyl chloride (3.9 g, 26 mmol). This mixture stirred at ambient temperature for 2 hours and was quenched with 10 mL of saturated aqueous NH$_4$Cl. The layers were separated and the aqueous layer was extracted with three 5 mL of portions of CH$_2$Cl$_2$. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 307 (M+H)$^+$.

Example 302B (cis-3-(tert-butyldimethylsilyloxy)cyclobutyl)methanol

A solution of Example 302A (3.7 g, 12 mmol) in 20 mL of ethanol was degassed and the flask was flushed with N$_2$. This was repeated two additional times. Pd/C (0.37 g, 10 wt %) was added and the mixture was degassed again and flushed with N$_2$. This was repeated two additional times then the flask was put under 1 atm. of H$_2$ and the reaction mixture was allowed to stir at ambient temperature for 48 hours. The mixture was degassed and the flask was filled with N$_2$ then the reaction mixture was filtered, concentrated under reduced pressure and purified by column chromatography (SiO$_2$, 50% hexanes in ethyl acetate) to afford the title compound. MS (DCI/NH$_3$) m/z 217 (M+NH$_4$)$^+$.

Example 302C (cis-3-(tert-butyldimethylsilyloxy)cyclobutyl)methyl 4-methylbenzenesulfonate Example 302B (1.2 g, 5.5 mmol) and p-toluenesulfonyl chloride (1.1 g, 5.5 mmol) in 7 mL of CH$_2$Cl$_2$ and 7 mL of pyridine were processed as in Example 203A to afford the title compound. MS (DCI/NH$_3$) m/z 371 (M+H)$^+$, 388 (M+NH$_4$)$^-$.

Example 302D 5-tert-butyl-3-((cis-3-(tert-butyldimethylsilyloxy) cyclobutyl)methyl)thiazol-2(3H)-imine Example 240A (0.72 g, 4.6 mmol), Example 302C (1.7 g, 4.6 mmol) and tetrabutylammonium iodide (0.85 g, 2.3 mmol) in 1.5 mL of N,N-dimethylformamide were processed as in Example 240C to afford the title compound. MS (DCI/NH$_3$) m/z 355 (M+H)$^+$.

Example 302E (Z)—N-(5-tert-butyl-3-((cis-3-(tert-butyldimethylsilyloxy)cyclobutyl)methyl)thiazol-2(3H)-ylidene)-5-chloro-2-methoxybenzamide Example 302D (0.57 g, 1.6 mmol), triethylamine (0.67 mL, 4.8 mmol) and Example 205B (1.6 mmol) in 10 mL of tetrahydrofuran were processed as in Example 208D to afford the title compound. MS (DCI/NH$_3$) m/z 523 (M+H)$^+$.

Example 302F

N-[(2Z)-5-tert-butyl-3-[(cis)-(3-hydroxycyclobutyl) methyl]-1,3-thiazol-2(3H)-ylidene]-5-chloro-2-methoxybenzamide To Example 302E (0.78 g, 1.5 mmol) in 10 mL of tetrahydrofuran at ambient temperature was added tetrabutylammonium fluoride (1 M in tetrahydrofuran, 1.8 mL, 1.8 mmol)

dropwise via syringe pump over 30 minutes. The reaction mixture was stirred at ambient temperature for 2 hours and was concentrated under reduced pressure and purified by column chromatography ($SiO_2$, 50% hexanes in ethyl acetate then 100% ethyl acetate) to afford the title compound. $^1$H NMR (300 MHz, $CD_3OD$) δ ppm 1.38 (s, 9H), 1.70-1.82 (m, 2H), 2.25-2.42 (m, 3H), 3.86 (s, 3H), 4.00-4.10 (m, 1H), 4.28 (d, J=6.4 Hz, 2H), 7.07 (d, J=9.2 Hz, 1H), 7.12 (s, 1H), 7.39 (dd, J=8.8, 2.7 Hz, 1H), 7.80 (d, J=2.7 Hz, 1H); MS (DCI/$NH_3$) m/z 409 (M+H)$^-$.

Example 303

N-[(2Z)-5-tert-butyl-3-[((cis)-3-hydroxy-3-methylcyclobutyl)methyl]-1,3-thiazol-2(3H)-ylidene]-5-chloro-2-methoxybenzamide

Example 303A (Z)—N-(5-tert-butyl-3-((3-oxocyclobutyl)methyl)thiazol-2(3H)-ylidene)-5-chloro-2-methoxybenzamide To Example 302F (0.57 g, 1.4 mmol) in 15 mL of $CH_2Cl_2$ was added 4-methylmorpholine N-oxide (0.82 g, 7.0 mmol) followed by approximately 0.5 g powdered 4 Å molecular sieves. This mixture was stirred at ambient temperature for 15 minutes and was cooled to 0° C. and tetrapropylammonium perruthenate (49 mg, 0.14 mmol) was added in portions over 5 minutes. The mixture was stirred at 0° C. for 5 minutes and was allowed to warm to ambient temperature and stirred for an additional 90 minutes. The mixture was filtered through Celite, concentrated under reduced pressure and purified by column chromatography ($SiO_2$, 20% hexanes in ethyl acetate) to afford the title compound. MS (DCI/$NH_3$) m/z 407 (M+H)$^-$.

Example 303B

N-[(2Z)-5-tert-butyl-3-[((cis)-3-hydroxy-3-methylcyclobutyl)methyl]-1,3-thiazol-2(3H)-ylidene]-5-chloro-2-methoxybenzamide To Example 302A (0.21 g, 0.52 mmol) in 10 mL of tetrahydrofuran at −78° C. was added a 1.6 M solution of methyllithium in diethyl ether (1.0 mL, 1.6 mmol) dropwise over 5 minutes. The mixture was stirred at −78° C. for 2 hours and was slowly warmed to ambient temperature and was allowed to stir for 18 hours. The mixture was quenched with 5 mL of saturated aqueous $NH_4Cl$ and diluted with 5 mL of ethyl acetate. The layers were separated and the aqueous layer was extracted twice with 5 mL of ethyl acetate. The combined organic extracts were dried over anhydrous $Na_2SO_4$, filtered and concentrated under reduced pressure. Purification via column chromatography ($SiO_2$, 30% hexanes in ethyl acetate) afforded the title compound. $^1$H NMR (300 MHz, $CD_3OD$) δ ppm 1.32 (s, 3H), 1.38 (s, 9H), 1.90-2.00 (m, 2H), 2.06-2.16 (m, 2H), 2.35-2.52 (m, 1H), 3.86 (s, 3H), 4.30 (d, J=7.1 Hz, 2H), 7.07 (d, J=8.8 Hz, 1H), 7.12 (s, 1H), 7.39 (dd, J=8.8, 2.7 Hz, 1H), 7.80 (d, J=3.1 Hz, 1H); MS (DCI/$NH_3$) m/z 423 (M+H)$^+$. Anal. Calculated for $C_{21}H_{27}ClN_2O_3S.0.1H_2O$: C, 59.38; H, 6.45; N, 6.59. Found: C, 59.17; H, 6.62; N, 6.28.

Example 304

5-chloro-N-[(2Z)-5-(1-hydroxy-1-methylethyl)-3-[((cis)-3-methoxycyclobutyl)methyl]-4-methyl-1,3-thiazol-2(3H)-ylidene]-2-methoxybenzamide

Example 304A (Z)—N-(5-acetyl-3-(((cis)-3-methoxycyclobutyl)methyl)-4-methylthiazol-2(3H)-ylidene)-5-chloro-2-methoxybenzamide Example 238A (0.57 g, 1.8 mmol), Example 301C (0.48 g, 1.8 mmol) and potassium tert-butoxide (0.42 g, 3.5 mmol) were processed as described in the procedure for Example 238B to afford the title compound. MS (DCI/$NH_3$) m/z 423 (M+H)$^+$.

Example 304B 5-chloro-N-[(2Z)-5-(1-hydroxy-1-methylethyl)-3-[((cis)-3-methoxycyclobutyl)methyl]-4-methyl-1,3-thiazol-2(3H)-ylidene]-2-methoxybenzamide Example 304A (20 mg, 0.047 mmol) and methyllithium (1.6 M in ether, 88 μL, 0.14 mmol) in 1 mL of tetrahydrofuran were processed as described in Example 239 to afford the title compound. $^1$H NMR (300 MHz, $CD_3OD$) δ ppm 1.61 (s, 6H), 1.80-1.87 (m, 2H), 2.32-2.43 (m, 2H), 2.49 (s, 3H), 3.20-3.24 (m, 1H), 3.20 (s, 3H), 3.34-3.41 (m, 1H), 3.68-3.78 (m, 1H), 3.86 (s, 3H), 4.38 (d, J=6.1 Hz, 2H), 7.06 (d, J=8.8 Hz, 1H), 7.39 (dd, J=8.8, 2.7 Hz, 1H), 7.86 (d, J=2.7 Hz, 1H) MS (DCI/$NH_3$) m/z 439 (M+H)$^+$.

Example 305

N-[(2Z)-5-tert-butyl-3-[2-(2-methoxyethoxy)ethyl]-1,3-thiazol-2(3H)-ylidene]-5-chloro-2-methoxybenzamide

Example 305A 5-tert-butyl-3-(2-(2-methoxyethoxy)ethyl)thiazol-2(3H)-imine hydrobromide A mixture of Example 240A (0.20 g, 1.3 mmol) and 1-bromo-2-(2-methoxyethoxy)ethane (0.27 g, 1.4 mmol) was warmed to 85° C. and was allowed to stir for 24 hours. The mixture was cooled to ambient temperature and the crude solids were triturated with ethanol and ether to afford the title compound. MS (DCI/$NH_3$) m/z 259 (M+H)$^-$.

Example 305B

N-[(2Z)-5-tert-butyl-3-[2-(2-methoxyethoxy)ethyl]-1,3-thiazol-2(3H)-ylidene]-5-chloro-2-methoxybenzamide Example 305A (0.3 g, 0.88 mmol), triethylamine (0.49 mL, 3.5 mmol) and Example 205B (0.88 mmol) in 10 mL of tetrahydrofuran and 1.5 mL of N,N-dimethylformamide were processed as described in Example 208D to afford the title compound. $^1$H NMR (300 MHz, $CD_3OD$) δ ppm 1.38 (s, 9H), 3.31 (s, 3H), 3.47-3.52 (m, 2H), 3.59-3.65 (m, 2H), 3.87 (dd, J=5.4 Hz, 2H), 3.86 (s, 3H), 4.42 (dd, J=5.1 Hz, 2H), 7.07 (d, J=8.8 Hz, 1H), 7.18 (s, 1H), 7.39 (dd, J=8.8, 2.7 Hz, 1H), 7.82 (d, J=2.7 Hz, 1H); MS (DCI/$NH_3$) m/z 427 (M+H)$^+$. Anal.

Calculated for $C_{20}H_{27}ClN_2O_4S$: C, 56.26; H, 6.37; N, 6.56. Found: C, 56.06; H, 5.50; N, 6.43.

Example 306

N-[(2Z)-5-tert-butyl-3-(3-methoxypropyl)-1,3-thiazol-2(3H)-ylidene]-5-chloro-2-methoxybenzamide

Example 306A 5-tert-butyl-3-(3-methoxypropyl)thiazol-2(3H)-imine

A mixture of Example 240A (0.20 g, 1.3 mmol) and 1-bromo-3-methoxypropane (0.22 g, 1.4 mmol) was warmed to 85° C. and was allowed to stir for 24 hours. The mixture was cooled to ambient temperature, concentrated under reduced pressure and purified via column chromatography ($SiO_2$, 10% methanol in ethyl acetate then 9:1:0.1 $CH_2Cl_2$:methanol:$NH_4OH$) to afford the title compound. MS (DCI/$NH_3$) m/z 229 (M-PH)$^+$.

Example 306B

N-[(2Z)-5-tert-butyl-3-(3-methoxypropyl)-1,3-thiazol-2(3H)-ylidene]-5-chloro-2-methoxybenzamide Example 306A (0.25 g, 0.81 mmol), triethylamine (0.34 mL, 2.4 mmol) and Example 205B (0.81 mmol) in 10 mL of tetrahydrofuran and 1 mL of N,N-dimethylformamide were processed as in Example 208D to afford the title compound. $^1$H NMR (300 MHz, $CD_3OD$) δ ppm 1.38 (s, 9H), 2.05-2.17 (m, 2H), 3.32 (s, 3H), 3.41 (t, J=5.9 Hz, 2H), 3.86 (s, 3H), 4.33 (t, J=7.0 Hz, 2H), 7.07 (d, J=8.8 Hz, 1H), 7.11 (s, 1H), 7.40 (dd, J=9.0, 2.9 Hz, 1H), 7.89 (d, J=2.7 Hz, 1H); MS (DCI/$NH_3$) m/z 397 (M+H)$^+$. Anal. Calculated for $C_{19}H_{25}ClN_2O_3S$: C, 57.49; H, 6.35; N, 7.06. Found: C, 57.18; H, 6.21; N, 6.94.

Example 307

N-[(2Z)-5-tert-butyl-3-(2-ethoxyethyl)-1,3-thiazol-2(3H)-ylidene]-5-chloro-2-methoxybenzamide

Example 307A 5-tert-butyl-3-(2-ethoxyethyl)thiazol-2(3H)-imine

A mixture of Example 240A (0.17 g, 1.1 mmol) and 2-(bromoethyl)ether (0.20 g, 1.2 mmol) was warmed to 85° C. and was allowed to stir for 24 hours. The mixture was cooled to ambient temperature, concentrated and purified via column chromatography ($SiO_2$, 10% methanol in ethyl acetate then 9:1:0.1 $CH_2Cl_2$:methanol:$NH_4OH$) to afford the title compound. MS (DCI/$NH_3$) m/z 229 (M+H)$^+$.

Example 307B

N-[(2Z)-5-tert-butyl-3-(2-ethoxyethyl)-1,3-thiazol-2(3H)-ylidene]-5-chloro-2-methoxybenzamide Example 307A (0.24 g, 1.05 mmol), triethylamine (0.44 mL, 3.2 mmol) and Example 205B (1.05 mmol) in 15 mL of tetrahydrofuran were processed as in Example 208D to afford the title compound. $^1$H NMR (300 MHz, $CD_3OD$) δ ppm 1.14 (t, J=7.0 Hz, 3H), 1.38 (s, 9H), 3.52 (q, J=6.9 Hz, 2H), 3.81 (t, J=5.3 Hz, 2H), 3.86 (s, 3H), 4.41 (t, J=5.3 Hz, 2H), 7.07 (d, J=8.8 Hz, 1H), 7.14 (s, 1H), 7.39 (dd, J=8.8, 2.7 Hz, 1H), 7.83 (d, J=3.1 Hz, 1H); MS (DCI/$NH_3$) m/z 397 (M+H)$^+$. Anal. Calculated for $C_{19}H_{25}ClN_2O_3S$: C, 57.49; H, 6.35; N, 7.06. Found: C, 57.34; H, 6.04; N, 6.94.

Example 308

N-[(2Z)-5-tert-butyl-3-(3-hydroxy-3-methylbutyl)-1,3-thiazol-2(3H)-ylidene]-5-chloro-2-methoxybenzamide

Example 308A 3-hydroxy-3-methylbutyl 4-methylbenzenesulfonate

To a solution of 3-methylbutane-1,3-diol (2.13 mL, 20 mmol) in pyridine (20 mL) at 0° C. was added para-toluenesulfonyl chloride (3.8 g, 20 mmol) in pyridine (10 mL) dropwise over 15 minutes. This mixture stirred at ambient temperature for 3 hours and 35 mL $H_2O$ was added and the mixture was extracted with ethyl acetate (2×50 mL). The combined organics were washed with $H_2O$ (2×50 mL), dried over $MgSO_4$, filtered, concentrated under reduced pressure and dried under vacuum (~1 mm Hg) to afford the title compound. MS (ESI) m/z 276 (M+18)$^+$.

Example 308B

N-[(2Z)-5-tert-butyl-3-(3-hydroxy-3-methylbutyl)-1,3-thiazol-2(3H)-ylidene]-5-chloro-2-methoxybenzamide A solution of Example 244A (75 mg, 0.23 mmol) in N,N-dimethylformamide (2 mL) was treated with NaH 60% dispersion in oil (9.5 mg, 0.23 mmol) followed by Example 308A (60 mg, 0.23 mmol). The reaction mixture was stirred at room temperature for 18 hours, poured into water and extracted with ethyl acetate. The organic layer was washed with $H_2O$ (2×50 mL), dried over $MgSO_4$, filtered, concentrated under reduced pressure and dried under vacuum (~1 mm Hg) to afford the title compound. $^1$H NMR (300 MHz, dimethylsulfoxide-$d_6$) δ ppm 1.17 (s, 6H), 1.32 (s, 9H), 1.76-1.91 (m, 2H), 3.79 (s, 3H), 4.14-4.31 (m, 2H), 4.43 (s, 1H), 7.10 (d, J=8.8 Hz, 1H), 7.31 (s, 1H), 7.44 (dd, J=9.0, 2.9 Hz, 1H), 7.76 (d, J=3.1 Hz, 1H); MS (ESI) m/z 411 (M+H)$^n$ Anal. Calculated for $C_{20}H_{27}ClN_2O_3SC$, 58.45; H, 6.62; N, 6.82. Found C, 58.30; H, 6.51; N, 6.71.

Example 309

N-[(2Z)-5-tert-butyl-3-(3-hydroxy-3-methylbutyl)-4-methyl-1,3-thiazol-2(3H)-ylidene]-5-chloro-2-methoxybenzamide

Example 309A (Z)—N-(5-tert-butyl-4-methylthiazol-2(3H)-ylidene)-5-chloro-2-methoxybenzamide A mixture of 5-tert-butyl-4-methylthiazol-2(3H)-imine (250 mg, 1.5 mmol) in tetrahydrofuran (10 mL) was treated with triethylamine (0.25 mL, 1.8 mmol) and 5-chloro-2-methoxybenzoylchloride (307 mg, 1.5 mmol). The reaction mixture was stirred at 60° C. for 18 hours then concentrated under reduced pressure. The residue was diluted with ethyl acetate and $H_2O$. The organic extract was dried over $MgSO_4$, filtered, concentrated under reduced pressure and dried under vacuum to afford the title compound (490 mg, 96% yield). MS (ESI) m/z 339 (M+H)+.

Example 309B

N-[(2Z)-5-tert-butyl-3-(3-hydroxy-3-methylbutyl)-4-methyl-1,3-thiazol-2(3H)-ylidene]-5-chloro-2-methoxybenzamide Example 308A and Example 309A were processed using the method described in Example 308B to afford the title compound. $^1$H NMR (300 MHz, dimethylsulfoxide-$d_6$) δ ppm 1.19 (s, 6H), 1.38 (s, 9H), 1.65-1.81 (m, 2H), 2.41 (s, 3H), 3.78 (s, 3H), 4.17-4.33 (m, 2H), 4.49 (s, 1H), 7.09 (d, J=8.8 Hz, 1H), 7.43 (dd, J=8.8, 3.1 Hz, 1H), 7.78 (d, J=2.7 Hz, 1H). MS (ESI) m/z 425 (M+H)+. Anal. Calculated for $C_{21}H_{29}ClN_2O_3S$ C, 59.35; H, 6.88; N, 6.55. Found C, 58.83; H, 7.13; N, 6.41.

Example 310

N-[(2Z)-5-tert-butyl-3-(2-methoxyethyl)-1,3-thiazol-2(3H)-ylidene]-5-chloro-2-methoxybenzamide Commercially available 2-bromoethyl methyl ether (Aldrich) and Example 244A were processed using the method described in Example 246 to afford the title compound. $^1$H NMR (300 MHz, dimethylsulfoxide-$d_6$) δ ppm 1.35 (s, 9H), 3.36 (s, 3H), 3.68-3.84 (m, 2H), 3.90 (s, 3H), 4.36 (t, J=5.1 Hz, 2H), 6.77 (s, 1H), 6.90 (d, J=8.8 Hz, 1H), 7.32 (dd, J=8.8, 2.7 Hz, 1H), 7.95 (d, J=2.7 Hz, 1H); MS (ESI−) m/z 383 (M+H)+; Anal. Calculated for $C_{18}H_{23}ClN_2O_3S$: C, 56.46; H, 6.05; N, 7.32. Found: C, 56.69; H, 6.02; N, 7.42.

Example 311

5-chloro-N-[(2Z)-5-(1-hydroxy-1-methylethyl)-3-(2-methoxyethyl)-4-methyl-1,3-thiazol-2(3H)-ylidene]-2-methoxybenzamide

Example 311A (Z)—N-(5-acetyl-3-(2-methoxyethyl)-4-methylthiazol-2(3H)-ylidene)-5-chloro-2-methoxybenzamide Commercially available 2-bromoethyl methyl ether (Aldrich) and Example 238A were processed using the method described in Example 246 to afford the title compound. MS (ESI+) m/z 383 (M+H)+.

Example 311B 5-chloro-N-[(2Z)-5-(1-hydroxy-1-methylethyl)-3-(2-methoxyethyl)-4-methyl-1,3-thiazol-2(3H)-ylidene]-2-methoxybenzamide Example 311A and commercially available methyllithium (Aldrich, 1.6 M in diethyl ether) were processed using the method described in Example 255 to afford the title compound. $^1$H NMR (300 MHz, dimethylsulfoxide-$d_6$) δ ppm 1.50 (s, 6H), 2.42 (s, 3H), 3.25 (s, 3H), 3.68 (t, J=5.4 Hz, 2H), 3.78 (s, 3H), 4.30 (t, J=5.4 Hz, 2H), 5.62 (s, 1H), 7.09 (d, J=9.2 Hz, 1H), 7.43 (dd, 1H), 7.63 (d, J=2.7 Hz, 1H); MS (ESI+) m/z 399 (M+H)+; Anal. Calculated for $C_{18}H_{23}ClN_2O_4S$: C, 54.20; H, 5.81; N, 7.02. Found: C, 54.30; H, 5.68; N, 6.91.

Example 312

N-[(2Z)-5-tert-butyl-3-(2-methoxy-2-methylpropyl)-1,3-thiazol-2(3H)-ylidene]-5-chloro-2-methoxybenzamide Example 244A and 1-bromo-2-methoxy-2-methylpropane were processed using the method described in Example 246 to afford the title compound. $^1$H NMR (500 MHz, CDCl$_3$) δ ppm 1.23 (s, 6H) 1.36 (s, 9H) 3.22 (s, 3H) 3.89 (s, 3H) 4.32 (s, 2H) 6.89 (s, 1H) 6.91 (s, 1H) 7.33 (dd, J=8.9, 2.8 Hz, 1H) 7.92 (d, J=2.8 Hz, 1H); MS (ESI) m/z 411 (M+H)+.

Example 313

N-[(2Z)-3-butyl-5-(1-hydroxy-1-methylethyl)-4-methyl-1,3-thiazol-2(3H)-ylidene]-5-chloro-2-methoxybenzamide

Example 313A (Z)—N-(5-acetyl-3-butyl-4-methylthiazol-2(3H)-ylidene)-5-chloro-2-methoxybenzamide A mixture of Example 238A (0.40 g, 1.2 mmol), 1-bromobutane (0.16 mL, 1.5 mmol), and potassium t-butoxide (0.22 g, 1.9 mmol) in 5 mL N,N-dimethylformamide was warmed to 65° C. and stirred for 20 hours. The mixture was cooled to ambient temperature quenched with 5 mL of saturated aqueous NH$_4$Cl and diluted with 5 mL of ethyl acetate. The layers were separated and the aqueous phase was extracted twice with 5 mL of ethyl acetate. The combined organic extracts were dried over anhydrous Na$_2$SO$_4$, filtered and concentrated under reduced pressure. Purification via column chromatography (SiO$_2$, 40% hexanes in ethyl acetate) afforded the title compound. $^1$H NMR (300 MHz, CD$_3$OD) δ ppm 1.04 (t, J=7.3 Hz, 3H), 1.42-1.55 (m, 2H), 1.77-1.90 (m, 2H), 2.51 (s, 3H), 2.76 (s, 3H), 3.88 (s, 3H), 4.32-4.41 (m, 2H), 7.10 (d, J=8.8 Hz, 1H), 7.45 (dd, J=8.8, 2.7 Hz, 1H), 7.99 (d, J=3.1 Hz, 1H); MS (DCI/NH$_3$) m/z 381 (M+H)+. Anal. Calculated for $C_{18}H_{21}ClN_2O_3S$: C, 56.76; H, 5.56; N, 7.35. Found: C, 56.68; H, 5.49; N, 7.26.

Example 313B

N-[(2Z)-3-butyl-5-(1-hydroxy-1-methylethyl)-4-methyl-1,3-thiazol-2(3H)-ylidene]-5-chloro-2-methoxybenzamide To the product of Example 313A (90 mg, 0.24 mmol) in 5 mL of THF at −78° C. was added a solution of methyllithium (1.6 M in diethyl ether, 0.44 mL, 0.71 mmol) dropwise over 5 minutes. The mixture was stirred at −78° C. for 4 hours and was slowly warmed to ambient temperature and allowed to stir for 12 hours. The mixture was quenched with 3 mL of saturated aqueous NH$_4$Cl and diluted with 5 mL of ethyl acetate. The layers were separated and the aqueous phase was extracted twice with 5 mL ethyl acetate. The combined organic extracts were dried over anhydrous Na$_2$SO$_4$, filtered and concentrated under reduced pressure. Purification via column chromatography (SiO$_2$, 20% hexanes in ethyl acetate) afforded the title compound. $^1$H NMR (300 MHz, CD$_3$OD) δ ppm 1.02 (t, J=7.3 Hz, 3H), 1.39-1.54 (m, 2H), 1.61 (s, 6H), 1.71-1.84 (m, 2H), 2.51 (s, 3H), 3.85 (s, 3H), 4.23-4.31 (m, 2H), 7.06 (d, J=8.8 Hz, 1H), 7.39 (dd, J=9.0, 2.9 Hz, 1H), 7.87 (d, J=3.1 Hz, 1H); MS (DCI/NH$_3$) m/z 397

(M+H)⁺. Anal. Calculated for C₁₉H₂₅ClN₂O₃S: C, 57.49; H, 6.35; N, 7.06. Found: C, 57.36; H, 6.33; N, 6.85.

Example 314

(5-chloro-N-[(2Z)-3-(cyclobutylmethyl)-5-(1-hydroxy-1-methylethyl)-4-methyl-1,3-thiazol-2(3H)-ylidene]-2-methoxybenzamide

Example 314A (Z)—N-(5-acetyl-3-(cyclobutylmethyl)-4-methylthiazol-2(3H)-ylidene)-5-chloro-2-methoxybenzamide A mixture of the product of Example 238A (0.75 g, 2.3 mmol), (bromomethyl)cyclobutane (0.31 mL, 2.8 mmol), and potassium t-butoxide (0.41 g, 3.5 mmol) in 7 mL N,N-dimethylformamide was warmed to 65° C. and stirred for 16 hours. The mixture was cooled to ambient temperature, quenched with 5 mL of saturated aqueous NH₄Cl and diluted with 10 mL of ethyl acetate. The layers were separated and the aqueous phase was extracted twice with 7 mL of ethyl acetate. The combined organic extracts were dried over anhydrous Na₂SO₄, filtered and concentrated under reduced pressure. Purification via column chromatography (SiO₂, 40% hexanes in ethyl acetate) afforded the title compound. ¹H NMR (300 MHz, CD₃OD) δ ppm 1.88-2.15 (m, 6H), 2.51 (s, 3H), 2.75 (s, 3H), 2.83-2.96 (m, 1H), 3.89 (s, 3H), 4.46 (d, J=7.5 Hz, 2H), 7.11 (d, J=9.2 Hz, 1H), 7.45 (dd, J=8.8, 2.7 Hz, 1H), 7.99 (d, J=3.1 Hz, 1H); MS (DCI/NH₃) m/z 393 (M+H)⁺. Anal. Calculated for C₁₉H₂₁ClN₂O₃S: C, 58.08; H, 5.39; N, 7.13. Found: C, 58.06; H, 5.20; N, 7.06.

Example 314B (5-chloro-N-[(2Z)-3-(cyclobutylmethyl)-5-(1-hydroxy-1-methylethyl)-4-methyl-1,3-thiazol-2(3H)-ylidene]-2-methoxybenzamide To the product of Example 314A (0.13 g, 0.33 mmol) in 5 mL of tetrahydrofuran at −78° C. was added a solution of methyllithium (1.6 M in diethyl ether, 0.62 mL, 0.99 mmol) dropwise over 5 minutes. The mixture was stirred at −78° C. for 1 hour then slowly warmed to ambient temperature and allowed to stir for 16 hours. The mixture was quenched with 5 mL of saturated aqueous NH₄Cl and diluted with 5 mL of ethyl acetate. The layers were separated and the aqueous phase was extracted twice with 5 mL ethyl acetate. The combined organic extracts were dried over anhydrous Na₂SO₄, filtered and concentrated under reduced pressure. Purification via column chromatography (SiO₂, 30% hexanes in ethyl acetate) afforded the title compound. ¹H NMR (300 MHz, CD₃OD) δ ppm 1.61 (s, 6H), 1.86-2.13 (m, 6H), 2.49 (s, 3H), 2.79-2.93 (m, 1H), 3.86 (s, 3H), 4.37 (d, J=7.1 Hz, 2H), 7.06 (d, J=8.8 Hz, 1H), 7.39 (dd, J=8.8, 2.7 Hz, 1H), 7.87 (d, J=2.7 Hz, 1H); MS (DCI/NH₃) m/z 409 (M+H)⁺. Anal. Calculated for C₂₀H₂₅ClN₂O₃S: C, 58.74; H, 6.16; N, 6.85. Found: C, 58.70; H, 6.12; N, 6.74.

Example 315

N-[(2Z)-5-tert-butyl-3-[(2S)-tetrahydrofuran-2-ylmethyl]-1,3-thiazol-2(3H)-ylidene]-5-chloro-2-methoxybenzamide

Example 315A 5-tert-Butyl-3-[(S)-1-(tetrahydro-furan-2-yl)methyl]-3H-thiazol-2-ylideneamine To a solution of 3,3-dimethylbutanal (Aldrich) (1.52 mL, 12.1 mmol) and (S)-(tetrahydrofuran-2-yl)methanamine (Aldrich) (1.00 g, 9.89 mmol) in 12 mL of acetonitrile was added 1.20 g of molecular sieves (4 Å beads, 8-12 mesh). The mixture was stirred for 12 h at 22° C. The mixture was filtered and to the filtrate was added potassium thiocyanate (1.42 g, 14.6 mmol). The temperature was adjusted at 50° C. and the mixture was stirred until all solids were dissolved, then iodine (5.58 g, 22.0 mmol) was added. The reaction was stirred at 50° C. for 12 h. The reaction was cooled to room temperature and diluted with EtOAc. The solution was washed with a solution of sodium bisulfate. The aqueous layers was brought to pH=9 by adding aq. NaOH (25%) and extracted with EtOAc. The organic extracts were combined, dried with sodium sulfate, filtered, and concentrated. The residue was crystallized from EtOAc/Hexane to give the title compound. MS (ESI⁻) m/z 241 (M+H)⁺.

Example 315B

N-[(2Z)-5-tert-butyl-3-[(2S)-tetrahydrofuran-2-ylmethyl]-1,3-thiazol-2(3H)-ylidene]-5-chloro-2-methoxybenzamide The products from Example 315A and 5-chloro-2-methoxy-benzoic acid were processed using the method described in Example 300 to afford the title compound. ¹H NMR (300 MHz, CDCl₃) δ ppm 1.35 (s, 9H), 1.62-1.95 (m, 3H), 2.00-2.12 (m, 1H), 3.72-3.87 (m, 2H), 3.90 (s, 3H), 4.18-4.34 (m, 2H), 4.42 (dd, J=12.0, 2.4 Hz, 1H), 6.86 (s, 1H), 6.90 (d, J=8.8 Hz, 1H), 7.32 (dd, J=8.8, 2.7 Hz, 1H), 7.95 (d, J=2.7 Hz, 1H). MS (ESI⁺) m/z 409 (M+H)⁺.

Example 316

5-chloro-2-methoxy-N-[(2Z)-4,4,6,6-tetramethyl-3-[(2R)-tetrahydrofuran-2-ylmethyl]-4,6-dihydrofuro[3,4-d][1,3]thiazol-2(3H)-ylidene]benzamide

Example 316A 4,4,6,6-Tetramethyl-3-[(R)-1-(tetrahydro-furan-2-yl)methyl]-4,6-dihydro-3H-furo[3,4-a]thiazol-2-ylideneamine 2,2,5,5-tetramethyldihydrofuran-3(2H)-one (Aldrich) and (R)-(tetrahydrofuran-2-yl)methanamine (Aldrich) were processed using the method described in Example 315A to afford the title compound. MS (ESI⁺) m/z 283 (M+H)⁺.

Example 316B 5-chloro-2-methoxy-N-[(2Z)-4,4,6,6-tetramethyl-3-[(2R)-tetrahydrofuran-2-ylmethyl]-4,6-dihydrofuro[3,4-d][1,3]thiazol-2(3H)-ylidene]benzamide The product from Example 316A and 5-chloro-2-methoxy-benzoic acid were processed using the method described in Example 300 to afford the title compound. ¹H NMR (300 MHz, CDCl₃) δ ppm 1.52 (s, 3H), 1.55 (s, 3H), 1.58 (s, 3H), 1.66 (s, 3H), 1.70-1.82 (m, 1H), 1.90-2.02 (m, 2H), 2.10-2.24 (m, 1H), 3.70-3.82 (m, 2H), 3.83-3.89 (m, 1H), 3.90 (s, 3H), 4.42 (dd, J=13.6, 3.7 Hz, 1H), 4.54-4.66 (m, 1H), 6.91 (d, J=8.8 Hz, 1H), 7.35 (dd, J=8.8, 2.7 Hz, 1H), 7.99 (d, J=2.7 Hz, 1H). MS (ESI⁺) m/z 451 (M+H)⁺.

Example 317

N-[(2Z)-5-tert-butyl-3-[(2R)-tetrahydrofuran-2-ylmethyl]-1,3-thiazol-2(3H)-ylidene]-5-cyano-2-methoxybenzamide

Example 317A 5-tert-butyl-3-[(R)-1-(tetrahydro-furan-2-yl)methyl]-3H-thiazol-2-ylideneamine 3,3-dimethylbutanal (Aldrich) and (R)-(tetrahydrofuran-2-yl)methanamine (Aldrich) were processed using the method described in Example 315A to afford the title compound. MS (ESI$^+$) m/z 241 (M+H)$^+$.

Example 317B 5-cyano-2-methoxy-benzoic acid methyl ester

A mixture of 3-bromo-4-methoxybenzonitrile (Aldrich) (10.0 g, 47.2 mmol), PdCl$_2$(dppf)-CH$_2$Cl$_2$ adduct (Aldrich) (1.00 g, 1.22 mmol) and triethylamine (12.5 mL, 89.7 mmol) in 100 mL of methanol in a high pressure vessel was heated to 100° C. at 60 psi of CO$_2$ for 4 h. The mixture was cooled to room temperature and filtered. The mixture was concentrated under reduced pressure to afford the title compound. $^1$H NMR (500 MHz, CDCl$_3$) δ ppm 3.91 (s, 3H), 3.98 (s, 3H), 7.06 (d, J=8.5 Hz, 1H), 7.76 (dd, J=8.7, 2.3 Hz, 1H), 8.10 (d, J=2.1 Hz, 1H).

Example 317C 5-cyano-2-methoxy-benzoic

A mixture of Example 317B (6.10 g, 31.9 mmol) and lithium hydroxide monohydrate (5.36 g, 128 mmol) in 150 mL of THF/water (2/1) was stirred at 22° C. for 3 h. The organic solvent was evaporated under reduced pressure and the aqueous solution was acidified to pH 2 with 6 N HCl. The mixture was extracted with dichloromethane. The organic extracts were dried over sodium sulfate, filtered, and concentrated under reduced pressure to afford the title compound. $^1$H NMR (500 MHz, CDCl$_3$) δ ppm 4.15 (s, 3H), 7.17 (d, J=8.8 Hz, 1H), 7.86 (dd, J=8.7, 2.3 Hz, 1H), 8.47 (d, J=2.1 Hz, 1H), 9.50-10.21 (brs, 1H).

Example 317D

N-[(2Z)-5-tert-butyl-3-[(2R)-tetrahydrofuran-2-ylmethyl]-1,3-thiazol-2(3H)-ylidene]-5-cyano-2-methoxybenzamide The products from Example 317A and Example 317C were processed using the method described in Example 300 to afford the title compound. $^1$H NMR (300 MHz, CDCl$_3$) δ ppm 1.36 (s, 9H), 1.60-1.97 (m, 3H), 2.01-2.16 (m, 1H), 3.73-3.89 (m, 2H), 3.97 (s, 3H), 4.18-4.34 (m, 2H), 4.39 (dd, J=12.0, 2.4 Hz, 1H), 6.90 (s, 1H), 7.03 (d, J=8.8 Hz, 1H), 7.67 (dd, J=8.8, 2.4 Hz, 1H), 8.29 (d, J=2.4 Hz, 1H). MS (ESI$^+$) m/z 400 (M+H)$^+$.

Example 318

N-[(2Z)-4-tert-butyl-3-[(2R)-tetrahydrofuran-2-ylmethyl]-1,3-thiazol-2(3H)-ylidene]-5-chloro-2-methoxybenzamide

Example 318A 4-tert-butyl-3-[(R)-1-(tetrahydro-furan-2-yl)methyl]-3H-thiazol-2-ylideneamine 3,3-dimethylbutan-2-one (Aldrich) and (R)-(tetrahydrofuran-2-yl)methanamine (Aldrich) were processed using the method described in Example 315A to afford the title compound. MS (ESI$^+$) m/z 241 (M+H)$^+$.

Example 318B

N-[(2Z)-4-tert-butyl-3-[(2R)-tetrahydrofuran-2-ylmethyl]-1,3-thiazol-2(3H)-ylidene]-5-chloro-2-methoxybenzamide The product from Example 318A and 5-chloro-2-methoxy-benzoic acid were processed using the method described in Example 300 to afford the title compound. $^1$H NMR (300 MHz, CDCl$_3$) −2.23 (m, 1H), 3.67-3.76 (m, 1H), 3.83-3.89 (m, 1H), 3.90 (s, 3H), 4.40 (dd, J=15.0, 7.5 Hz, 1H), 4.57-4.68 (m, 2H), 6.35 (s, 1H), 6.91 (d, J=8.7 Hz, 1H), 7.33 (dd, J=8.7, 2.8 Hz, 1H), 8.04 (d, J=2.8 Hz, 1H). MS (ESI$^+$) m/z 409 (M+H)$^+$.

Example 319

N-[(2Z)-5-tert-butyl-4-methyl-3-[(2R)-tetrahydrofuran-2-ylmethyl]-1,3-thiazol-2(3H)-ylidene]-5-chloro-2-methoxybenzamide

Example 319A

N-(5-tert-butyl-4-methylthiazol-2-yl)-5-chloro-2-methoxybenzamide

To 5-tert-butyl-4-methylthiazol-2-amine (Matrix, 204 mg, 1.2 mmol) in CH$_2$Cl$_2$ (10 ml) at 0° C. was added Example 205B (246 mg, 1.2 mmol), followed by triethylamine (0.2 ml, 1.44 mmol). The mixture was stirred at room temperature for 4 hours and checked with LC/MS. When the starting material disappeared, water (20 ml) and CH$_2$Cl$_2$ (20 ml) were added. The organic layer was washed with brine and concentrated under reduced pressure. The residue was purified by chromatography on a silica gel cartridge, eluting with ethyl acetate/hexane in 5-30% gradient to yield the title compound (305 mg, 75%). $^1$H NMR (300 MHz, DMSO-d$_6$) δ ppm 11.64 (s, 1H), 7.47-7.77 (m, 2H), 7.22 (d, J=8.82 Hz, 1H), 3.89 (s, 3H), 2.34 (s, 3H), 1.39 (s, 9H). MS (ESI) m/z 339 [M+H]$^+$, 337 {M−H}$^−$.

Example 319B

N-[(2Z)-5-tert-butyl-4-methyl-3-[(2R)-tetrahydrofuran-2-ylmethyl]-1,3-thiazol-2(3H)-ylidene]-5-chloro-2-methoxybenzamide To the mixture of Example 319A (160 mg, 0.472 mmol), Example 208A (182 mg, 0.71 mmol) and K$_2$CO$_3$ (131 mg, 0.944 mmol) in toluene (6 ml) were added phase transfer agents of n-Bu$_4$NI (5%) and n-Bu$_4$NHSO$_4$ (5%). The reaction mixture was heated at 100° C. for 24 hrs, and then cooled to ambient temperature and filtered. The solid was washed with ethyl acetate (10 mL×2) and the filtrate was concentrated under reduced pressure. The residue was purified by preparative reverse phase HPLC using a gradient of 10% to 100% acetonitrile: ammonium acetate (10 mM) to afford the title compound (101 mg, 50.6%). $^1$H NMR (300 MHz, DMSO-d6) δ ppm 7.64 (d, J=2.71 Hz, 1H), 7.40-7.46 (m, 1H), 7.09 (d, J=8.81 Hz, 1H), 4.23-4.38 (m, 2H), 4.03-4.13 (m, 1H), 3.74-3.83 (m, 4H), 3.59-3.68 (m, 1H), 2.41 (s, 3H), 1.63-2.02 (m, 4H), 1.38 (s, 9H); MS (ESI) m/z 423 [M+H]$^+$.

Example 320

5-chloro-2-methoxy-N-{(2Z)-3-[(2R)-tetrahydrofuran-2-ylmethyl]-3,4,5,6,7,8-hexahydro-2H-4,7-epoxycyclohepta[d][1,3]thiazol-2-ylidene}benzamide Example 320A 3-[(2R)-tetrahydrofuran-2-ylmethyl]-3,4,5,6,7,8-hexahydro-2H-4,7-epoxycyclohepta[d][1,3]thiazol-2-imine A mixture of 8-oxabicyclo[3.2.1]octan-2-one (obtained as described in Vogel et al. *Tetrahedron* 1993, 49 (8), 1649-1664) (0.53 g, 4.2 mmol), (R)-(tetrahydrofuran-2-yl)methanamine (0.43 mL, 4.2 mmol) and 1 g of 4 Å molecular sieves (8-12 mesh beads) in acetonitrile (4 mL) was stirred at ambient temperature for 16 h. The material was filtered through Celite® with acetonitrile (additional 10 mL) then the filtrate treated with potassium thiocyanate (0.54 g, 5.6 mmol) was added and the mixture was warmed to 50° C. Iodine (2.1 g, 8.4 mmol) was added and the mixture stirred at 50° C. for 72 h. The mixture was cooled to ambient temperature and was concentrated under reduced pressure. The crude material was diluted with 20 mL CH$_2$Cl$_2$ and was stirred with sodium metabisulfite (20 mL of 20% aqueous solution) for 15 min. The layers were separated and the aqueous layer was extracted 3×10 mL CH$_2$Cl$_2$. The combined organics were dried over Na$_2$SO$_4$, filtered and concentrated under reduced pressure to give the crude material (1.0 g, 3.8 mmol, 89% yield) which was carried on without further purification. MS (DCI/NH$_3$) m/z 267 (M+H)$^+$.

Example 320B 5-chloro-2-methoxy-N-{(2Z)-3-[(2R)-tetrahydrofuran-2-ylmethyl]-3,4,5,6,7,8-hexahydro-2H-4,7-epoxycyclohepta[d][1,3]thiazol-2-ylidene}benzamide To a solution of the product of Example 320A (1.0 g, 3.8 mmol) in THF (25 mL) was added triethylamine (1.6 mL, 11.3 mmol). To this mixture was added Example 205B (0.77 g, 3.8 mmol). The mixture was warmed to 50° C. and allowed to stir for 16 hours. The mixture was cooled to ambient temperature then was quenched with saturated, aqueous NaHCO$_3$, extracted with EtOAc, dried over Na$_2$SO$_4$, filtered and concentrated under reduced pressure. The mixture was purified by column chromatography (SiO$_2$, 40% hexanes in EtOAc) and then was further purified by HPLC (Waters XTerra RP18 5µ column, 30×100 mm, 40 mL/min flow rate, 5-95% gradient of acetonitrile in 0.1% aqueous trifluoroacetic acid over 22 min, UV detection at 254 nm) to give the title compound (0.40 g, 0.92 mmol, 25% yield). $^1$H NMR (300 MHz, CDCl$_3$) δ ppm 1.64-2.02 (m, 4H), 2.08-2.33 (m, 5H), 3.19 (dt, J=10.9, 5.4 Hz, 1H), 3.69-3.88 (m, 2H), 3.88-3.95 (m, 1H), 3.90 (s, 3H), 4.17-4.78 (m, 2H), 4.80-4.89 (m, 1H), 5.29 (dd, J=12.2, 5.8 Hz, 1H), 6.91 (d, J=8.8 Hz, 1H), 7.36 (ddd, J=8.8, 2.7, 1.4 Hz, 1H), 7.96 (d, J=2.7 Hz, 1H); MS (DCI/NH$_3$) m/z 435 (M+H)$^+$; Anal. calculated for C$_{21}$C$_{23}$ClN$_2$O$_4$S.0.5 CF$_3$CO$_2$H: C, 53.71; H, 4.81; N, 5.69. Found: C, 53.95; H, 4.95; N, 5.80.

Example 321

5-chloro-2-methoxy-N-[(2Z)-3-[(2R)-tetrahydrofuran-2-ylmethyl]-6,7-dihydro-4H-pyrano[3,4-d][1,3]thiazol-2(3H)-ylidene]benzamide Example 321A (R)-3-((tetrahydrofuran-2-yl)methyl)-3,4,6,7-tetrahydro-2H-pyrano[3,4-d]thiazol-2-imine Commercially available dihydro-2H-pyran-3(4H)-one (Small Molecules Inc), (R)-(tetrahydrofuran-2-yl)methanamine (Aldrich), potassium thiocyanate (Aldrich) and iodine (Aldrich) were processed using the method described in Example 315A to afford the title compound. LCMS (ESI$^+$) m/z 241 (M+H)$^+$.

Example 321B 5-chloro-2-methoxy-N-[(2Z)-3-[(2R)-tetrahydrofuran-2-ylmethyl]-6,7-dihydro-4H-pyrano[3,4-d][1,3]thiazol-2(3H)-ylidene]benzamide Example 321A and 5-chloro-2-methoxybenzoic acid (Aldrich) were processed using the method described in Example 58 to afford the title compound. $^1$H NMR (300 MHz, DMSO-d$_6$) δ ppm 1.49-1.74 (m, 1H), 1.75-1.89 (m, 2H), 1.91-2.06 (m, 1H), 2.67 (t, J=5.4 Hz, 2H), 3.57-3.68 (m, 1H), 3.72-3.83 (m, 1H), 3.79 (s, 3H), 3.87-3.95 (m, 3H), 4.16-4.35 (m, 2H), 4.59-4.78 (m, 2H), 7.12 (d, J=8.8 Hz, 1H), 7.46 (dd, J=8.8, 2.7 Hz, 1H), 7.69 (d, J=2.7 Hz, 1H); MS (ESI$^+$) m/z 409 (M+H); Anal. Calculated for C$_{19}$H$_{21}$ClN$_2$O$_4$S: C, 55.81; H, 5.18; N, 6.85. Found: C, 55.88; H, 5.00; N, 6.84.

Example 322

5-chloro-2-methoxy-N-{(2Z)-1-[(2R)-tetrahydrofuran-2-ylmethyl]-1,4,6,7-tetrahydro-2H-pyrano[4,3-d][1,3]thiazol-2-ylidene}benzamide Example 322A 6,7-dihydro-4H-pyrano[4,3-d]thiazol-2-amine Commercially available dihydro-2H-pyran-4(3H)-one (Aldrich), pyrrolidine (Aldrich), p-toluenesulfonic acid monohydrate (Aldrich) sulfur (Aldrich) and cyanamide (Aldrich) were processed using the method described in Example 240A to afford the title compound. MS (ESI$^+$) m/z 157 (M+H)$^+$.

Example 322B (Z)-5-chloro-N-(6,7-dihydro-1H-pyrano[4,3-d]thiazol-2(4H)-ylidene)-2-methoxybenzamide Example 322A and 5-chloro-2-methoxybenzoic acid (Aldrich) were processed using the method described in Example 58 to afford the title compound. MS (ESI$^+$) m/z 325 (M+H)$^+$.

Example 322C 5-chloro-2-methoxy-N-{(2Z)-1-[(2R)-tetrahydrofuran-2-ylmethyl]-1,4,6,7-tetrahydro-2H-pyrano[4,3-d][1,3]thiazol-2-ylidene}benzamide Example 322B and Example 208A were processed using the method described in Example 246 to afford the title compound. $^1$H NMR (300 MHz, DMSO-$d_6$) δ ppm 1.60-2.05 (m, 4H), 2.64-2.88 (m, 2H), 3.56-3.69 (m, 1H), 3.73-3.84 (m, 1H), 3.79 (s, 3H), 3.95 (t, J=5.6 Hz, 2H), 3.97-4.12 (m, 1H), 4.19-4.34 (m, 2H), 4.58 (s, 2H), 7.12 (d, J=9.2 Hz, 1H), 7.46 (dd, J=8.8, 2.7 Hz, 1H), 7.69 (d, J=2.7 Hz, 1H); MS (ESI$^+$) m/z 409 (M+H)$^-$; Anal. Calculated for $C_{19}H_{21}ClN_2O_4S$: C, 55.81; H, 5.18; N, 6.85. Found: C, 55.77; H, 4.93; N, 6.72.

Example 323

N-[(2Z)-5-tert-butyl-3-(2-morpholin-4-ylethyl)-1,3-thiazol-2(3H)-ylidene]-5-chloro-2-methoxybenzamide

Example 323A 5-tert-butyl-3-(2-morpholinoethyl)thiazol-2(3H)-imine

Commercially available 3,3-dimethylbutanal (Aldrich), 2-morpholinoethanamine (Aldrich), potassium thiocyanate (Aldrich) and iodine (EMD chemicals) were processed using the method described in Example 315A to afford the title compound. MS (ESI$^+$) m/z 270 (M+H)$^+$.

Example 323B

N-[(2Z)-5-tert-butyl-3-(2-morpholin-4-ylethyl)-1,3-thiazol-2(3H)-ylidene]-5-chloro-2-methoxybenzamide Example 323A and Example 205B were processed using the method described in Example 244A to afford the title compound. $^1$H NMR (300 MHz, DMSO-$d_6$) δ ppm 1.32 (s, 9H), 2.39-2.49 (m, 4H), 2.69 (t, J=6.3 Hz, 2H), 3.46-3.58 (m, 4H), 3.78 (s, 3H), 4.25 (t, J=6.5 Hz, 2H), 7.10 (d, J=8.7 Hz, 1H), 7.30 (s, 1H), 7.44 (dd, J=8.7, 2.8 Hz, 1H), 7.66 (d, J=2.8 Hz, 1H); MS (ESI$^+$) m/z 438 (M+H)$^+$.

Example 324

N-[(2Z)-5-tert-butyl-3-[(2R)-tetrahydrofuran-2-ylmethyl]-1,3-thiazol-2(3H)-ylidene]-5-chloro-2-hydroxybenzamide Example 317A and 5-chloro-2-hydroxybenzoic acid (Aldrich) were processed using the method described in Example 58 to afford the title compound. $^1$H NMR (300 MHz, DMSO-$d_6$) δ ppm 1.34 (s, 9H), 1.59-1.75 (m, 1H), 1.77-1.94 (m, 2H), 1.94-2.08 (m, 1H), 3.58-3.72 (m, 1H), 3.75-3.88 (m, 1H), 4.23-4.34 (m, 3H), 6.94 (d, J=8.8 Hz, 1H), 7.37-7.48 (m, 1H), 7.45 (s, 1H), 7.95 (d, J=2.7 Hz, 1H), 13.02 (s, 1H); MS (ESI$^+$) m/z 395 (M+H)$^+$.

Example 325

N-[(2Z)-5-tert-butyl-3-[(2R)-tetrahydrofuran-2-ylmethyl]-1,3-thiazol-2(3H)-ylidene]-2-methoxy-5-(trifluoromethyl)benzamide Example 317A and 2-methoxy-5-(trifluoromethyl)benzoyl chloride (JRD Fluorochemicals Ltd) were processed using the method described in Example 244A to afford the title compound. $^1$H NMR (300 MHz, DMSO-$d_6$) δ ppm 1.32 (s, 9H), 1.58-1.73 (m, 1H), 1.74-1.86 (m, 2H), 1.85-1.96 (m, 1H), 3.57-3.71 (m, 1H), 3.73-3.83 (m, 1H), 3.87 (s, 3H), 4.19 (dd, J=5.9, 1.6 Hz, 2H), 4.31 (dd, 1H), 7.29 (s, 1H), 7.27 (s, 1H), 7.77 (dd, J=9.1, 2.4 Hz, 1H), 7.97 (d, J=2.4 Hz, 1H); MS (ESI$^+$) m/z 443 (M+H)$^+$.

Example 326

N-[(2Z)-5-tert-butyl-3-tetrahydro-2H-pyran-4-yl-1,3-thiazol-2(3H)-ylidene]-5-chloro-2-methoxybenzamide

Example 326A 5-tert-butyl-3-(tetrahydro-2H-pyran-4-yl)thiazol-2(3H)-imine

Commercially available 3,3-dimethylbutanal (Aldrich), tetrahydro-2H-pyran-4-amine (Matrix), potassium thiocyanate (Aldrich) and iodine (EMD chemicals) were processed using the method described in Example 315A to afford the title compound. MS (ESI$^+$) m/z 241 (M+H)$^+$.

Example 326B

N-[(2Z)-5-tert-butyl-3-tetrahydro-2H-pyran-4-yl-1,3-thiazol-2(3H)-ylidene]-5-chloro-2-methoxybenzamide Example 326A and Example 205B were processed using the method described in Example 244A to afford the title compound. $^1$H NMR (300 MHz, DMSO-$d_6$) δ ppm 1.32 (s, 9H), 1.86 (dd, J=12.0, 2.5 Hz, 2H), 2.03-2.22 (m, 2H), 3.46 (t, J=11.7 Hz, 2H), 3.79 (s, 3H), 3.93-4.03 (m, 2H), 4.81-5.16 (m, 1H), 7.11 (d, J=8.8 Hz, 1H), 7.39 (s, 1H), 7.44 (dd, J=8.8, 2.7 Hz, 1H), 7.62 (d, J=3.1 Hz, 1H); MS (ESI m/z 409 (M+H); Anal. Calculated for $C_{20}C_{25}ClN_2O_3S$: C, 58.74; H, 6.16; N, 6.85. Found: C, 58.59; H, 6.24; N, 6.76.

Example 327

N-[(2Z)-5-tert-butyl-3-{2-[(cis)-2,6-dimethylmorpholin-4-yl]ethyl}-1,3-thiazol-2(3H)-ylidene]-5-chloro-2-methoxybenzamide

Example 327A 5-tert-butyl-3-(2-((cis)-2,6-dimethylmorpholino)ethyl)thiazol-2(3H)-imine Commercially available 3,3-dimethylbutanal (Aldrich), 4-(2-aminoethyl)-cis-2,6-dimethylmorpholine (Oakwood), potassium thiocyanate (Aldrich) and iodine (EMD chemicals) were processed using the method described in Example 315A to afford the title compound. MS (ESI$^+$) m/z 298 (M+H)$^+$.

Example 327B

N-[(2Z)-5-tert-butyl-3-{2-[(cis)-2,6-dimethylmorpholin-4-yl]ethyl}-1,3-thiazol-2(3H)-ylidene]-5-chloro-2-methoxybenzamide Example 327A and 5-chloro-2-methoxybenzoic acid (Aldrich) were processed using the method described in Example 58 to afford the title compound. $^1$H NMR (300 MHz, DMSO-$d_6$) δ ppm 0.97 (s, 3H), 0.99 (s, 3H), 1.31 (s, 9H), 1.68 (t, J=10.5 Hz, 2H), 2.66 (t, J=6.4 Hz, 2H), 2.80 (d, J=10.2 Hz, 2H), 3.35-3.50 (m, 2H), 3.78 (s, 3H), 4.25 (t, J=6.3 Hz, 2H), 7.10 (d, J=8.8 Hz, 1H), 7.30 (s, 1H), 7.44 (dd, J=8.8, 2.7 Hz, 1H), 7.67 (d, J=2.7 Hz, 1H); MS (ESI$^+$) m/z 466 (M+H)$^+$; Anal. Calculated for $C_{23}H_{32}ClN_3O_3S \cdot 0.5H_2O \cdot 0.1C_4H_8O_2$: C, 58.09; H, 7.04; N, 8.68. Found: C, 57.84; H, 6.96; N, 8.58.

Example 328

N-[(2Z)-5-tert-butyl-3-{[(2R)-5-oxotetrahydrofuran-2-yl]methyl}-1,3-thiazol-2(3H)-ylidene]-5-chloro-2-methoxybenzamide Example 328A (R)-5-(tosylmethyl)dihydrofuran-2(3H)-one (R)-5-(hydroxymethyl)dihydrofuran-2(3H)-one (1.0 g, 8.6 mmol) was processed using the method described in Example 162A to afford the title compound. MS (ESI) m/z 288 (M+18)$^+$.

Example 328B

N-[(2Z)-5-tert-butyl-3-{[(2R)-5-oxotetrahydrofuran-2-yl]methyl}-1,3-thiazol-2(3H)-ylidene]-5-chloro-2-methoxybenzamide Example 244A and Example 328A were processed using the method described in Example 238B to afford the title compound. 1H NMR (500 MHz, CDCl$_3$) δ ppm 1.35 (s, 9H) 2.08-2.19 (m, 1H) 2.34-2.48 (m, 2H) 2.49-2.61 (m, 1H) 3.90 (s, 3H) 4.39 (dd, J=14.34, 6.10 Hz, 1H) 4.55 (dd, J=14.65, 3.05 Hz, 1H) 4.92-4.99 (m, 1H) 6.75 (s, 1H) 6.91 (d, J=8.85 Hz, 1H) 7.34 (dd, J=8.85, 2.75 Hz, 1H) 7.92 (d, J=2.75 Hz, 1H); MS (ESI) m/z 423 (M+H)$^+$.

Example 329

5-chloro-N-[(2Z)-5-(1-hydroxy-1-methylethyl)-4-methyl-3-[(2R)-tetrahydrofuran-2-ylmethyl]-1,3-thiazol-2(3H)-ylidene]-2-(2,2,2-trifluoroethoxy)benzamide Example 280 B was processed using the method described in Example 255 to afford the title compound. 1H NMR (500 MHz, CDCl$_3$) δ ppm 1.63-1.74 (m, 1H) 1.66 (d, J=10.68 Hz, 6H) 1.88-1.98 (m, 3H) 2.08-2.16 (m, 1H) 2.56 (s, 3H) 3.74 (dd, J=14.04, 7.32 Hz, 1H) 3.88 (dd, J=15.26, 7.02 Hz, 1H) 3.97 (dd, J=14.04, 7.93 Hz, 1H) 4.33-4.40 (m, 1H) 4.46 (dd, J=17.09, 8.54 Hz, 2H) 4.55 (dd, J=13.73, 3.05 Hz, 1H) 7.02 (d, J=8.85 Hz, 1H) 7.33 (dd, J=8.85, 2.75 Hz, 1H) 7.99 (d, J=2.75 Hz, 1H); MS (ESI) m/z 493 (M+H)$^+$.

Example 330

N-[(2Z)-5-tert-butyl-3-[(2R)-tetrahydrofuran-2-ylmethyl]-1,3-thiazol-2(3H)-ylidene]-5-chloro-2-[(E)-(hydroxyimino)methyl]benzamide A mixture of Example 331B (0.020 g, 0.054 mmmol) and hydroxylamine hydrochloride (0.004 g, 0.054 mmol) in pyridine (5 mL) was stirred at room temperature for 8 h. The mixture was concentrated under reduced pressure and the residue was partitioned between EtOAc and water. The organic layer was washed with water, brine, dried with MgSO$_4$, filtered, and concentrated under reduced pressure to afford 17 mg of product. $^1$H NMR (300 MHz-DMSO-$d_6$) δ 1.33 (s, 9H), 1.62 (m, 1H), 1.84 (m, 2H), 1.99 (m, 1H), 3.65 (m, 1H), 3.80 (m, 1H), 4.26 (m, 3H), 7.36 (s, 1H), 7.55 (dd, J=9 Hz, 3 Hz, 1H), 7.78 (d, J=9 Hz, 1H), 8.04 (d, J=3 Hz, 1H), 8.87 (s, 1H), 11.27 (s, 1H); MS (DCI/NH$_3$) m/z 422 (M+H)$^+$.

Example 331

N-[(2Z)-5-tert-butyl-3-[(2R)-tetrahydrofuran-2-ylmethyl]-1,3-thiazol-2(3H)-ylidene]-5-chloro-2-formylbenzamide Example 331A methyl N-[(2Z)-5-tert-butyl-3-[(2R)-tetrahydrofuran-2-ylmethyl]-1,3-thiazol-2(3H)-ylidene]-N'-cyanoimidothiocarbamate A mixture of Example 240C (0.361 g, 1.5 mmol) and dimethyl cyanocarbonimidodithioate (0.219 g, 1.5 mmol) in THF (35 mL) was treated with triethylamine (0.21 mL, 1.5 mmol) and the resulting mixture was stirred at 45° C. for 12 h. The mixture was concentrated under reduced pressure and the residue was purified by chromatography (hexane-EtOAc 1:1) to afford 430 mg of the title compound. $^1$H NMR (300 MHz-DMSO-$d_6$) δ 1.31 (s, 9H), 1.60 (m, 1H), 1.82 (quintet, J=7 Hz, 2H), 1.95 (m, 1H), 2.53 (s, 3H), 3.65 (m, 1H), 3.75 (m, 1H), 4.26 (m, 3H), 7.43 (s, 1H); MS (DCI/NH$_3$) m/z 339 (M+H)$^+$.

Example 331B

N-[(2Z)-5-tert-butyl-3-[(2R)-tetrahydrofuran-2-ylmethyl]-1,3-thiazol-2(3H)-ylidene]-5-chloro-2-formylbenzamide To a mixture of Example 331A (0.102 g, 0.3 mmol), 5-chloro-2-formylboronic acid (0.184 g, 1 mmol), copper(1) acetate (0.123 g, 1 mmol) in DME (25 mL) were added tris(dibenzylideneacetone)dipalladium(0) 0.045 g, 0.05 mmol) and triethyl phosphate (0.024 mg, 0.14 mmol) and the mixture was refluxed for 16 h. The mixture was then concentrated under reduced pressure and the residue was chromatographed (SiO$_2$; hexane-EtOAc 1:1) to afford 30 mg of the title compound. $^1$H NMR (300 MHz-DMSO-$d_6$) δ 1.33 (s, 9H), 1.62 (m, 1H), 1.84 (m, 2H), 1.99 (m, 1H), 3.65 (m, 1H), 3.80 (m, 1H), 4.26 (m, 3H), 7.36 (s, 1H), 7.70 (m, 2H), 8.06 (d, J=3 Hz, 1H), 10.53 (s, 1H); MS (DCI/NH$_3$) m/z 407 (M+H)$^+$.

Example 332

N-[(2Z)-5-tert-butyl-3-[(2R)-tetrahydrofuran-2-ylmethyl]-1,3-thiazol-2(3H)-ylidene]-N'-(1,1-dimethylpropyl)urea Example 332A (R,Z)-4-nitrophenyl 5-tert-butyl-3-((tetrahydrofuran-2-yl)methyl)thiazol-2(3H)-ylidenecarbamate In a 20 mL vial, Example 317A was dissolved in dichloromethane (5 ml). Triethylamine (0.417 g, 4.12 mmol) was added followed by addition of 4-nitrophenylcarbonyl chloridate (0.755 g, 3.74 mmol) and the reaction was stirred for 2 hrs. The reaction was washed with water, dried with sodium sulfate, filtered, and concentrated in vacuo. The residue was purified by silica gel flash chromatography using 0-30% ethyl acetate in hexanes provided the title compound as a white solid. $^1$H NMR (300 MHz, DMSO-d$_6$) δ ppm 1.29 (s, 9H) 1.73-1.87 (m, 3H) 1.87-1.96 (m, 1H) 3.65 (m, 1H) 3.75 (m, 1H) 4.03 (m, 2H) 4.19 (m, 1H) 7.22 (s, 1H) 7.41-7.49 (m, 2H) 8.24-8.30 (m, 2H). MS (DCI) m/z 406 (M+H)$^+$.

Example 332B

N-[(2Z)-5-tert-butyl-3-[(2R)-tetrahydrofuran-2-ylmethyl]-1,3-thiazol-2(3H)-ylidene]-N'-(1,1-dimethylpropyl)urea To a 10 mL microwave vial, Example 332A (100 mg, 0.247 mmol) was dissolved in acetonitrile (1.5 ml) followed by addition of 2-methylbutan-2-amine (32.2 mg, 0.370 mmol) and heated in a microwave reactor at 140° C. for 10 min. The reaction was concentrated and the residue was purified by reverse phase HPLC using a Waters Sunfire C8 column (30×5 mm) eluting with a gradient of acetonitrile and 0.1% trifluoroacetic acid in water at a flow rate of 50 mL/min. Fractions selected by mass spectrometry to provide the title compound as a TFA salt. $^1$H NMR (300 MHz, DMSO-D6) δ ppm 0.79 (t, J=7.34 Hz, 3H) 1.23 (s, 6H) 1.27 (s, 9H) 1.54 (m, 1H) 1.67 (m, 2H) 1.77-1.88 (m, 2H) 1.95 (m, 1H) 3.61-3.69 (m, 1H) 3.75-3.83 (m, 1H) 3.98-4.11 (m, 2H) 4.19 (m, 1H) 6.65 (s, 1H) 7.11 (s, 1H). MS (DCI) m/z 354 (M+H)$^+$.

Example 333

N-[(2Z)-5-tert-butyl-3-[(2R)-tetrahydrofuran-2-ylmethyl]-1,3-thiazol-2(3H)-ylidene]-N'-(1-methyl-1-phenylethyl)urea The title compound was prepared and purified as described in Example 332B, substituting cumylamine for 2-methylbutan-2-amine. $^1$H NMR (300 MHz, CDCl$_3$) δ ppm 1.20-1.30 (m, 9H) 1.55 (s, 6H) 1.65 (s, 2H) 1.79-1.90 (m, 2H) 3.72-3.86 (m, 2H) 3.93 (dd, J=14.48, 6.54 Hz, 1H) 4.11 (s, 1H) 4.19 (s, 1H) 5.53 (s, 1H) 6.56 (s, 1H) 7.12-7.22 (m, 1H) 7.27-7.35 (m, 2H) 7.46 (d, J=7.54 Hz, 2H). MS (DCI) m/z 402 (M+H)$^+$. Anal. Calculated for C$_{16}$H$_{16}$BrClN$_2$O$_2$S: C, 65.41; H, 7.74; N, 10.23. Found: C, 65.8; H, 7.78; N, 10.46.

Example 334

N-[(2Z)-5-tert-butyl-3-[(2R)-tetrahydrofuran-2-ylmethyl]-1,3-thiazol-2(3H)-ylidene]-N'-(2-hydroxy-1,1-dimethylethyl)urea The title compound was prepared and purified as described in Example 332B, substituting 2-amino-2-methyl-1-propanol for 2-methylbutan-2-amine $^1$H NMR (300 MHz, CD$_3$OD) δ ppm 1.34 (s, 6H) 1.38 (s, 9H) 1.64 (m, 1H) 1.88-1.98 (m, 2H) 2.12 (m, 1H) 3.58 (s, 2H) 3.76 (m, 1H) 3.90 (m, 1H) 4.13 (m, 1H) 4.26 (m, 2H) 7.26 (s, 1H). MS (DCI) m/z 356 (M+H)$^+$.

Example 335 methyl N-({[(2Z)-5-tert-butyl-3-[(2R)-tetrahydrofuran-2-ylmethyl]-1,3-thiazol-2(3H)-ylidene]amino}carbonyl)-2-methylalaninate In a 20 mL microwave vial, Example 332A (60 mg, 0.148 mmol) was dissolved in acetonitrile (1.5 ml), followed by addition of triethylamine (0.045 ml, 0.326 mmol) and 2-amino isobutyric acid methyl ester hydrochloride (45.5 mg, 0.296 mmol). The reaction mixture was microwaved at 120° C. for 20 min. The reaction was concentrated and the residue was purified according to Example 332B. $^1$H NMR (300 MHz, CD$_3$OD) δ ppm 1.34 (s, 9H) 1.52 (s, 6H) 1.63 (m, 1H) 1.91 (m, 2H) 2.09 (m, 1H) 3.63-3.74 (s, 3H) 3.77 (m, 1H) 3.90 (m, 1H) 4.07 (m, 1H) 4.23 (m, 2H), 7.08 (s, 1H). MS (DCI) m/z 384 (M+H)$^+$. Anal. Calculated for C$_{18}$H$_{29}$N$_3$O$_4$S 0.75 TFA: C, 49.94; H, 6.39; N, 8.96. Found: C, 50.28; H, 6.02; N, 9.05.

Example 336

N-[(2Z)-5-tert-butyl-3-(1,3-oxazol-2-ylmethyl)-1,3-thiazol-2(3H)-ylidene]-5-chloro-2-methoxybenzamide Example 244A (0.125 g, 0.386 mmol) in DMF (2 mL) was treated with NaH (11 mg, 0.462 mmol), then 2-(chloromethyl)-oxazole (54 mg, 0.46 mmol) followed by stirring at room temperature overnight. After workup, the product was purified by silica gel chromatography. $^1$H NMR (CDCl$_3$, 300 MHz) δ ppm 1.33 (s, 9H), 3.75 (s, 3H), 5.51 (s, 2H), 7.08 (d, 1H), 7.21 (d, 1H), 7.42 (s, 1H), 7.44 (dd, 1H), 7.57 (d, 1H), 8.11 (d, 1H); MS (ESI$^+$) m/z 406 (M+H)$^+$.

Example 337

N-[(2Z)-5-tert-butyl-3-(1,2,4-oxadiazol-3-ylmethyl)-1,3-thiazol-2(3H)-ylidene]-5-chloro-2-methoxybenzamide Example 244A and commercially available 3-(chloromethyl)-1,2,4-oxadiazole (May bridge) were processed using the method described in Example 266 to afford the title compound. $^1$H NMR (300 MHz, DMSO-d$_6$) δ ppm 1.33 (s, 9H), 3.74 (s, 3H), 5.59 (s, 2H), 7.08 (d, J=9.2 Hz, 1H), 7.39-7.49 (m, 1H), 7.43 (s, 1H), 7.59 (d, J=2.7 Hz, 1H), 9.63 (s, 1H); MS (ESI$^+$) m/z 407 (M+H)$^+$; Anal. Calculated for C$_{18}$H$_{19}$ClN$_4$O$_3$S: C, 53.13; H, 4.71; N, 13.77. Found: C, 53.14; H, 4.57; N, 13.56.

Example 338

N-[(2Z)-5-tert-butyl-3-(2-furylmethyl)-1,3-thiazol-2(3H)-ylidene]-5-chloro-2-methoxybenzamide

Example 338A 5-tert-butyl-3-(furan-2-ylmethyl)thiazol-2(3H)-imine

Commercially available 3,3-dimethylbutanal (Aldrich), 2-furan-2-ylmethanamine (Aldrich), potassium thiocyanate (Aldrich) and iodine (EMD chemicals) were processed using the method described in Example 315A to afford the title compound. MS (ESI$^+$) m/z 237 (M+H)$^+$.

Example 338B (Z)—N-(5-tert-butyl-3-(furan-2-ylmethyl)thiazol-2(3H)-ylidene)-5-chloro-2-methoxybenzamide Example 338A and Example 205B were processed using the method described in Example 244A to afford the title compound. $^1$H NMR (300 MHz, DMSO-d$_6$) δ ppm 1.31 (s, 9H), 3.79 (s, 3H), 5.37 (s, 2H), 6.22-6.59 (m, 2H), 7.12 (d, J=8.7 Hz, 1H), 7.30 (s, 1H), 7.46 (dd, J=8.9, 3.0 Hz, 1H), 7.65 (dd, J=1.8, 1.0 Hz, 1H), 7.73 (d, J=2.8 Hz, 1H); MS (ESI$^+$) m/z 405 (M+H)$^+$.

Example 339

5-chloro-N-[(2Z)-4,5-dimethyl-3-[(3-methylisoxazol-5-yl)methyl]-1,3-thiazol-2(3H)-ylidene]-2-methoxybenzamide

Example 339A 4,5-dimethyl-3-(prop-2-ynyl)thiazol-2(3H)-imine hydrobromide

To a solution of 4,5-dimethylthiazol-2-amine (2.5 g, 19.5 mmol) in 10 mL toluene was added propargyl bromide (2.78 g, 23.4 mmol). The reaction was heated at 85° C. for 12 h then cooled. The crude material was diluted with diethyl ether and the solid was collected via filtration to give 3.5 g of the title compound which was used without further purification. m/z 167.1 (M+H)$^+$.

Example 339B 5-chloro-N-[(2Z)-4,5-dimethyl-3-prop-2-yn-1-yl-1,3-thiazol-2(3H)-ylidene]-2-methoxybenzamide To a solution of Example 339A (0.5 g, 2.03 mmol) in 15 mL acetonitrile was added Example 205B (0.54 g, 2.69 mmol) and triethylamine (0.81 g, 8.12 mmol). The reaction was heated at 65° C. for 6 h, then at room temperature overnight. The crude reaction was triturated with methylene chloride/hexane and the resulting solid collected. The filtrate was chromatographed over silica gel (gradient elution, 20-40% ethyl acetate/hexane) and combined with the material from the aforementioned trituration to give 0.3 g of the title compound. m/z 334.9 (M+H)$^-$.

Example 339C 5-chloro-N-[(2Z)-4,5-dimethyl-3-[(3-methylisoxazol-5-yl)methyl]-1,3-thiazol-2(3H)-ylidene]-2-methoxybenzamide To a solution of acetaldehyde oxime (0.085 g, 2.24 mmol) in 10 mL chloroform was added N-chlorosuccinimide (0.27 g, 2 mmol) and a drop of pyridine. The solution was stirred at ambient temperature for 4 h when Example 339B (0.15 g, 0.45 mmol) and triethylamine (0.224 g, 2.24 mmol) were added. The reaction was held at ambient temperature overnight, then diluted with ethyl acetate, washed with water, brine, dried over MgSO$_4$, filtered, and concentrated. The material was purified by flash chromatography over silica gel (50% ethyl acetate/hexane) to give 0.075 g of the title compound. $^1$H NMR (300 MHz, DMSO-d$_6$) δ ppm 2.20 (s, 3H) 2.23 (s, 3H) 2.26 (s, 3H) 3.77 (s, 3H) 5.57 (s, 2H) 6.28 (s, 1H) 7.10 (d, J=9.15 Hz, 1H) 7.34-7.59 (m, 1H) 7.69 (d, J=2.71 Hz, 1H). m/z 392.0 (M+H)$^+$.

Example 340

5-chloro-2-methoxy-N-[(2Z)-5-methyl-3-{[5-(trifluoromethyl)-2-furyl]methyl}-1,3-thiazol-2(3H)-ylidene]benzamide

Example 340A 5-chloro-2-methoxy-N-(5-methylthiazol-2-yl)benzamide

To a solution of 5-methylthiazol-2-amine (0.25 g, 2.25 mmol) in 15 mL acetonitrile was added Example 205B (0.5 g, 2.7 mmol) and triethylamine (0.45 g, 4.5 mmol). The reaction was heated at reflux for 4 h and then 65° C. overnight. The reaction was cooled, diluted with ethyl acetate and washed with NaHCO$_3$, brine, dried over MgSO$_4$, filtered, and concentrated to give 0.4 g of the crude title compound, which was used without further purification. m/z 282.9 (M+H)$^+$.

Example 340B 5-chloro-2-methoxy-N-[(2Z)-5-methyl-3-{[5-(trifluoromethyl)-2-furyl]methyl}-1,3-thiazol-2(3H)-ylidene]benzamide To a solution of Example 340A (0.1 g, 0.36 mmol) in 5 mL DMF was added sodium hydride (0.01 g, 0.39 mmol, 95%). The solution was allowed to stir at ambient temperature for 30 min when 2-(bromomethyl)-5-(trifluoromethyl)furan (0.09 g, 0.39 mmol) was added. The reaction was held at ambient temperature overnight and then quenched with water. The crude was extracted with ethyl acetate and the organics washed with water, then dried over MgSO$_4$, filtered, and concentrated. Flash chromatography over silica gel (50% ethyl acetate/hexane) gave 0.05 g of the title compound. $^1$H NMR (300 MHz, DMSO-d$_6$) δ ppm 2.28 (d, J=1.36 Hz, 3H) 3.78 (s, 3H) 5.47 (s, 2H) 6.66 (d, J=2.71 Hz, 1H) 7.11 (d, J=8.81 Hz, 1H) 7.22 (dd, J=3.39, 1.36 Hz, 1H) 7.31-7.39 (m, J=1.36 Hz, 1H) 7.41-7.52 (m, 1H) 7.72 (d, J=2.71 Hz, 1H). m/z 431.0 (M+H)$^+$.

Example 341

5-chloro-N-[(2Z)-3-(2-furylmethyl)-5-methyl-1,3-thiazol-2(3H)-ylidene]-2-methoxybenzamide To a solution of Example 340A (0.15 g, 0.53 mmol) in 5 mL DMF was added sodium hydride (0.016 g, 0.67 mmol, 95%). After the solution was allowed to stir at ambient temperature for 30 min, 2-(chloromethyl)furan (0.08 g, 0.67 mmol) was added. The reaction was held at ambient temperature overnight and then quenched with water. The crude was extracted with ethyl acetate and the organics washed with water, then dried over MgSO$_4$, filtered, and concentrated. Flash chromatography over silica gel (50% ethyl acetate/hexane) gave 0.075 g of the title compound. $^1$H NMR (300 MHz, DMSO-d$_6$) δ ppm 2.26 (d, J=1.36 Hz, 3H) 3.80 (s, 3H) 5.18 (s, 2H) 6.54 (s, 1H) 7.12 (d, J=8.81 Hz, 1H) 7.29 (d, J=1.36 Hz, 1H) 7.46 (dd, J=8.81, 2.71 Hz, 1H) 7.64 (t, J=1.70 Hz, 1H) 7.67-7.76 (m, 2H). m/z 363.0 (M+H)$^+$.

Example 342

5-chloro-N-[(2Z)-3-(3-furylmethyl)-5-methyl-1,3-thiazol-2(3H)-ylidene]-2-methoxybenzamide To a solution of Example 340A (0.15 g, 0.53 mmol) in 5 mL DMF was added sodium hydride (0.016 g, 0.67 mmol, 95%). After the solution was allowed to stir at ambient temperature for 30 min, 3-(chloromethyl)furan (0.08 g, 0.67 mmol) was added. The reaction was held at ambient temperature overnight and then quenched with water. The crude was extracted with ethyl acetate and the organics washed with water, then dried over $MgSO_4$, filtered, and concentrated. Flash chromatography over silica gel (50% ethyl acetate/hexane) gave 0.035 g of the title compound. $^1$H NMR (300 MHz, DMSO-$d_6$) δ ppm 2.27 (d, J=1.36 Hz, 3H) 3.80 (s, 3H) 5.38 (s, 2H) 6.39-6.55 (m, 2H) 7.12 (d, J=8.82 Hz, 1H) 7.26 (d, J=1.36 Hz, 1H) 7.46 (dd, J=8.82, 2.71 Hz, 1H) 7.64 (s, 1H) 7.75 (d, J=2.71 Hz, 1H). m/z 363.0 (M+H)$^+$.

Example 343

N-[(2Z)-5-tert-butyl-3-[(2R)-tetrahydrofuran-2-ylmethyl]-1,3-thiazol-2(3H)-ylidene]-2-ethoxy-5-(trifluoromethyl)benzamide

Example 343A

N-[(2Z)-5-tert-butyl-3-[(2R)-tetrahydrofuran-2-ylmethyl]-1,3-thiazol-2(3H)-ylidene]-2-fluoro-5-(trifluoromethyl)benzamide To the product of Example 240C (0.62 g, 1.5 mmol) in THF (15 mL) was added triethylamine (1.1 mL, 7.7 mmol) followed by 2-fluoro-5-(trifluoromethyl)benzoyl chloride (0.39 mL, 2.6 mmol). This mixture was warmed to 50° C. and was allowed to stir for 4 h. The mixture was cooled to ambient temperature then was quenched with saturated, aqueous $NH_4Cl$ (5 mL) and was diluted with EtOAc (5 mL). The layers were separated and the aqueous layer was extracted with EtOAc (3×5 mL). The combined organics were dried over anhydrous $Na_2SO_4$, filtered and concentrated under reduced pressure. The crude material was purified by column chromatography ($SiO_2$, 60% hexanes in EtOAc) to give the title compound (0.44 g, 1.0 mmol, 66% yield). MS (DCI/$NH_3$) m/z 431 (M+H)$^+$.

Example 343B

N-[(2Z)-5-tert-butyl-3-[(2R)-tetrahydrofuran-2-ylmethyl]-1,3-thiazol-2(3H)-ylidene]-2-ethoxy-5-(trifluoromethyl)benzamide To ethanol (0.13 mL, 2.15 mmol) in 5 mL THF was added potassium tert-butoxide (0.23 g, 2.0 mmol). The mixture was stirred at ambient temperature for 20 min then the product of Example 343A (0.44 g, 1.0 mmol) in THF (10 mL) was added via cannula. The mixture was stirred for 1 h at ambient temperature then was quenched with saturated, aqueous $NH_4Cl$ (5 mL) and was diluted with EtOAc (5 mL). The layers were separated, the aqueous layer was extracted with EtOAc (3×5 mL) and the combined organics were dried over anhydrous $Na_2SO_4$, filtered and concentrated under reduced pressure. The crude material was purified by column chromatography ($SiO_2$, 60% hexanes in EtOAc) to give the title compound (0.45 g, 0.99 mmol, 96% yield). $^1$H NMR (300 MHz, $CDCl_3$) δ ppm 1.36 (s, 9H), 1.48 (t, J=7.0 Hz, 3H), 1.62-1.77 (m, 1H), 1.76-1.95 (m, 2H), 1.99-2.12 (m, 1H), 3.73-3.90 (m, 2H), 4.16-4.24 (m, 3H), 4.29 (dt, J=13.1, 6.7, 2.5 Hz, 1H), 4.42 (dd, J=13.6, 3.1 Hz, 1H), 6.86 (s, 1H), 7.01 (d, J=8.5 Hz, 1H), 7.59 (dd, J=9.0, 2.2 Hz, 1H), 8.24 (d, J=2.4 Hz, 1H); MS (DCI/NH3) m/z 457 (M+H)+. Anal. Calculated for $C_{22}H_{27}F_3N_2O_3S$; Calc: C, 57.88; H, 5.96; N, 6.14. Found: C, 57.91; H, 5.91; N, 6.10.

Example 344

5-chloro-2-methoxy-N-[(2Z)-5-methyl-3-(2-morpholin-4-ylethyl)-1,3-thiazol-2(3H)-ylidene]benzamide

Example 344A 5-methyl-3-(2-morpholinoethyl)thiazol-2(3H)-imine

A mixture of 2-amino-5-methylthiazole (1.0 g, 8.8 mmol), 4-(2-chloroethyl)-morpholine hydrochloride (1.7 g, 9.2 mmol) and $Et_3N$ (3.7 mL, 26 mmol) in DMF (5 mL) was warmed to 80° C. and was allowed to stir for 24 h. The mixture was then cooled to ambient temperature, quenched with saturated aqueous $NaHCO_3$ (5 mL), and diluted with $CH_2Cl_2$ (5 mL). The layers were separated and the aqueous layer was extracted with $CH_2Cl_2$ (3×5 mL). The combined organics were dried over anhydrous $Na_2SO_4$, filtered, concentrated under reduced pressure and purified via column chromatography ($SiO_2$, 10% $CH_3OH$ in EtOAc then 9:1:0.1 $CH_2Cl_2$:$CH_3OH$:$NH_4OH$) to give the title compound (0.88 g, 3.9 mmol, 44% yield). MS (DCI/$NH_3$) m/z 228 (M+H)$^+$.

Example 344B 5-chloro-2-methoxy-N-[(2Z)-5-methyl-3-(2-morpholin-4-ylethyl)-1,3-thiazol-2(3H)-ylidene]benzamide To a solution of the product of Example 344A (0.15 g, 0.66 mmol) in THF (10 mL) was added $Et_3N$ (0.28 mL, 2.0 mmol) followed by Example 205B (0.66 mmol) in 5 mL THF via cannula. This mixture was warmed to 50° C. and was stirred for 4 h. The mixture was cooled to ambient temperature, was quenched with saturated, aqueous $NaHCO_3$ (5 mL) and was diluted with EtOAc (5 mL). The layers were separated and the aqueous layer was extracted with EtOAc (3×5 mL). The combined organics were dried over anhydrous $Na_2SO_4$, filtered, concentrated under reduced pressure and purified via column chromatography ($SiO_2$, 9:1:0.1 $CH_2Cl_2$:$CH_3OH$:$NH_4OH$) to give the title compound (0.16 g, 0.39 mmol, 59% yield). $^1$H NMR (300 MHz, $CD_3OD$) δ ppm 2.34 (d, J=1.4 Hz, 3H), 2.59-2.65 (m, 4H), 2.86 (t, J=6.4 Hz, 2H), 3.59-3.67 (m, 4H), 3.86 (s, 3H), 4.40 (t, J=6.3 Hz, 2H), 7.08 (d, J=8.8 Hz, 1H), 7.16 (d, J=1.4 Hz, 1H), 7.40 (dd, J=8.8, 2.7 Hz, 1H), 7.85 (d, J=3.1 Hz, 1H); MS (DCI/NH3) m/z 396 (M+H)$^+$. Anal. Calculated for $C_{18}H_{22}ClN_3O_3S \cdot 0.5H_2O$; Calc: C, 53.39; H, 5.73; N, 10.38. Found: C, 53.62; H, 5.33; N, 10.00.

Example 345

N-[(2Z)-5-tert-butyl-3-{[(4S)-2-oxo-1,3-oxazolidin-4-yl]methyl}-1,3-thiazol-2(3H)-ylidene]-5-chloro-2-methoxybenzamide A mixture of Example 244A (180 mg, 0.55 mmol), (S)-(2-oxo-oxazolidin-4-yl)methyl 4-methylbenzenesulfonate (180 mg, 0.67 mmol), potassium carbonate (153 mg, 1.1 mmol), tetrabutylammonium iodide (10 mg, 0.03 mmol), tetrabutylammonium hydrogen sulfate (10 mg, 0.03 mmol) and tetraethylammonium iodide (10 mg, 0.04 mmol) in toluene (35 mL) was refluxed for 14 h. The mixture was washed with water, brine, dried with $MgSO_4$, filtered, and concentrated under reduced pressure. The residue was purified by chromatography over silica gel (EtOAc as eluent) to afford 100 mg of the title compound. $^1$H NMR (300 MHz, $CDCl_3$) δ ppm 1.36 (s, 9H), 3.92 (s, 3H), 4.11-4.26 (m, 2H), 4.30-4.41 (m, 2H), 4.57 (t, J=8.6 Hz, 1H), 6.33 (s, 1H), 6.62 (s, 1H), 6.93 (d, J=8.8 Hz, 1H), 7.35 (dd, J=9.0, 2.9 Hz, 1H), 7.79 (d, J=2.7 Hz, 1H). MS (DCI/NH$_3$) m/z 424 (M+H)$^+$.

Example 346

2-[(1-aminocyclopentyl)methoxy]-N-[(2Z)-5-tert-butyl-3-[(2R)-tetrahydrofuran-2-ylmethyl]-1,3-thiazol-2(3H)-ylidene]-5-(trifluoromethyl)benzamide A mixture of Example 343A (215 mg, 0.5 mmol), (1-aminocyclopentyl)methanol (115 mg, 1.0 mmol) and potassium tert-butoxide (1N solution in THF) (0.75 mL, 0.75 mmol) in THF (15 mL) was stirred at room temperature for 2 h. The mixture was then acidified to pH 5 with acetic acid and concentrated under reduced pressure. The residue was treated with a saturated solution of NaHCO$_3$ and extracted with ethyl acetate. The organic layer was washed with brine, dried with MgSO$_4$, filtered, and concentrated under reduced pressure. The residue was purified by chromatography over silica gel (EtOAc-MeOH 4:1 as eluent) to afford 175 mg of the title compound. $^1$H NMR (300 MHz, DMSO-d$_6$) δ ppm 1.32 (s, 9H), 1.37-2.08 (m, 14H), 3.59-3.66 (m, 1H), 3.77 (t, J=7.3 Hz, 1H), 3.92 (s, 2H), 4.15-4.35 (m, 3H), 7.20-7.32 (m, 2H), 7.74 (dd, J=8.7, 2.4 Hz, 1H), 8.02 (d, J=2.4 Hz, 1H). MS (DCI/NH$_3$) m/z 526 (M+H)$^+$. Anal. calculated for C$_{26}$H$_{34}$F$_3$N$_3$O$_3$S: C, 59.41; H, 6.52; N, 7.99. Found: C, 59.37; H, 6.74; N, 7.60.

Example 347

N-[(2Z)-5-tert-butyl-3-[(2R)-tetrahydrofuran-2-ylmethyl]-1,3-thiazol-2(3H)-ylidene]-2-{[(3S)-1-(2-oxopropyl)pyrrolidin-3-yl]oxy}-5-(trifluoromethyl)benzamide

Example 347A

N-[(2Z)-5-tert-butyl-3-[(2R)-tetrahydrofuran-2-ylmethyl]-1,3-thiazol-2(3H)-ylidene]-2-[(3S)-pyrrolidin-3-yloxy]-5-(trifluoromethyl)benzamide A mixture of Example 343A (860 mg, 2 mmol), (S)-pyrrolidin-3-ol (348 mg, 4.0 mmol) and potassium tert-butoxide (1N solution in THF) (3 mL, 3 mmol) in THF (15 mL) was stirred at room temperature for 1 h. The mixture was then acidified to pH 5 with acetic acid and concentrated under reduced pressure. The residue was treated with a saturated solution of NaHCO$_3$ and extracted with ethyl acetate. The organic layer was washed with brine, dried with MgSO$_4$, filtered, and concentrated under reduced pressure to afford 950 mg of the crude title compound. MS (DCI/NH$_3$) m/z 498 (M+H)$^+$.

Example 347B

N-[(2Z)-5-tert-butyl-3-[(2R)-tetrahydrofuran-2-ylmethyl]-1,3-thiazol-2(3H)-ylidene]-2-{[(3S)-1-(2-oxopropyl)pyrrolidin-3-yl]oxy}-5-(trifluoromethyl)benzamide To a mixture of Example 347A (400 mg, 0.8 mmol) and K$_2$CO$_3$ (222 mg, 1.6 mmol) in acetonitrile (35 mL) was added at ambient temperature 1-chloropropan-2-one (91 mg, 1 mmol) and the resulting mixture was stirred at room temperature for 15 h. The mixture was concentrated under reduced pressure, the residue was dissolved in EtOAc, washed with water, brine, dried with MgSO$_4$, filtered, and concentrated under reduced pressure. The residue was purified by chromatography (EtOAc-MeOH 9:1 as eluent) to afford 370 mg of the title compound. $^1$H NMR (300 MHz, DMSO-d$_6$) δ ppm 1.29-1.36 (m, 9H), 1.58-1.67 (m, 1H), 1.71-1.98 (m, 6H), 2.04 (s, 3H), 2.21-2.35 (m, J=13.6, 6.4 Hz, 1H), 2.53-2.59 (m, J=6.4 Hz, 1H), 2.65-2.77 (m, 2H), 3.01 (dd, J=10.3, 6.3 Hz, 1H), 3.60-3.71 (m, 1H), 3.73-3.83 (m, 1H), 4.14-4.35 (m, 3H), 4.94-5.07 (m, 1H), 7.16-7.30 (m, 2H), 7.72 (dd, J=8.8, 2.0 Hz, 1H), 7.97 (d, J=2.0 Hz, 1H). MS (DCI/NH$_3$) m/z 554 (M+H)$^+$.

Example 348

N-[(2Z)-5-tert-butyl-3-[(2R)-tetrahydrofuran-2-ylmethyl]-1,3-thiazol-2(3H)-ylidene]-2-({1-[2-(hydroxyimino)propyl]azetidin-3-yl}oxy)-5-(trifluoromethyl)benzamide

Example 348A

N-[(2Z)-5-tert-butyl-3-[(2R)-tetrahydrofuran-2-ylmethyl]-1,3-thiazol-2(3H)-ylidene]-2-{[1-(2-oxopropyl)azetidin-3-yl]oxy}-5-(trifluoromethyl)benzamide To a mixture of Example 382B (485 mg, 1 mmol) and K$_2$CO$_3$ (348 mg, 2.5 mmol) in acetonitrile (35 mL) was added at ambient temperature 1-chloropropan-2-one (139 mg, 1.5 mmol) and the resulting mixture was stirred at room temperature for 16 h. The mixture was concentrated under reduced pressure, the residue was dissolved in EtOAc, washed with water, brine, dried with MgSO$_4$, filtered, and concentrated under reduced pressure. The residue was purified by chromatography (CH$_2$Cl$_2$-MeOH 9:1 as eluent) to afford 200 mg of the title compound. MS (DCI/NH$_3$) m/z 540 (M+H)$^+$.

Example 348B

N-[(2Z)-5-tert-butyl-3-[(2R)-tetrahydrofuran-2-ylmethyl]-1,3-thiazol-2(3H)-ylidene]-2-({1-[2-(hydroxyimino)propyl]azetidin-3-yl}oxy)-5-(trifluoromethyl)benzamide A mixture of Example 348A (162 mg, 0.3 mmol) and hydroxylamine hydrochloride (31 mg, 0.45 mmol) in pyridine (10 mL) was stirred at room temperature for 14 h and then was concentrated under reduced pressure. A saturated solution of sodium bicarbonate was added to the residue and the mixture was extracted with ethyl acetate. The ethyl acetate extract was washed with water, brine, dried with MgSO$_4$, filtered, and concentrated under reduced pressure. Purification by silica gel chromatography (Ethyl acetate-MeOH 9:1) afforded 60 mg of the title compound. $^1$H NMR (300 MHz, DMSO-d$_6$) δ ppm 1.33 (s, 9H), 1.58-2.00 (m, 7H), 3.00-3.04 (m, 2H), 3.10 (s, 2H), 3.62-3.85 (m, 4H), 4.19-4.39 (m, 3H), 4.94 (t, J=5.8 Hz, 1H), 7.01 (d, J=8.8 Hz, 1H), 7.22-7.33 (m, 1H), 7.70 (dd, J=8.5, 2.0 Hz, 1H), 8.01 (d, J=2.0 Hz, 1H), 10.52 (s, 1H). MS (DCI/NH$_3$) m/z 555 (M+H)$^+$.

Example 349

5-chloro-2-(4-chlorophenoxy)-N-[(2Z)-3-(2-methoxyethyl)-5-methyl-1,3-thiazol-2(3H)-ylidene]benzamide

Example 349A 5-chloro-2-fluoro-N-[(2Z)-3-(2-methoxyethyl)-5-methyl-1,3-thiazol-2(3H)-ylidene]benzamide Example 140A and 5-chloro-2-fluorobenzoic acid were processed using the method described in Example 223A to afford the title compound. MS (ESI) m/z 329 (M+H)$^+$.

Example 349B 5-chloro-2-(4-chlorophenoxy)-N-[(2Z)-3-(2-methoxyethyl)-5-methyl-1,3-thiazol-2(3H)-ylidene]benzamide Example 349A and 4-chlorophenol were processed using the method described in Example 280B to afford the title compound. $^1$H NMR (400 MHz, DMSO-d$_6$) δ ppm 2.25 (s, 3H) 3.18 (s, 3H) 3.44 (t, J=5.22 Hz, 2H) 4.06 (t, J=5.22 Hz, 2H) 6.87-6.94 (m, 2H) 7.10 (d, J=8.90 Hz, 1H) 7.18 (d, J=1.53 Hz, 1H) 7.33-7.40 (m, 2H) 7.56 (dd, J=8.59, 2.76 Hz, 1H) 7.91 (d, J=2.76 Hz, 1H); MS (ESI) m/z 437 (M+H)$^+$.

Example 350

5-chloro-N-[(2Z)-3-(2-methoxyethyl)-5-methyl-1,3-thiazol-2(3H)-ylidene]-2-(tetrahydrofuran-3-yloxy)benzamide Example 349A and tetrahydrofuran-3-ol were processed using the method described in Example 280B to afford the title compound. $^1$H NMR (500 MHz, DMSO-d$_6$) δ ppm 1.93-2.00 (m, 1H) 2.12-2.21 (m, 1H) 2.28 (s, 3H) 3.26 (s, 3H) 3.68 (t, J=5.19 Hz, 2H) 3.70-3.75 (m, 1H) 3.75-3.84 (m, 2H) 3.88 (dd, J=10.07, 4.88 Hz, 1H) 4.32 (t, J=5.19 Hz, 2H) 5.02-5.07 (m, 1H) 7.09 (d, J=8.85 Hz, 1H) 7.24 (d, J=1.22 Hz, 1H) 7.42 (dd, J=8.85, 2.75 Hz, 1H) 7.68 (d, J=2.75 Hz, 1H); MS (ESI) m/z 397 (M+H)$^+$.

Example 351

N-[(2Z)-5-tert-butyl-4-methyl-3-[(2R)-tetrahydrofuran-2-ylmethyl]-1,3-thiazol-2(3H)-ylidene]-2-fluoro-3-(trifluoromethyl)benzamide The title compound was prepared according to the procedure described in Examples 319A and 319B, replacing Example 205B with 2-fluoro-3-(trifluoromethyl)benzoyl chloride in 67.7% yield. $^1$H NMR (300 MHz, DMSO-d$_6$) δ ppm 1.39 (s, 9H), 1.58-2.05 (m, 4H), 2.44 (s, 3H), 3.63 (q, J=7.54 Hz, 1H), 3.72-3.84 (m, 1H), 4.07-4.21 (m, 1H), 4.22-4.34 (m, 1H), 4.42 (dd, J=13.88, 2.78 Hz, 1H), 7.45-7.52 (m, 1H), 7.84-7.94 (m, 1H), 8.19-8.34 (m, 1H); MS (ESI) m/z 445 [M+H]$^+$, 443 [M−H].

Example 352

N-[(2Z)-5-tert-butyl-3-[(2R)-tetrahydrofuran-2-ylmethyl]-1,3-thiazol-2(3H)-ylidene]-2-[2-(dimethylamino)ethoxy]-5-(trifluoromethyl)benzamide To a solution of 2-(dimethylamino)ethanol (89 mg, 1.0 mmol) in THF (2 mL) was added potassium tert-butoxide 1.0M solution in THF (1 mL). The mixture was stirred at room temperature for 10 min and then Example 372B (215 mg, 0.5 mmol) was added and stirred at room temperature for another 2 hrs. The reaction mixture was quenched with saturated aqueous ammonium chloride and extracted by ethyl acetate (3×10 mL). The combined organic layers were washed with brine, dried over MgSO$_4$, filtered, and concentrated. Purification by column chromatography eluting with NH$_3$/MeOH (1:9) in 5-30% gradient in ethyl acetate afforded the title compound (190 mg, 76%). $^1$H NMR (300 MHz, DMSO-d$_6$) δ ppm 1.32 (s, 9H), 1.57-2.01 (m, 4H), 2.36-2.46 (m, 6H), 2.90 (s, 2H), 3.59-3.84 (m, 2H), 4.17-4.35 (m, 5H), 7.26-7.37 (m, 2H), 7.77 (dd, J=8.72, 1.98 Hz, 1H), 8.00 (d, J=2.38 Hz, 1H); MS (ESI) m/z 500 [M+H]$^+$.

Example 353

N-[(2Z)-5-tert-butyl-3-[(2R)-tetrahydrofuran-2-ylmethyl]-1,3-thiazol-2(3H)-ylidene]-2-[2-(dimethylamino)-2-methylpropoxy]-5-(trifluoromethyl)benzamide The title compound was prepared according to the procedure described in Example 352, replacing 2-(dimethylamino)ethanol with 2-(dimethylamino)-2-methylpropan-1-ol in 80% yield. $^1$H NMR (300 MHz, DMSO-d$_6$) δ ppm 1.10 (s, 6H), 1.29-1.40 (m, 9H), 1.55-1.69 (m, 1H), 1.73-1.97 (m, 3H), 2.06-2.34 (m, 6H), 3.59-3.68 (m, 1H), 3.73-3.83 (m, 1H), 3.94 (s, 2H), 4.15-4.31 (m, 3H), 7.21-7.37 (m, 2H), 7.73 (d, J=9.12 Hz, 1H), 7.95 (s, 1H); MS (ESI) m/z 528 [M+H]$^+$.

Example 354

N-[(2Z)-5-tert-butyl-3-[(2R)-tetrahydrofuran-2-ylmethyl]-1,3-thiazol-2(3H)-ylidene]-2-(2-morpholin-4-ylethoxy)-5-(trifluoromethyl)benzamide The title compound was prepared according to the procedure described in Example 352, replacing 2-(dimethylamino)ethanol with 2-morpholinoethanol in 85% yield. $^1$H NMR (300 MHz, DMSO-d$_6$) δ ppm 1.32 (s, 9H), 1.57-1.69 (m, 1H), 1.73-1.94 (m, 3H), 2.36-2.48 (m, 4H), 2.69 (t, J=5.93 Hz, 2H), 3.45-3.57 (m, 4H), 3.58-3.71 (m, 1H), 3.72-3.85 (m, 1H), 4.12-4.37 (m, 5H), 7.22-7.34 (m, 2H), 7.73 (dd, J=8.82, 2.03 Hz, 1H), 7.92 (d, J=2.37 Hz, 1H); MS (ESI) m/z 542 [M+H]$^+$.

Example 355

N-[(2Z)-5-tert-butyl-3-[(2R)-tetrahydro furan-2-ylmethyl]-1,3-thiazol-2(3H)-ylidene]-2-[2-(diethylamino)ethoxy]-5-(trifluoromethyl)benzamide The title compound was prepared according to the procedure described in Example 352, replacing 2-(dimethylamino)

ethanol with 2-(diethylamino)ethanol in 82% yield. ¹H NMR (300 MHz, DMSO-d$_6$) δ ppm 0.73-1.19 (m, 6H), 1.32 (s, 9H), 1.55-2.02 (m, 4H), 2.49-2.67 (m, 4H), 2.69-2.98 (m, 2H), 3.58-3.84 (m, 2H), 3.92-4.55 (m, 5H), 7.14-7.41 (m, 2H), 7.75 (s, 1H), 7.95 (s, 1H); MS (ESI) m/z 528 [M+H]⁺.

Example 356

N-[(2Z)-5-tert-butyl-3-[(2R)-tetrahydrofuran-2-ylmethyl]-1,3-thiazol-2(3H)-ylidene]-2-[2-(1,1-dioxidothiomorpholin-4-yl)ethoxy]-5-(trifluoromethyl)benzamide The title compound was prepared according to the procedure described in Example 352, replacing 2-(dimethylamino)ethanol with 4-(2-hydroxyethyl)thiomorpholine-1,1-dioxide in 80% yield. ¹H NMR (300 MHz, DMSO-d$_6$) δ ppm 1.32 (s, 9H), 1.55-2.01 (m, 4H), 2.93 (t, J=5.55 Hz, 2H), 2.96-3.10 (m, 8H), 3.60-3.68 (m, 1H), 3.72-3.82 (m, 1H), 4.11-4.36 (m, 5H), 7.24-7.33 (m, 2H), 7.75 (dd, J=8.92, 2.58 Hz, 1H), 7.95 (d, J=2.38 Hz, 1H); MS (ESI) m/z 590 [M+H]⁺.

Example 357

N-[(2Z)-5-tert-butyl-3-[(2R)-tetrahydrofuran-2-ylmethyl]-1,3-thiazol-2(3H)-ylidene]-2-(2-piperidin-1-ylethoxy)-5-(trifluoromethyl)benzamide The title compound was prepared according to the procedure described in Example 352, replacing 2-(dimethylamino)ethanol with 2-(piperidin-1-yl)ethanol in 69% yield. ¹H NMR (300 MHz, DMSO-d$_6$) δ ppm 1.32 (s, 9H), 1.33-1.39 (m, 2H), 1.39-1.49 (m, 4H), 1.57-1.70 (m, 1H), 1.74-1.86 (m, 2H), 1.86-1.98 (m, 1H), 2.36-2.46 (m, 4H,) 2.65 (t, J=6.35 Hz, 2H), 3.61-3.70 (m, 1H), 3.74-3.83 (m, 1H), 4.15-4.23 (m, 4H), 4.24-4.33 (m, 1H), 7.25 (s, 1H), 7.30 (d, J=9.12 Hz, 1H), 7.73 (dd, J=8.73, 2.38 Hz, 1H), 7.92 (d, J=2.38 Hz, 1H); MS (+DCI) m/z 540 [M+H]⁺.

Example 358

N-[(2Z)-5-tert-butyl-3-[(2R)-tetrahydrofuran-2-ylmethyl]-1,3-thiazol-2(3H)-ylidene]-2-(3-methoxy-3-methylbutoxy)-5-(trifluoromethyl)benzamide The title compound was prepared according to the procedure described in Example 352, replacing 2-(dimethylamino)ethanol with 3-methoxy-3-methylbutan-1-ol in 55% yield. ¹H NMR (300 MHz, DMSO-d$_6$) δ ppm 1.15 (s, 6H), 1.32 (s, 9H), 1.58-1.70 (m, 1H), 1.75-1.98 (m, 5H), 3.10 (s, 3H), 3.60-3.70 (m, 1H), 3.73-3.83 (m, 1H), 4.10-4.35 (m, 5H), 7.23-7.32 (m, 2H), 7.73 (dd, J=8.72, 2.38 Hz, 1H), 7.94 (d, J=2.38 Hz, 1H); MS (+DCI) m/z 529 [M+H]⁺.

Example 359

N-[(2Z)-5-tert-butyl-3-[(2R)-tetrahydrofuran-2-ylmethyl]-1,3-thiazol-2(3H)-ylidene]-2-[2-(2-oxopyrrolidin-1-yl)ethoxy]-5-(trifluoromethyl)benzamide The title compound was prepared according to the procedure described in Example 352, replacing 2-(dimethylamino)ethanol with 1-(2-hydroxyethyl)pyrrolidin-2-one in 35% yield. ¹H NMR (300 MHz, DMSO-d$_6$) δ ppm) δ ppm 1.32 (s, 9H) 1.54-1.97 (m, 6H) 2.11-2.22 (m, 2H) 3.43 (t, J=6.95 Hz, 2H) 3.52 (t, J=5.43 Hz, 2H) 3.59-3.70 (m, 1H) 3.72-3.83 (m, 1H) 4.13-4.34 (m, 5H) 7.23-7.33 (m, 2H) 7.74 (dd, J=8.82, 2.03 Hz, 1H) 7.93 (d, J=2.03 Hz, 1H); MS (+DCI) m/z 540 [M+H]⁺.

Example 360

1-benzyl-3-tert-butyl-N-[(2Z)-5-tert-butyl-3-[(2R)-tetrahydrofuran-2-ylmethyl]-1,3-thiazol-2(3H)-ylidene]-1H-pyrazole-5-carboxamide To a solution of Example 372A (737 mg, 2.0 mmol) and triethylamine (1.4 mL, 10.0 mmol) in dichloromethane (10 mL) was added 1-benzyl-3-(tert-butyl)-1H-pyrazole-5-carbonyl chloride (720 mg, 1.3 mmol) dropwise. The mixture was stirred at room temperature for 2 hr, and then water (10 mL) was added. The reaction mixture was extracted with dichloromethane (10 mL×2). The combined organic layer was washed with brine, dried over magnesium sulfate and concentrated. The residue was purified by column chromatography over silica gel eluting with ethyl acetate in hexane in 5-30% gradient to provide the title compound (680 mg, 70.7% yield). ¹H NMR (300 MHz, DMSO-d$_6$) δ ppm 1.26 (s, 9H), 1.29 (s, 9H), 1.46-1.60 (m, 1H), 1.70-1.92 (m, 3H), 3.57-3.66 (m, 1H), 3.70-3.80 (m, 1H), 4.12-4.24 (m, 3H), 5.79-5.92 (m, 2H), 6.77 (s, 1H), 7.06 (d, J=7.14 Hz, 2H), 7.18-7.33 (m, 4H); MS (+ESI) m/z 526 [M+H]⁺.

Example 361 methyl 2-({[(2Z)-5-tert-butyl-3-[(2R)-tetrahydrofuran-2-ylmethyl]-1,3-thiazol-2(3H)-ylidene]amino}carbonyl)-4-(trifluoromethyl)benzoate To Example 386B (2.6 g, 5.29 mmol) and MeOH (50 mL) in a 250 mL stainless steel pressure bottle was added Pd-dppf (Heraeus) (0.194 g, 0.265 mmol) and triethylamine (1.475 mL, 10.58 mmol). The mixture was pressurized with carbon monoxide (60 psi) and stirred at 95° C. for 16 hrs. The reaction mixture was concentrated to dryness and purified by column chromatography over silica gel eluting with ethyl acetate in hexane in 5-30% gradient to provide the title compound (2.3 g, 92% yield). ¹H NMR (300 MHz, DMSO-d$_6$) δ ppm 1.33 (s, 9H), 1.52-2.02 (m, 4H), 3.60-3.69 (m, 1H), 3.73-3.83 (m, 4H), 4.14-4.34 (m, 3H), 7.32 (s, 1H), 7.89 (s, 1H), 7.96 (d, J=8.33 Hz, 1H), 8.16 (d, J=7.93 Hz, 1H); MS (+ESI) m/z 526 [M+H]⁺.

Example 362

3-tert-butyl-N-[(2Z)-5-tert-butyl-3-[(2R)-tetrahydrofuran-2-ylmethyl]-1,3-thiazol-2(3H)-ylidene]-1-methyl-1H-pyrazole-5-carboxamide The title compound was prepared according to the procedure described in Example 360, replacing 1-benzyl-3-(tert-butyl)-1H-pyrazole-5-carbonyl chloride with 3-tert-butyl-1-methyl-1H-pyrazole-5-carbonyl chloride in 79% yield. ¹H NMR (300 MHz, DMSO-d$_6$) δ ppm 1.25 (s, 9H) 1.31 (s, 9H) 1.56-2.04 (m, 4H) 3.59-3.70 (m, 1H) 3.73-3.84 (m, 1H) 4.10 (s, 3H) 4.19-4.33 (m, 3H) 6.67 (s, 1H) 7.26 (s, 1H); MS (+ESI) m/z 417 [M+H]⁺.

Example 363

N-[(2Z)-5-tert-butyl-3-[(2R)-tetrahydrofuran-2-ylmethyl]-1,3-thiazol-2(3H)-ylidene]-1-methyl-3-(trifluoromethyl)-1H-pyrazole-5-carboxamide The mixture of 1-methyl-3-(trifluoromethyl)-1H-pyrazole-5-carboxylic acid (234 mg, 1.2 mmol) and O-benzotriazol-1-yl-N,N,N',N'-tetramethyluronium tetrafluoroborate (TBTU) (383 mg, 1.5 mmol) in DMF (4 mL) was stirred at room temperature for 10 min, and then Example 372A (241 mg, 1.0 mmol) was added, followed by triethylamine (0.14 mL, 0.1 mmol) dropwise. The mixture was stirred for another 2 hrs and monitored by LC/MS. Water (10 mL) and ethyl acetate (20 mL) were added and the organic layer was washed with saturated $NaHCO_3$ and brine and concentrated. Purification by column chromatography over silica gel eluting with ethyl acetate in hexane in 5-40% gradient yielded the title compound (340 mg, 82% yield). $^1$H NMR (300 MHz, DMSO-$d_6$) δ ppm 1.32 (s, 9H), 1.55-2.05 (m, 4H), 3.58-3.71 (m, 1H), 3.72-3.83 (m, 1H), 4.26 (s, 3H), 4.27-4.33 (m, 3H), 7.23 (s, 1H), 7.33 (s, 1H); MS (+ESI) m/z 417 $[M+H]^+$.

Example 364

2-[2-(tert-butylamino)ethoxy]-N-[(2Z)-5-tert-butyl-3-[(2R)-tetrahydrofuran-2-ylmethyl]-1,3-thiazol-2(3H)-ylidene]-5-(trifluoromethyl)benzamide The title compound was prepared according to the procedure described in Example 352, replacing 2-(dimethylamino)ethanol with 2-(tert-butylamino)ethanol in 89% yield. $^1$H NMR (300 MHz, DMSO-$d_6$) δ ppm 0.96-1.18 (m, 9H), 1.32 (s, 9H), 1.56-2.02 (m, 4H), 2.89 (s, 2H), 3.59-3.70 (m, 1H), 3.72-3.84 (m, 1H), 4.08-4.35 (m, 5H), 7.25-7.39 (m, 2H), 7.77 (dd, J=8.81, 2.03 Hz, 1H), 8.01 (s, 1H); MS (+ESI) m/z 528 $[M+H]^+$.

Example 365 tert-butyl 3-{[3-tert-butyl-5-({[(2Z)-5-tert-butyl-3-[(2R)-tetrahydrofuran-2-ylmethyl]-1,3-thiazol-2(3H)-ylidene]amino}carbonyl)-1H-pyrazol-1-yl]methyl}azetidine-1-carboxylate Example 365A 3-tert-butyl-N-[(2Z)-5-tert-butyl-3-[(2R)-tetrahydrofuran-2-ylmethyl]-1,3-thiazol-2(3H)-ylidene]-1H-pyrazole-5-carboxamide To Example 360 (600 mg, 1.248 mmol) and ethanol (5 mL) in a 20 mL pressure bottle was added 20% Pd(OH)$_2$/C, wet (300 mg, 2.135 mmol) and hydrochloric acid (0.208 mL, 2.497 mmol). The mixture was stirred at 50° C. under hydrogen (60 psi) for 2.5 days. HPLC analysis showed conversion completed. The mixture was, filtered, and concentrated to dryness to afford the title compound (450 mg, 92% yield). LC/MS (TFA-method) 391 $[M+H]^+$.

Example 365B tert-butyl 3-{[3-tert-butyl-5-({[2Z)-5-tert-butyl-3-[(2R)-tetrahydrofuran-2-ylmethyl]-1,3-thiazol-2(3H)-ylidene]amino}carbonyl)-1H-pyrazol-1-yl]methyl}azetidine-1-carboxylate Example 365A (155 mg, 0.397 mmol), potassium tert-butoxide (89 mg, 0.794 mmol), and tert-butyl 3-(iodomethyl)azetidine-1-carboxylate (142 mg, 0.476 mmol) in dimethylacetamide (4 mL) were reacted at ambient temperature for 2 hrs. The reaction was quenched with saturated $NaHCO_3$ and diluted with ethyl acetate. The water layer was extracted with ethyl acetate (10 mL×2). The combined organics were washed with brine and dried over $MgSO_4$, filtered, and concentrated. Purification by column chromatography (silica gel, ethyl acetate in hexane in 5-40% gradient) provided the title compound (145 mg, 65.3% yield). $^1$H NMR (300 MHz, DMSO-$d_6$) δ ppm 1.31 (s, 9H), 1.35 (s, 9H), 1.43 (s, 9H), 1.61-2.14 (m, 4H), 3.06-3.23 (m, 1H), 3.70-3.98 (m, 6H), 4.14-4.45 (m, 3H), 4.88 (t, J=6.95 Hz, 2H), 6.74 (s, 1H), 6.86 (s, 1H); MS (+ESI) m/z 560 $[M+H]^+$.

Example 366

1-(azetidin-3-ylmethyl)-3-tert-butyl-N-[(2Z)-5-tert-butyl-3-[(2R)-tetrahydrofuran-2-ylmethyl]-1,3-thiazol-2(3H)-ylidene]-1H-pyrazole-5-carboxamide A mixture of Example 365B (140 mg, 0.25 mmol) and 2,2,2-trifluoroacetic acid (0.193 mL, 2.5 mmol) in $CH_2Cl_2$ (5 mL) was stirred at room temperature overnight. The mixture was concentrated under reduced pressure and the residue was purified by HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to yield the title compound (78 mg, 67.8% yield) as a TFA salt. $^1$H NMR (300 MHz, DMSO-$d_6$) δ ppm 1.24-1.29 (m, 9H), 1.32 (s, 9H), 1.62-1.70 (m, 1H), 1.79-1.88 (m, 2H), 1.92-2.02 (m, 1H), 3.20-3.34 (m, 1H), 3.66 (q, J=7.08 Hz, 1H), 3.76-3.83 (m, 1H), 3.84-4.01 (m, 4H), 4.18-4.43 (m, 3H), 4.81 (d, J=6.92 Hz, 2H), 6.74 (s, 1H), 7.29-7.31 (m, 1H), 8.63 (s, 1H); MS (+ESI) m/z 460 $[M+H]^+$.

Example 367

N-[(2Z)-5-tert-butyl-3-[(5-methylisoxazol-3-yl)methyl]-1,3-thiazol-2(3H)-ylidene]-5-chloro-2-methoxybenzamide A solution of Example 244A (275 mg, 0.84 mmol) in DMF at 0° C. was treated with 60% NaH in mineral oil (40 mg, 1.03 mmol). After the gas evolution subsided, the reaction mixture was allowed to stir for 30 min and then treated with commercially available 3-(chloromethyl)-5-methylisoxazole (111 mg, 0.847 mmol). The resulting mixture was stirred at room temperature for 18 hr, poured into brine and extracted with EtOAc. The organics were combined and washed with water and brine, dried over $MgSO_4$, filtered, and concentrated. The residue was purified by flash chromatography over silica gel using 20% EtOAc in hexane to afford the title compound (165 mg, 37% yield). $^1$H NMR (500 MHz, DMSO-$d_6$) δ ppm 1.32 (s, 9H), 2.38 (s, 3H), 3.77 (s, 3H), 5.39 (s, 2H), 6.23 (s, 1H), 7.10 (d, J=8.8 Hz, 1H), 7.39 (s, 1H), 7.45 (dd, J=9.0, 2.9 Hz, 1H), 7.65 (d, J=3.1 Hz, 1H). MS (DCI) m/z 420 $(M+H)^+$. Elemental analysis calculated for $C_{20}H_{22}ClN_3O_3S$: C, 57.20; H, 5.28; N, 10.01. Found: C, 57.16; H, 5.42; N, 9.75.

Example 368

N-[(2Z)-5-tert-butyl-3-[(2R)-tetrahydrofuran-2-ylmethyl]-1,3-thiazol-2(3H)-ylidene]-2-({(3S)-1-[2-(hydroxyimino)propyl]pyrrolidin-3-yl}oxy)-5-(trifluoromethyl)benzamide A solution of Example 347B (340 mg, 0.614 mmol) in pyridine (5 mL) was treated with commercially available hydroxylamine hydrochloride (51 mg, 0.73 mmol) and stirred at room temperature for 14 h. The reaction mixture was concentrated under reduced pressure and the residue was partitioned between saturated sodium bicarbonate and ethyl acetate. The organic layer was washed with brine, dried with MgSO$_4$, filtered, and concentrated under reduced pressure. The residue was purified by flash chromatography over silica gel using EtOAc: MeOH (9:1) as eluent to afford the title compound (320 mg, 91% yield). $^1$H NMR (300 MHz, DMSO-d$_6$) δ ppm 1.32 (s, 9H), 1.54-2.04 (m, 9H), 2.30 (dd, J=13.4, 6.6 Hz, 1H), 2.41-2.75 (m, 3H), 2.91 (dd, J=10.2, 6.4 Hz, 1H), 3.06 (s, 1H), 3.52-3.90 (m, 2H), 4.11-4.45 (m, 3H), 5.00 (s, 1H), 7.10-7.32 (m, 2H), 7.71 (dd, J=8.6, 1.9 Hz, 1H), 7.95 (d, J=2.0 Hz, 1H), 10.45 (s, 1H). MS (DCI) m/z 569 (M+H)$^+$. Anal. calculated for C$_{27}$H$_{35}$F$_3$N$_4$O$_4$S.0.4H$_2$O: C, 56.31; H, 6.27; N, 9.73; N. Found: C, 56.33; H, 6.39; N, 9.46.

Example 369

N-[(2Z)-5-tert-butyl-3-(2-hydroxyethyl)-1,3-thiazol-2(3H)-ylidene]-5-chloro-2-methoxybenzamide

Example 369A 2-(5-tert-butyl-2-iminothiazol-3(2H)-yl)ethanol

Commercially available 3,3-dimethylbutanal (Aldrich), 2-aminoethanol (Aldrich), potassium thiocyanate (Aldrich) and iodine (EMD chemicals) were processed using the method described in Example 315A to afford the title compound. MS (ESI$^+$) m/z 201 (M+H)$^+$.

Example 369B

N-[(2Z)-5-tert-butyl-3-(2-hydroxyethyl)-1,3-thiazol-2(3H)-ylidene]-5-chloro-2-methoxybenzamide Example 369A and 5-chloro-2-methoxybenzoic acid (Aldrich) were processed using the method described in Example 58 to afford the title compound. $^1$H NMR (300 MHz, DMSO-d$_6$) δ ppm 1.32 (s, 9H), 3.71-3.83 (m, 2H), 3.78 (s, 3H), 4.20 (t, J=5.4 Hz, 2H), 4.95 (t, 1H), 7.10 (d, J=8.8 Hz, 1H), 7.23 (s, 1H), 7.44 (dd, J=8.8, 2.7 Hz, 1H), 7.62 (d, J=2.7 Hz, 1H); MS (ESI$^+$) m/z 369 M+H)$^+$, Anal. Calculated for C$_{17}$H$_{21}$ClN$_2$O$_3$S: C, 55.35; H, 5.74; N, 7.59. Found: C, 55.02; H, 6.16; N, 7.28.

Example 370

5-chloro-N-[(2Z)-5-(4,4-difluorocyclohexyl)-3-(2-methoxyethyl)-1,3-thiazol-2(3H)-ylidene]-2-methoxybenzamide

Example 370A (4,4-difluorocyclohexyl)methanol

To a suspension of lithium aluminum hydride (2.6 g, 69 mmol) in diethyl ether (160 mL) was added slowly a solution of commercially available ethyl 4,4-difluorocyclohexanecarboxylate (Matrix, 11.0 g, 57 mmol) in diethyl ether (20 mL). The reaction mixture was refluxed for 4 hours, then cooled in an ice bath, quenched cautiously with sequential addition of water (2.6 mL), 15% NaOH (2.6 mL) and water (7.8 mL) and extracted with ethyl acetate (3×100 mL). The mixture was filtered and concentrated to afford the title compound.

Example 370B (4,4-difluorocyclohexyl)methyl 4-methylbenzenesulfonate

To a solution of Example 370A (8.5 g, 57 mmol) in dichloromethane (100 mL) were added triethylamine (Aldrich, 25 mL, 180 mmol) and tosyl chloride (Aldrich, 11.4 g, 60 mmol). The reaction mixture was stirred at room temperature for 16 hours and washed with water (50 mL) and brine (50 mL). The organic layer was dried over anhydrous Na$_2$SO$_4$, filtered and concentrated under reduced pressure. The residue was purified by column chromatography using an Analogix® Intelliflash280™ (SiO$_2$, 0-50% ethyl acetate in hexanes) to afford the title compound. $^1$H NMR (300 MHz, CDCl$_3$) δ ppm 1.17-1.42 (m, 2H), 1.57-1.69 (m, 1H), 1.70-1.91 (m, 4H), 1.93-2.18 (m, 2H), 2.46 (s, 3H), 3.86 (d, J=6.4 Hz, 2H), 7.35 (d, J=8.5 Hz, 2H), 7.78 (d, J=8.1 Hz, 2H).

Example 370C 2-(4,4-difluorocyclohexyl)acetonitrile

To a solution of Example 370B (4.5 g, 15 mmol) in dimethylsulfoxide (100 mL) was added sodium cyanide (Aldrich, 2.2 g, 45 mmol). The reaction mixture was stirred at 80° C. for 14 hours, cooled to room temperature, quenched with saturated aqueous NaHCO$_3$ (50 mL) and extracted with diethyl ether (3×50 mL). The combined organic extracts were dried over anhydrous MgSO$_4$, filtered and concentrated under reduced pressure. The residue was purified by column chromatography using an Analogix® Intelliflash280™ (SiO$_2$, 50% pentane in ether) to afford the title compound. MS (ESI$^+$) m/z 177 (M+NH$_4$)$^+$.

Example 370D 2-(4,4-difluorocyclohexyl)acetaldehyde

To a solution of Example 370C (3.8 g, 24 mmol) in dichloromethane (50 mL) was added diisobutylaluminum hydride (1.6M in cyclohexane, 22.5 mL, 36 mmol), dropwise. The reaction mixture was stirred at room temperature for 3 hours. The reaction mixture was quenched with 1M tartaric acid (40 mL), stirred for 1 hour and the layers were separated. The aqueous layer was extracted with dichloromethane (3×50 mL). The combined organic extracts were dried over anhydrous MgSO$_4$, filtered and concentrated under reduced pressure to afford the title compound. MS (ESI$^+$) m/z 162 (M+NH$_4$—H$_2$O)$^+$.

Example 370E 5-(4,4-difluorocyclohexyl)-2,3-dihydrothiazol-2-amine

Example 370D, pyrrolidine, p-toluenesulfonic acid monohydrate, sulfur and cyanamide were processed using the method described in Example 202A to obtain the title compound. MS (ESI$^+$) m/z 219 (M+H)$^+$.

Example 370F 5-(4,4-difluorocyclohexyl)-3-(2-methoxyethyl)thiazol-2(3H)-imine hydrobromide A mixture of Example 370E and commercially available 2-bromoethyl methyl ether (Aldrich) was processed using the method described in Example 12A to afford the title compound. MS (ESI$^-$) m/z 277 (M+H)$^+$.

Example 370G 5-chloro-N-[(2Z)-5-(4,4-difluorocyclohexyl)-3-(2-methoxyethyl)-1,3-thiazol-2(3H)-ylidene]-2-methoxybenzamide Example 370F and 5-chloro-2-methoxybenzoic acid (Aldrich) were processed using the method described in Example 58 to afford the title compound. $^1$H NMR (300 MHz, DMSO-$d_6$) δ ppm 1.44-1.76 (m, 2H), 1.80-2.21 (m, 6H), 2.80-2.99 (m, 1H), 3.26 (s, 3H), 3.72 (t, J=5.4 Hz, 2H), 3.78 (s, 3H), 4.32 (t, J=5.3 Hz, 2H), 7.11 (d, J=9.2 Hz, 1H), 7.34 (s, 1H), 7.45 (dd, J=8.8, 3.1 Hz, 1H), 7.65 (d, J=2.7 Hz, 1H); MS (ESI$^+$) m/z 445 (M+H)$^-$, Anal. Calculated for $C_{20}H_{23}ClF_2N_2O_3S$: C, 53.99; H, 5.21; N, 6.30. Found: C, 54.03; H, 5.19; N, 6.27.

Example 371

N-[(2Z)-5-tert-butyl-3-[(2R)-tetrahydrofuran-2-ylmethyl]-1,3-thiazol-2(3H)-ylidene]-2-cyano-5-(trifluoromethyl)benzamide A mixture of Example 343A (180 mg, 0.42 mmol) and sodium cyanide (41.0 mg, 0.84 mmol) in 0.4 mL of DMSO was heated at 120° C. for 2 h. The reaction was cooled to room temperature and diluted with ether. The mixture was washed with brine, and the layers were separated. The aqueous layer was extracted with ether (2×10 mL). The combined organic extracts were dried (MgSO$_4$), filtered, and concentrated. The residue was purified by column chromatography using an Analogix® Intelliflash280™ (SiO$_2$, 0-50% ethyl acetate in hexanes) to afford the title compound. $^1$H NMR (300 MHz, CDCl$_3$) δ ppm 1.38 (s, 9H), 1.58-1.72 (m, 1H), 1.73-1.95 (m, 2H), 2.09-2.23 (m, 1H), 3.73-3.89 (m, 2H), 4.25-4.39 (m, 2H), 4.65-4.79 (m, 1H), 6.98 (s, 1H), 7.78 (dd, J=8.0, 1.9 Hz, 1H), 7.90 (d, J=7.9 Hz, 1H), 8.69 (d, J=1.6 Hz, 1H); MS (ESI$^+$) m/z 438 (M+H)$^+$.

Example 372

2-tert-butoxy-N-[(2Z)-5-tert-butyl-3-[(2R)-tetrahydrofuran-2-ylmethyl]-1,3-thiazol-2(3H)-ylidene]-5-(trifluoromethyl)benzamide

Example 372A 5-tert-butyl-3-[(2R)-tetrahydrofuran-2-ylmethyl]-1,3-thiazol-2(3H)-imine hydroiodide To a solution of 3,3-dimethylbutanal (9.90 g, 99 mmol) in acetonitrile (60 mL) were added molecular sieves (8 g) and (R)-(tetrahydrofuran-2-yl)methanamine (10 g, 99 mmol). The reaction mixture was stirred at room temperature for 24 hr and then filtered. To the filtrate was added potassium thiocyanate (12.78 g, 131 mmol). The temperature was adjusted to 50° C. and the mixture was stirred until the solids were dissolved. Then, iodine (25.09 g, 99 mmol) was added to the mixture and stirred at 50° C. for 24 hr. The reaction mixture was cooled, and to the mixture was added sodium metabisulfite (20%, 100 mL) and stirred for 30 min. The organic layer was separated. The aqueous layer was washed with dichloromethane (3×40 mL). The combined organic extracts were dried with sodium sulfate, filtered and concentrated to obtain the crude product as a yellow solid. The residue was taken into dichloromethane (20 mL) and ethyl acetate (80 mL) was added, the mixture was warmed to 40° C., sonicated, and left in the refrigerator overnight. The solid was collected and washed with cold ethyl acetate to obtain the title compound as a white solid (18.2 g, 50%). $^1$H NMR (300 MHz, DMSO-$d_6$) δ ppm 1.27 (s, 9H) 1.48-1.61 (m, 1H) 1.78-1.93 (m, 2H) 1.94-2.07 (m, 1H) 3.62-3.71 (m, 1H) 3.76-3.84 (m, 1H) 3.92-4.08 (m, 2H) 4.11-4.20 (m, 1H) 7.19 (s, 1H) 9.39 (s, 2H); MS (DCI/NH$_3$); m/z 241 (M+H)$^+$.

Example 372B

N-[(2Z)-5-tert-butyl-3-[(2R)-tetrahydrofuran-2-ylmethyl]-1,3-thiazol-2(3H)-ylidene]-2-fluoro-5-(trifluoromethyl)benzamide In a 250 mL round-bottomed flask, Example 372A (6 g, 24.96 mmol) was dissolved in dichloromethane (50 mL), triethylamine (8.70 mL, 62.4 mmol) was added followed by addition of 2-fluoro-5-(trifluoromethyl)benzoyl chloride (3.78 mL, 24.96 mmol) dropwise and stirred for 2 hr. The reaction was washed with water and dried with sodium sulfate. The solution was filtere and concentrated, and the residue was purified by column chromatography using an Analogix® Intelliflash280™ (SiO$_2$, 0-30% ethyl acetate in hexane over 25 min) The product was concentrated to provide the title compound as a viscous liquid (7.14 g, 66.4% yield). $^1$H NMR (300 MHz, DMSO-$d_6$) δ ppm 1.33 (s, 9H) 1.62-1.72 (m, 1H) 1.78-1.88 (m, 2H) 1.89-1.99 (m, 1H) 3.62-3.70 (m, 1H) 3.75-3.83 (m, 1H) 4.22-4.29 (m, 2H) 4.29-4.37 (m, 1H) 7.34 (s, 1H) 7.48-7.57 (m, 1H) 7.86-7.97 (m, 1H) 8.31 (dd, J=6.78, 2.37 Hz, 1H); MS (DCI/NH$_3$) m/z 431 (M+H)$^+$.

Example 372C 2-tert-butoxy-N-[(2Z)-5-tert-butyl-3-[(2R)-tetrahydrofuran-2-ylmethyl]-1,3-thiazol-2(3H)-ylidene]-5-(trifluoromethyl)benzamide To a solution of potassium tert-butoxide in tetrahydrofuran (1 M, 2 mL) was added Example 372B (163 mg, 0.38 mmol). The mixture was stirred at room temperature overnight. The reaction was quenched with saturated aqueous ammonium chloride and extracted by ethyl acetate (3×10 mL). The organic layers were combined, washed with water, dried, filtered, and concentrated, and the residue was purified by column chromatography using an Analogix® Intelliflash280™ (SiO$_2$, 0-100% ethyl acetate in hexane) to afford the title compound (0.16 g, 80%). $^1$H NMR (300 MHz, DMSO-$d_6$) δ ppm 1.32 (s, 9H) 1.33 (s, 9H) 1.57-1.68 (m, 1H) 1.77-1.92 (m, 3H) 3.60-3.68 (m, 1H) 3.78 (dt, J=8.39, 6.49 Hz, 1H) 4.17-4.22 (m, 2H) 4.24-4.33 (m, 1H) 7.26 (s, 1H) 7.32 (d, J=8.48 Hz, 1H) 7.67 (dd, J=8.99, 2.20 Hz, 1H) 7.88 (d, J=2.37 Hz, 1H); MS (DCI/NH$_3$) m/z 485 (M+H)$^+$.

Example 373

N-[(2Z)-5-tert-butyl-3-[(2R)-tetrahydrofuran-2-ylmethyl]-1,3-thiazol-2(3H)-ylidene]-2-{[(3R)-1-methylpyrrolidin-3-yl]oxy}-5-(trifluoromethyl)benzamide To a solution of (R)-1-methylpyrrolidin-3-ol (162 mg, 1.6 mmol) in tetrahydrofuran (2 mL) was added sodium tert-butoxide (161 mg, 1.68 mmol). The mixture was stirred at room temperature for 20 min before a solution of Example 372B (344 mg, 0.8 mmol) in tetrahydrofuran (1 mL) was added dropwise. The mixture was stirred at room temperature for 2 hr before it was quenched with saturated aqueous ammonium chloride and extracted by ethyl acetate (3×10 mL). The organic layers were combined, washed with brine, dried, filtered, concentrated and the residue was purified by column chromatography using an Analogix® Intelliflash280™ (SiO$_2$, gradient elution over 25 min with solvents A:B (100:0 to 10:90); solvent A=CH$_2$Cl$_2$; solvent B=7M NH$_3$/MeOH (1):CH$_2$Cl$_2$ (9)) to afford the title compound (150 mg, 37%). $^1$H NMR (300 MHz, DMSO-d$_6$) δ ppm 1.32 (s, 9H) 1.57-1.70 (m, 1H) 1.76-1.83 (m, 3H) 1.88-1.96 (m, 1H) 2.25 (s, 3H) 2.29-2.44 (m, 2H) 2.60-2.73 (m, 2H) 2.78-2.84 (m, 1H) 3.61-3.69 (m, 1H) 3.74-3.83 (m, 1H) 4.18-4.24 (m, 2H) 4.25-4.33 (m, 1H) 4.96-5.04 (m, 1H) 7.18 (d, J=8.73 Hz, 1H) 7.26 (s, 1H) 7.72 (dd, J=8.73, 2.78 Hz, 1H) 7.96 (d, J=2.78 Hz, 1H); MS (DCI/NH$_3$) m/z 512 (M+H)$^+$. Anal. calcd C$_{24}$H$_{31}$F$_3$N$_2$O$_3$S: C, 58.69; H, 6.3; N, 8.21. Found: C, 58.58; H, 6.29; N, 8.18.

Example 374

N-[(2Z)-5-tert-butyl-3-[(2R)-tetrahydrofuran-2-ylmethyl]-1,3-thiazol-2(3H)-ylidene]-2-{[(3S)-1-methylpyrrolidin-3-yl]oxy}-5-(trifluoromethyl)benzamide The title compound was prepared and isolated as described in Example 373, substituting (S)-1-methylpyrrolidin-3-ol for (R)-1-methylpyrrolidin-3-ol in 42% yield. $^1$H NMR (300 MHz, DMSO-d$_6$) δ ppm 1.31 (s, 9H) 1.58-1.69 (m, 1H) 1.74-1.85 (m, 3H) 1.87-1.98 (m, 1H) 2.25 (s, 3H) 2.29-2.41 (m, 2H) 2.59-2.69 (m, 2H) 2.78-2.84 (m, 1H) 3.60-3.69 (m, 1H) 3.74-3.83 (m, 1H) 4.18-4.32 (m, 3H) 4.95-5.04 (m, 1H) 7.18 (d, J=8.73 Hz, 1H) 7.26 (s, 1H) 7.71 (dd, J=9.12, 2.38 Hz, 1H) 7.97 (d, J=2.38 Hz, 1H); MS (DCI/NH$_3$) m/z 512 (M+H)$^+$. Anal. calcd C$_{24}$H$_{31}$F$_3$N$_2$O$_3$S.0.5 H$_2$O: C, 57.68; H, 6.39; N, 8.18. Found: C, 57.79; H, 6.39; N, 8.04.

Example 375

N-[(2Z)-5-tert-butyl-3-[(2R)-tetrahydrofuran-2-ylmethyl]-1,3-thiazol-2(3H)-ylidene]-2-formyl-5-(trifluoromethyl)benzamide

Example 375A 2-formyl-5-(trifluoromethyl)benzoic acid

To a 250 mL round-bottomed flask, was added 2.5 M n-butyllithium/hexane (8.92 mL, 22.30 mmol) in tetrahydrofuran (40 mL) and cooled to −78° C., followed by dropwise addition of 2-bromo-5-(trifluoromethyl)benzoic acid (3 g, 11.15 mmol) in tetrahydrofuran (20 mL). After 30 min N,N-dimethylformamide (0.978 g, 13.38 mmol) was added and the solution slowly allowed to warm to rt. To the reaction was added saturated ammonium chloride solution, followed by addition of saturated NaHCO$_3$ solution until basic. The aqueous layer was separated, and 2 N HCl was added until acidic. The mixture was extracted with ethyl acetate (3×20 mL). The organic layers were combined, dried, filtered, and concentrated. The resulting solid was used without further purification. MS (DCI/NH$_3$) m/z 512 (M+NH$_4$)$^+$.

Example 375B 2-formyl-5-(trifluoromethyl)benzoyl chloride

A solution of Example 375A (0.6 g) and thionyl chloride (3.27 g, 27.5 mmol) was refluxed for 2 hr. The reaction solution was cooled to room temperature, concentrated, azeotroped with toluene, and used without further purification.

Example 375C

N-[(2Z)-5-tert-butyl-3-[(2R)-tetrahydrofuran-2-ylmethyl]-1,3-thiazol-2(3H)-ylidene]-2-formyl-5-(trifluoromethyl)benzamide The title compound was prepared and isolated as described in Example 372B, substituting Example 375B for 2-fluoro-(5-trifluoromethyl)benzoyl chloride in 25% yield. $^1$H NMR (300 MHz, DMSO-d$_6$) δ ppm 1.34 (s, 9H) 1.58-1.70 (m, 1H) 1.77-1.92 (m, 2H) 1.93-2.04 (m, 1H) 3.62-3.70 (m, 1H) 3.76-3.84 (m, 1H) 4.22-4.32 (m, 3H) 7.39 (s, 1H) 7.81 (d, J=8.14 Hz, 1H) 8.00-8.03 (m, 1H) 8.37-8.38 (m, 1H) 10.62 (s, 1H); MS (APCI) m/z 441 (M+H)$^-$.

Example 376

N-[(2Z)-5-tert-butyl-3-[(2R)-tetrahydrofuran-2-ylmethyl]-1,3-thiazol-2(3H)-ylidene]-3-(trifluoromethyl) benzamide The title compound was obtained as a side product from Example 375C. $^1$H NMR (300 MHz, DMSO-d$_6$) δ ppm 1.33 (s, 9H) 1.64-1.76 (m, 1H) 1.78-1.90 (m, 2H) 1.91-2.04 (m, 1H) 3.62-3.72 (m, 1H) 3.76-3.85 (m, 1H) 4.26-4.39 (m, 3H) 7.32 (s, 1H) 7.71-7.77 (m, 1H) 7.89-7.92 (m, 1H) 8.41-8.47 (m, 2H); MS (DCI/NH$_3$) m/z 413 (M+H)$^+$.

Example 377

2-(azetidin-1-ylmethyl)-N-[(2Z)-5-tert-butyl-3-[(2R)-tetrahydrofuran-2-ylmethyl]-1,3-thiazol-2 (3H)-ylidene]-5-(trifluoromethyl)benzamide In a 20 mL vial, to a solution of Example 375C (52 mg, 0.118 mmol) in dichloromethane (2 mL) was added azetidine (20.22 mg, 0.354 mmol), followed by addition of acetic acid (7.09 mg, 0.118 mmol) and sodium triacetoxyborohydride (37.5 mg, 0.177 mmol) and the mixture was stirred for 2 hr. The reaction was quenched with saturated NaHCO$_3$ and extracted with dichloromethane (3×5 mL). The organics were combined, dried, filtered, concentrated and the residue was purified by column chromatography using an Analogix® Intelliflash280™ (SiO$_2$, gradient elution over 25 min with solvents A:B (100:0 to 10:90); solvent A=CH$_2$Cl$_2$; solvent B=7M NH$_3$/MeOH (1):CH$_2$Cl$_2$ (9)) to afford the title compound in 79% yield. $^1$H NMR (300 MHz, DMSO-d$_6$) δ ppm 1.34 (s, 9H) 1.61-1.76 (m, 1H) 1.79-1.91 (m, 2H) 1.91-2.06 (m, 3H) 3.18 (t, J=6.94 Hz, 4H) 3.60-3.71 (m, 1H) 3.74-3.85 (m, 1H) 4.06 (s, 2H) 4.23-4.36 (m, 3H) 7.32 (s, 1H) 7.74-7.78 (m, 2H) 8.21-8.25 (m, 1H); MS (DCI/NH$_3$) m/z 482 (M+H)$^+$. Anal. calcd C$_{25}$H$_{32}$F$_3$N$_3$O$_2$S.0.3 C$_6$H$_6$: C, 62.02; H, 6.56; N, 8.10. Found: C, 61.94; H, 6.43; N, 8.38.

Example 378

N-[(2Z)-5-tert-butyl-3-[(2R)-tetrahydrofuran-2-ylmethyl]-1,3-thiazol-2(3H)-ylidene]-2-(pyrrolidin-1-ylmethyl)-5-(trifluoromethyl)benzamide The title compound was prepared and isolated as described in Example 377, substituting pyrrolidine for azetidine in 72% yield. $^1$H NMR (300 MHz, DMSO-d$_6$) δ ppm 1.33 (s, 9H) 1.62-1.72 (m, 5H) 1.79-1.88 (m, 2H) 1.90-1.98 (m, 1H) 2.43-2.50 (m, 4H) 3.62-3.70 (m, 1H) 3.76-3.83 (m, 1H) 4.10 (s, 2H) 4.22-4.33 (m, 3H) 7.30 (s, 1H) 7.76-7.86 (m, 2H) 8.16 (d, J=1.70 Hz, 1H); MS (DCI/NH$_3$) m/z 496 (M+H)$^+$.

Example 379

N-[(2Z)-5-tert-butyl-3-[(2R)-tetrahydrofuran-2-ylmethyl]-1,3-thiazol-2(3H)-ylidene]-2-{[(3R)-3-hydroxypyrrolidin-1-yl]methyl}-5-(trifluoromethyl)benzamide The title compound was prepared as described in Example 377, substituting (R)-pyrrolidin-3-ol for azetidine, and isolated by preparative HPLC on a Phenomenex Luna Combi-HTS C8(2) column (5 μm, 100 Å, 2.1 mm×30 mm), using a gradient of 10-100% acetonitrile (A) and 10 mM ammonium acetate in water (B), at a flow rate of 2.0 mL/min (0-0.1 min 10%A, 0.1-2.6 min 10-100%A, 2.6-2.9 min 100%A, 2.9-3.0 min 100-10% A. 0.5 min post-run delay) in 70% yield. $^1$H NMR (300 MHz, DMSO-d$_6$) δ ppm 1.33 (s, 9H) 1.53-1.69 (m, 2H) 1.78-1.89 (m, 2H) 1.92-2.04 (m, 2H) 2.35 (dd, J=9.52, 3.57 Hz, 1H) 2.42-2.48 (m, 1H) 2.58-2.74 (m, 2H) 3.61-3.71 (m, 1H) 3.75-3.84 (m, 1H) 4.09-4.11 (d, J=5.95 Hz, 2H) 4.16-4.27 (m, 3H) 4.29-4.33 (m, 1H) 4.67 (d, J=4.36 Hz, 1H) 7.30 (s, 1H) 7.76-7.81 (m, 1H) 7.83-7.88 (m, 1H) 8.17-8.18 (m, 1H); MS (DCI/NH$_3$) m/z 512 (M+H)$^+$.

Example 380

N-[(2Z)-5-tert-butyl-3-[(2R)-tetrahydrofuran-2-ylmethyl]-1,3-thiazol-2(3H)-ylidene]-2-{[(3S)-3-hydroxypyrrolidin-1-yl]methyl}-5-(trifluoromethyl)benzamide The title compound was prepared as described in Example 377, substituting (S)-pyrrolidin-3-ol for azetidine, and isolated by preparative HPLC on a Phenomenex Luna Combi-HTS C8(2) column (5 μm, 100 Å, 2.1 mm×30 mm), using a gradient of 10-100% acetonitrile (A) and 10 mM ammonium acetate in water (B), at a flow rate of 2.0 mL/min (0-0.1 min 10%A, 0.1-2.6 min 10-100%A, 2.6-2.9 min 100%A, 2.9-3.0 min 100-10% A. 0.5 min post-run delay) in 60% yield. $^1$H NMR (300 MHz, DMSO-d$_6$) δ ppm 1.33 (s, 9H) 1.53-1.60 (m, 1H) 1.62-1.69 (m, 1H) 1.77-1.89 (m, 2H) 1.92-2.04 (m, 2H) 2.32-2.47 (m, 2H) 2.59-2.74 (m, 2H) 3.62-3.70 (m, 1H) 3.75-3.84 (m, 1H) 4.02-4.13 (m, 2H) 4.17-4.33 (m, 4H) 4.67 (d, J=4.07 Hz, 1H) 7.30 (s, 1H) 7.76-7.81 (m, 1H) 7.83-7.88 (m, 1H) 8.17 (s, 1H); MS (DCI/NH$_3$) m/z 512 (M+H)$^+$.

Example 381

N-[(2Z)-5-tert-butyl-3-[(2R)-tetrahydrofuran-2-ylmethyl]-1,3-thiazol-2(3H)-ylidene]-2-methyl-5-(trifluoromethyl)benzamide Example 381A 2-methyl-5-(trifluoromethyl)benzoyl chloride The title compound was prepared and isolated using the method described in Example 375B, substituting 2-methyl-5-trifluoromethyl benzoic acid for Example 375A.

Example 381B

N-[(2Z)-5-tert-butyl-3-[(2R)-tetrahydrofuran-2-ylmethyl]-1,3-thiazol-2(3H)-ylidene]-2-methyl-5-(trifluoromethyl)benzamide The title compound was prepared and isolated as described in Example 372B, substituting Example 381A for 2-fluoro-(5-trifluoro)benzoyl chloride in 63% yield. $^1$H NMR (300 MHz, DMSO-d$_6$) δ ppm 1.33 (s, 9H) 1.60-1.72 (m, 1H) 1.78-1.86 (m, 2H) 1.87-1.99 (m, 1H) 2.67 (s, 3H) 3.62-3.70 (m, 1H) 3.75-3.83 (m, 1H) 4.23-4.34 (m, 3H) 7.31 (s, 1H) 7.50 (d, J=8.14 Hz, 1H) 7.70 (dd, J=7.97, 1.86 Hz, 1H) 8.28 (d, J=2.03 Hz, 1H); MS (DCI/NH$_3$) m/z 427 (M+H)$^+$.

Example 382

2-(azetidin-3-yloxy)-N-[(2Z)-5-tert-butyl-3-[(2R)-tetrahydrofuran-2-ylmethyl]-1,3-thiazol-2(3H)-ylidene]-5-(trifluoromethyl)benzamide Example 382A tert-butyl 3-[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]azetidine-1-carboxylate To a solution of tert-butyl 3-hydroxyazetidine-1-carboxylate (4 g, 23.09 mmol) in tetrahydrofuran (30 mL) was added sodium tert-butoxide (2.330 g, 24.25 mmol). The mixture was stirred at room temperature for 20 minutes before Example 372B (4.97 g, 11.55 mmol) was added. The mixture was stirred at room temperature for 2 hr, quenched with saturated aqueous ammonium chloride and extracted with ethyl acetate (3×30 mL). The organic layers were combined, washed with brine, dried, filtered, concentrated and the residue was purified by column chromatography using an Analogix® Intelliflash280™ (SiO$_2$, 0-100% ethyl acetate in hexane over 25 min) to afford the title compound (6.32 g, 10.83 mmol, 94% yield). $^1$H NMR (300 MHz, DMSO-d$_6$) δ ppm 1.33 (s, 9H) 1.39 (s, 9H) 1.58-1.69 (m, 1H) 1.76-1.87 (m, 2H) 1.88-1.99 (m, 1H) 3.60-3.70 (m, 1H) 3.75-3.86 (m, 3H) 4.20-4.22 (m, 2H) 4.29-4.35 (m, 3H) 5.09-5.17 (m, 1H) 7.00 (d, J=8.48 Hz, 1H) 7.73 (dd, J=8.82, 2.37 Hz, 1H) 8.04 (d, J=2.37 Hz, 1H); MS (DCI/NH$_3$) m/z 584 (M+H)$^+$.

Example 382B 2-(azetidin-3-yloxy)-N-[(2Z)-5-tert-butyl-3-[(2R)-tetrahydrofuran-2-ylmethyl]-1,3-thiazol-2(3H)-ylidene]-5-(trifluoromethyl)benzamide To a solution of Example 382A (500 mg, 0.857 mmol) in ethyl acetate (1 mL) was added sulfuric acid (84 mg, 0.857 mmol) in ethyl acetate (0.5 mL). The mixture was stirred at room temperature for 6 hr. More sulfuric acid (84 mg, 0.857 mmol) was added and the reaction was heated at 75° C. overnight. The reaction mixture was cooled to room temperature and filtered. The solid was washed with ethyl acetate. The title compound was obtained as a disulfate salt (175 mg, 30%). $^1$H NMR (300 MHz, CD$_3$OD) δ ppm 1.44 (s, 9H) 1.64-1.76 (m, 1H) 1.83-2.00 (m, 2H) 2.08-2.19 (m, 1H) 3.74-3.90 (m, 2H) 4.30-4.38 (m, 3H) 4.39-4.48 (m, 1H) 4.54-4.66 (m, 3H) 5.34-5.41 (m, 1H) 7.06 (d, J=8.72 Hz, 1H) 7.47 (s, 1H) 7.84 (dd, J=9.12, 2.38 Hz, 1H) 8.26 (d, J=2.38 Hz, 1H); (DCI/NH$_3$) m/z 484 (M+H)$^+$. Anal. calcd C$_{23}$H$_{28}$F$_3$N$_3$O$_3$S.2H$_2$SO$_4$: C, 40.64; H, 4.75; N, 6.18. Found: C, 40.66; H, 4.57; N, 6.04.

Example 383

N-[(2Z)-5-tert-butyl-3-[(2R)-tetrahydrofuran-2-ylmethyl]-1,3-thiazol-2(3H)-ylidene]-2-[(1-methylazetidin-3-yl)oxy]-5-(trifluoromethyl)benzamide

Example 383A 2-(azetidin-3-yloxy)-N-[(2Z)-5-tert-butyl-3-[(2R)-tetrahydrofuran-2-ylmethyl]-1,3-thiazol-2(3H)-ylidene]-5-(trifluoromethyl)benzamide To a solution of Example 382A (0.619 g, 1.06 mmol) in dichloromethane (2 mL) was added 2,2,2-trifluoroacetic acid (1 mL, 10.60 mmol). The mixture was stirred at room temperature for 2 hr and then concentrated as the TFA salt.

Example 383B

N-[(2Z)-5-tert-butyl-3-[(2R)-tetrahydrofuran-2-ylmethyl]-1,3-thiazol-2(3H)-ylidene]-2-[(1-methylazetidin-3-yl)oxy]-5-(trifluoromethyl)benzamide To Example 383A (317 mg, 0.53 mmol) in dichloromethane (5 mL) was added a solution of formaldehyde in water (318 μL, 30%, 95 mg), sodium acetate (130 mg, 1.590 mmol) and sodium triacetoxyborohydride (674 mg, 3.18 mmol). The mixture was stirred at room temperature overnight and quenched with saturated aqueous $NaHCO_3$ and extracted with dichloromethane (3×10 mL). The combined organic layers were dried, filtered, concentrated under reduced pressure, and the residue was purified by column chromatography using an Analogix® Intelliflash280™ ($SiO_2$, gradient elution over 25 min with solvents A:B (100:0 to 10:90); solvent A=$CH_2Cl_2$; solvent B=7M $NH_3$/MeOH (1):$CH_2Cl_2$ (9)) to provide the title compound (105 mg, 0.211 mmol, 39.8% yield). $^1$H NMR (300 MHz, DMSO-$d_6$) δ ppm 1.33 (s, 9H) 1.67-1.70 (m, 1H) 1.76-1.85 (m, 2H) 1.88-1.93 (m, 1H) 2.29 (s, 3H) 2.96-3.02 (m, 2H) 3.63-3.67 (m, 1H) 3.73-3.83 (m, 3H) 4.21-4.23 (m, 2H) 4.31-4.33 (m, 1H) 4.87-4.89 (m, 1H) 6.99-7.02 (m, 1H), 7.27 (s, 1H) 7.70-7.73 (m, 1H) 8.00-8.02 (m, 1H); MS (DCI/$NH_3$) m/z 498 (M+H)$^+$.

Example 384

N-[(2Z)-5-tert-butyl-3-[(2R)-tetrahydrofuran-2-ylmethyl]-1,3-thiazol-2(3H)-ylidene]-2-[(3R)-pyrrolidin-3-yloxy]-5-(trifluoromethyl)benzamide

Example 384A tert-butyl(3R)-3-[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]pyrrolidine-1-carboxylate The title compound was prepared and isolated as described in Example 373, substituting (R)-tert-butyl 3-hydroxypyrrolidine-1-carboxylate for (R)-1-methylpyrrolidin-3-ol in 88% yield. $^1$H NMR (300 MHz, DMSO-$d_6$) δ ppm 1.32 (s, 9H) 1.38 (s, 9H) 1.57-1.68 (m, 1H) 1.75-1.84 (m, 2H) 1.86-1.95 (m, 1H) 2.10-2.16 (m, 2H) 3.34-3.45 (m, 3H) 3.53-3.68 (m, 2H) 3.73-3.82 (m, 1H) 4.15-4.22 (m, 2H) 4.22-4.31 (m, 1H) 5.13-5.20 (m, 1H) 7.27 (s, 1H) 7.30-7.34 (m, 1H) 7.75 (dd, J=8.92, 2.18 Hz, 1H) 7.97-7.99 (m, 1H); MS (DCI/$NH_3$) m/z 598 (M+H)$^+$.

Example 384B

N-[(2Z)-5-tert-butyl-3-[(2R)-tetrahydrofuran-2-ylmethyl]-1,3-thiazol-2(3H)-ylidene]-2-[(3R)-pyrrolidin-3-yloxy]-5-(trifluoromethyl)benzamide To a solution of Example 384A (1.223 g, 2.046 mmol) in dichloromethane (5 mL) was added 2,2,2-trifluoroacetic acid (2.333 g, 20.46 mmol). The mixture was stirred at room temperature for 2 hr and then concentrated. The mixture was taken up in dichloromethane and washed with sodium bicarbonate. The organic layers were combined, dried and concentrated to give the title compound (0.92 g, 90%). $^1$H NMR (300 MHz, CDCl$_3$) δ ppm 1.37 (s, 9H) 1.58-1.72 (m, 1H) 1.79-1.94 (m, 2H) 2.01-2.15 (m, 3H) 2.96-3.06 (m, 2H) 3.23-3.34 (m, 2H) 3.74-3.89 (m, 2H) 4.14-4.21 (m, 1H) 4.24-4.32 (m, 1H) 4.39-4.46 (m, 1H) 4.97-5.03 (m, 1H) 6.88 (s, 1H) 7.05 (d, J=8.73 Hz, 1H) 7.60 (dd, J=8.72, 2.38 Hz, 1H) 8.17 (d, J=2.38 Hz, 1H); MS (DCI/$NH_3$) m/z 498 (M+H)$^+$. Anal. calcd $C_{24}H_{30}F_3N_3O_3S.1.2 H_2O$: C, 55.52; H, 6.29; N, 8.09. Found: C, 55.39; H, 6.63; N, 8.01.

Example 385

N-[(2Z)-5-tert-butyl-3-[(2R)-tetrahydrofuran-2-ylmethyl]-1,3-thiazol-2(3H)-ylidene]-2-[(3S)-pyrrolidin-3-yloxy]-5-(trifluoromethyl)benzamide

Example 385A tert-butyl(3S)-3-[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]pyrrolidine-1-carboxylate The title compound was prepared and isolated as described in Example 373, substituting (S)-tert-butyl 3-hydroxypyrrolidine-1-carboxylate for (R)-1-methylpyrrolidin-3-ol in 84% yield. $^1$H NMR (300 MHz, CDCl$_3$) δ ppm 1.36 (s, 9H) 1.45 (s, 9H) 1.67-1.72 (m, 1H) 1.75-1.91 (m, 2H) 1.91-2.15 (m, 2H) 2.23-2.29 (m, 1H) 3.46-3.61 (m, 3H) 3.65-3.69 (m, 1H) 3.73-3.88 (m, 2H) 4.13-4.29 (m, 2H) 4.36-4.48 (m, 1H) 4.99-5.03 (m, 1H) 6.88 (s, 1H) 6.97 (d, J=8.72 Hz, 1H) 7.57-7.61 (m, 1H) 8.18 (d, J=2.38 Hz, 1H); MS (DCI/$NH_3$) m/z 598 (M+H)$^+$.

Example 385B

N-[(2Z)-5-tert-butyl-3-[(2R)-tetrahydrofuran-2-ylmethyl]-1,3-thiazol-2(3H)-ylidene]-2-[(3S)-pyrrolidin-3-yloxy]-5-(trifluoromethyl)benzamide The title compound was prepared and isolated as described in Example 384B, substituting Example 385A for Example 384A in 61% yield. $^1$H NMR (300 MHz, DMSO-$d_6$) δ ppm 1.32 (s, 9H) 1.60-1.69 (m, 1H) 1.77-1.86 (m, 2H) 1.87-1.98 (m, 2H) 2.03-2.15 (m, 1H) 2.95-3.11 (m, 3H) 3.20-3.26 (m, 2H) 3.61-3.69 (m, 1H) 3.75-3.83 (m, 1H) 4.21-4.22 (m, 2H) 4.24-4.33 (m, 1H) 5.11-5.14 (m, 1H) 7.28 (s, 1H) 7.31 (d, J=8.82 Hz, 1H) 7.76 (dd, J=8.82, 2.03 Hz, 1H) 8.03 (d, J=2.03 Hz, 1H); MS (DCI/$NH_3$) m/z 498 (M+H)$^+$. Anal. calcd $C_{24}H_{30}F_3N_3O_3S.0.4$ EtOAc.0.3 $CH_2Cl_2$: C, 53.18; H, 5.79; N, 7.27. Found: C, 53.33; H, 5.47; N, 6.94.

Example 386

Xueqing Wang

N-[(2Z)-5-tert-butyl-3-[(2R)-tetrahydrofuran-2-ylmethyl]-1,3-thiazol-2(3H)-ylidene]-5-(trifluoromethyl)-2-vinylbenzamide

Example 386A 2-bromo-5-(trifluoromethyl)benzoyl chloride

The title compound was prepared using the method described in Example 375B, substituting 2-bromo-5-(trifluoromethyl)benzoic acid for Example 375A.

Example 386B 2-bromo-N-[(2Z)-5-tert-butyl-3-[(2R)-tetrahydrofuran-2-ylmethyl]-1,3-thiazol-2(3H)-ylidene]-5-(trifluoromethyl)benzamide The title compound was prepared as described in Example 372B, substituting Example 386A for 2-fluoro-5-(trifluoromethyl)benzoyl chloride in 88% yield. $^1$H NMR (300 MHz, DMSO-$d_6$) δ ppm 1.33 (s, 9H) 1.54-1.69 (m, 1H) 1.77-1.86 (m, 2H) 1.88-1.97 (m, 1H) 3.61-3.69 (m, 1H) 3.74-3.82 (m, 1H) 4.21-4.34 (m, 3H) 7.34 (s, 1H) 7.71 (dd, J=8.33, 2.38 Hz, 1H) 7.93 (d, J=8.33 Hz, 1H) 8.08 (d, J=2.38 Hz, 1H); MS (DCI/NH$_3$) m/z 491 (M+H)$^+$.

Example 386C

N-[(2Z)-5-tert-butyl-3-[(2R)-tetrahydrofuran-2-ylmethyl]-1,3-thiazol-2(3H)-ylidene]-5-(trifluoromethyl)-2-vinylbenzamide To a solution Example 386B (200 mg, 0.407 mmol) and dibutylvinylboronate (150 mg, 0.814 mmol) in 1,2-dimethoxyethane (1 mL) and methyl alcohol (0.500 mL) was added palladium tetrakistriphenylphosphine (47.0 mg, 0.041 mmol) and cesium fluoride (185 mg, 1.22 mmol). This mixture was heated in a microwave at 110° C. for 15 min. The reaction mixture was cooled to room temperature and concentrated, and the residue was purified by column chromatography using an Analogix® Intelliflash280™ (SiO$_2$, 0-30% ethyl acetate in hexane over 25 min) to obtain the title compound (150 mg, 84%). $^1$H NMR (300 MHz, CDCl$_3$) δ ppm 1.36 (s, 9H) 1.61-1.73 (m, 1H) 1.79-1.95 (m, 2H) 2.02-2.13 (m, 1H) 3.75-3.89 (m, 2H) 4.14-4.24 (m, 1H) 4.27-4.33 (m, 1H) 4.42-4.48 (m, 1H) 5.34-5.41 (m, 1H) 5.64-5.72 (m, 1H) 6.88 (s, 1H) 7.60-7.73 (m, 3H) 8.39 (s, 1H); MS (DCI/NH$_3$) m/z 439 (M+H)$^+$.

Example 387 tert-butyl 4-[2-({[(2Z)-5-tert-butyl-3-[(2R)-tetrahydrofuran-2-ylmethyl]-1,3-thiazol-2(3H)-ylidene] amino}carbonyl)-4-trifluoromethyl)phenyl]-3,6-dihydropyridine-1(2H)-carboxylate The title compound was prepared and isolated as described in Example 386C, substituting 1-(tert-butoxycarbonyl)-1,2,3,6-tetrahydropyridin-4-ylboronic acid for dibutylvinylboronate in 93% yield. $^1$H NMR (300 MHz, CDCl$_3$) δ ppm 1.36 (s, 9H) 1.48 (s, 9H) 1.64-1.70 (m, 1H) 1.79 (m, 2H) 1.99-2.10 (m, 1H) 2.42-2.46 (m, 1H) 3.59-3.63 (m, 2H) 3.70- 3.88 (m, 3H) 4.03-4.07 (m, 2H) 4.10-4.17 (m, 1H) 4.22-4.27 (m, 1H) 4.39-4.45 (m, 1H) 5.63-5.67 (m, 1H) 6.88 (s, 1H) 7.31 (d, J=7.93 Hz, 1H) 7.60 (dd, J=7.73, 1.78 Hz, 1H) 8.21-8.24 (m, 1H); MS (DCI/NH$_3$) m/z 594 (M+H)$^+$.

Example 388

N-[(2Z)-5-tert-butyl-3-[(2R)-tetrahydrofuran-2-ylmethyl]-1,3-thiazol-2(3H)-ylidene]-2-(1,2,3,6-tetrahydropyridin-4-yl)-5-(trifluoromethyl)benzamide The title compound was prepared and isolated using the method in Example 384B, substituting Example 387 for example 384A in 61% yield. $^1$H NMR (300 MHz, CDCl$_3$) δ ppm 1.36 (s, 9H) 1.64-1.68 (m, 1H) 1.81-1.91 (m, 2H) 2.03-2.11 (m, 2H) 2.31-2.33 (m, 1H) 3.10 (t, J=5.55 Hz, 2H) 3.51-3.55 (m, 2H) 3.75-3.90 (m, 2H) 4.10-4.21 (m, 1H) 4.25-4.32 (m, 1H) 4.46 (dd, J=13.68, 2.97 Hz, 1H) 5.68-5.72 (m, 1H) 6.88 (s, 1H) 7.32 (d, J=7.93 Hz, 1H) 7.60 (dd, J=8.13, 1.78 Hz, 1H) 8.20 (d, J=1.59 Hz, 1H); MS (DCI/NH$_3$) m/z 494 (M+H)$^+$.

Example 389

N-[(2Z)-5-tert-butyl-3-[(2R)-tetrahydrofuran-2-ylmethyl]-1,3-thiazol-2(3H)-ylidene]-2-ethyl-5-(trifluoromethylbenzamide A mixture of Example 386C (120 mg, 0.274 mmol) and palladium hydroxide (19.22 mg, 0.137 mmol) in methyl alcohol (2.0 mL) was hydrogenated under 1 atm H$_2$ at 20° C. for 4 hr. The reaction was filtered and the filtrate concentrated. The residue was isolated by preparative HPLC on a Phenomenex Luna Combi-HTS C8(2) column (5 μm, 100 Å, 2.1 mm×30 mm), using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100%A, 2.9-3.0 min 100-10%A 0.5 min post-run delay) to provide the title compound (92 mg, 76%). $^1$H NMR (300 MHz, DMSO-$d_6$) δ ppm 1.19 (t, J=7.29 Hz, 3H) 1.33 (s, 9H) 1.59-1.70 (m, 1H) 1.78-1.87 (m, 2H) 1.88-1.99 (m, 1H) 3.09 (q, J=7.46 Hz, 2H) 3.62-3.70 (m, 1H) 3.75-3.83 (m, 1H) 4.22-4.32 (m, 3H) 7.30 (s, 1H) 7.52 (d, J=8.14 Hz, 1H) 7.72 (d, J=7.12 Hz, 1H) 8.19 (s, 1H); MS (DCI/NH$_3$) m/z 441 (M+H)$^+$. Anal. calcd C$_{22}$H$_{27}$F$_3$N$_2$O$_2$S.0.3 H$_2$O: C, 59.26; H, 6.24; N, 6.28. Found: C, 59.14; H, 6.06; N, 6.20.

Example 390

N-[(2Z)-5-tert-butyl-3-[(2R)-tetrahydrofuran-2-ylmethyl]-1,3-thiazol-2(3H)-ylidene]-2-[(E)-2-(methylsulfonyl)vinyl]-5-(trifluoromethyl)benzamide To a solution of Example 386B (172 mg, 0.350 mmol), triethylamine (53 mg, 0.525 mmol) and methylvinylsulfone (55.7 mg, 0.525 mmol) in acetonitrile (1 mL) was added palladium acetate (4.72 mg, 0.021 mmol) and tri(o-tolyl)phosphine (23.44 mg, 0.077 mmol). This mixture was heated in a microwave at 140° C. for 30 min. The reaction was heated another 30 min at 180° C. The reaction mixture was cooled to room temperature and filtered. The residue was purified by preparative HPLC on a Phenomenex Luna Combi-HTS C8(2) column (5 μm, 100 Å, 2.1 mm×30 mm), using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to provide the title compound (85 mg, 47%). ¹H NMR (300 MHz, CDCl₃) δ ppm 1.38 (s, 9H) 1.62-1.71 (m, 1H) 1.76-1.92 (m, 2H) 2.02-2.14 (m, 1H) 3.08 (s, 3H) 3.73-3.87 (m, 2H) 4.22-4.34 (m, 2H) 4.50 (d, J=11.10 Hz, 1H) 6.80 (d, J=15.47 Hz, 1H) 6.97 (s, 1H) 7.59-7.72 (m, 2H) 8.52 (s, 1H) 8.83 (d, J=15.47 Hz, 1H); MS (DCI/NH₃) m/z 517 (M+H)⁺.

Example 391

N-[(2Z)-5-tert-butyl-3-[(2R)-tetrahydrofuran-2-ylmethyl]-1,3-thiazol-2(3H)-ylidene]-2-[2-(methylsulfonyl)ethyl]-5-(trifluoromethyl)benzamide The title compound was prepared and isolated using the method described in Example 389, substituting Example 390 for Example 386C in 87% yield. ¹H NMR (300 MHz, CDCl₃) δ ppm 1.38 (m, 9H) 1.64-1.74 (m, 1H) 1.81-1.97 (m, 2H) 2.04-2.15 (m, 1H) 3.01 (s, 3H) 3.40-3.47 (m, 2H) 3.59-3.67 (m, 2H) 3.75-3.90 (m, 2H) 4.18-4.26 (m, 1H) 4.27-4.34 (m, 1H) 4.46 (dd, J=13.39, 2.88 Hz, 1H) 6.91 (s, 1H) 7.43 (d, J=8.14 Hz, 1H) 7.60-7.66 (m, 1H) 8.51 (d, J=1.70 Hz, 1H); MS (DCI/NH₃) m/z 519 (M+H)⁺.

Example 392

N-[(2Z)-5-tert-butyl-3-[(2R)-tetrahydrofuran-2-ylmethyl]-1,3-thiazol-2(3H)-ylidene]-2-{[(2S)-2-(hydroxymethyl)pyrrolidin-1-yl]methyl}-5-(trifluoromethyl)benzamide In a vial (5 mL), a mixture of Example 375C (88 mg, 0.200 mmol), support-bound cyanoborohydride resin (0.256 g, 0.599 mmol), (S)-pyrrolidin-2-ylmethanol (60 mg, 0.593 mmol), and acetic acid (18 mg, 0.300 mmol) in dichloromethane (1 mL) and methyl alcohol (1 mL) was shaken on an orbit shaker for 2 hr. The reaction was filtered, concentrated and the residue was purified by preparative HPLC on a Phenomenex Luna Combi-HTS C8(2) column (5 μm, 100 Å, 2.1 mm×30 mm), using a gradient of 10-100% acetonitrile (A) and 0.1% trifluoroacetic acid in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) in 38% yield as TFA salt. ¹H NMR (300 MHz, CD₃OD) δ ppm 1.41 (s, 9H) 1.72-1.81 (m, 1H) 1.88-1.99 (m, 2H) 2.05-2.20 (m, 3H) 2.27-2.41 (m, 1H) 3.34-3.42 (m, 1H) 3.52-3.66 (m, 1H) 3.67-3.82 (m, 4H) 3.85-3.96 (m, 1H) 4.36-4.46 (m, 3H) 4.57 (d, J=12.69 Hz, 1H) 4.86-4.93 (m, 2H) 7.28 (s, 1H) 7.76-7.82 (m, 1H) 7.87-7.94 (m, 1H) 8.73-8.75 (m, 1H); MS (DCI/NH₃) m/z 526 (M+H)⁺. Anal. calcd calcd C₂₆H₃₄F₃N₃O₃S.1.9 CF₃CO₂H: C, 48.22; H, 4.87; N, 5.66. Found: C, 48.28; H, 4.63; N, 5.67.

Example 393

N-[(2Z)-5-tert-butyl-3-[(2R)-tetrahydrofuran-2-ylmethyl]-1,3-thiazol-2(3H)-ylidene]-2-(morpholin-4-ylmethyl)-5-(trifluoromethyl)benzamide The title compound was prepared and purified as described in Example 392, substituting morpholine for (S)-pyrrolidin-2-ylmethanol in 42% yield as the TFA salt. ¹H NMR (300 MHz, CD₃OD) δ ppm 1.41 (s, 9H) 1.71-1.82 (m, 1H) 1.88-1.98 (m, 2H) 2.06-2.13 (m, 1H) 3.36-3.40 (m, 2H) 3.46-3.57 (m, 2H) 3.75-3.91 (m, 4H) 4.05-4.16 (m, 2H) 4.37-4.47 (m, 3H) 4.68 (s, 2H) 7.29 (s, 1H) 7.76 (d, J=7.93 Hz, 1H) 7.92 (dd, J=7.93, 1.98 Hz, 1H) 8.79 (s, 1H); MS (DCI/NH₃) m/z 512 (M+H)⁺. Anal. Calcd C₂₅H₃₂F₃N₃O₃S.1.9 CF₃CO₂H: C, 47.50; H, 4.69; N, 5.67. Found: C, 47.62; H, 4.67; N, 5.86.

Example 394

N-[(2Z)-5-tert-butyl-3-[(2R)-tetrahydrofuran-2-ylmethyl]-1,3-thiazol-2(3H)-ylidene]-2-(thiomorpholin-4-ylmethyl)-5-(trifluoromethyl)benzamide The TFA salt of the title compound was prepared and purified as described in Example 392, substituting thiomorpholine for (S)-pyrrolidin-2-ylmethanol in 45% yield. ¹H NMR (300 MHz, CD₃OD) δ ppm 1.40 (s, 9H) 1.70-1.81 (m, 1H) 1.88-1.98 (m, 2H) 2.15-2.15 (m, 1H) 2.93-3.02 (m, 2H) 3.04-3.14 (m, 2H) 3.40-3.48 (m, 2H) 3.73-3.93 (m, 4H) 4.37-4.47 (m, 3H) 4.66 (s, 2H) 7.29 (s, 1H) 7.74-7.76 (m, 1H) 7.90-7.92 (m, 1H) 8.75-8.77 (m, 1H); MS (DCI/NH₃) m/z 528 (M+H)⁺. Anal. calcd C₂₅H₃₂F₃N₃O₂S₂.1.1 CF₃CO₂H: C, 50.02; H, 5.11; N, 6.43. Found: C, 49.97; H, 5.05; N, 6.40.

Example 395

N-[(2Z)-5-tert-butyl-3-[(2R)-tetrahydrofuran-2-ylmethyl]-1,3-thiazol-2(3H)-ylidene]-2-[(4-methylpiperazin-1-yl)methyl]-5-(trifluoromethyl)benzamide The TFA salt of the title compound was prepared and purified as described in Example 392, substituting N-methyl piperidine for (S)-pyrrolidin-2-ylmethanol in 45% yield. ¹H NMR (300 MHz, CD₃OD) δ ppm 1.40 (s, 9H) 1.66-1.78 (m, 1H) 1.87-1.97 (m, 2H) 2.02-2.14 (m, 1H) 2.81 (s, 3H) 2.94-3.08 (m, 4H) 3.18-3.28 (m, 4H) 3.72-3.81 (m, 1H) 3.85-3.93 (m, 1H) 4.28-4.41 (m, 5H) 7.23 (s, 1H) 7.71-7.80 (m, 2H) 8.33 (s, 1H); MS (DCI/NH₃) m/z 525 (M+H)⁺. Anal. calcd C₂₆H₃₅F₃N₄O₂S.2.0 CF₃CO₂H: C, 47.87; H, 4.95; N, 7.44. Found: C, 47.69; H, 4.92; N, 7.38.

Example 396

N-[(2Z)-5-tert-butyl-3-[(2R)-tetrahydrofuran-2-ylmethyl]-1,3-thiazol-2(3H)-ylidene]-2-{[(cyanomethyl)(methyl)amino]methyl}-5-(trifluoromethyl)benzamide The title compound was prepared and purified as described in Example 392, substituting 2-(methylamino)acetonitrile for (S)-pyrrolidin-2-ylmethanol in 45% yield. ¹H NMR (300 MHz, CD₃OD) δ ppm 1.40 (s, 9H) 1.69-1.75 (m, 1H) 1.85-1.97 (m, 2H) 2.04-2.17 (m, 1H) 2.53 (s, 3H) 3.73-3.80 (m, 1H) 3.85-3.92 (m, 3H) 4.29 (s, 2H), 4.30-4.42 (m, 3H) 7.21 (s, 1H) 7.71-7.80 (m, 2H) 8.28-8.30 (m, 1H); MS (DCI/NH₃) m/z 495 (M+H)⁺.

Example 397

N-[(2Z)-5-tert-butyl-3-[(2R)-tetrahydrofuran-2-ylmethyl]-1,3-thiazol-2(3H)-ylidene]-2-{[(2R)-2-(hydroxymethyl)pyrrolidin-1-yl]methyl}-5-(trifluoromethyl)benzamide The TFA salt of the title compound was prepared and purified as described in Example 392, substituting (R)-pyrrolidin-2-ylmethanol for (S)-pyrrolidin-2-ylmethanol in 60% yield. ¹H NMR (300 MHz, CD₃OD) δ ppm 1.41 (s, 9H) 1.70-1.82 (m, 1H) 1.88-1.98 (m, 2H) 2.05-2.22 (m, 4H) 2.33-2.37 (m, 1H) 3.33-3.40 (m, 1H) 3.51-3.59 (m, 1H) 3.68-3.82 (m, 4H) 3.86-3.94 (m, 1H) 4.36-4.44 (m, 3H) 4.53-4.61 (m, 1H) 4.88-4.92 (m, 1H) 7.28 (s, 1H) 7.75-7.81 (m, 1H) 7.90 (dd, J=7.97, 1.53 Hz, 1H) 8.74 (d, J=1.70 Hz, 1H); MS (DCI/NH$_3$) m/z 526 (M+H)$^+$. Anal. calcd C$_{26}$H$_{34}$F$_3$N$_3$O$_3$S.2.0 CF$_3$CO$_2$H: C, 47.81; H, 4.81; N, 5.58. Found: C, 47.72; H, 4.91; N, 5.49.

Example 398

2-[(tert-butylamino)methyl]-N-[(2Z)-5-tert-butyl-3-[(2R)-tetrahydrofuran-2-ylmethyl]-1,3-thiazol-2 (3H)-ylidene]-5-(trifluoromethyl)benzamide The TFA salt of the title compound was prepared and purified as described in Example 392, substituting tert-butyl amine for (S)-pyrrolidin-2-ylmethanol in 80% yield. $^1$H NMR (300 MHz, CD$_3$OD) δ ppm 1.40 (s, 9H) 1.55 (s, 9H) 1.71-1.82 (m, 1H) 1.88-1.98 (m, 2H) 2.04-2.15 (m, 1H) 3.73-3.81 (m, 1H) 3.86-3.94 (m, 1H) 4.36-4.46 (m, 3H), 4.48 (s, 2H) 7.27 (s, 1H) 7.76 (d, J=8.14 Hz, 1H) 7.88 (dd, J=7.97, 1.86 Hz, 1H) 8.69 (d, J=1.36 Hz, 1H); MS (DCI/NH$_3$) m/z 498 (M+H)$^+$. Anal. calcd C$_{25}$H$_{34}$F$_3$N$_3$O$_2$S.1.0 CF$_3$CO$_2$H: C, 53.02; H, 5.77; N, 6.87. Found: C, 52.92; H, 5.71; N, 6.80.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound according to formula (I),

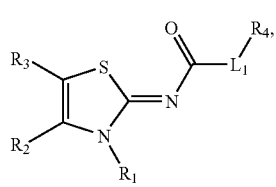

or a pharmaceutically acceptable salt, prodrug, salt of a prodrug, or a combination thereof, wherein
  R$_1$ is A, or A-alkylene-;
  R$_2$ is hydrogen, alkoxy, alkoxyalkyl, alkoxycarbonyl, alkoxycarbonylalkyl, alkyl, alkyl-S(O)$_2$—, aryl, arylalkyl, arylalkenyl, azidoalkyl, cyano, cycloalkyl, halo, haloalkyl, heteroaryl, heterocycle, —(CR$_{21}$R$_{22}$)$_m$—OH, R$_a$R$_b$N—, R$_a$R$_b$N-alkyl-, R$_c$R$_d$NC(O)—, or R$_8$—R$_7$—;
  R$_3$ is alkoxy, alkoxyalkyl, n-propyl, tert-butyl, alkylcarbonyl, alkyl-S(O)$_2$—, cyano, cycloalkyl, halo, haloalkyl, —(CR$_{31}$R$_{32}$)$_m$—OH, R$_a$R$_b$N—, R$_a$R$_b$N-alkyl-, or R$_8$—R$_7$—; or
  R$_2$ and R$_3$, together with the carbon atoms to which they are attached, form a 4-, 5-, 6-, or 7-membered monocyclic ring, optionally fused to benzo or oxadiazole, said monocyclic ring contains zero or one additional double bond, zero or one oxygen atom, and zero or one nitrogen atom as ring atoms; two non-adjacent atoms of said monocyclic ring are optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; with the proviso that when R$_2$ and R$_3$, together with the carbon atom to which they are attached, form a ring as represented by formula (viii), (ix), or (xi),

then R$_1$ is A or A-alkylene-;
  and with a further proviso that when R$_2$ and R$_3$ are other than forming a ring with the carbon atoms to which they are attached, then R$_1$ is alkoxyalkoxyalkyl, A or A-alkylene-;
  R$_4$ is alkyl, alkynyl, cycloalkyl, cycloalkenyl, or aryl; wherein the alkyl group is optionally substituted with one substituent selected from the group consisting of alkoxy, alkoxycarbonyl, carboxy, halo, —OH, and R$_e$R$_f$N—;
  R$_7$ and R$_8$ are each independently aryl, cycloalkyl, cycloalkenyl, heteroaryl, or heterocycle;
  R$_a$ and R$_b$, at each occurrence, are each independently hydrogen, alkoxycarbonyl, alkyl, alkylcarbonyl, alkyl-S(O)$_2$—, or arylalkyl;
  R$_c$ and R$_d$, are each independently hydrogen or alkyl;
  R$_e$ and R$_f$, are each independently hydrogen, alkyl, or alkylcarbonyl;
  A is a 4-, 5-, 6-, 7-, 8-, or 9-membered monocyclic heterocycle containing zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; or A is furanyl, oxazolyl, isoxazolyl, or oxadiazolyl; each ring A is optionally fused with a monocyclic ring selected from the group consisting of benzo, cycloalkyl, cycloalkenyl, heterocycle and heteroaryl; and each A is independently unsubstituted or substituted with 1, 2, 3, 4, 5, or 6 substituents independently selected from the group consisting of oxo, alkyl, halo, —OH, —O(alkyl), and haloalkyl;
  L$_1$ is a single bond or —NR$_g$—;
  R$_g$ is hydrogen or alkyl;

the aryl, cycloalkyl, cycloalkenyl, heterocycle, or heteroaryl moieties, as a substituent, or as part of a substituent, as represented by $R_2$, $R_3$, $R_4$, $R_a$, $R_b$, $R_7$, and $R_8$, are each independently unsubstituted or substituted with 1, 2, 3, 4, 5, or 6 substituents independently selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$—(CR$_{41}$R$_{42}$)$_p$=C(R$_{41}$)—, alkyl-S(O)$_2$—(CR$_{41}$R$_{42}$)$_p$—, alkyl-S—, alkyl-S—(CR$_{41}$R$_{42}$)$_p$—, alkynyl, carboxy, carboxyalkyl, cyano, cyanoalkyl, formyl, formylalkyl, halogen, haloalkyl, haloalkoxy, hydroxy, hydroxyalkyl, oxo, —SH, N(O)$_2$, —C(R$_{41}$)=N—O(R$_{42}$), —(CR$_{41}$R$_{42}$)$_p$—C(R$_{41}$)=N—O(R$_{42}$), =N—O(alkyl), =N—OH, NZ$_1$Z$_2$—(CR$_{41}$R$_{42}$)$_p$—O—, —O—(CR$_{41}$R$_{42}$)$_p$-G$_1$, G$_1$, —NZ$_1$Z$_2$, —(CR$_{41}$R$_{42}$)$_p$—NZ$_1$Z$_2$, and (NZ$_3$Z$_4$)carbonyl;

G$_1$ is a 4-, 5-, 6-, or 7-membered monocyclic heterocycle containing one nitrogen atom and optionally 1 or 2 additional heteroatom in the ring, wherein said ring is attached to the parent moiety through the nitrogen atom, and said ring is optionally substituted with 1, 2, 3, 4, or 5 substituents selected from the group consisting of alkyl, alkenyl, alkynyl, halo, haloalkyl, =N—CN, =N—OR$_{51}$, —CN, oxo, —OR$_{51}$, —OC(O)R$_{51}$, —OC(O)N(R$_{51}$)$_2$, —S(O)$_2$R$_{52}$, —S(O)$_2$N(R$_{51}$)$_2$, —C(O)R$_{51}$, —C(O)OR$_{51}$, —C(O)N(R$_{51}$)$_2$, —N(R$_{51}$)$_2$, —N(R$_{51}$)C(O)R$_{51}$, —N(R$_{51}$)S(O)$_2$R$_{52}$, —N(R$_{51}$)C(O)O(R$_{52}$), —N(R$_{51}$)C(O)N(R$_{51}$)$_2$, —(CR$_{1c}$R$_{1d}$)$_q$—OR$_{51}$, —(CR$_{1c}$R$_{1d}$)$_q$—OC(O)R$_{51}$, —(CR$_{1c}$R$_{1d}$)$_q$—OC(O)N(R$_{51}$)$_2$, —(CR$_{1c}$R$_{1d}$)$_q$—S(O)$_2$R$_{52}$, —(CR$_{1c}$R$_{1d}$)$_q$—S(O)$_2$N(R$_{51}$)$_2$, —(CR$_{1c}$R$_{1d}$)$_q$—C(O)R$_{51}$, —(CR$_{1c}$R$_{1d}$)$_q$—C(O)OR$_{51}$, —(CR$_{1c}$R$_{1d}$)$_q$—C(O)N(R$_{51}$)$_2$, —(CR$_{1c}$R$_{1d}$)$_q$—N(R$_{51}$)$_2$, —(CR$_{1c}$R$_{1d}$)$_q$—N(R$_{51}$)C(O)R$_{51}$, —(CR$_{1c}$R$_{1d}$)$_q$—N(R$_{51}$)S(O)$_2$R$_{52}$, —(CR$_{1c}$R$_{1d}$)$_q$—N(R$_{51}$)C(O)O(R$_{52}$), —(CR$_{1c}$R$_{1d}$)$_q$—N(R$_{51}$)C(O)N(R$_{51}$)$_2$, and —(CR$_{1c}$R$_{1d}$)$_q$—CN;

R$_{51}$, at each occurrence, is independently hydrogen, C$_1$-C$_4$ alkyl, C$_1$-C$_4$ haloalkyl, —(CR$_{2c}$R$_{2d}$)$_u$—OR$^{53}$, monocyclic cycloalkyl, or —(CR$_{2c}$R$_{2d}$)$_u$-(monocyclic cycloalkyl); wherein R$_{53}$ is hydrogen, C$_1$-C$_4$ alkyl, C$_1$-C$_4$ haloalkyl, monocyclic cycloalkyl, or —(CR$_{2c}$R$_{2d}$)$_u$-(monocyclic cycloalkyl);

R$_{52}$, at each occurrence, is independently C$_1$-C$_4$ alkyl, C$_1$-C$_4$ haloalkyl, monocyclic cycloalkyl, or —(CR$_{2c}$R$_{2d}$)$_u$-(monocyclic cycloalkyl);

the monocyclic cycloalkyl moiety, as a substituent, or as part of a substituent, as represented by R$_{51}$, R$_{52}$, and R$_{53}$ are each independently unsubstituted or substituted with 1, 2, 3, or 4 substituents selected from the group consisting of C$_1$-C$_4$ alkyl, halo, hydroxy, C$_1$-C$_4$ alkoxy, C$_1$-C$_4$ haloalkoxy, and C$_1$-C$_4$ haloalkyl;

R$_{21}$, R$_{22}$, R$_{31}$, R$_{32}$, R$_{41}$, R$_{42}$, R$_{1c}$, R$_{1d}$, R$_{2c}$, and R$_{2d}$, at each occurrence, are each independently hydrogen, alkyl, haloalkyl, or halo;

m, p, q, and u, at each occurrence, are each independently 1, 2, 3, or 4;

Z$_1$ and Z$_2$ are each independently hydrogen, alkyl, alkoxyalkyl, alkylcarbonyl, cyanoalkyl, haloalkyl, or formyl; and Z$_3$ and Z$_4$ are each independently hydrogen, alkyl, haloalkyl, phenyl or benzyl; wherein the phenyl moiety is optionally substituted with 1, 2, 3, or 4 substituents selected from the group consisting of alkyl, hydroxyl, and haloalkyl.

2. The compound of claim 1, or a pharmaceutically acceptable salt, prodrug, salt of a prodrug, or a combination thereof, wherein A is a 4-, 5-, 6-, 7-, 8-, or 9-membered monocyclic heterocycle containing zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; each ring A is optionally fused with a monocyclic ring selected from the group consisting of benzo, cycloalkyl, cycloalkenyl, heterocycle, and heteroaryl; and each A is independently unsubstituted or substituted with 1, 2, 3, 4, 5, or 6 substituents independently selected from the group consisting of oxo, alkyl, halo, —OH, —O(alkyl), and haloalkyl.

3. The compound of claim 2, or a pharmaceutically acceptable salt, prodrug, salt of a prodrug, or a combination thereof, wherein R$_2$ is hydrogen, alkoxycarbonyl, alkoxycarbonylalkyl, alkyl, aryl, halo, haloalkyl, or —(CR$_{21}$R$_{22}$)$_m$—OH;

R$_3$ is n-propyl, tert-butyl, alkylcarbonyl, cycloalkyl, halo, haloalkyl, or —(CR$_{31}$R$_{32}$)$_m$—OH;

L$_1$ is a bond; and

R$_4$ is aryl, cycloalkyl, alkynyl, or alkyl; wherein the alkyl is optionally substituted with one substituent selected from the group consisting of alkoxycarbonyl, —OH, and R$_e$R$_f$N—.

4. The compound of claim 3, or a pharmaceutically acceptable salt, prodrug, salt of a prodrug, or a combination thereof, wherein R$_4$ is optionally substituted phenyl.

5. The compound of claim 2, or a pharmaceutically acceptable salt, prodrug, salt of a prodrug, or a combination thereof, wherein R$_2$ is hydrogen or alkyl;

R$_3$ is n-propyl, tert-butyl, or —(CR$_{31}$R$_{32}$)$_m$—OH;

L$_1$ is a bond;

R$_4$ is optionally substituted phenyl.

6. The compound of claim 2, or a pharmaceutically acceptable salt, prodrug, salt of a prodrug, or a combination thereof, wherein R$_2$ is hydrogen, alkoxycarbonyl, alkoxycarbonylalkyl, alkyl, aryl, halo, haloalkyl, or —(CR$_{21}$R$_{22}$)$_m$—OH;

R$_3$ is n-propyl, tert-butyl, alkylcarbonyl, cycloalkyl, halo, haloalkyl, or —(CR$_{31}$R$_{32}$)$_m$—OH;

L$_1$ is a NR$_g$; and

R$_4$ is cyclolalkyl, or alkyl; wherein the alkyl is optionally substituted with one substituent selected from the group consisting of alkoxycarbonyl, —OH, and R$_e$R$_f$N—.

7. The compound of claim 1, or a pharmaceutically acceptable salt, prodrug, salt of a prodrug, or a combination thereof, wherein R$_1$ is A-alkylene- and A is furanyl, oxazolyl, isoxazolyl, or oxadiazolyl, each of which is optionally substituted.

8. The compound of claim 7, or a pharmaceutically acceptable salt, prodrug, salt of a prodrug, or a combination thereof, wherein R$_2$ is hydrogen, alkoxycarbonyl, alkoxycarbonylalkyl, alkyl, aryl, halo, haloalkyl, or —(CR$_{21}$R$_{22}$)$_m$—OH;

R$_3$ is n-propyl, tert-butyl, alkylcarbonyl, cycloalkyl, halo, haloalkyl, or —(CR$_{31}$R$_{32}$)$_m$—OH;

L$_1$ is a bond; and $R_4$ is aryl, cycloalkyl, alkynyl, or alkyl; wherein the alkyl is optionally substituted with one substituent selected from the group consisting of alkoxycarbonyl, —OH, and $R_eR_fN$—.

9. The compound of claim 7, or a pharmaceutically acceptable salt, prodrug, salt of a prodrug, or a combination thereof, wherein $R_2$ is hydrogen or alkyl;

$R_3$ is n-propyl, tert-butyl, or —$(CR_{31}R_{32})_m$—OH;

$L_1$ is a bond;

$R_4$ is optionally substituted phenyl.

10. The compound of claim 7, or a pharmaceutically acceptable salt, prodrug, salt of a prodrug, or a combination thereof, wherein $R_2$ is hydrogen, alkoxycarbonyl, alkoxycarbonylalkyl, alkyl, aryl, halo, haloalkyl, or —$(CR_{21}R_{22})_m$—OH;

$R_3$ is n-propyl, tert-butyl, alkylcarbonyl, cycloalkyl, halo, haloalkyl, or —$(CR_{31}R_{32})_m$—OH;

$L_1$ is a $NR_g$; and $R_4$ is cyclolalkyl, or alkyl; wherein the alkyl is optionally substituted with one substituent selected from the group consisting of alkoxycarbonyl, —OH, and $R_eR_fN$—.

11. The compound of claim 1, or a pharmaceutically acceptable salt, prodrug, salt of a prodrug, or a combination thereof, wherein $R_2$ and $R_3$, together with the carbon atoms to which they are attached, form a 4-, 5-, 6-, or 7-membered monocyclic ring optionally fused to benzo or oxadiazole, said monocyclic ring contains zero or one additional double bond, zero oxygen atom and zero nitrogen atom as ring atoms; two non-adjacent atoms of said monocyclic ring are linked by an alkenylene bridge of 2, 3, or 4 carbon atoms, or linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl.

12. The compound of claim 11, or a pharmaceutically acceptable salt, prodrug, salt of a prodrug, or a combination thereof, wherein $R_4$ is aryl, cycloalkyl, alkynyl, or alkyl; wherein the alkyl is optionally substituted with one substituent selected from the group consisting of alkoxycarbonyl, —OH, and $R_eR_fN$—.

13. The compound of claim 1, or a pharmaceutically acceptable salt, prodrug, salt of a prodrug, or a combination thereof, wherein $R_2$ and $R_3$, together with the carbon atoms to which they are attached, form an optionally substituted ring as represented by

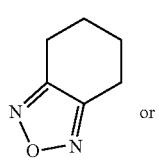

or

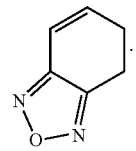

14. The compound of claim 1, or a pharmaceutically acceptable salt, prodrug, salt of a prodrug, or a combination thereof, wherein $R_2$ and $R_3$, together with the carbon atoms to which they are attached, form a 4-, 5-, 6-, or 7-membered monocyclic ring optionally fused to benzo or oxadiazole, said monocyclic ring contains zero or one additional double bond, and one oxygen atom and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl.

15. The compound of claim 14, or a pharmaceutically acceptable salt, prodrug, salt of a prodrug, or a combination thereof, wherein $R_4$ is aryl, cycloalkyl, alkynyl, or alkyl; wherein the alkyl is optionally substituted with one substituent selected from the group consisting of alkoxycarbonyl, —OH, and $R_eR_fN$—.

16. The compound of claim 1, or a pharmaceutically acceptable salt, prodrug, salt of a prodrug, or a combination thereof, wherein $R_2$ and $R_3$, together with the carbon atoms to which they are attached, form a ring as represented by

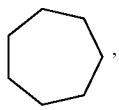

17. The compound of claim 1 selected from the group consisting of 5-chloro-2-methoxy-N-[(2Z)-5-propyl-3-(tetrahydrofuran-2-ylmethyl)-1,3-thiazol-2(3H)-ylidene]benzamide;

5-chloro-N-[(2Z)-5-chloro-3-(tetrahydrofuran-2-ylmethyl)-1,3-thiazol-2(3H)-ylidene]-2-methoxybenzamide;

5-bromo-N-[(2Z)-5-tert-butyl-3-[(2R)-tetrahydrofuran-2-ylmethyl]-1,3-thiazol-2(3H)-ylidene]-2-methoxybenzamide;

N-[(2Z)-5-acetyl-4-methyl-3-[(2R)-tetrahydrofuran-2-ylmethyl]-1,3-thiazol-2(3H)-ylidene]-5-chloro-2-methoxybenzamide;
5-chloro-N-[(2Z)-5-(1-hydroxy-1-methylethyl)-4-methyl-3-[(2R)-tetrahydrofuran-2-ylmethyl]-1,3-thiazol-2(3H)-ylidene]-2-methoxybenzamide;
N-[(2Z)-5-tert-butyl-3-[(2R)-tetrahydrofuran-2-ylmethyl]-1,3-thiazol-2(3H)-ylidene]-5-chloro-2-methoxybenzamide;
N-[(2Z)-5-tert-butyl-3-(1,3-dioxolan-2-ylmethyl)-1,3-thiazol-2(3H)-ylidene]-5-chloro-2-methoxybenzamide;
5-chloro-N-[(2Z)-5-chloro-3-[(2R)-tetrahydrofuran-2-ylmethyl]-1,3-thiazol-2(3H)-ylidene]-2-methoxybenzamide;
5-chloro-N-[(2Z)-5-chloro-3-(tetrahydro-2H-pyran-4-ylmethyl)-1,3-thiazol-2(3H)-ylidene]-2-methoxybenzamide;
N-[(2Z)-5-tert-butyl-3-[(3-methyl-4,5-dihydroisoxazol-5-yl)methyl]-1,3-thiazol-2(3H)-ylidene]-5-chloro-2-methoxybenzamide;
N-[(2Z)-5-tert-butyl-3-(tetrahydro-2H-pyran-4-ylmethyl)-1,3-thiazol-2(3H)-ylidene]-5-chloro-2-methoxybenzamide;
5-chloro-2-methoxy-N-[(2Z)-3-(tetrahydro-2H-pyran-4-ylmethyl)-4,5,6,7-tetrahydro-1,3-benzothiazol-2(3H)-ylidene]benzamide;
N-[(2Z)-5-acetyl-4-methyl-3-(oxetan-2-ylmethyl)-1,3-thiazol-2(3H)-ylidene]-5-chloro-2-methoxybenzamide;
5-chloro-N-[(2Z)-4,4-dimethyl-1-(oxetan-2-ylmethyl)-1,4,6,7-tetrahydro-2H-pyrano[4,3-d][1,3]thiazol-2-ylidene]-2-methoxybenzamide;
5-chloro-N-{(2Z)-4,4-dimethyl-1-[(2R)-tetrahydrofuran-2-ylmethyl]-1,4,6,7-tetrahydro-2H-pyrano[4,3-d][1,3]thiazol-2-ylidene}-2-methoxybenzamide;
N-[(2Z)-5-acetyl-4-methyl-3-(tetrahydro-2H-pyran-2-ylmethyl)-1,3-thiazol-2(3H)-ylidene]-5-chloro-2-methoxybenzamide;
N-[(2Z)-5-acetyl-4-methyl-3-(tetrahydro-2H-pyran-3-ylmethyl)-1,3-thiazol-2(3H)-ylidene]-5-chloro-2-methoxybenzamide;
5-chloro-N-[(2Z)-5-(1-hydroxy-1-methylethyl)-4-methyl-3-(tetrahydro-2H-pyran-2-ylmethyl)-1,3-thiazol-2(3H)-ylidene]-2-methoxybenzamide;
5-chloro-2-methoxy-N-[(2Z)-4-methyl-3-[(2R)-tetrahydrofuran-2-ylmethyl]-5-[2,2,2-trifluoro-1-hydroxy-1-(trifluoromethyl)ethyl]-1,3-thiazol-2(3H)-ylidene]benzamide;
5-chloro-N-[(2Z)-5-(1-hydroxy-1-methylethyl)-4-methyl-3-(tetrahydro-2H-pyran-3-ylmethyl)-1,3-thiazol-2(3H)-ylidene]-2-methoxybenzamide;
5-chloro-N-[(2Z)-3-{[(4R)-2,2-dimethyl-1,3-dioxolan-4-yl]methyl}-5-(1-hydroxy-1-methylethyl)-4-methyl-1,3-thiazol-2(3H)-ylidene]-2-methoxybenzamide;
5-chloro-N-[(2Z)-6,6-dimethyl-4-oxo-3-[(2R)-tetrahydrofuran-2-ylmethyl]-4,6-dihydrofuro[3,4-d][1,3]thiazol-2(3H)-ylidene]-2-methoxybenzamide;
5-chloro-N-[(2Z)-3-{[(4S)-2,2-dimethyl-1,3-dioxolan-4-yl]methyl}-5-(1-hydroxy-1-methylethyl)-4-methyl-1,3-thiazol-2(3H)-ylidene]-2-methoxybenzamide;
N-[(2Z)-5-acetyl-3-(1,4-dioxan-2-ylmethyl)-4-methyl-1,3-thiazol-2(3H)-ylidene]-5-chloro-2-methoxybenzamide;
5-chloro-N-[(2Z)-5-(1-hydroxy-1-methylethyl)-4-methyl-3-(oxetan-2-ylmethyl)-1,3-thiazol-2(3H)-ylidene]-2-methoxybenzamide;
5-chloro-N-[(2Z)-5-(1-hydroxy-1-methylethyl)-4-methyl-3-(tetrahydrofuran-3-ylmethyl)-1,3-thiazol-2(3H)-ylidene]-2-methoxybenzamide;
5-chloro-N-[(2Z)-3-(1,4-dioxan-2-ylmethyl)-5-(1-hydroxy-1-methylethyl)-4-methyl-1,3-thiazol-2(3H)-ylidene]-2-methoxybenzamide;
N-[(2Z)-5-tert-butyl-3-[(2R)-tetrahydrofuran-2-ylmethyl]-1,3-thiazol-2(3H)-ylidene]-3-methoxy-2-naphthamide;
N-[(2Z)-5-tert-butyl-3-[(3-methyloxetan-3-yl)methyl]-1,3-thiazol-2(3H)-ylidene]-5-chloro-2-methoxybenzamide;
5-chloro-2-methoxy-N-[(2Z)-3-(tetrahydrofuran-2-ylmethyl)-3,4,5,6-tetrahydro-2H-cyclopenta[d][1,3]thiazol-2-ylidene]benzamide;
5-chloro-2-methoxy-N-[(2Z)-3-(tetrahydro-2H-pyran-4-ylmethyl)-3,4,5,6-tetrahydro-2H-cyclopenta[d][1,3]thiazol-2-ylidene]benzamide;
N-[(2Z)-5-tert-butyl-3-(oxetan-2-ylmethyl)-1,3-thiazol-2(3H)-ylidene]-5-chloro-2-methoxybenzamide;
N-[(2Z)-5-tert-butyl-3-(tetrahydro-2H-pyran-2-ylmethyl)-1,3-thiazol-2(3H)-ylidene]-5-chloro-2-methoxybenzamide;
N-[(2Z)-5-tert-butyl-3-(1,4-dioxan-2-ylmethyl)-1,3-thiazol-2(3H)-ylidene]-5-chloro-2-methoxybenzamide;
N-[(2Z)-5-tert-butyl-3-{[(4S)-2,2-dimethyl-1,3-dioxolan-4-yl]methyl}-1,3-thiazol-2(3H)-ylidene]-5-chloro-2-methoxybenzamide;
N-[(2Z)-5-tert-butyl-3-{[(4R)-2,2-dimethyl-1,3-dioxolan-4-yl]methyl}-1,3-thiazol-2(3H)-ylidene]-5-chloro-2-methoxybenzamide;
N-[(2Z)-5-tert-butyl-3-(tetrahydrofuran-3-ylmethyl)-1,3-thiazol-2(3H)-ylidene]-5-chloro-2-methoxybenzamide;
N-[(2Z)-5-tert-butyl-3-(tetrahydro-2H-pyran-3-ylmethyl)-1,3-thiazol-2(3H)-ylidene]-5-chloro-2-methoxybenzamide;
N-[(2Z)-5-tert-butyl-3-{[(2S)-5-oxotetrahydrofuran-2-yl]methyl}-1,3-thiazol-2(3H)-ylidene]-5-chloro-2-methoxybenzamide;
N-[(2Z)-5-acetyl-4-methyl-3-[(2R)-tetrahydrofuran-2-ylmethyl]-1,3-thiazol-2(3H)-ylidene]-5-chloro-2-(2,2,2-trifluoroethoxy)benzamide;
N-[(2Z)-5-tert-butyl-3-[(5-methyltetrahydrofuran-2-yl)methyl]-1,3-thiazol-2(3H)-ylidene]-5-chloro-2-methoxybenzamide;
N-[(2Z)-5-tert-butyl-3-[(5,5-dimethyltetrahydrofuran-2-yl)methyl]-1,3-thiazol-2(3H)-ylidene]-5-chloro-2-methoxybenzamide;
N-[(2Z)-5-tert-butyl-3-[(2R)-tetrahydrofuran-2-ylmethyl]-1,3-thiazol-2(3H)-ylidene]-5-chloro-2-(2-methoxyethoxy)benzamide;
5-chloro-2-methoxy-N-[(2Z)-5-(1-methylcyclopropyl)-3-[(2R)-tetrahydrofuran-2-ylmethyl]-1,3-thiazol-2(3H)-ylidene]benzamide;
5-chloro-N-[(2Z)-5-(1-hydroxy-3-iodo-1-methylpropyl)-3-[(2R)-tetrahydrofuran-2-ylmethyl]-1,3-thiazol-2(3H)-ylidene]-2-methoxybenzamide;
N-[(2Z)-5-tert-butyl-3-[(2R)-tetrahydrofuran-2-ylmethyl]-1,3-thiazol-2(3H)-ylidene]-5-chloro-2-isopropoxybenzamide;
N-[(2Z)-5-tert-butyl-3-[(2R)-tetrahydrofuran-2-ylmethyl]-1,3-thiazol-2(3H)-ylidene]-5-chloro-2-ethoxybenzamide;
N-[(2Z)-5-tert-butyl-3-[(2R)-tetrahydrofuran-2-ylmethyl]-1,3-thiazol-2(3H)-ylidene]-5-chloro-2-[(2-methoxyethyl)(methyl)amino]benzamide;

N-[(2Z)-5-tert-butyl-3-[(2R)-tetrahydrofuran-2-ylmethyl]-1,3-thiazol-2(3H)-ylidene]-5-chloro-2-(difluoromethoxy)benzamide;
N-[(2Z)-5-tert-butyl-3-[(2R)-tetrahydrofuran-2-ylmethyl]-1,3-thiazol-2(3H)-ylidene]-5-chloro-2-(trifluoromethoxy)benzamide;
N-[(2Z)-5-tert-butyl-3-[(2R)-tetrahydrofuran-2-ylmethyl]-1,3-thiazol-2(3H)-ylidene]-5-chloro-2-(2,2,2-trifluoroethoxy)benzamide;
N-[(2Z)-5-tert-butyl-3-[(2R)-tetrahydrofuran-2-ylmethyl]-1,3-thiazol-2(3H)-ylidene]-5-chloro-2-[3-(dimethylamino)propoxy]benzamide;
N-[(2Z)-5-tert-butyl-3-[(2S)-tetrahydrofuran-2-ylmethyl]-1,3-thiazol-2(3H)-ylidene]-5-chloro-2-methoxybenzamide;
5-chloro-2-methoxy-N-[(2Z)-4,4,6,6-tetramethyl-3-[(2R)-tetrahydrofuran-2-ylmethyl]-4,6-dihydrofuro[3,4-d][1,3]thiazol-2(3H)-ylidene]benzamide;
N-[(2Z)-5-tert-butyl-3-[(2R)-tetrahydrofuran-2-ylmethyl]-1,3-thiazol-2(3H)-ylidene]-5-cyano-2-methoxybenzamide;
N-[(2Z)-5-tert-butyl-4-methyl-3-[(2R)-tetrahydrofuran-2-ylmethyl]-1,3-thiazol-2(3H)-ylidene]-5-chloro-2-methoxybenzamide;
5-chloro-2-methoxy-N-{(2Z)-3-[(2R)-tetrahydrofuran-2-ylmethyl]-3,4,5,6,7,8-hexahydro-2H-4,7-epoxycyclohepta[d][1,3]thiazol-2-ylidene}benzamide;
5-chloro-2-methoxy-N-[(2Z)-3-[(2R)-tetrahydrofuran-2-ylmethyl]-6,7-dihydro-4H-pyrano[3,4-d][1,3]thiazol-2(3H)-ylidene]benzamide;
5-chloro-2-methoxy-N-{(2Z)-1-[(2R)-tetrahydrofuran-2-ylmethyl]-1,4,6,7-tetrahydro-2H-pyrano[4,3-d][1,3]thiazol-2-ylidene}benzamide;
N-[(2Z)-5-tert-butyl-3-(2-morpholin-4-ylethyl)-1,3-thiazol-2(3H)-ylidene]-5-chloro-2-methoxybenzamide;
N-[(2Z)-5-tert-butyl-3-[(2R)-tetrahydrofuran-2-ylmethyl]-1,3-thiazol-2(3H)-ylidene]-5-chloro-2-hydroxybenzamide;
N-[(2Z)-5-tert-butyl-3-[(2R)-tetrahydrofuran-2-ylmethyl]-1,3-thiazol-2(3H)-ylidene]-2-methoxy-5-(trifluoromethyl)benzamide;
N-[(2Z)-5-tert-butyl-3-tetrahydro-2H-pyran-4-yl-1,3-thiazol-2(3H)-ylidene]-5-chloro-2-methoxybenzamide;
N-[(2Z)-5-tert-butyl-3-{2-[cis-2,6-dimethylmorpholin-4-yl]ethyl}-1,3-thiazol-2(3H)-ylidene]-5-chloro-2-methoxybenzamide;
N-[(2Z)-5-tert-butyl-3-{[(2R)-5-oxotetrahydrofuran-2-yl]methyl}-1,3-thiazol-2(3H)-ylidene]-5-chloro-2-methoxybenzamide;
5-chloro-N-[(2Z)-5-(1-hydroxy-1-methylethyl)-4-methyl-3-[(2R)-tetrahydrofuran-2-ylmethyl]-1,3-thiazol-2(3H)-ylidene]-2-(2,2,2-trifluoroethoxy)benzamide;
N-[(2Z)-5-tert-butyl-3-[(2R)-tetrahydrofuran-2-ylmethyl]-1,3-thiazol-2(3H)-ylidene]-5-chloro-2-[(E)-(hydroxyimino)methyl]benzamide;
N-[(2Z)-5-tert-butyl-3-[(2R)-tetrahydrofuran-2-ylmethyl]-1,3-thiazol-2(3H)-ylidene]-5-chloro-2-formylbenzamide;
N-[(2Z)-5-tert-butyl-3-[(2R)-tetrahydrofuran-2-ylmethyl]-1,3-thiazol-2(3H)-ylidene]-N'-(1,1-dimethylpropyl)urea;
N-[(2Z)-5-tert-butyl-3-[(2R)-tetrahydrofuran-2-ylmethyl]-1,3-thiazol-2(3H)-ylidene]-N'-(2-hydroxy-1,1-dimethylethyl)urea;
methyl N-({[(2Z)-5-tert-butyl-3-[(2R)-tetrahydrofuran-2-ylmethyl]-1,3-thiazol-2(3H)-ylidene]amino}carbonyl)-2-methylalaninate;
N-[(2Z)-5-tert-butyl-3-(1,3-oxazol-2-ylmethyl)-1,3-thiazol-2(3H)-ylidene]-5-chloro-2-methoxybenzamide;
N-[(2Z)-5-tert-butyl-3-(1,2,4-oxadiazol-3-ylmethyl)-1,3-thiazol-2(3H)-ylidene]-5-chloro-2-methoxybenzamide;
N-[(2Z)-5-tert-butyl-3-(2-furylmethyl)-1,3-thiazol-2(3H)-ylidene]-5-chloro-2-methoxybenz amide;
N-[(2Z)-5-tert-butyl-3-[(2R)-tetrahydrofuran-2-ylmethyl]-1,3-thiazol-2(3H)-ylidene]-2-ethoxy-5-(trifluoromethyl)benzamide;
N-[(2Z)-5-tert-butyl-3-{[(4S)-2-oxo-1,3-oxazolidin-4-yl]methyl}-1,3-thiazol-2(3H)-ylidene]-5-chloro-2-methoxybenzamide;
N-[(2Z)-5-tert-butyl-4-methyl-3-[(2R)-tetrahydrofuran-2-ylmethyl]-1,3-thiazol-2(3H)-ylidene]-2-fluoro-3-(trifluoromethyl)benzamide;
N-[(2Z)-5-tert-butyl-3-[(2R)-tetrahydrofuran-2-ylmethyl]-1,3-thiazol-2(3H)-ylidene]-2-[2-(dimethylamino)ethoxy]-5-(trifluoromethyl)benzamide;
N-[(2Z)-5-tert-butyl-3-[(2R)-tetrahydrofuran-2-ylmethyl]-1,3-thiazol-2(3H)-ylidene]-2-[2-(dimethylamino)-2-methylpropoxy]-5-(trifluoromethyl)benzamide;
N-[(2Z)-5-tert-butyl-3-[(2R)-tetrahydrofuran-2-ylmethyl]-1,3-thiazol-2(3H)-ylidene]-2-(2-morpholin-4-ylethoxy)-5-(trifluoromethyl)benzamide;
N-[(2Z)-5-tert-butyl-3-[(2R)-tetrahydrofuran-2-ylmethyl]-1,3-thiazol-2(3H)-ylidene]-2-[2-(diethylamino)ethoxy]-5-(trifluoromethyl)benzamide;
N-[(2Z)-5-tert-butyl-3-[(2R)-tetrahydrofuran-2-ylmethyl]-1,3-thiazol-2(3H)-ylidene]-2-[2-(1,1-dioxidothiomorpholin-4-yl)ethoxy]-5-(trifluoromethyl)benzamide;
N-[(2Z)-5-tert-butyl-3-[(2R)-tetrahydrofuran-2-ylmethyl]-1,3-thiazol-2(3H)-ylidene]-2-(2-piperidin-1-ylethoxy)-5-(trifluoromethyl)benzamide;
N-[(2Z)-5-tert-butyl-3-[(2R)-tetrahydrofuran-2-ylmethyl]-1,3-thiazol-2(3H)-ylidene]-2-(3-methoxy-3-methylbutoxy)-5-(trifluoromethyl)benzamide;
N-[(2Z)-5-tert-butyl-3-[(2R)-tetrahydrofuran-2-ylmethyl]-1,3-thiazol-2(3H)-ylidene]-2-[2-(2-oxopyrrolidin-1-yl)ethoxy]-5-(trifluoromethyl)benzamide;
methyl 2-({[(2Z)-5-tert-butyl-3-[(2R)-tetrahydrofuran-2-ylmethyl]-1,3-thiazol-2(3H)-ylidene]amino}carbonyl)-4-(trifluoromethyl)benzoate;
2-[2-(tert-butylamino)ethoxy]-N-[(2Z)-5-tert-butyl-3-[(2R)-tetrahydrofuran-2-ylmethyl]-1,3-thiazol-2(3H)-ylidene]-5-(trifluoromethyl)benzamide;
N-[(2Z)-5-tert-butyl-3-[(5-methylisoxazol-3-yl)methyl]-1,3-thiazol-2(3H)-ylidene]-5-chloro-2-methoxybenzamide;
N-[(2Z)-5-tert-butyl-3-[(2R)-tetrahydrofuran-2-ylmethyl]-1,3-thiazol-2(3H)-ylidene]-2-cyano-5-(trifluoromethyl)benzamide;
2-tert-butoxy-N-[(2Z)-5-tert-butyl-3-[(2R)-tetrahydrofuran-2-ylmethyl]-1,3-thiazol-2(3H)-ylidene]-5-(trifluoromethyl)benzamide;
N-[(2Z)-5-tert-butyl-3-[(2R)-tetrahydrofuran-2-ylmethyl]-1,3-thiazol-2(3H)-ylidene]-2-formyl-5-(trifluoromethyl)benzamide;
N-[(2Z)-5-tert-butyl-3-[(2R)-tetrahydrofuran-2-ylmethyl]-1,3-thiazol-2(3H)-ylidene]-3-(trifluoromethyl)benzamide;

N-[(2Z)-5-tert-butyl-3-[(2R)-tetrahydrofuran-2-ylmethyl]-1,3-thiazol-2(3H)-ylidene]-2-methyl-5-(trifluoromethyl)benzamide;

N-[(2Z)-5-tert-butyl-3-[(2R)-tetrahydrofuran-2-ylmethyl]-1,3-thiazol-2(3H)-ylidene]-5-(trifluoromethyl)-2-vinylbenzamide;

tert-butyl 4-[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenyl]-3,6-dihydropyridine-1(2H)-carboxylate;

N-[(2Z)-5-tert-butyl-3-[(2R)-tetrahydrofuran-2-ylmethyl]-1,3-thiazol-2(3H)-ylidene]-2-(1,2,3,6-tetrahydropyridin-4-yl)-5-(trifluoromethyl)benzamide;

N-[(2Z)-5-tert-butyl-3-[(2R)-tetrahydrofuran-2-ylmethyl]-1,3-thiazol-2(3H)-ylidene]-2-ethyl-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(E)-2-(methylsulfonyl)vinyl]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[2-(methylsulfonyl)ethyl]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(cyanomethyl)(methyl)amino]methyl}-5-(trifluoromethyl)benzamide;

and

2-[(tert-butylamino)methyl]-N-[(2Z)-5-tert-butyl-3-[(2R)-tetrahydrofuran-2-ylmethyl]-1,3-thiazol-2(3H)-ylidene]-5-(trifluoromethyl)benzamide;

or a pharmaceutical acceptable salt thereof.

18. A pharmaceutical composition comprising therapeutically effective amount of a compound of claim 1 having formula (I) or a pharmaceutically acceptable salt thereof, in combination with a pharmaceutically acceptable carrier.

* * * * *